US010857293B2

(12) United States Patent
Kamen et al.

(10) Patent No.: US 10,857,293 B2
(45) Date of Patent: *Dec. 8, 2020

(54) APPARATUS FOR INFUSING FLUID

(71) Applicant: DEKA Products Limited Partnership, Manchester, NH (US)

(72) Inventors: Dean Kamen, Bedford, NH (US); John M. Kerwin, Manchester, NH (US); Colin H. Murphy, Cambridge, MA (US); Jonathan Parker, Contoocook, NH (US); Daniel F. Pawlowski, Raymond, NH (US); Dirk A. van der Merwe, Canterbury, NH (US); Larry B. Gray, Merrimack, NH (US); Christopher C. Langenfeld, Nashua, NH (US); Michael S. Place, Manchester, NH (US); Michael J. Slate, Merrimack, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 402 days.

This patent is subject to a terminal disclaimer.

(21) Appl. No.: 15/584,376

(22) Filed: May 2, 2017

(65) Prior Publication Data

US 2017/0266378 A1 Sep. 21, 2017

Related U.S. Application Data

(63) Continuation of application No. 13/840,339, filed on Mar. 15, 2013, now Pat. No. 9,675,756, which is a
(Continued)

(51) Int. Cl.
*A61M 5/168* (2006.01)
*G06F 19/00* (2018.01)
(Continued)

(52) U.S. Cl.
CPC ...... *A61M 5/16859* (2013.01); *A61M 5/1411* (2013.01); *A61M 5/1689* (2013.01);
(Continued)

(58) Field of Classification Search
CPC .... F04B 43/08; F04B 43/082; F04B 43/1223; A61M 5/16859; A61M 5/1411; A61M 5/16827; A61M 5/14228; A61M 5/16809
(Continued)

(56) References Cited

U.S. PATENT DOCUMENTS 2,546,852 A 3/1951 Corneil
2,877,714 A 3/1959 Sorg et al.
(Continued)

FOREIGN PATENT DOCUMENTS

AU 736366 B2 7/2001
CN 1938061 A 3/2007
(Continued)

OTHER PUBLICATIONS

English Translation of WO-2011080193-A1 obtained Jun. 11, 2019 (Year: 2019).*
(Continued)

*Primary Examiner* — Connor J Tremarche
(74) *Attorney, Agent, or Firm* — James D. Wyninegar, Jr.

(57) ABSTRACT

A pump for pumping fluid includes a tube platen, a plunger, a bias member, inlet and outlet valves, an actuator mechanism, a position sensor, and a processor. The plunger is configured for actuation toward and away from the infusion-tube when the tube platen is disposed opposite to the plunger. The tube platen can hold an intravenous infusion tube. The bias member is configured to urge the plunger toward the tube platen.

19 Claims, 280 Drawing Sheets

Related U.S. Application Data continuation-in-part of application No. 13/333,574, filed on Dec. 21, 2011, now Pat. No. 10,453,157, and a continuation-in-part of application No. PCT/US2011/066588, filed on Dec. 21, 2011, and a continuation-in-part of application No. 13/723,238, filed on Dec. 21, 2012, now Pat. No. 9,759,369, which is a continuation-in-part of application No. 13/333,574, and a continuation-in-part of application No. PCT/US2011/066588, said application No. 13/840,339 is a continuation-in-part of application No. 13/723,235, filed on Dec. 21, 2012, now Pat. No. 9,400,873, which is a continuation-in-part of application No. 13/333,574, and a continuation-in-part of application No. PCT/US2011/066588, said application No. 13/840,339 is a continuation-in-part of application No. PCT/US2012/071131, filed on Dec. 21, 2012, which is a continuation-in-part of application No. 13/333,574, and a continuation-in-part of application No. PCT/US2011/066588, said application No. 13/840,339 is a continuation-in-part of application No. 13/724,568, filed on Dec. 21, 2012, now Pat. No. 9,295,778, which is a continuation-in-part of application No. 13/333,574, and a continuation-in-part of application No. PCT/US2011/066588, filed on Dec. 21, 2011, said application No. 13/840,339 is a continuation-in-part of application No. 13/725,790, filed on Dec. 21, 2012, now Pat. No. 9,677,555, which is a continuation-in-part of application No. 13/333,574, and a continuation-in-part of application No. PCT/US2011/066588, said application No. 13/840,339 is a continuation-in-part of application No. PCT/US2012/071490, filed on Dec. 21, 2012, and a continuation-in-part of application No. 13/333,574, and a continuation-in-part of application No. PCT/US2011/066588, said application No. 13/840,339 is a continuation-in-part of application No. 13/723,239, filed on Dec. 21, 2012, now Pat. No. 10,108,785, which is a continuation-in-part of application No. 13/333,574, and a continuation-in-part of application No. PCT/US2011/066588, said application No. 13/840,339 is a continuation-in-part of application No. 13/723,242, filed on Dec. 21, 2012, said application No. 13/840,339 is a continuation-in-part of application No. 13/723,244, filed on Dec. 21, 2012, now Pat. No. 9,151,646, which is a continuation-in-part of application No. 13/333,574, and a continuation-in-part of application No. PCT/US2011/066588, said application No. 13/840,339 is a continuation-in-part of application No. PCT/US2012/071142, filed on Dec. 21, 2012, which is a continuation-in-part of application No. 13/333,574, and a continuation-in-part of application No. PCT/US2011/066588, said application No. 13/840,339 is a continuation-in-part of application No. 13/723,251, filed on Dec. 21, 2012, now Pat. No. 9,636,455, which is a continuation-in-part of application No. 13/333,574, and a continuation-in-part of application No. PCT/US2011/066588, said application No. 13/840,339 is a continuation-in-part of application No. PCT/US2012/071112, filed on Dec. 21, 2012, which is a continuation-in-part of application No. 13/333,574, and a continuation-in-part of application No. PCT/US2011/066588, said application No. 13/840,339 is a continuation-in-part of application No. 13/723,253, filed on Dec. 21, 2012, which is a continuation-in-part of application No. 13/333,574, and a continuation-in-part of application No. PCT/US2011/066588, filed on Dec. 21, 2011.

(60) Provisional application No. 61/679,117, filed on Aug. 3, 2012, provisional application No. 61/651,322, filed on May 24, 2012, provisional application No. 61/578,649, filed on Dec. 21, 2011, provisional application No. 61/578,658, filed on Dec. 21, 2011, provisional application No. 61/578,674, filed on Dec. 21, 2011.

(51) Int. Cl.
| | |
|---|---|
| *A61M 5/14* | (2006.01) |
| *F04B 43/08* | (2006.01) |
| *F04B 43/12* | (2006.01) |
| *A61M 5/142* | (2006.01) |
| *A61M 5/145* | (2006.01) |

(52) U.S. Cl.
CPC .... *A61M 5/16827* (2013.01); *A61M 5/16831* (2013.01); *G06F 19/3418* (2013.01); *G06F 19/3456* (2013.01); *G06F 19/3468* (2013.01); *A61M 5/1415* (2013.01); *A61M 5/1417* (2013.01); *A61M 5/1452* (2013.01); *A61M 5/1456* (2013.01); *A61M 5/1458* (2013.01); *A61M 5/14216* (2013.01); *A61M 5/14224* (2013.01); *A61M 5/14228* (2013.01); *A61M 2005/16863* (2013.01); *A61M 2005/16868* (2013.01); *A61M 2205/12* (2013.01); *A61M 2205/14* (2013.01); *A61M 2205/18* (2013.01); *A61M 2205/332* (2013.01); *A61M 2205/3306* (2013.01); *A61M 2205/3317* (2013.01); *A61M 2205/3375* (2013.01); *A61M 2205/3576* (2013.01); *A61M 2205/50* (2013.01); *A61M 2205/505* (2013.01); *A61M 2205/52* (2013.01); *A61M 2209/082* (2013.01); *A61M 2209/086* (2013.01); *F04B 43/08* (2013.01); *F04B 43/082* (2013.01); *F04B 43/1223* (2013.01); *G06F 19/326* (2013.01)

(58) Field of Classification Search
USPC .......................................................... 417/44.2
See application file for complete search history.

(56) References Cited

U.S. PATENT DOCUMENTS

| | | |
|---|---|---|
| 3,128,716 A | 4/1964 | Stallman et al. |
| 3,173,372 A | 3/1965 | Baldwin |
| 3,384,336 A | 5/1968 | Pulman |
| 3,658,445 A | 4/1972 | Pulman et al. |
| 3,981,633 A | 9/1976 | Wall |
| 4,236,880 A | 12/1980 | Archibald |
| 4,273,121 A | 6/1981 | Jassawalla |
| 4,277,226 A | 7/1981 | Archibald |
| 4,303,376 A | 12/1981 | Siekmann |
| D263,997 S | 4/1982 | Preussner |
| 4,373,525 A | 2/1983 | Kobayashi |
| 4,392,849 A | 7/1983 | Petre et al. |
| 4,561,830 A | 12/1985 | Bradley |
| 4,648,812 A | 3/1987 | Kobayashi et al. |
| D289,395 S | 4/1987 | Bowers |
| 4,725,205 A | 2/1988 | Cannon et al. |
| 4,728,265 A | 3/1988 | Cannon |
| D309,662 S | 7/1990 | Gorton |
| 4,952,124 A | 8/1990 | Ogami |
| 5,039,279 A | 8/1991 | Natwick et al. |
| 5,055,001 A | 10/1991 | Natwick et al. |
| 5,055,013 A | 10/1991 | Faeser |

(56) References Cited

U.S. PATENT DOCUMENTS

| | | | |
|---|---|---|---|
| 5,078,362 A | 1/1992 | Lawless et al. | |
| 5,087,245 A | 2/1992 | Doan | |
| 5,103,211 A | 4/1992 | Daoud et al. | |
| 5,116,203 A | 5/1992 | Natwick et al. | |
| 5,131,816 A * | 7/1992 | Brown | A61M 5/142 417/2 |
| 5,158,437 A | 10/1992 | Natwick et al. | |
| 5,180,287 A | 1/1993 | Natwick et al. | |
| 5,213,573 A | 5/1993 | Sorich et al. | |
| RE34,413 E | 10/1993 | McCullough | |
| 5,256,157 A | 10/1993 | Samiotes et al. | |
| 5,322,422 A | 6/1994 | Natwick et al. | |
| D348,730 S | 7/1994 | Walker et al. | |
| 5,357,827 A | 10/1994 | Natwick et al. | |
| D353,667 S | 12/1994 | Tsubota et al. | |
| 5,395,321 A | 3/1995 | Kawahara et al. | |
| 5,413,252 A | 5/1995 | Magnus et al. | |
| 5,478,211 A | 12/1995 | Dominiak et al. | |
| 5,482,446 A * | 1/1996 | Williamson | A61M 5/142 417/234 |
| 5,505,709 A | 4/1996 | Funderburk et al. | |
| 5,577,891 A | 11/1996 | Loughnane et al. | |
| 5,609,576 A | 3/1997 | Voss et al. | |
| 5,637,095 A | 6/1997 | Nason et al. | |
| 5,681,285 A | 10/1997 | Ford et al. | |
| 5,695,473 A | 12/1997 | Olsen | |
| D390,654 S | 2/1998 | Alsberg et al. | |
| D393,072 S | 3/1998 | Rogler | |
| 5,755,563 A | 5/1998 | Clegg et al. | |
| 5,781,442 A | 7/1998 | Engleson et al. | |
| 5,791,881 A | 8/1998 | Moubayed et al. | |
| 5,800,387 A | 9/1998 | Duffy et al. | |
| 5,836,910 A | 11/1998 | Duffy et al. | |
| 5,842,841 A | 12/1998 | Danby et al. | |
| 5,868,712 A | 2/1999 | Briggs et al. | |
| 5,938,413 A | 8/1999 | Makino et al. | |
| 5,954,697 A | 9/1999 | Srisathapat et al. | |
| D425,017 S | 5/2000 | Leung | |
| 6,064,797 A | 5/2000 | Crittendon et al. | |
| 6,106,249 A | 8/2000 | Barak | |
| 6,158,965 A | 12/2000 | Butterfield et al. | |
| 6,193,480 B1 | 2/2001 | Butterfield | |
| D440,575 S | 4/2001 | Wang et al. | |
| 6,228,047 B1 | 5/2001 | Dadson | |
| 6,234,773 B1 | 5/2001 | Hill et al. | |
| 6,241,704 B1 | 6/2001 | Peterson et al. | |
| 6,253,968 B1 | 7/2001 | Van Dijk et al. | |
| 6,261,262 B1 * | 7/2001 | Briggs | A61M 5/142 251/7 |
| 6,267,559 B1 | 7/2001 | Mossman et al. | |
| 6,305,908 B1 | 10/2001 | Hermann et al. | |
| 6,328,712 B1 | 12/2001 | Cartledge | |
| 6,346,886 B1 | 2/2002 | De La Huerga | |
| 6,347,553 B1 | 2/2002 | Morris et al. | |
| 6,348,777 B1 | 2/2002 | Brown et al. | |
| 6,358,225 B1 | 3/2002 | Butterfield | |
| 6,362,591 B1 | 3/2002 | Moberg | |
| 6,362,887 B1 | 3/2002 | Meisberger | |
| 6,394,771 B2 | 5/2002 | Butterfield | |
| 6,408,330 B1 | 6/2002 | DeLaHuerga | |
| 6,416,291 B1 | 7/2002 | Butterfield et al. | |
| 6,422,057 B1 | 7/2002 | Anderson | |
| 6,475,180 B2 | 11/2002 | Peterson et al. | |
| 6,503,221 B1 | 1/2003 | Briggs et al. | |
| 6,519,569 B1 | 2/2003 | White et al. | |
| D475,134 S | 5/2003 | Randolph | |
| 6,561,262 B1 | 5/2003 | Osakabe et al. | |
| 6,616,633 B1 | 9/2003 | Butterfield et al. | |
| 6,629,955 B2 | 10/2003 | Morris et al. | |
| 6,635,033 B1 | 10/2003 | Hill et al. | |
| D491,523 S | 6/2004 | Chi et al. | |
| 6,790,198 B1 | 9/2004 | White et al. | |
| D499,740 S | 12/2004 | Ombao et al. | |
| 6,869,425 B2 | 3/2005 | Briggs et al. | |
| D512,151 S | 11/2005 | Ward et al. | |
| 6,997,905 B2 | 2/2006 | Gillespie, Jr. et al. | |
| 7,104,763 B2 | 9/2006 | Bouton et al. | |
| 7,206,715 B2 | 4/2007 | Vanderveen et al. | |
| 7,217,108 B2 | 5/2007 | Herwig et al. | |
| 7,258,534 B2 | 8/2007 | Fathallah et al. | |
| D551,243 S | 9/2007 | Young | |
| 7,267,661 B2 | 9/2007 | Susi | |
| D557,272 S | 12/2007 | Glaser et al. | |
| D559,262 S | 1/2008 | Young | |
| D568,814 S | 5/2008 | Hung | |
| 7,520,859 B2 * | 4/2009 | Nunome | A61B 5/02116 600/490 |
| 7,553,291 B2 | 6/2009 | Duffy et al. | |
| 7,553,295 B2 | 6/2009 | Susi | |
| 7,556,616 B2 | 7/2009 | Fathallah et al. | |
| 7,561,986 B2 | 7/2009 | Vanderveen et al. | |
| 7,565,301 B2 | 7/2009 | Moubayed et al. | |
| D599,373 S | 9/2009 | Kobayashi et al. | |
| D604,740 S | 11/2009 | Matheny et al. | |
| 7,611,498 B2 | 11/2009 | Hasler | |
| 7,611,503 B2 | 11/2009 | Spohn et al. | |
| 7,621,893 B2 | 11/2009 | Moberg et al. | |
| 7,632,249 B2 | 12/2009 | Momeni et al. | |
| 7,651,489 B2 | 1/2010 | Estes et al. | |
| 7,654,976 B2 | 2/2010 | Peterson et al. | |
| 7,668,731 B2 | 2/2010 | Martucci et al. | |
| 7,678,071 B2 | 3/2010 | Lebel et al. | |
| 7,699,806 B2 | 4/2010 | Ware et al. | |
| 7,713,241 B2 | 5/2010 | Cartledge et al. | |
| 7,727,222 B2 | 6/2010 | Da Silva et al. | |
| 7,736,354 B2 | 6/2010 | Gelfand et al. | |
| 7,743,975 B2 | 6/2010 | Miller | |
| 7,762,989 B2 | 7/2010 | Simpson | |
| D622,730 S | 8/2010 | Krum et al. | |
| D625,322 S | 10/2010 | Guntaur et al. | |
| D625,323 S | 10/2010 | Matsushima et al. | |
| 7,819,843 B2 | 10/2010 | Mann et al. | |
| 7,873,489 B2 | 1/2011 | Dolgos et al. | |
| 7,890,881 B1 | 2/2011 | Skidgel | |
| 7,893,876 B2 | 2/2011 | Brown et al. | |
| 7,895,053 B2 | 2/2011 | Holland et al. | |
| D633,517 S | 3/2011 | Weir et al. | |
| 7,896,572 B2 | 3/2011 | Fathallah et al. | |
| 7,896,842 B2 | 3/2011 | Palmroos et al. | |
| 7,904,822 B2 | 3/2011 | Monteleone et al. | |
| 7,911,353 B2 | 3/2011 | Bedingfield | |
| 7,933,780 B2 | 4/2011 | De La Huerga | |
| 7,934,912 B2 | 5/2011 | Voltenburg, Jr. et al. | |
| 7,938,796 B2 | 5/2011 | Moubayed et al. | |
| 7,941,534 B2 | 5/2011 | de la Huerga | |
| 7,945,452 B2 | 5/2011 | Fathallah et al. | |
| D640,376 S | 6/2011 | Amano et al. | |
| D640,377 S | 6/2011 | Amano et al. | |
| 7,955,060 B2 | 6/2011 | Gottschalk | |
| 7,976,508 B2 | 7/2011 | Hoag | |
| 7,981,082 B2 | 7/2011 | Wang et al. | |
| 8,025,634 B1 | 9/2011 | Moubayed et al. | |
| 8,029,253 B2 | 10/2011 | Rotem et al. | |
| 8,032,226 B2 | 10/2011 | Miller et al. | |
| 8,062,008 B2 | 11/2011 | Voltenburg, Jr. et al. | |
| 8,062,257 B2 | 11/2011 | Moberg et al. | |
| D649,973 S | 12/2011 | Matas | |
| 8,075,514 B2 | 12/2011 | Butterfield et al. | |
| 8,082,112 B2 | 12/2011 | Butterfield et al. | |
| 8,083,503 B2 | 12/2011 | Voltenburg, Jr. et al. | |
| D652,050 S | 1/2012 | Chaudhri | |
| 8,105,269 B2 | 1/2012 | Zhou | |
| 8,105,282 B2 | 1/2012 | Susi et al. | |
| 8,109,898 B2 | 2/2012 | Wolff | |
| 8,118,778 B2 | 2/2012 | Haylor et al. | |
| D655,301 S | 3/2012 | Ray et al. | |
| 8,133,197 B2 | 3/2012 | Blomquist et al. | |
| 8,134,459 B2 | 3/2012 | Smith et al. | |
| 8,142,400 B2 | 3/2012 | Rotem et al. | |
| 8,149,131 B2 | 4/2012 | Blomquist | |
| 8,150,493 B2 | 4/2012 | Susi | |
| D660,313 S | 5/2012 | Williams et al. | |
| 8,177,739 B2 | 5/2012 | Cartledge et al. | |
| 8,182,461 B2 | 5/2012 | Pope et al. | |

(56) References Cited

U.S. PATENT DOCUMENTS

| | | |
|---|---|---|
| 8,185,322 B2 | 5/2012 | Schroeder et al. |
| D662,051 S | 6/2012 | Saunders et al. |
| 8,192,394 B2 | 6/2012 | Estes et al. |
| 8,197,235 B2 | 6/2012 | Davis |
| 8,211,061 B2 | 7/2012 | Sen |
| 8,231,578 B2 | 7/2012 | Fathallah et al. |
| D664,988 S | 8/2012 | Gleasman et al. |
| D665,401 S | 8/2012 | Rai et al. |
| D666,208 S | 8/2012 | Spears et al. |
| 8,235,938 B2 | 8/2012 | Eggers et al. |
| 8,250,483 B2 | 8/2012 | Blomquist |
| 8,257,066 B2 | 9/2012 | Kasai et al. |
| D668,262 S | 10/2012 | Gleasman et al. |
| D669,096 S | 10/2012 | Katsura |
| D669,165 S | 10/2012 | Estes et al. |
| D671,550 S | 11/2012 | Chen et al. |
| D671,551 S | 11/2012 | Deng et al. |
| 8,308,457 B2 | 11/2012 | Rotem et al. |
| 8,313,308 B2 | 11/2012 | Lawless et al. |
| D673,168 S | 12/2012 | Frijlink et al. |
| 8,337,168 B2 | 12/2012 | Rotem et al. |
| D675,224 S | 1/2013 | Lee et al. |
| 8,359,338 B2 | 1/2013 | Butterfield et al. |
| D675,727 S | 2/2013 | Collins et al. |
| 8,371,832 B2 | 2/2013 | Rotem et al. |
| D678,320 S | 3/2013 | Kanalakis, Jr. et al. |
| 8,414,523 B2 | 4/2013 | Blomquist et al. |
| 8,435,206 B2 | 5/2013 | Evans et al. |
| D685,817 S | 7/2013 | Kunieda et al. |
| D689,195 S | 9/2013 | Nelsen |
| D690,729 S | 10/2013 | Abratowski et al. |
| D691,259 S | 10/2013 | Estes et al. |
| D692,378 S | 10/2013 | Esses |
| D696,684 S | 12/2013 | Yuk et al. |
| D696,686 S | 12/2013 | Yuk et al. |
| D698,362 S | 1/2014 | Ramesh et al. |
| D701,232 S | 3/2014 | Na et al. |
| D704,213 S | 5/2014 | Agnew |
| D705,244 S | 5/2014 | Arnold et al. |
| D705,248 S | 5/2014 | McCormack et al. |
| D708,626 S | 7/2014 | Klein et al. |
| D708,627 S | 7/2014 | Klein et al. |
| D709,085 S | 7/2014 | Wen |
| D712,920 S | 9/2014 | Sloo et al. |
| D715,320 S | 10/2014 | McCormack et al. |
| D716,332 S | 10/2014 | Chotin et al. |
| D717,814 S | 11/2014 | Zuckerberg et al. |
| D718,776 S | 12/2014 | Hobbs et al. |
| D718,777 S | 12/2014 | Hobbs et al. |
| D718,778 S | 12/2014 | Hobbs et al. |
| D719,963 S | 12/2014 | Hobbs et al. |
| D719,964 S | 12/2014 | Hobbs et al. |
| D721,719 S | 1/2015 | Lee |
| D722,612 S | 2/2015 | Lee et al. |
| D722,614 S | 2/2015 | Williams et al. |
| D723,052 S | 2/2015 | Lai et al. |
| D725,670 S | 3/2015 | Zhang et al. |
| D728,779 S | 5/2015 | Sabin et al. |
| D731,509 S | 6/2015 | Sueishi et al. |
| D732,062 S | 6/2015 | Kwon |
| D732,063 S | 6/2015 | Kwon |
| D732,567 S | 6/2015 | Moon et al. |
| D733,740 S | 7/2015 | Lee et al. |
| D733,741 S | 7/2015 | Lee et al. |
| D735,319 S | 7/2015 | Sabin et al. |
| D735,746 S | 8/2015 | Zuckerberg et al. |
| D736,370 S | 8/2015 | Sabin et al. |
| D740,848 S | 10/2015 | Bolts et al. |
| D741,358 S | 10/2015 | Seo et al. |
| 9,151,646 B2 | 10/2015 | Kamen et al. |
| D745,661 S | 12/2015 | Collins et al. |
| D749,206 S | 2/2016 | Johnson et al. |
| D751,689 S | 3/2016 | Peret et al. |
| D751,690 S | 3/2016 | Peret et al. |
| D752,209 S | 3/2016 | Peret et al. |
| 9,295,778 B2 | 3/2016 | Kamen et al. |
| D754,065 S | 4/2016 | Gray et al. |
| D756,386 S | 5/2016 | Kendler et al. |
| D758,399 S | 6/2016 | Kendler et al. |
| D760,288 S | 6/2016 | Kendler et al. |
| D760,289 S | 6/2016 | Kendler et al. |
| 9,364,394 B2 | 6/2016 | Demers et al. |
| 9,372,486 B2 | 6/2016 | Peret et al. |
| D760,782 S | 7/2016 | Kendler et al. |
| D760,888 S | 7/2016 | Gill et al. |
| 9,400,873 B2 | 7/2016 | Kamen et al. |
| 9,408,966 B2 | 8/2016 | Kamen |
| D767,756 S | 9/2016 | Sabin |
| 9,435,455 B2 | 9/2016 | Peret et al. |
| D768,716 S | 10/2016 | Kendler et al. |
| 9,465,919 B2 | 10/2016 | Kamen et al. |
| 9,488,200 B2 | 11/2016 | Kamen et al. |
| D774,645 S | 12/2016 | Gill et al. |
| 9,518,958 B2 | 12/2016 | Wilt et al. |
| 9,636,455 B2 | 5/2017 | Kamen et al. |
| D789,516 S | 6/2017 | Gill et al. |
| 9,675,756 B2 | 6/2017 | Kamen et al. |
| 9,677,555 B2 | 6/2017 | Kamen et al. |
| 9,687,417 B2 | 6/2017 | Demers et al. |
| D792,963 S | 7/2017 | Gill |
| D795,424 S | 8/2017 | Sloss |
| D795,805 S | 8/2017 | Gray et al. |
| 9,719,964 B2 | 8/2017 | Blumberg |
| 9,724,465 B2 | 8/2017 | Peret et al. |
| 9,724,466 B2 | 8/2017 | Peret et al. |
| 9,724,467 B2 | 8/2017 | Peret et al. |
| 9,730,731 B2 | 8/2017 | Langenfeld et al. |
| 9,744,300 B2 | 8/2017 | Kamen et al. |
| 9,746,093 B2 | 8/2017 | Peret et al. |
| 9,746,094 B2 | 8/2017 | Peret et al. |
| 9,759,343 B2 | 9/2017 | Peret et al. |
| 9,759,369 B2 | 9/2017 | Gray et al. |
| 9,772,044 B2 | 9/2017 | Peret et al. |
| D799,025 S | 10/2017 | Johnson et al. |
| 9,789,247 B2 | 10/2017 | Kamen et al. |
| 2001/0044602 A1 | 11/2001 | Angersbach et al. |
| 2002/0165503 A1 | 11/2002 | Morris et al. |
| 2003/0106553 A1 | 6/2003 | Vanderveen |
| 2003/0190246 A1 | 10/2003 | Corwin et al. |
| 2003/0217962 A1 | 11/2003 | Childers et al. |
| 2004/0158193 A1 | 8/2004 | Bui et al. |
| 2005/0029277 A1 | 2/2005 | Tachibana |
| 2005/0050301 A1 | 3/2005 | Whittle et al. |
| 2005/0267827 A1 | 12/2005 | Grant, Jr. et al. |
| 2006/0140798 A1 | 6/2006 | Kutsuzawa |
| 2006/0258985 A1 | 11/2006 | Russell |
| 2007/0109325 A1 | 5/2007 | Eveleigh |
| 2008/0038128 A1 | 2/2008 | Haar |
| 2009/0040875 A1 | 2/2009 | Buzescu et al. |
| 2009/0088687 A1* | 4/2009 | Yardimci ............ A61M 1/3626 604/122 |
| 2009/0107902 A1* | 4/2009 | Childers ................ A61M 1/16 210/196 |
| 2009/0112155 A1 | 4/2009 | Zhao et al. |
| 2009/0144620 A1 | 6/2009 | Bauchot et al. |
| 2009/0153058 A1 | 6/2009 | Feng et al. |
| 2009/0153463 A1 | 6/2009 | Arrizza et al. |
| 2009/0203329 A1 | 8/2009 | White et al. |
| 2009/0270810 A1 | 10/2009 | DeBelser et al. |
| 2009/0276167 A1 | 11/2009 | Glaser et al. |
| 2009/0286692 A1 | 11/2009 | Wainwright et al. |
| 2010/0036322 A1 | 2/2010 | Rotem |
| 2010/0040481 A1 | 2/2010 | Wolff |
| 2010/0114027 A1 | 5/2010 | Jacobson et al. |
| 2010/0153872 A1 | 6/2010 | Ahn et al. |
| 2010/0169389 A1 | 7/2010 | Weber et al. |
| 2010/0169783 A1 | 7/2010 | Weber et al. |
| 2011/0004186 A1 | 1/2011 | Butterfield |
| 2011/0085778 A1 | 4/2011 | Iwase et al. |
| 2011/0161806 A1 | 6/2011 | Stern et al. |
| 2011/0172594 A1 | 7/2011 | Yodfat et al. |
| 2011/0231204 A1 | 9/2011 | De La Huerga |
| 2011/0241878 A1 | 10/2011 | Hoag |
| 2011/0264033 A1 | 10/2011 | Jensen et al. |

(56) References Cited

U.S. PATENT DOCUMENTS

| | | |
|---|---|---|
| 2011/0271221 A1 | 11/2011 | Lategan |
| 2011/0301472 A1 | 12/2011 | Grober et al. |
| 2011/0313789 A1 | 12/2011 | Kamen et al. |
| 2011/0318198 A1 | 12/2011 | Johnson et al. |
| 2011/0318208 A1 | 12/2011 | Goldor et al. |
| 2011/0320049 A1 | 12/2011 | Chossat et al. |
| 2012/0004624 A1 | 1/2012 | Brown et al. |
| 2012/0016295 A1 | 1/2012 | Tsoukalis |
| 2012/0029941 A1 | 2/2012 | Malave et al. |
| 2012/0035581 A1 | 2/2012 | Travis |
| 2012/0053533 A1 | 3/2012 | Butterfield et al. |
| 2012/0066609 A1 | 3/2012 | Howard et al. |
| 2012/0078222 A1 | 3/2012 | Smith et al. |
| 2012/0079416 A1 | 3/2012 | Fagans |
| 2012/0083760 A1 | 4/2012 | Ledford et al. |
| 2012/0124174 A1 | 5/2012 | Nudelman et al. |
| 2012/0130308 A1 | 5/2012 | Silkaitis et al. |
| 2012/0157920 A1 | 6/2012 | Flachbart et al. |
| 2012/0172802 A1 | 7/2012 | Blomquist |
| 2012/0176394 A1 | 7/2012 | Vik et al. |
| 2012/0177507 A1 | 7/2012 | Bennett et al. |
| 2012/0179130 A1 | 7/2012 | Barnes et al. |
| 2012/0185267 A1 | 7/2012 | Kamen et al. |
| 2012/0209197 A1 | 8/2012 | Lanigan et al. |
| 2012/0241525 A1 | 9/2012 | Borges et al. |
| 2012/0254044 A1 | 10/2012 | Flanagan et al. |
| 2012/0266964 A1 | 10/2012 | West et al. |
| 2012/0283638 A1 | 11/2012 | Susi |
| 2012/0283691 A1 | 11/2012 | Barnes et al. |
| 2012/0310205 A1 | 12/2012 | Lee et al. |
| 2012/0323212 A1 | 12/2012 | Murphy et al. |
| 2013/0012880 A1 | 1/2013 | Blomquist |
| 2013/0023848 A1 | 1/2013 | Nelson et al. |
| 2013/0045115 A1 | 2/2013 | Flachbart et al. |
| 2013/0053820 A1 | 2/2013 | Estes et al. |
| 2013/0091191 A1 | 4/2013 | Levin et al. |
| 2013/0104120 A1 | 4/2013 | Arrizza et al. |
| 2013/0127870 A1 | 5/2013 | Baudel et al. |
| 2013/0133036 A1 | 5/2013 | Wang et al. |
| 2013/0141329 A1 | 6/2013 | Halbert et al. |
| 2013/0177455 A1 | 7/2013 | Kamen |
| 2013/0182381 A1 | 7/2013 | Gray |
| 2013/0184676 A1 | 7/2013 | Kamen |
| 2013/0188040 A1 | 7/2013 | Kamen |
| 2013/0191513 A1 | 7/2013 | Kamen |
| 2013/0197693 A1 | 8/2013 | Kamen |
| 2013/0204188 A1 | 8/2013 | Kamen |
| 2013/0272773 A1 | 10/2013 | Kamen |
| 2013/0281965 A1 | 10/2013 | Kamen |
| 2013/0297330 A1 | 11/2013 | Kamen |
| 2013/0310990 A1 | 11/2013 | Peret et al. |
| 2013/0317753 A1 | 11/2013 | Kamen |
| 2013/0317837 A1 | 11/2013 | Ballantyne |
| 2013/0318429 A1 | 11/2013 | Dantas et al. |
| 2013/0325154 A1 | 12/2013 | Oh et al. |
| 2013/0336814 A1 | 12/2013 | Kamen |
| 2013/0339049 A1 | 12/2013 | Blumberg, Jr. |
| 2013/0346108 A1 | 12/2013 | Kamen |
| 2014/0165703 A1 | 6/2014 | Wilt |
| 2014/0180711 A1 | 6/2014 | Kamen |
| 2014/0188076 A1 | 7/2014 | Kamen |
| 2014/0188516 A1 | 7/2014 | Kamen |
| 2014/0195639 A1 | 7/2014 | Kamen |
| 2014/0207057 A1 | 7/2014 | Zhu |
| 2014/0227021 A1 | 8/2014 | Kamen |
| 2014/0237419 A1 | 8/2014 | Ryu |
| 2014/0243745 A1 | 8/2014 | Ueda et al. |
| 2014/0318639 A1 | 10/2014 | Peret |
| 2014/0343492 A1 | 11/2014 | Kamen |
| 2014/0359443 A1 | 12/2014 | Hwang |
| 2015/0002667 A1 | 1/2015 | Peret et al. |
| 2015/0002668 A1 | 1/2015 | Peret et al. |
| 2015/0002677 A1 | 1/2015 | Peret et al. |
| 2015/0018766 A1 | 1/2015 | Nakanishi et al. |
| 2015/0023808 A1 | 1/2015 | Zhu |
| 2015/0033823 A1 | 2/2015 | Blumberg, Jr. |
| 2015/0089364 A1 | 3/2015 | Meller et al. |
| 2015/0151057 A1 | 6/2015 | Nakanishi |
| 2015/0154364 A1 | 6/2015 | Biasi et al. |
| 2015/0157791 A1 | 6/2015 | Desch et al. |
| 2015/0238228 A1 | 8/2015 | Langenfeld et al. |
| 2015/0257974 A1 | 9/2015 | Demers et al. |
| 2015/0314083 A1 | 11/2015 | Blumberg, Jr. et al. |
| 2015/0332009 A1 | 11/2015 | Kane et al. |
| 2016/0055397 A1 | 2/2016 | Peret et al. |
| 2016/0055649 A1 | 2/2016 | Peret et al. |
| 2016/0061641 A1 | 3/2016 | Peret et al. |
| 2016/0063353 A1 | 3/2016 | Peret et al. |
| 2016/0073063 A1 | 3/2016 | Peret et al. |
| 2016/0084434 A1 | 3/2016 | Janway et al. |
| 2016/0097382 A1 | 4/2016 | Kamen et al. |
| 2016/0131272 A1 | 5/2016 | Yoo et al. |
| 2016/0158437 A1 | 6/2016 | Biasi et al. |
| 2016/0179086 A1 | 6/2016 | Peret et al. |
| 2016/0184510 A1 | 6/2016 | Kamen et al. |
| 2016/0203292 A1 | 7/2016 | Kamen et al. |
| 2016/0262977 A1 | 9/2016 | Demers et al. |
| 2016/0319850 A1 | 11/2016 | Kamen et al. |
| 2016/0346056 A1 | 12/2016 | Demers et al. |
| 2016/0362234 A1 | 12/2016 | Peret et al. |
| 2017/0011202 A1 | 1/2017 | Kamen et al. |
| 2017/0045478 A1 | 2/2017 | Wilt et al. |
| 2017/0216516 A1 | 8/2017 | Dale et al. |
| 2017/0224909 A1 | 8/2017 | Kamen et al. |
| 2017/0259230 A1 | 9/2017 | Demers et al. |
| 2017/0266378 A1 | 9/2017 | Kamen et al. |
| 2017/0268497 A1 | 9/2017 | Kamen et al. |
| 2017/0284968 A1 | 10/2017 | Blumberg, Jr. |

FOREIGN PATENT DOCUMENTS

| | | |
|---|---|---|
| EP | 477551 A1 | 4/1992 |
| EP | 681847 A2 | 11/1995 |
| EP | 960627 A2 | 12/1999 |
| EP | 1640028 A2 | 3/2006 |
| EP | 1722310 A1 | 11/2006 |
| EP | 2319551 A2 | 5/2011 |
| EP | 2700424 A1 | 2/2014 |
| GB | 2020735 | 11/1979 |
| GB | 2020735 A | 11/1979 |
| JP | S58163843 A | 9/1983 |
| JP | 07171213 A | 7/1995 |
| JP | 10503688 A | 3/1996 |
| JP | 8191890 | 7/1996 |
| JP | 08509898 A | 10/1996 |
| JP | 11500338 A | 3/1997 |
| JP | 2000504964 A | 2/1998 |
| JP | 11148462 A | 6/1999 |
| JP | 200349779 A | 12/2000 |
| JP | 2004523305 | 8/2004 |
| JP | 2006514856 A | 5/2006 |
| JP | 2007516798 T | 6/2007 |
| JP | 3957322 B9 | 8/2007 |
| JP | 2007528236 A | 10/2007 |
| JP | 2007530860 A | 11/2007 |
| JP | 2009521998 A | 6/2009 |
| JP | 2011245354 A | 12/2011 |
| WO | WO9304285 A1 | 3/1993 |
| WO | WO9310835 A1 | 6/1993 |
| WO | WO9524229 A2 | 9/1995 |
| WO | WO9603168 A1 | 2/1996 |
| WO | WO9734084 A1 | 9/1997 |
| WO | WO9737703 A1 | 10/1997 |
| WO | WO9814234 A1 | 4/1998 |
| WO | WO2002068018 A2 | 9/2002 |
| WO | WO02100262 A1 | 12/2002 |
| WO | WO03094091 A1 | 11/2003 |
| WO | WO2004012043 A2 | 2/2004 |
| WO | WO2004029853 A2 | 4/2004 |
| WO | WO2004035116 A1 | 4/2004 |
| WO | WO2005065750 A1 | 7/2005 |
| WO | WO2005089263 A2 | 9/2005 |
| WO | WO2005094919 A1 | 10/2005 |
| WO | WO2006008465 A1 | 1/2006 |

(56) References Cited

FOREIGN PATENT DOCUMENTS

| | | | |
|---|---|---|---|
| WO | WO2006086723 A2 | 8/2006 | |
| WO | WO2008022880 A1 | 2/2008 | |
| WO | WO2009055639 A2 | 4/2009 | |
| WO | WO2010129720 A2 | 11/2010 | |
| WO | WO2011021098 A1 | 2/2011 | |
| WO | WO2011066556 A1 | 6/2011 | |
| WO | WO-2011080193 A1 * | 7/2011 | .......... A61M 1/3653 |
| WO | WO2011091998 A1 | 8/2011 | |
| WO | WO2011119810 A1 | 9/2011 | |
| WO | WO2013095459 A9 | 6/2013 | |
| WO | WO2013096713 A2 | 6/2013 | |
| WO | WO2013096718 A2 | 6/2013 | |
| WO | WO2013096722 A2 | 6/2013 | |
| WO | WO2013096909 A2 | 6/2013 | |
| WO | WO2013176770 A2 | 11/2013 | |
| WO | WO2013177357 A1 | 11/2013 | |
| WO | WO2014100557 A2 | 6/2014 | |
| WO | WO2014100571 A2 | 6/2014 | |
| WO | WO2014100658 A1 | 6/2014 | |
| WO | WO2014100687 A2 | 6/2014 | |
| WO | WO2014100736 A2 | 6/2014 | |
| WO | WO2014100744 A2 | 6/2014 | |
| WO | WO2014144557 A2 | 9/2014 | |
| WO | PCT/US15/16796 | 2/2015 | |
| WO | WO2015017275 A1 | 2/2015 | |
| WO | PCT/US15/49952 | 9/2015 | |
| WO | PCT/US2015/63359 | 12/2015 | |
| WO | PCT/US2017/15382 | 1/2017 | |

OTHER PUBLICATIONS

Second Office Action dated May 15, 2017, received in Republic of China Patent Application No. 201380039475.5, 10 pgs.
Rule 161 Communication from the European Patent Office for Patent Application 15771376.9, dated May 8, 2017, 2 pgs.
Notice for Reason for Rejection, dated Jun. 6, 2017, received in Japanese patent application National Publication No. 2016-132343, 2 pgs.
First Examination Report from the Intellectual Property Office of New Zealand for Application 735908, dated Oct. 26, 2017, 3 pgs.
Notice for Reason for Rejection, dated Aug. 29, 2017, received in Japanese patent application National Publication No. 2016-161815, 5 pgs.
U.S. Appl. No. 15/616,325, filed Jun. 7, 2017, US20170268497A1.
U.S. Appl. No. 15/808,099, filed Nov. 9, 2017.
AAMI and FDA, Infusing Patients Safely: Priority Issues from the AAMI/FDA Infusion Device Summit, Symposium, Oct. 5-6, 2010, pp. 1-48, AAMI, Arlington, VA, USA.
Alaris Medical Systems, Signature Edition GOLD: Infusion Pump Models 7130/7131 and 7230/7231, directions for use, 132 pgs., ALARIS Medical Systems, Inc. (Publication date unknown but assumed to be prior to the filing date.).
B. Braun, B. Braun Space Infusion Systems: Automated Infusion Systems, brochure, 24 pgs., B. Braun Melsungen AG (Publication date unknown but assumed to be prior to the filing date.).
B. Braun, B. Braun SpaceStation MRI: Automated Infusion Systems, B. Braun Melsungen AG; (available not before Feb. 2008); No. 6064504; 2 pgs.
B. Braun, Infusomat Space and Accessories, Date of last revision: Nov. 2010, 68 pgs., B. Braun Meslungen AG; www.bbraun.com.
B. Braun, Outlook 200 with DoseScan, Operator's Manual, 2003, 73 pgs., B. Braun Medical Inc.
B. Braun, Outlook ES Safety Infusion System, © 2008, 16 pgs., Bethlehem, PA, United States, B. Braun Medical Inc.
B. Braun, SpaceControl for Automated Glucose Control, instructions for use, Date of last revision: Dec. 2010, 44 pgs., B. Braun Melsungen AG.
B. Braun, Technical Data, 5 pgs., B. Braun Melsungen AG; (Publication date unknown but assumed to be prior to the filing date.).
B. Braun, Vista basic Infusion Pump: Quick Reference, manual, 950853-Rev Jun. 2002, 2 pgs., B. Braun Medical Inc.
B. Braun, Vista Basic: Software IFVB, instructions for use, 2002, 3 pgs., B. Bran Medical Inc.
Baxter, Flo-Gard 6201: Volumetric Infusion Pump, Service Manual, 1992/1995, 202 pgs., Baxter Healthcare Corporation, United States.
Butterfield, Alaris SE Pump, Monitoring and Detection of IV Line Occlusions, 2010, 4 pgs., CareFusion Corporation.
Carayon et al., Observing Nurse Interaction with Infusion Pump Technologies, Advances in Patient Safety, pp. 349-364, vol. 2: Observing Medication Administration; Study 2001-2004.
Cardinal Health, Alaris DS Docking Station, Technical Service Manual, 2002-2007, pp. 131, Issue 2, Cardinal Health, Inc.
Cardinal Health, Alaris GP Volumetric Pump, Technical Service Manual, 2006-2008, pp. 184, Issue 3, Cardinal Health, Inc.
Cardinal Health, Alaris GW Volumetric Pump, Technical Service Manual, 2003-2006, pp. 1-77, Issue 4, Cardinal Health, Inc.
Cardinal Health, IVAC Variable Pressure Volumetric Pump: Models 571 & 572, Technical Service Manual, 1994-2008, pp. 1-104, Issue 2, Cardinal Health, Inc.
Cardinal Health, IVAC Volumetric Pump: Models 597 & 598, Technical Service Manual, 1998-2006, pp. 1-76, Issue 3, Cardinal Health, Inc.
Care Everywhere, Gateway User Manual: V1.0.13 W/CQI 1.6: For use with the Sigma Spectrum Pump: Care Everywhere Document No. CE-100-003-IFU, manual, 1-55, CareEverywhere LLC, 9 Tech Circle, Natick, MA, USA. © 2010.
Carefusion, Alaris SE Pump: Models 7100/7130 and 7200/7230, User Manual, Apr. 2011, 134 pgs., CareFusion Corporation.
Carefusion, Directions for Use: Alaris System (with Alaris PC unit, Model 8015), directions for use, Dec. 2011, 360 pgs., CareFusion Corporation.
Carefusion, Infusion Products, brochure, 2011, 16 pgs., CareFusion Corporation.
Carefusion, MedSystem III Infusion Pump Model 2865: With Advanced Dose Rate Calculation and Drug List Editor, User Manual, Nov. 2012, 102 pgs., CareFusion Corporation.
ECRI Institute, Evaluation: Large-Volume Infusion Pumps, Health Devices, Dec. 2009, pp. 402-410, Dec. 2009 issue, ECRI Institute, www.ecri.org.
ECRI Institute, Healthcare Product Comparison System: Infusion Pumps, General Purpose, 2007, pp. 1-54, ECRI Institute.
ECRI, Product Comparison: Infusion Pumps, General-Purpose, Aug. 2005, pp. 1-47, ECRI.
FDA, Medical Devices: SEDASYS Computer-Assisted Personalized Sedation System—P080009, Recently-Approved Devices, May 24, 2013, 2 pgs., U.S. Food and Drug Administration.
First Examination Report from The Intellectual Property Office of New Zealand for Application 626630, dated Apr. 1, 2015, 2 pgs.
First Examination Report from the Intellectual Property Office of New Zealand for Application 702122, dated Nov. 3, 2015, 5 pgs.
Fresenius Deutshsland, Technisches Handbuch: Volumed micro-VP5000, 101 pgs., Fresenius Deutschland; (Publication date unknown but assumed to be prior to the filing date.).
Fresenius Kabi, Applix Smart—Enteral Feeding Pump: Instructions for Use, manual, Feb. 2011, 40 pgs., Fresenius Kabi AG.
Fresenius Kabi, Applix Smart: Technical Guide, service manual, 50 pgs., Fresenius Kabi; (Publication date unknown but assumed to be prior to the filing date.).
Fresenius Kabi, Volumat Agilia, customer presentation, 29 pgs., Fresenius Kabi; (Publication date unknown but assumed to be prior to the filing date.).
Fresenius Kabi, Volumat MC Agilia: Advanced Volumetric Infusion Pump, Medical Devices, specifications, 2 pgs., Fresenius Kabi; (Publication date unknown but assumed to be prior to the filing date.).
Fresenius Medical Care, multiFiltrate Service Manual, service manual, 150 pgs., Fresenius Medical Care multiFiltrate; (Publication date unknown but assumed to be prior to the filing date.).
Fresenius Transfusions GMBH, Fresenius HemoCare: Technical Manual for COM.TEC, service manual, 342 pgs., Fresenius Transfusions GmbH; (Publication date unknown but assumed to be prior to the filing date.).

(56) References Cited

OTHER PUBLICATIONS

Fresenius USA, Inc., Fresenius 2008H Hemodialysis System, Troubleshooting Guide, 1998-1999, 90 pgs., Fresenius USA, Inc.
Fresenius Vial S.A., Optima PT-VS-ST: Technical Manual, service manual, 2007, 106 pgs., Fresenius Vial S.A.
Gieras, Innovative Infusion Pump Technologies, Jun. 15, 2010, pp. 1-53, IEEE.
Goldman et al., Advancing the Adoption of Medical Device "Plug-and-Play" Interoperability to Improve Patient Safety and Healthcare Efficiency, a white paper from the MD PnP Program, 2006-2009 (rev Sep. 2009), pp. 1-3, MD PnP Program.
Hawk, III, The Role of Color Coding in Medication Error Reduction, Action of the AMA House of Delegates 2004 Annual Meeting: Report of the Council on Scientific Affairs, CSA Report 5-A-04, pp. 1-8.
Hoenich et al., Research & Technology: The Current Status and Future Directions of Hemodialysis Machine Technology, Hemodialysis Horizons, pp. 38-44, AAMI.org; (Publication date unknown but assumed to be prior to the filing date.).
Hofmann, Modeling Medical Devices for Plug-and-Play Interoperability, Master of Engineering thesis, Massachusetts Institute of Technology, Jun. 2007, pp. 1-187, Robert Matthew Hofmann, MMVII.
Infusion Nurses Society, Infusion Nursing: Standards of Practice, Journal of Infusion Nursing, 2011, 115 pgs., vol. 34, No. 1S, Jan./Feb. 2011 issue, Infusion Nurses Society.
Infusion Nurses Society, Policies and Procedures for Infusion Nursing, 2011, pts. 1-162, 4th edition, Infusion Nurses Society.
International Search Report & Written Opinion dated Oct. 1, 2013, received in International patent application No. PCT/US2012/071490, 20 pgs.
International Search Report & Written Opinion dated Dec. 4, 2013, received in International patent application No. PCT/US2013/032445, 20 pgs.
International Search Report & Written Opinion dated Nov. 7, 2013, received in International patent application No. PCT/US2013/042350, 18 pgs.
International Preliminary Report on Patentability dated Jul. 3, 2014, received in International patent application No. PCT/US2012/071490, 14 pgs.
International Preliminary Report on Patentability dated Dec. 4, 2014, received in International patent application No. PCT/US2013/032445, 12 pgs.
International Preliminary Report on Patentability dated Dec. 4, 2014, received in International patent application No. PCT/US2013/042350, 13 pgs.
Invitation to Pay Additional Fees and, Where Applicable, Protest Fees, dated May 28, 2013, received in International patent application PCT /US2012/071490, 8 pgs.
Invitation to Pay Additional Fees and, Where Applicable, Protest Fee dated Sep. 9, 2013, received in International patent application No. PCT/US2013/032445, 10 pgs.
Invitation to Pay Additional Fees and, Where Applicable, Protest Fee dated Sep. 26, 2013, received in International patent application No. PCT/US2013/042350, 7 pgs.
Israelski, The Symbiq (Next-Generation) IV Infusion Pump: A Feature-Filled "Intelligent" Pump Developed with and for the End-User, May 2007, 4 pgs., Hospira, Inc.
Jetley et al., Safety Requirements based Analysis of Infusion Pump Software, 4 pgs., US Food and Drug Administration; (Publication date unknown but assumed to be prior to the filing date.)
King et al., Prototyping Closed Loop Physiologic Control with the Medical Device Coordination Framework, 200X, 11 pgs., MD PnP www.mdpnp.org; (Publication date unknown but assumed to be prior to the filing date.).
MHRA, Volumetric Pump—Fresenius Vial MVP MS, evaluation, Feb. 2004, pp. 1-16, MHRA.
National Patient Safety Agency, Design for Patient Safety: A Guide to the Design of Electronic Infusion Devices, booklet, 2010, pp. 1-96, Edition 1, National Patient Safety Agency, London, USA.

Nemeth et al., Making Information Technology a Team Player in Safety: The Case of Infusion Devices, Advances in Patient Safety: Interface Design for Infusion Devices, pp. 319-330, vol. 1; (Publication date unknown but assumed to be prior to the filing date.).
Notice for Reason for Rejection, dated Nov. 17, 2015, received in Japanese patent application No. 2015-514014 with English Translation, 9 pgs.
Notice for Reason for Rejection, dated Oct. 6, 2015, received in Japanese patent application No. 2014-548986 with English Translation, 10 pgs.
Pfiedler Enterprises, A Comprehensive Surgical Checklist: Using Technology to Help Optimize Preparedness, Patient Safety and Performance (A Continuing Education Self-Study Activity), 2011, pp. 1-20, Pfiedler Enterprises.
Prusch et al., IV Interoperability: Smart Pump and BCMA Integration, Oct. 5, 2010, Lancaster General Health; 13 pgs.
Rafferty, Proposal for Wireless Transmission of Non-invasive Respiratory Data to the Servo Module of an Opioid Infusion-Pump for Real-Time Patient Safety Feedback Control, 1pg., Yale School of Medecine; (Publication date unknown but assumed to be prior to the filing date.).
Search Report and Written Opinion from the Intellectual Property Office of Singapore for Application 11201403511Y, dated Nov. 28, 2014, 20 pgs.
Sigma, Service Manual Sigma International Model Spectrum Infusion Pump, Service Manual, Aug. 2009, 58 pgs., SIGMA International, Inc., Medina, New York, United States.
Technical Data: Infusomat Space, Perfusor Space, 7 pgs.; (Publication date unknown but assumed to be prior to the filing date.).
Vanderveen, Technology Focus: Using Data to Improve Smart Intravenous Infusion Pumps, Human Factors Horizons, 2010, pp. 57-63, Human Factors Horizons.
Written Opinion from the Intellectual Property Office of Singapore for Application 11201403511Y, dated Jun. 19, 2015, 11 pgs.
Invitation to Pay Additional Fees and, Where Applicable, Protest Fee dated Jan. 25, 2016, received in International patent application No. PCT/US2015/049952, 7 pgs.
International Search Report and Written Opinion dated Apr. 7, 2016, received in International patent application No. PCT/US2015/049952, 18 pgs.
Extended European Search Report & Written Opinion dated Jul. 18, 2016, received in European patent application No. 16166215.0, 9 pgs.
First Examination Report from IP Australia for Australian Application 2012358221, dated Sep. 28, 2016, 3 pgs.
Notice of Acceptance from IP Australia for Australian Application 2012358221, dated Dec. 13, 2016, 3 pgs.
First Rule 71(3) Communication from the European Patent Office for EPO Application No. 12 826 641.8-116. dated Jun. 23, 2015, 8 pgs.
Second Rule 71(3) Communication from the European Patent Office for EPO Application No. 12 826 641.8-116, dated Jan. 28, 2016, 8 pgs.
Decision to Grant from the European Patent Office for EPO Application No. 12 826 641.8-116, dated Jul. 21, 2016, 3 pgs.
Second Examination Report from the Intellectual Property Office of New Zealand for Application 626630, dated Dec. 23, 2015, 2 pgs.
Notice of Acceptance and Extract from the Intellectual Property Office of New Zealand for Application 626630, dated May 30, 2016, 4 pgs.
Notice of Intention to Refuse Patent Application and Examination Report from the Intellectual Property Office of Singapore for Application 11201403511Y, dated May 4, 2016, 12 pgs.
First Examination Report from the IP Australia of the Australian Government for Australian Patent Application No. 2013266864, dated Oct. 31, 2016, 3 pgs.
First Office Action dated Aug. 30, 2016, received in Republic of China Patent Application No. 201380039475.5, 10 pgs.
Notification of Paying the Restoration Fee for Unity of Invention dated May 20, 2016, received in Republic of China Patent Application No. 201380039475.5, 1 pgs.

(56) References Cited

OTHER PUBLICATIONS

Report of substantive examination from Superintendent of Industry and Commerce of Colombia for Patent Application 14.283.126, dated Jun. 24, 2016, 6 pgs.
Article 94(3) Communication from the European Patent Office for EPO Application No. 13 728 549.0-1662, dated Mar. 4, 2016, 3 pgs.
Notice for Reason for Rejection, dated Nov. 17, 2015, received in Japanese patent application No. 2015-514014, 4 pgs.
Decision to Grant, dated Jun. 7, 2016, received in Japanese patent application No. 2015-514014, 3 pg.
Further Examination Report (Second) from the Intellectual Property Office of New Zealand for Application 702122, dated Nov. 9, 2016, 2 pgs.
First Examination Report from the Intellectual Property Office of New Zealand for Application 714766, dated Jun. 8, 2016, 2 pgs.
Further (Second) Examination Report from the Intellectual Property Office of New Zealand for Application 714766, dated Aug. 26, 2016, 2 pgs.
Further (Third) Examination Report from the Intellectual Property Office of New Zealand for Application 714766, dated Dec. 23, 2015, 2 pgs.
Notice of Acceptance and Extract from the Intellectual Property Office of New Zealand for Application 714766, dated Nov. 16, 2016, 4 pgs.
First Examination report from the New Zealand Intellectual Property Office for New Zealand IP No. 720136, dated Jun. 8, 2016, 2 pgs.
First Examination report from the New Zealand Intellectual Property Office for New Zealand IP No. 724959, dated Oct. 31, 2016, 3 pgs.
First Examination Report from the Intellectual Property Office of New Zealand for Application 720767, dated Sep. 5, 2016, 4 pgs.
Notice of Acceptance from the Intellectual Property Office of New Zealand for Application 720767, dated Dec. 14, 2016, 1 pg.
Decision to Grant, dated Jul. 26, 2016, received in Japanese patent application No. 2014548986, 3 pg.
Notice of Eligibility for Grant and Examination Review Report from the Intellectual Property Office of Singapore for Application 11201403511Y, dated Jan. 31, 2017, 7 pgs.
Notice of Acceptance from the IP Australia of the Australian Government for Australian Patent Application No. 2013266864, dated Mar. 24, 2017, 3 pgs.
International Preliminary Report on Patentability and Written Opinion dated Mar. 21, 2017, received in International patent application No. PCT/US2015/049952, 11 pgs.
Further Examination report from the New Zealand Intellectual Property Office for New Zealand IP No. 720136, dated Dec. 22, 2016, 2 pgs.
Report of substantive examination from Superintendent of Industry and Commerce of Colombia for Patent Application 14.283.126, dated Jan. 17, 2017, 6 pgs.
Further Examination report from the New Zealand Intellectual Property Office for New Zealand IP No. 724959, dated Apr. 26, 2017, 2 pgs.
U.S. Appl. No. 61/297,544, filed Jan. 22, 2010.
U.S. Appl. No. 13/011,543, filed Jan. 21, 2011, US20110313789A1.
U.S. Appl. No. 61/578,674, filed Dec. 21, 2011.
U.S. Appl. No. 13/333,574, filed Dec. 21, 2011, US20120185267A1.
PCT/US11/66588, Dec. 21, 2011, WO2013095459A1.
U.S. Appl. No. 61/578,649, filed Dec. 21, 2011.
U.S. Appl. No. 61/578,658, filed Dec. 21, 2011.
U.S. Appl. No. 61/651,322, filed May 24, 2012.
U.S. Appl. No. 61/679,117, filed Aug. 3, 2012.
U.S. Appl. No. 61/738,447, filed Dec. 18, 2012.
U.S. Appl. No. 13/723,242, filed Dec. 21, 2012, US20130317753A1.
PCT/US12/71112, Dec. 21, 2012, WO2013096713A1.
U.S. Appl. No. 13/723,251, filed Dec. 21, 2012, US20130204188A1.
U.S. Appl. No. 61/740,474, filed Dec. 21, 2012.
PCT/US12/71142, Dec. 21, 2012, WO2013096722A1.
U.S. Appl. No. 13/723,244, filed Dec. 21, 2012, US20130188040A1.
U.S. Appl. No. 13/723,239, filed Dec. 21, 2012, US20130297330A1.
PCT/US12/71490, Dec. 21, 2012, WO2013096909A1.
U.S. Appl. No. 13/725,790, filed Dec. 21, 2012, US20130177455A1.
U.S. Appl. No. 13/723,253, filed Dec. 21, 2012, US20130191513A1.
U.S. Appl. No. 13/723,238, filed Dec. 21, 2012, US20130182381A1.
U.S. Appl. No. 13/724,568, filed Dec. 21, 2012, US20130184676A1.
PCT/US12/71131, Dec. 21, 2012, WO2013096718A1.
U.S. Appl. No. 13/723,235, filed Dec. 21, 2012, US20130197693A1.
U.S. Appl. No. 13/840,339, filed Mar. 15, 2013, US20130336814A1.
U.S. Appl. No. 13/833,432, filed Mar. 15, 2013, US20130281965A1.
U.S. Appl. No. 13/833,712, filed Mar. 15, 2013, US20130272773A1.
PCT/US13/32445, Mar. 15, 2013, WO2013176770A1.
U.S. Appl. No. 13/834,030, filed Mar. 15, 2013, US20130310990A1.
U.S. Appl. No. 13/836,497, filed Mar. 15, 2013, US20130346108A1.
U.S. Appl. No. 13/900,655, filed May 23, 2013, US20130317837A1.
PCT/US13/42350, May 23, 2013, WO/2013/177357A1.
U.S. Appl. No. 29/457,522, filed Jun. 11, 2013, U.S. Pat. No. D736,370S.
U.S. Appl. No. 29/457,521, filed Jun. 11, 2013, U.S. Pat. No. D767,756S.
U.S. Appl. No. 29/457,520, filed Jun. 11, 2013, U.S. Pat. No. D735,319S.
U.S. Appl. No. 29/457,516, filed Jun. 11, 2013, U.S. Pat. No. D728,779S.
U.S. Appl. No. 61/843,574, filed Jul. 8, 2013.
U.S. Appl. No. 61/860,398, filed Jul. 31, 2013.
U.S. Appl. No. 13/971,258, filed Aug. 20, 2013, US20130339049A1.
U.S. Appl. No. 61/894,801, filed Oct. 23, 2013.
U.S. Appl. No. 61/900,431, filed Nov. 6, 2013.
U.S. Appl. No. 29/471,856, filed Nov. 6, 2013, U.S. Pat. No. D751,689S.
U.S. Appl. No. 29/471,858, filed Nov. 6, 2013, U.S. Pat. No. D751,690S.
U.S. Appl. No. 29/471,859, filed Nov. 6, 2013, U.S. Pat. No. D745,661S.
U.S. Appl. No. 29/471,861, filed Nov. 6, 2013, U.S. Pat. No. D749,206S.
U.S. Appl. No. 29/471,864, filed Nov. 6, 2013, U.S. Pat. No. D752,209S.
U.S. Appl. No. 61/904,123. filed Nov. 14, 2013.
U.S. Appl. No. 14/101,848, filed Dec. 10, 2013, US20140165703A1.
PCT/US13/77258, Dec. 20, 2013, WO2014100736A1.
U.S. Appl. No. 29/477,232, filed Dec. 20, 2013, U.S. Pat. No. D768,716S.
U.S. Appl. No. 29/477,233, filed Dec. 20, 2013, U.S. Pat. No. D760,782S.
U.S. Appl. No. 29/477,236, filed Dec. 20, 2013, U.S. Pat. No. D760,288S.
U.S. Appl. No. 29/477,237, filed Dec. 20, 2013, U.S. Pat. No. D760,289S.
U.S. Appl. No. 29/477,242, filed Dec. 20, 2013, U.S. Pat. No. D756,386S.
U.S. Appl. No. 29/477,231, filed Dec. 20, 2013, U.S. Pat. No. D758,399S.
PCT/US13/77077, Dec. 20, 2013, WO/2014/100658A1.
PCT/US13/77135, Dec. 20, 2013, WO/2014/100687A1.
U.S. Appl. No. 14/136,243, filed Dec. 20, 2013, US20140188516A1.
U.S. Appl. No. 14/137,562, Dec. 20, 2013, US20140227021A1.
PCT/US13/76851, Dec. 20, 2013, WO2014100557A1.
U.S. Appl. No. 14/135,784, filed Dec. 20, 2013, US20140188076A1.
PCT/US13/76886, Dec. 20, 2013, WO/2014/100571A1.
U.S. Appl. No. 14/135,809, filed Dec. 20, 2013, US20140195639A1.
U.S. Appl. No. 29/477,249, filed Dec. 20, 2013, U.S. Pat. No. D760,888S.
U.S. Appl. No. 14/137,421, filed Dec. 20, 2013, US20140180711A1.
PCT/US13/77270, Dec. 20, 2013, WO/2014/100744A1.
U.S. Appl. No. 61/942,986, filed Feb. 21, 2014.
U.S. Appl. No. 14/191,827, filed Feb. 27, 2014, US20150238228A1.
U.S. Appl. No. 14/213,373, filed Mar. 14, 2014, US20140318639A1.
PCT/US14/29020, Mar. 14, 2014, WO/2014/144557A1.
U.S. Appl. No. 61/953,036, filed Mar. 14, 2014.
U.S. Appl. No. 61/987,742, filed May 2, 2014.
U.S. Appl. No. 61/990,330, filed May 8, 2014.

(56) References Cited

OTHER PUBLICATIONS

PCT/US2014/48227, Jul. 25, 2014, WO2015017275A1.
U.S. Appl. No. 14/341,207, filed Jul. 25, 2014, US20150033823A1.
U.S. Appl. No. 14/451,904, filed Aug. 5, 2014, US20140343492A1.
U.S. Appl. No. 62/052,008, filed Sep. 18, 2014.
U.S. Appl. No. 14/491,128, filed Sep. 19, 2014, US20150002667A1.
U.S. Appl. No. 14/491,143, filed Sep. 19, 2014, US20150002668A1.
U.S. Appl. No. 14/491,161, filed Sep. 19, 2014, US20150002677A1.
U.S. Appl. No. 62/086,356, filed Dec. 2, 2014.
U.S. Appl. No. 14/616,079, filed Feb. 6, 2015, US20150154364A1.
U.S. Appl. No. 29/517,099, filed Feb. 10, 2015, U.S. Pat. No. D. 774,645S.
U.S. Appl. No. 29/517,101, filed Feb. 10, 2015.
U.S. Appl. No. 29/517,100, filed Feb. 10, 2015.
U.S. Appl. No. 29/517,098, filed Feb. 10, 2015, U.S. Pat. No. D. 754,065S.
U.S. Appl. No. 29/517,097, filed Feb. 10, 2015.
U.S. Appl. No. 29/517,095, filed Feb. 10, 2015.
U.S. Appl. No. 29/517,096, filed Feb. 10, 2015.
U.S. Appl. No. 14/627,287, filed Feb. 20, 2015, US20150157791A1.
U.S. Appl. No. 14/656,945, filed Mar. 13, 2015, US20150257974A1.
U.S. Appl. No. 14/679,364, Apr. 6, 2015, US20150314083A1.
U.S. Appl. No. 62/168,343, filed May 29, 2015.
U.S. Appl. No. 29/531,366, filed Jun. 25, 2015.
U.S. Appl. No. 29/532,660, filed Jul. 9, 2015.
U.S. Appl. No. 14/812,149, filed Jul. 29, 2015, US20150332009A1.
U.S. Appl. No. 29/538,153, filed Sep. 1, 2015.
U.S. Appl. No. 62/212,871, filed Sep. 1, 2015.
U.S. Appl. No. 14/853,300, filed Sep. 14, 2015, US20160158437A1.
U.S. Appl. No. 14/873,515, filed Oct. 2, 2015, US20160097382A1.
U.S. Appl. No. 14/931,928, filed Nov. 4, 2015, US20160055397A1.
U.S. Appl. No. 14/932,291, filed Nov. 4, 2015, US20160055649A1.
U.S. Appl. No. 14/938,368, filed Nov. 11, 2015, US20160061641A1.
U.S. Appl. No. 14/938,083, filed Nov. 11, 2015, US20160073063A1.
U.S. Appl. No. 14/939,015, filed Nov. 12, 2015, US20160063353A1.
U.S. Appl. No. 14/939,586, filed Nov. 12, 2015, US20160131272A1.
U.S. Appl. No. 14/956,648, filed Dec. 2, 2015, US20160084434A1.
U.S. Appl. No. 29/547,402, filed Dec. 3, 2015.
U.S. Appl. No. 29/547,405, filed Dec. 3, 2015.
U.S. Appl. No. 29/548,225, filed Dec. 11, 2015.
U.S. Appl. No. 29/552,303, filed Jan. 21, 2016.
U.S. Appl. No. 29/552,942, filed Jan. 27, 2016.
U.S. Appl. No. 29/552,943, filed Jan. 27, 2016.
U.S. Appl. No. 62/288,132, field Jan. 28, 2016.
U.S. Appl. No. 29/553,094, filed Jan. 28, 2016.
U.S. Appl. No. 29/556,048, filed Feb. 26, 2016.
U.S. Appl. No. 15/055,941, filed Feb. 29, 2016, US20160179086A1.
U.S. Appl. No. 15/059,394, filed Mar. 3, 2016, US20160184510A1.
U.S. Appl. No. 15/077,389, filed Mar. 22, 2016, US20160203292A1.
U.S. Appl. No. 29/561,572, filed Apr. 18, 2016.
U.S. Appl. No. 29/564,750, filed May 16, 2016.
U.S. Appl. No. 15/161,876, filed May 23, 2016, US20160262977A1.
U.S. Appl. No. 62/341,396, filed May 25, 2016.
U.S. Appl. No. 15/163,906, filed May 25, 2016.
U.S. Appl. No. 29/565,908, filed May 25, 2016.
U.S. Appl. No. 29/569,450, filed Jun. 28, 2016.
U.S. Appl. No. 29/569,460, filed Jun. 28, 2016.
U.S. Appl. No. 15/205,538, filed Jul. 8, 2016, US20160319850A1.
U.S. Appl. No. 29/570,648, filed Jul. 11, 2016.
U.S. Appl. No. 29/571,387, filed Jul. 18, 2016.
U.S. Appl. No. 29/575,316, filed Aug. 24, 2016.
U.S. Appl. No. 29/575,331, filed Aug. 24, 2016.
U.S. Appl. No. 15/248,200, filed Aug. 26, 2016, US20160362234A1.
U.S. Appl. No. 15/270,321, filed Sep. 20, 2016.
U.S. Appl. No. 15/341,611, filed Nov. 2, 2016.
U.S. Appl. No. 15/418,096, filed Jan. 27, 2017.
U.S. Appl. No. 15/467,196, filed Mar. 23, 2017.

* cited by examiner

| Lens focal length | Lens separation from the camera | Focus separation from the camera | Field of view | Depth of Field ($D_{blur}/D_{pixel}$)=1 | Depth of Field ($D_{blur}/D_{pixel}$)=2 |
|---|---|---|---|---|---|
| 20mm | 0mm | 18.6mm | ±9.7mm | ±2mm | ±4mm |
| 20mm | 60mm | 78.2mm | ±12.3mm | ±3mm | ±6mm |
| 40mm | 0mm | 34.8mm | ±18.2mm | ±5mm | ≥10mm |
| 40mm | 60mm | 93.5mm | ±22.6mm | ±10mm | ≥10mm |
| 60mm | 0mm | 48.9mm | ±25.6mm | ≥10mm | ≥10mm |
| 60mm | 60mm | 106.4mm | ±31.4mm | ≥10mm | ≥10mm |

FIG. 11

Typical background image

Droplet image, background image, and difference between the background image and the droplet

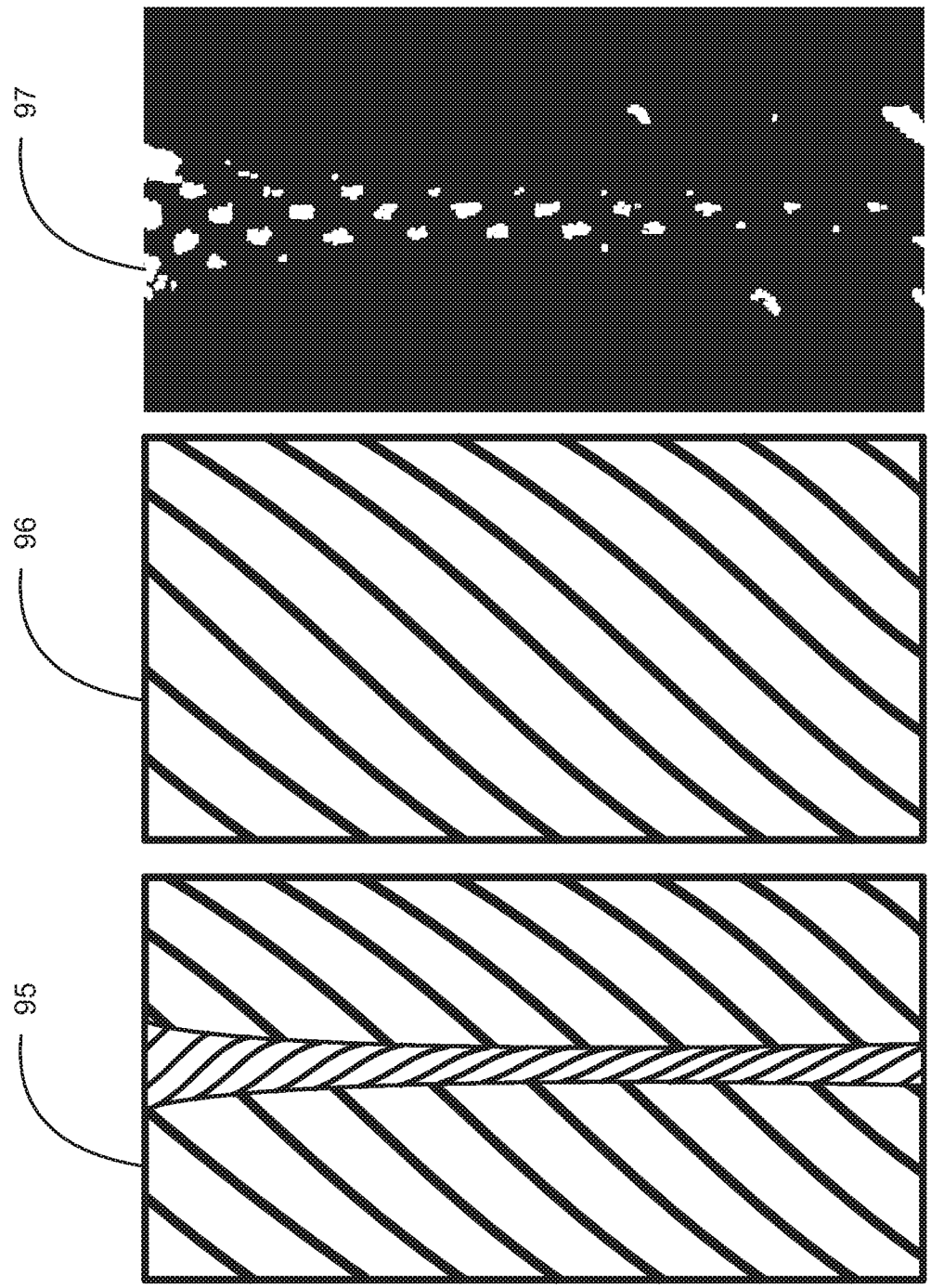

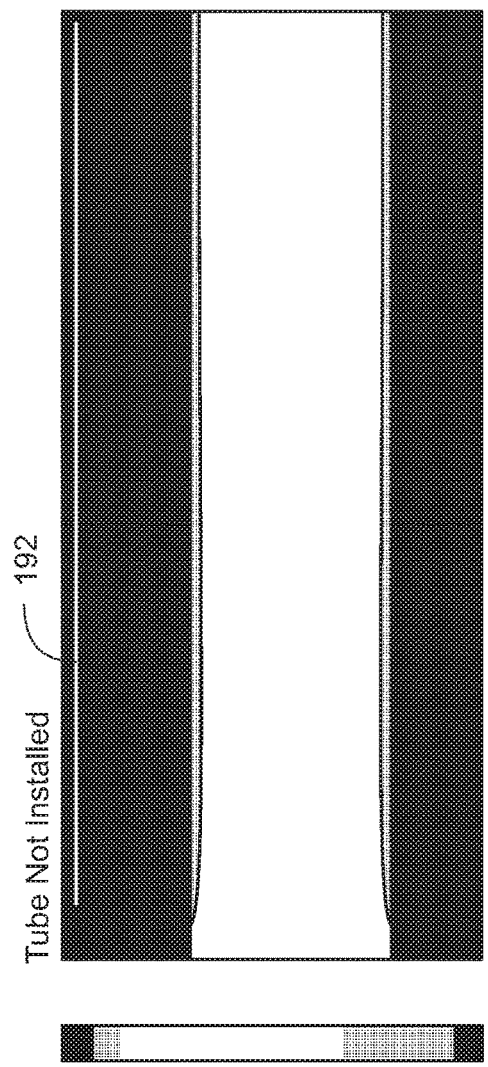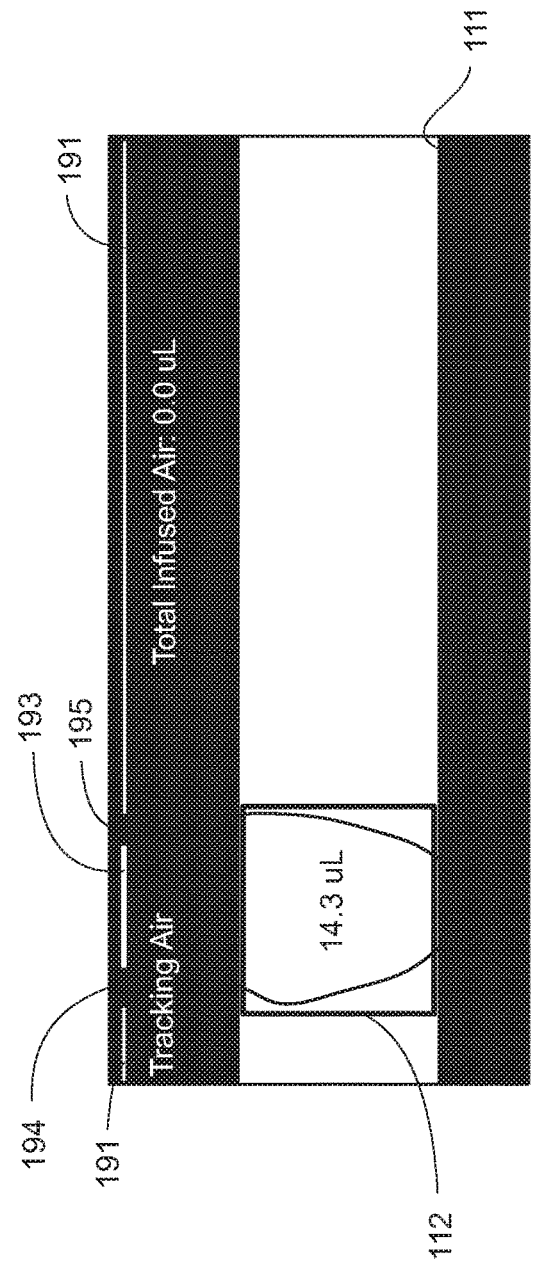

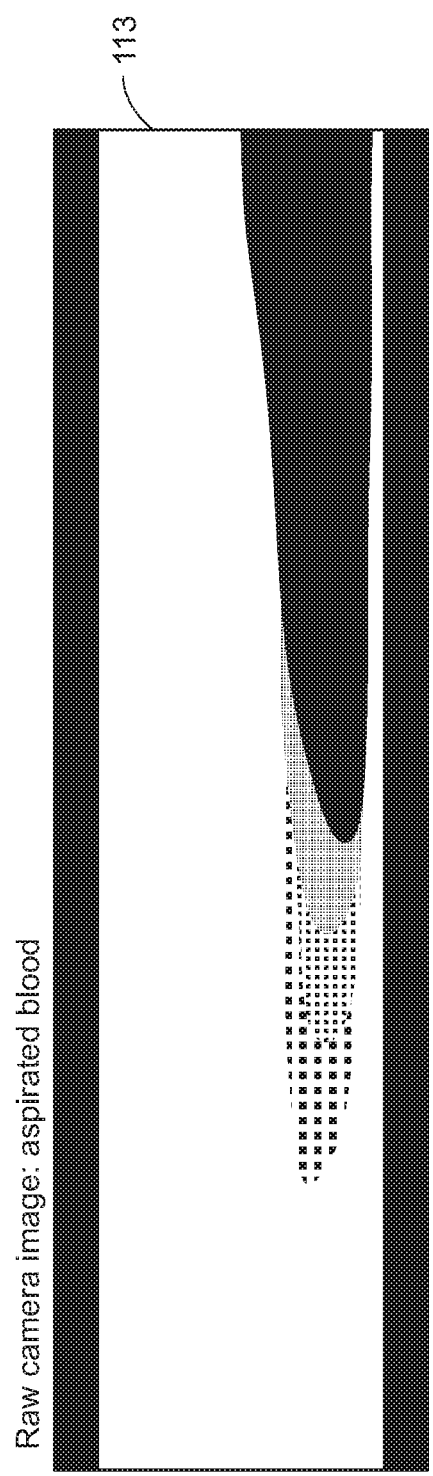
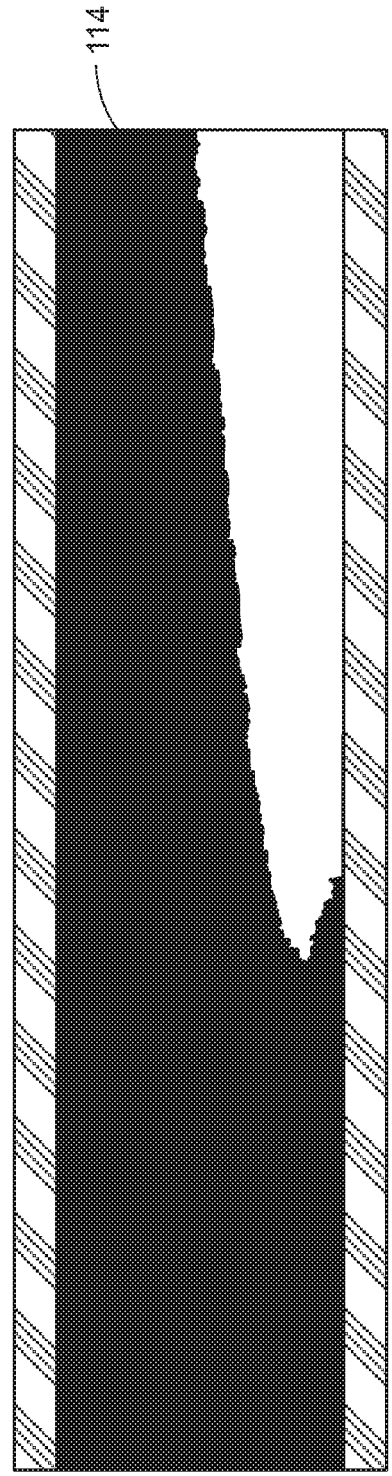
FIG. 37
FIG. 38

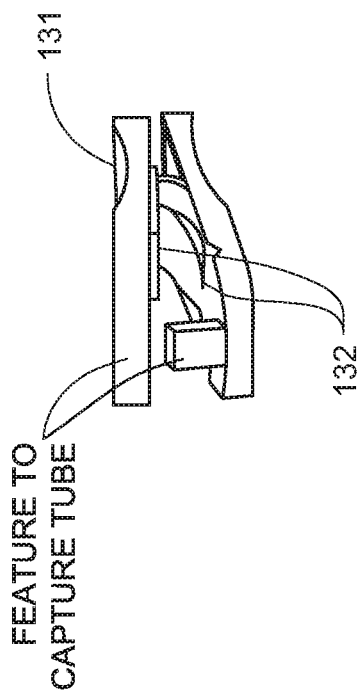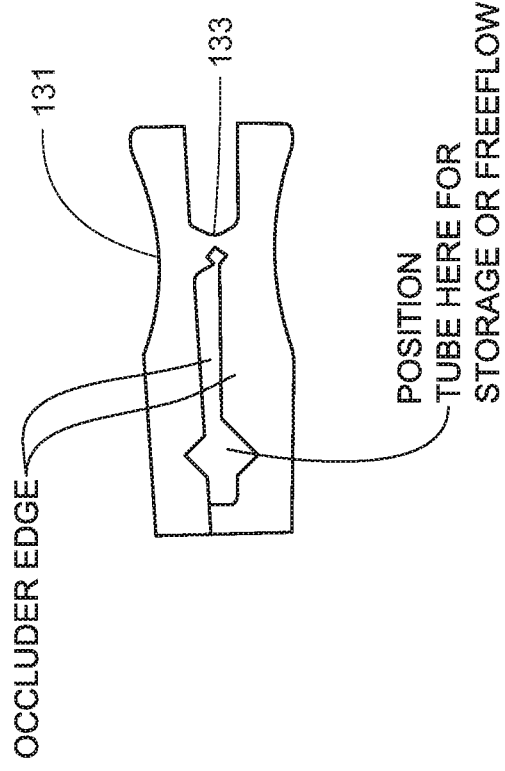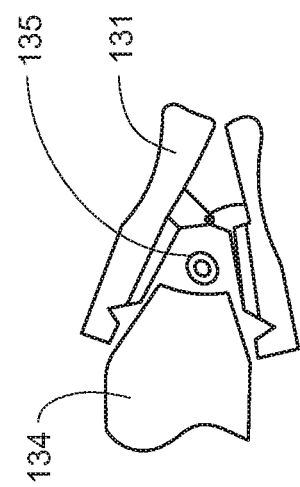

Fig. 2.1 Two-Layer Singe

Fig. 3.2 Double Sided AVS with Integral Perimeter Seal Valves

Fig. 3.3 3-D AVS with Integral Perimeter Seal Valves

Fig. 3.4 Three-Layer Single Sided AVS with Piston Valves

Figure 1: Example Active Fill/Passive Empty Pumping AVS

Figure 1: Example Optical Line Pressure

——— Electrical Circuit
PC: Pneumatic Control features
HC: Hydraulic Control features
PS: Pressure Sensors
SPK: AVS speaker
MIC: AVS microphones
OPT: Optical proximity sensor
 AVS Temperature Sensor
 AVS Speaker
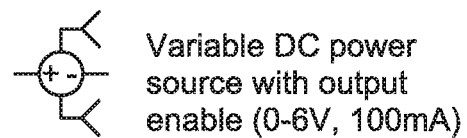 Variable DC power source with output enable (0-6V, 100mA)
 AVS Microphone
 SPST switch
 Optical proximity sensor
FIG. 80

—— Pneumatic Circuit
V: Pneumatic volume
P: Pneumatic pressure
 Two-way valve shown in normally closed position (+/-5 PSI, <50 ms response)
 Pressure sensor (0-5PSI, +/-0.1 PSI)
 Atmosphere vent
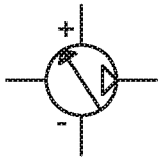 Variable flow/pressure pump (>2 LPM / > 3PSI and < - 2 LPM / < -3 PSI)
 Accumulator reservoir (5cc, +/-5psi max)
FIG. 81

——— Hydraulic Circuit
V: Hydraulic volume
 One-way valve shown in normally closed position (> 2x PSI withstand of pump pressure)
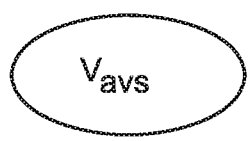 AVS compliant chamber volume (0.5 cc nom)
Note: Valve in disposable
FIG. 82

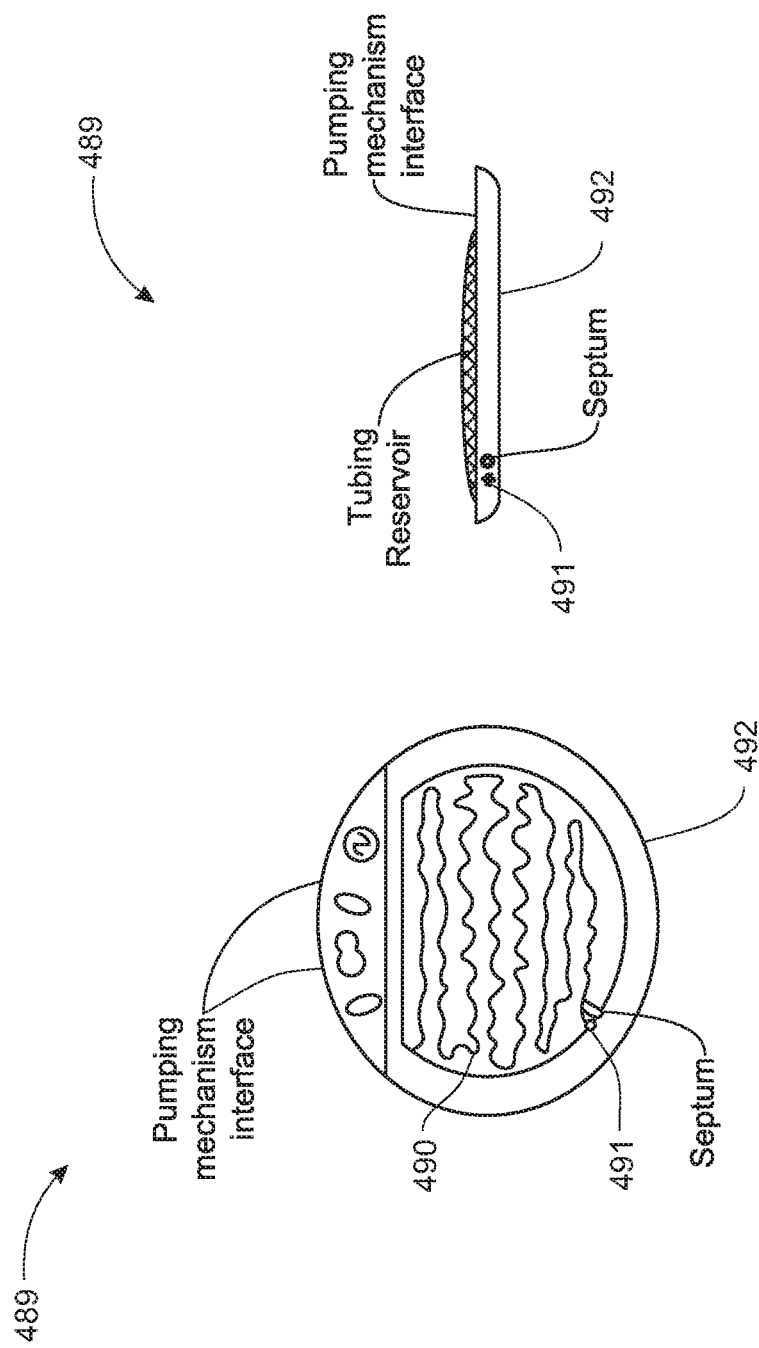

Mechanically actuated cassette free avs pumping design

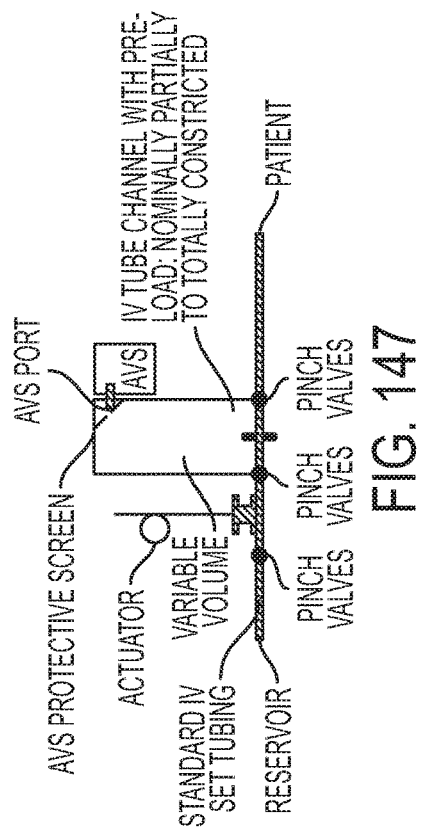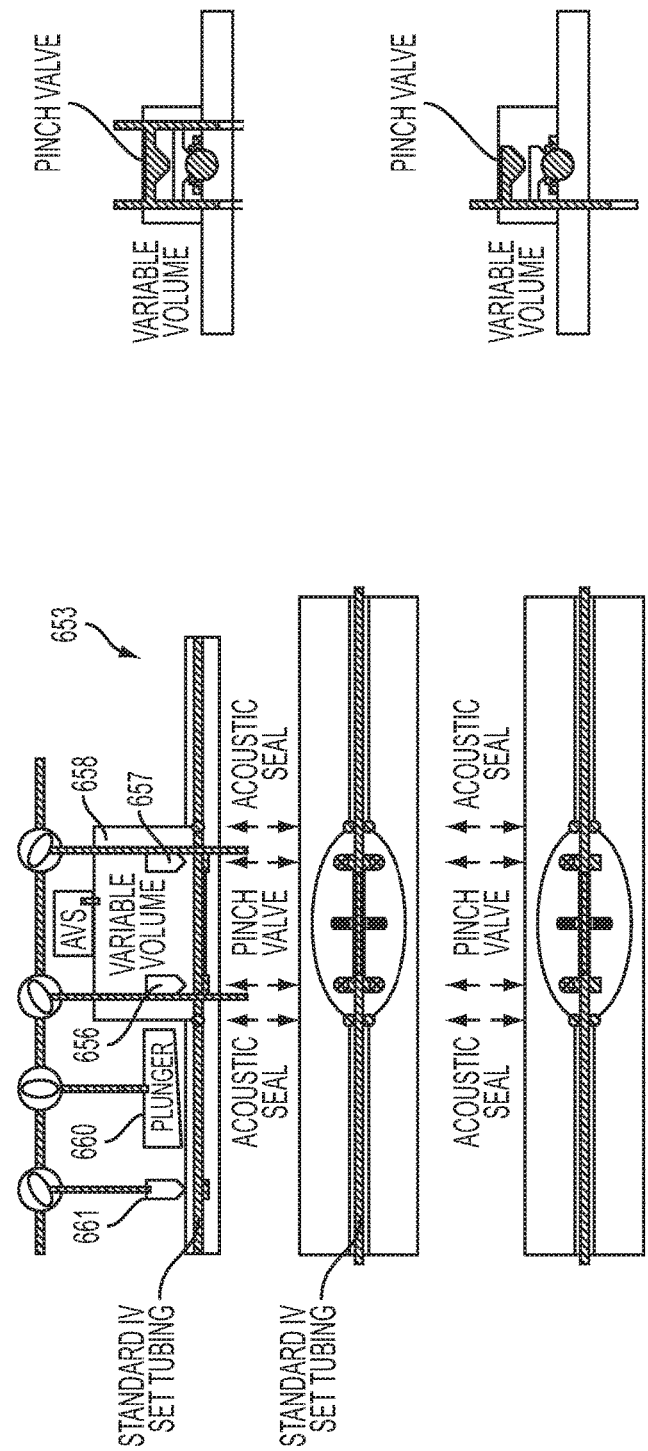

EMPTY RESERVOIR/UPSTREAM OCCLUSION DETECTION
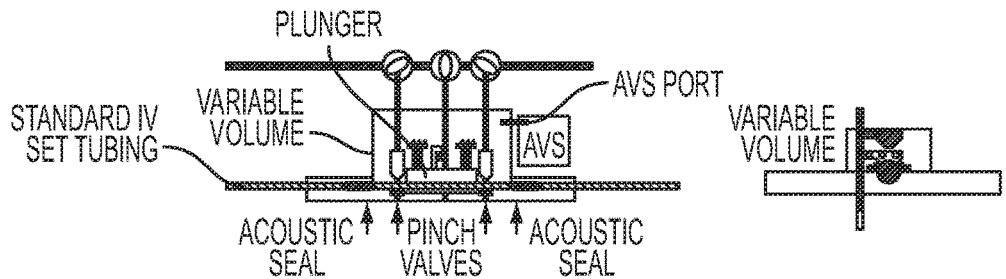
PREVIOUS DELIVERIES
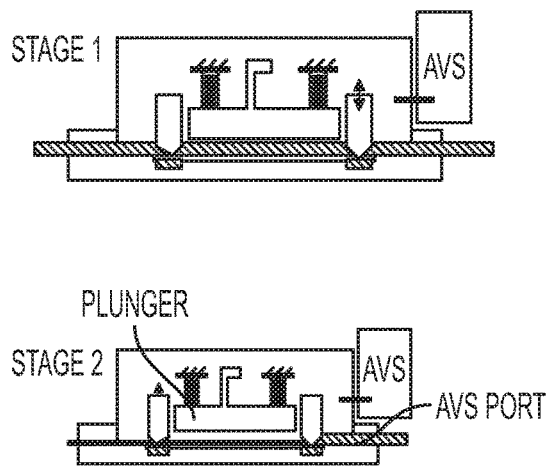
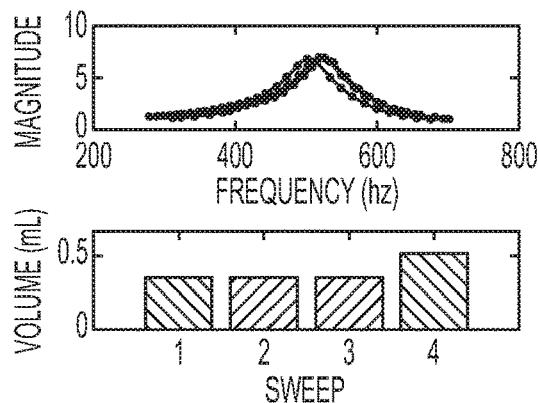
CURRENT DELIVERIES
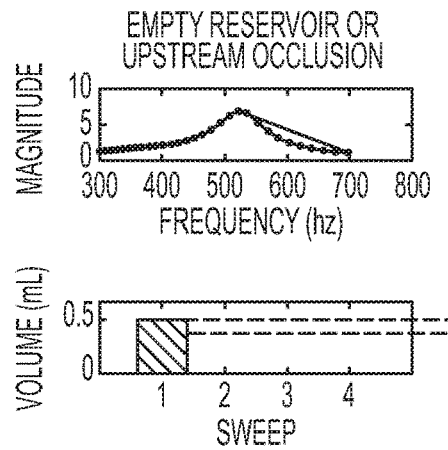
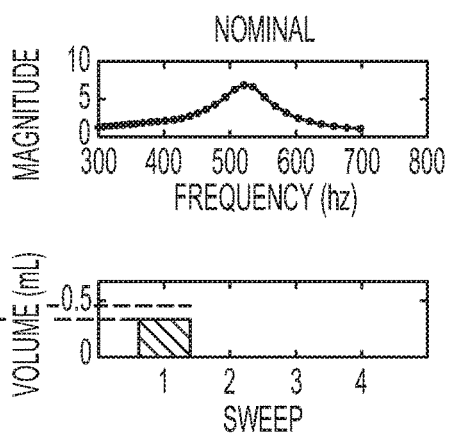
FIG. 154

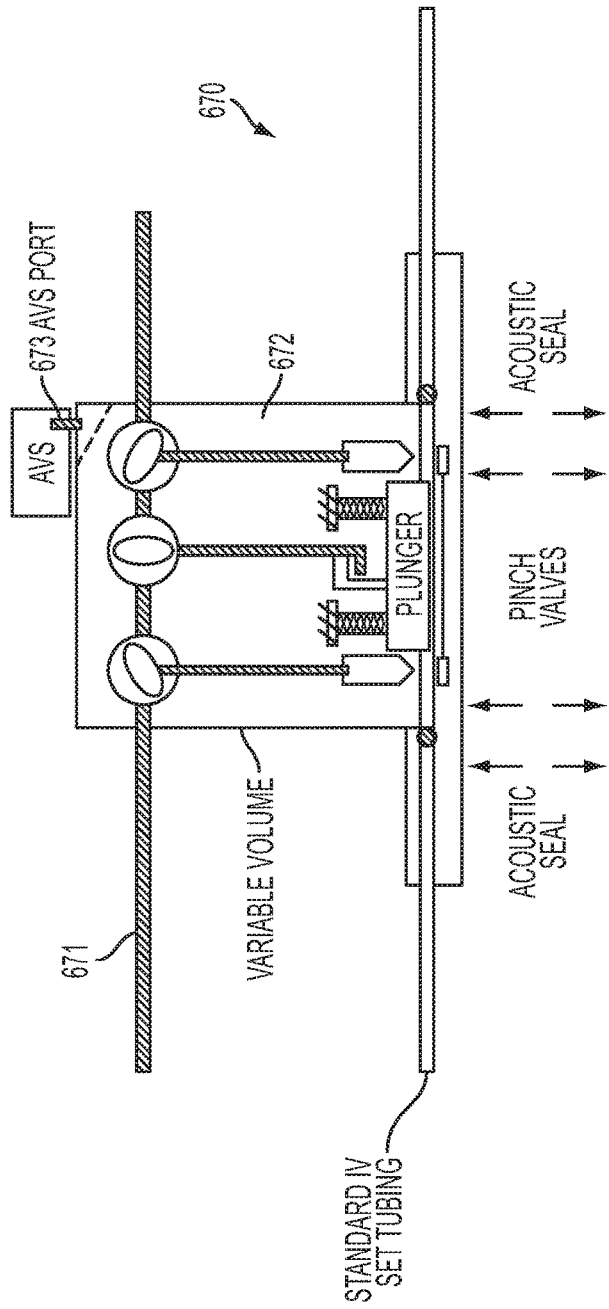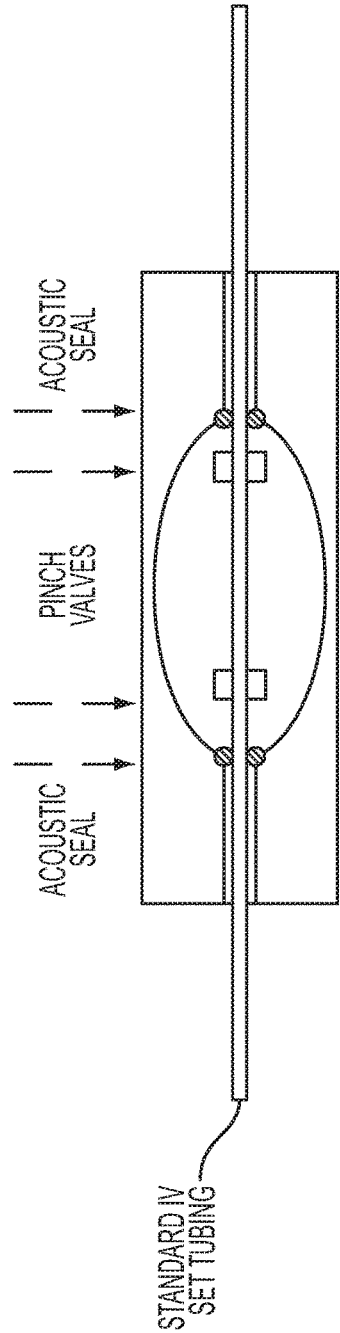

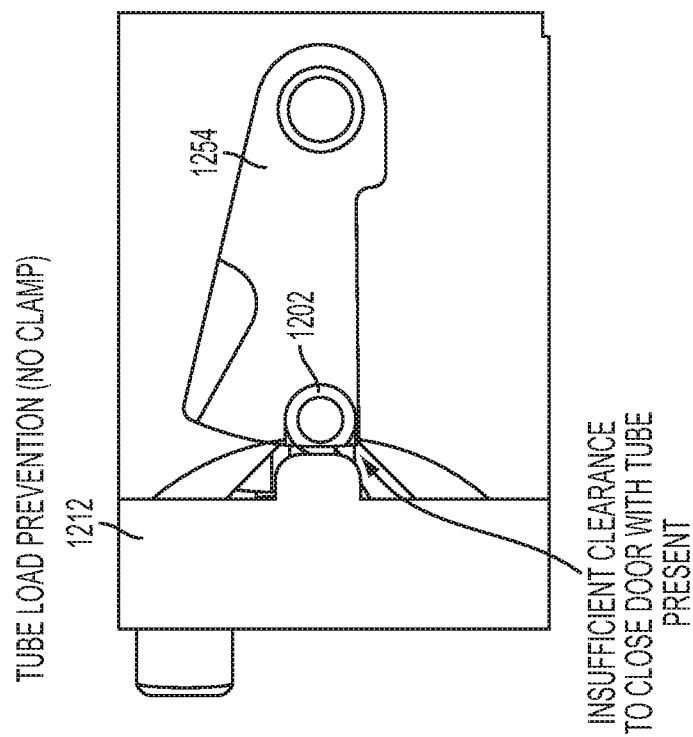
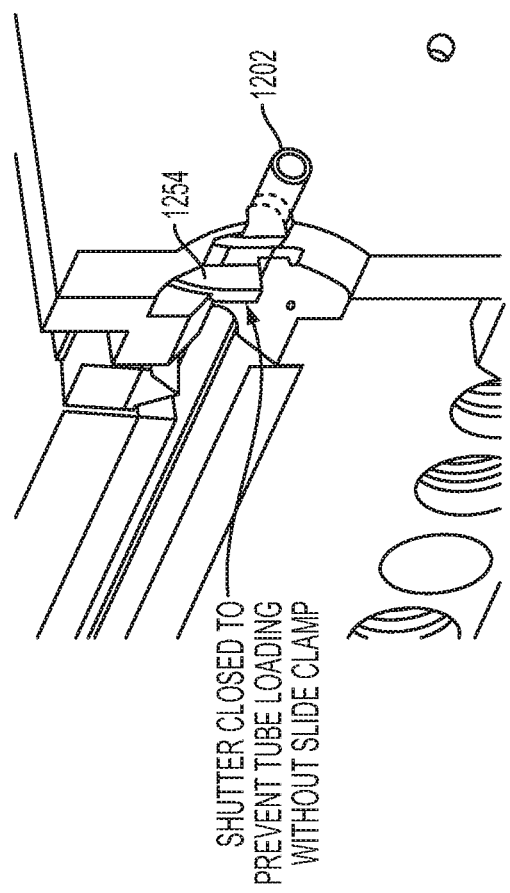
FIG. 211
FIG. 212

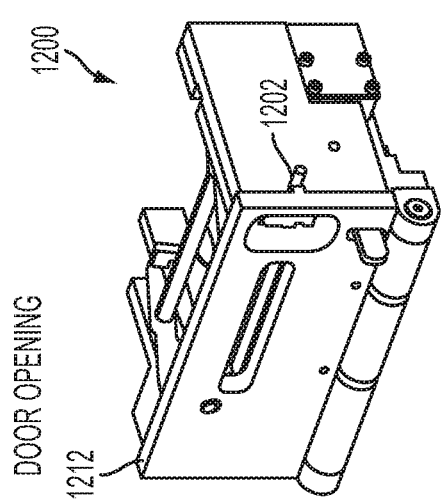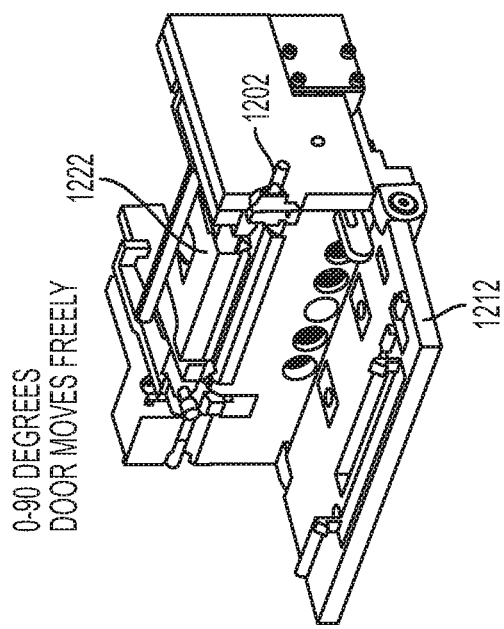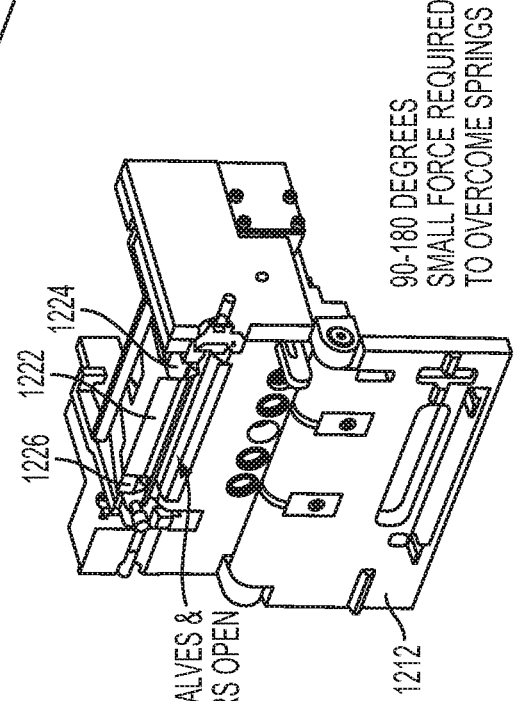

DOOR BARS PULL LEVERS AWAY FROM CAMS

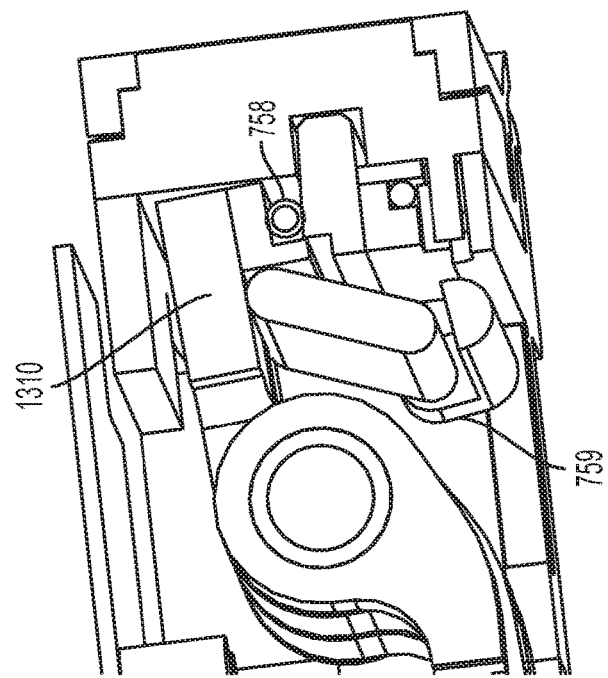
FIG. 227 PLUNGERS ENGAGED
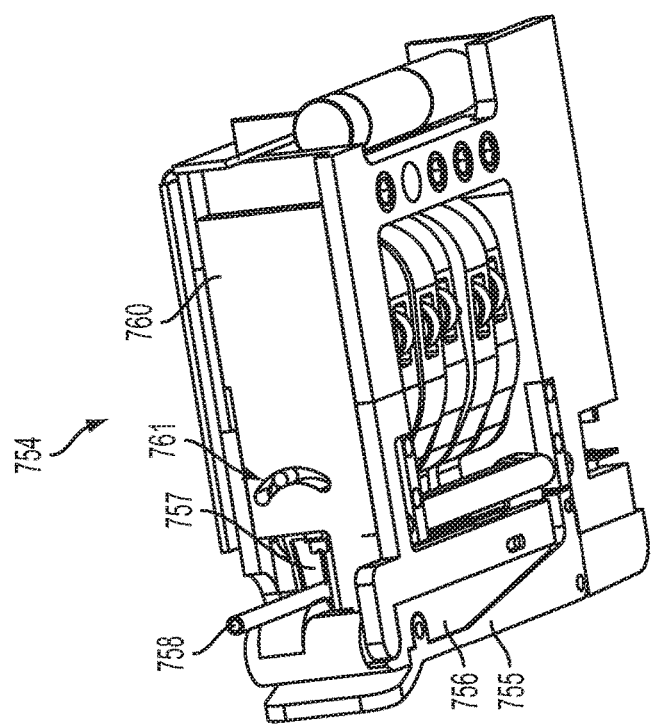
FIG. 226

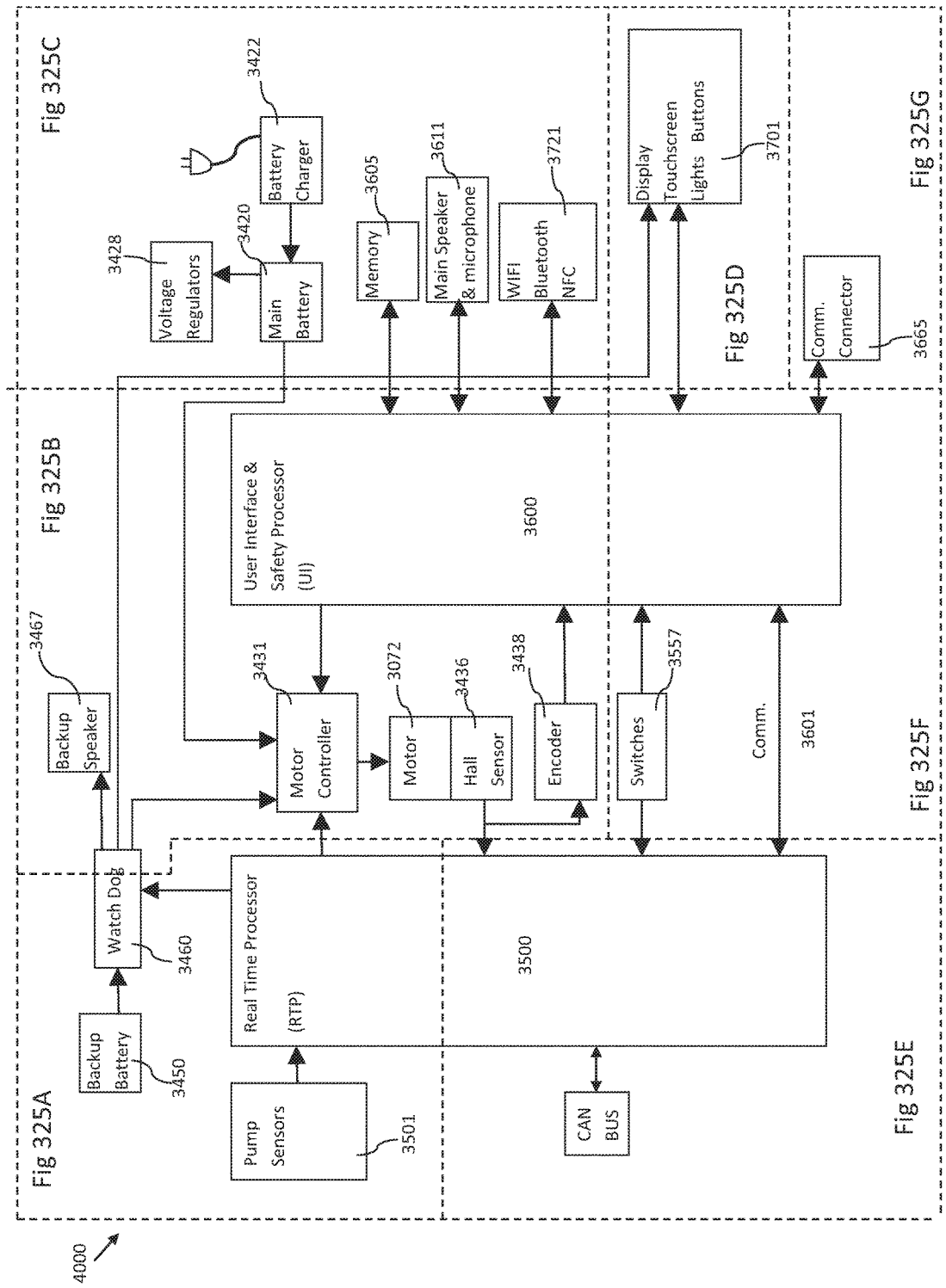

TPS3813 PIN CONFIGURATIONS

WDT, WDR = 00 = 10-200 MS WINDOW
WDT, WDR = 01 = 2.5-200 MS WINDOW
WDT, WDR = 10 = 100-2000 MS WINDOW
WDT, WDR = 11 = 25-2000 MS WINDOW

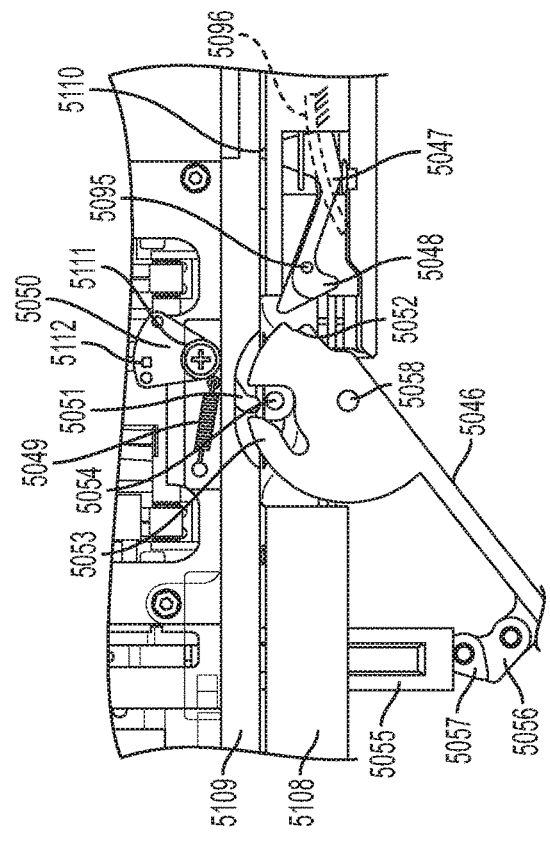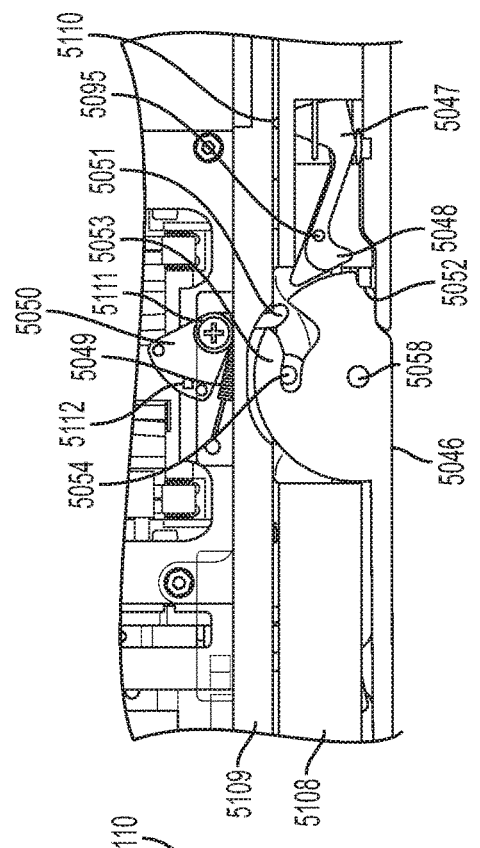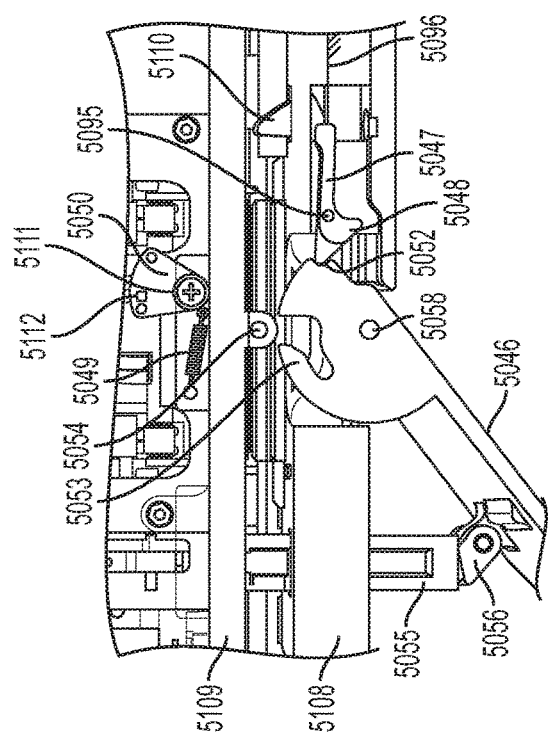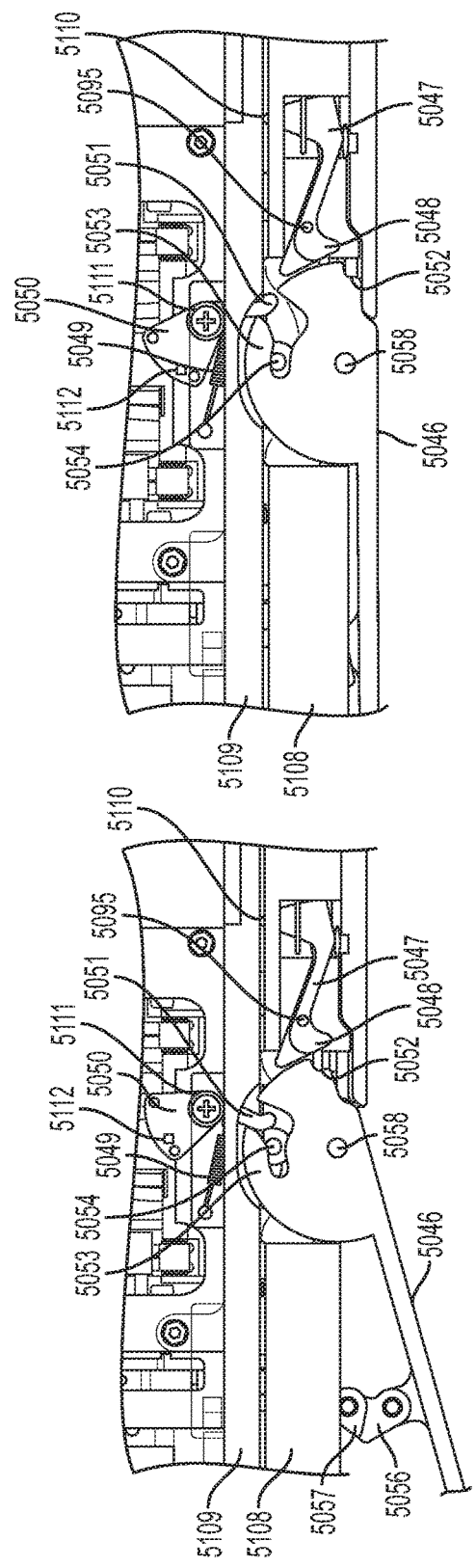

APPARATUS FOR INFUSING FLUID

CROSS REFERENCE TO RELATED APPLICATIONS

The present application is a Continuation application of U.S. patent application Ser. No. 13/840,339, filed Mar. 15, 2013 and entitled Apparatus for Infusing Fluid, now U.S. Publication No. US-2013-0336814-A1, published Dec. 19, 2013 which claims priority to and the benefit of the following:

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, both of which are hereby incorporated herein by reference in their entireties.

U.S. patent application Ser. No. 13/840,339 claims priority to and is also a Continuation-In-Part application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/840,339 claims priority to and is also a Continuation-in-Part application of U.S. patent application Ser. No. 13/723,238, filed Dec. 21, 2012 and entitled System, Method, and Apparatus for Clamping, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, each of which is hereby incorporated herein by reference in its entirety.

U.S. patent application Ser. No. 13/723,238 claims priority to and is a Continuation-In-Part application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/840,339 claims priority to and is also a Continuation-in-Part application of U.S. patent application Ser. No. 13/723,235, filed Dec. 21, 2012 and entitled System, Method, and Apparatus for Dispensing Oral Medications, which claims priority to and benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, each of which is hereby incorporated herein by reference in its entirety.

U.S. patent application Ser. No. 13/723,235 claims priority to and is a Continuation-In-Part application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/840,339 is also a Continuation-In-Part application of PCT Application Serial No. PCT/US12/71131, filed Dec. 21, 2012 and entitled System, Method, and Apparatus for Dispensing Oral Medications, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

PCT Application Serial No. PCT/US12/71131 claims priority to and is a Continuation-In-Part application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/840,339 claims priority to and is also a Continuation-In-Part application of U.S.

patent application Ser. No. 13/724,568, filed Dec. 21, 2012 and entitled System, Method, and Apparatus for Estimating Liquid Delivery, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, each of which is hereby incorporated herein by reference in its entirety.

U.S. patent application Ser. No. 13/724,568 claims priority to and is a Continuation-In-Part application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/840,339 claims priority to and is also a Continuation-In-Part application of U.S. patent application Ser. No. 13/725,790, filed Dec. 21, 2012 and entitled System, Method, and Apparatus for Infusing Fluid, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, each of which is hereby incorporated herein by reference in its entirety.

U.S. patent application Ser. No. 13/725,790 claims priority to and is a Continuation-In-Part application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/840,339 is also a Continuation-In-Part application of PCT Application Serial No. PCT/US12/71490, filed Dec. 21, 2012 and entitled System, Method, and Apparatus for Infusing Fluid, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/679,117, filed Aug. 3, 2012 and entitled System, Method, and Apparatus for Monitoring, Regulating, or Controlling Fluid Flow; and U.S. Provisional Patent Application Ser. No. 61/651,322, filed May 24, 2012 and entitled System, Method, and Apparatus for Electronic Patient Care, each of which is hereby incorporated herein by reference in its entirety.

PCT Application Serial No. PCT/US12/71490 claims priority to and is a Continuation-In-Part application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/840,339 claims priority to and is also a Continuation-In-Part application of U.S. patent application Ser. No. 13/723,239, filed Dec. 21, 2012 and entitled System, Method, and Apparatus for Electronic Patient Care, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

U.S. patent application Ser. No. 13/723,239 claims priority to and is a Continuation-In-Part application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/840,339 claims priority to and is also a Continuation-In-Part application of U.S. patent application Ser. No. 13/723,242, filed Dec. 21, 2012 and entitled System, Method, and Apparatus for Electronic Patient Care, which claims priority to and the benefit of the following:

U.S. Provisional Patent Application Ser. No. 61/651,322, filed May 24, 2012 and entitled System, Method, and Apparatus for Electronic Patient Care, which is hereby incorporated herein by reference in its entirety.

U.S. patent application Ser. No. 13/840,339 claims priority to and is also a Continuation-In-Part application of U.S. patent application Ser. No. 13/723,244, filed Dec. 21, 2012 and entitled System, Method, and Apparatus for Monitoring, Regulating, or Controlling Fluid Flow, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

U.S. patent application Ser. No. 13/723,244 claims priority to and is a Continuation-In-Part application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/840,339 claims priority to and is also a Continuation-In-Part application of PCT Application Serial No. PCT/US12/71142, filed Dec. 21, 2012 and entitled System, Method, and Apparatus for Monitoring, Regulating, or Controlling Fluid Flow, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

PCT Application Serial No. PCT/US12/71142 claims priority to and is a Continuation-In-Part application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/840,339 claims priority to and is also a Continuation-In-Part application of U.S. patent application Ser. No. 13/723,251, filed Dec. 21, 2012 and entitled System, Method, and Apparatus for Estimating Liquid Delivery, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

U.S. patent application Ser. No. 13/723,251 claims priority to and is a Continuation-In-Part application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/840,339 is also a Continuation-In-Part application of PCT Application Serial No. PCT/US12/71112, filed Dec. 21, 2012 and entitled System, Method, and Apparatus for Estimating Liquid Delivery, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

PCT Application Serial No. PCT/US12/71112 claims priority to and is a Continuation-In-Part application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/840,339 claims priority to and is also a Continuation-In-Part application of U.S. patent application Ser. No. 13/723,253, filed Dec. 21, 2012 and entitled System, Method, and Apparatus for Electronic Patient Care, which claims priority to and the benefit of the following:

U.S. Provisional Patent Application Ser. No. 61/578,649, filed Dec. 21, 2011 and entitled System, Method, and Apparatus for Infusing Fluid;

U.S. Provisional Patent Application Ser. No. 61/578,658, filed Dec. 21, 2011 and entitled System, Method, and Apparatus for Estimating Liquid Delivery;

U.S. Provisional Patent Application Ser. No. 61/578,674, filed Dec. 21, 2011 and entitled System, Method, and Apparatus for Dispensing Oral Medications;

U.S. Provisional Patent Application Ser. No. 61/651,322, filed May 24, 2012 and entitled System, Method, and Apparatus for Electronic Patient Care; and U.S. Provisional Patent Application Ser. No. 61/679,117, filed Aug. 3, 2012 and entitled System, Method, and Apparatus for Monitoring, Regulating, or Controlling Fluid Flow, each of which is hereby incorporated herein by reference in its entirety.

U.S. patent application Ser. No. 13/723,253 claims priority to and is a Continuation-In-Part application of the following:

U.S. patent application Ser. No. 13/333,574, filed Dec. 21, 2011 and entitled System, Method, and Apparatus for Electronic Patient Care, now U.S. Publication No. US-2012-0185267-A1, published Jul. 19, 2012, and PCT Application Serial No. PCT/US11/66588, filed Dec. 21, 2011 and entitled System, Method, and Apparatus for Electronic Patient Care, both of which are hereby incorporated herein by reference in their entireties.

U.S. patent application Ser. No. 13/840,339 may also be related to one or more of the following U.S. patent applications filed on even date herewith, all of which are hereby incorporated herein by reference in their entireties:

PCT Application for Apparatus for Infusing Fluid;

Nonprovisional application for Syringe Pump and Related Method;

Nonprovisional application for System and Apparatus for Electronic Patient Care;

Nonprovisional application for System, Method and Apparatus for Clamping; and

Nonprovisional application for System, Method, and Apparatus for Monitoring, Regulating, or Controlling Fluid Flow.

BACKGROUND

Relevant Field

The present disclosure relates to infusing fluid. More particularly, the present disclosure relates to an apparatus for infusing fluid into a patient, e.g., using a pump.

Description of Related Art

Providing patient care in a hospital generally necessitates the interaction of numerous professionals and caregivers (e.g., doctors, nurses, pharmacists, technicians, nurse practitioners, etc.) and any number of medical devices/systems needed for treatment of a given patient. Despite the existence of systems intended to facilitate the care process, such as those incorporating electronic medical records ("EMR") and computerized provider order entry ("CPOE"), the process of providing comprehensive care to patients including ordering and delivering medical treatments, such as medications, is associated with a number of non-trivial issues.

Peristaltic pumps are used in a variety of applications such as medical applications, especially fluid transfer applications that would benefit from isolation of fluid from the system and other fluids. Some peristaltic pumps work by compressing or squeezing a length of flexible tubing. A mechanical mechanism pinches a portion of the tubing and pushes any fluid trapped in the tubing in the direction of rotation. There are rotary peristaltic pumps and finger peristaltic pumps.

Rotary peristaltic pumps typically move liquids through flexible tubing placed in an arc-shaped raceway. Rotary peristaltic pumps are generally made of two to four rollers placed on a roller carrier driven rotationally by a motor. A typical rotary peristaltic pump has a rotor assembly with pinch rollers that apply pressure to the flexible tubing at spaced locations to provide a squeezing action on the tubing against an occlusion bed. The occlusion of the tubing creates increased pressure ahead of the squeezed area and reduced pressure behind that area, thereby forcing a liquid through the tubing as the rotor assembly moves the pinch rollers along the tubing. In order to operate, there must always be an occlusion zone; in other words, at least one of the rollers is always pressing on the tube.

Finger peristaltic pumps are made of a series of fingers moving in cyclical fashion to flatten a flexible tube against a counter surface. The fingers move essentially vertically, in wave-like fashion, forming a zone of occlusion that moves from upstream to downstream. The last finger—the furthest downstream—raises up when the first finger—the furthest upstream—presses against the counter surface. The most commonly used finger pumps are linear, meaning that the counter surface is flat and the fingers are parallel. In this case, the fingers are controlled by a series of cams arranged one behind another, each cam cooperating with a finger. These cams are placed helically offset on a shared shaft driven rotationally by a motor. There are also rotary-finger peristaltic pumps, which attempt to combine the advantages of roller pumps with those of finger pumps. In this type of pump, the counter surface is not flat, but arc-shaped, and the fingers are arranged radially inside the counter surface. In this case, a shared cam with multiple knobs placed in the center of the arc is used to activate the fingers.

SUMMARY

In an embodiment of the present disclosure, a pump for pumping fluid includes a tube platen, a plunger, a bias member, inlet and outlet valves, an actuator mechanism, a position sensor, and a processor. The plunger is configured for actuation toward and away from the tube platen when the tube platen is disposed opposite to the plunger. The tube platen can hold an intravenous infusion tube. The bias member is configured to urge the plunger toward the tube platen. Optionally, the plunger may be an L-shaped plunger.

The inlet valve is upstream of the plunger and is configured for actuation between an occluding position and a non-occluding position. The outlet valve is downstream of the plunger and is configured for actuation between an occluding position and a non-occluding position. The actuator mechanism controls the actuation of the plunger, the inlet valve and the outlet valve. The position sensor estimates a position of the plunger. The actuator mechanism may be or includes a cam shaft. The processor is coupled to the position sensor to receive the estimated position of the plunger therefrom. The processor detects an anomaly based in part on the estimated plunger position when the inlet valve is in the occluding position and the outlet valve is in the occluding position. The processors may be configured to detect a leak based on a rate of change of the estimated position of the plunger.

The pump may further include an ultrasonic sensor sensitive to gas in an infusion tube. The ultrasonic sensor may be located downstream of the plunger and communicates with the processor. The processor distinguishes between an upstream occlusion and a presence of air in the fluid using the ultrasonic sensor. The processor may determine the volume of air pumped downstream based on the plunger position when both the inlet and outlet valves occlude the infusion tube and based upon the sensed gas sensed by the ultrasonic sensor.

The pump may include a housing and door pivotally coupled to the housing. The door pivots to an open position and to a closed position. The tube platen may be disposed on the door. The tube platen, the door, and the plunger are configured such that the plunger is configured for actuation toward and away from the infusion-tube when the door is in a closed position.

The pump may include a lever pivotally coupled to the door and has at least first and second positions. The pump may also include a latch coupled to the door. The lever latches the door onto the housing when in the first position. The first position may be a position in which the lever is pivoted toward to the door.

The pump may include a carrier having first and second portions pivotally coupled together. The door and the carrier co-pivot together. The housing includes a first slot in which the first portion of the carrier is at least partially disposed when the door is in the open position a second slot in which the second portion of the carrier is disposed within when the door is in the open position. The lever is operatively coupled to the second portion of the carrier such that when the door is in the closed position, lever actuation toward the first position pushes the first and second portions of the carrier into the first slot of the housing.

The actuator mechanism may include a cam shaft, an inlet-valve cam, an outlet-valve cam, and a plunger. The inlet-valve cam is coupled to the cam shaft and actuates the inlet valve. The outlet-valve cam is coupled to the cam shaft and actuates the outlet valve. The plunger cam is coupled to the cam shaft to actuate the plunger. The plunger cam is configured to lift the plunger away from the tube platen. The processor may detect the anomaly when only a force of the bias member forces the plunger toward the tube platen. The processor may communicate data (e.g., the anomaly) to a monitoring client. That is, the data may include an indication of the anomaly.

In yet another embodiment of the present disclosure, a pump includes a tube platen, a plunger, a bias member, inlet and outlet valves, an actuator mechanism, a pressure sensor, and a processor. The plunger is configured for actuation toward and away from the infusion-tube when the tube platen is disposed opposite to the plunger. The bias member urges the plunger toward the tube platen. The inlet valve is upstream of the plunger and is configured for actuation between an occluding position and a non-occluding position. The outlet valve is downstream of the plunger and is configured for actuation between an occluding position and a non-occluding position. The actuator mechanism is configured to control the actuation of the plunger, the inlet valve and the outlet valve. The pressure sensor is disposed adjacent to at least one of the inlet valve, the outlet valve, and the plunger. The processor is coupled to the pressure sensor to receive a pressure signal from the pressure sensor. The inlet valve, the outlet valve, and the plunger are configured to pump fluid in a plurality of cycles, each cycle having a trough pressure level and a peak pressure level. The processor is configured to, using the pressure signal, determine a downstream occlusion exists when a difference between a peak pressure level and a trough pressure level is greater than a predetermined threshold in a cycle of the plurality of cycles. The cycle of the plurality of cycles may be a single cycle. The pressure signal may be filtered prior to being received by the processor. The pump may include an analog filter configured to filter the pressure signal prior to being received by the processor. Additionally or alternatively, the processor is configured to digitally filter the pressure signal prior to determining whether a downstream occlusion exists.

In yet another embodiment, a pump for pumping fluid includes a tube platen, a plunger, a bias member, inlet and outlet valves, an actuator mechanism, a pressure sensor and a processor. The plunger is configured for actuation toward and away from the tube platen when the tube platen is disposed opposite to the plunger. The bias member urges the plunger toward the tube platen. The inlet valve is upstream of the plunger and is configured for actuation between an occluding position and a non-occluding position. The outlet valve is downstream of the plunger and is configured for actuation between an occluding position and a non-occluding position. The actuator mechanism controls the actuation of the plunger, the inlet valve and the outlet valve. The pressure sensor is disposed adjacent to at least one of the inlet valve, the outlet valve, and the plunger. The processor coupled to the pressure sensor to receive a pressure signal from the pressure sensor. The inlet valve, the outlet valve, and the plunger are configured to pump fluid in a plurality of cycles, each cycle having a trough pressure level and a peak pressure level. The processor is configured to, using the pressure signal, determine a downstream occlusion exists when a difference between a first trough pressure level of a first cycle and a second trough pressure level of a second cycle is greater than a predetermined threshold.

The processor may be one or more of a microprocessor, a microcontroller, a PLD, a PLA, a CPLD, and/or an FPGA. The first and second cycles are cycles of the plurality of cycles. The first and second cycles may be sequential cycles.

The pressure signal may be filtered prior to being received by the processor. The pump may include an analog filter configured to filter the pressure signal prior to being received by the processor. The processor may digitally filter the pressure signal prior to determining whether a downstream occlusion exists.

In yet another embodiment, a pump for pumping fluid includes a tube platen, a plunger, a bias member, inlet and outlet valves, an actuator mechanism, a pressure sensor and a processor. The plunger is configured for actuation toward and away from the tube platen when the tube platen is disposed opposite to the plunger. The bias member urges the plunger toward the tube platen. The inlet valve is upstream of the plunger and is configured for actuation between an occluding position and a non-occluding position. The outlet valve is downstream of the plunger and is configured for actuation between an occluding position and a non-occluding position. The actuator mechanism controls the actuation of the plunger, the inlet valve and the outlet valve. The pressure sensor is disposed adjacent to at least one of the inlet valve, the outlet valve, and the plunger. The processor coupled to the pressure sensor to receive a pressure signal from the pressure sensor. The inlet valve, the outlet valve, and the plunger are configured to pump fluid in a plurality of cycles, each cycle having a trough pressure level and a peak pressure level. The processor is configured to, using the pressure signal, determine a downstream occlusion exists when a summation of each sequential trough-to-trough pressure value of the plurality of cycles is greater than a predetermined threshold.

The pressure signal may be filtered prior to being received by the processor. The pump may include an analog filter configured to filter the pressure signal prior to being received by the processor and/or a digital filter within the processor that filters the pressure signal prior to determining whether a downstream occlusion exists.

The processor may add an adjustment value to the summation such that the summation represents a difference between a trough level of a current cycle of the plurality of cycles relative to a lowest trough value of all of the plurality of cycles.

In yet another embodiment, a pump for pumping fluid includes a tube platen, a plunger, a bias member, inlet and outlet valves, an actuator mechanism, a pressure sensor and a processor. The plunger is configured for actuation toward and away from the tube platen when the tube platen is disposed opposite to the plunger. The bias member urges the plunger toward the tube platen. The inlet valve is upstream of the plunger and is configured for actuation between an occluding position and a non-occluding position. The outlet valve is downstream of the plunger and is configured for actuation between an occluding position and a non-occluding position. The actuator mechanism controls the actuation of the plunger, the inlet valve and the outlet valve. The pressure sensor is disposed adjacent to at least one of the inlet valve, the outlet valve, and the plunger. The processor coupled to the pressure sensor to receive a pressure signal from the pressure sensor. The inlet valve, the outlet valve, and the plunger are configured to pump fluid in a plurality of cycles, each cycle having a trough pressure level and a peak pressure level. The processor is configured to, using the pressure signal, determine a downstream occlusion exists when a trough of a cycle of the plurality of cycles is greater than a lowest trough of all of the plurality of cycles by a predetermined amount.

The pressure signal may be filtered prior to being received by the processor. The pump may include an analog filter configured to filter the pressure signal prior to being received by the processor. The processor may digitally filter the pressure signal prior to determining whether a downstream occlusion exists.

In yet another embodiment, a pump for pumping fluid includes a tube platen, a plunger, a bias member, inlet and outlet valves, an actuator mechanism, a pressure sensor and a processor. The plunger is configured for actuation toward and away from the tube platen when the tube platen is disposed opposite to the plunger. The bias member urges the plunger toward the tube platen. The inlet valve is upstream of the plunger and is configured for actuation between an occluding position and a non-occluding position. The outlet valve is downstream of the plunger and is configured for actuation between an occluding position and a non-occluding position. The actuator mechanism controls the actuation of the plunger, the inlet valve and the outlet valve. The pressure sensor is disposed adjacent to at least one of the inlet valve, the outlet valve, and the plunger. The processor coupled to the pressure sensor to receive a pressure signal from the pressure sensor. The inlet valve, the outlet valve, and the plunger are configured to pump fluid in a plurality of cycles, each cycle having a trough pressure level and a peak pressure level. The processor is configured to, using the pressure signal, determine a downstream occlusion exists when a difference is greater than a predetermined threshold where the difference is a subtraction of: (1) a filtered value of a sequential series of sequential trough-to-trough pressure values of the plurality of cycles from (2) a trough-to-trough value.

The pressure signal may be filtered prior to being received by the processor. The pump may include an analog filter configured to filter the pressure signal prior to being received by the processor. The processor may digitally filter the pressure signal prior to determining whether a downstream occlusion exists.

In yet another embodiment, a pump for pumping fluid includes a tube platen, a plunger, a bias member, inlet and outlet valves, an actuator mechanism, a pressure sensor and a processor. The plunger is configured for actuation toward and away from the tube platen when the tube platen is disposed opposite to the plunger. The bias member urges the plunger toward the tube platen. The inlet valve is upstream of the plunger and is configured for actuation between an occluding position and a non-occluding position. The outlet valve is downstream of the plunger and is configured for actuation between an occluding position and a non-occluding position. The actuator mechanism controls the actuation of the plunger, the inlet valve and the outlet valve. The pressure sensor is disposed adjacent to at least one of the inlet valve, the outlet valve, and the plunger. The processor coupled to the pressure sensor to receive a pressure signal from the pressure sensor. The inlet valve, the outlet valve, and the plunger are configured to pump fluid in a plurality of cycles, each cycle having a trough pressure level and a peak pressure level. The processor is configured, using the pressure signal, to: (1) determine a downstream occlusion exists if a difference between a peak pressure level and a trough pressure level is greater than a first predetermined threshold in any cycle of the plurality of cycles, (2) determine the downstream occlusion exists if a difference between a first trough pressure level of a first cycle and a second trough pressure level of a second cycle is greater than a second predetermined threshold, the first and second cycles are cycles of the plurality of cycles, (3) determine the downstream occlusion exists if a trough of the cycle of the plurality of cycles is greater than a lowest trough of all of the plurality of cycles by a third predetermined threshold, and (4) determine the downstream occlusion exists if a subtraction of a filtered value of a sequential series of sequential trough-to-trough pressure values of the plurality of cycles from a trough-to-trough value is greater than a fourth predetermined threshold.

The processor may perform all of the evaluations (1)-(4) to determine if the downstream occlusion exists. The processor is configured to communicate data to a monitoring client. The pressure signal may be filtered prior to being received by the processor. The pump may include an analog filter configured to filter the pressure signal prior to being received by the processor. The processor may digitally filter the pressure signal prior to determining whether a downstream occlusion exists.

The actuator mechanism may further includes an inlet-valve cam coupled to the cam shaft configured to actuate the inlet valve; an outlet-valve cam coupled to the cam shaft configured to actuate the outlet valve; and a plunger cam coupled to the cam shaft configured to actuate the plunger. The plunger cam may be configured to lift the plunger away from the tube platen. The plunger cam may be configured such that the plunger cam can only compress the bias member and not force the plunger toward the tube platen.

The plunger cam may be configured to only actuate the plunger away from the tube platen against the bias member, and the plunger cam and the bias member are configured such that only a force of the bias member can compress a tube disposed within the tube platen.

In another embodiment of the present disclosure, a pump includes a tube platen and a plunger. The plunger is configured to actuate toward the tube platen. An end of the plunger has a rounded end and a bottom of the tube platen has a generally U shape that provides a radial gap between the plunger and the tube platen about equal to from two to three times a wall thickness of an infusion tube. A minimum distance between the plunger and the tube platen along a path of motion of the plunger may be limited by a surface on the tube platen that contacts a portion of the plunger.

In another embodiment, a pump includes a tube platen and a plunger. The tube platen defines a well and a first contacting section. The plunger is configured to actuate toward the tube platen. The plunger has a rounded tip and a second contacting section. The tube platen and the plunger are configured such that actuation of the plunger toward the tube platen is impeded when the first and second contacting sections contact each other. The first and second contacting sections may be configured to contact each other to leave a predetermined gap between the well of the tube platen and the rounded tip of the plunger.

The predetermined gap may be configured to prevent an infusion tube disposed within the tube platen from fully closing. The predetermined gap may be configured to cause an infusion tube disposed within the tube platen to partially occlude fluid flow within the infusion tube.

In another embodiment, a pump includes a tube platen and a plunger. The tube platen defines a well and a first contacting section. The plunger is configured to actuate toward the tube platen, and the plunger has a rounded tip and a second contacting section. The tube platen and the plunger are configured such that actuation of the plunger toward the tube platen is impeded when the first and second contacting sections contact each other. The first and second contacting sections contact each other such that a gap between the rounded tip and the tube platen is about equal to about eight percent larger than twice a wall thickness of an infusion tube disposed within the tube platen. The rounded tip may have a width that is less than an uncompressed tube diameter of a tube disposed within the well of the tube platen. The tube platen may be configured to receive a predetermine range of infusion tube sizes and/or, the tube platen may be configured to receive a predetermine infusion tube size.

In yet another embodiment of the present disclosure, a pump includes a tube platen defining a well, and a plunger configured to actuate toward the tube platen. The plunger has a rounded tip. The rounded tip has a width that is less than an uncompressed tube diameter of a tube disposed within the well of the tube platen. The tube platen may be configured to receive a predetermine infusion tube size. In another embodiment, the rounded tip has a radius that is less than an uncompressed tube radius of a tube disposed within the well of the tube platen.

In another embodiment, a pump includes a tube platen defining a well and a first contacting section, and a plunger configured to actuate toward the tube platen. The plunger has a rounded tip and a second contacting section. The tube platen and the plunger are configured such that actuation of the plunger toward the tube platen is impeded when the first and second contacting sections contact each other. The first and second contacting section contact each other such that a gap between the rounded tip and the tube platen is about equal to slightly greater than twice a wall thickness a tube disposed within the well. The tube platen may be configured to receive a predetermine infusion tube size.

In another embodiment of the present disclosure, pump includes a housing, a door, a carrier, and a lever handle. The housing has a first slot. The door is pivotally coupled to the housing and has a platen configured to receive a tube. The door is configured to have a closed position and an open position. The door includes a second slot. The carrier has a pivot defining first and second portions pivotally coupled together. The first portion is slidingly disposed within the first slot of the housing and the second portion is slidingly disposed within the second slot of the door when the door is open. The lever handle is pivotally coupled to the door and is operatively coupled to the carrier.

The pump may further include a valve configured to occlude the tube. The carrier may be configured to retain a slide occluder. When the door is in the closed position and the lever handle is in a fully open position, the carrier is configured to retain the slide occluder within the first and second portions such that the slide occluder fully occludes the tube. An initial actuation of the lever handle toward the housing actuates the valve to occlude the tube prior to actuation of the carrier into the first slot of the door such that the tube is unoccluded by the slide occluder.

The lever handle may be operatively coupled to the second portion of the carrier such that actuation of the lever handle away from the housing moves the first and second portions of the carrier away from the first slot to thereby move a slide occluder disposed within the carrier into an occluded position such that at least some actuation of the lever handle away from the housing occurs without moving the slide occluder.

The door may be pivotally coupled to the housing via a hinge, the door may contact a face of the housing when the door is in the closed position, and the hinge may be configured to allow the door to move relative to the housing from a perpendicular position relative to the housing face when the door is in the open position to adjacent to the housing face when the door is in the closed position.

The second portion of the carrier may be keyed to receive a slide occluder in only a predetermined orientation. The door defines a key for the second portion of the carrier such that the second portion of the carrier receives a slide occluder in only a predetermined orientation.

The pump may include a slide occluder sensor configured to detect a presence of a slide occluder when the slide occluder is properly inserted into the carrier, the door is shut, and the lever handle is actuated fully toward the door.

In some embodiments, the pump may further include a valve configured to occlude the tube. The carrier is configured to retain a slide occluder. When the door is in the closed position and the lever handle is in a fully open position, the carrier is configured to retain the slide occluder within the first and second portions such that the slide occluder fully occludes the tube. An initial actuation of the lever handle when the lever handle is in a fully closed position away from the housing actuates the carrier to an occluding position prior to actuating the valve into a non-occluding position.

In some embodiments, the pump further includes a valve configured to occlude the tube. The carrier is configured to retain a slide occluder. When the door is in the closed position and the lever handle is in a fully closed position, the carrier is configured to retain the slide occluder within the first and second portions such that the slide occluder fully occludes the tube. An initial actuation of the lever handle away from the housing actuates the carrier to an occluding position prior to actuating the valve into a non-occluding position. The door may become unlatched from the housing after a substantial amount of actuation of the lever handle away from the door.

In yet another embodiment of the present disclosure, a pump includes a housing, a door, and a carrier. The housing has a first slot. The door is pivotally coupled to the housing and has a platen configured to receive a tube. The door is configured to have a closed position and an open position, and includes a second slot. The carrier has a pivot defining first and second portions pivotally coupled together, wherein the first portion is slidingly disposed within the first slot of the housing and the second portion is slidingly disposed within the second slot of the door when the door is open.

In another embodiment of the present disclosure, a pump includes a pumping mechanism, a motor, a rotation sensor, a counter, and first and second processors. The pumping mechanism is configured to pump fluid. The motor is coupled to the pumping mechanism to actuate the pumping mechanism. The rotation sensor is couple to the motor and is configured to generate a plurality of pulses where each pulse of the plurality of pulses indicates a rotation (e.g., a full rotation or a partial rotation, such as 2 degrees) of the motor. The counter is coupled to the rotation sensor to count each pulse of the plurality of pulses. The first processor is operatively coupled to the rotation sensor to monitor the plurality of pulses. The second processor is operatively coupled to the counter to monitor the counted pulses of the plurality of pulses. The first and second processors are in operative communication with each other. The first and second processors are configured to determine whether the monitored plurality of pulses determined by the first processor corresponds to the counted pulses as received by the second processor from the counter.

The monitored plurality of pulses determined by the first processor corresponds to the counted pulses as received by the second processor from the counter when the monitored plurality of pulses determined by the first processor agrees with counted pulses as received by the second processor from the counter by a predetermined amount. The predetermined amount may be a percentage amount, a predetermined number of pulses of the plurality of pulses, and/or a predetermined angular value. Each pulse of the plurality of pulses may correspond to a predetermined number of degrees of rotation by the motor.

The first processor may communicate a counted number of the monitored plurality of pulses to the second processor. The first processor may use the monitored plurality of pulses to determine a first estimated amount of volume delivered. The second processor may use the counted pulses of the plurality of pulses to determine a second estimated amount of volume delivered. One or both of the first and second processors may issue an alarm when the first and second estimated amounts of volume delivered do not agree by a predetermined amount.

In another embodiment, pump includes a pumping mechanism, a motor, a rotation sensor, a counter, and first and second processors. The pumping mechanism is configured to pump fluid. The motor is coupled to the pumping mechanism to actuate the pumping mechanism. The rotation sensor is couple to the motor and is configured to generate a plurality of pulses. Each pulse of the plurality of pulses may indicate a rotation of the motor. The counter coupled to the rotation sensor counts each pulse of the plurality of pulses. The first processor is operatively coupled to the rotation sensor to monitor the plurality of pulses to estimate a first volume of fluid pumped. The second processor is operatively coupled to the counter to monitor the counted pulses of the plurality of pulses to estimate a second volume of fluid pumped. The first and second processors are in operative communication with each other. The first and second processors are configured to determine whether the estimated first volume of fluid pumped is within a predetermined range relative to the estimated second volume of fluid pumped. The first processor may control the operation of the motor. The second processor may control the operation of the motor. The second processor may be coupled to a user interface to receive user input therefrom.

The predetermined range may be a percentage amount relative to one of the first and second estimated volumes of fluid pumped, a range relative to the estimated first volume of fluid pumped, and/or a range relative to the estimated second volume of fluid pumped.

One or both of the first and second processors may issue an alarm when the first and second estimated volumes of fluid pumped do not agree within the predetermined range. The first processor may communicate the estimated first volume of fluid pumped to the second processor such that the second processor determines whether the estimated first volume of fluid pumped is within the predetermined range relative to the estimated second volume of fluid pumped. The second processor may communicate the estimated second volume of fluid pumped to the first processor such that the first processor determines whether the estimated first volume of fluid pumped is within the predetermined range relative to the estimated second volume of fluid pumped.

In another embodiment of the present disclosure, a pump for pumping fluid includes a housing, a door, a tube platen, a plunger, a valve, one or more hook latches, and a lever. The housing has one or more pins. The door is pivotally coupled to the housing. The tube platen is dispose on the door. The plunger is configured for actuation toward and away from the infusion-tube when the tube platen is disposed opposite to the plunger. The valve is disposed upstream or downstream of the plunger and is configured for actuation between an occluding position and a non-occluding position. The lever handle is operatively coupled to the one or more hook latches to actuate the one or more hook latches to latch onto the one or more pins of the housing.

The pump may include a spring configured to urge the door toward the housing when the one or more hook latches are latched onto the one or more pins. The spring may be a leaf spring, and may provide mechanical engagement between the at least one hook latch and the door. Actuation of the lever handle to latch the one or more hook latches to the one or more pins may also actuate the valve to occlude a tube. Actuation of the lever handle to unlatch the one or more hook latches from the one or more pins also actuates the valve to a non-occluding position. A bias member may be configured to urge the plunger toward the tube platen.

In another embodiment of the present disclosure, a pump includes a housing and a door. The housing has a front, and first and second sides. The door is pivotally coupled to the first side and defines a cutout portion. The pump may include a lever handle pivotally coupled to the door. The pump may have a bumper coupled to the first side of the housing and disposed within the cutout portion of the door when the door is in a closed position. The lever handle includes a lever-cutout portion positioned such that the bumper is disposed within the lever-cutout portion when the door is in the closed position and the lever handle is in a closed position.

In another embodiment of the present disclosure, a pump includes a housing, a user interface, and an elongated light source. The housing has a front, and first and second sides. The user interface is operatively coupled to the front of the housing. The elongated light source is coupled at least partially around the user interface. The elongated light source may include a plurality of LEDs and a light diffuser. The elongated light source may be disposed fully around an outer periphery of the user interface. A processor may be operatively coupled to the elongated light source. The processor may be configured to control the elongated light source. The processor may be configured to indicate a status of the pump by controlling the elongated light source, e.g., by changing a color of the elongated light source and/or by changing a brightness of the elongated light source.

In another embodiment of the present disclosure, a pump includes a housing and a power supply. The power supply may be coupled to the housing such that the housing is configured as a heat sink for the power supply. The pump may be a peristaltic pump and/or a syringe pump. The housing may be die casted and may comprise at least one metal. The housing may be a unitary body. The pump may include a motor such that the motor is coupled to the housing so that the housing is a heat sink for the motor.

In another embodiment of the present disclosure, a pump includes a tube platen, a plunger, a cam shaft, a motor, a position sensor, a rotation sensor, and a processor. The plunger has a cam follower and is configured for actuation toward and away from the tube platen when the tube platen is disposed opposite to the plunger. The cam shaft has a plunger cam coupled to the cam shaft. The cam follower of the plunger is configured to engage the plunger cam such that rotation of the cam shaft actuates the plunger. The pump may include a bias member configured to urge the plunger toward the tube platen. The motor is operatively coupled to the cam shaft to rotate the cam shaft. The position sensor is configured to provide a first signal corresponding to a position of the plunger. The rotation sensor is configured to provide a second signal corresponding to rotation of the cam shaft. The processor coupled to the position sensor and the rotation sensor to receive the first and second signals, wherein the processor determines whether the first signal corresponds to the second signal.

The processor may be configured to continue to operate the motor when one of the first and second signals is inoperative. The processor may be configured to ignore the inoperative one of the first and second signals.

The pump may include a motor rotation sensor configured to provide a third signal to the processor. The third signal corresponds to rotation of the motor. The processor may be configured to determine whether the first, second and third signals correspond to each other.

The processor may be configured to continue to operate the motor when one of the first, second, and third signals is inoperative. The processor may be configured to ignore the inoperative one of the first, second and third signals.

The pump may include a redundant position sensor configured to provide a fourth signal corresponding to the position of the plunger. The processor receives the fourth signal. The processor may be configured to continue to operate the motor when one of the first, second, and fourth signals is inoperative. The processor may be configured to ignore the inoperative one of the first, second and fourth signals.

In another embodiment of the present disclosure, a pump includes a tube platen, inlet and outlet valves, a cam shaft, a motor, and a processor. The plunger is configured for actuation toward and away from the tube platen when the tube platen is disposed opposite to the plunger. The inlet valve is upstream of the plunger and is configured for actuation between an occluding position and a non-occluding position. The outlet valve is downstream of the plunger and is configured for actuation between an occluding position and a non-occluding position. The cam shaft is configured to actuate the plunger, the inlet valve and the outlet valve. The motor is operatively coupled to the cam shaft. The processor is operatively coupled to the motor and is configured to control the motor. The processor is configured to limit at least one of a rise of the inlet valve, a rise of the outlet valve, and a rise of the plunger to below a predetermined speed. The predetermined speed is selected to prevent an outgas of a fluid within a tube disposed on the tube platen. The predetermined speed is a function of a position of at least one of the inlet valve, the outlet valve, and the plunger. The predetermined speed may be less than a natural expansion speed of a tube disposed on the tube platen.

A pump includes a tube platen, a plunger, a bias member, inlet and outlet valves, an actuator mechanism, a position sensor, an air-in-line sensor, and a processor. The plunger is configured for actuation toward and away from the infusion-tube when the tube platen is disposed opposite to the plunger. The bias member is configured to urge the plunger toward the tube platen. The inlet valve is upstream of the plunger and is configured for actuation between an occluding position and a non-occluding position. The outlet valve is downstream of the plunger and is configured for actuation between an occluding position and a non-occluding position. The actuator mechanism is configured to control the actuation of the plunger, the inlet valve and the outlet valve. The inlet valve, the outlet valve, and the plunger are configured to pump fluid in a plurality of cycles where each cycle has a trough pressure level and a peak pressure level. Each cycle has an initial pressurization period corresponding to a full-volume measurement taken when the inlet and outlet valves are closed and only the bias member applies a force to the plunger toward the tube platen. The position sensor is operatively coupled to the plunger and is configured to measure a position of the plunger to determine the full-volume measurement. The position sensor may provide a first signal corresponding to the position of the plunger. The air-in-line sensor is positioned downstream to the plunger and is configured to detect air. The air-in-line sensor provides a second signal corresponding to the air. The processor is coupled to the position sensor to receive the first signal and to the air-in-line sensor to receive the second signal. The processor is configured to determine an underfill condition has occurred when the position of the plunger is within a predetermined range from the tube platen as indicated by the first signal during the initial pressurization period of a cycle of the plurality of cycles. The actuator mechanism may be a cam shaft.

The processor may determine whether the underfill condition is from air within a fluid tube using the second signal when the outlet valve is opened. The processor may determine whether the underfill condition is from an upstream occlusion using the second signal when the outlet valve is opened. The processor may determine whether the underfill condition is from an empty upstream fluid source using the second signal when the outlet valve is opened.

In another embodiment of the present disclosure, a pump for pumping fluid includes a housing, a user interface, and a gesture-recognition apparatus. The user interface is coupled to the housing. The gesture-recognition apparatus is configured to recognize at least one gesture performed near the user interface. The pumping mechanism is configured to pump fluid. The processor is coupled to the user interface and the gesture-recognition apparatus. The processor is configured to present a user with at least one option via the user interface and receive a selected one of the at least one option via the gesture-recognition apparatus. The pumping mechanism may be a peristaltic pumping mechanism and/or a syringe-pump mechanism.

In another embodiment of the present disclosure, a pump includes a housing, a user interface, a pumping mechanism, and a processor. The user interface is coupled to the housing. The pumping mechanism is configured to pump fluid. The processor coupled to the user interface and is configured to provide a plurality of pump parameter inputs where each of the plurality of pump parameter inputs is configured to receive a user inputted parameter. The processor is configured to determine whether all of the user inputted parameters of all of the plurality of pump parameters meets at least one predetermined safety criterion. Each of the plurality of pump parameter inputs may be present without another one of the plurality of pump parameters inputs.

In another embodiment of the present disclosure, a pump includes a housing, a user interface, a pumping mechanism, and a processor. The user interface is coupled to the housing. The pumping mechanism may be configured to pump fluid. The processor is coupled to the user interface. The processor may be configured to provide a plurality of pump parameter inputs, each of the plurality of pump parameter inputs is configured to receive a user inputted parameter, wherein the processor is configured to require that all of the plurality of pump parameter inputs are inputted within a predetermined amount of time. The processor may be configured to receive a corresponding user inputted parameter for the plurality of pump parameter inputs in any order.

In yet another embodiment of the present disclosure, pump for pumping fluid includes a tube platen, a plunger, an actuator mechanism, a light source, an image sensor, and a processor. The plunger is configured for actuation toward and away from the tube platen when the tube platen is disposed opposite to the plunger. The actuator mechanism is configured to control the actuation of the plunger. The light source configured to shine light toward or adjacent to the tube platen. The image sensor is configured to receive the light. The processor is in operative communication with the image sensor to receive image data and is configured to estimate a parameter of a tube disposed on the tube platen in accordance with the image data.

The light source may be disposed within the plunger. The plunger may be at least one of transparent and translucent to the light of the light source.

The light source may be disposed adjacent to the plunger and the plunger is at least one of transparent and translucent to the light of the light source. The light source and the plunger may be configured such that the light from the light source travels from the light source through the plunger and toward the tube platen.

The pump may include a first polarizer positioned to polarize the light from the light source prior to being shined on the tube platen. The pump may include a second polarizer positioned to polarize the light from the tube platen prior to entering the image sensor. The first and second polarizers may be configured to polarize light in orthogonal directions relative to each other.

In some embodiments, the parameter of the tube is determined using a birefringence effect.

The parameter of the tube may be an identification of a particle disposed within the tube, an identification of a liquid disposed within the tube, a determined material of the tube, a volume of fluid within the tube along a predetermined portion of the tube, an identification of a bubble within a liquid disposed within the tube, and/or whether the tube is present on the tube platen. The parameter of the tube may be used to calibrate a control system of the pump.

The processor and the image sensor may be configured to estimate the parameter using a color spectrum of the light affected by a birefringence effect. The processor and the image sensor may be configured to estimate the parameter using a moiré pattern of the light affected by a birefringence effect.

In some embodiments, the pump further comprising a first pattern positioned to affect the light from the light source prior to being shined on the tube platen. The pump may also include a second pattern positioned to affect the light from the well prior to entering the image sensor. The parameter of the tube is determined using a moiré pattern as seen from the image sensor.

The second pattern may be disposed adjacent to the tube and is deformed by compression of the tube against the tube platen when the plunger is actuated toward the tube platen.

The light source may be a monochromatic light source.

In yet another embodiment of the present disclosure, a pump for pumping fluid includes a tube platen, a plunger, an actuator mechanism, a layered structure, an image sensor, and a processor. The plunger is configured for actuation toward and away from the tube platen when the tube platen is disposed opposite to the plunger. The actuator mechanism may be configured to control the actuation of the plunger. The layered structure has a waveguide layer and a diffuser layer and is configured for placement against a tube to indicate a parameter of the tube. The image sensor is configured to receive the light from the layered structure. The processor is in operative communication with the image sensor to receive image data. The processor is configured to estimate the parameter of the tube disposed on the tube platen in accordance with the image data.

The layered structure may include a plurality of waveguide layers and a plurality of diffuser layers to determine a plurality of parameters of the tube. The layered structure may provide the parameter of the tube selected from the group of a polarization, an orientation, and a color. The waveguide layer may be configured to be disposed against the tube such that light is diverted within the waveguide into the tube.

In another embodiment of the present disclosure, a pump for pumping fluid includes a tube platen, a plunger, a bias member, inlet and outlet valves, an actuator mechanism, a position sensor, and a processor. The plunger is configured for actuation toward and away from the tube platen when the tube platen is disposed opposite to the plunger. The bias member may be configured to urge the plunger toward the tube platen. The inlet valve is upstream of the plunger and is configured for actuation between an occluding position and a non-occluding position. The outlet valve is downstream of the plunger and is configured for actuation between an occluding position and a non-occluding position. The actuator mechanism may be configured to control the actuation of the plunger, the inlet valve and the outlet valve. The inlet valve, the outlet valve, and the plunger may be configured to pump fluid in a plurality of cycles where each cycle has an initial pressurization period corresponding to a full-volume measurement taken when the inlet and outlet valves are closed and only the bias member applies a force to the plunger toward the tube platen. The position sensor may be operatively coupled to the plunger and is configured to measure a position of the plunger to determine the full-volume measurement. The position sensor may provide a first signal corresponding to the position of the plunger. The processor may be coupled to the position sensor to receive the first signal, and the processor is configured to determine a head height of a fluid source coupled to a fluid tube disposed within the tube platen using the first signal corresponding to the position of the plunger.

In yet another embodiment of the present disclosure, a medical device includes a user interface, an antenna, and a split-ring resonator. The user interface has a front side and a backside. The antenna may be disposed orthogonal to a surface defined by the back side of the user interface. The split-ring resonator may be disposed in spaced relation to the user interface and configured to operate with the antenna.

The user interface may include a touchscreen sensor. A frame may surround the touchscreen sensor and has a gap such that the frame defines the split-ring resonator. A dielectric may be disposed within the gap.

In yet another embodiment of the present disclosure, a pump includes a housing, a door, a lever, and an interlock. The housing has a pin. The door is pivotally coupled to the housing. The lever has a latch configured to latch the lever onto the pin of the housing, and the lever is pivotally coupled to the door. The interlock may be configured to lock the lever when in an open position and the door is in an open position. The pump may include a carrier operatively coupled to the lever.

The carrier may include a first portion and a second portion pivotally coupled to the first portion. The first portion may be positioned within a slot of the housing. The second portion may be positioned within a slot of door. The first and second portions are configured to retain a slide occluder.

BRIEF DESCRIPTION OF THE DRAWINGS

These and other aspects will become more apparent from the following detailed description of the various embodiments of the present disclosure with reference to the drawings wherein:

FIG. 11 shows a table illustrating the corresponding fields of view about the optical axis for the corners of the two configurations of FIGS. 9 and 10 in accordance with an embodiment of the present disclosure;

FIG. 21 is a graphic illustration of an image captured by the camera when a free flow condition exists thereby forming a stream within the drip chamber of FIG. 14 in accordance with an embodiment of the present disclosure;

FIG. 22 is a graphic illustration of an image captured by the camera of FIG. 14 for use as a background image in accordance with an embodiment of the present disclosure;

FIG. 23 is a graphic illustration of a difference between the images of FIGS. 20 and 21 with some additional processing for use in detecting a free flow condition in accordance with an embodiment of the present disclosure;

FIG. 34 shows a matching template for use in air detection in accordance with an embodiment of the present disclosure;

FIG. 35 illustrates an image captured by the camera of system of FIG. 33 for detecting that no tube is within a cavity in accordance with an embodiment of the present disclosure;

FIG. 36 illustrates an image captured by the camera of the system of FIG. 33 for detecting air bubbles in accordance with an embodiment of the present disclosure;

FIG. 37 illustrates an image captured by the camera of the system of FIG. 33 for detecting blood in accordance with an embodiment of the present disclosure;

FIG. 38 illustrates the image of FIG. 37 that has undergone image processing for detecting a threshold amount of red for detecting blood in accordance with an embodiment of the present disclosure;

FIG. 42 shows a perspective view of an occluder in accordance to an embodiment of the present disclosure;

FIG. 43 shows a side view of the occluder of FIG. 42 in accordance to an embodiment of the present disclosure;

FIG. 44 shows a side view of the occluder of FIG. 42 in operation in accordance to an embodiment of the present disclosure;

FIGS. 80-82 show legends for use in conjunction with FIGS. 79 and 83-98 in accordance with an embodiment of the present disclosure;

FIGS. 125 and 126 show a tube-based reservoir in accordance with an embodiment of the present disclosure;

FIG. 147 shows several views of a plunger pump having an AVS assembly with pinch valve disposed within the variable volume of the AVS assembly, and a plunger and pinch valve disposed outside the variable volume in accordance with an embodiment of the present disclosure;

FIG. 148 shows an two cross-sectional views of the plunger pump of FIG. 147 in accordance with an embodiment of the present disclosure;

FIG. 149 shows an alternative two cross-sectional views of the plunger pump of FIG. 147 in accordance with an embodiment of the present disclosure;

FIG. 150 illustrates the stages during normal operation of a plunger pump having a spring-biased plunger in accordance with an embodiment of the present disclosure;

FIG. 151 illustrates the stages for detecting an occlusion for a plunger pump having a spring-biased plunger in accordance with an embodiment of the present disclosure;

FIG. 152 illustrates the stages for leakage detection for a plunger pump having a spring-biased plunger in accordance with an embodiment of the present disclosure;

FIG. 153 illustrates the stages for detecting a failed valve and/or bubble detection for a plunger pump having a spring-biased plunger in accordance with an embodiment of the present disclosure;

FIG. 154 illustrates the stages for empty reservoir detection and/or upstream occlusion detection for a plunger pump having a spring-biased plunger in accordance with an embodiment of the present disclosure;

FIG. 155 illustrates the stages for free-flow prevention for a plunger pump having a spring-biased plunger in accordance with an embodiment of the present disclosure;

FIG. 156 illustrates the stages for a negative pressure valve check for a plunger pump having a spring-biased plunger in accordance with an embodiment of the present disclosure;

FIGS. 157-158 show views of a plunger pump having a cam shaft 671 that traverses the variable volume of an AVS assembly in accordance with an embodiment of the present disclosure;

FIGS. 159-162 illustrate several cam profiles in accordance with several embodiments of the present disclosure;

FIG. 163 illustrates a peristaltic pump having a plunger and a pinch valves outside of an AVS chamber with two pinch valves on the interface of the ACS chamber in accordance with an embodiment of the present disclosure;

Figure 163:
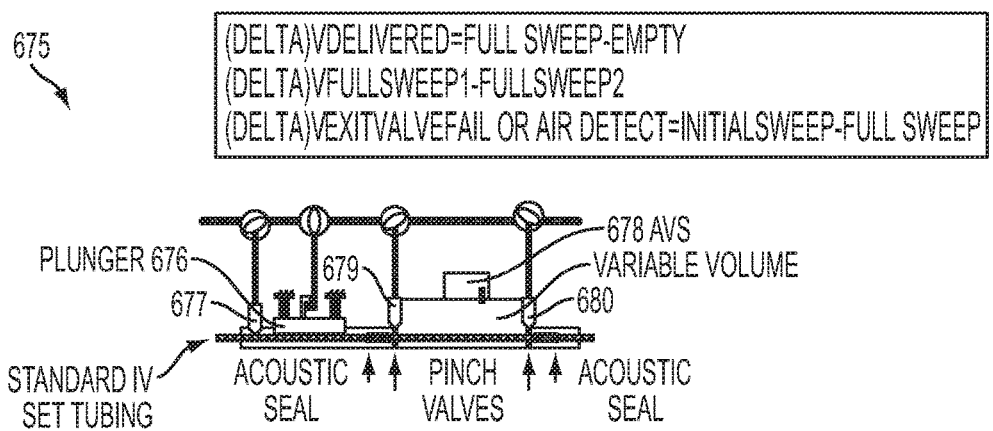
Figure 164:
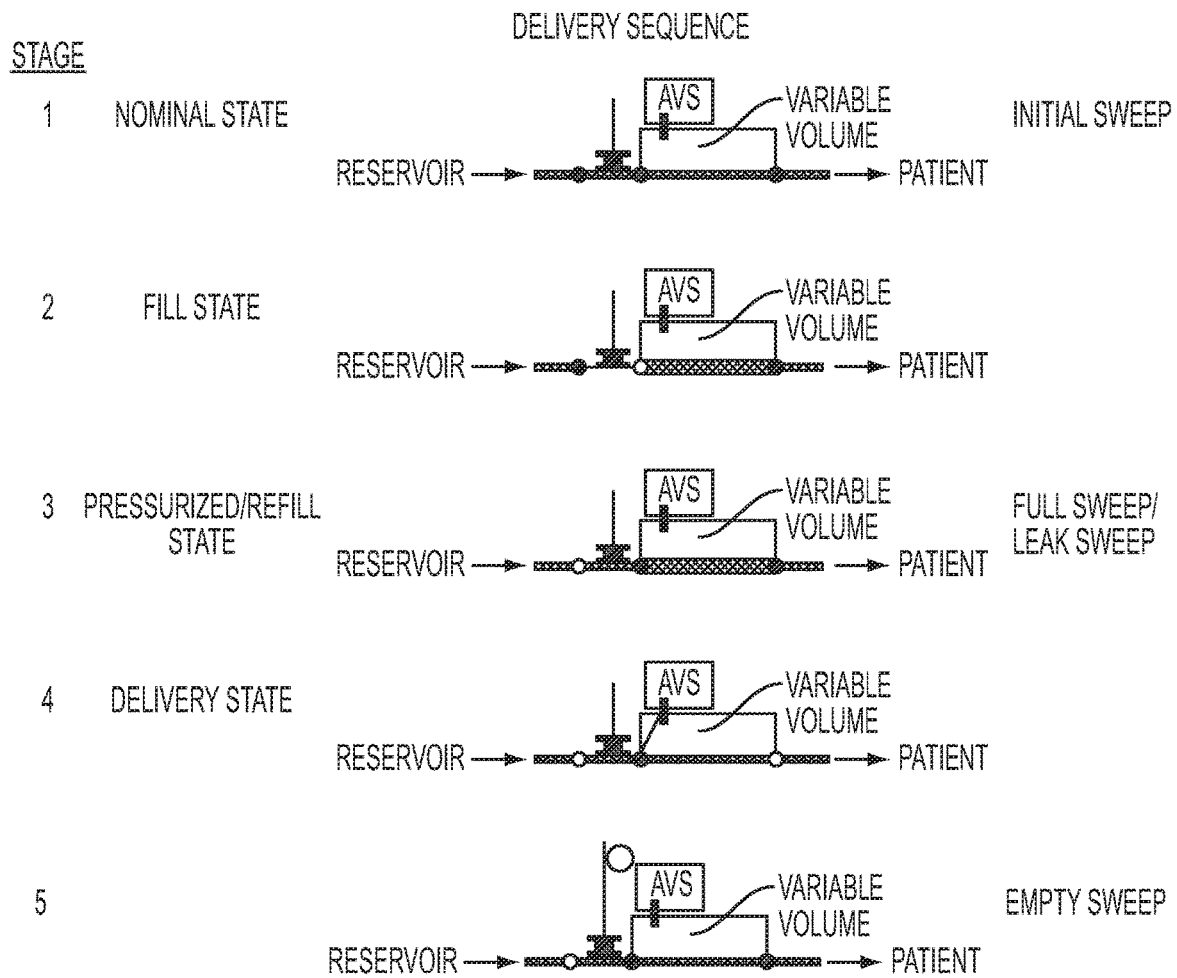
Figure 165:
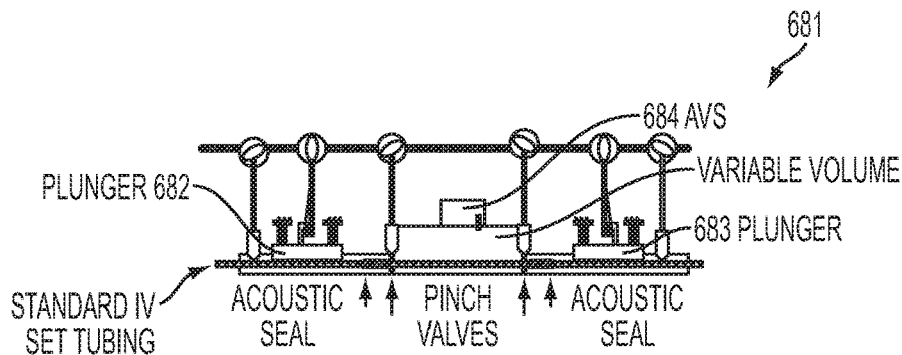
Figure 166:
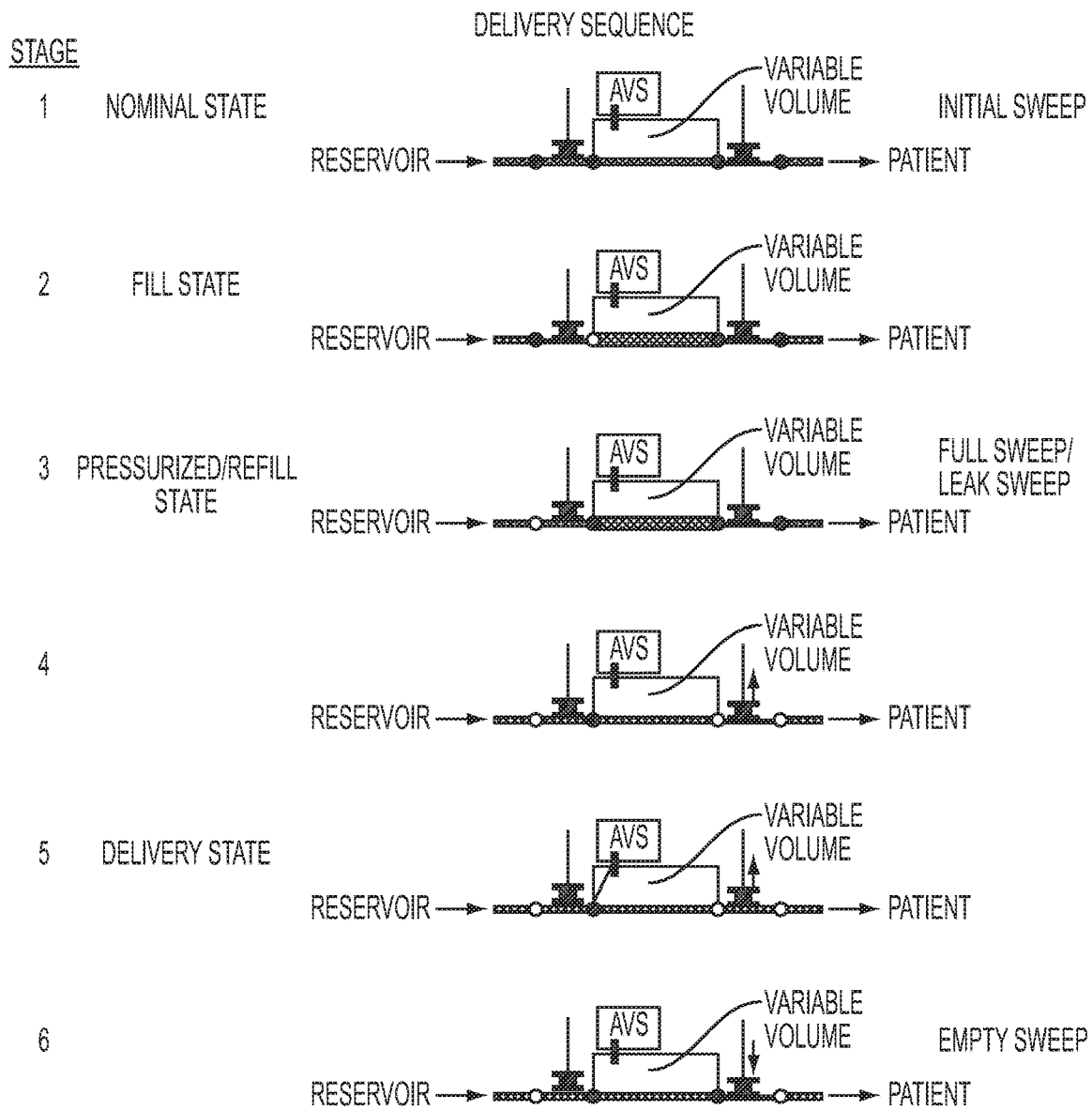
Figure 167:
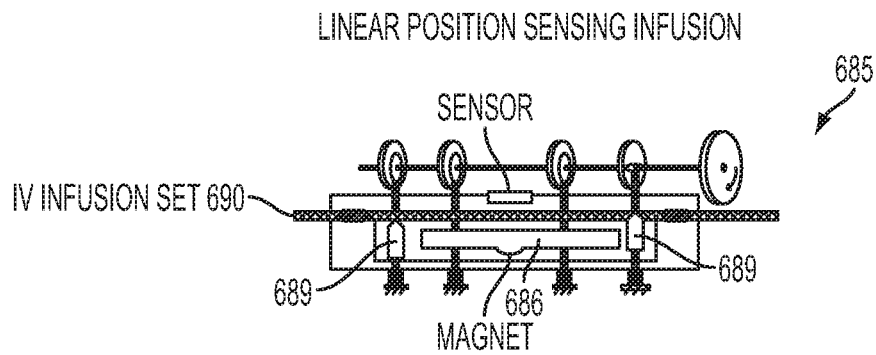
Figure 168:
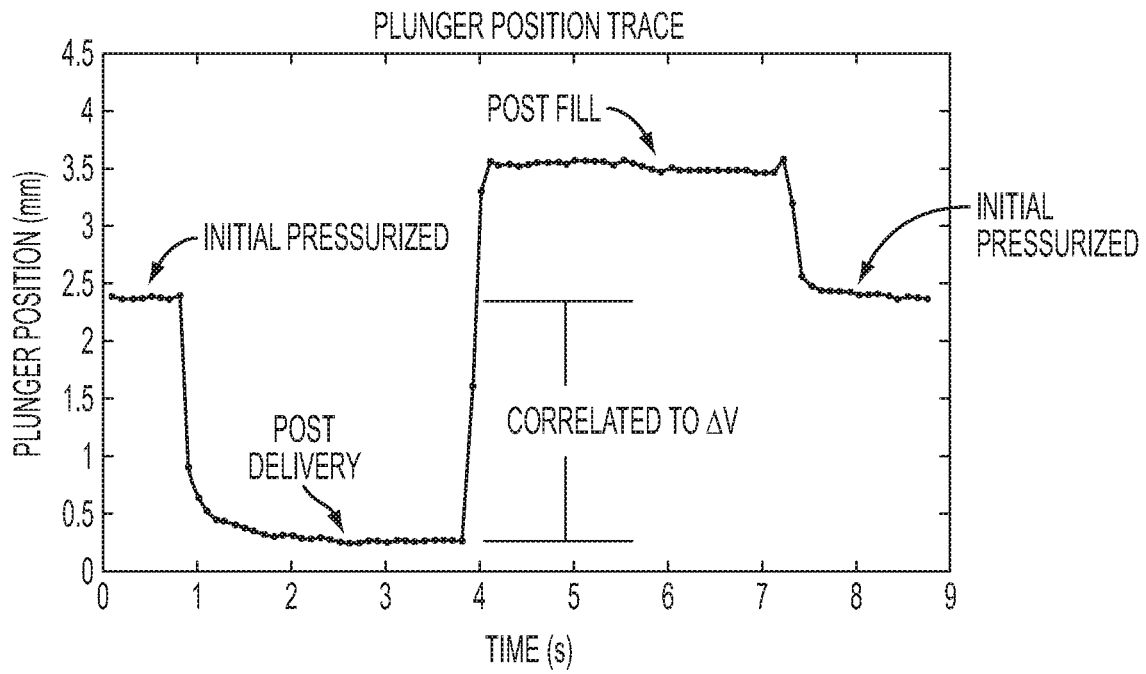
Figure 169:
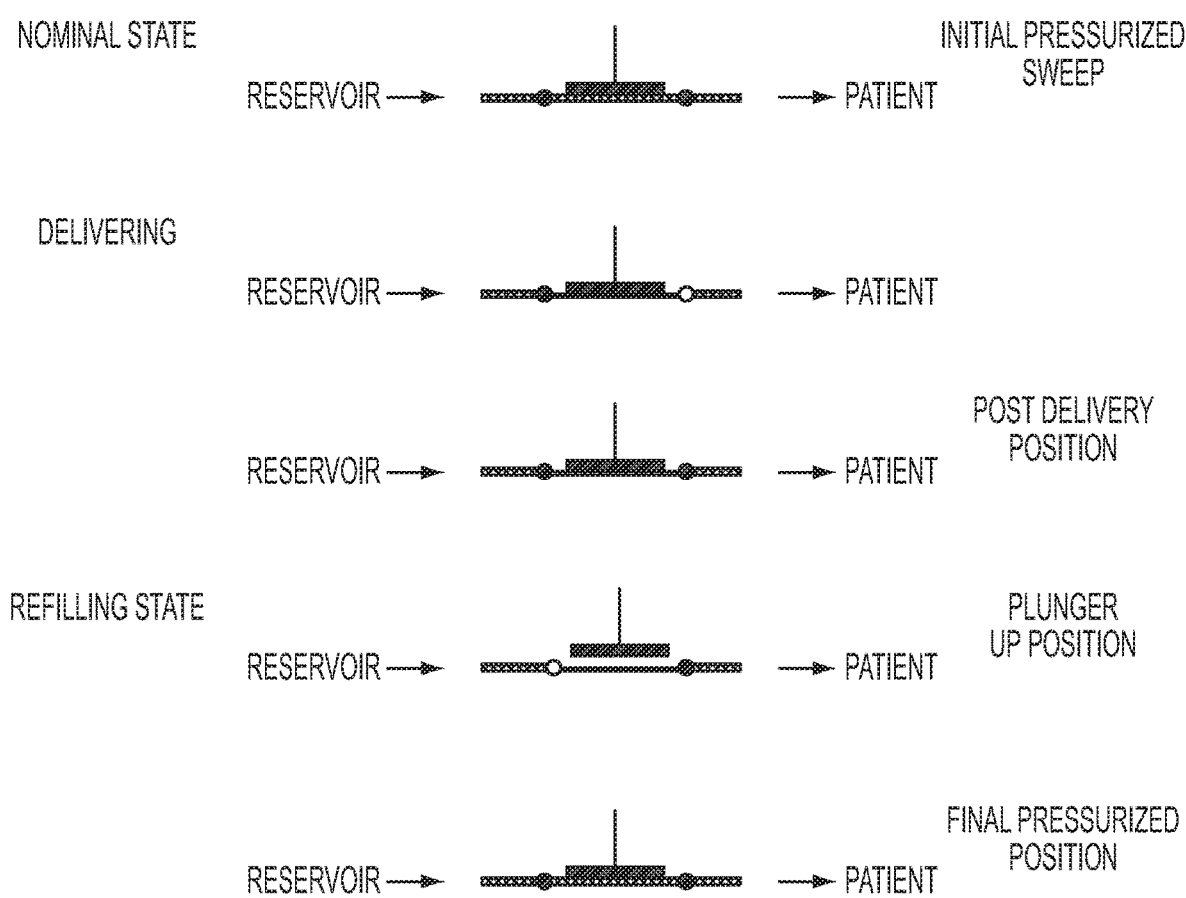
Figure 170:
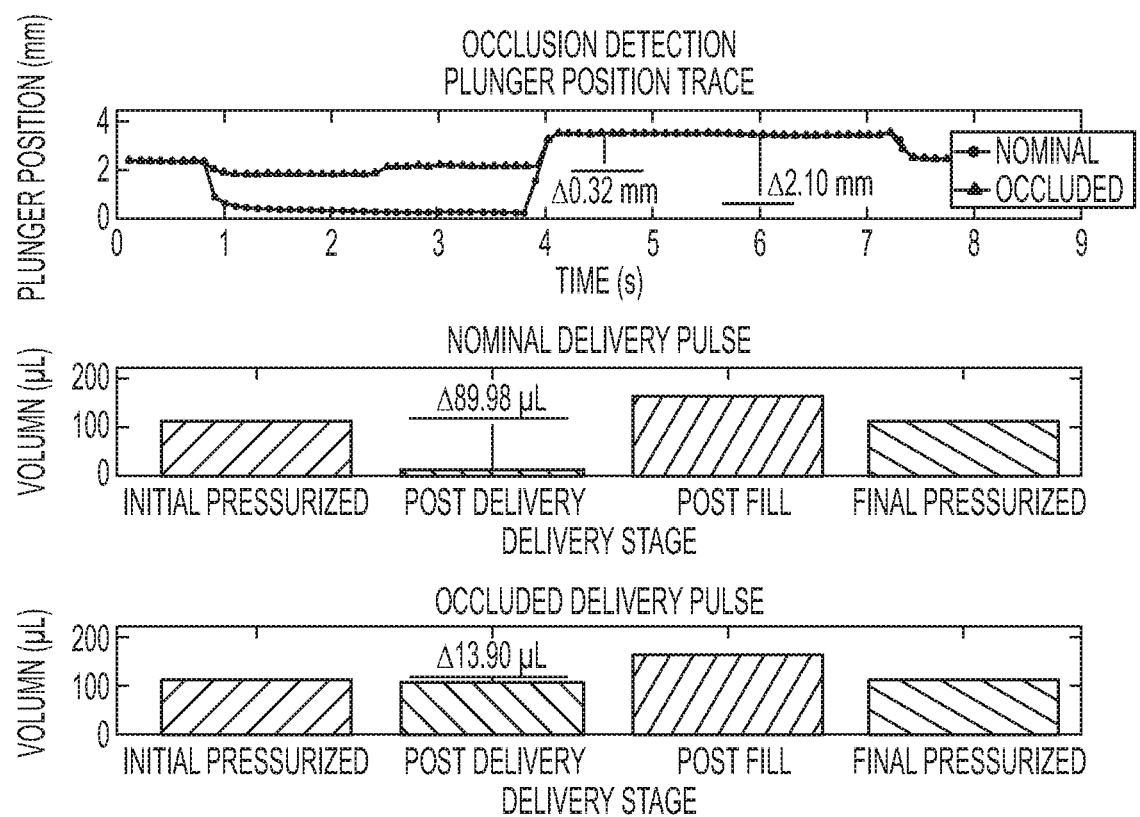
Figure 171:
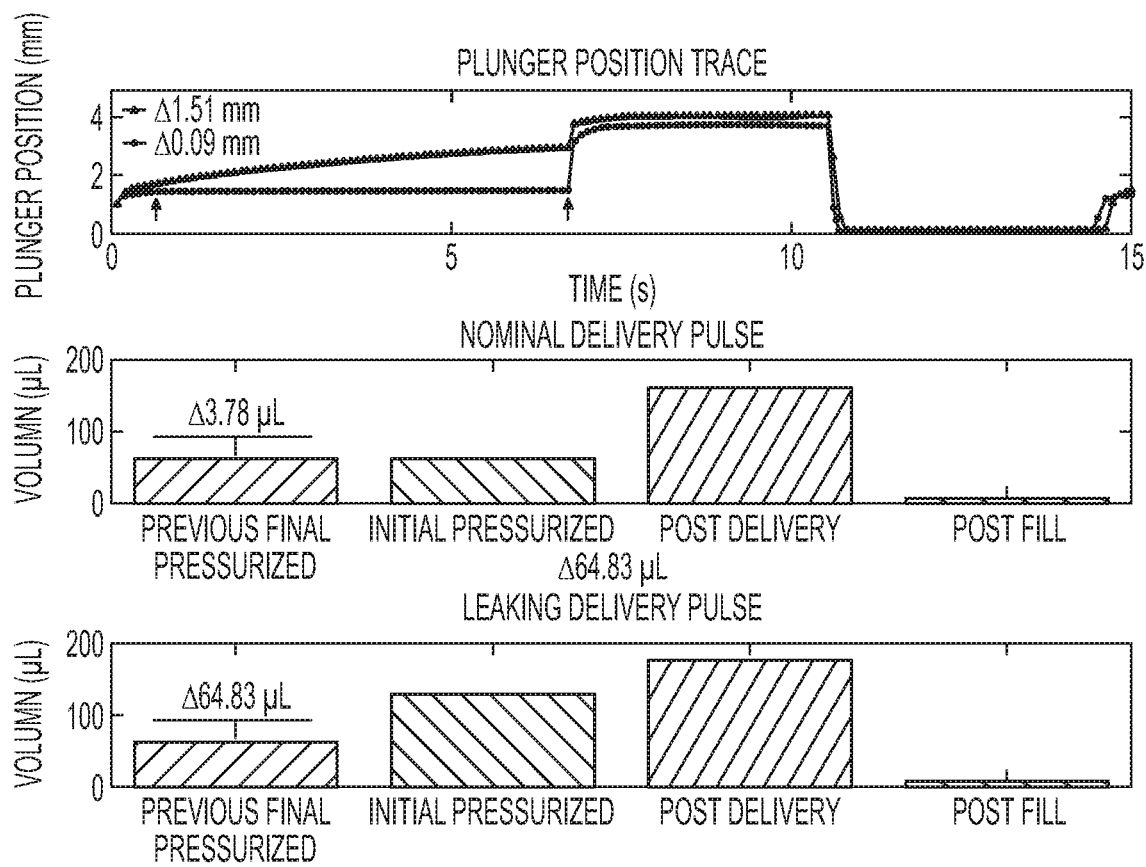
Figure 172:
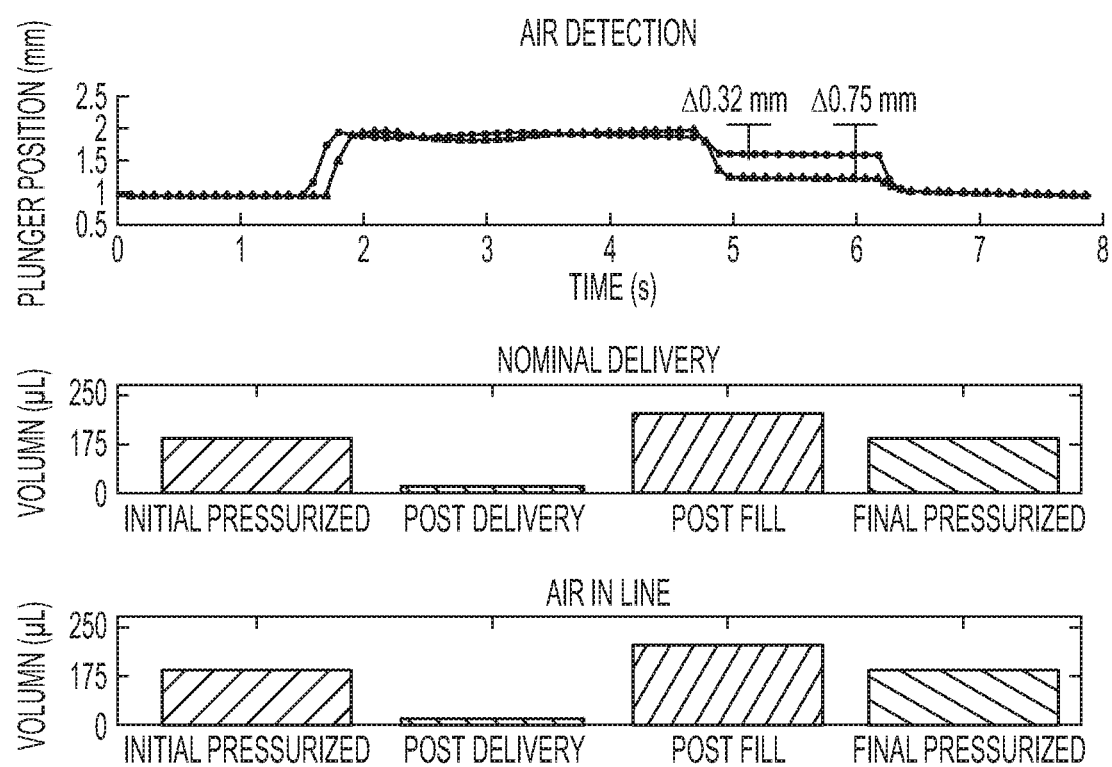
Figure 173:
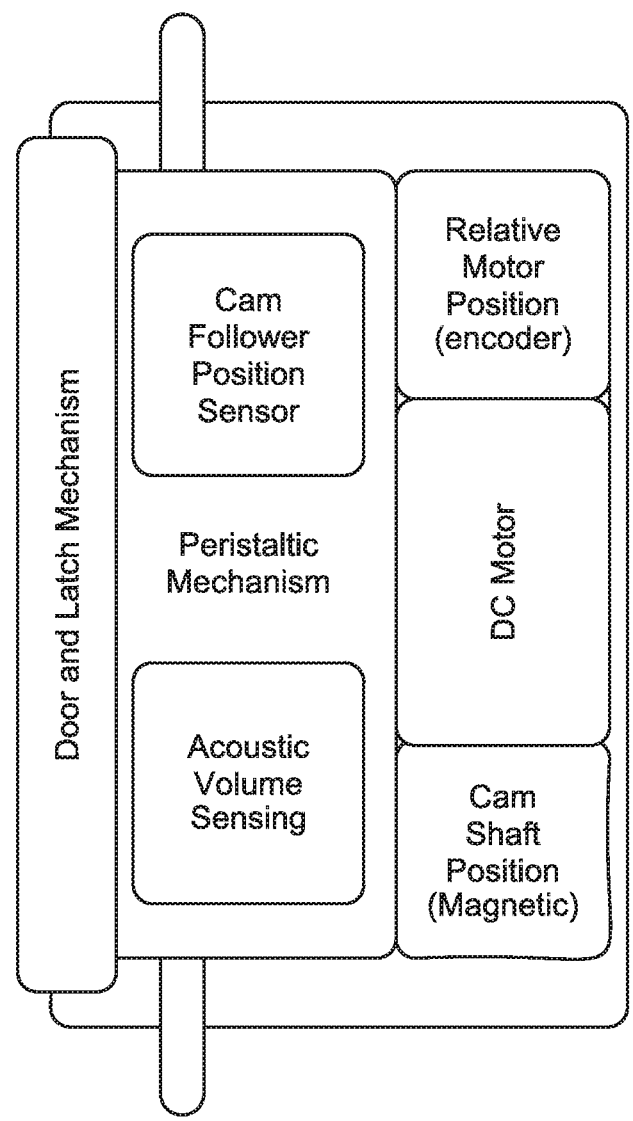
Figure 174:
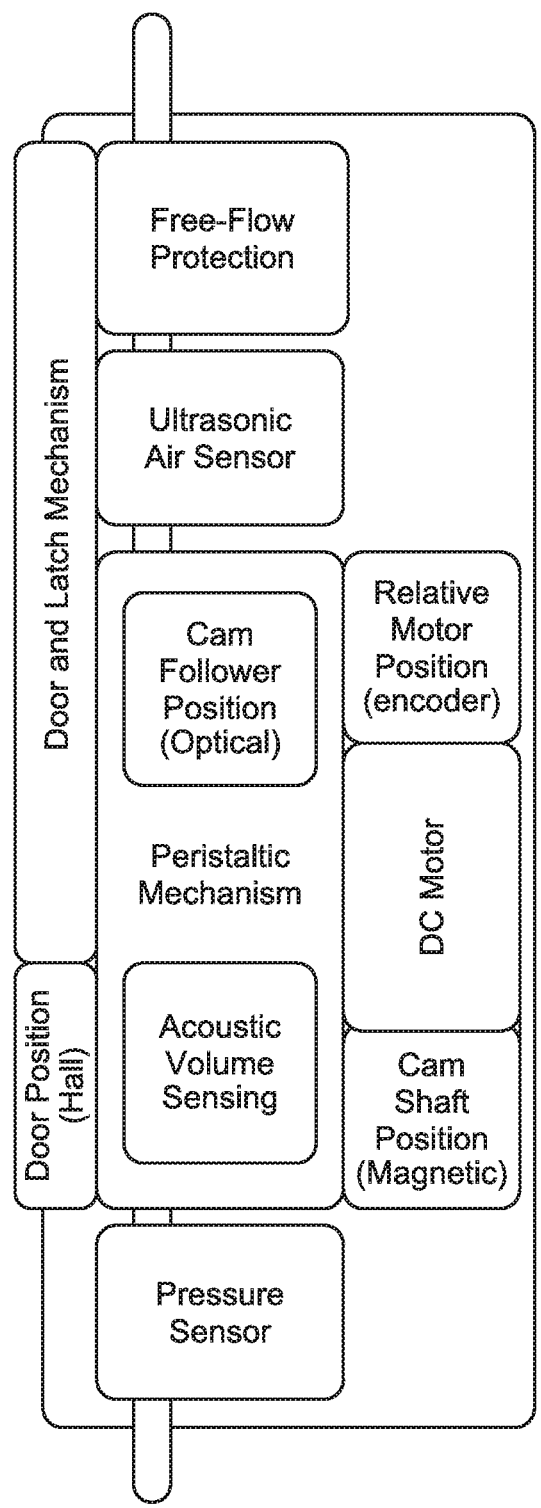
Figure 175:
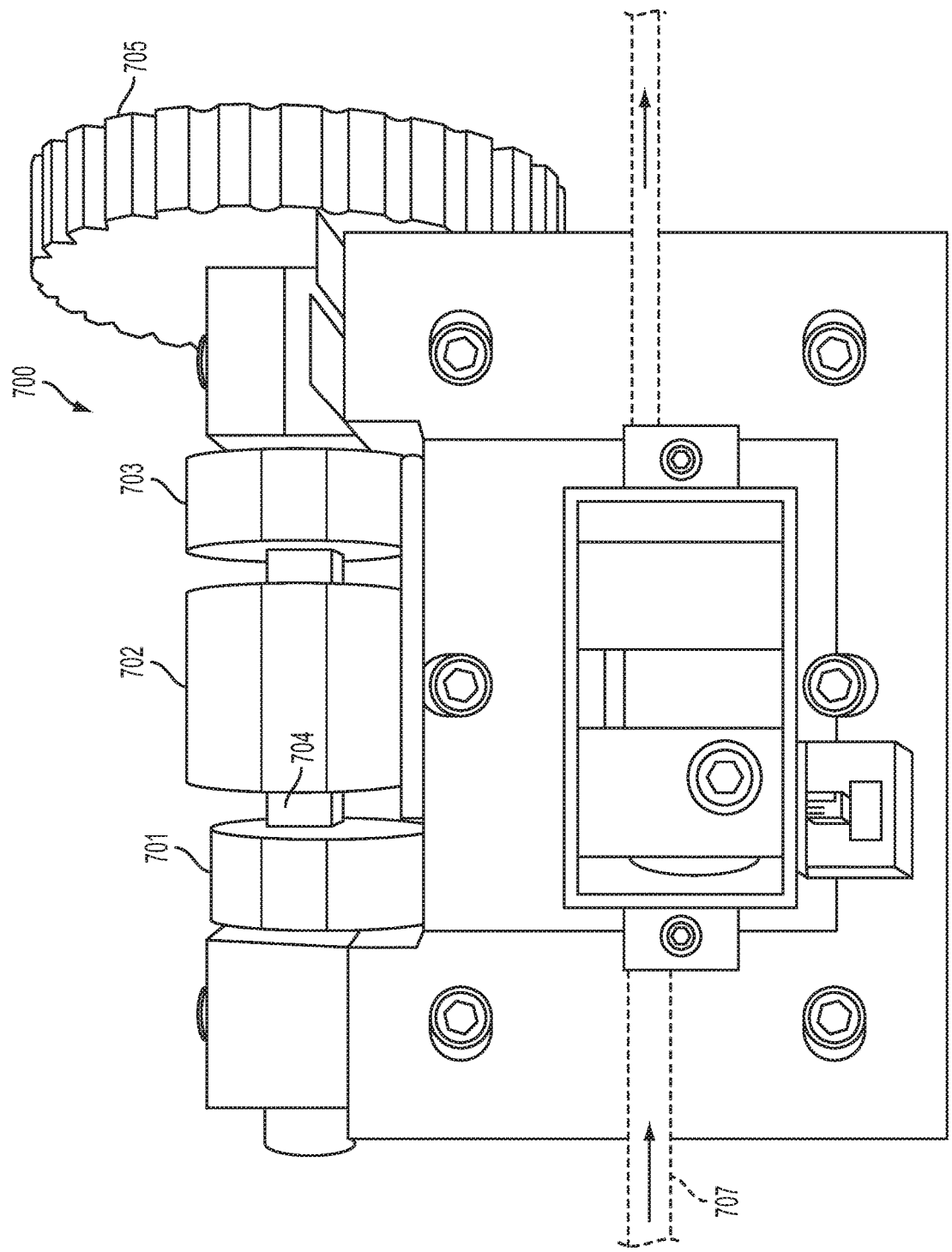
Figure 181:
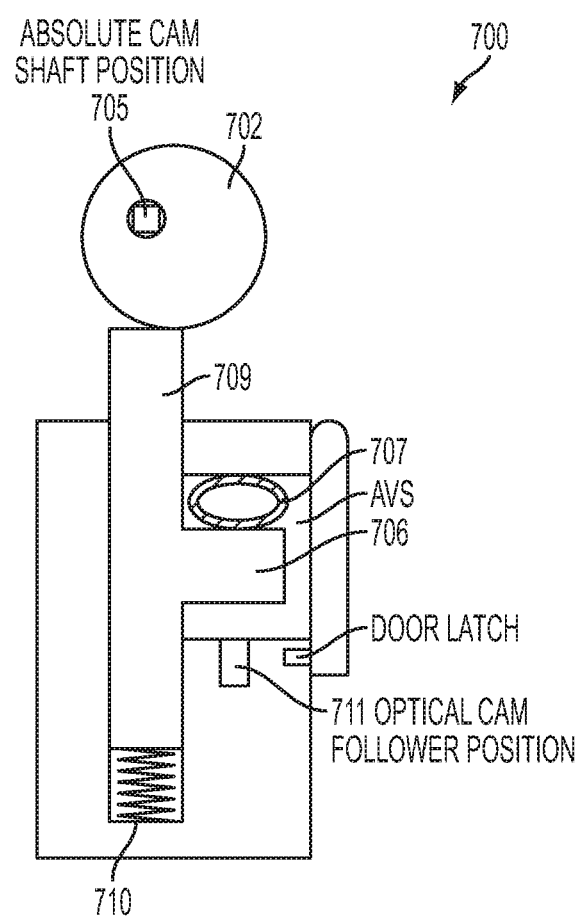
Figure 182C:
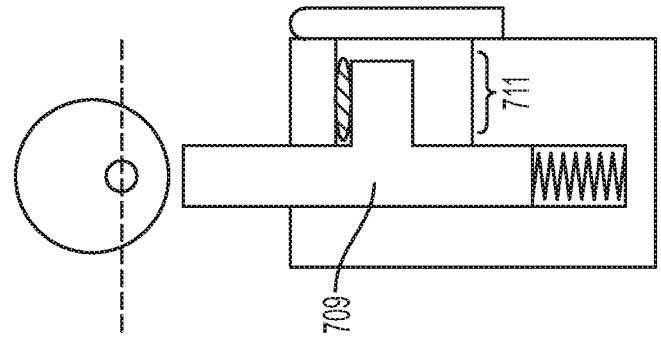
Figure 182B:
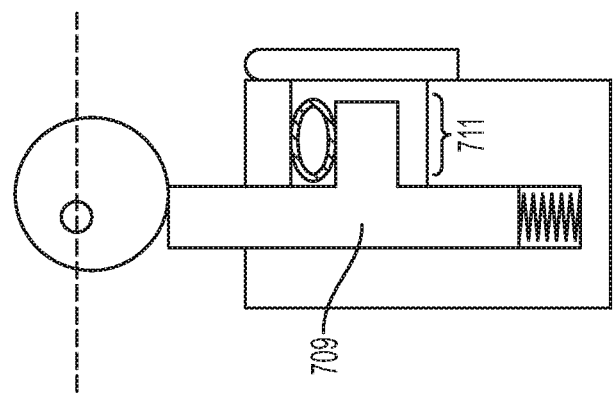
Figure 182A:
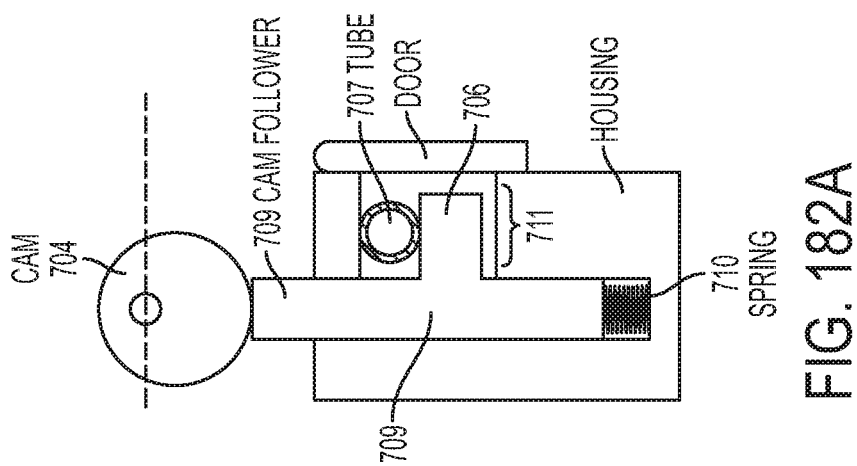
Figure 183C:
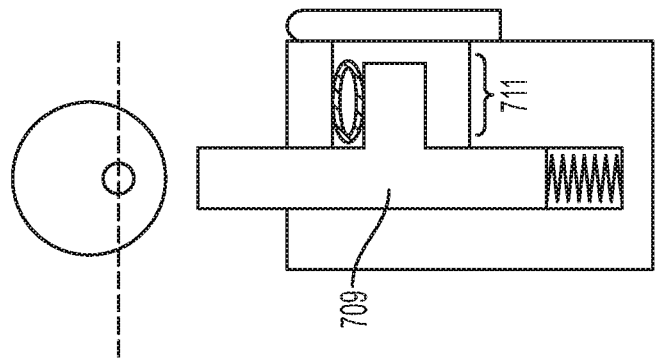
Figure 183B:
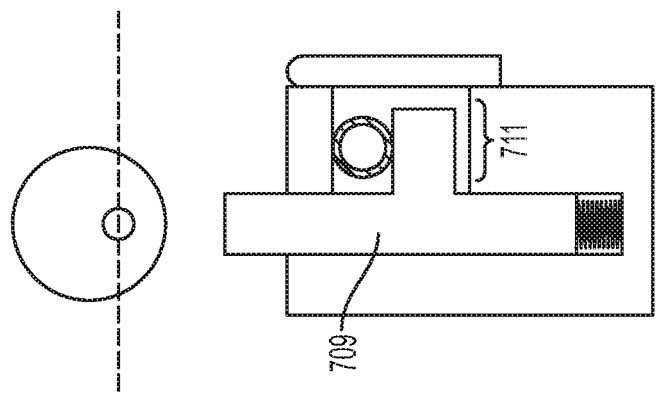
Figure 183A:
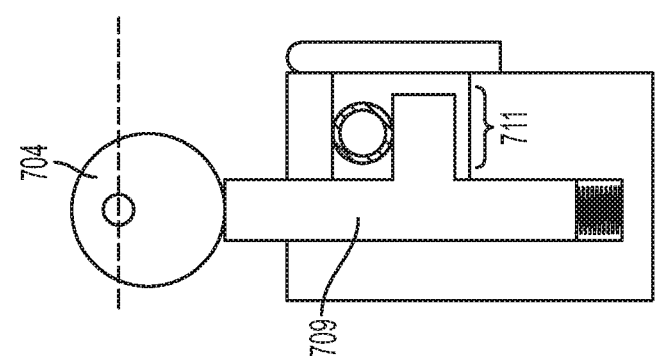
Figure 184:
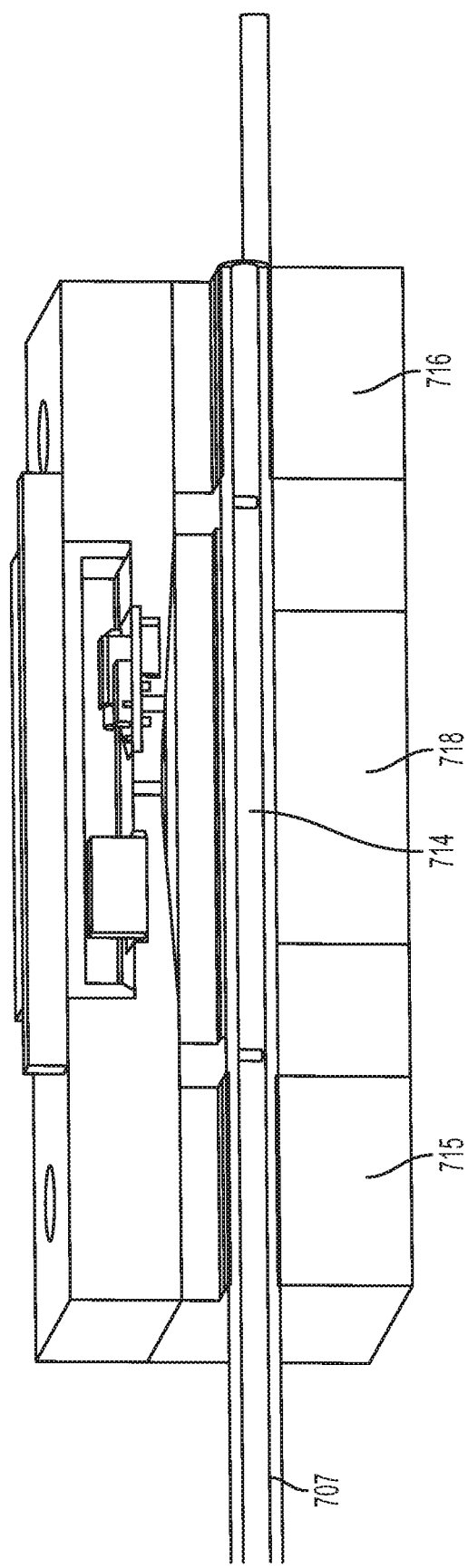
Figure 185:
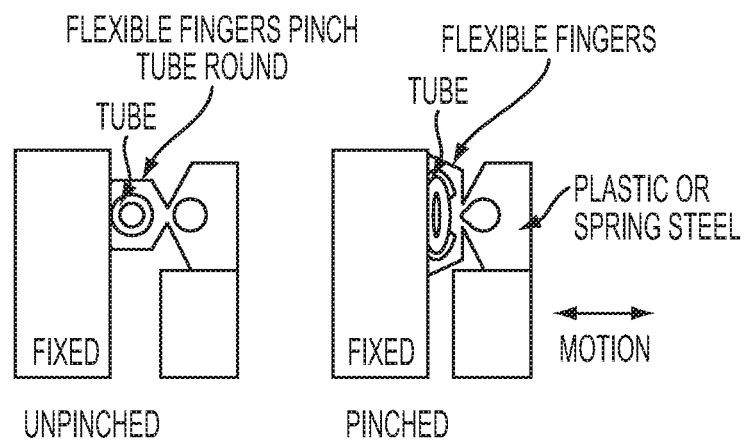
Figure 186:
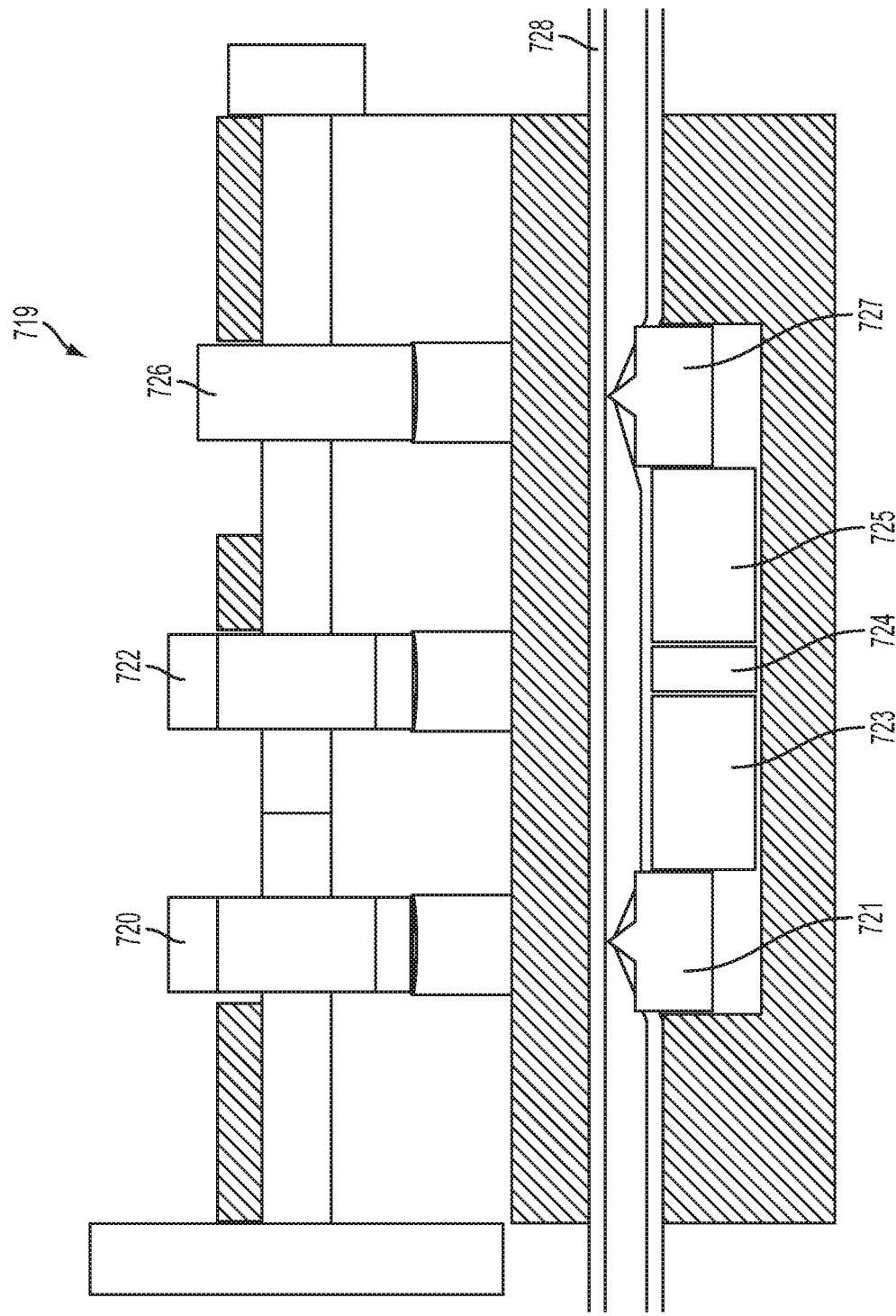
Figure 187:
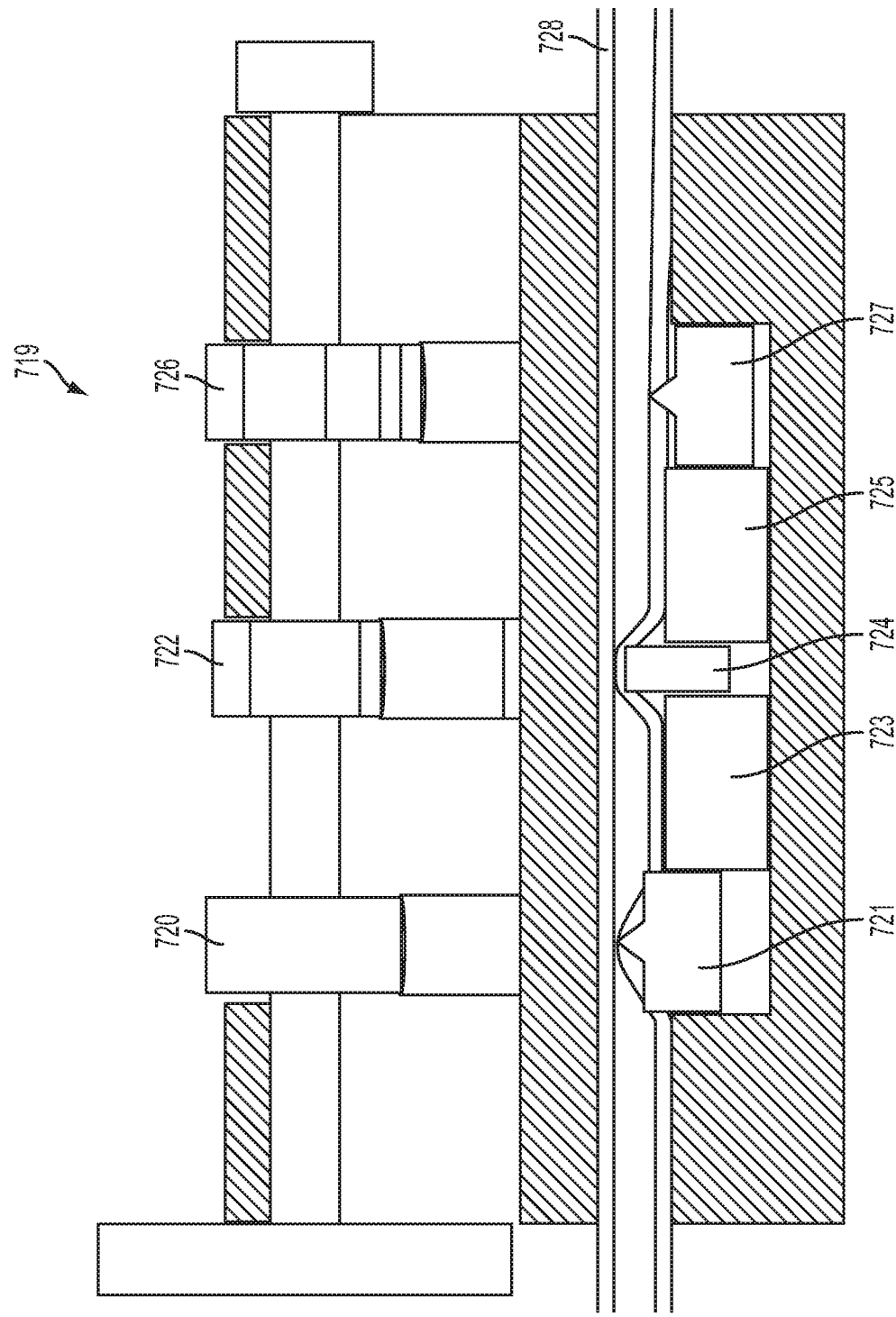
Figure 196A:
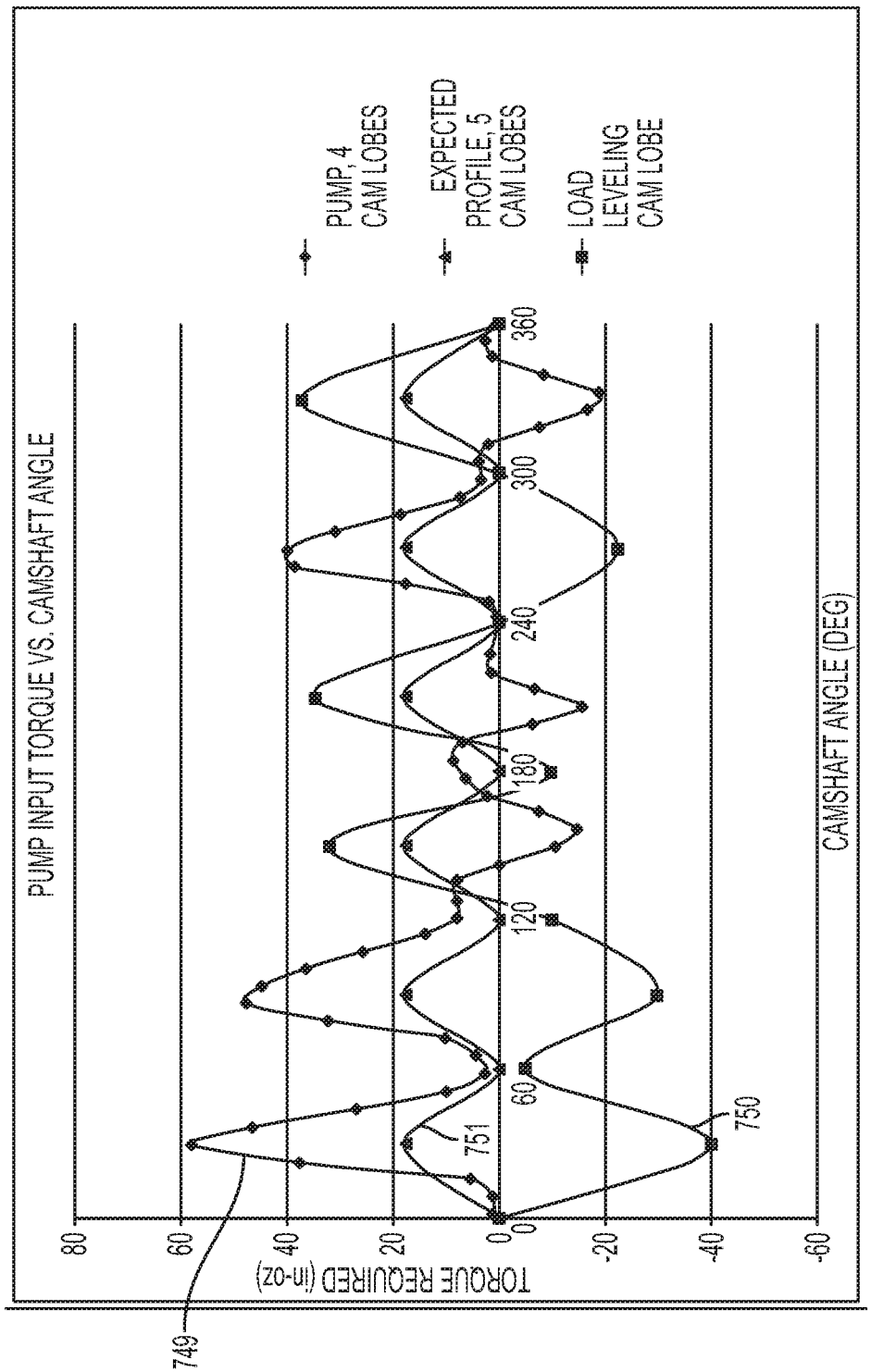
Figure 196B:
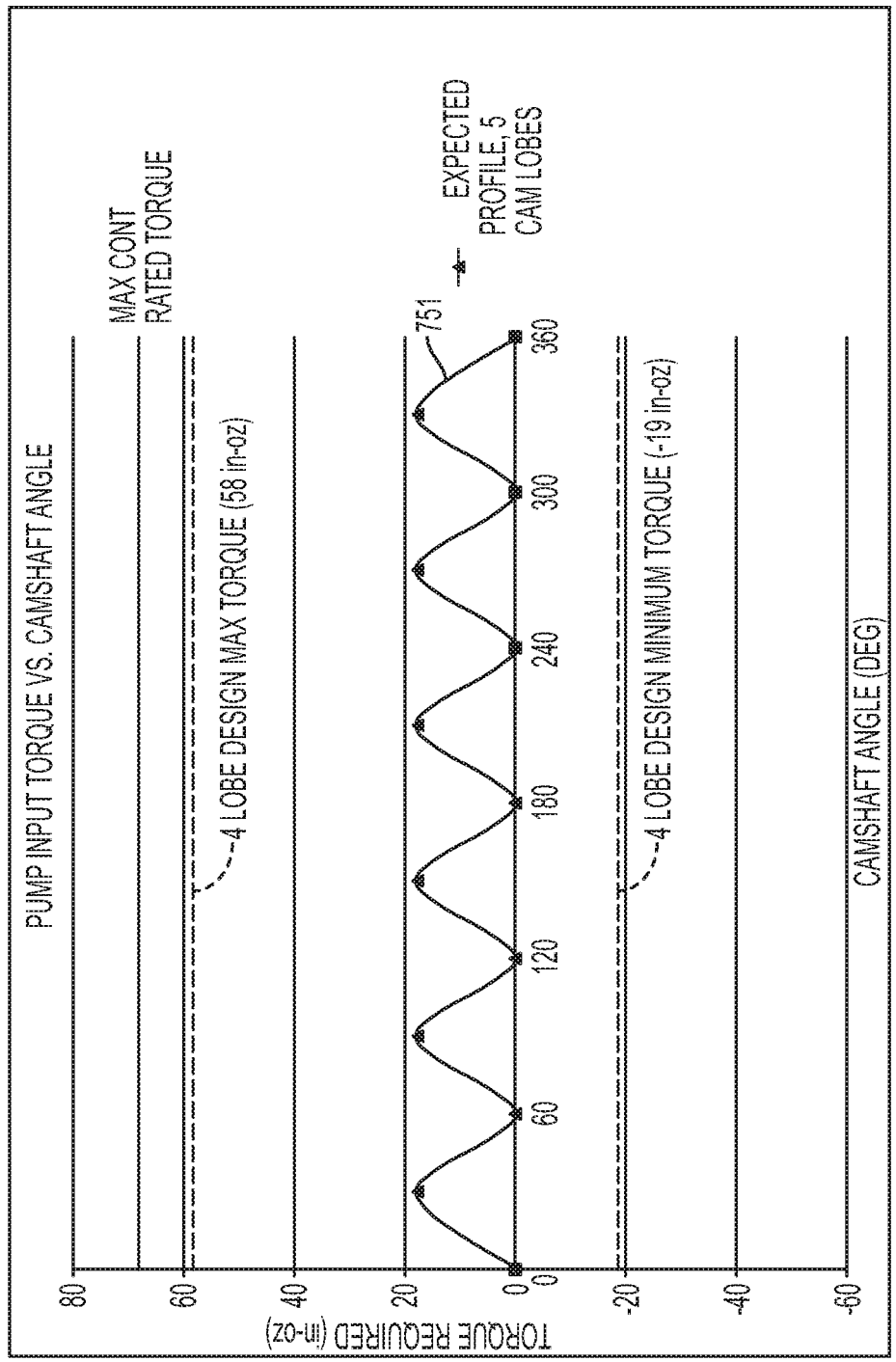
Figure 197:
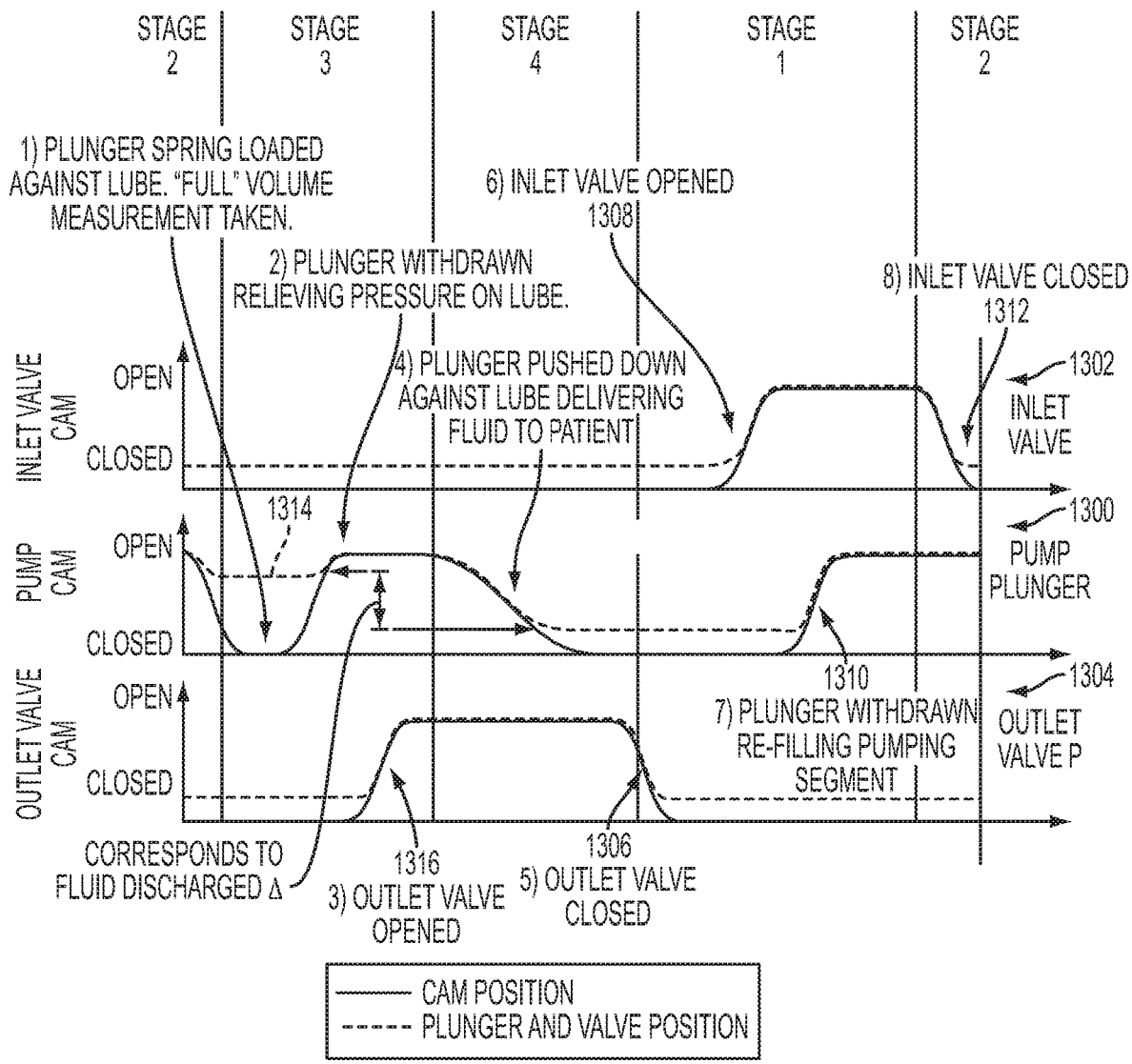
Figure 198:
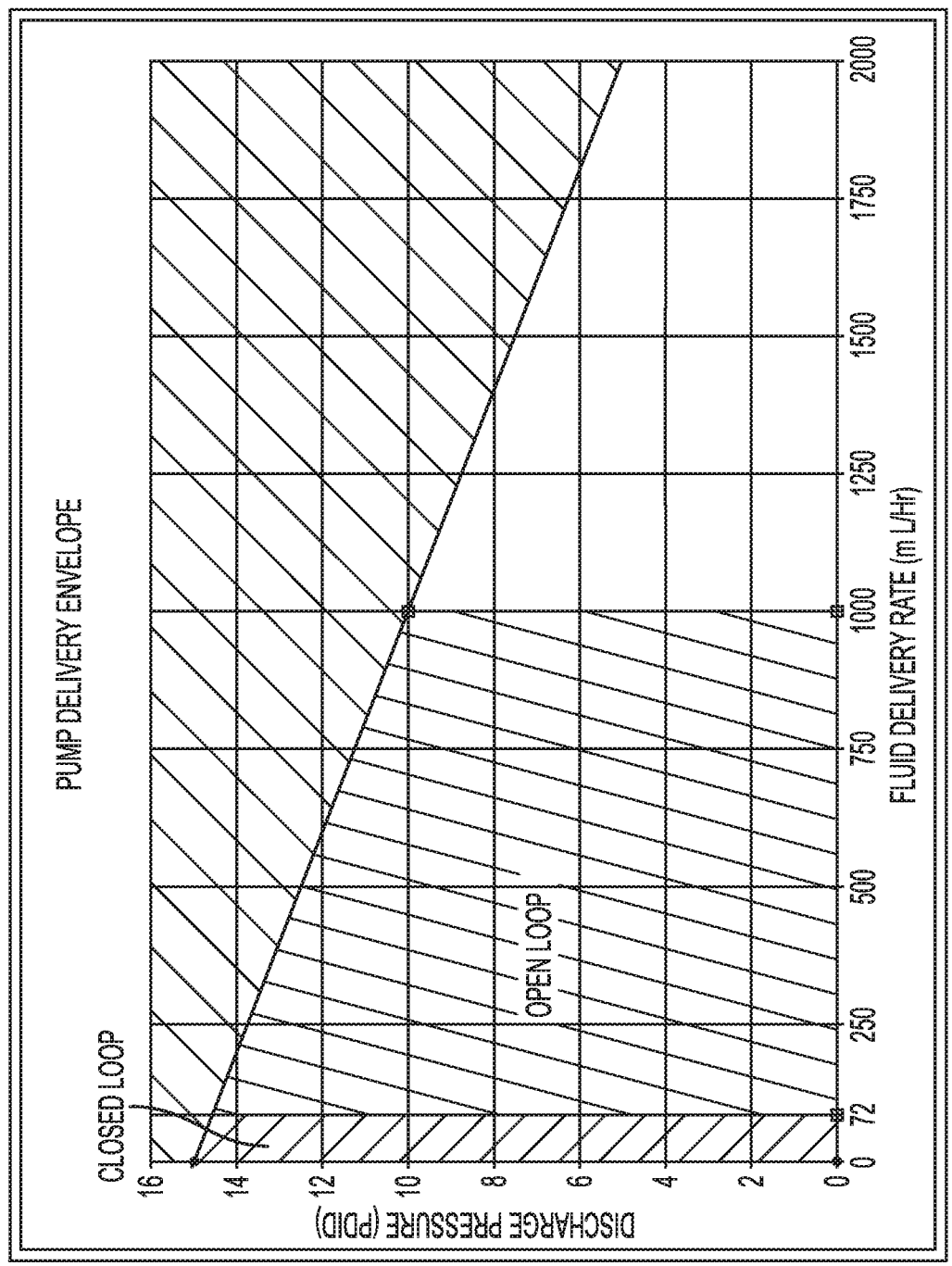
Figure 199:
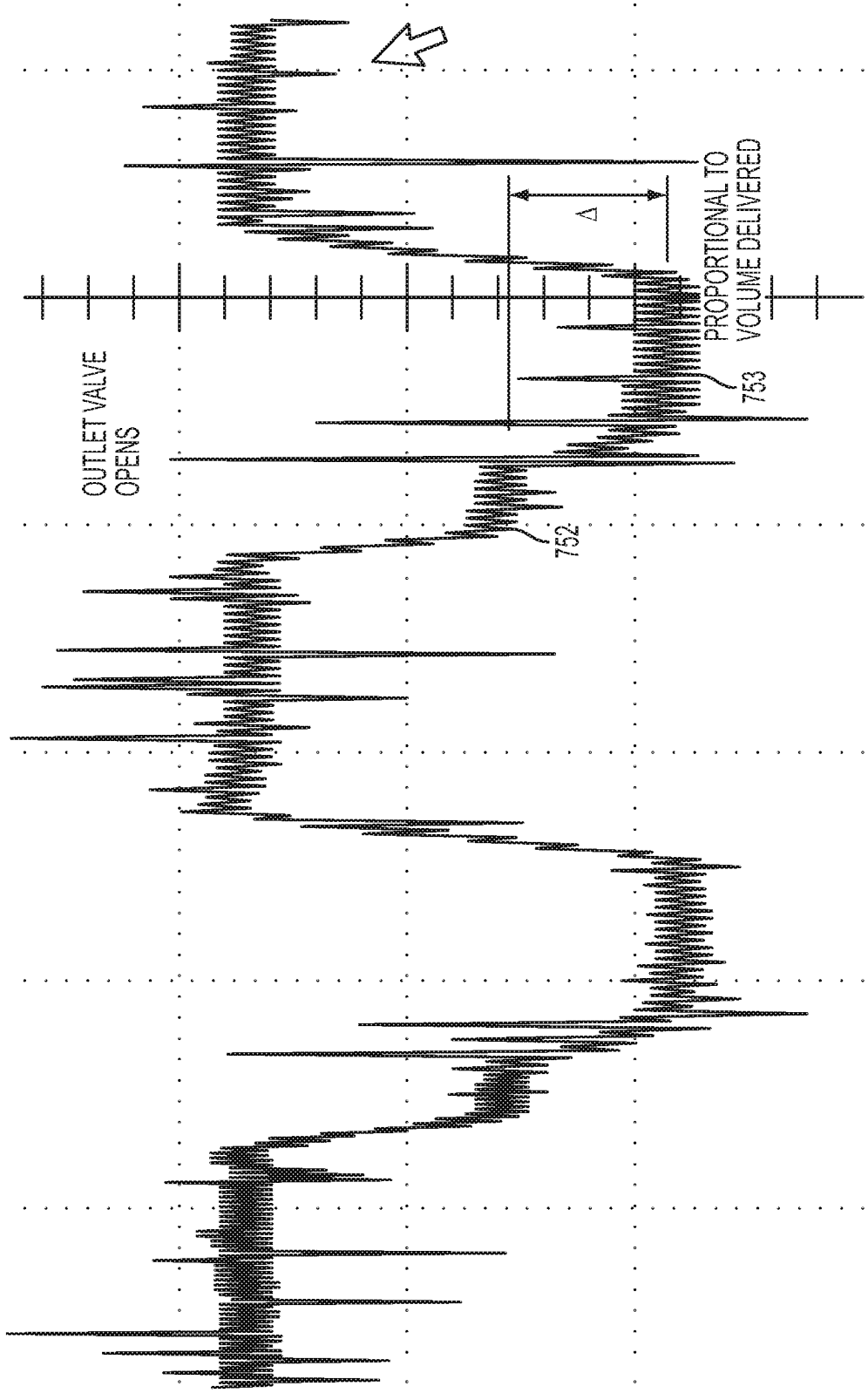
Figures 200, 201:
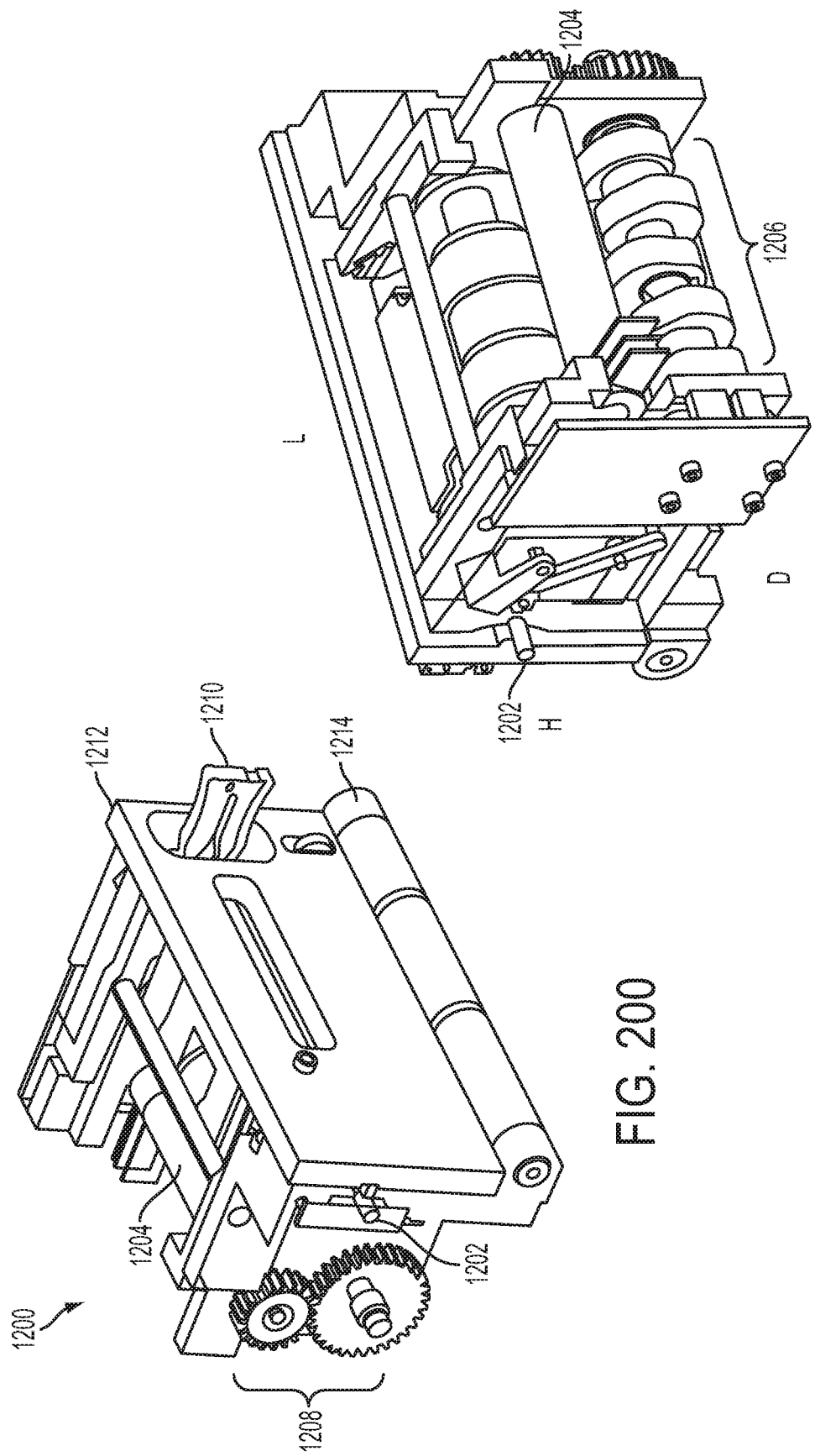
Figure 202:
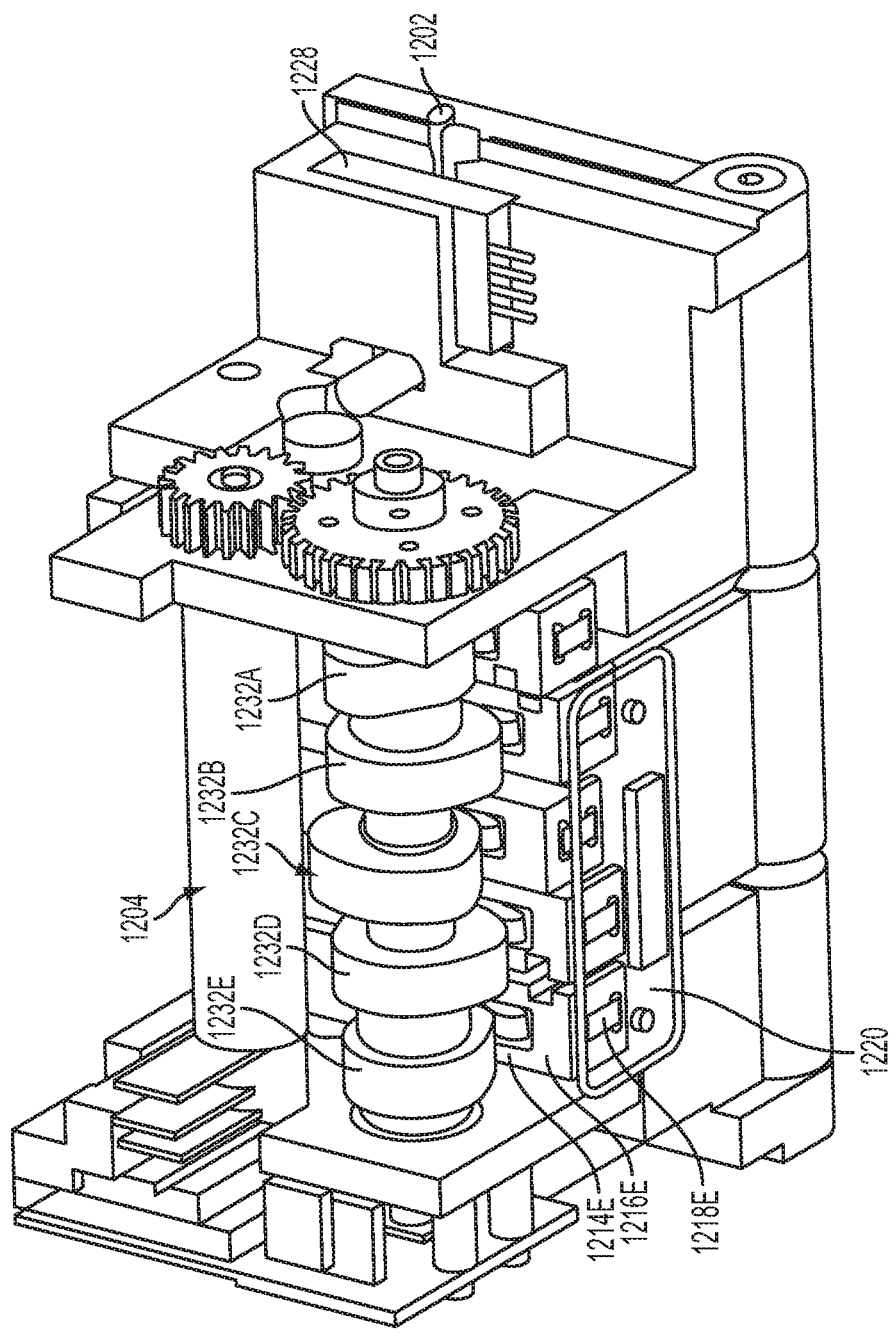
Figure 203:
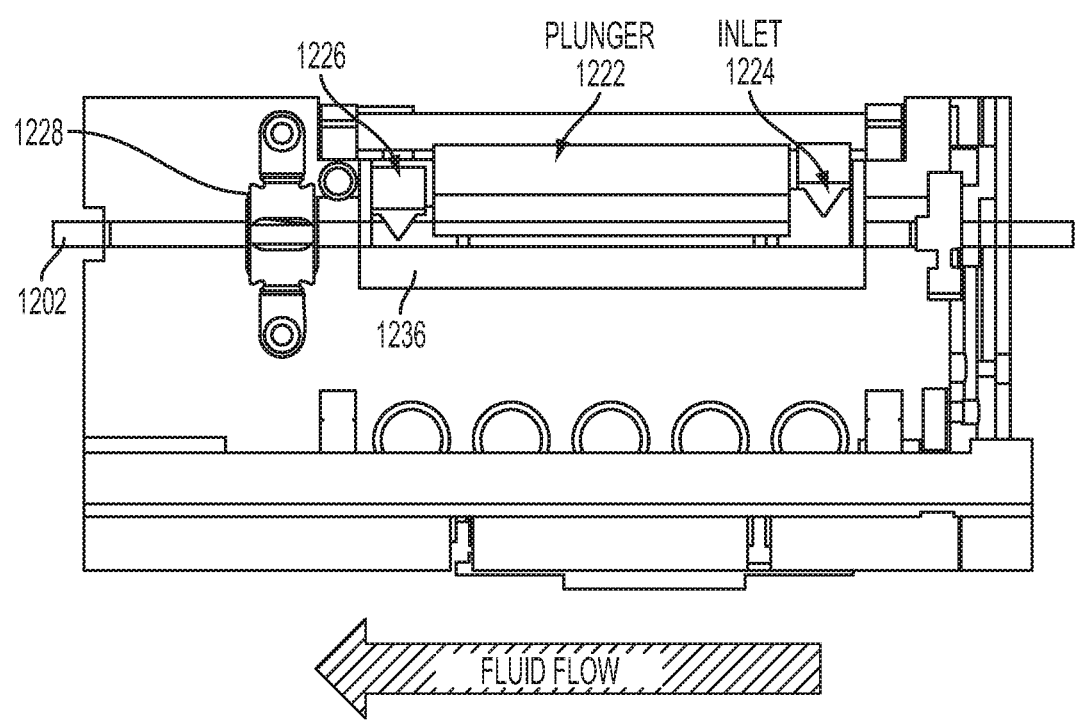
Figure 204:
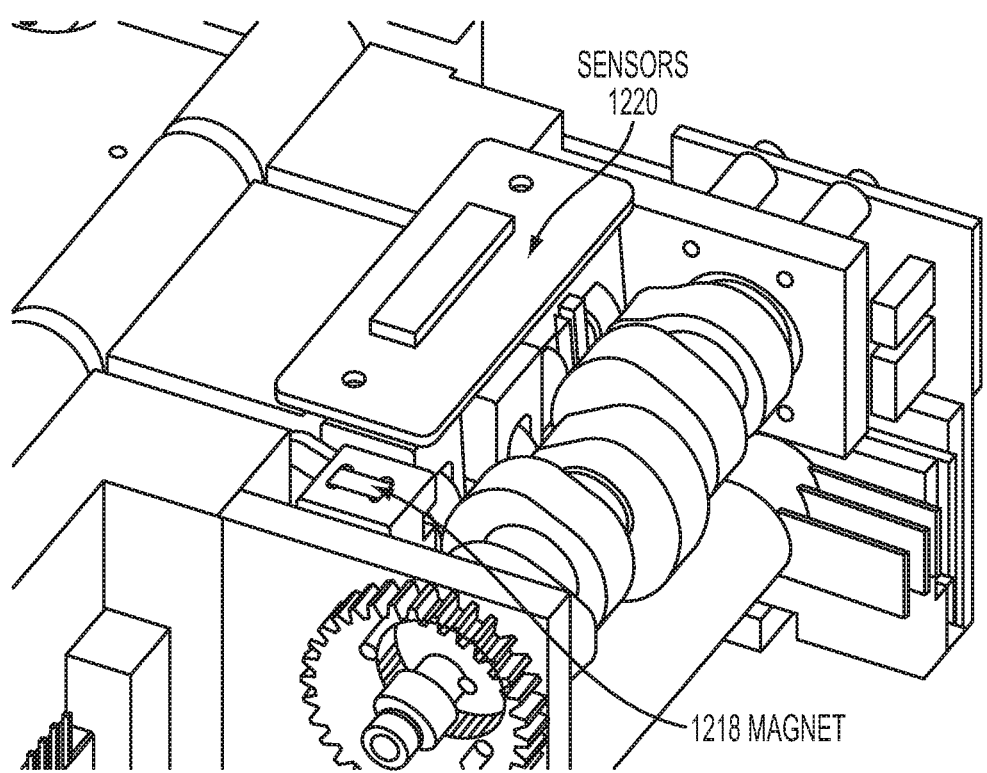
Figure 206:
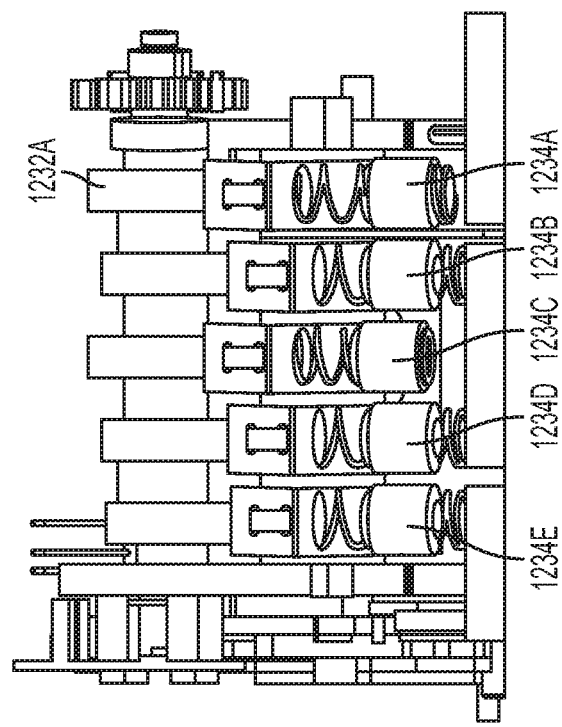
Figure 205:
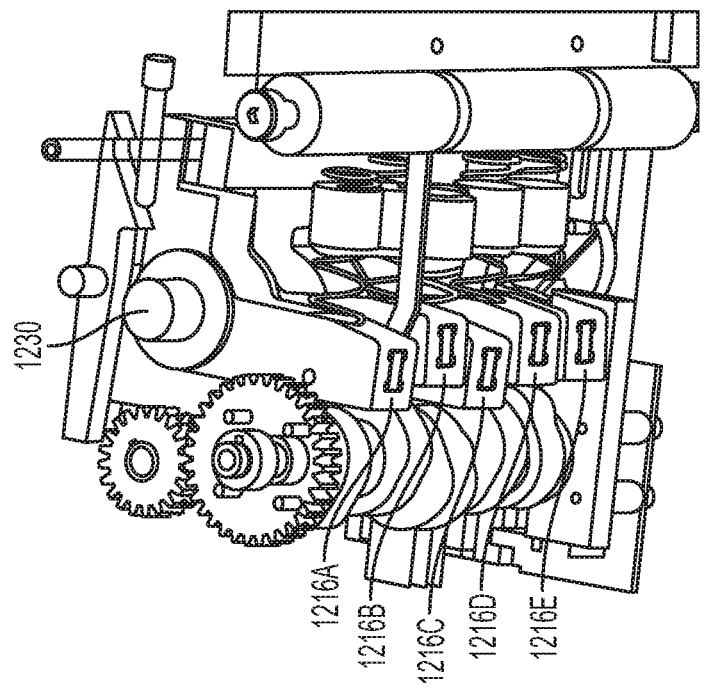
Figure 222:
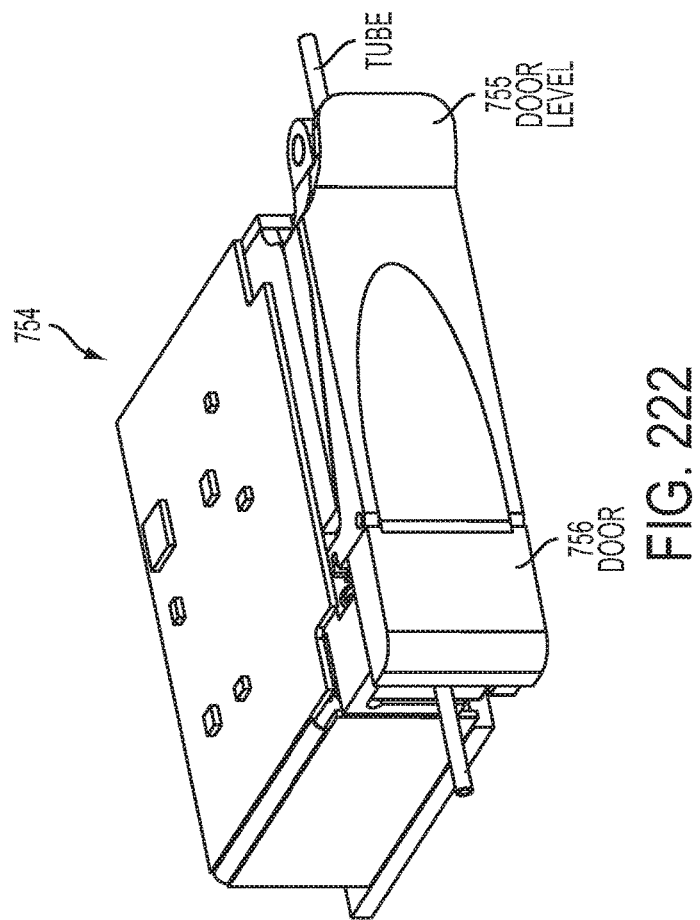
Figure 223:
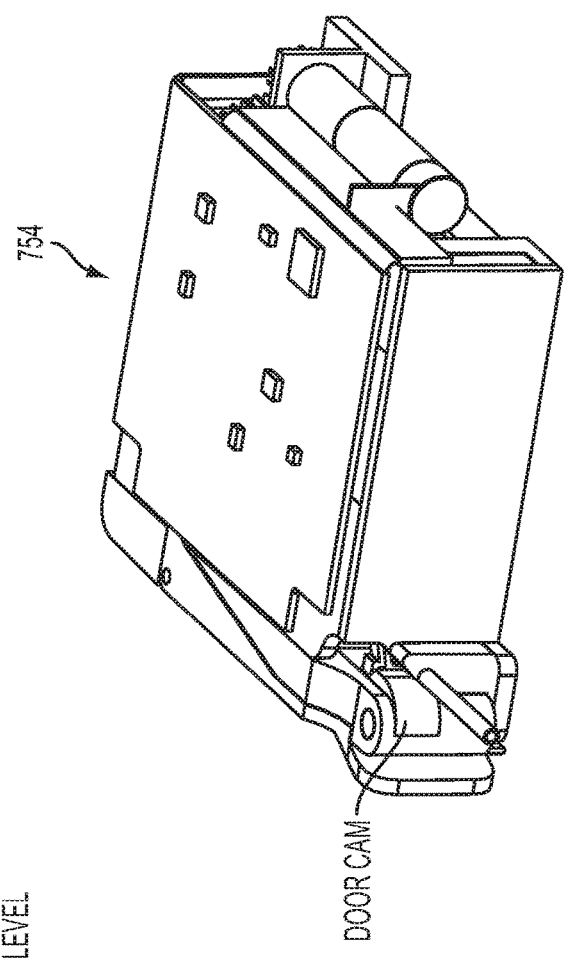
Figure 255:
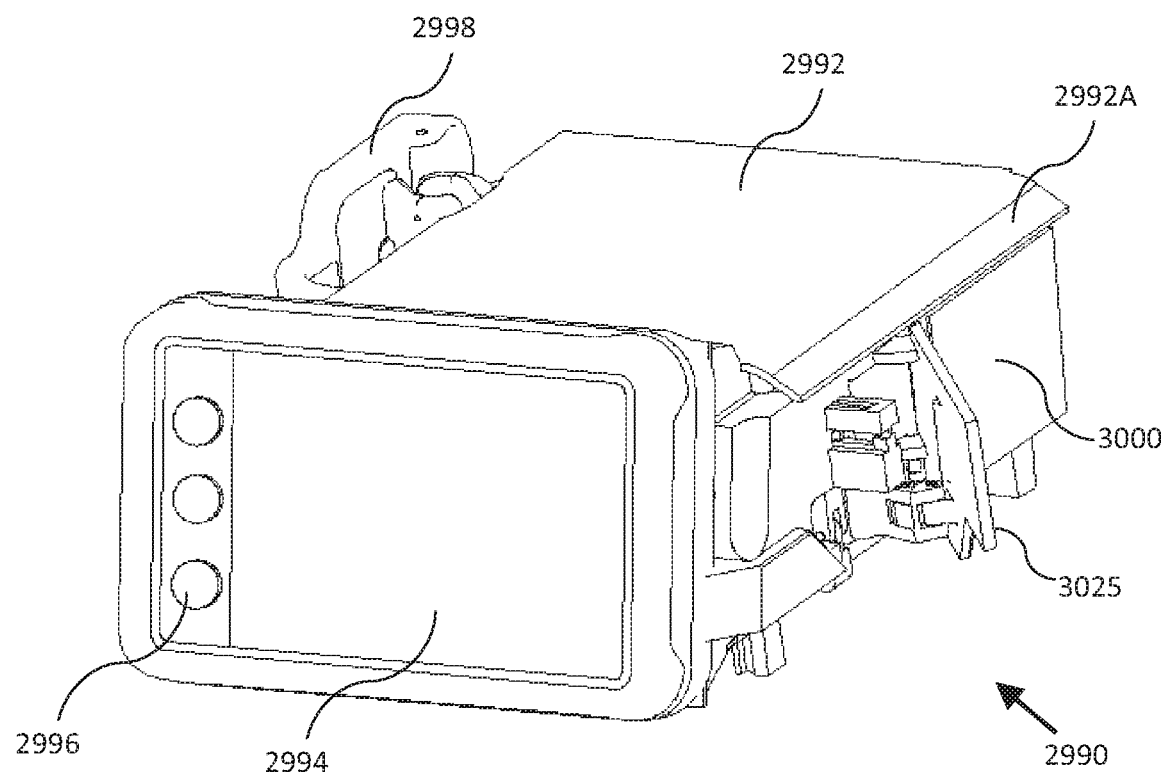
Figure 256A:
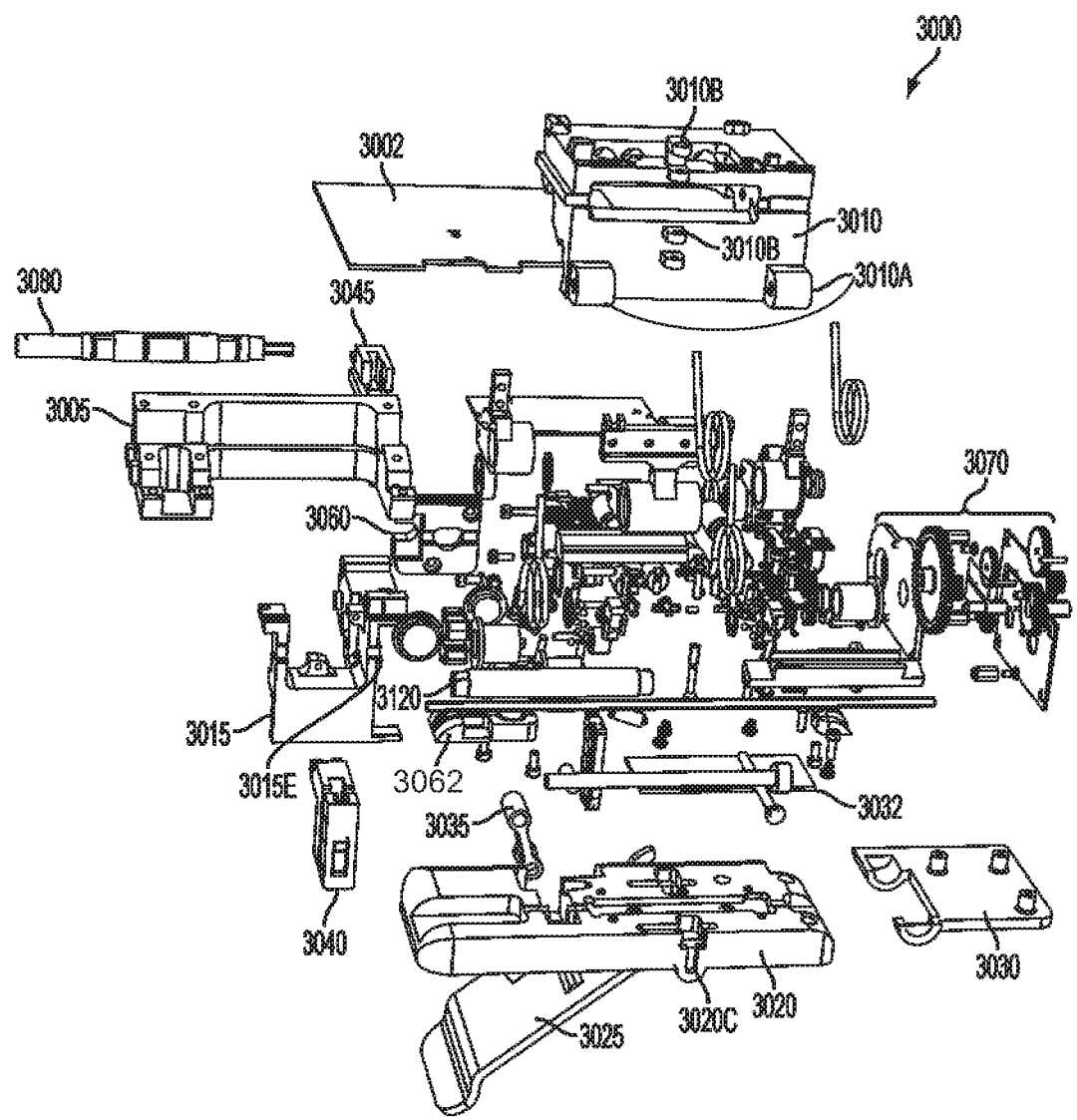
Figure 256B:
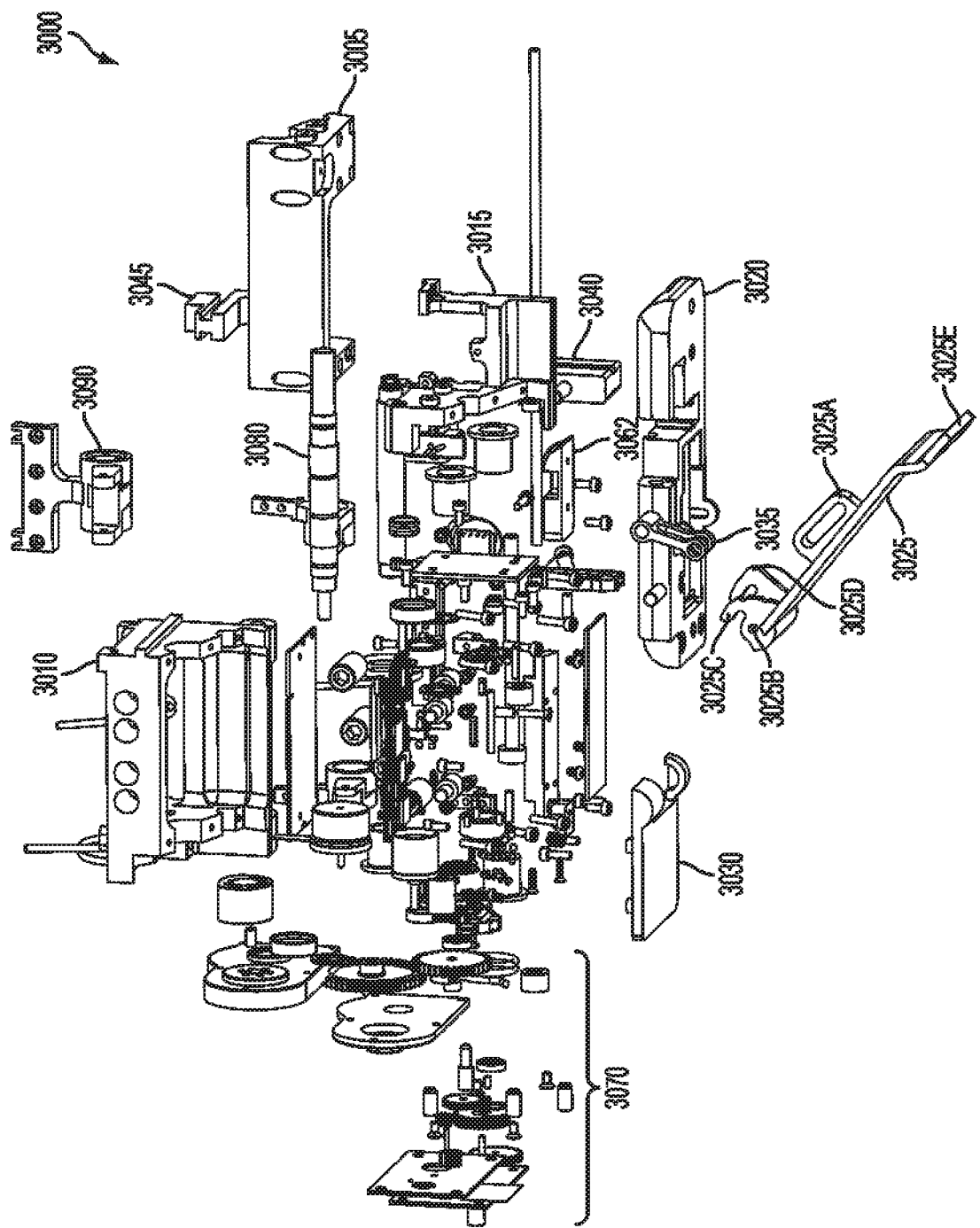
Figure 257:
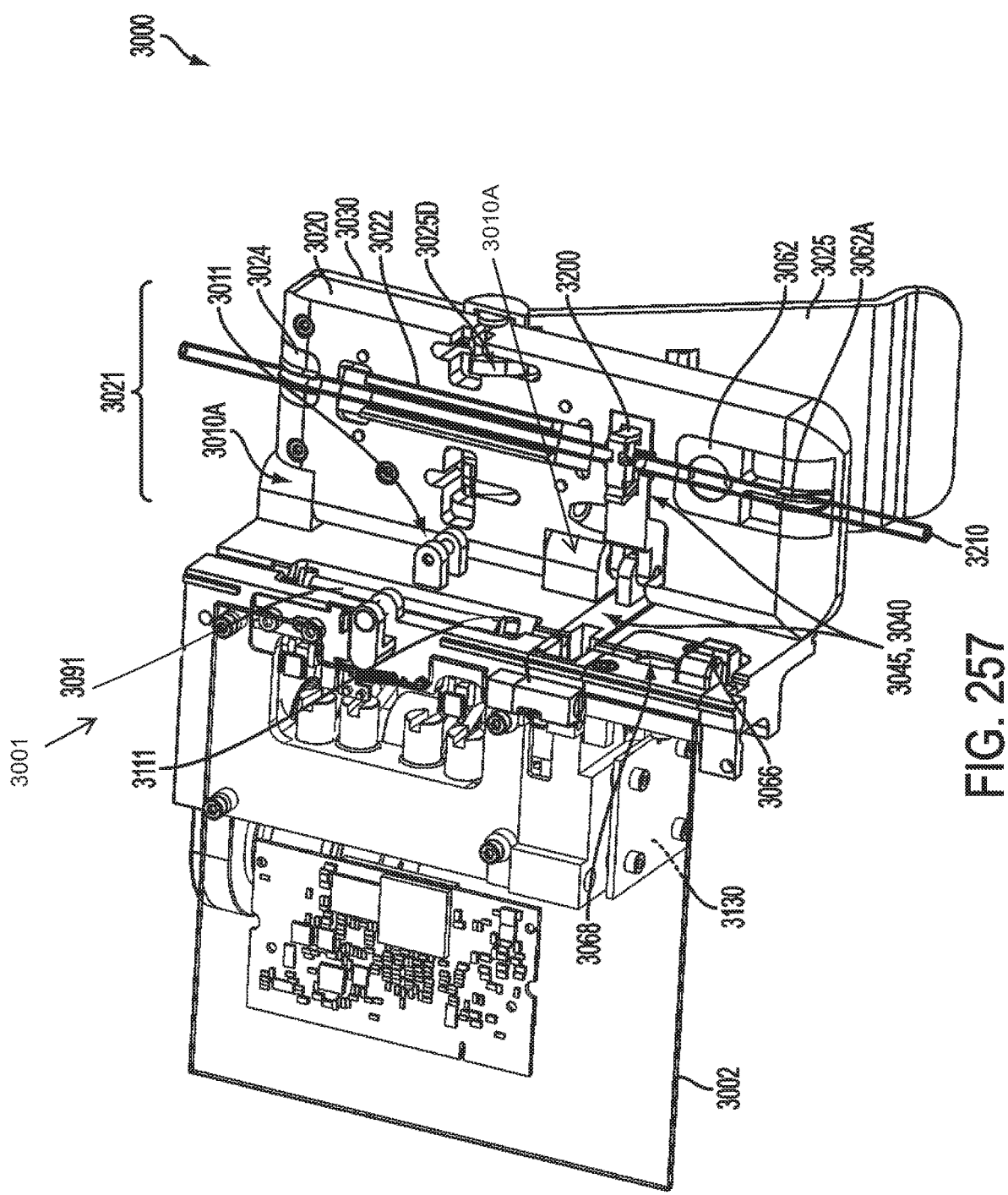
Figure 258:
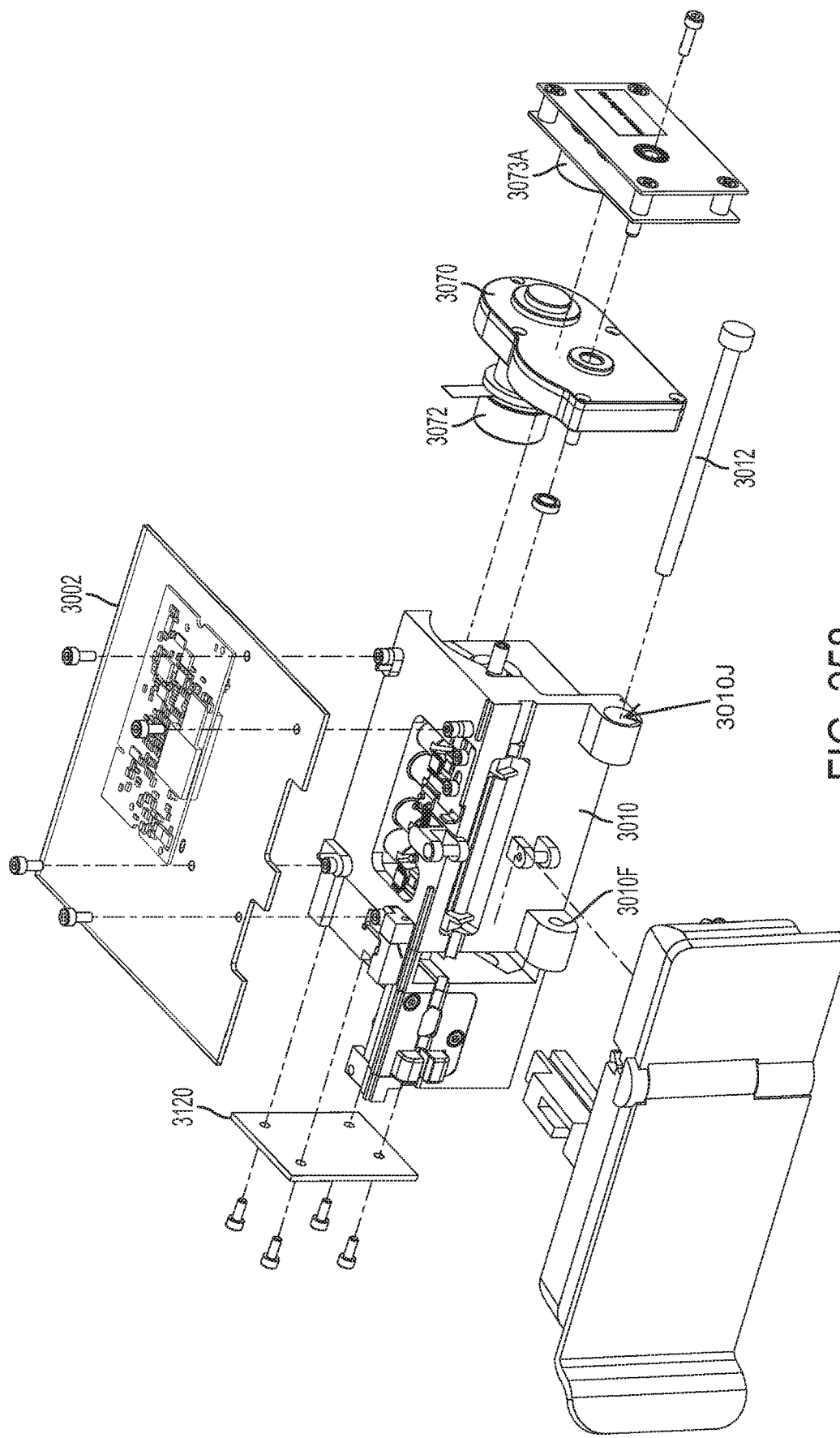
Figure 259:
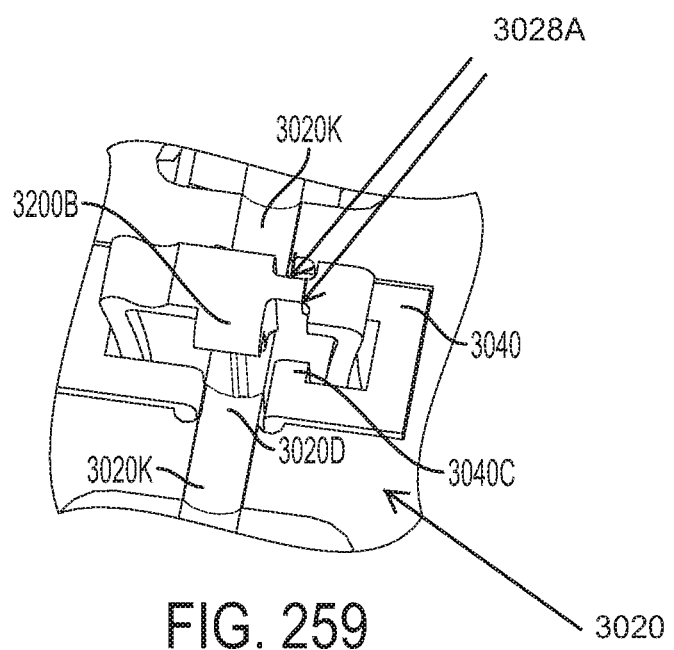
Figure 260:
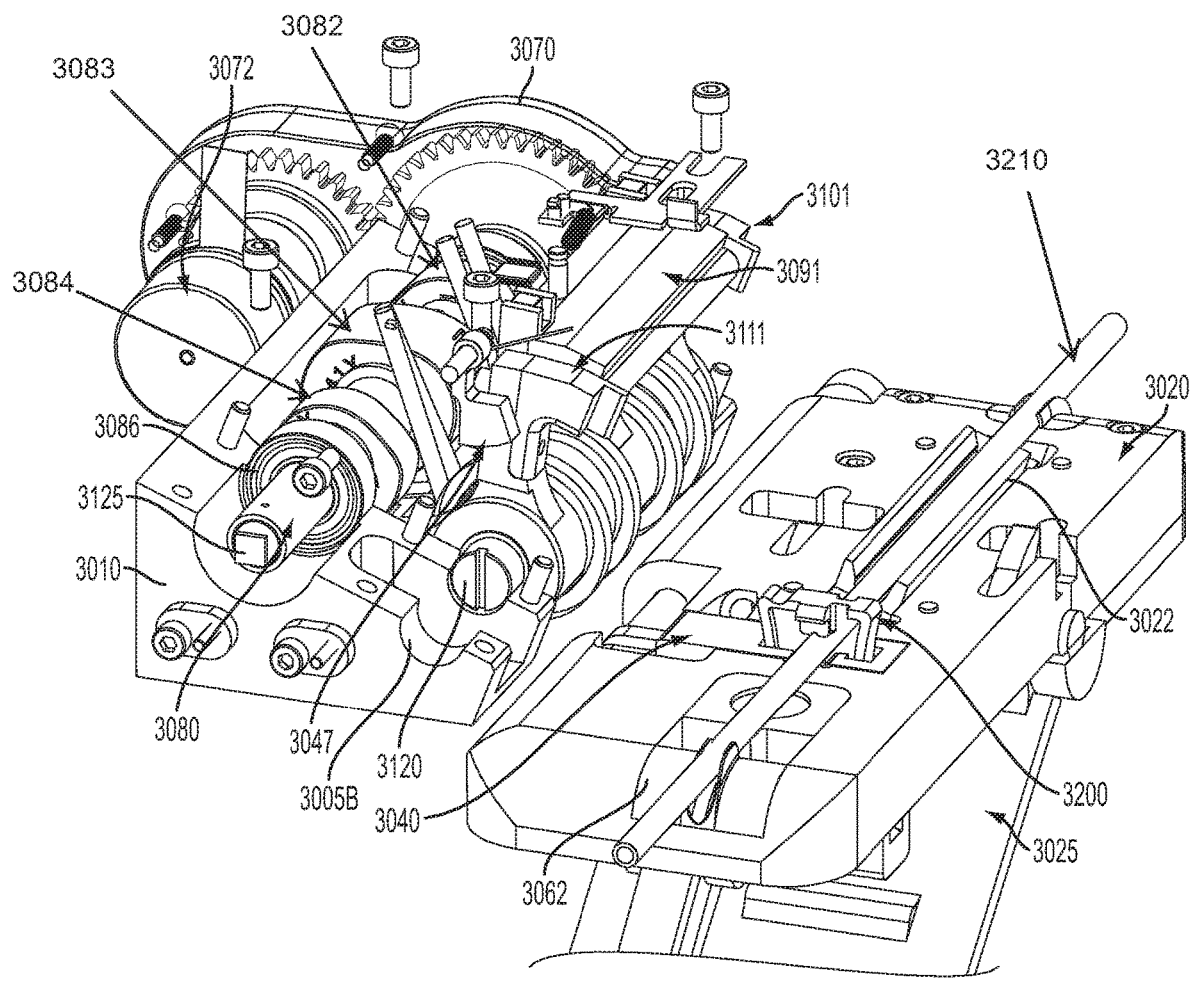
Figure 261:
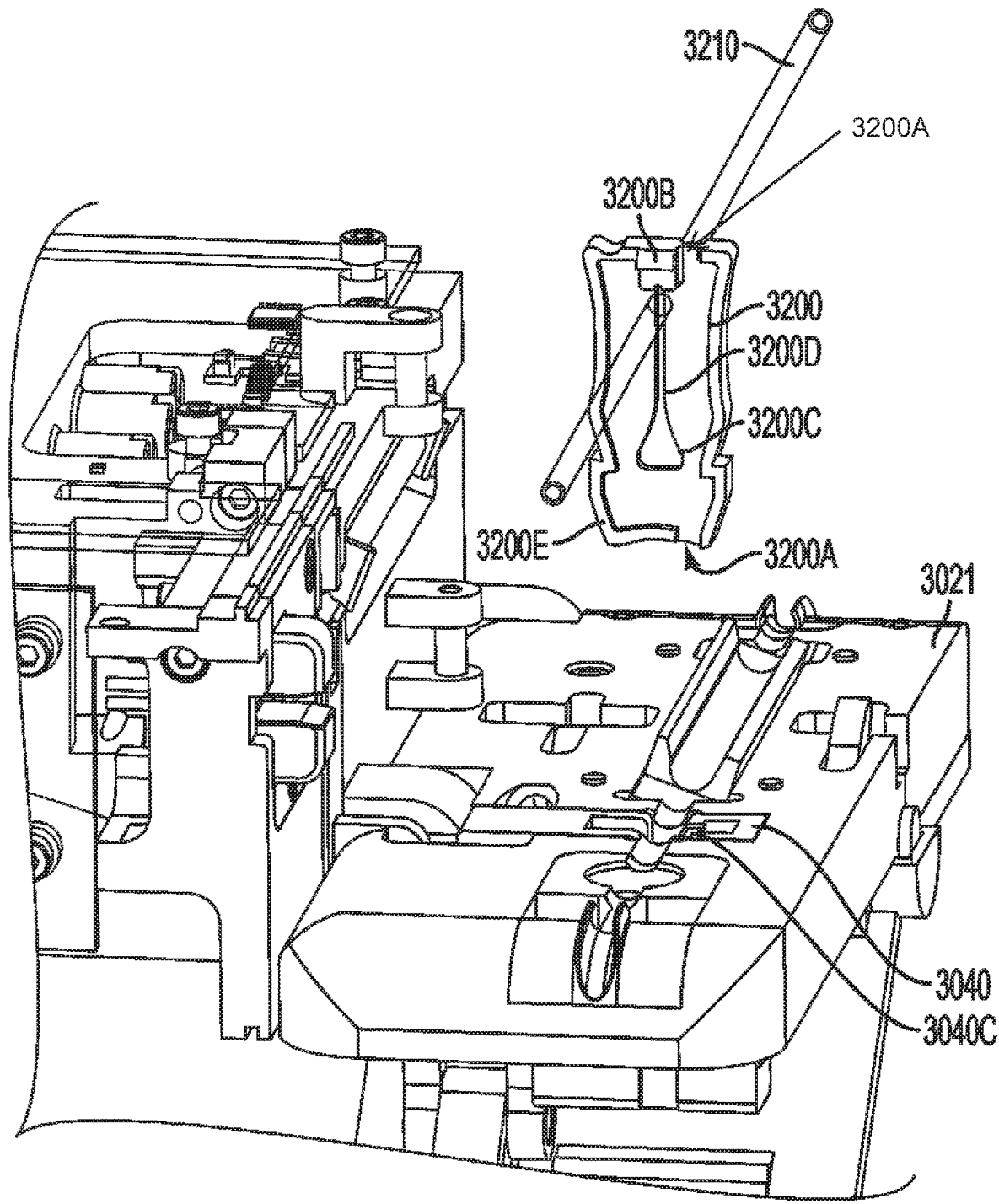
Figure 262:
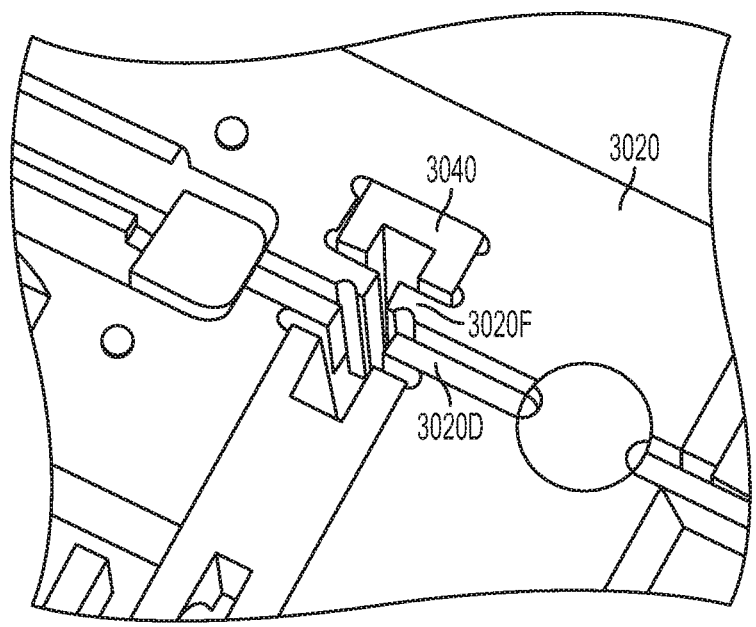
Figure 263:
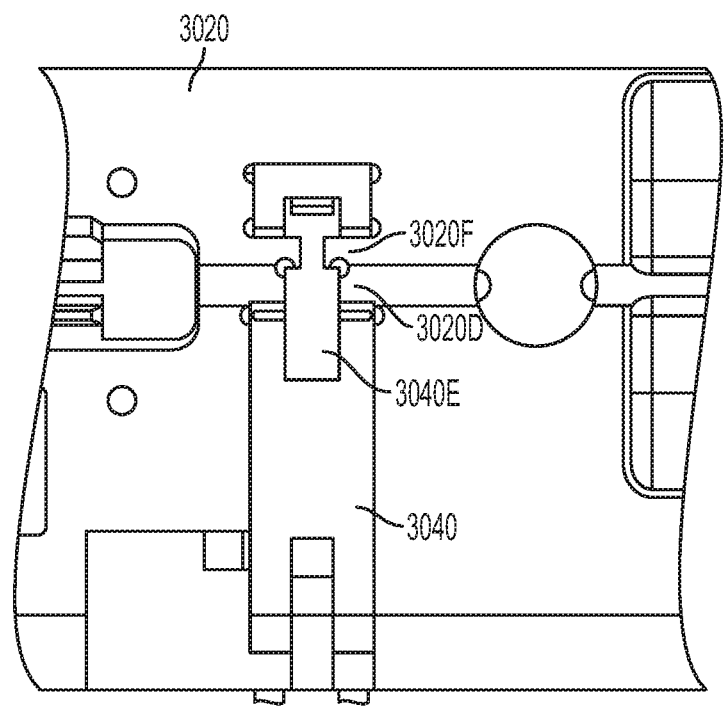
Figure 264:
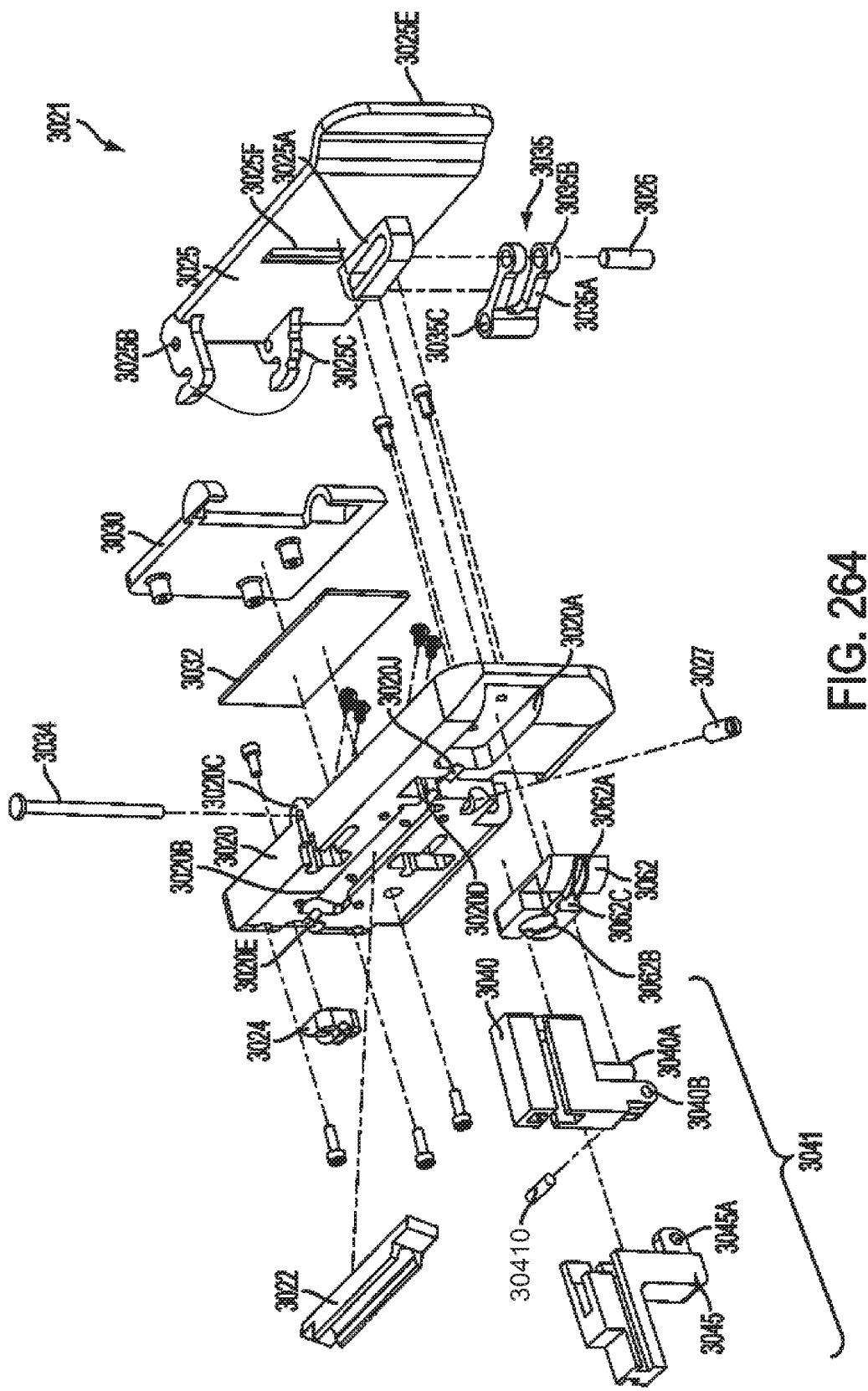
Figure 265:
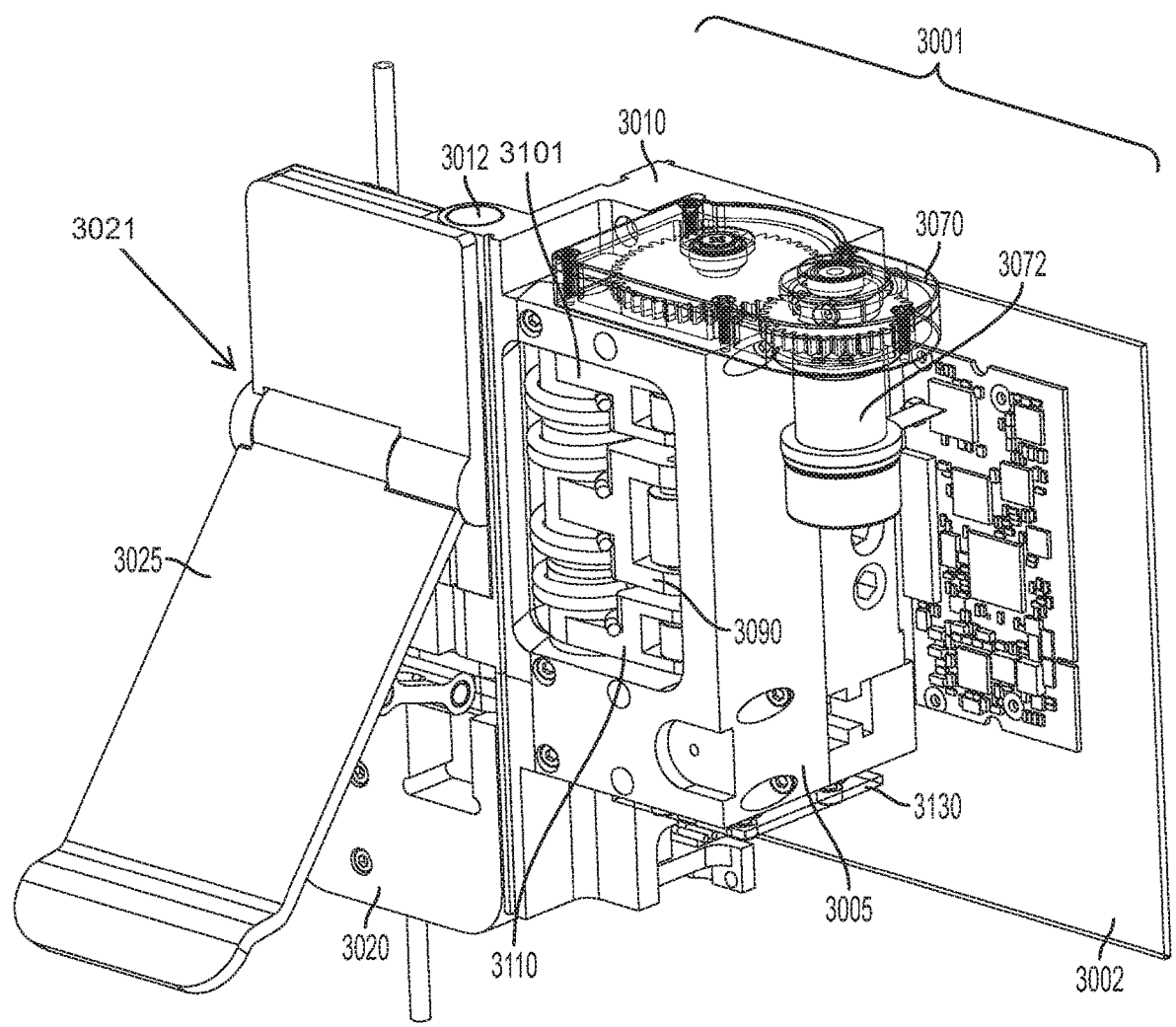
Figure 266:
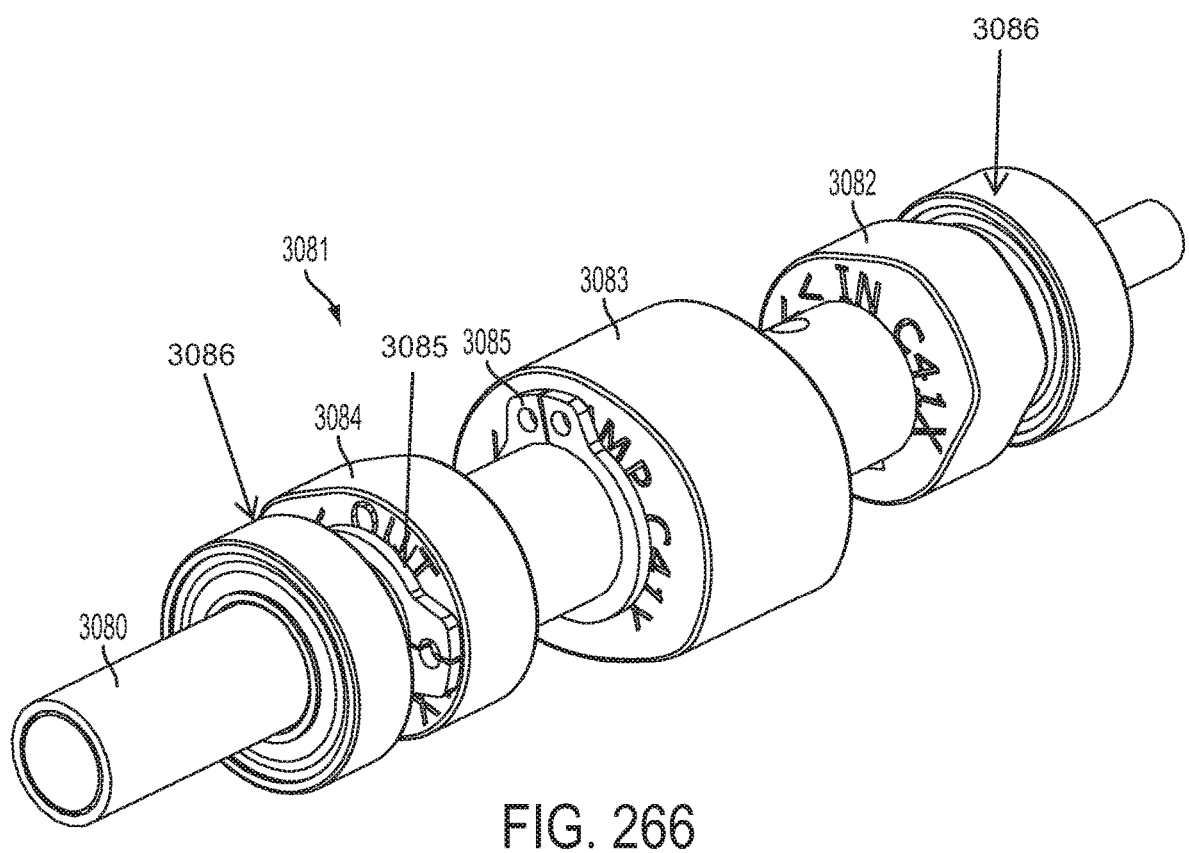
Figure 267:
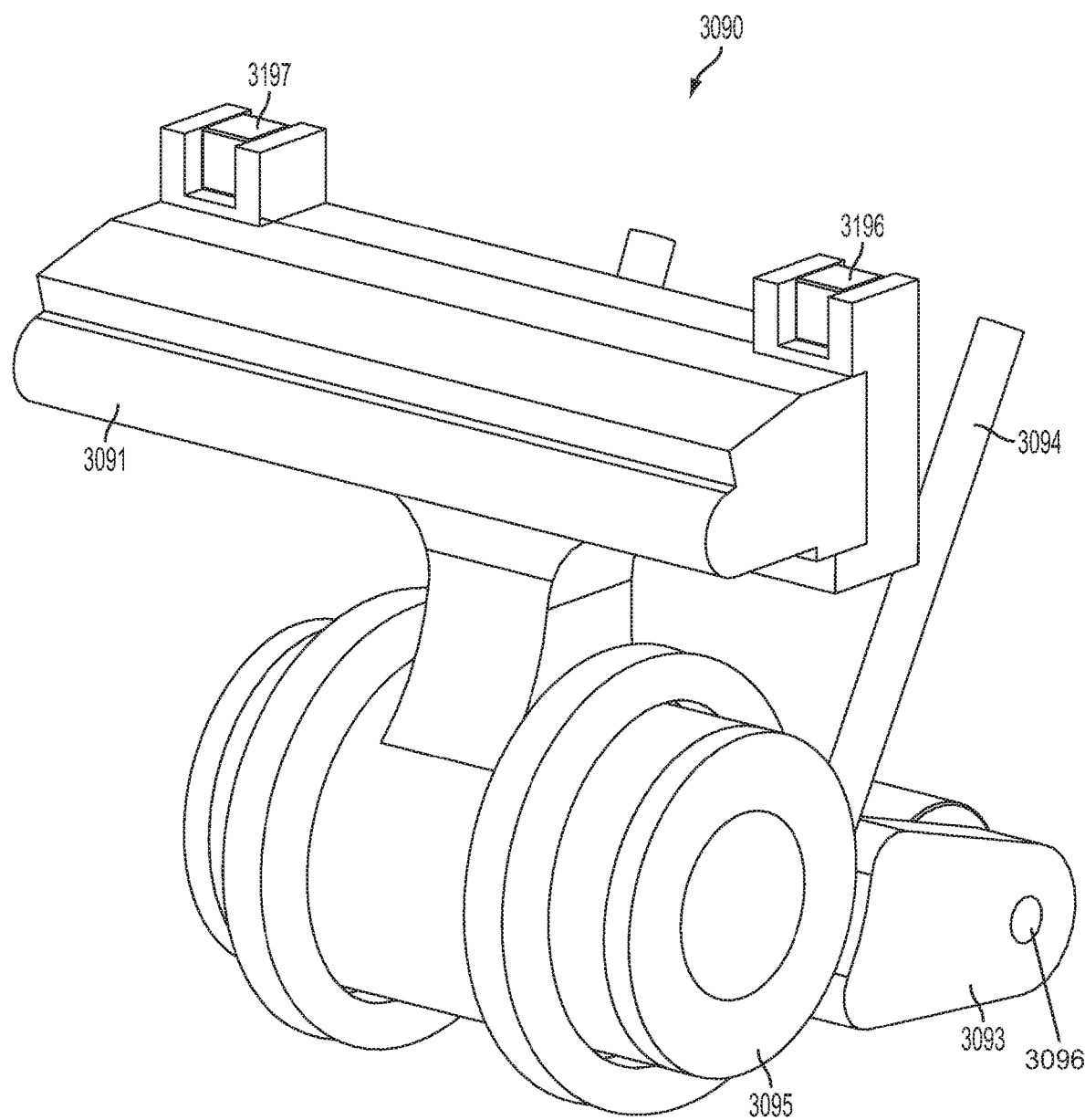
Figure 268:
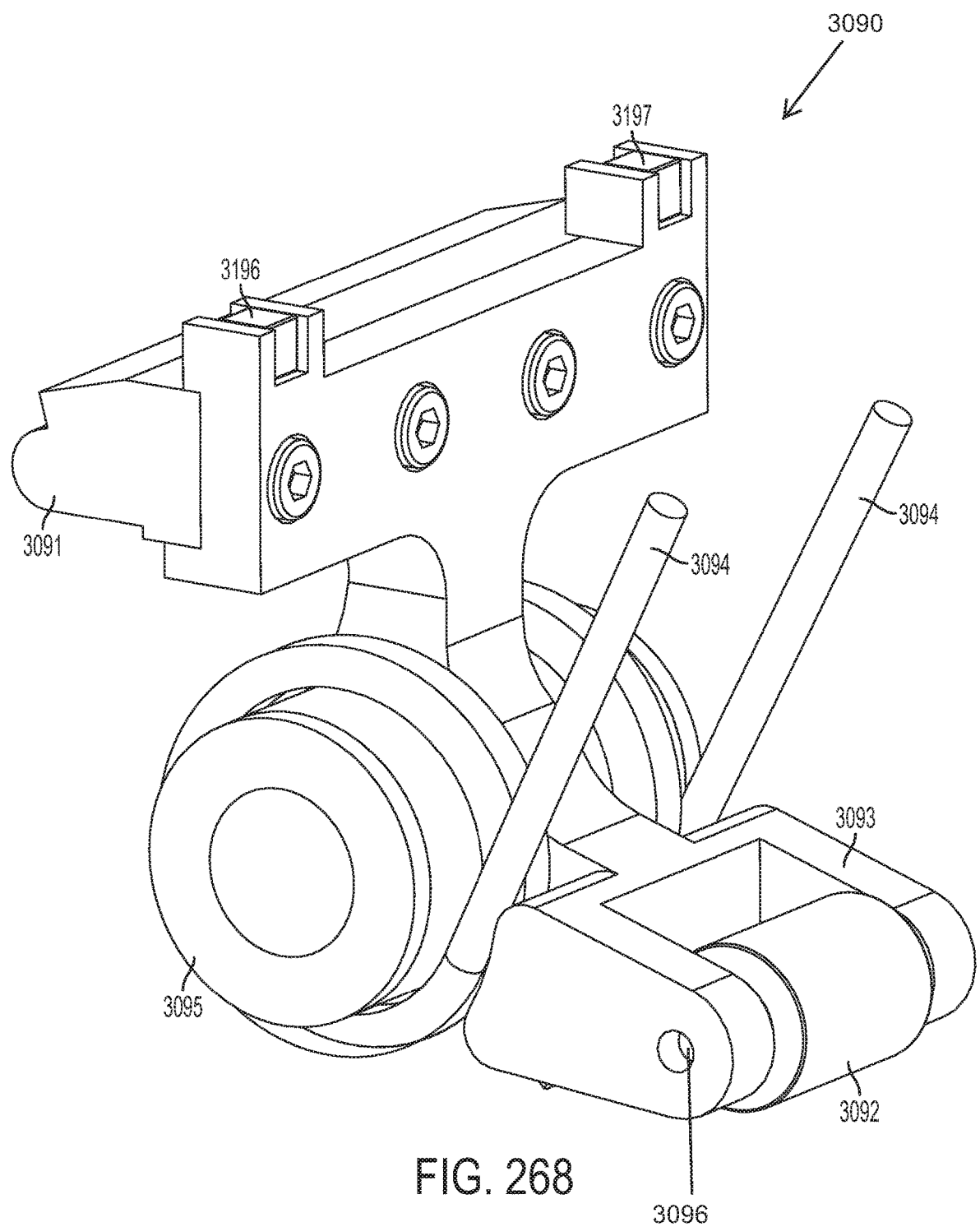
Figure 269:
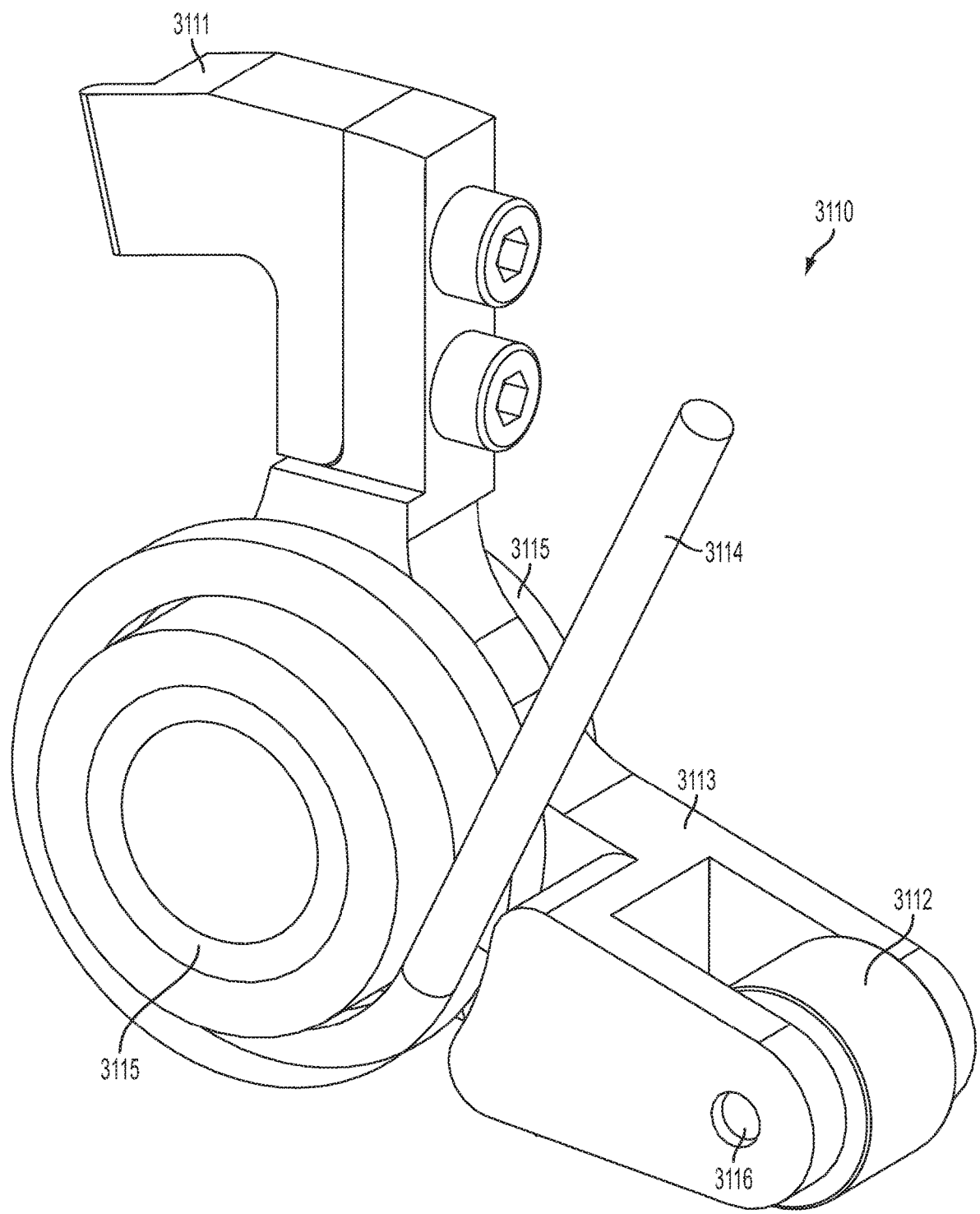
Figure 270:
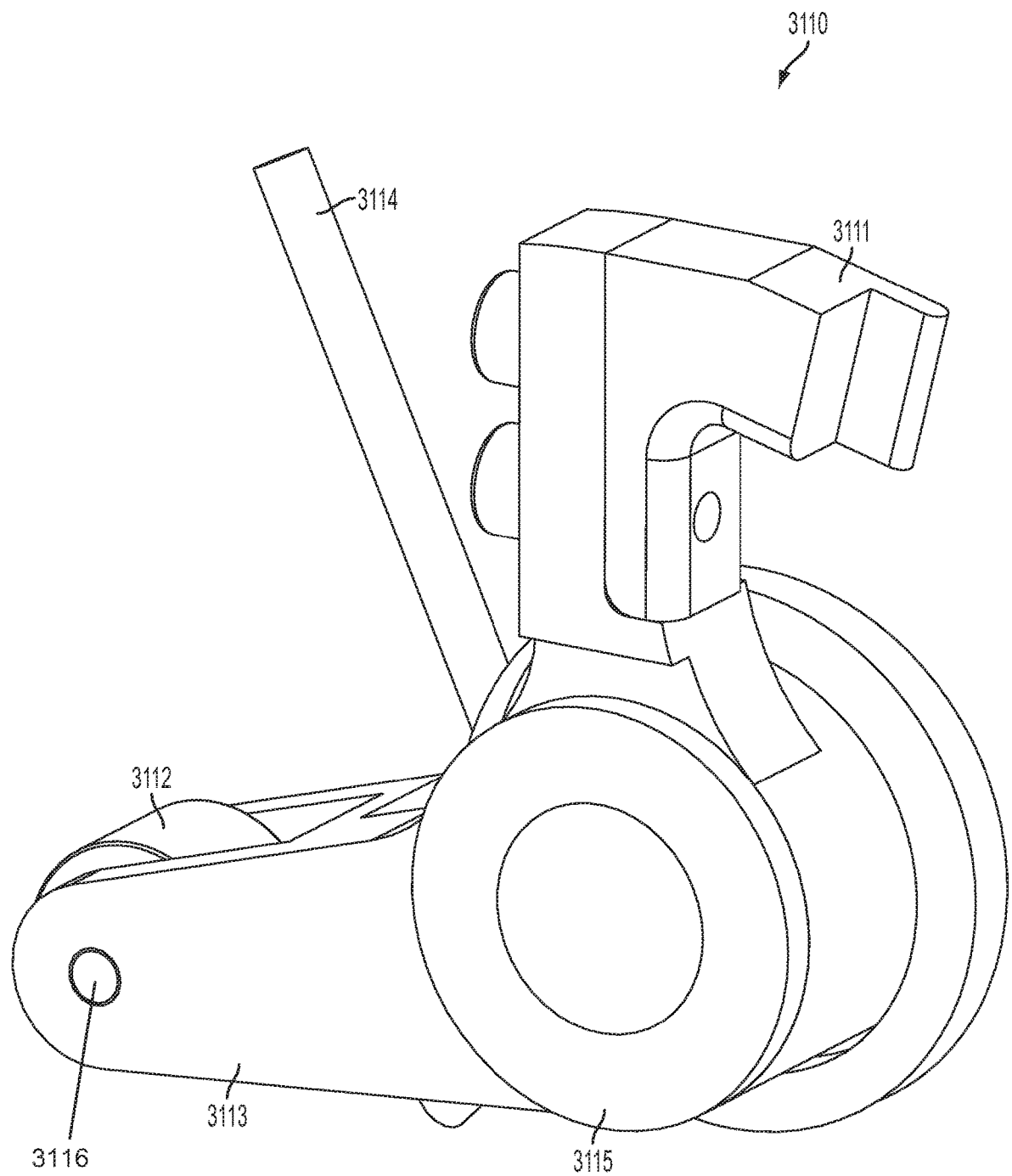
Figure 271:
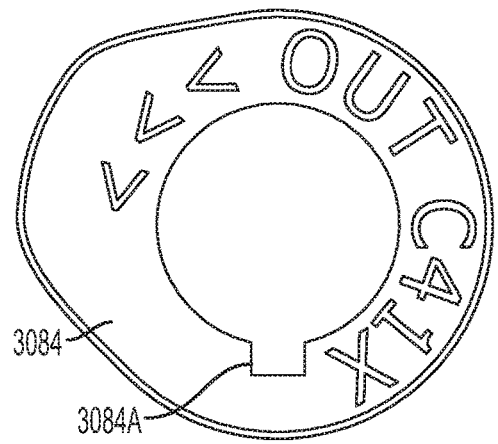
Figure 272:
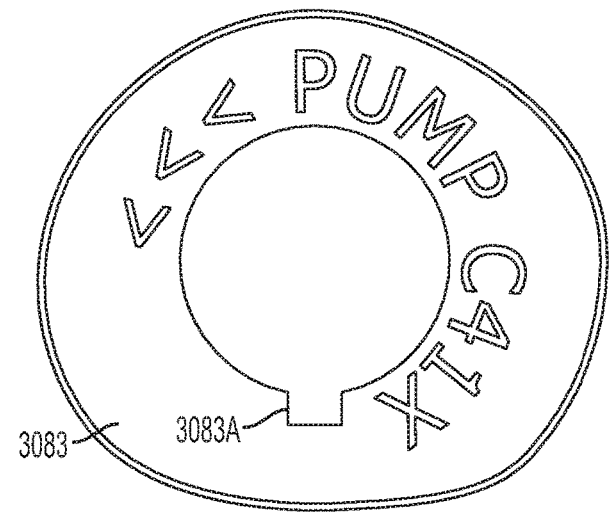
Figure 273:
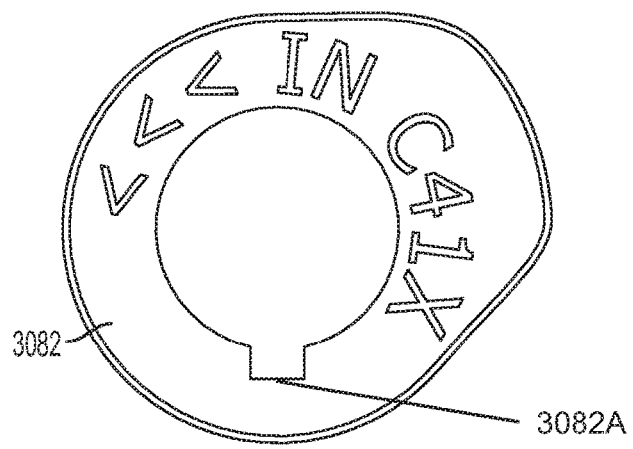
Figure 274:
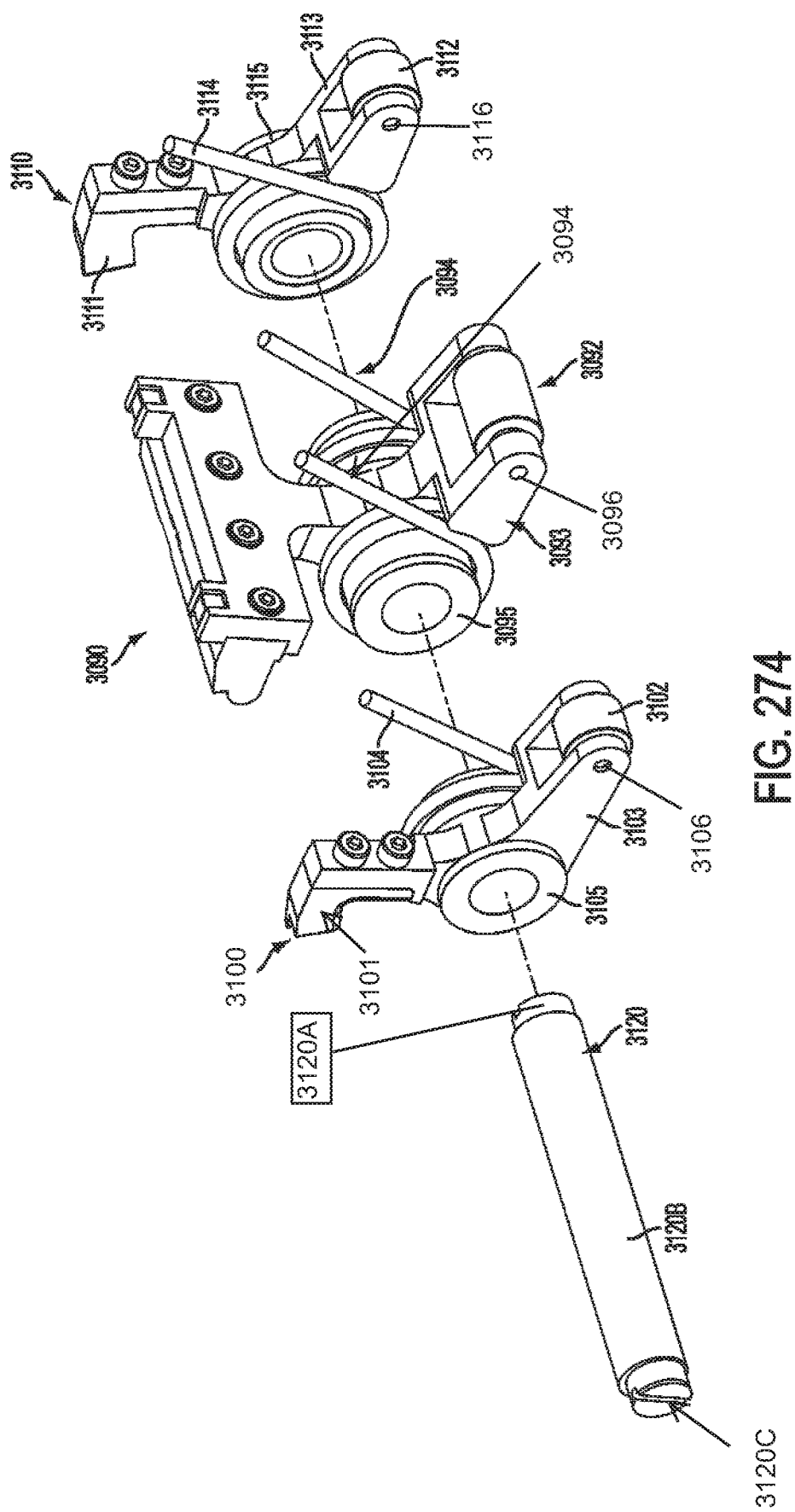
Figure 275:
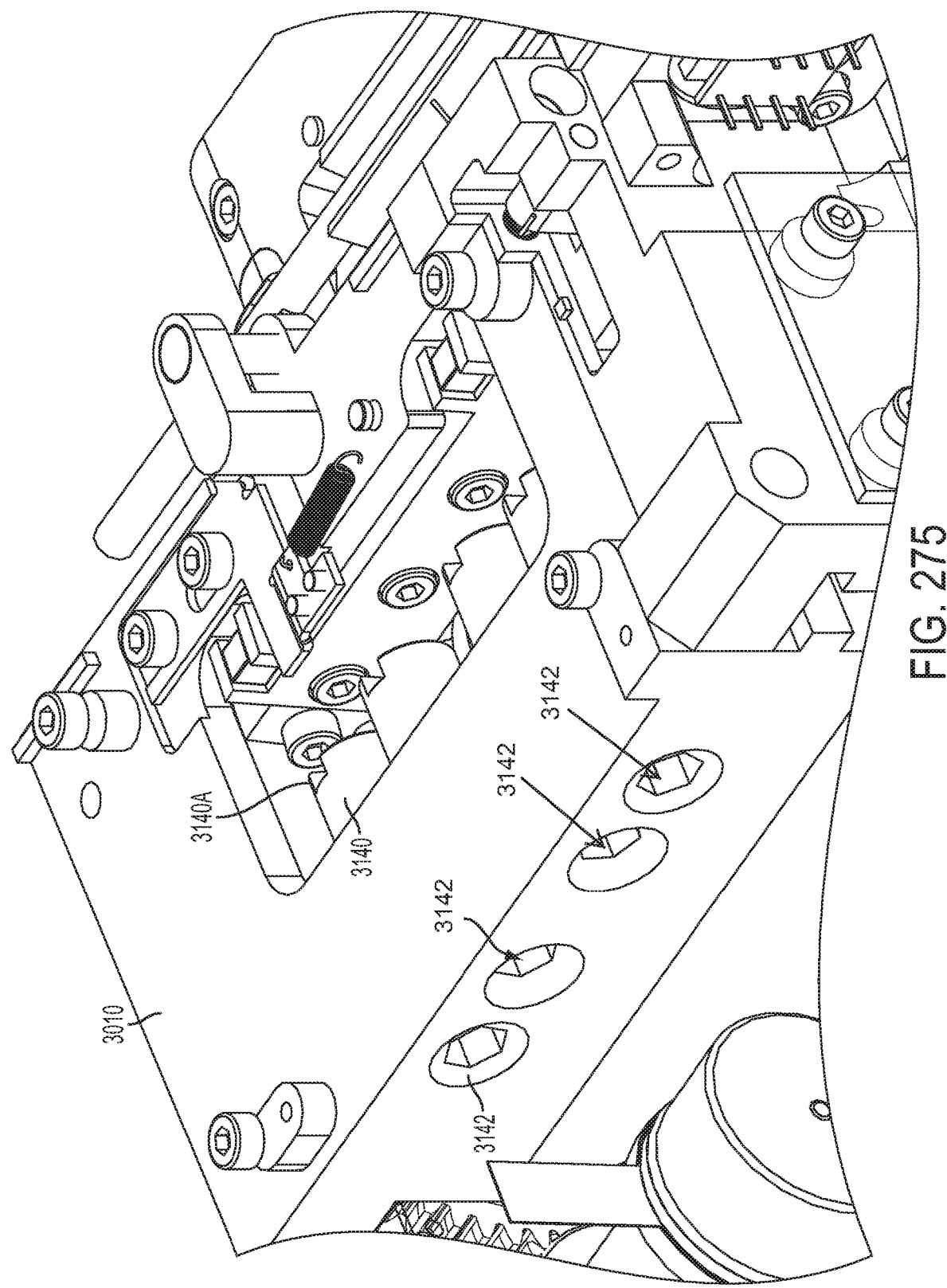
Figure 276:
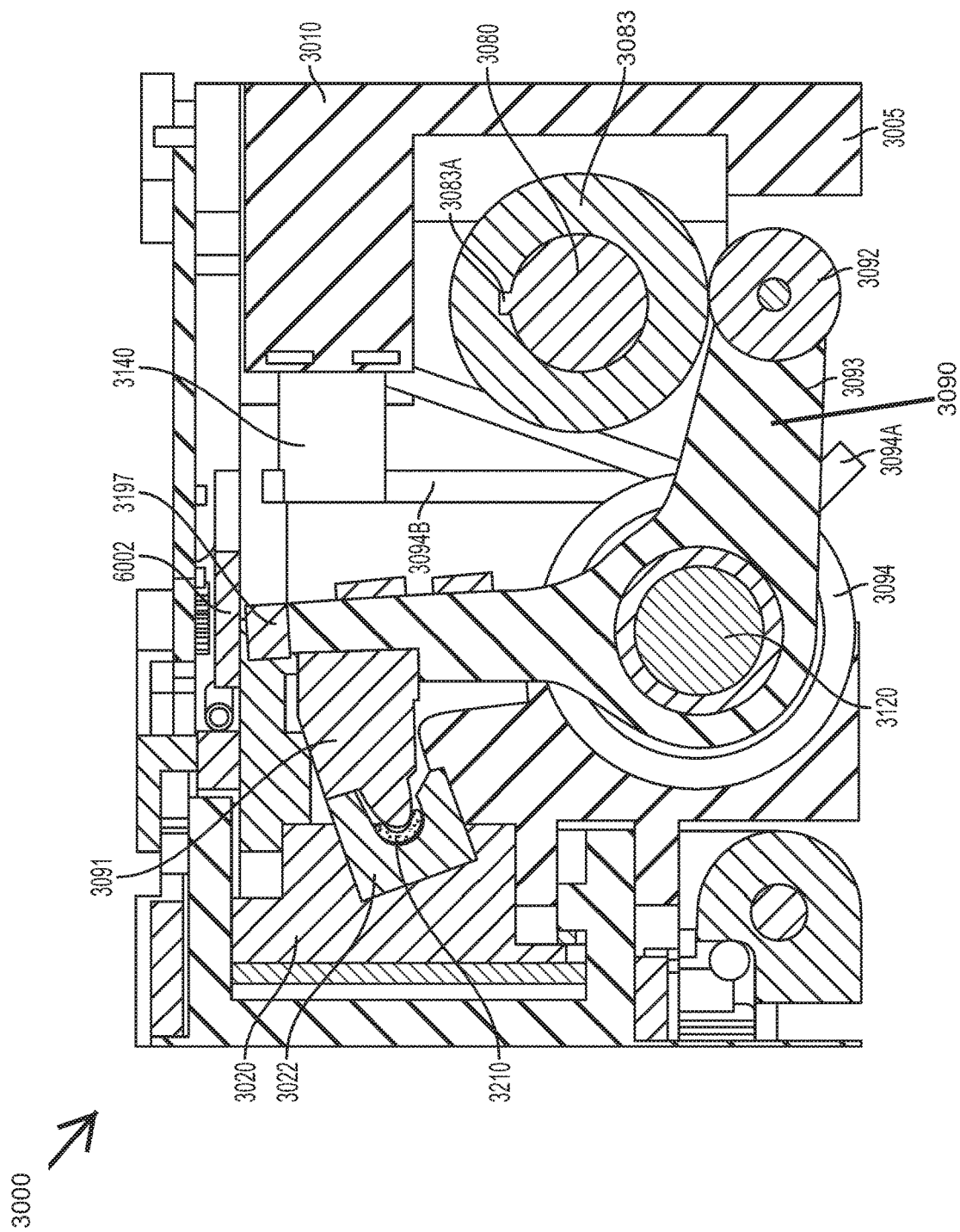
Figure 277:
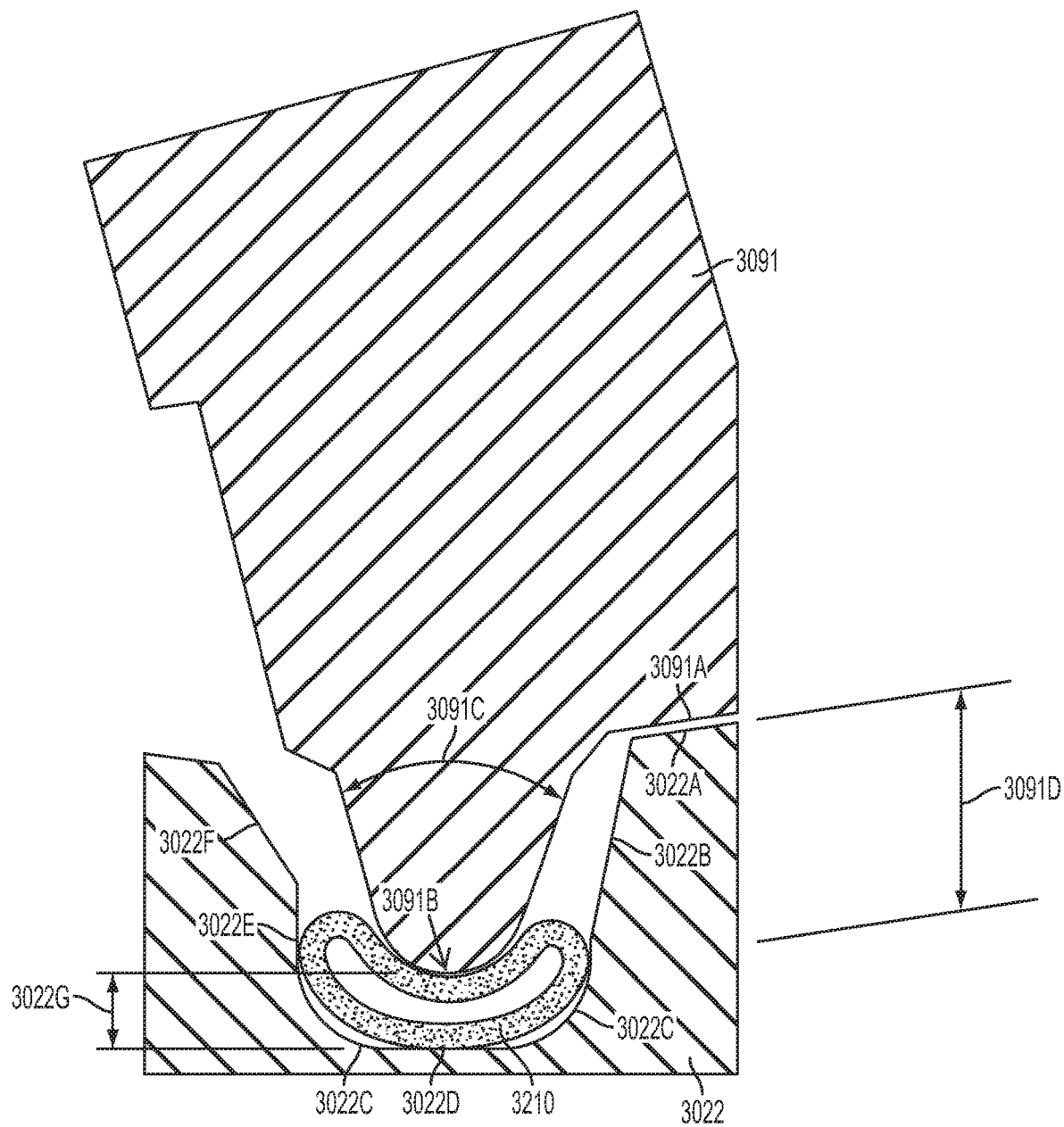
Figure 278:
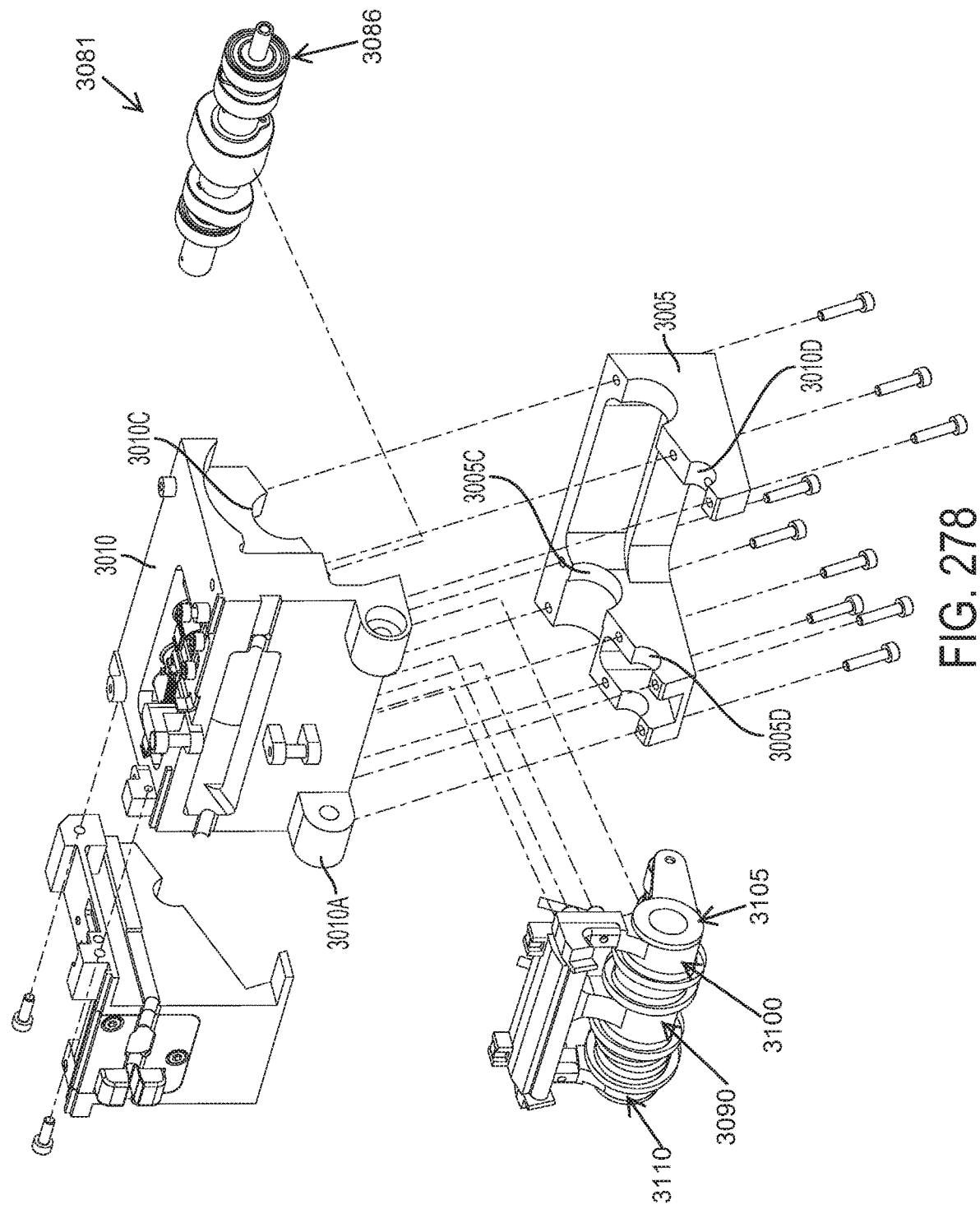
Figure 279:
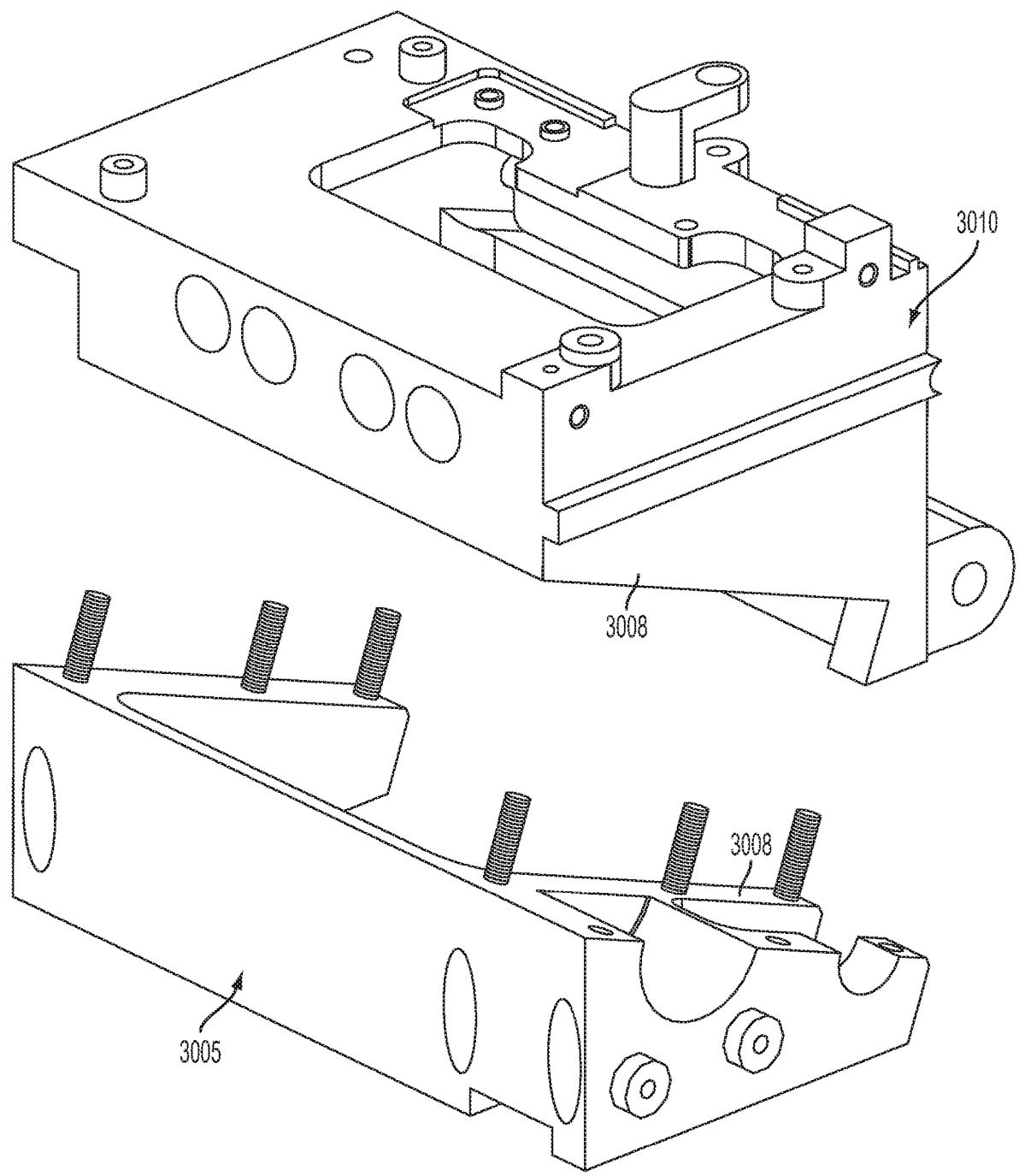
Figure 280:
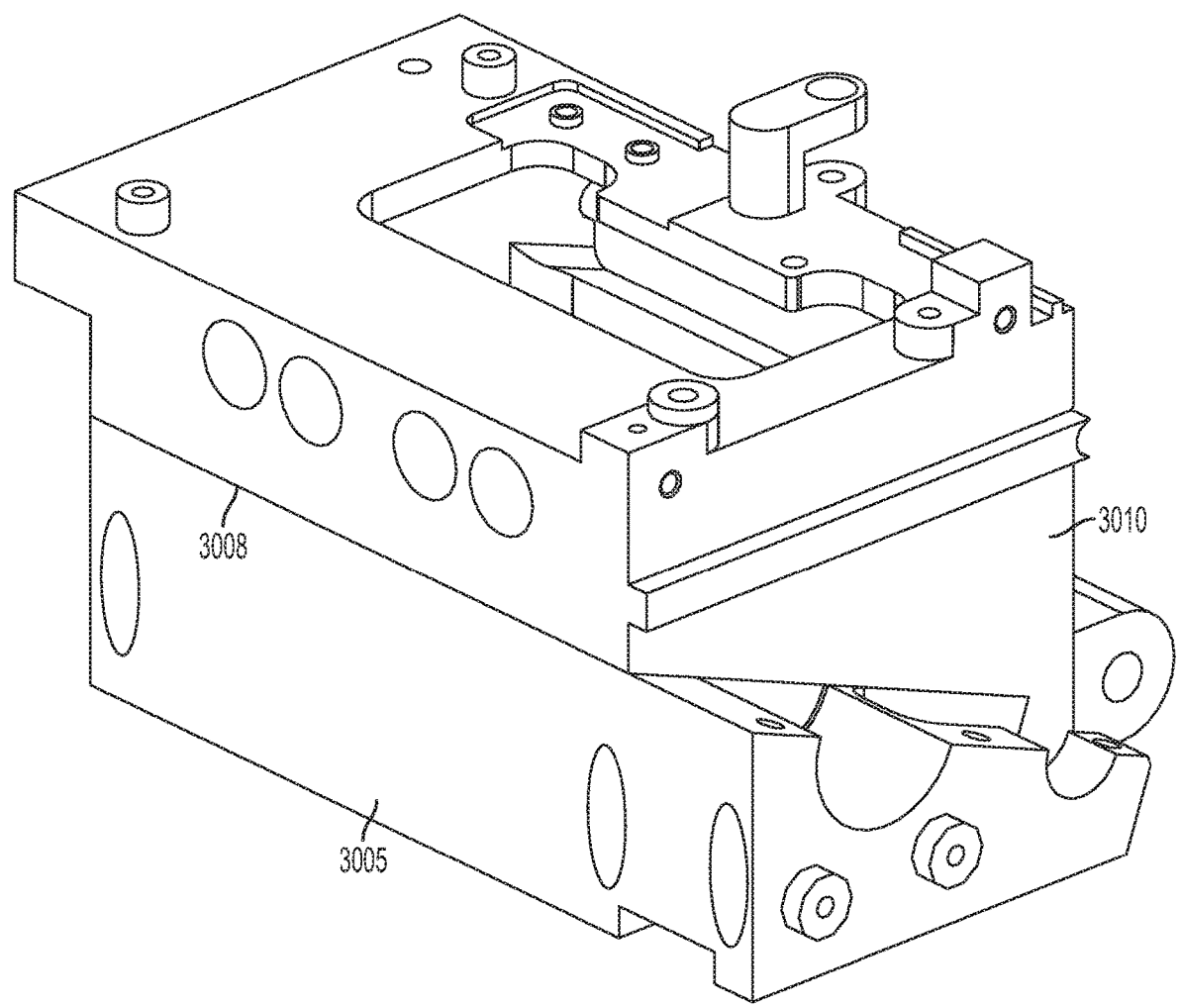
Figure 281:
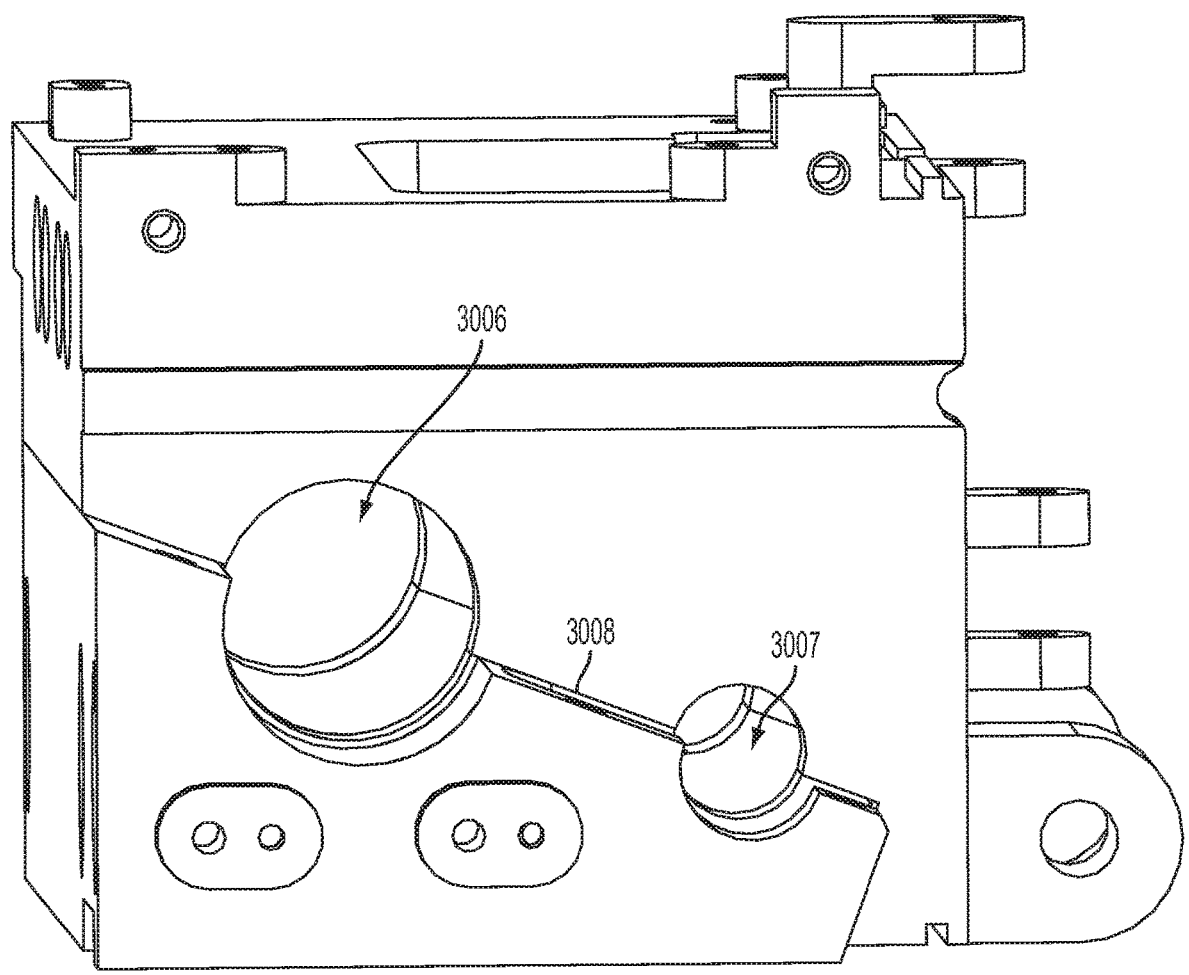
Figure 282:
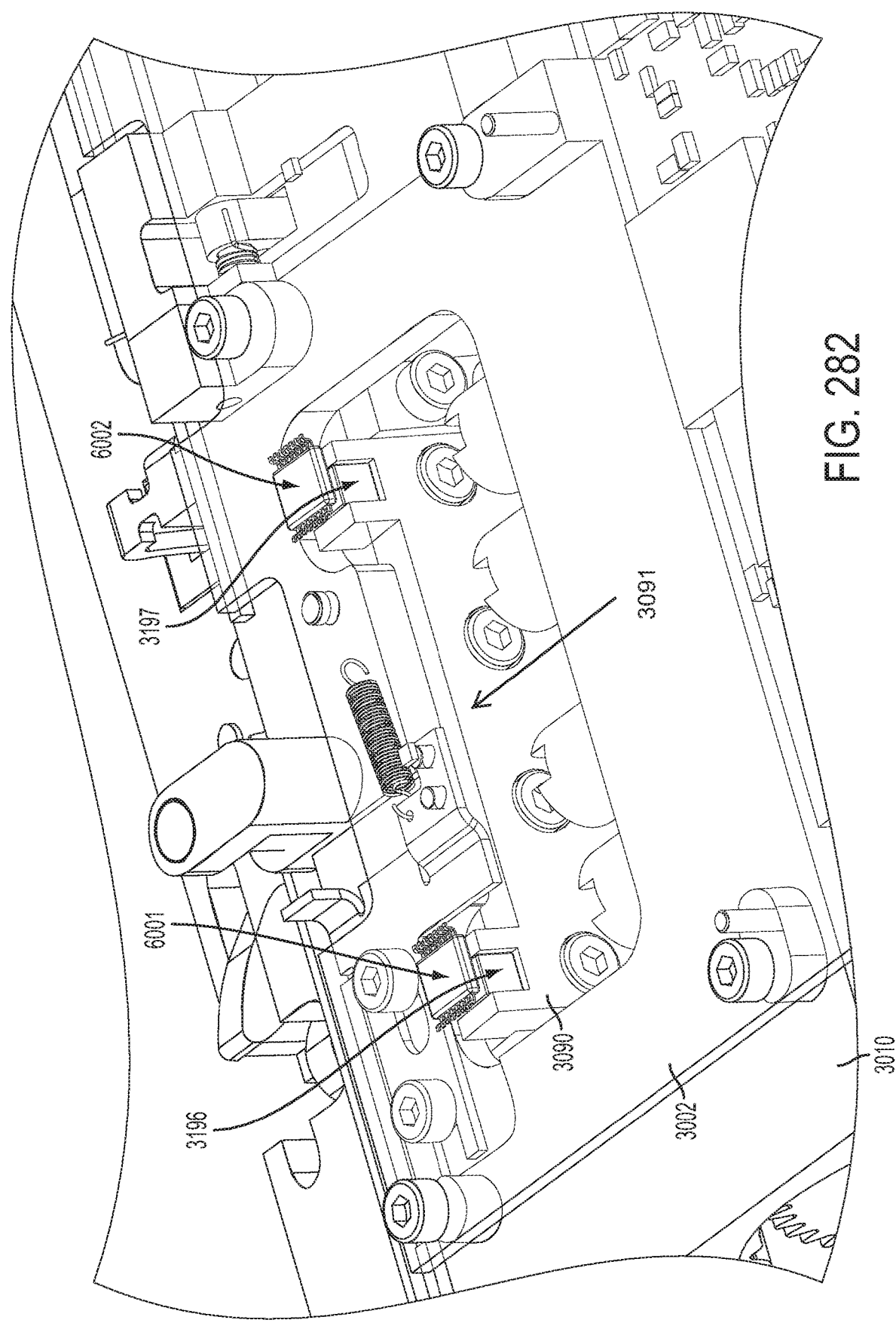
Figure 283:
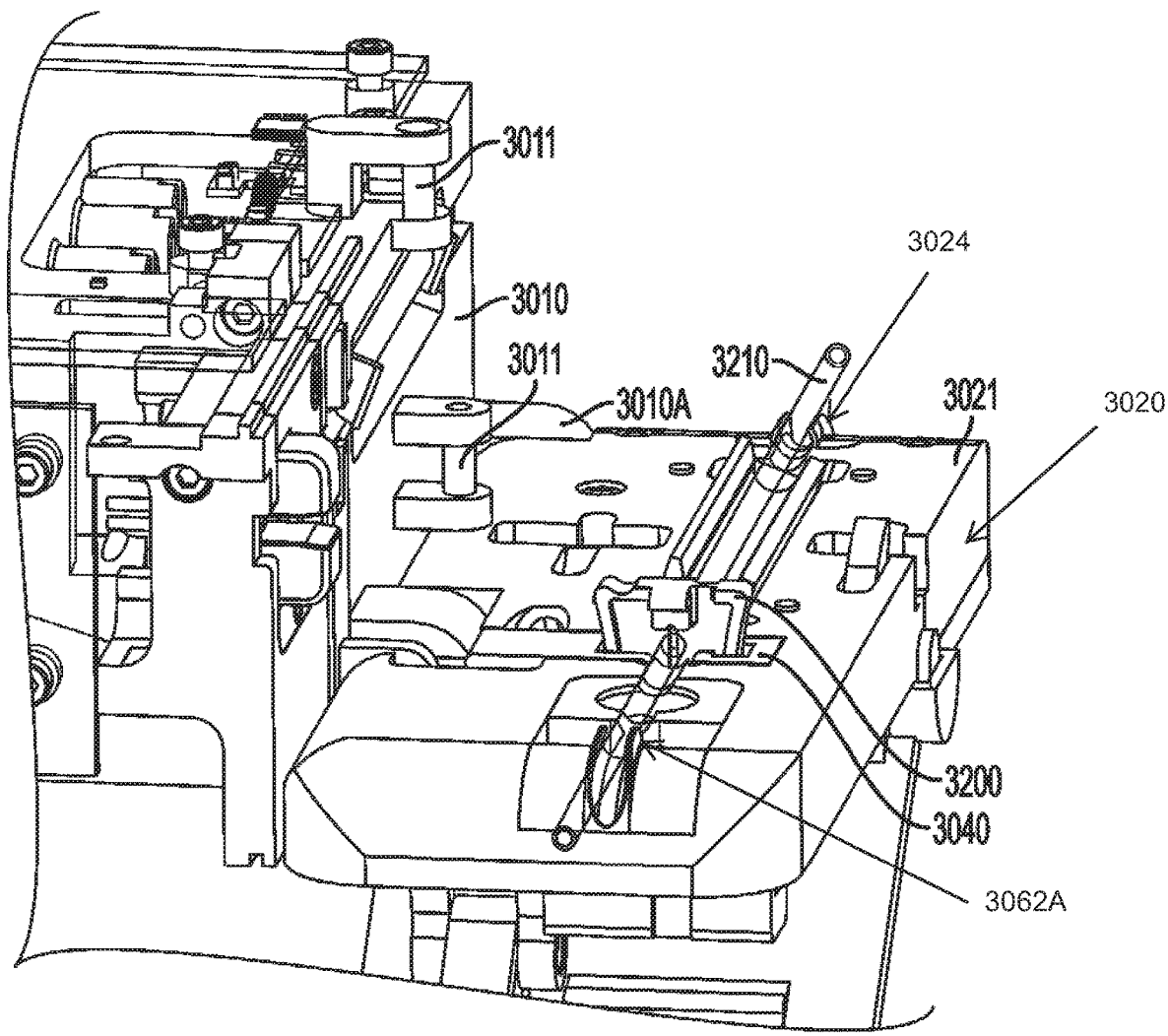
Figure 284:
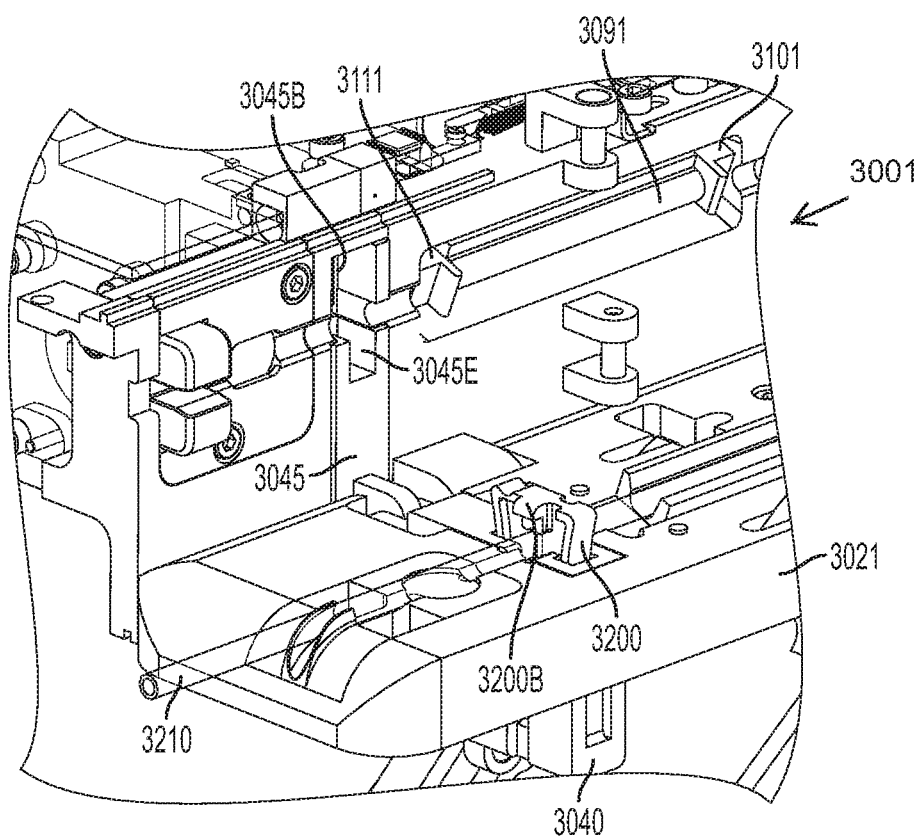
Figure 285:
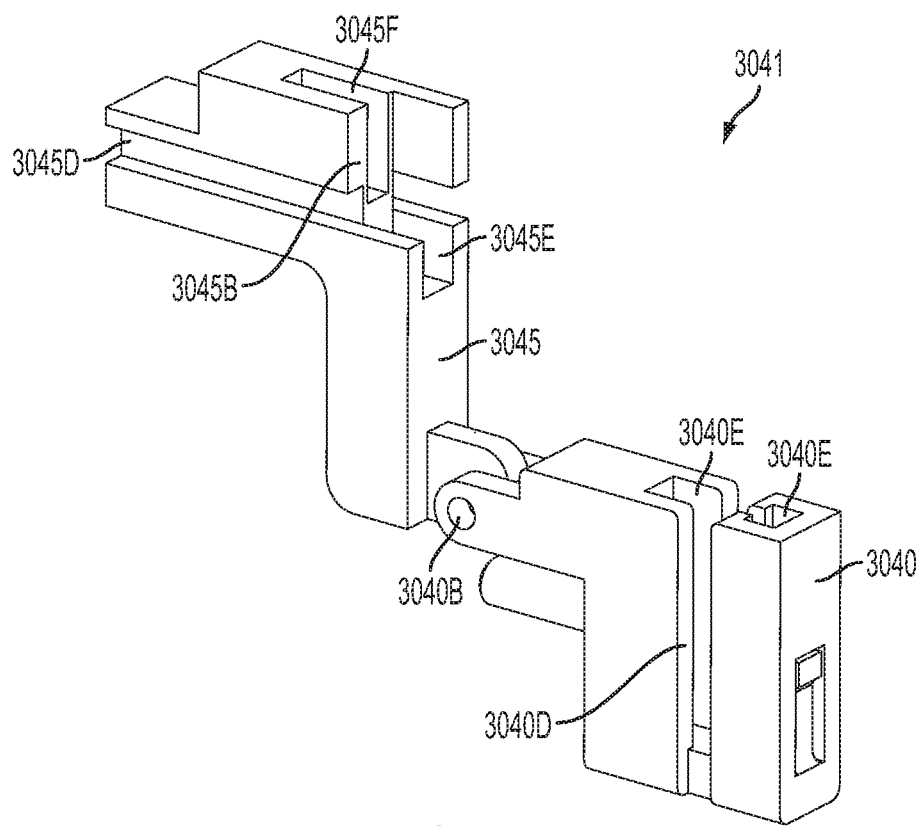
Figure 286:
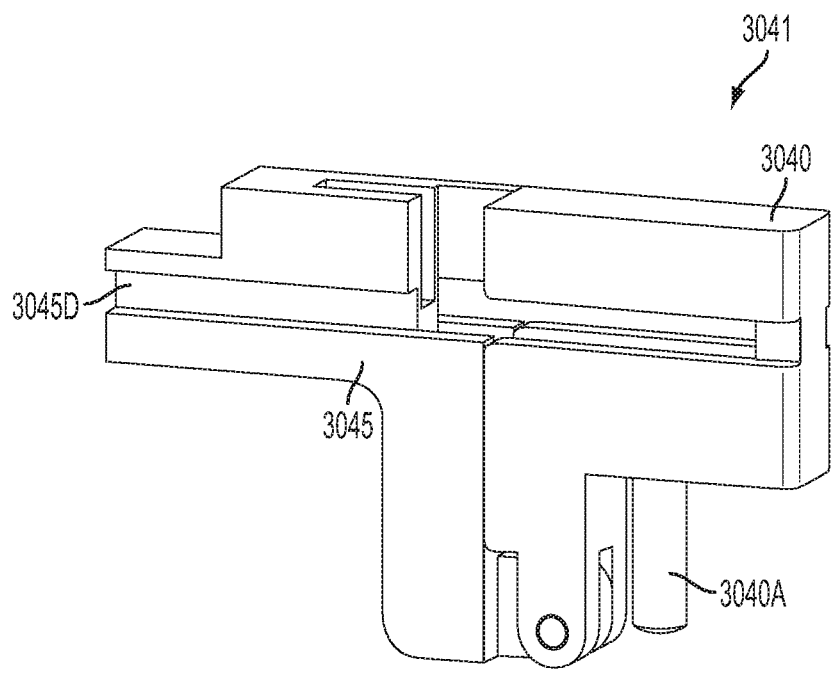
Figure 287:
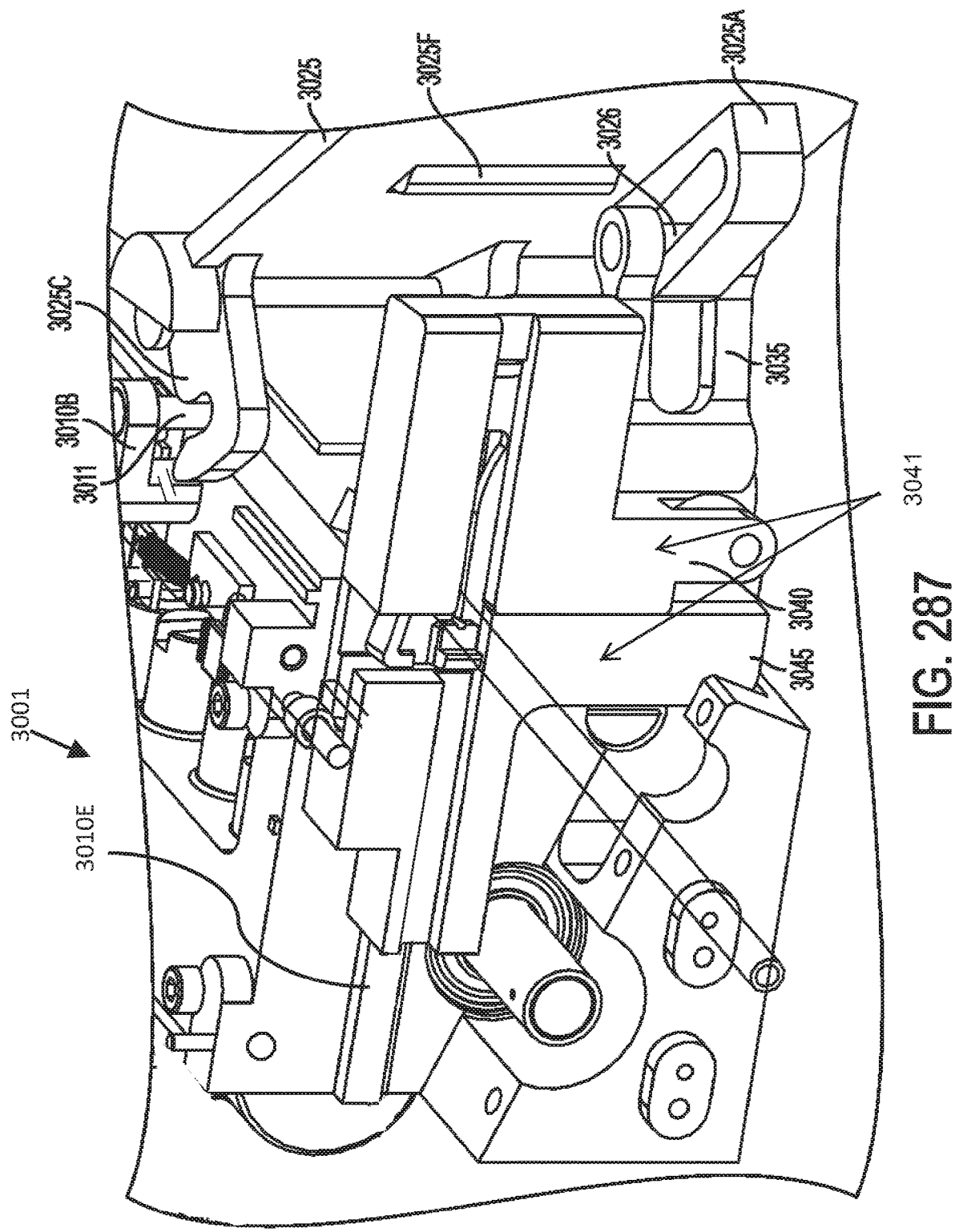
Figure 288:
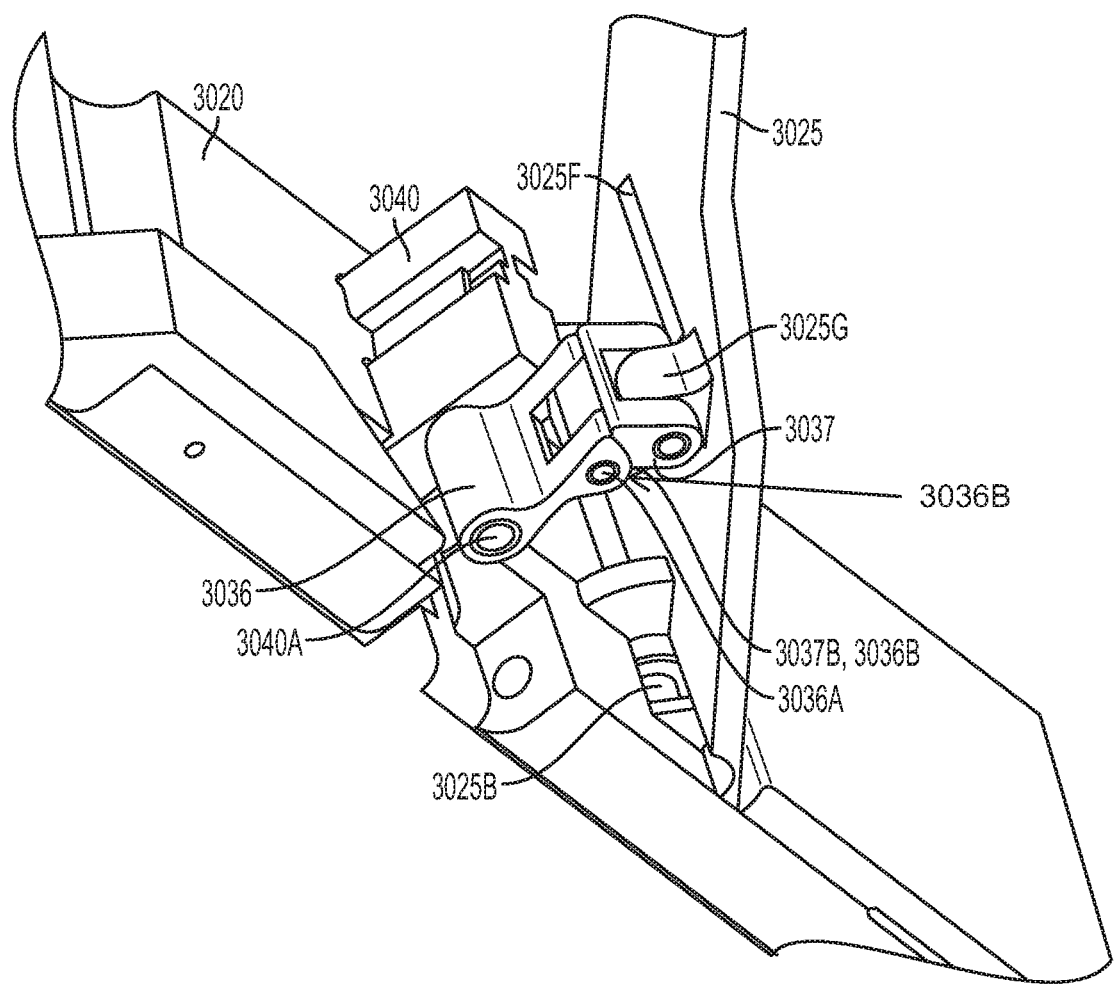
Figure 289:
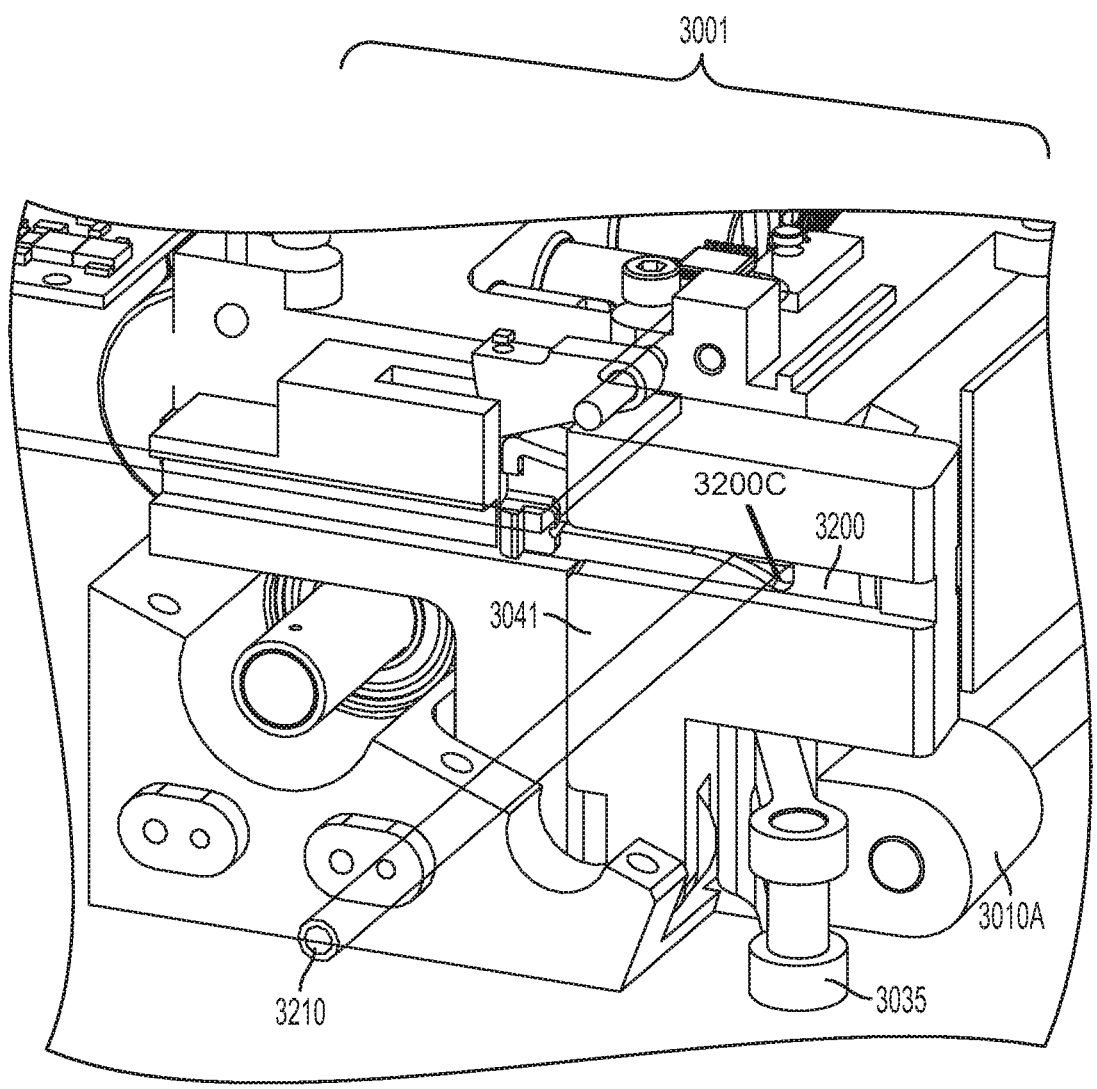
Figure 294:
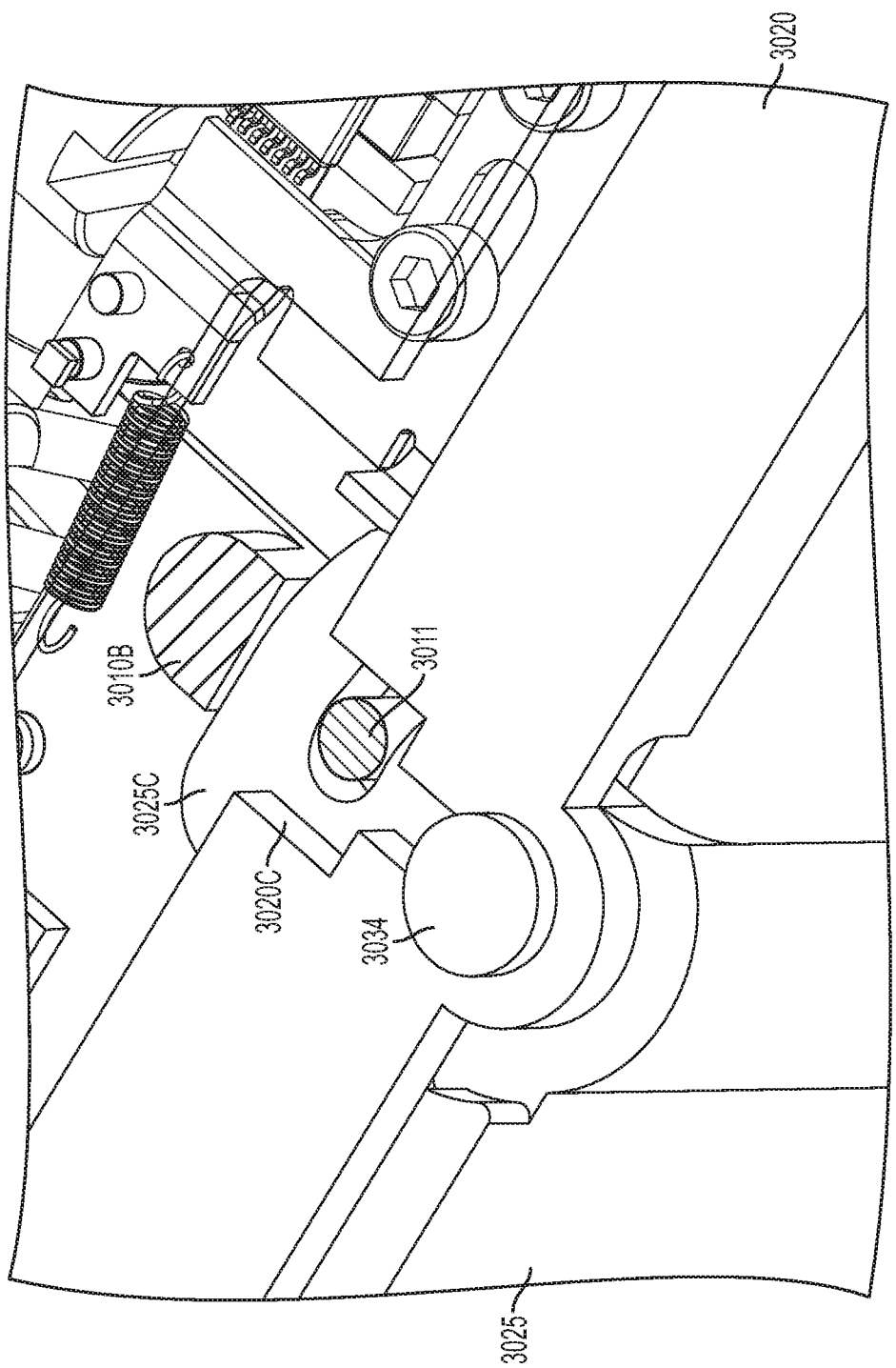
Figure 295:
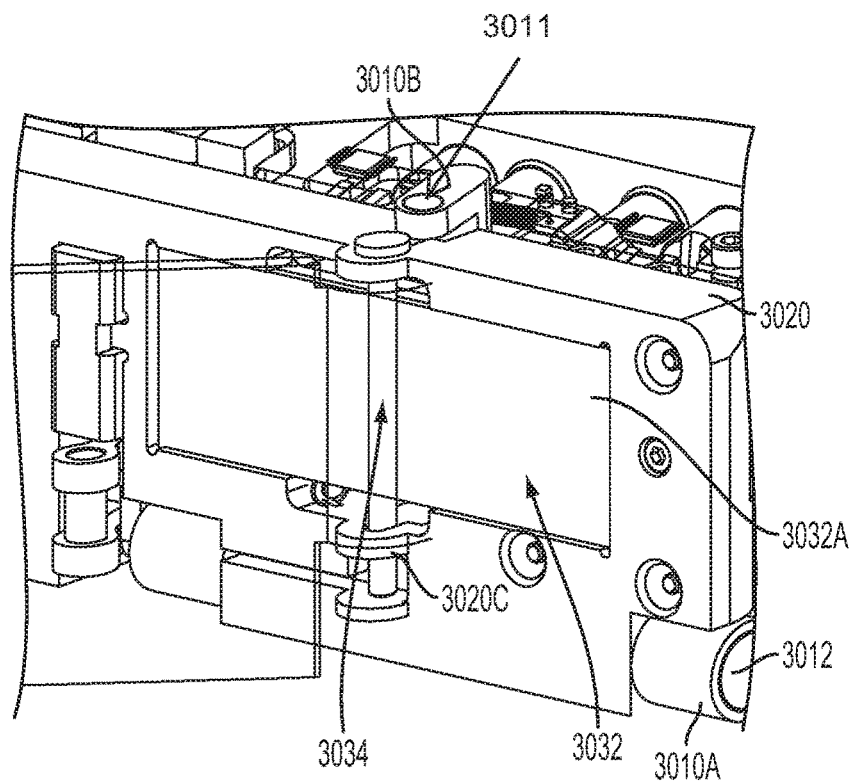
Figure 296:
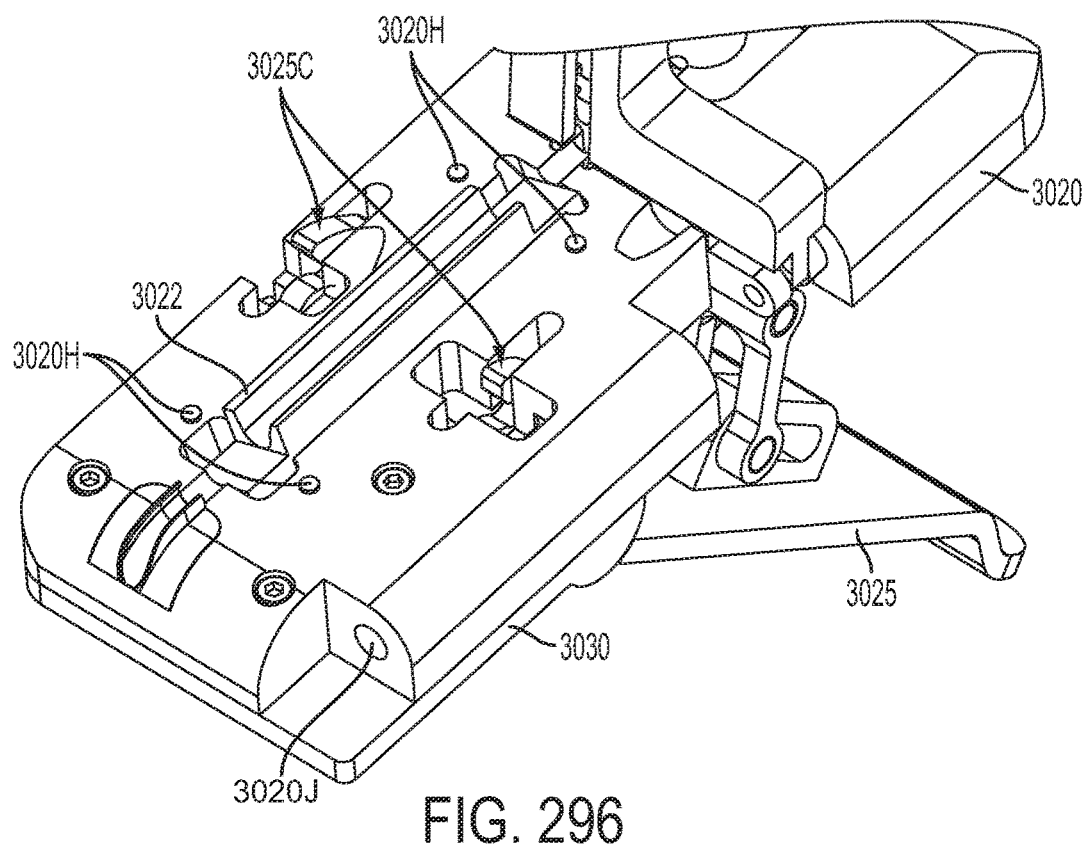
Figure 297:
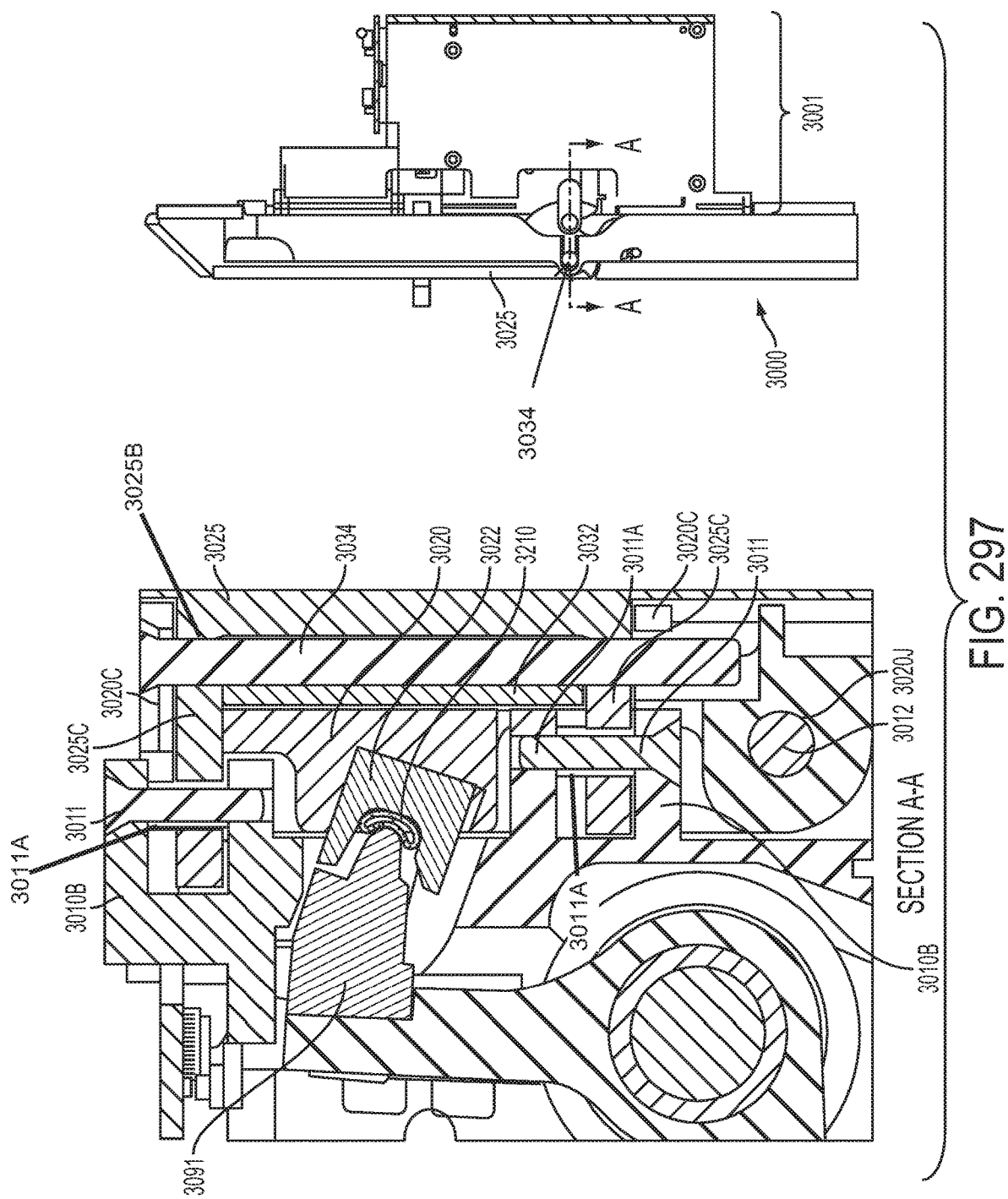
Figure 298:
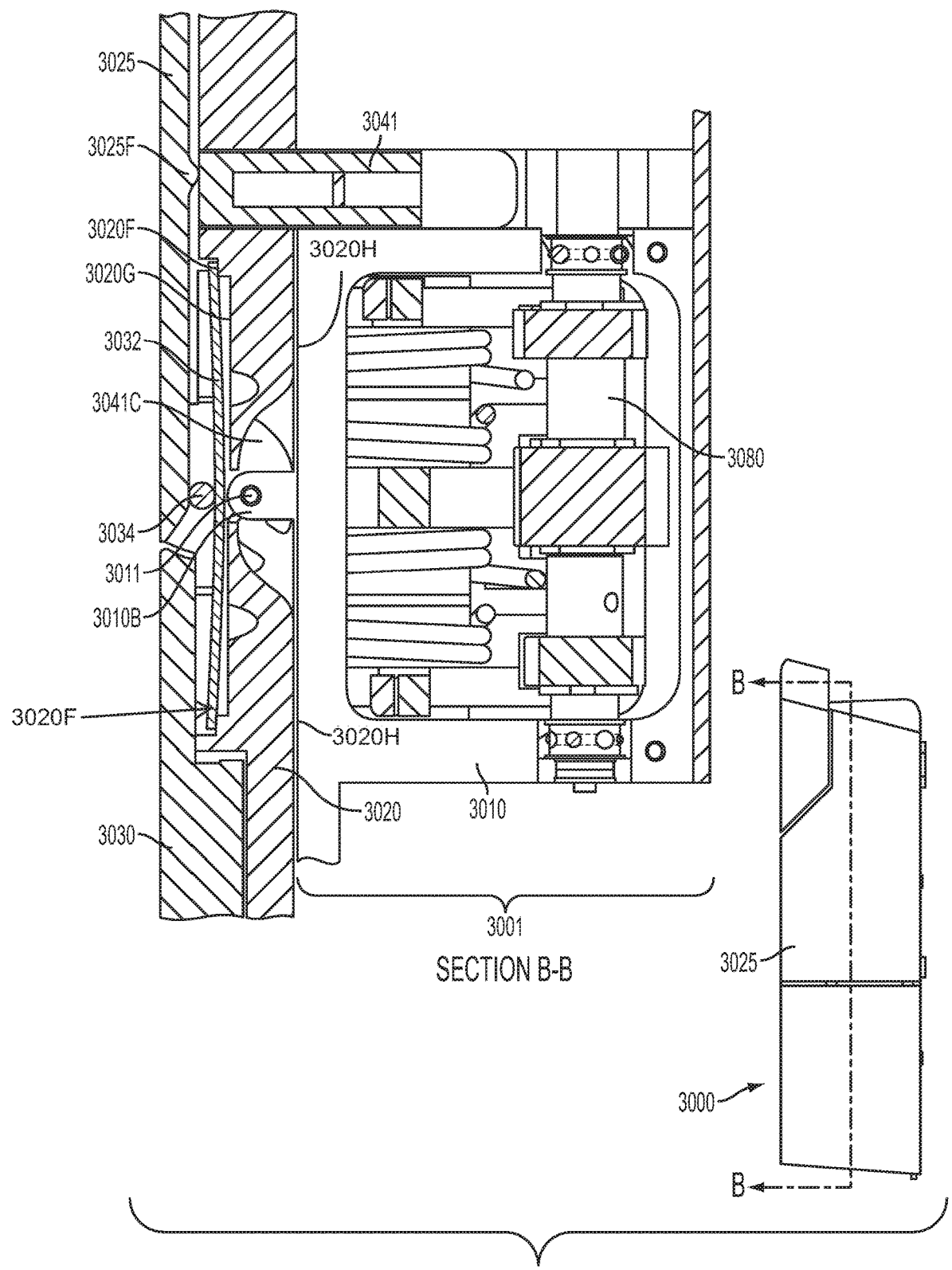
Figure 299:
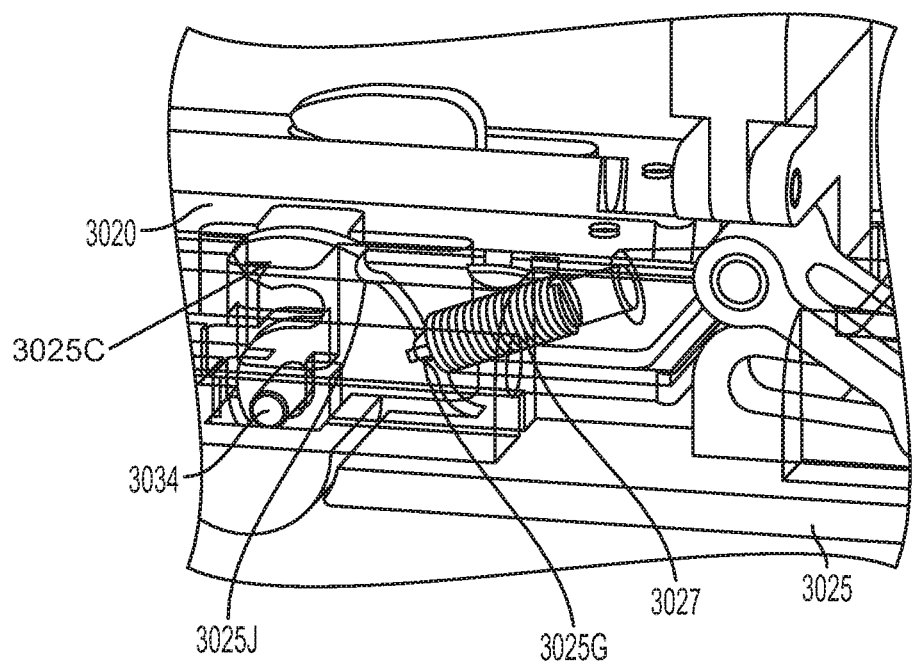
Figure 300:
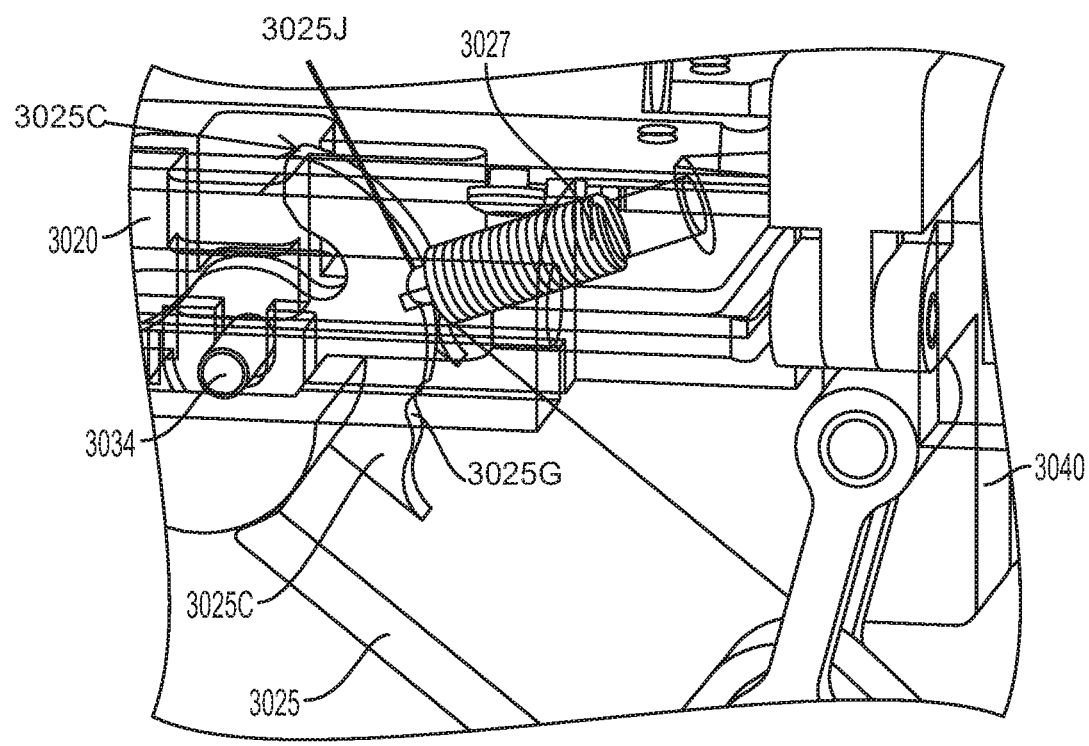
Figure 301:
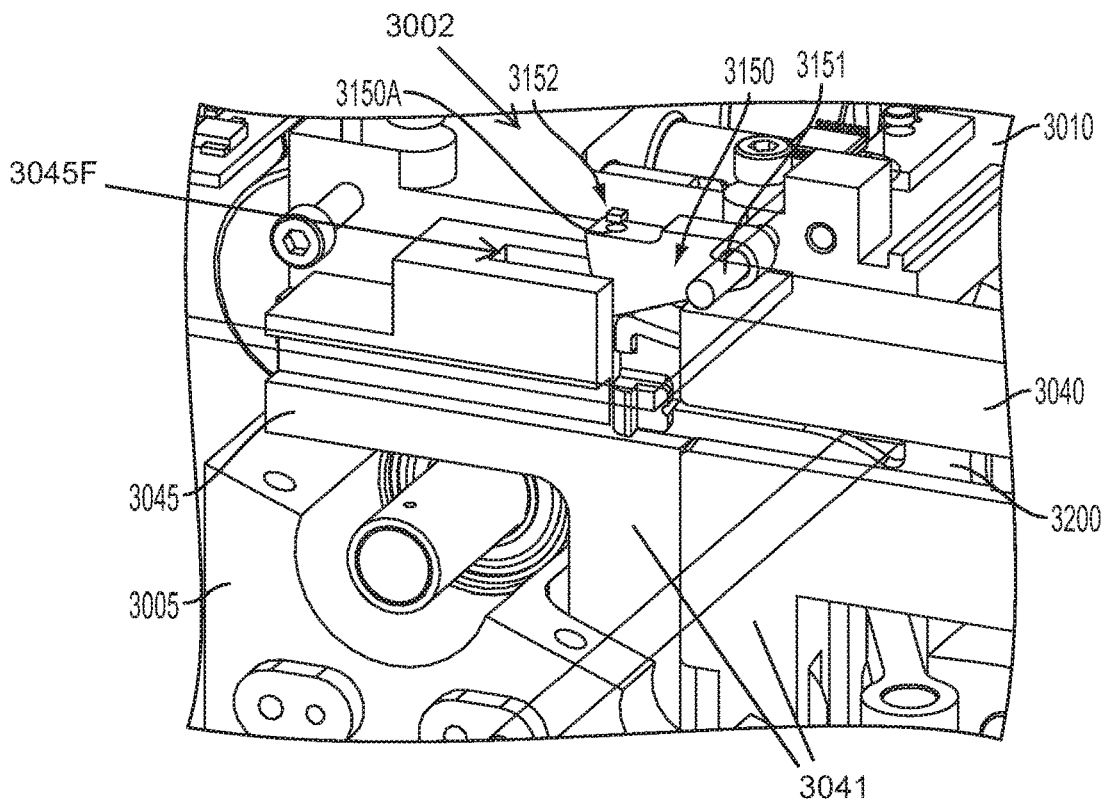
Figure 302:
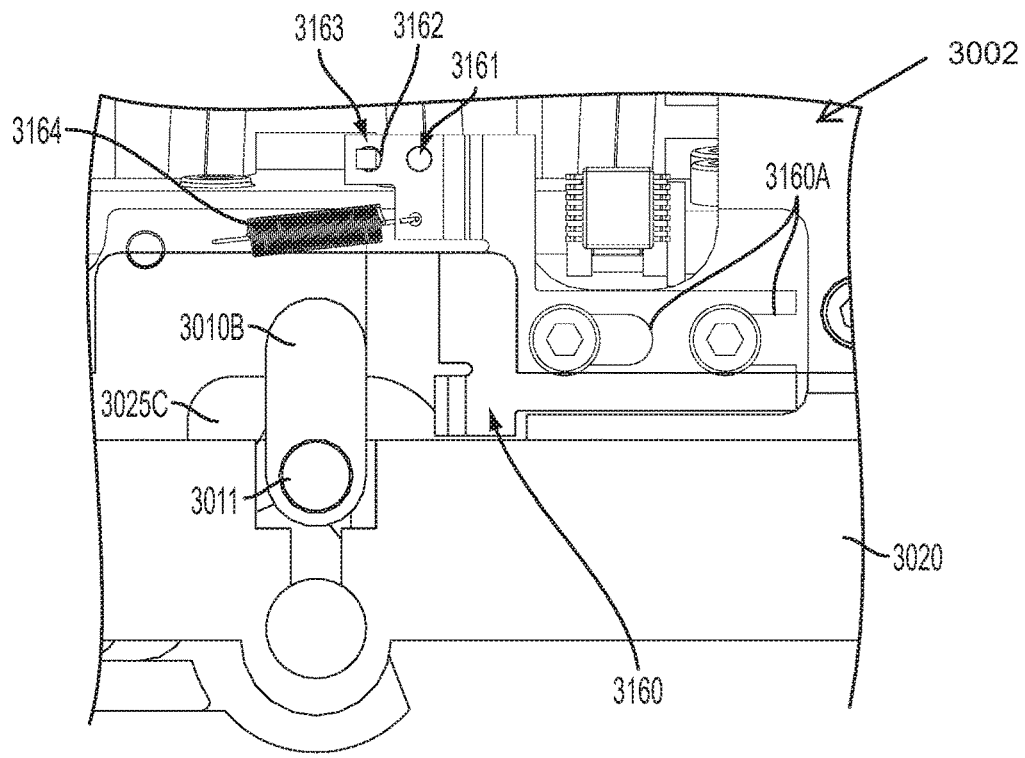
Figure 305:
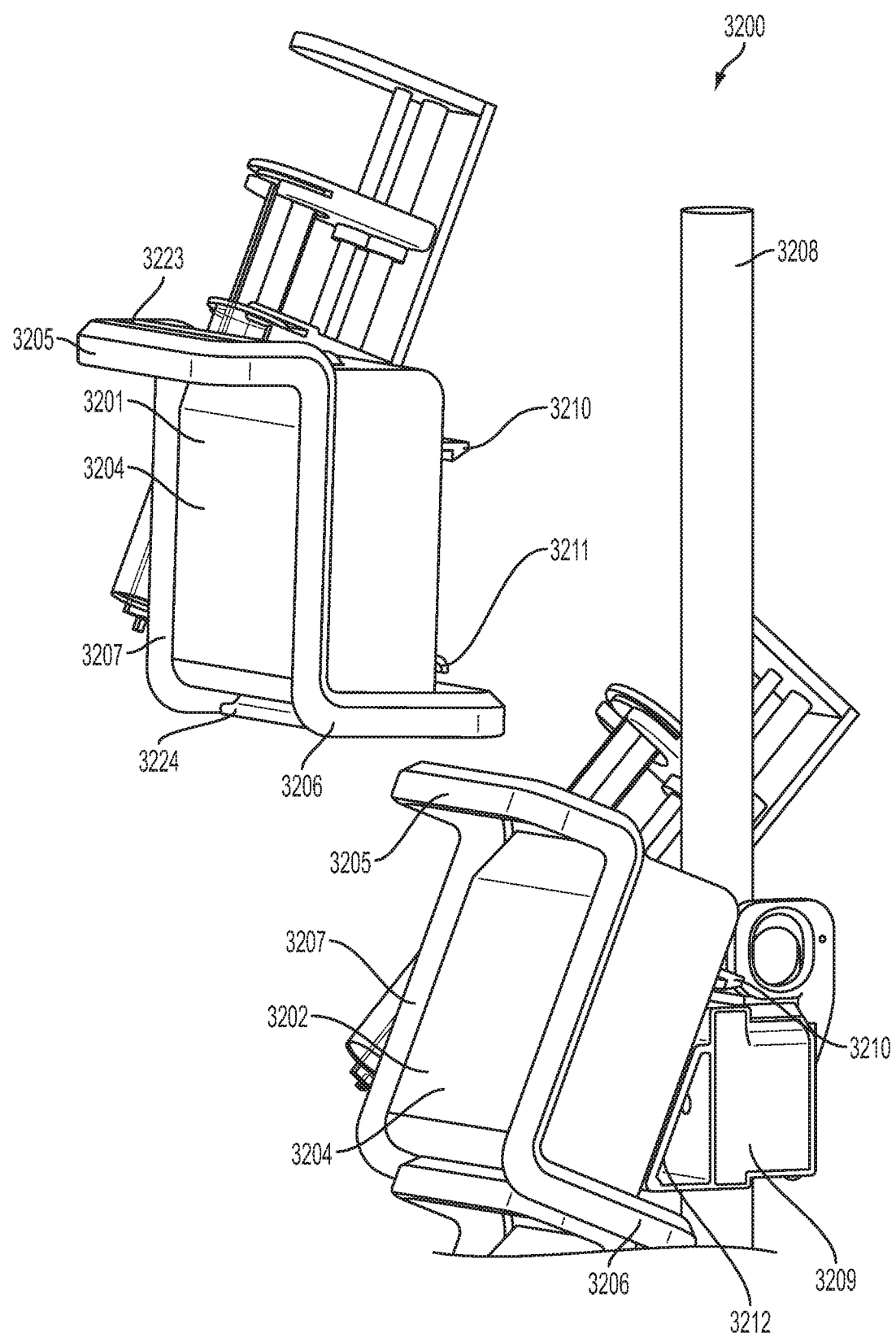
Figure 306:
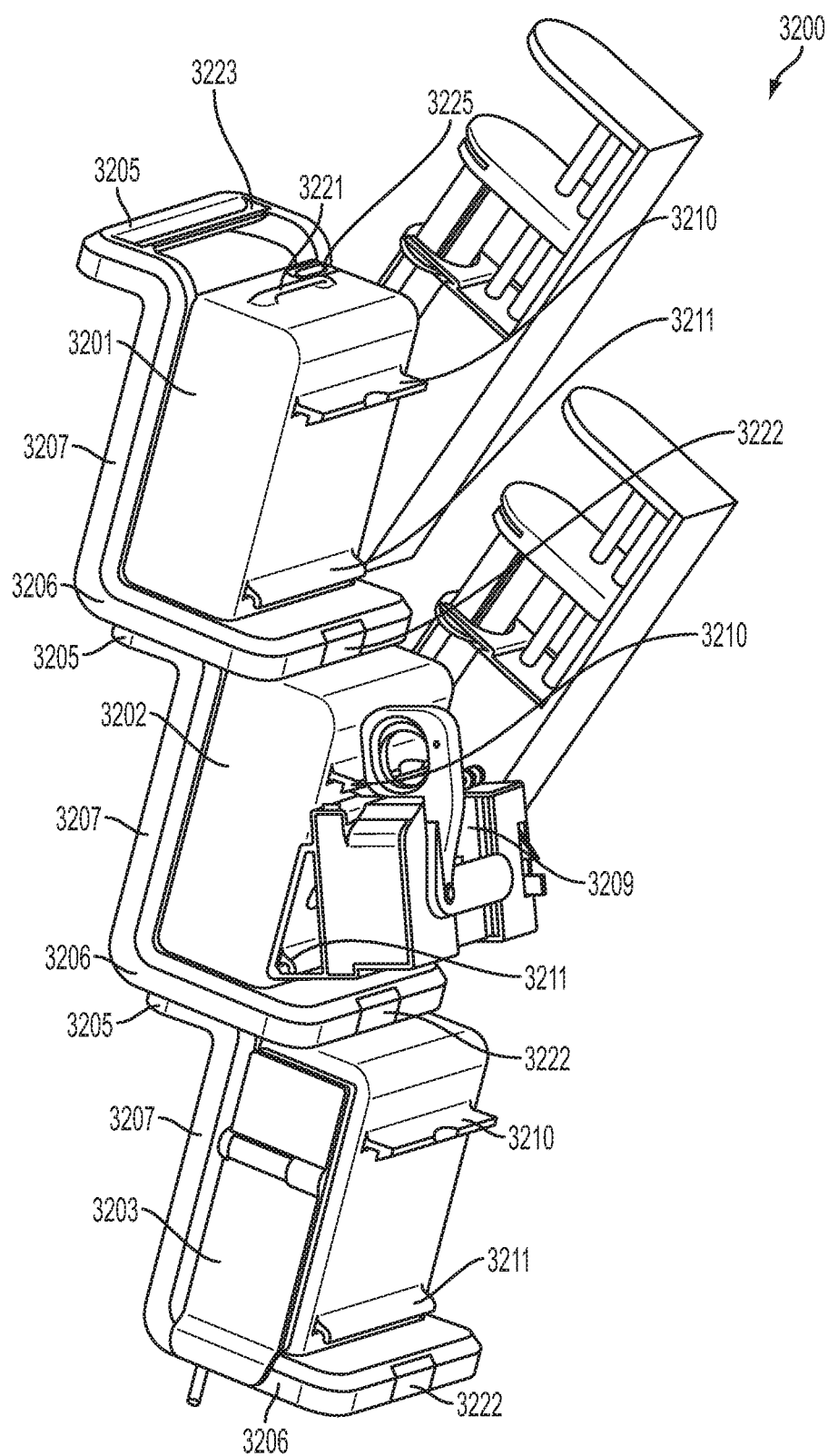
Figure 307:
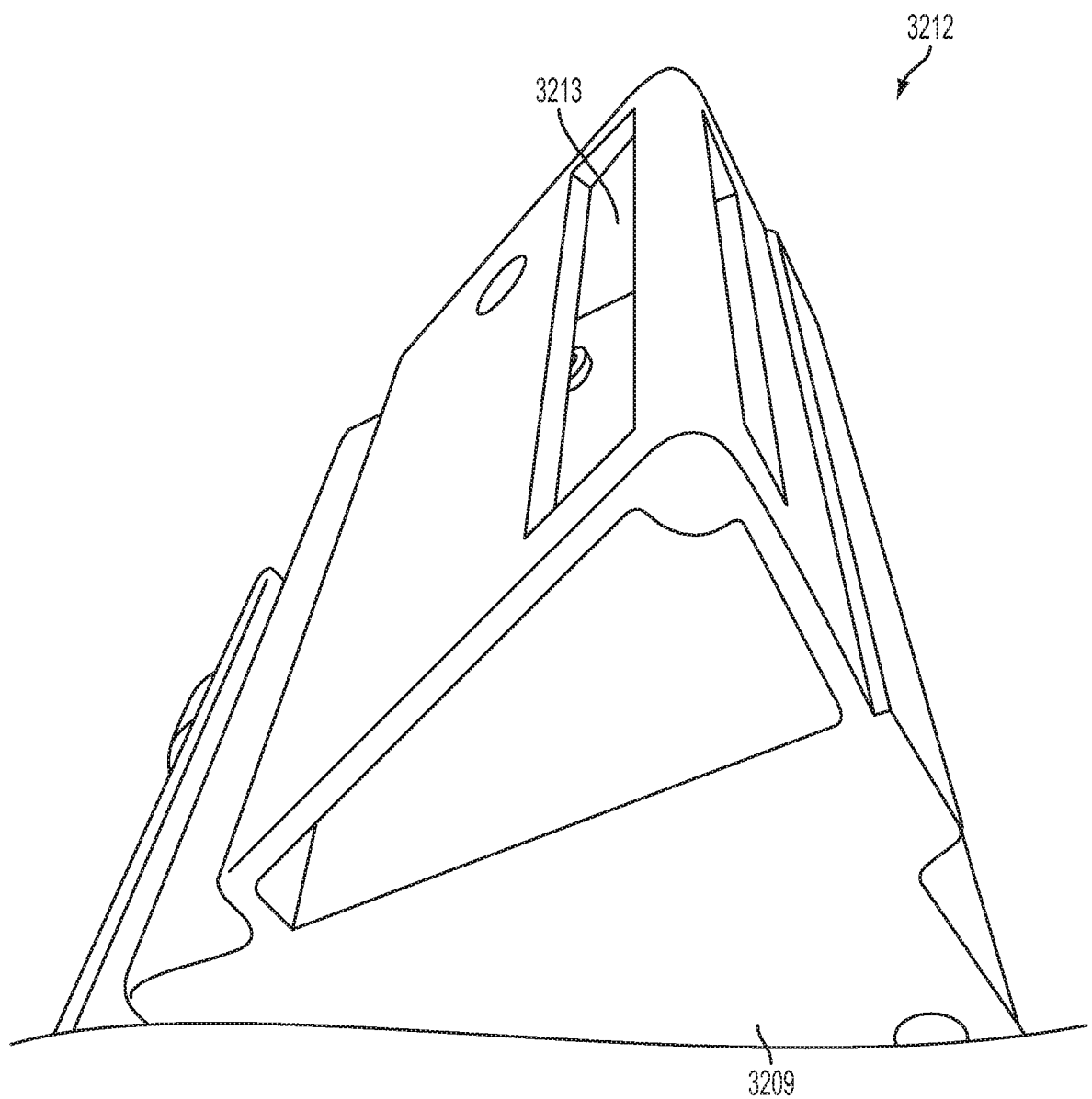
Figure 308:
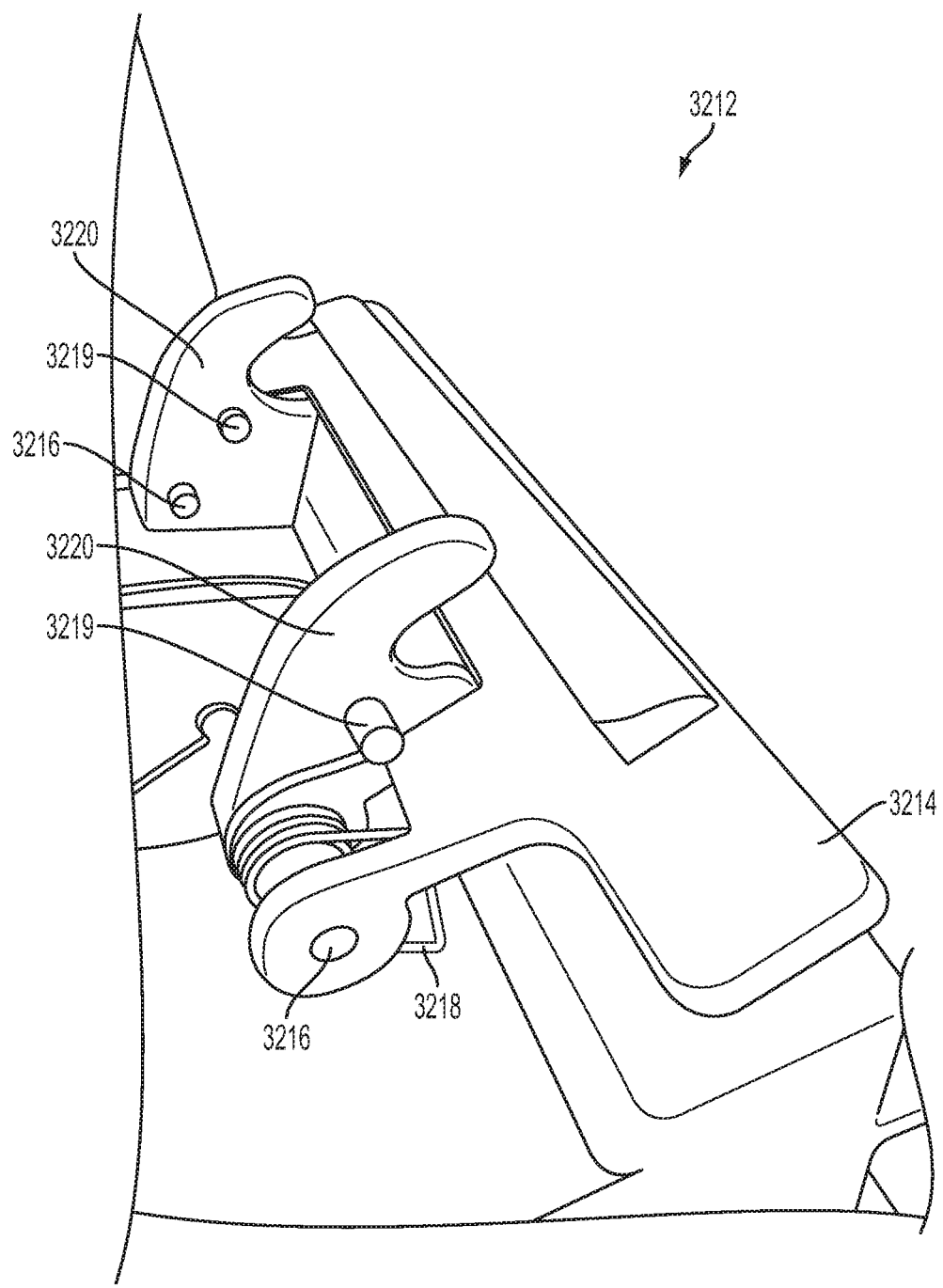
Figure 309:
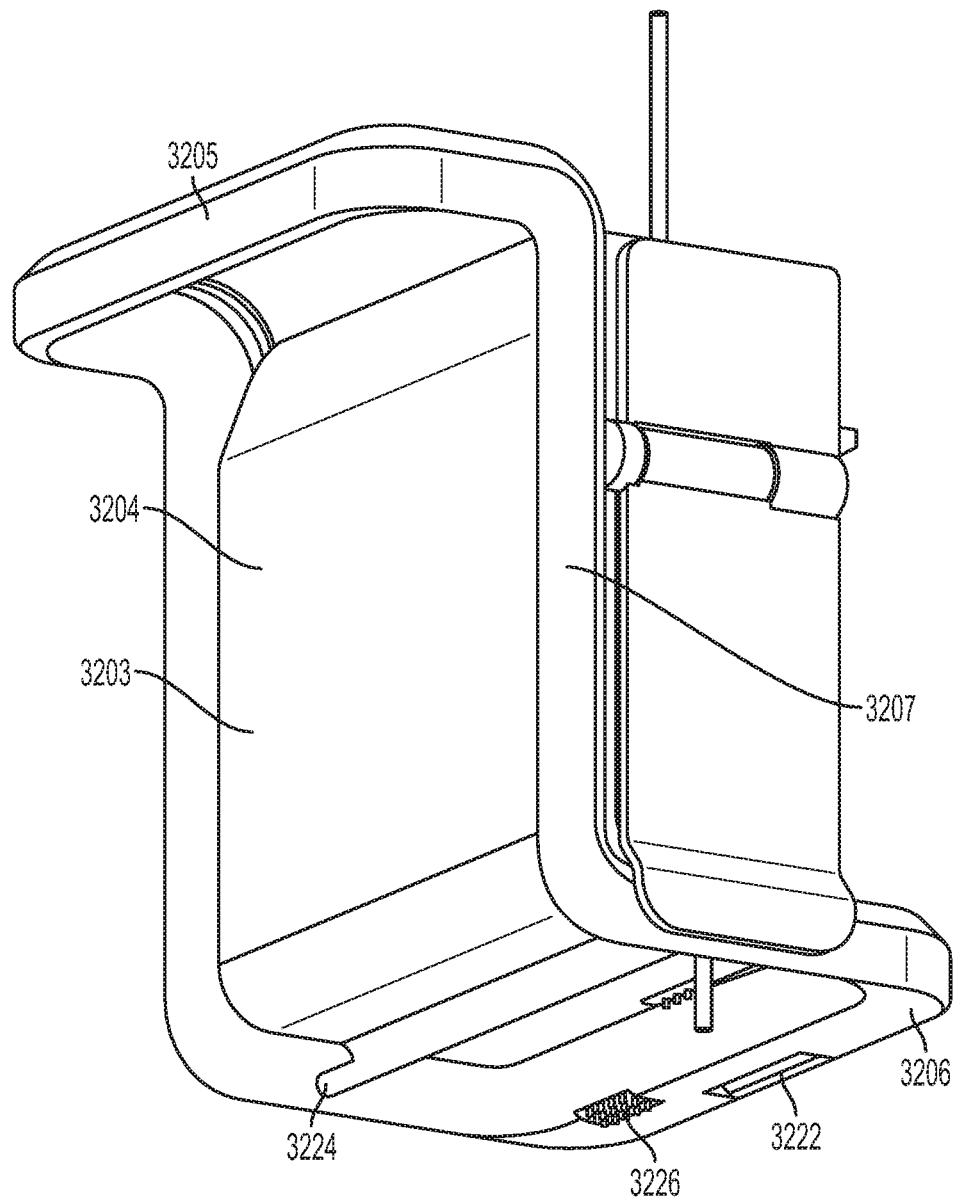
Figure 310:
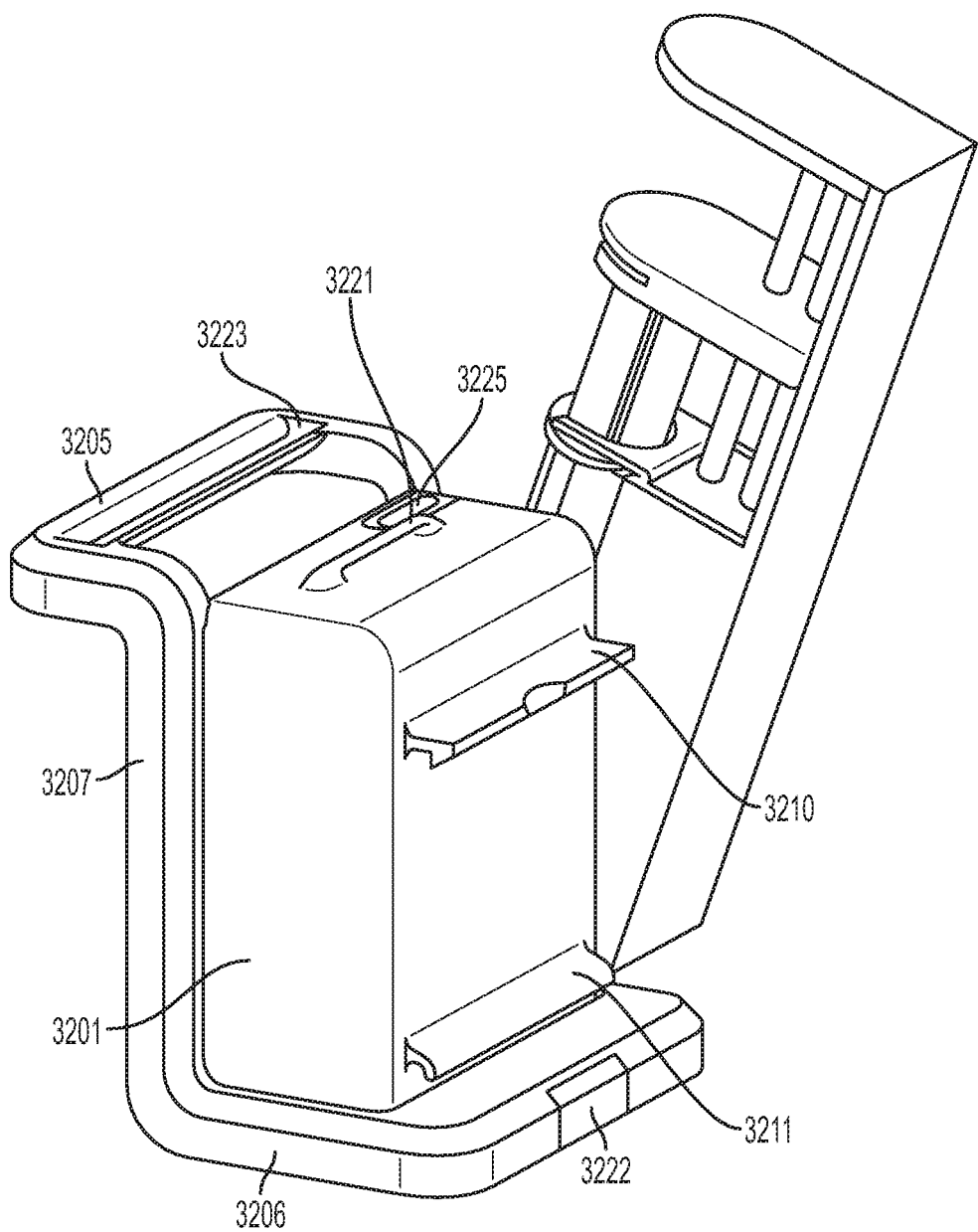
Figure 311:
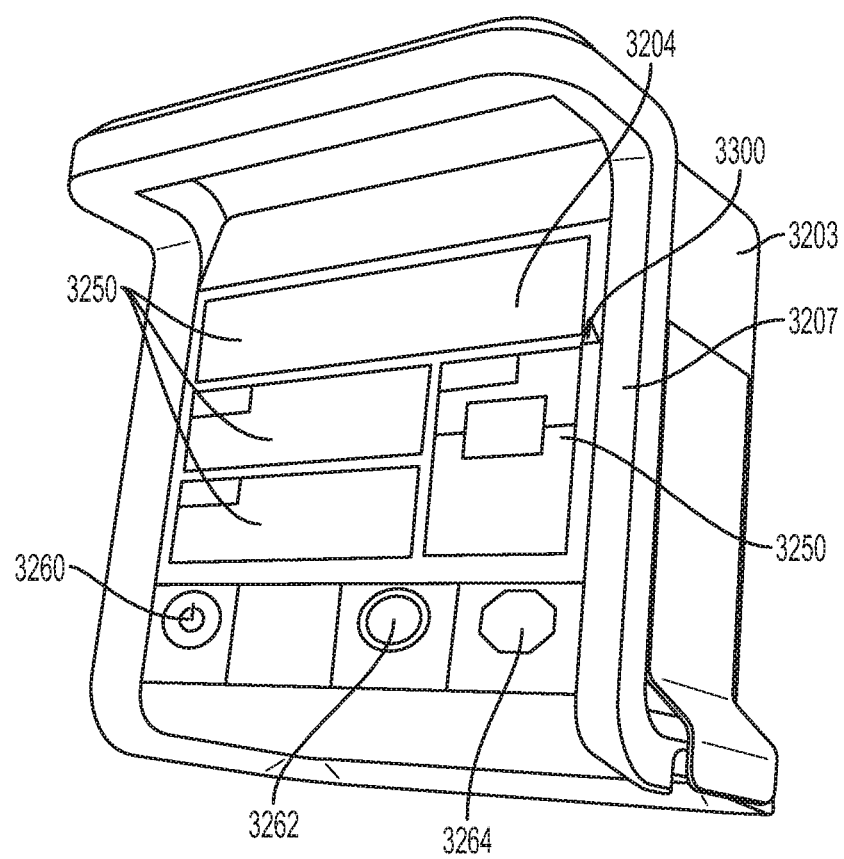
Figure 312:
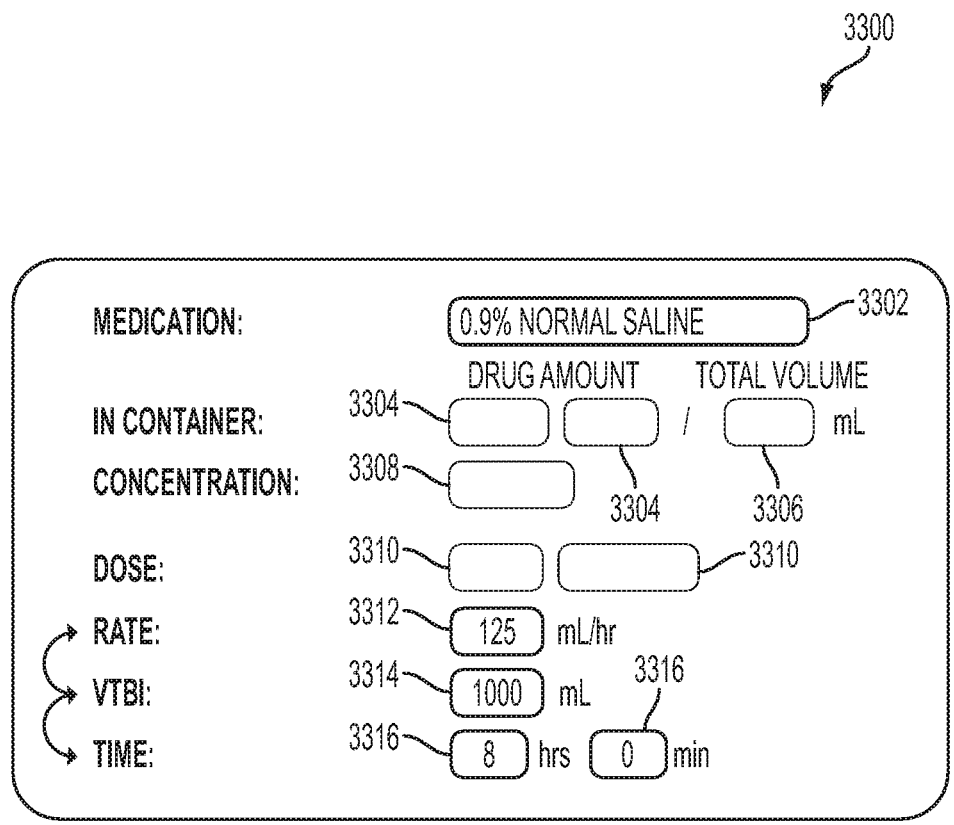
Figure 313:
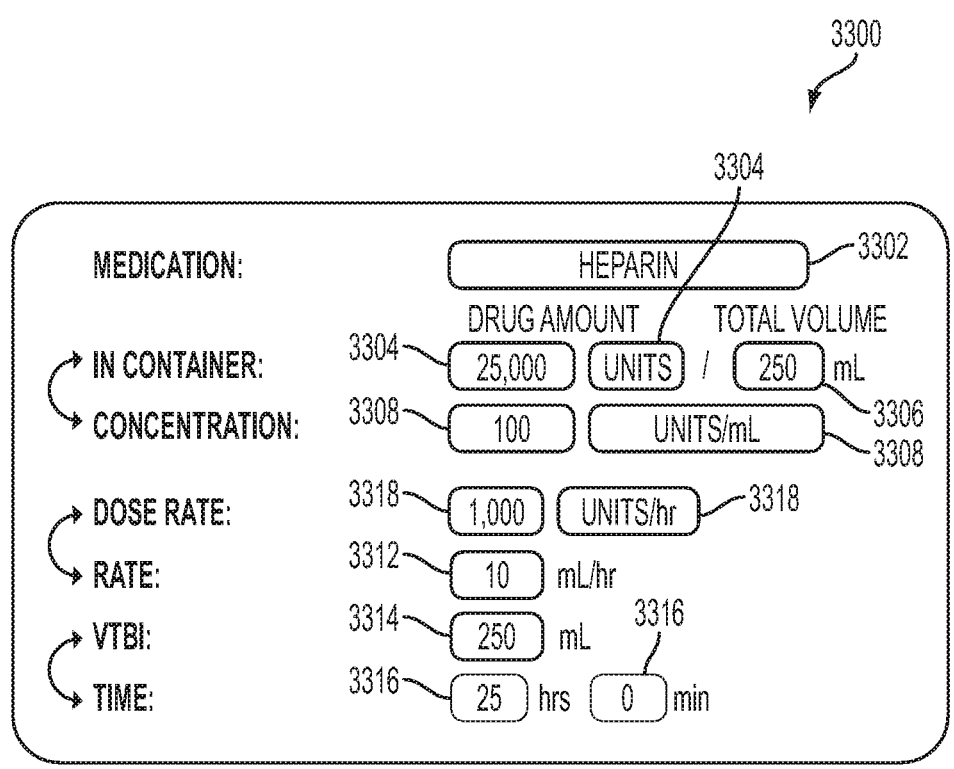
Figure 314:
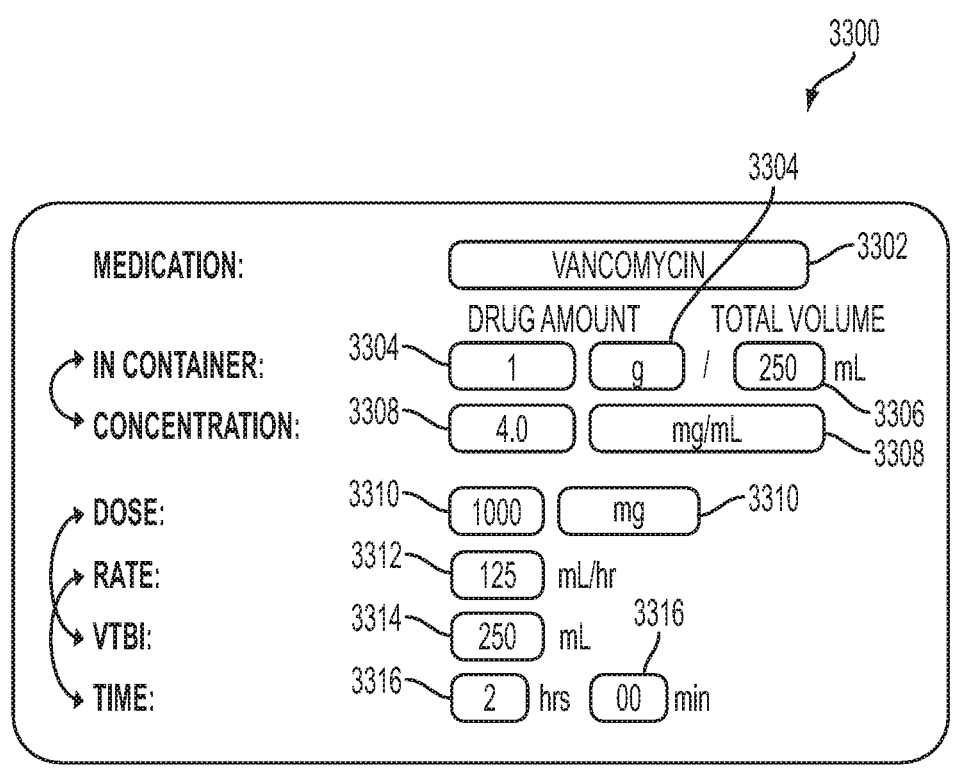
Figure 315:
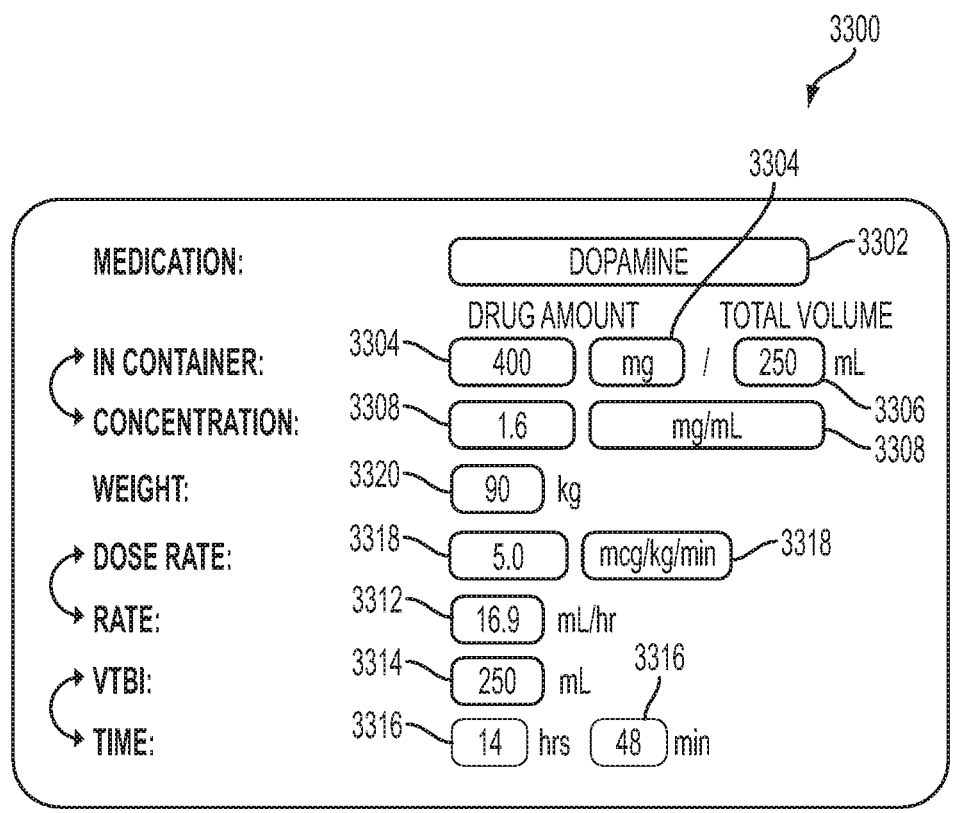
Figure 316:
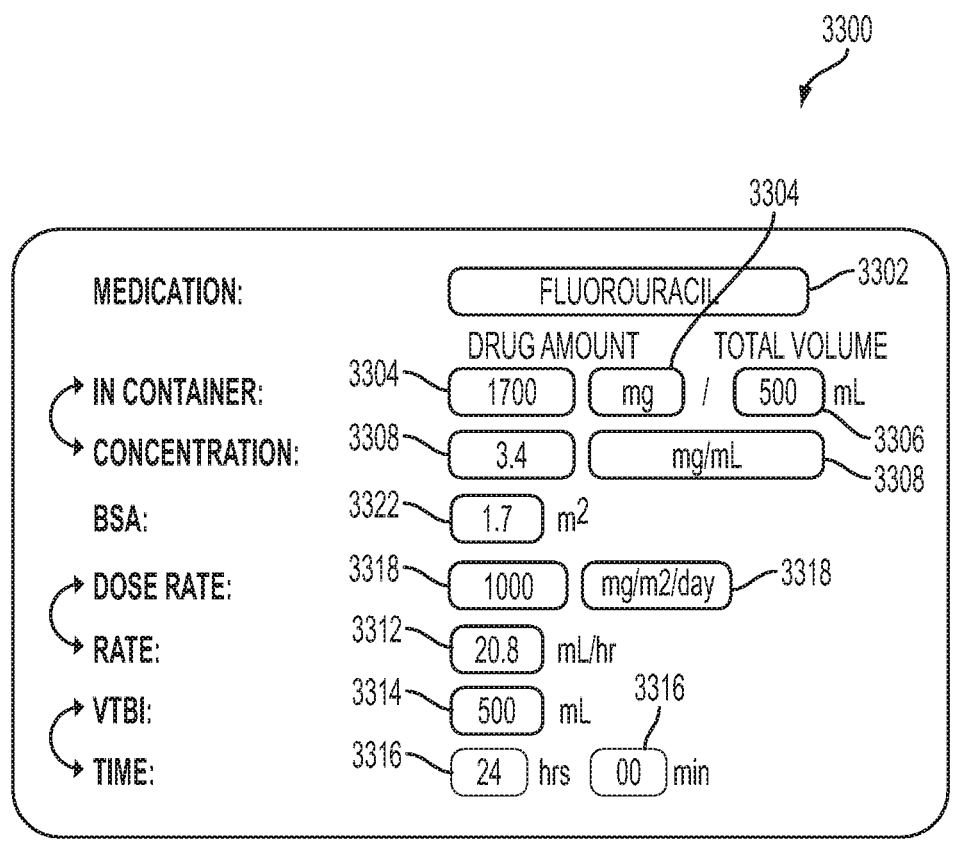
Figure 317:
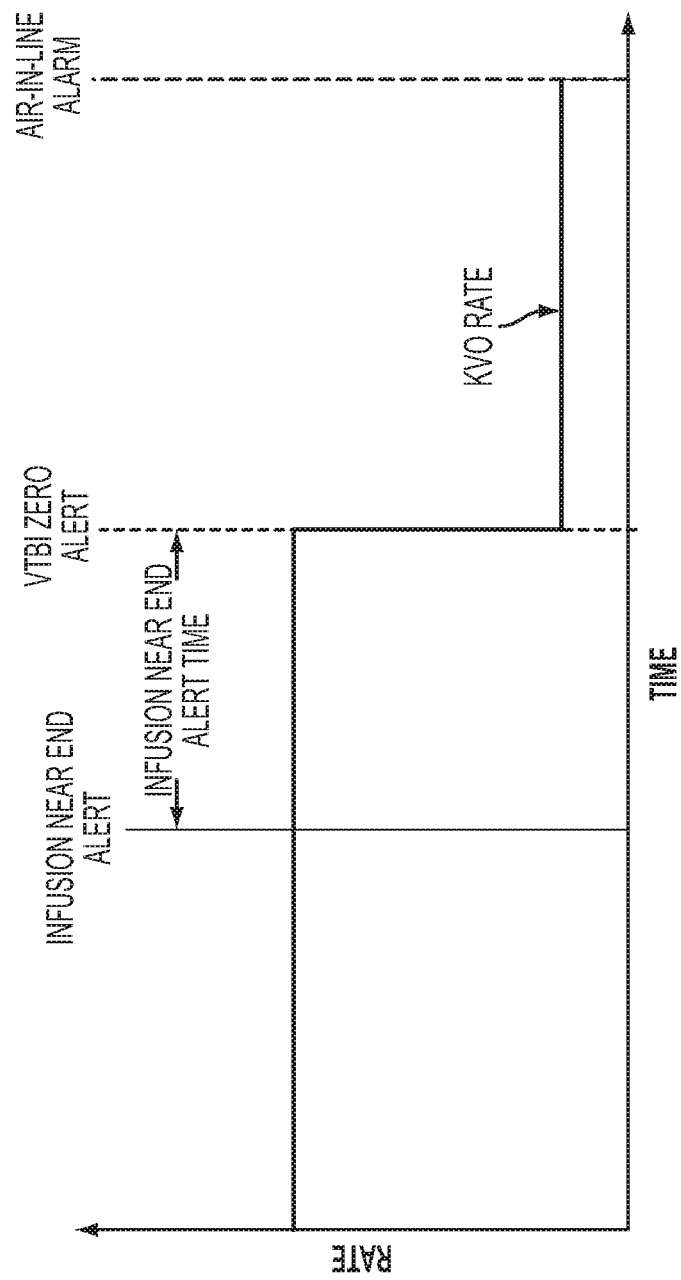
Figure 318:
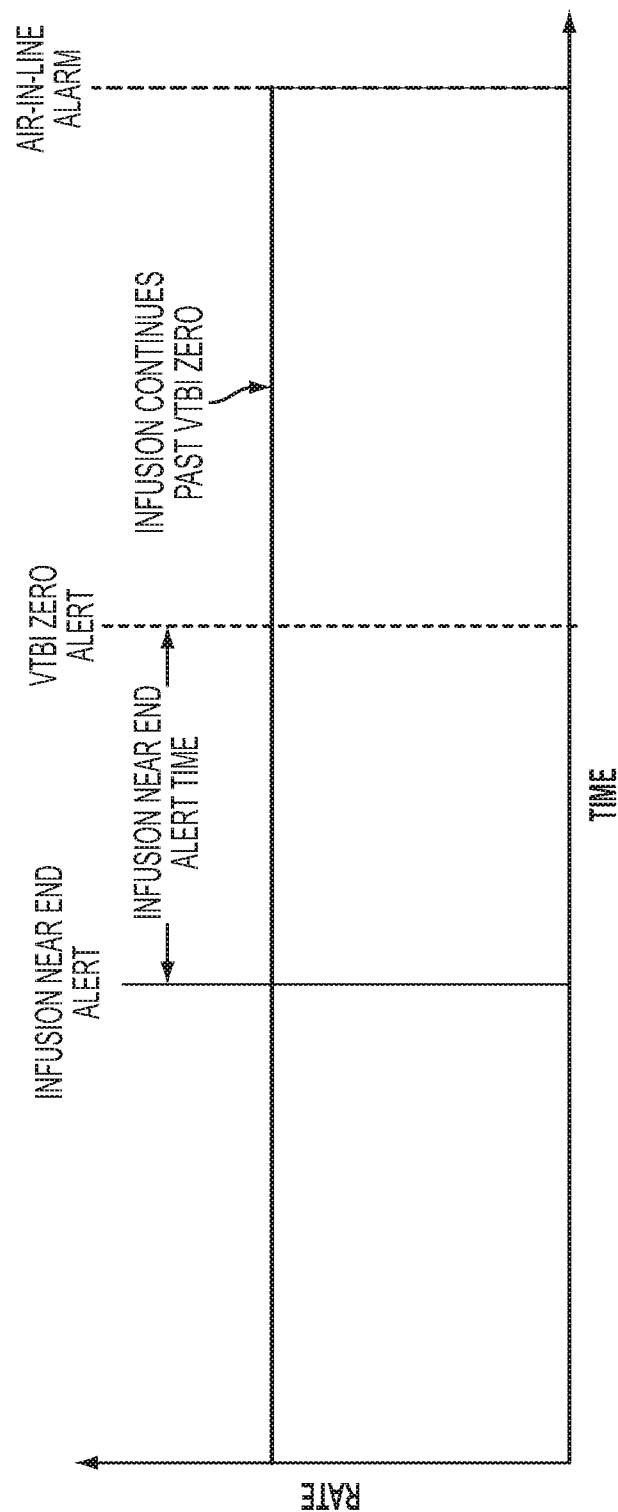
Figure 319:
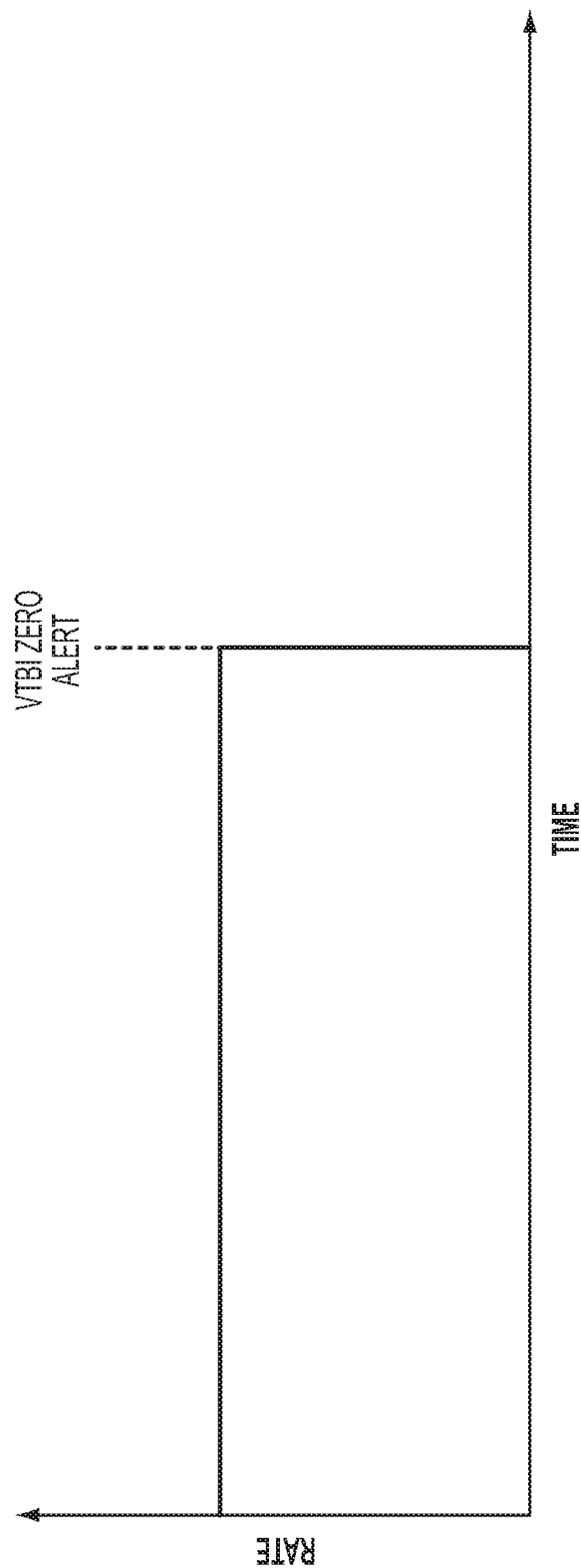
Figure 320:
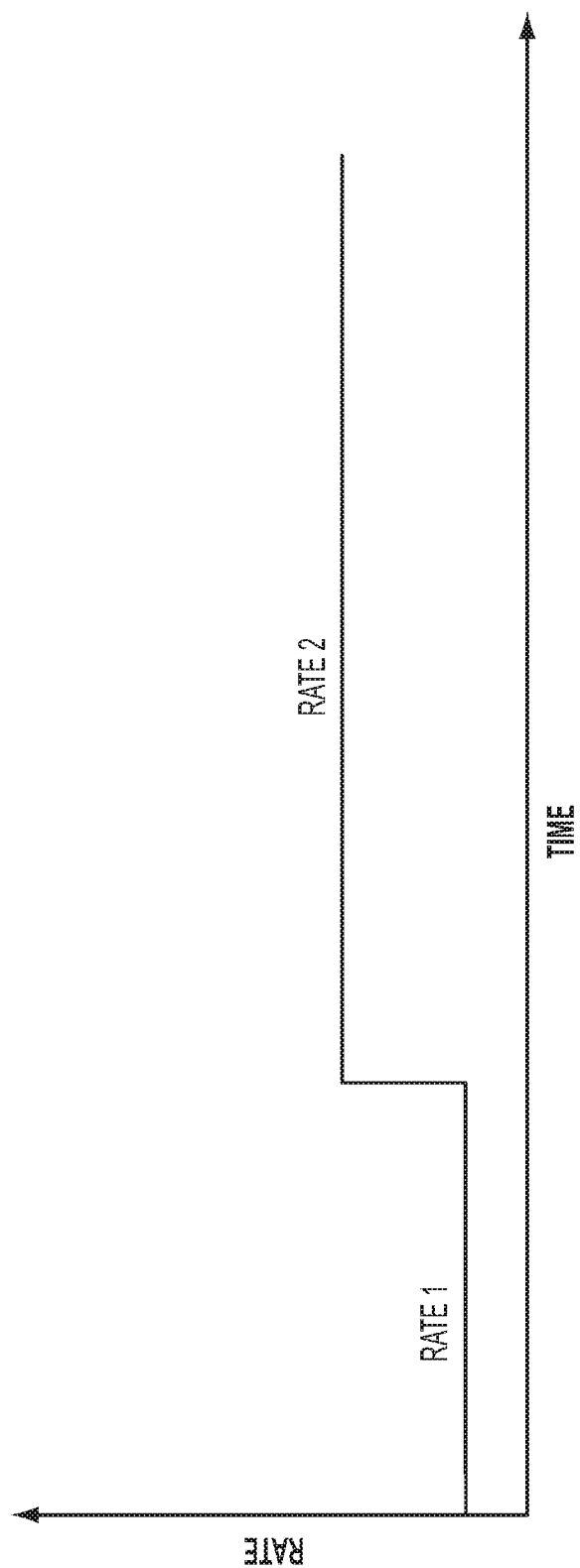
Figure 321:
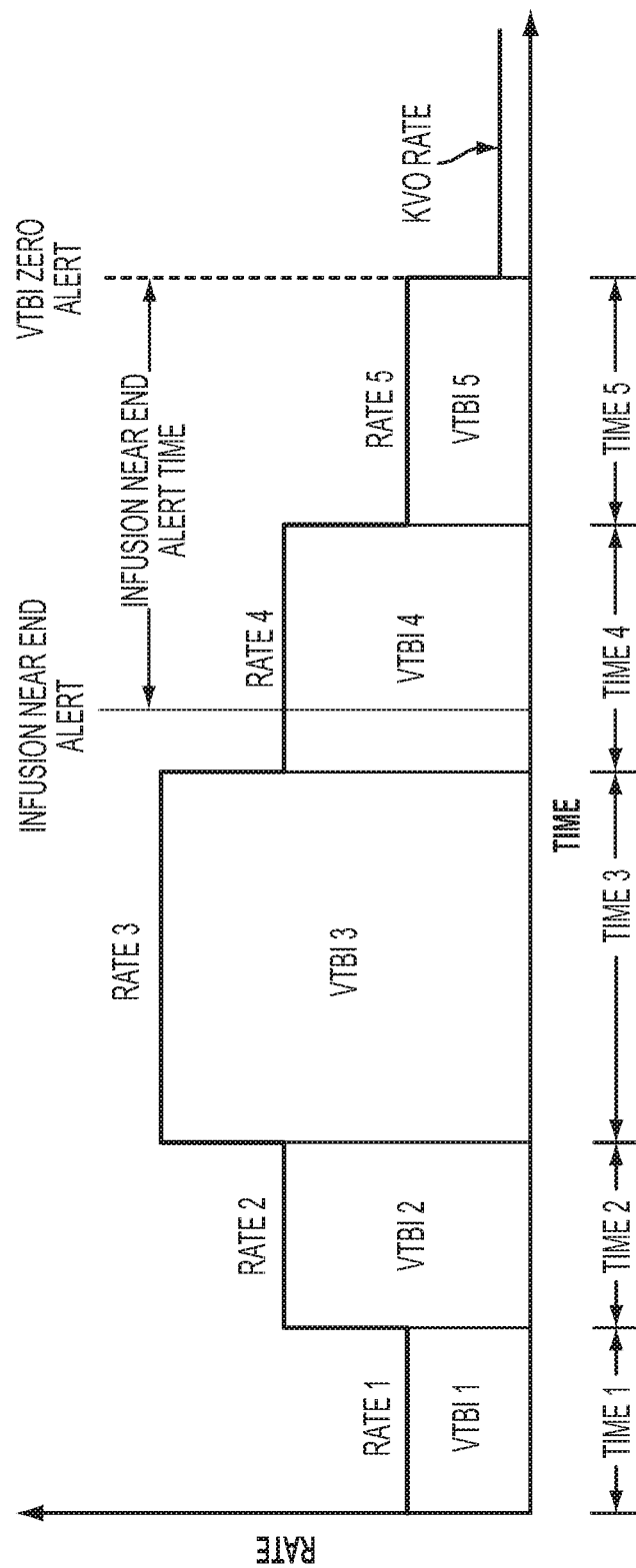
Figure 322:
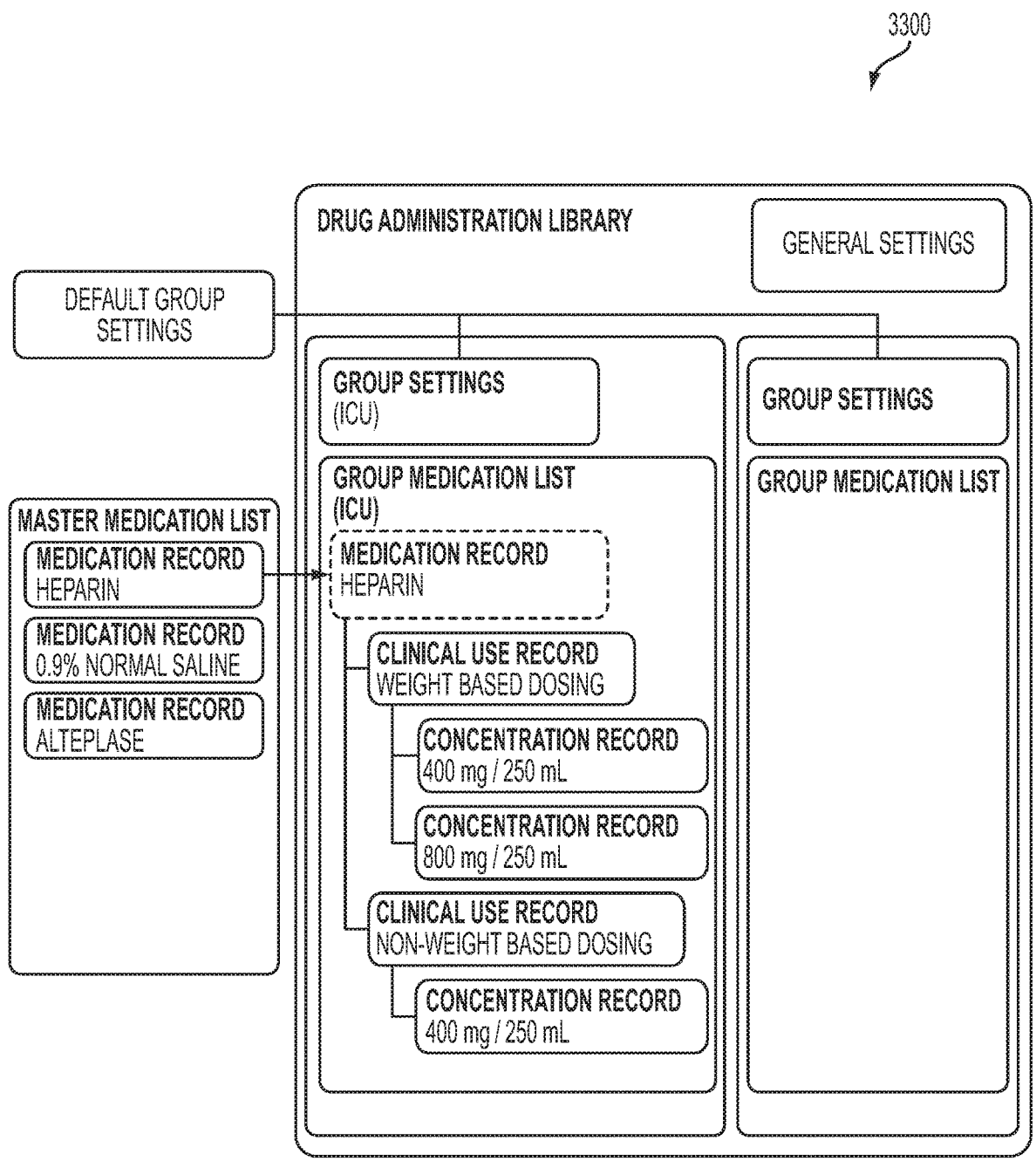
Figure 323:
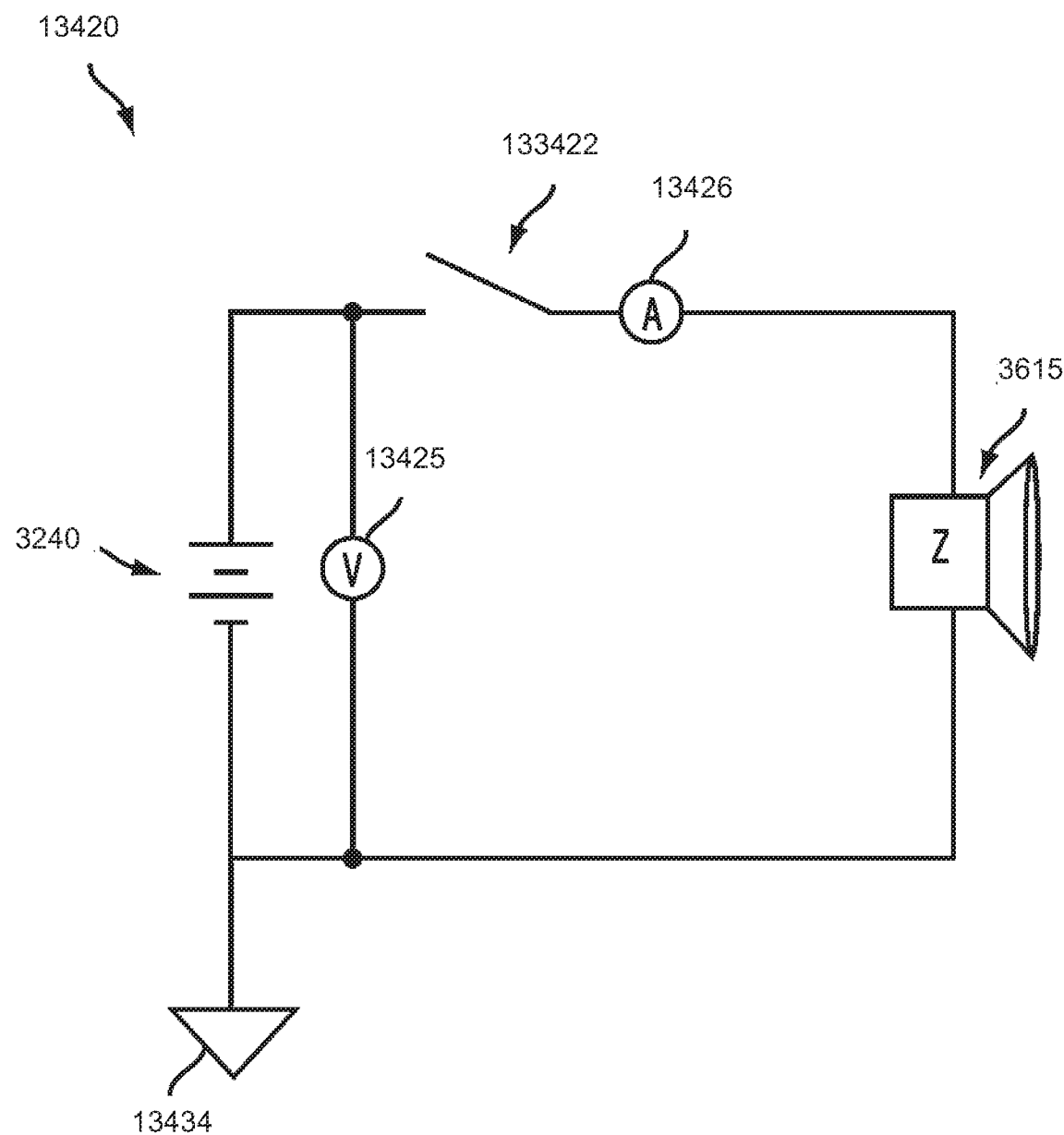
Figure 324:
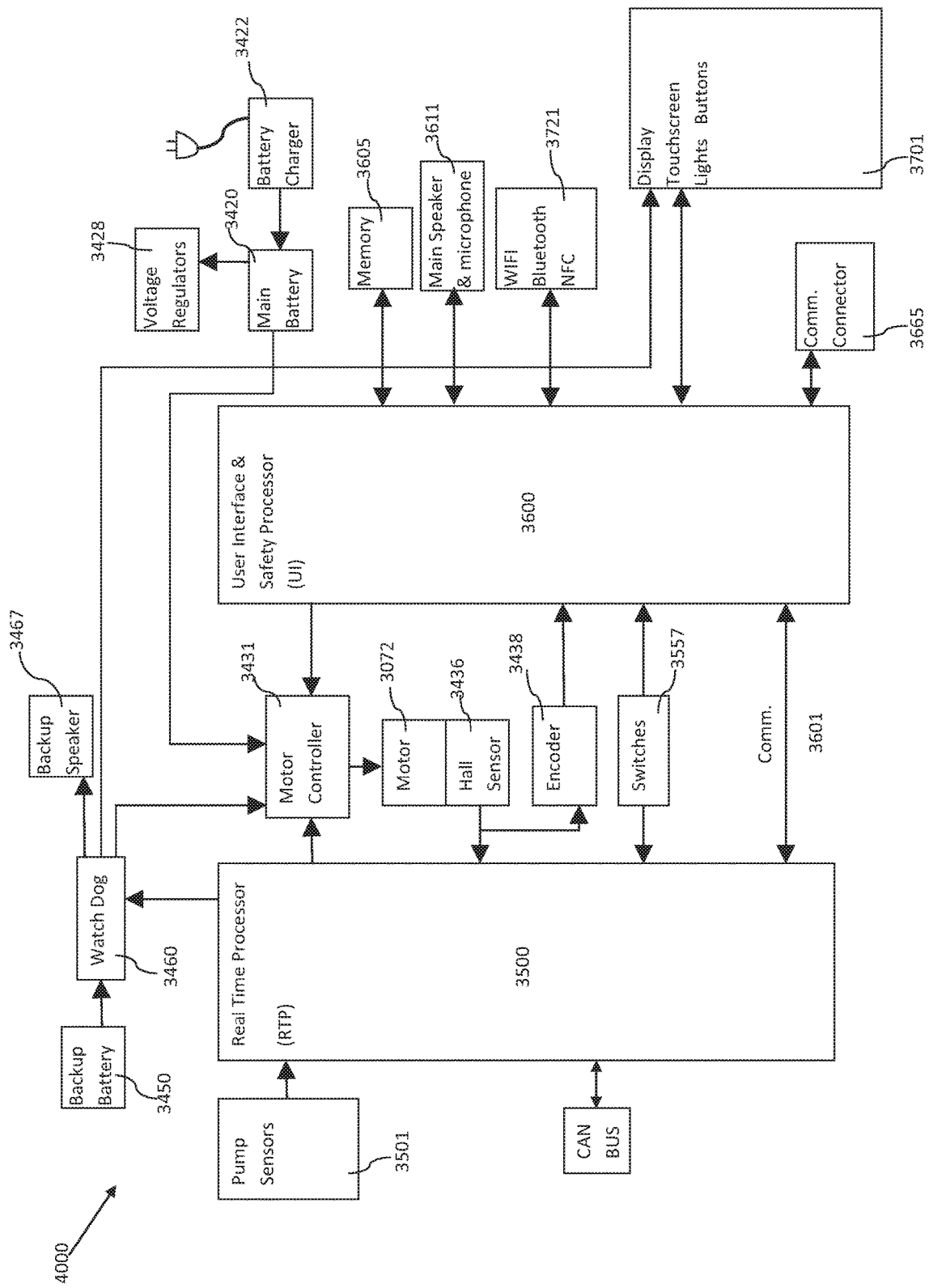
Figure 326:
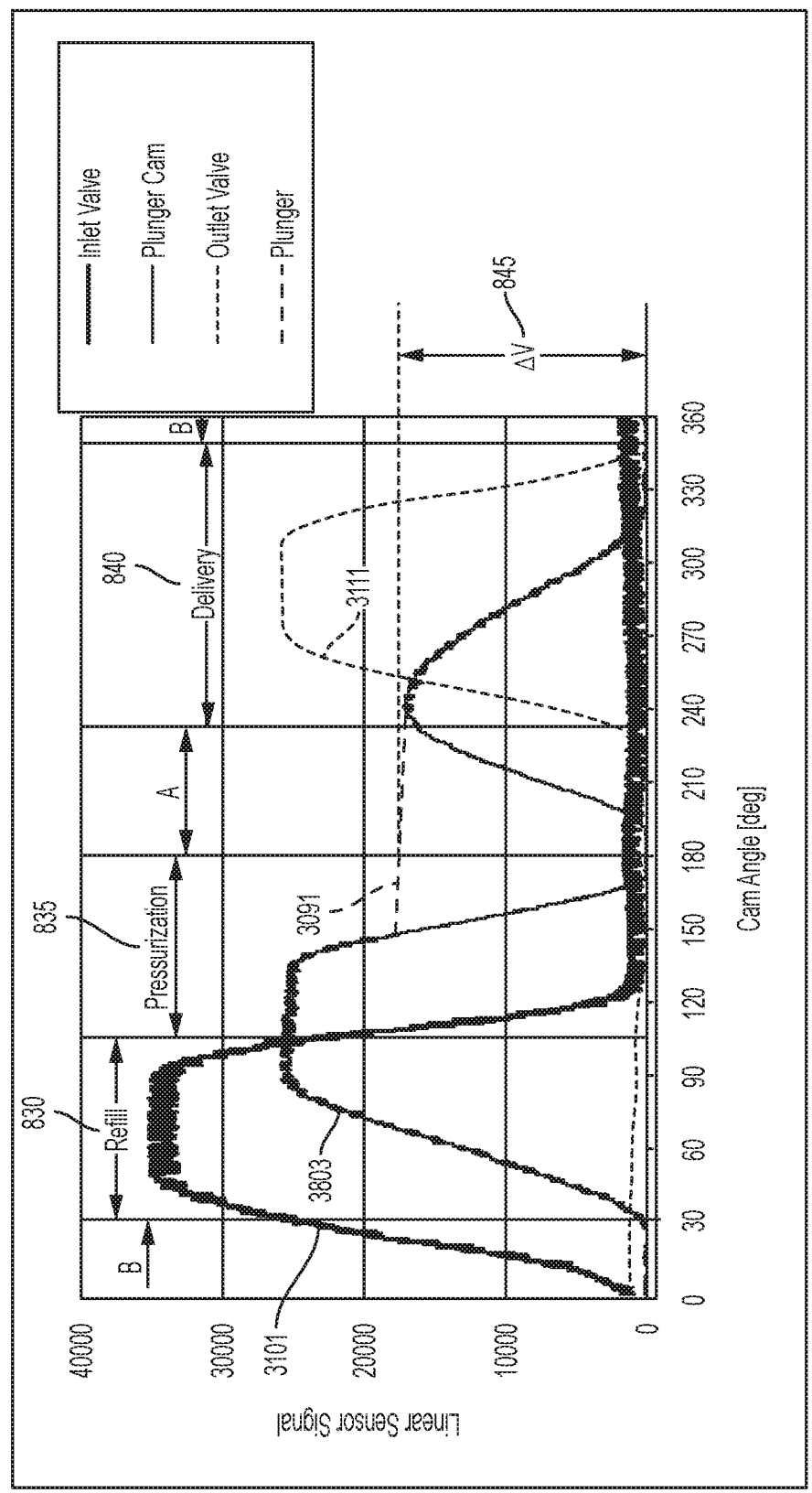
Figure 327:
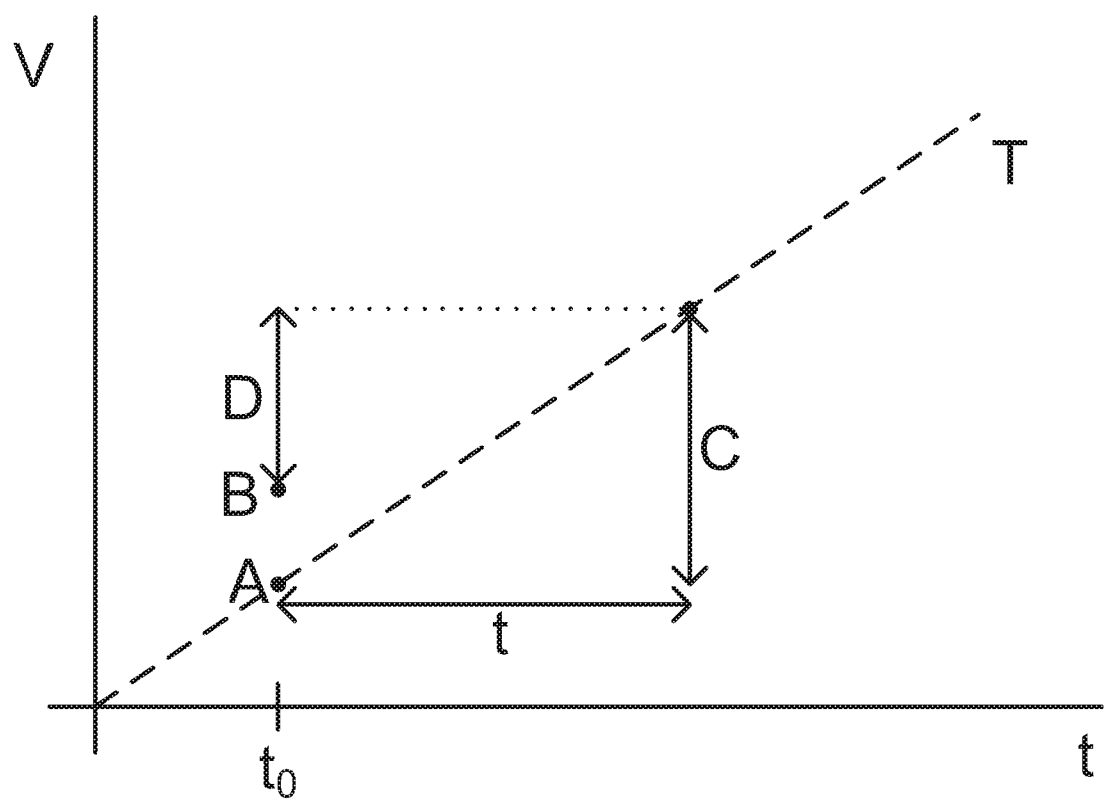
Figure 328:
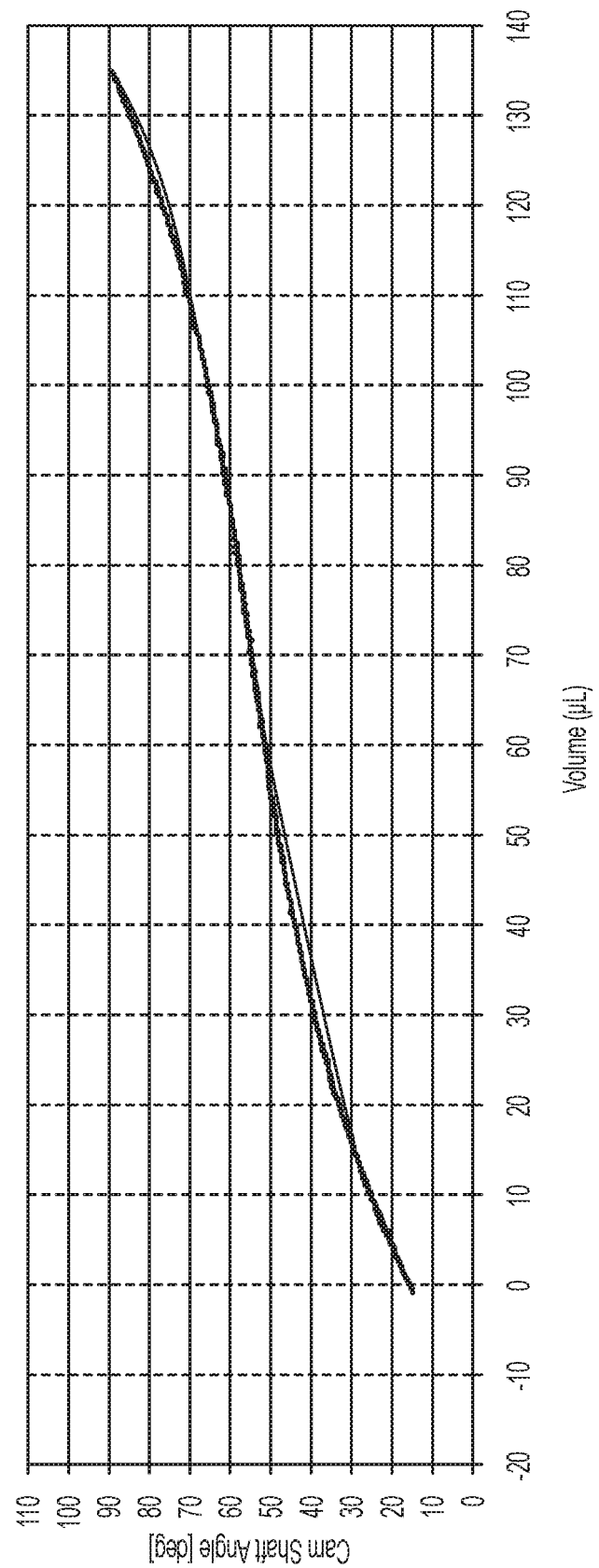
Figure 329:
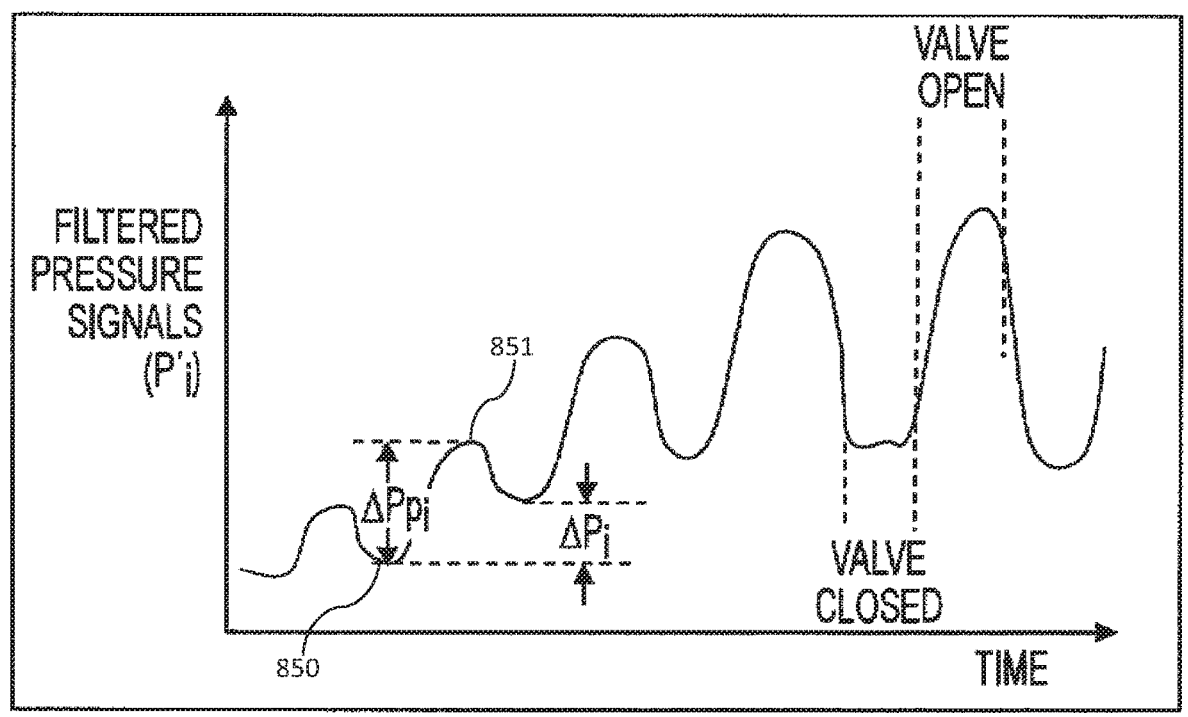
Figure 330:
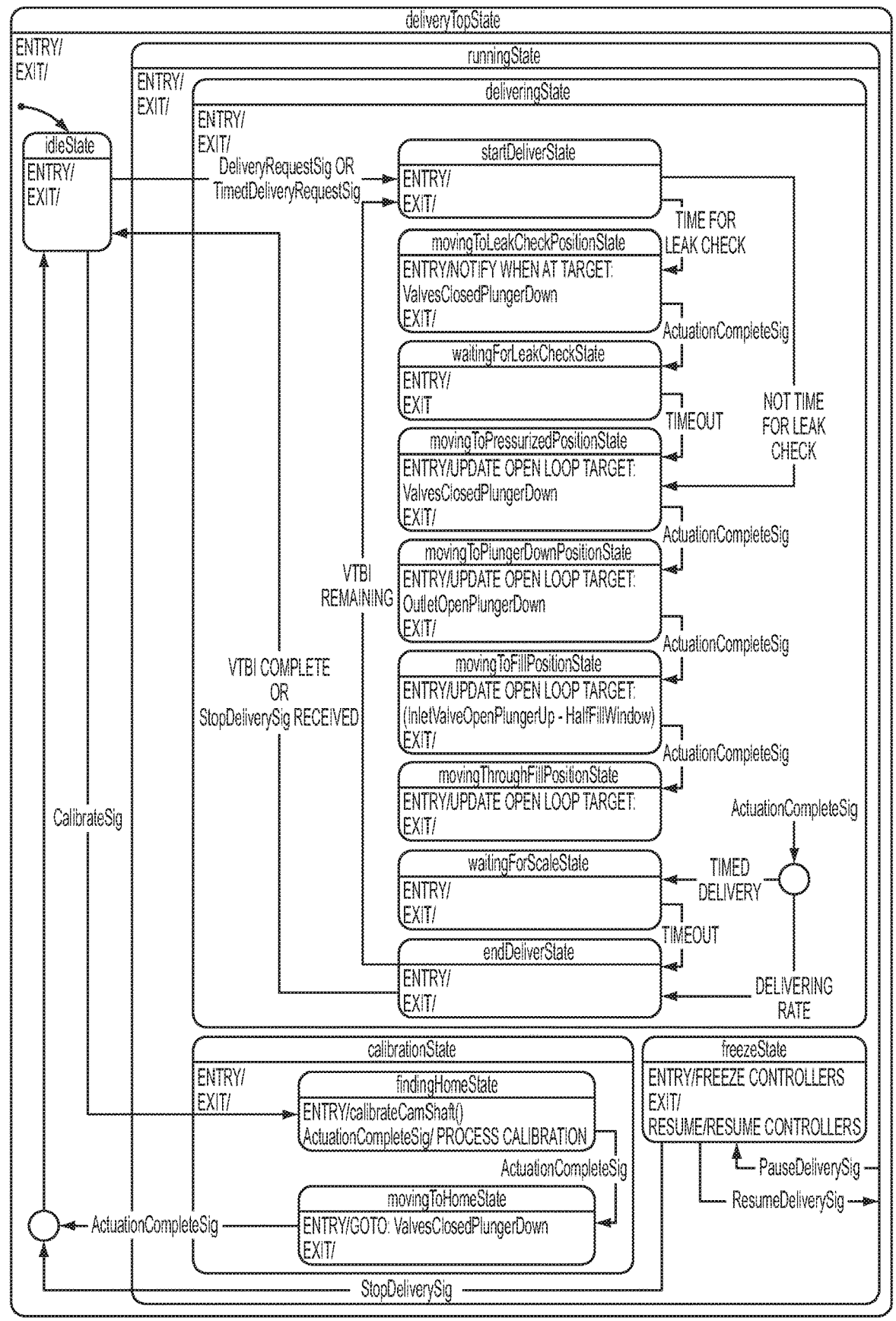
Figure 331:
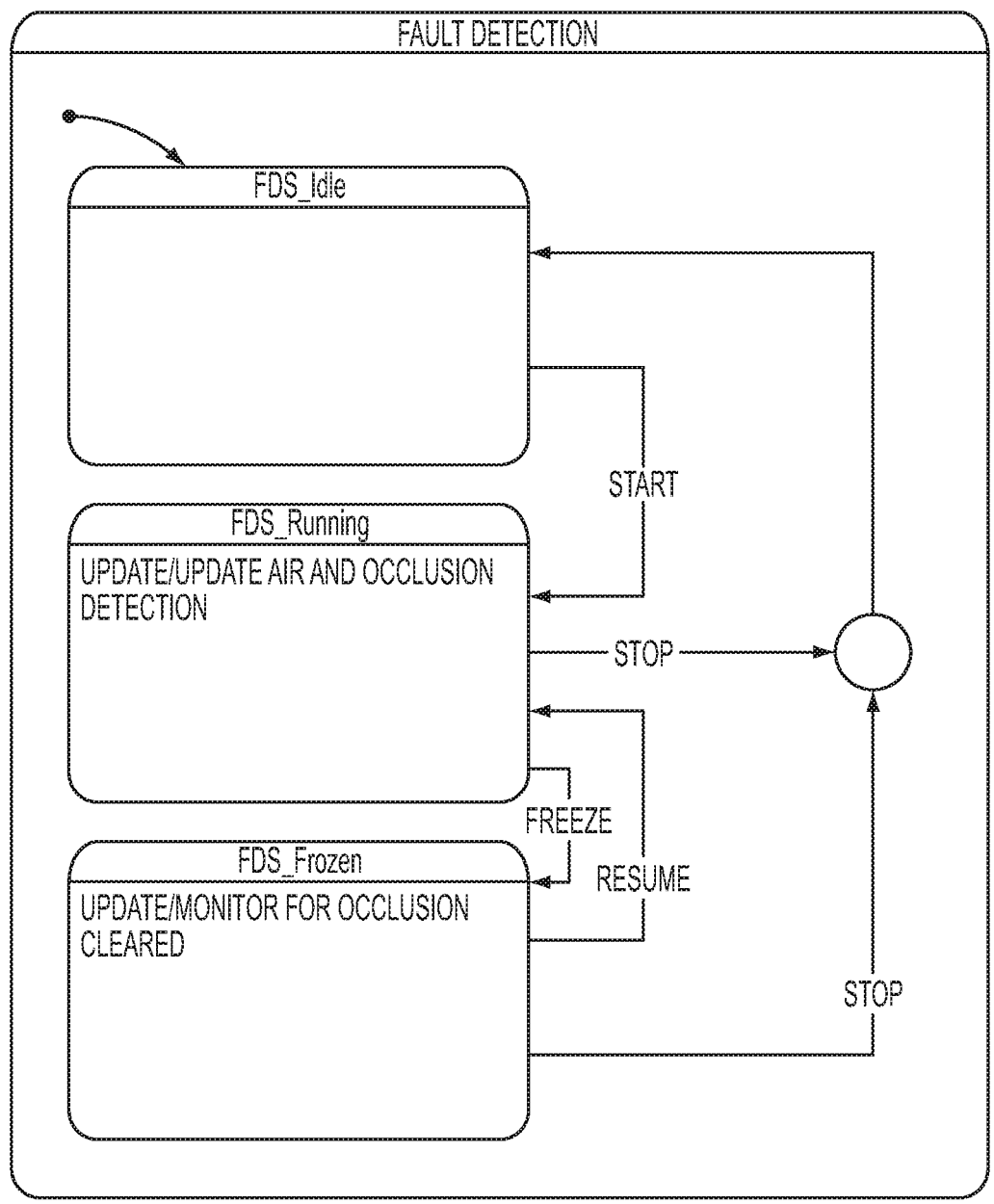
Figure 332:
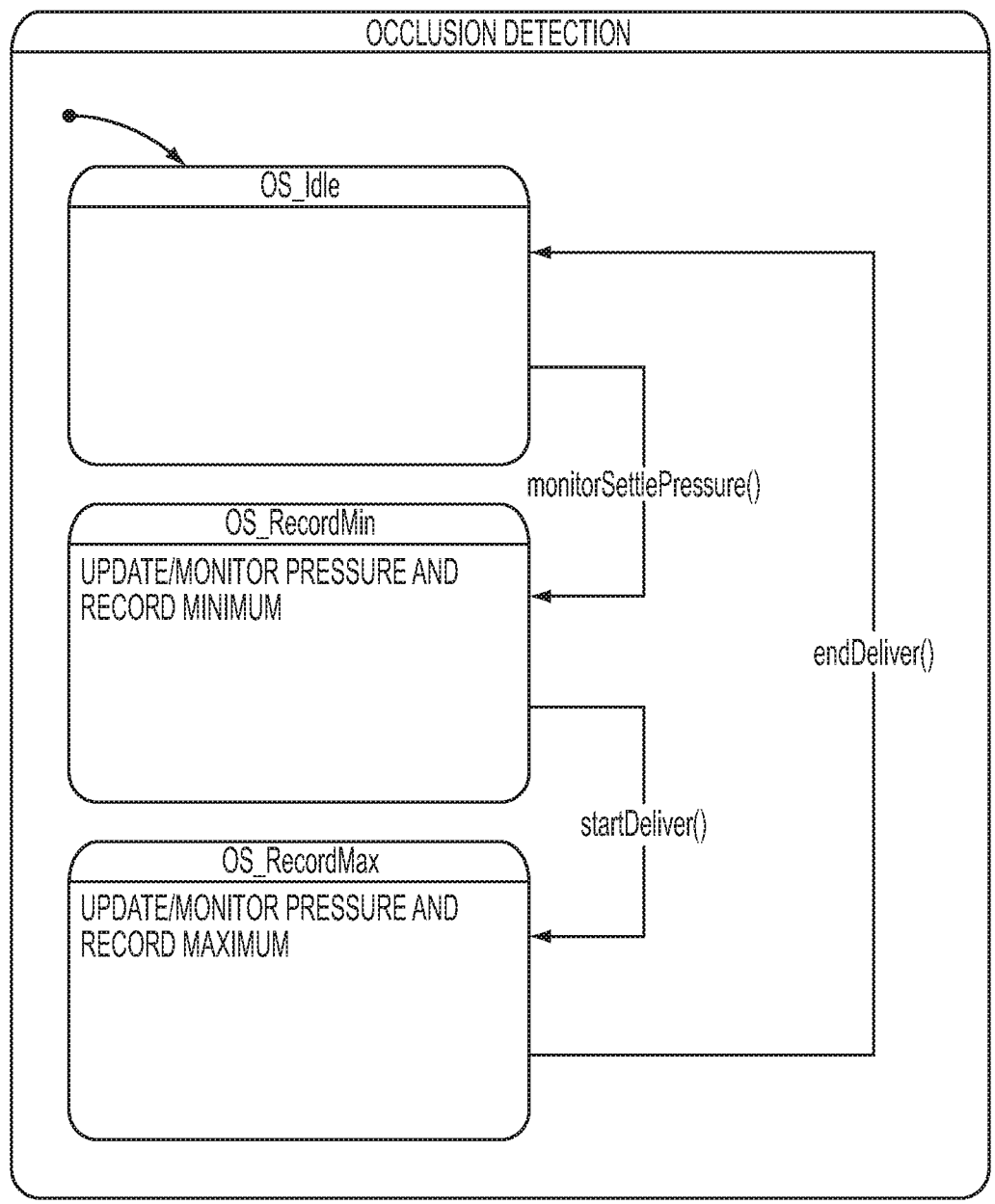
Figure 333:
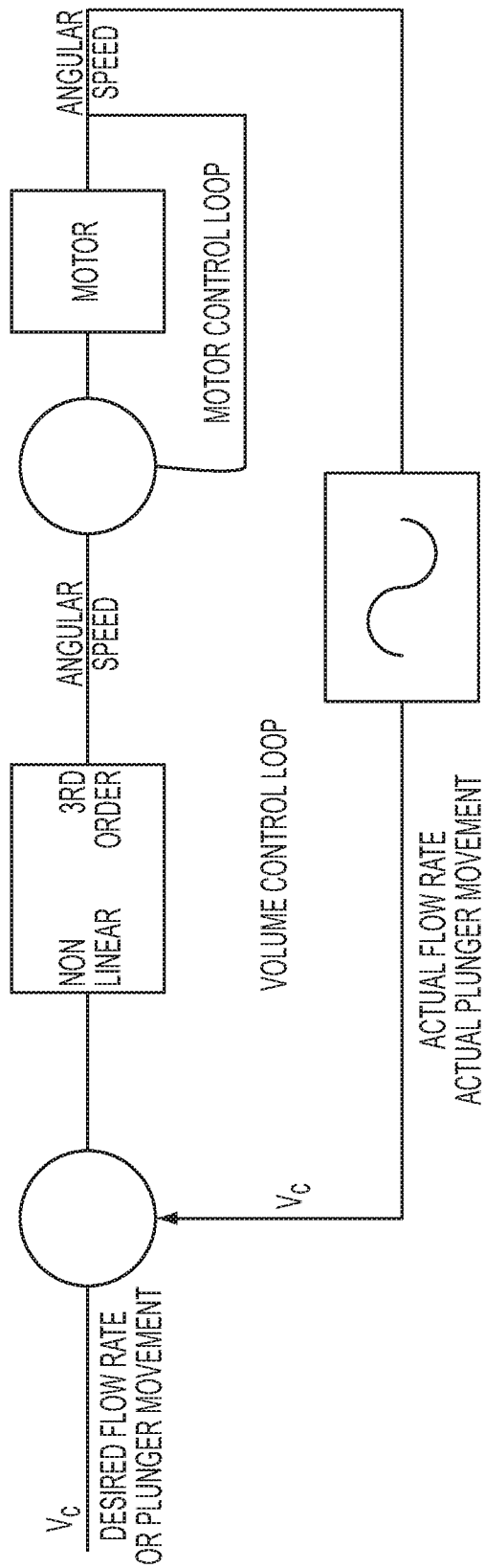
Figure 334:
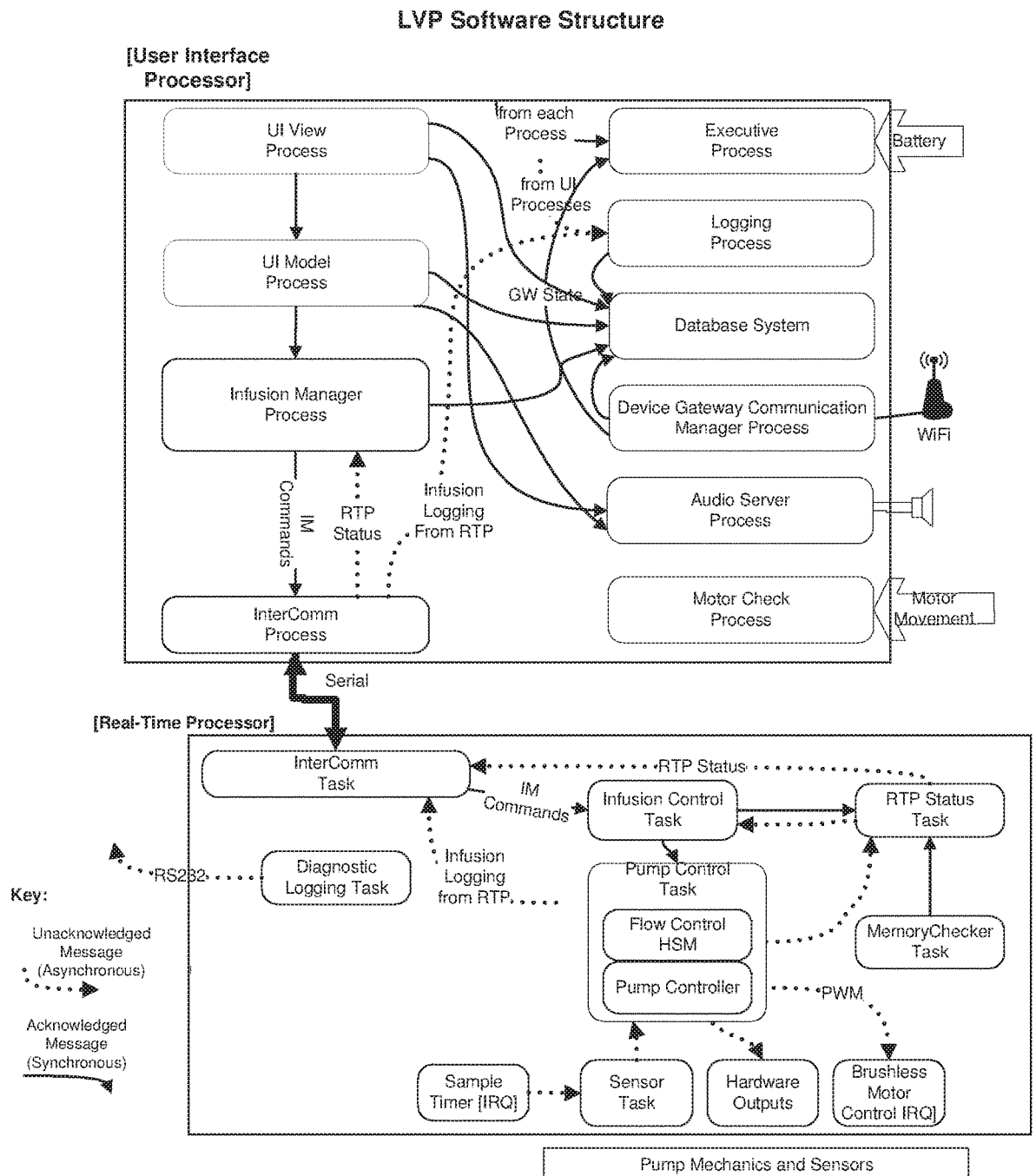
Figure 335:
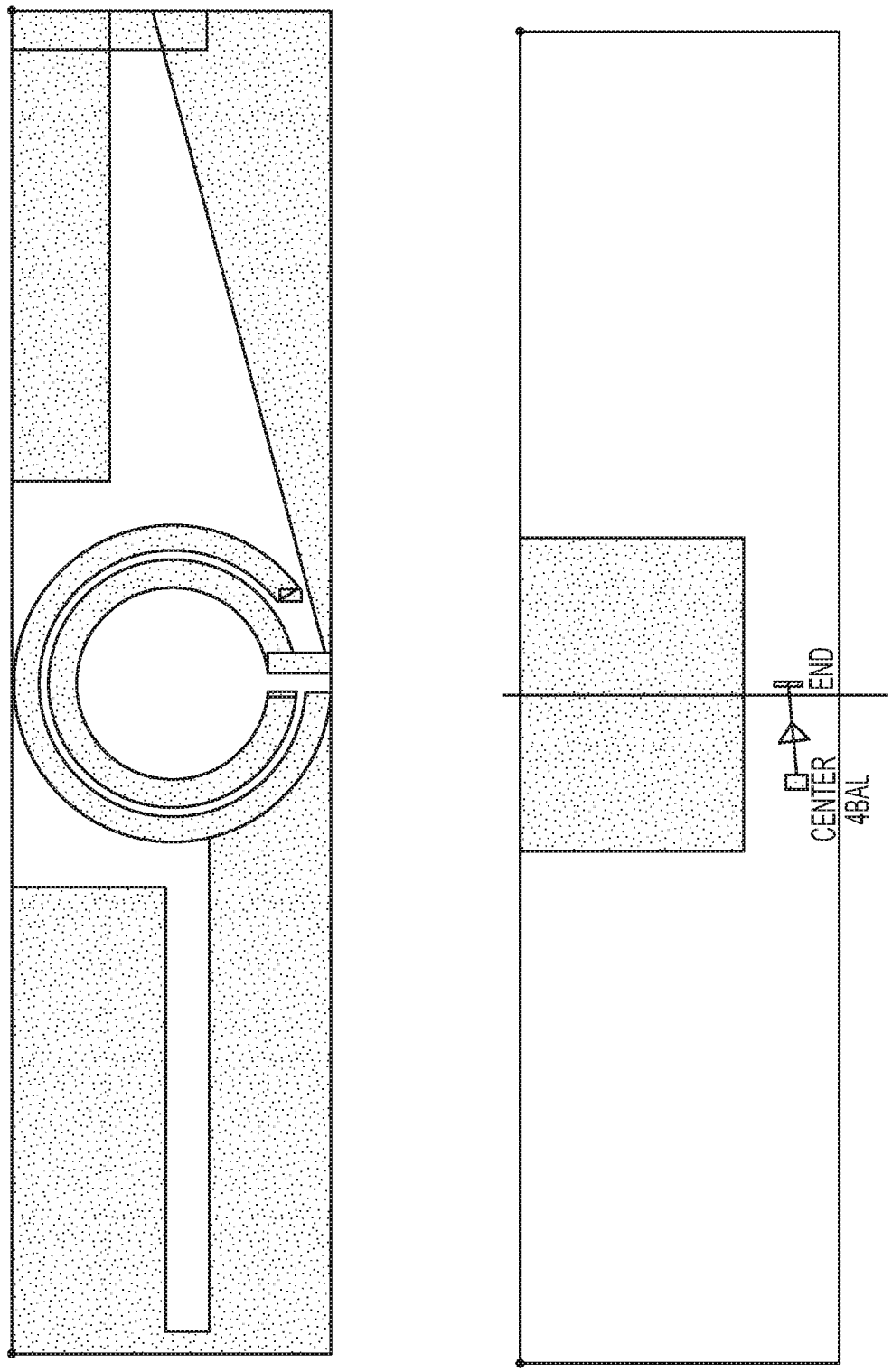
Figure 336:
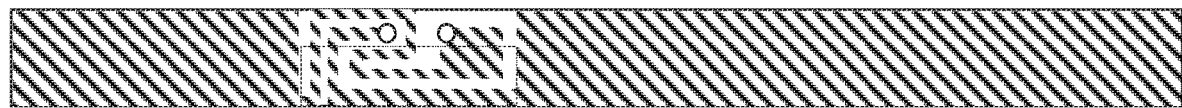
Figure 337:
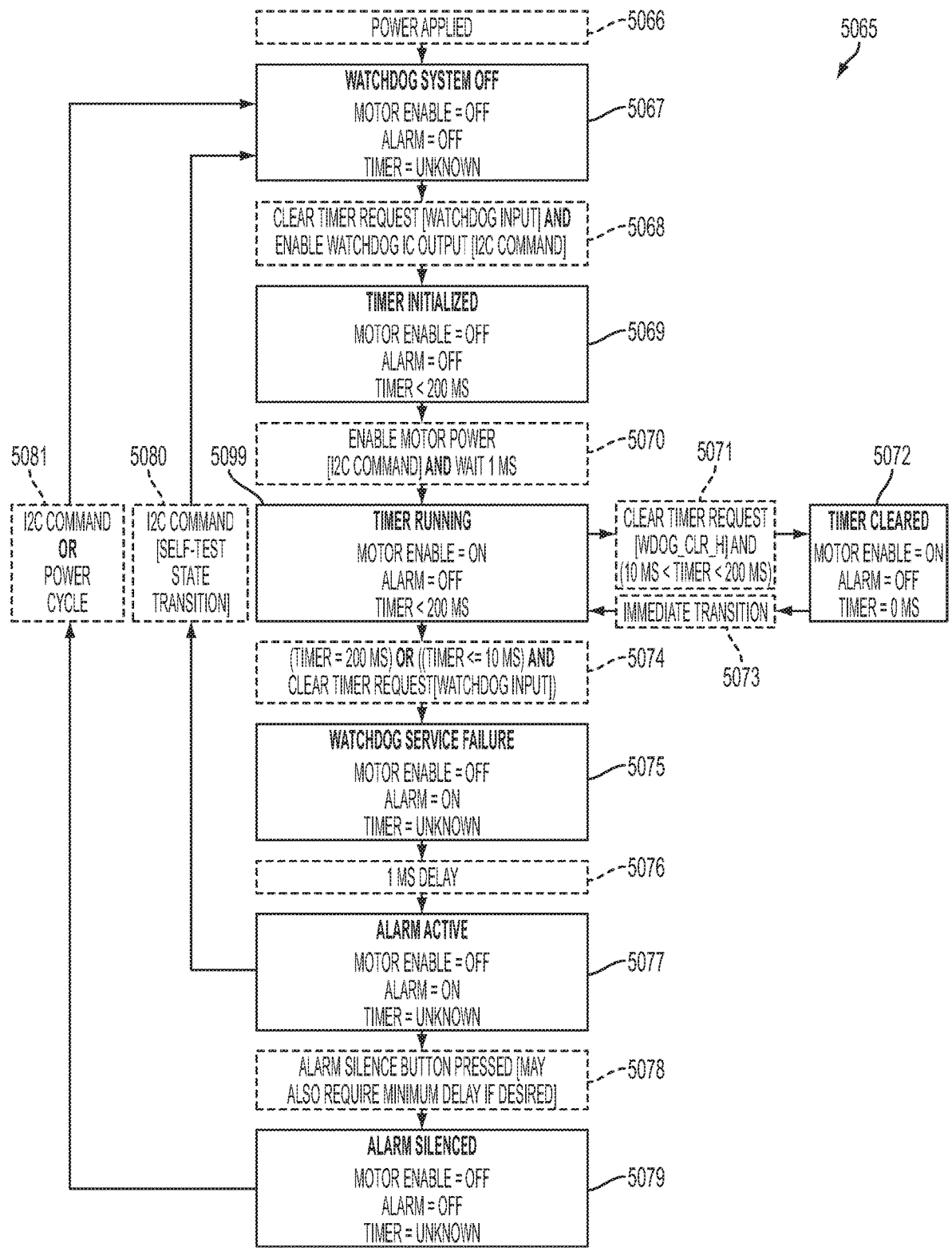
Figure 338A:
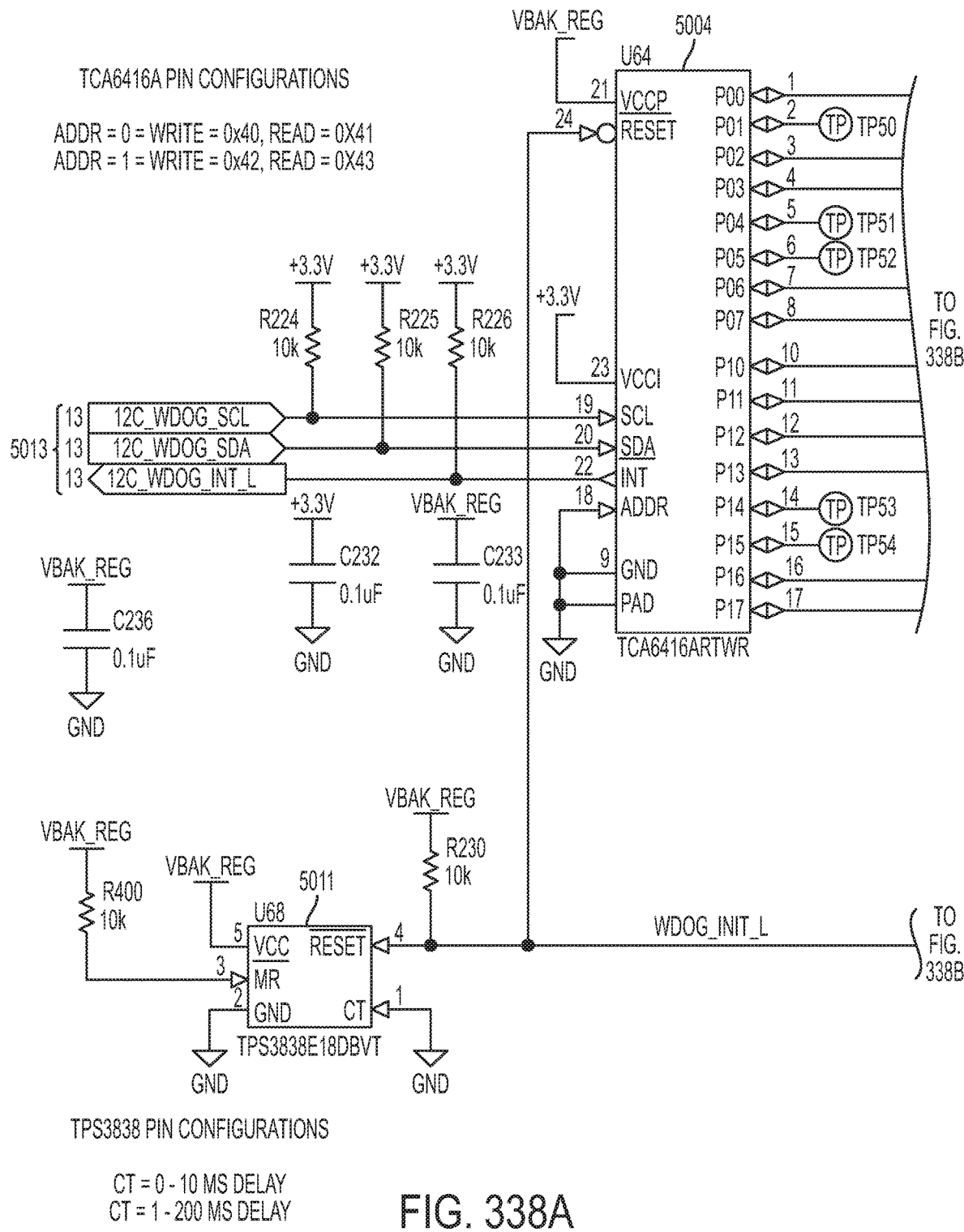
Figure 338B:
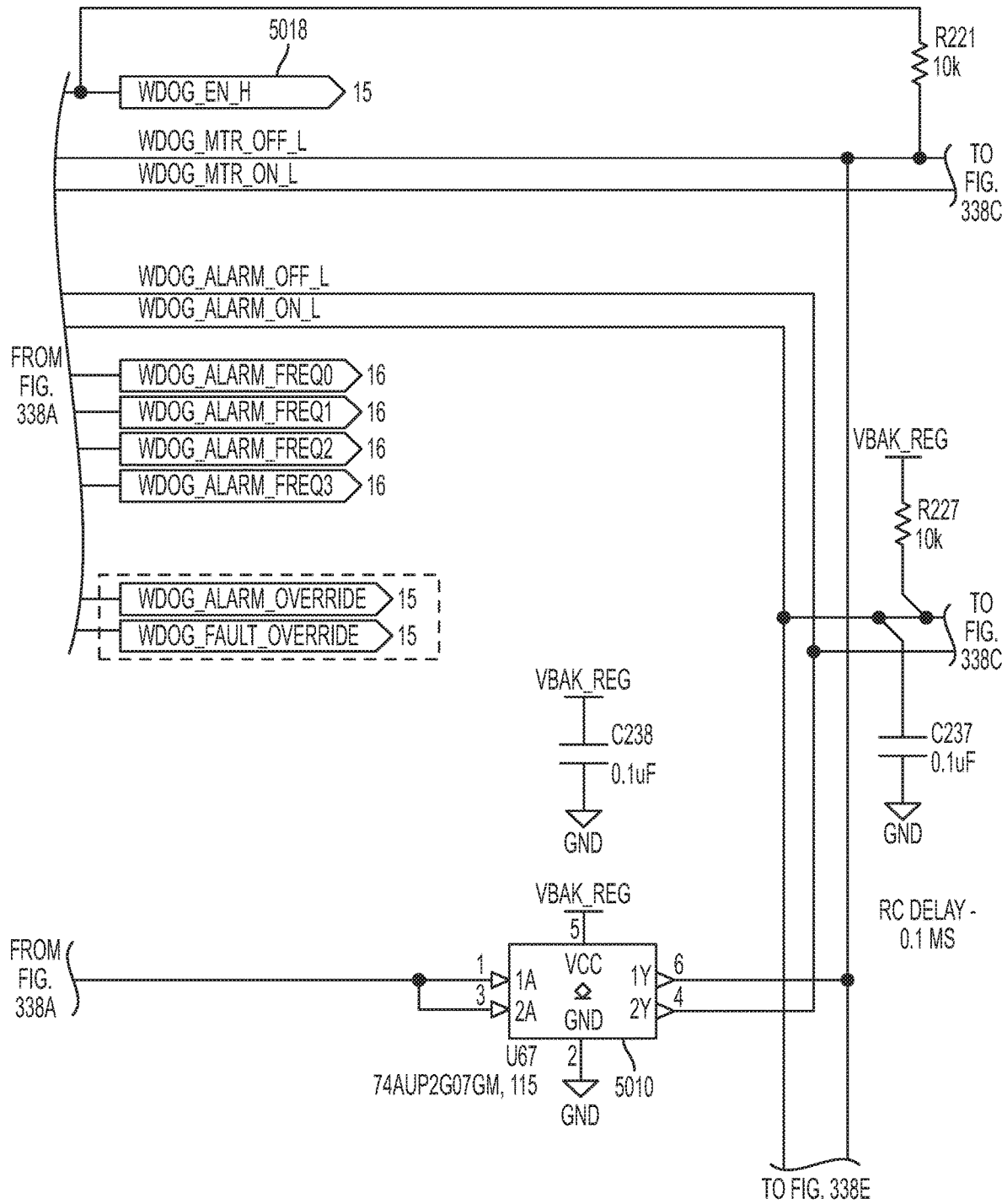
Figure 338C:
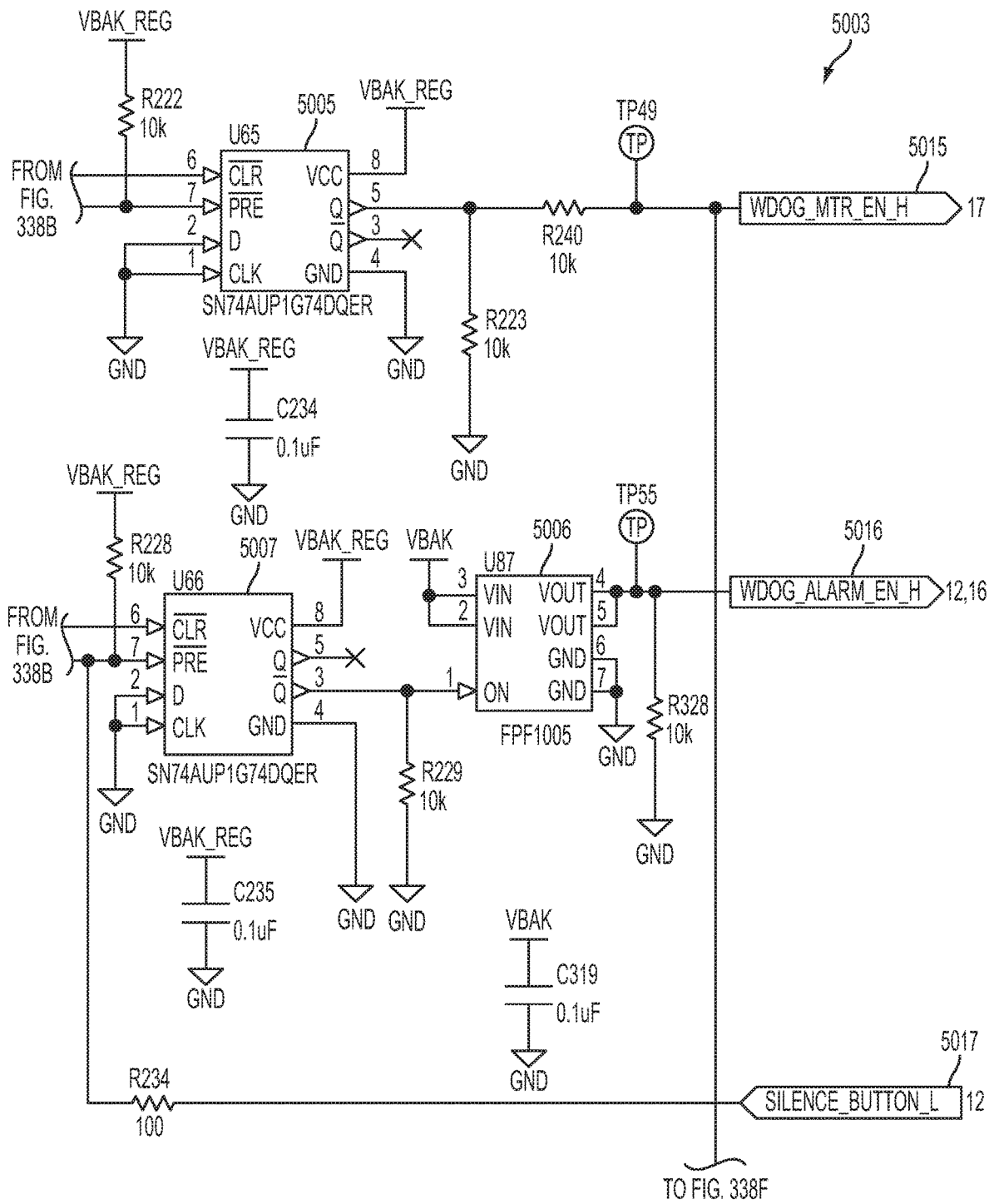
Figure 338D:
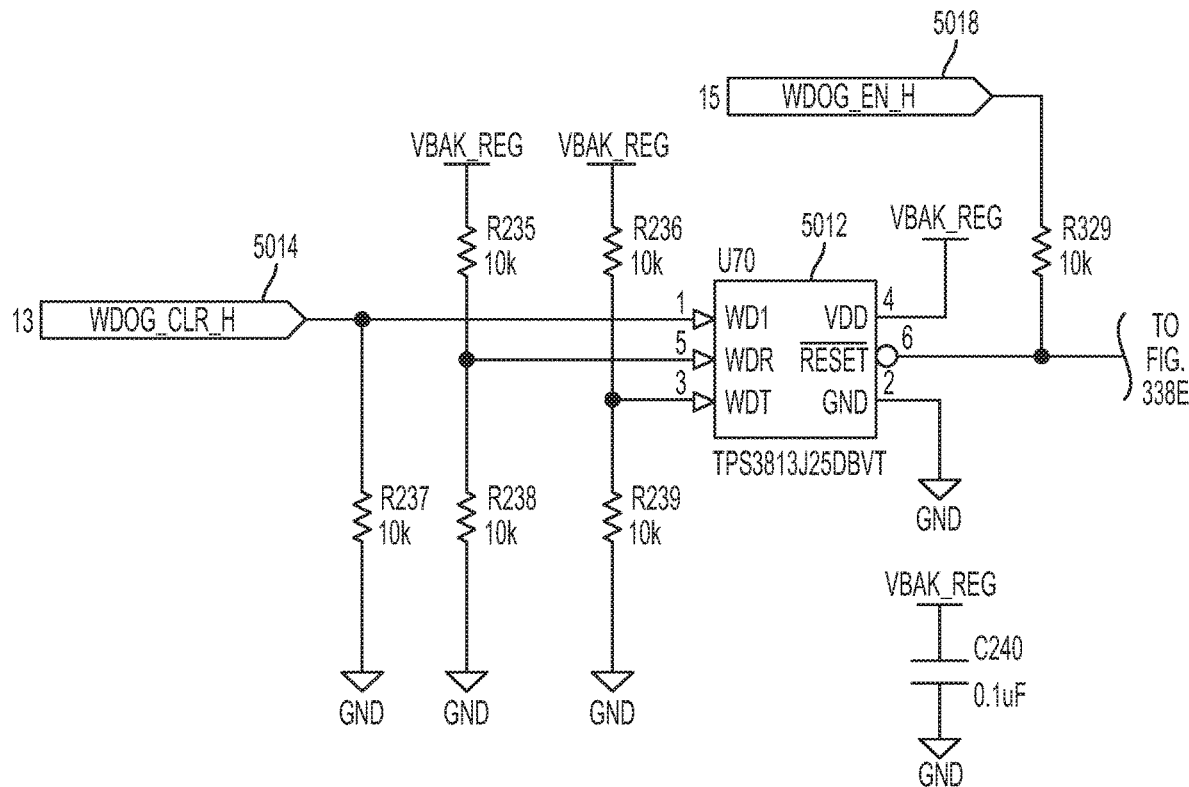
Figure 338E:
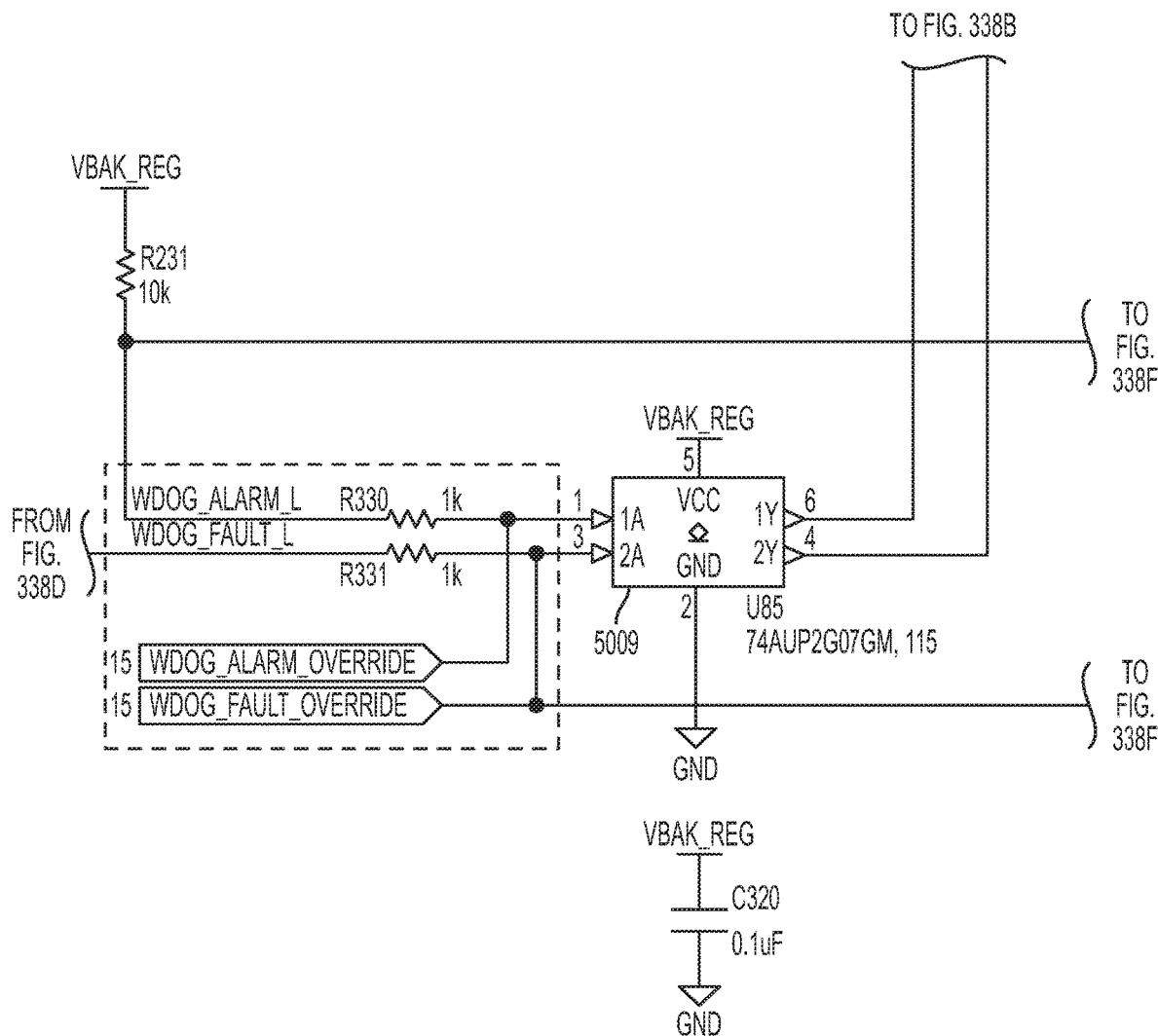
Figure 338F:
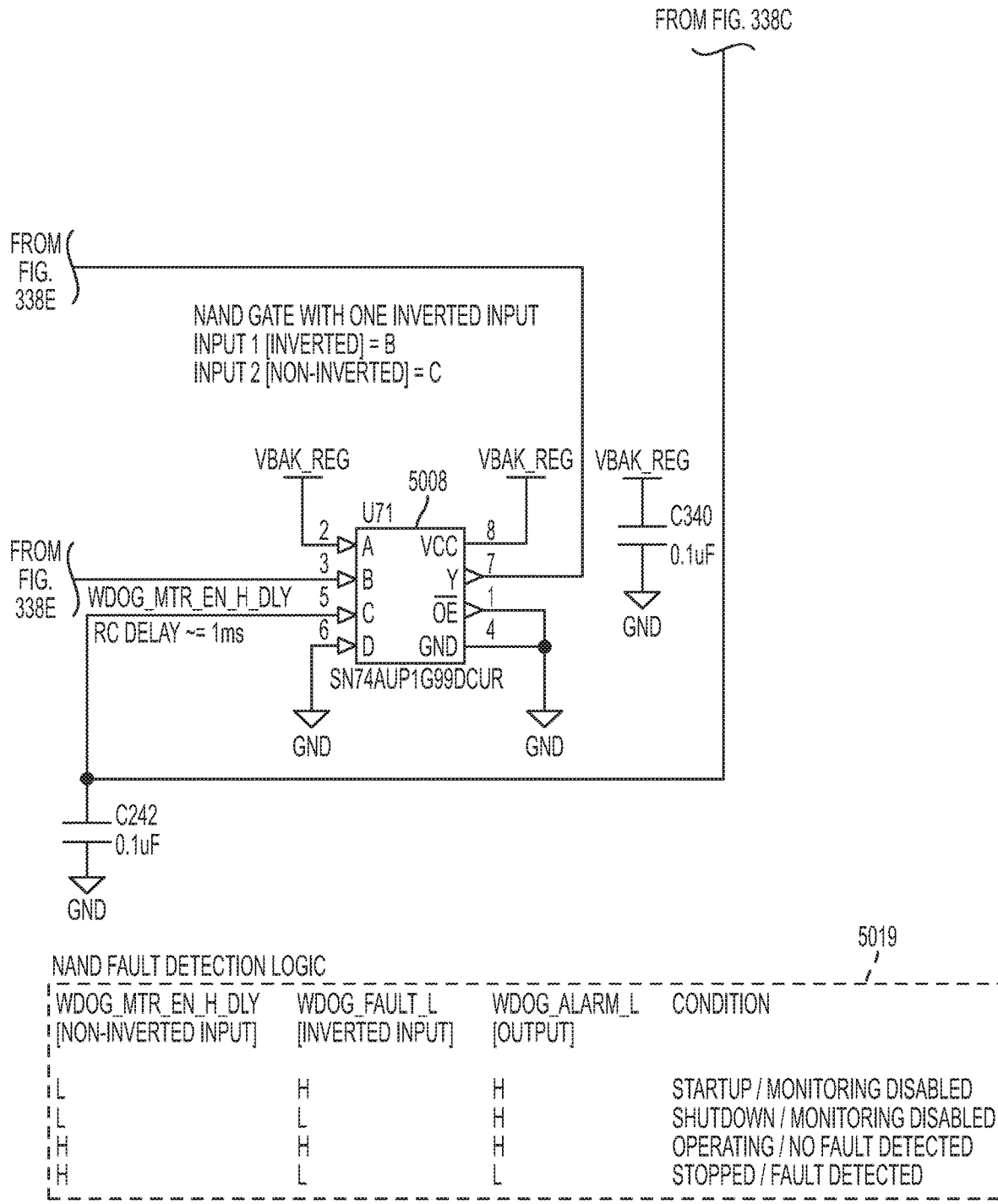
Figure 339:
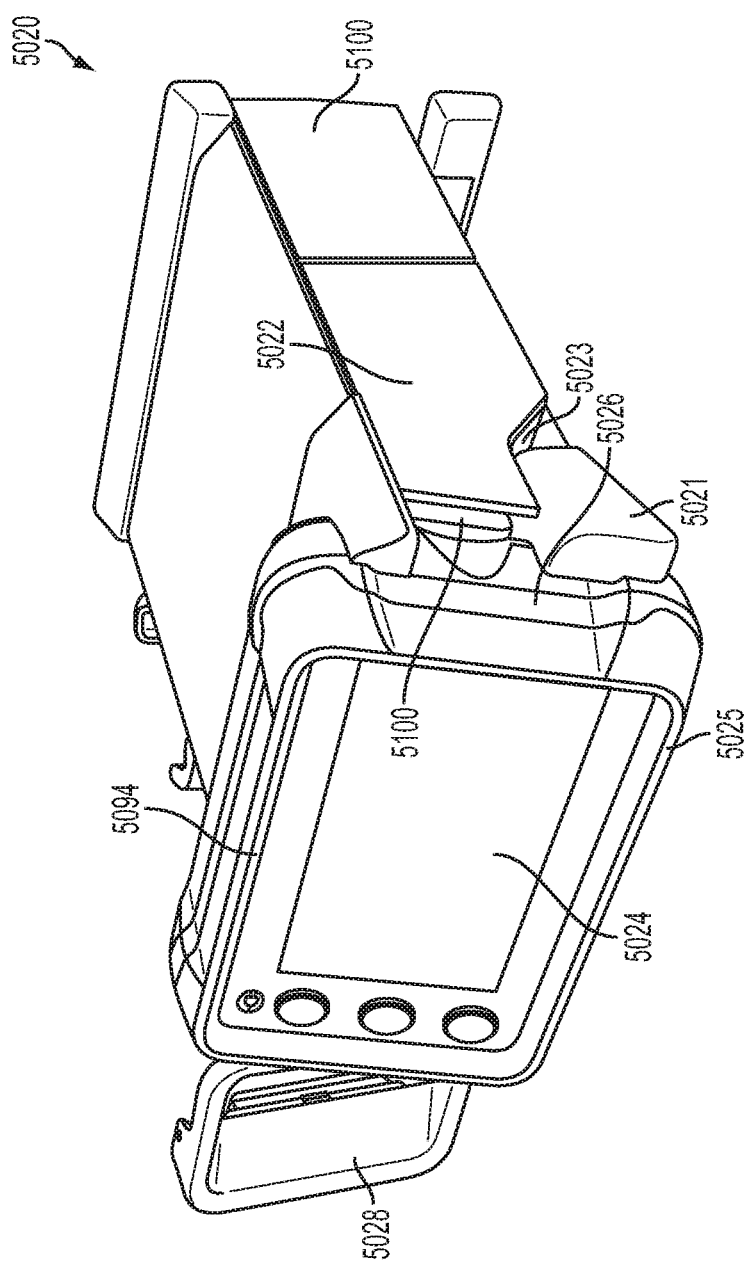
Figure 340:
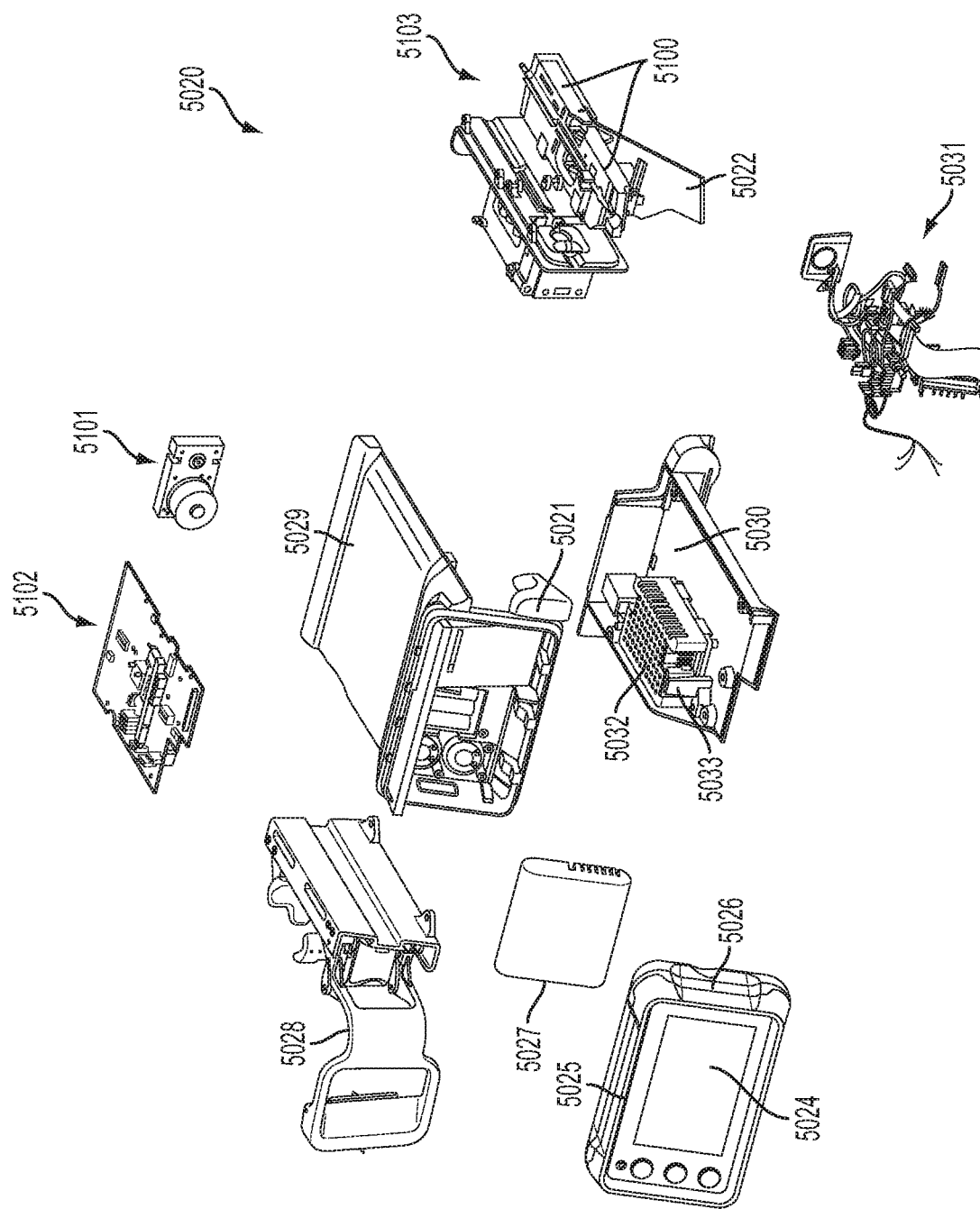
Figure 341:
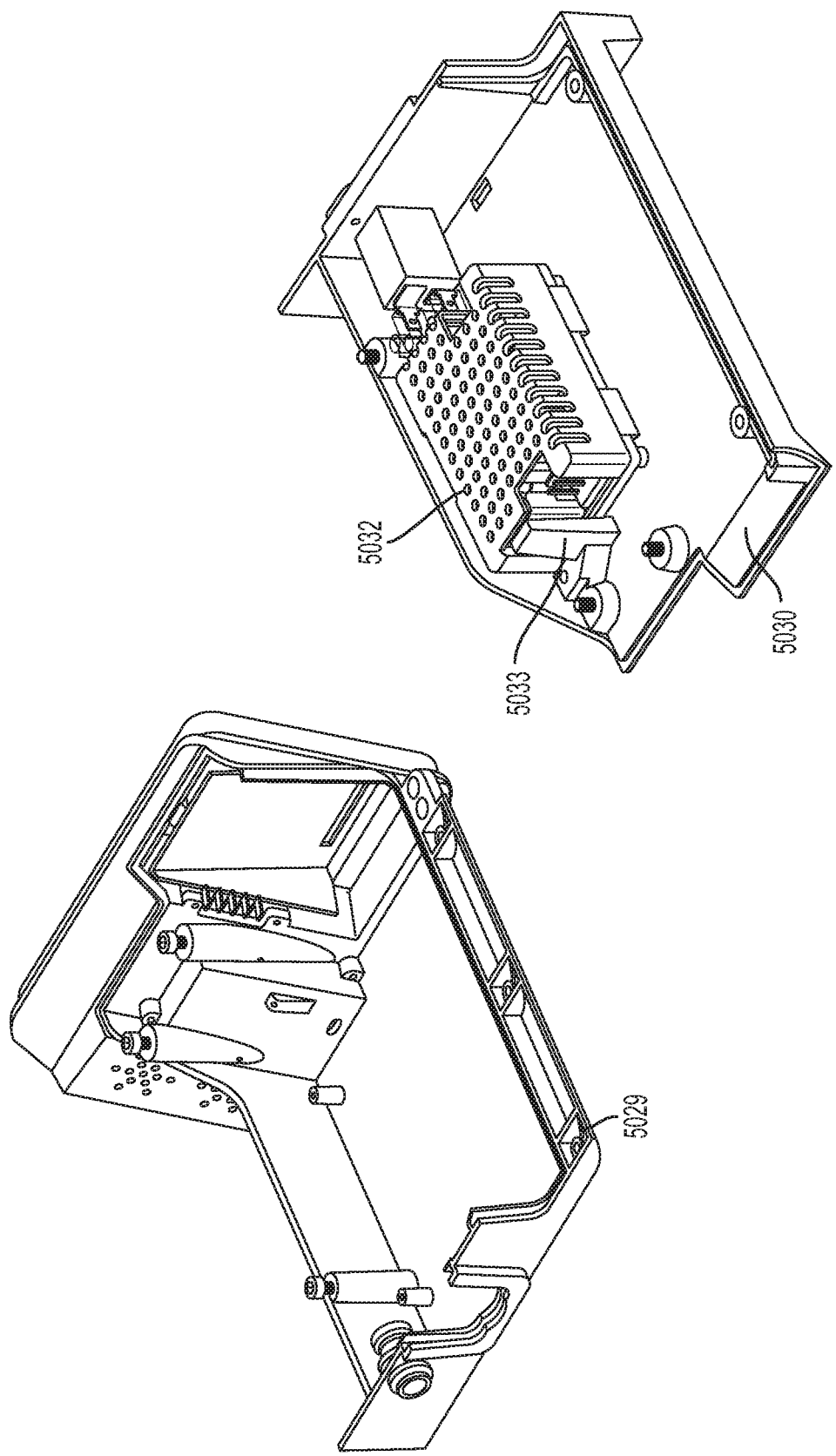
Figure 342B:
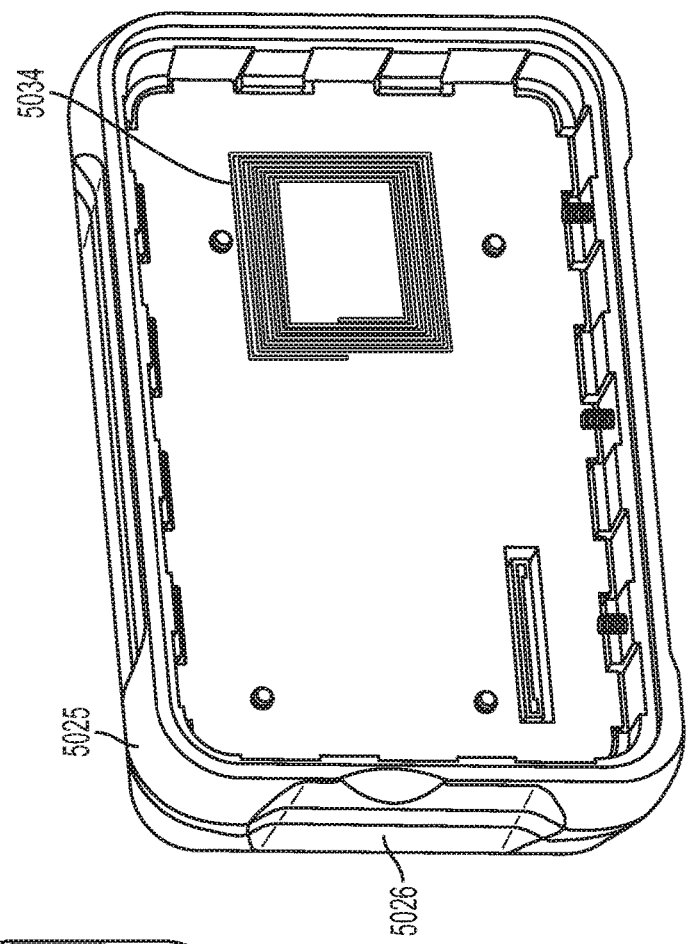
Figure 342A:
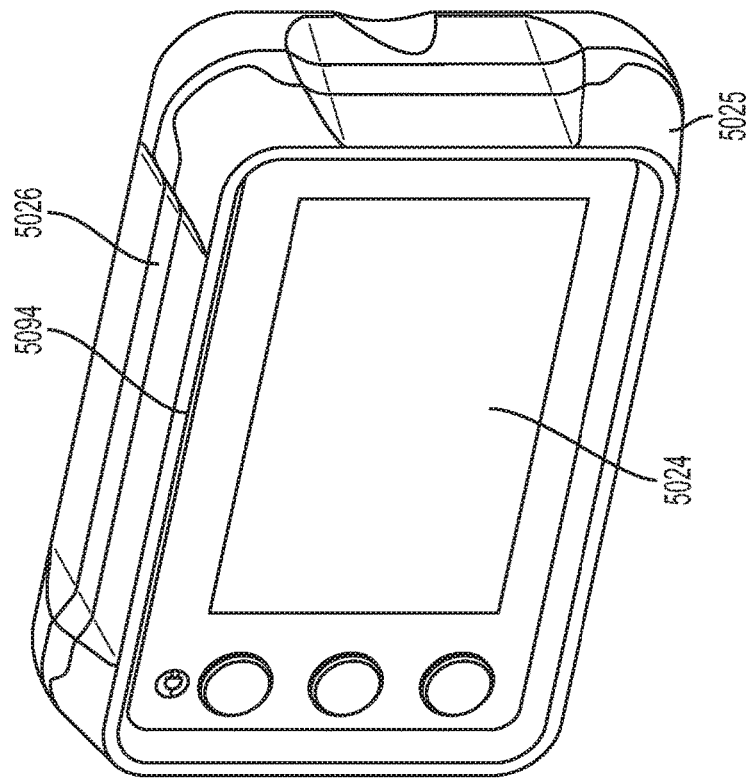
Figure 343:
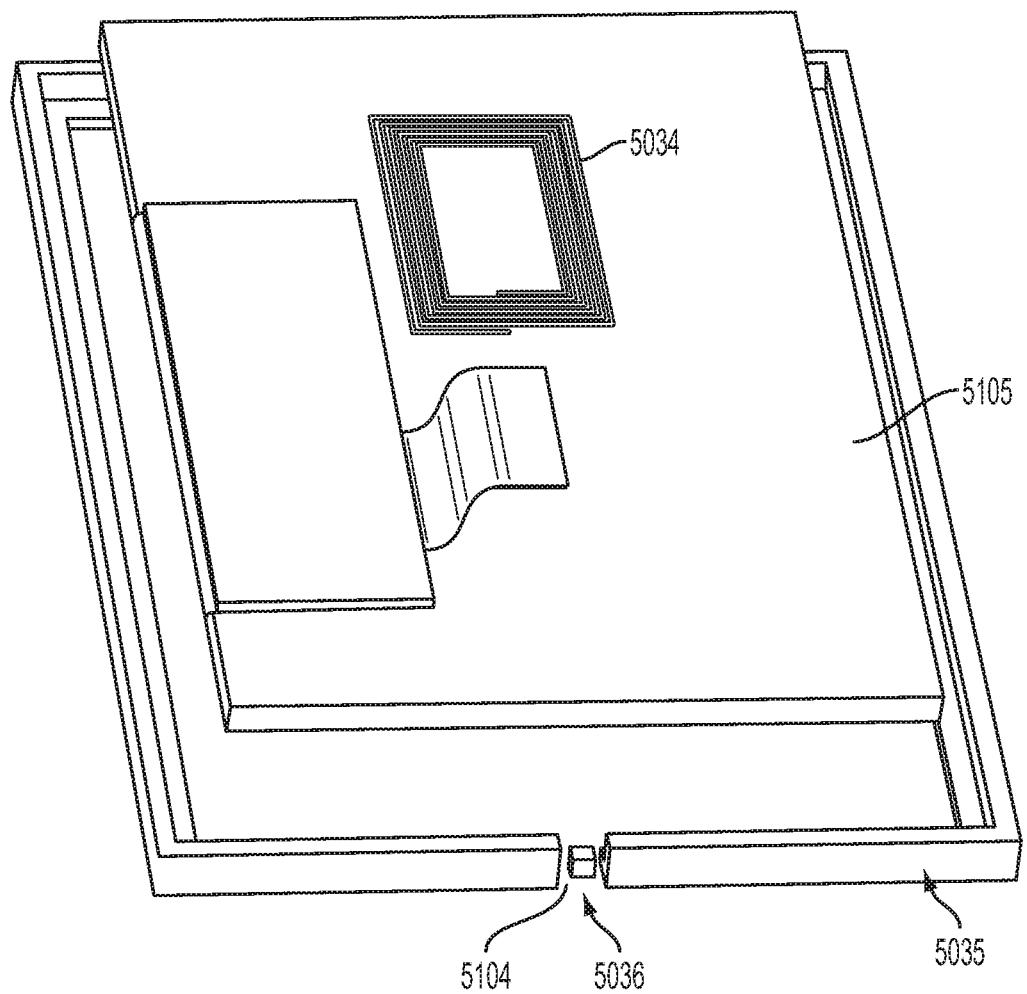
Figure 344:
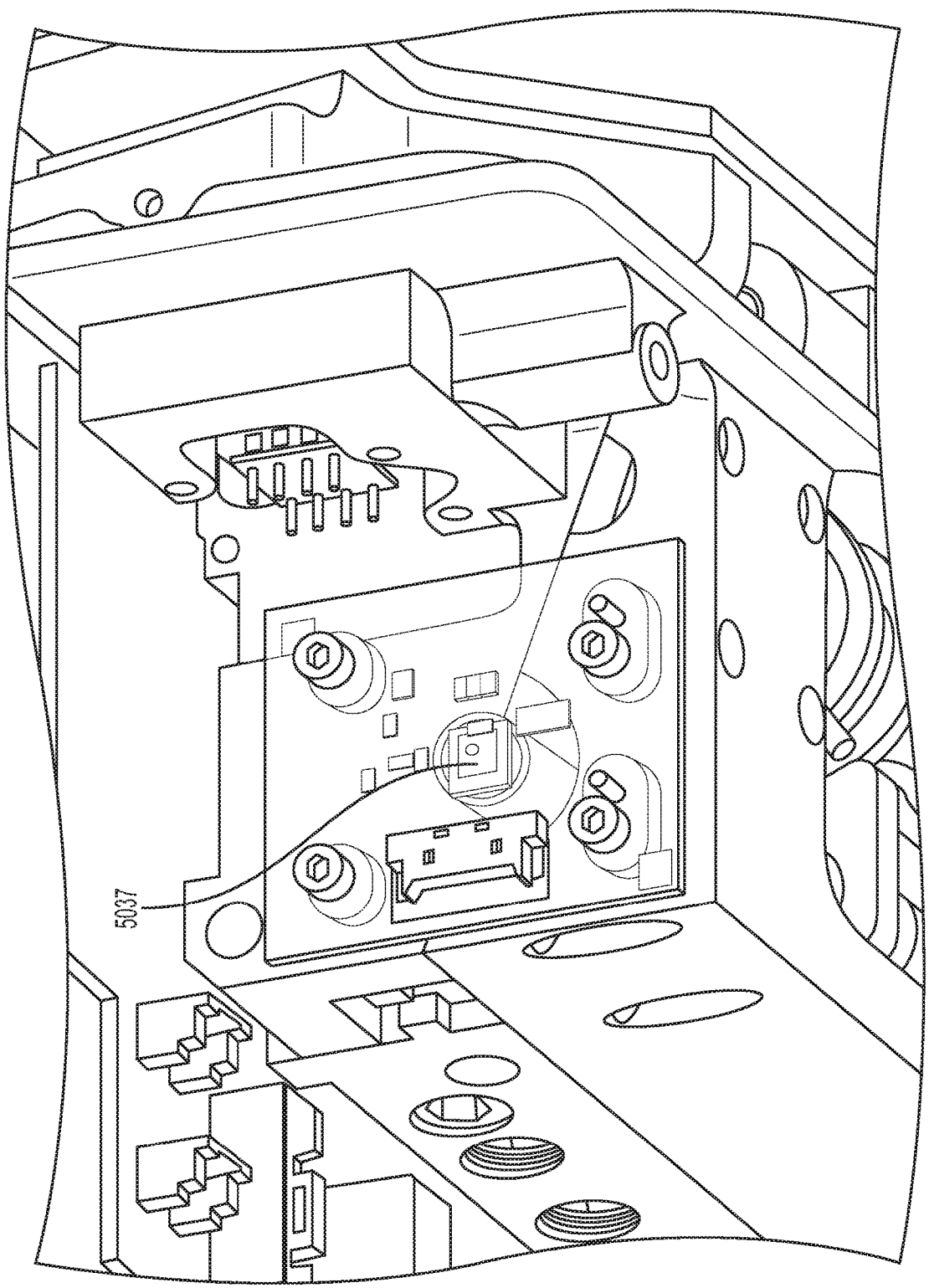
Figure 345:
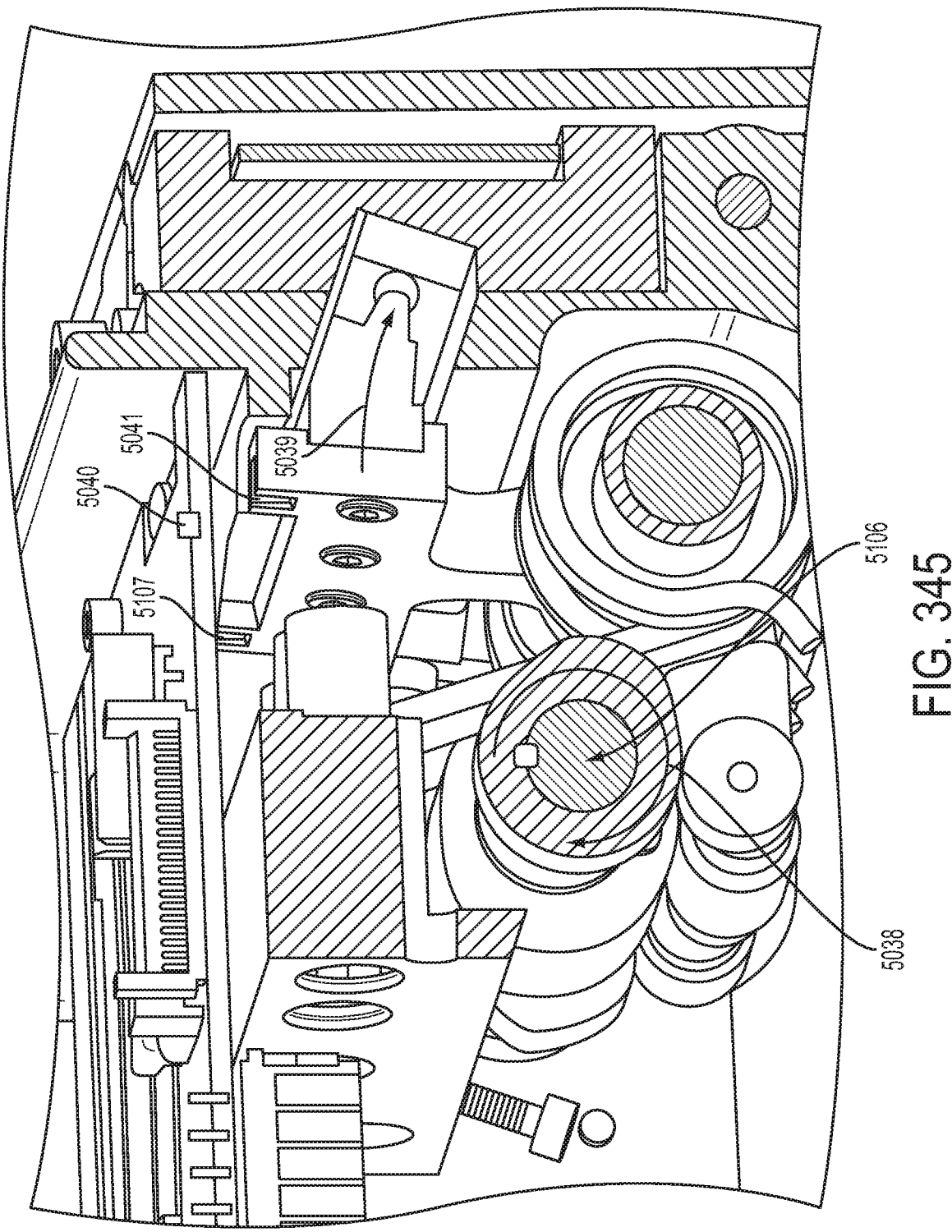
Figure 346:
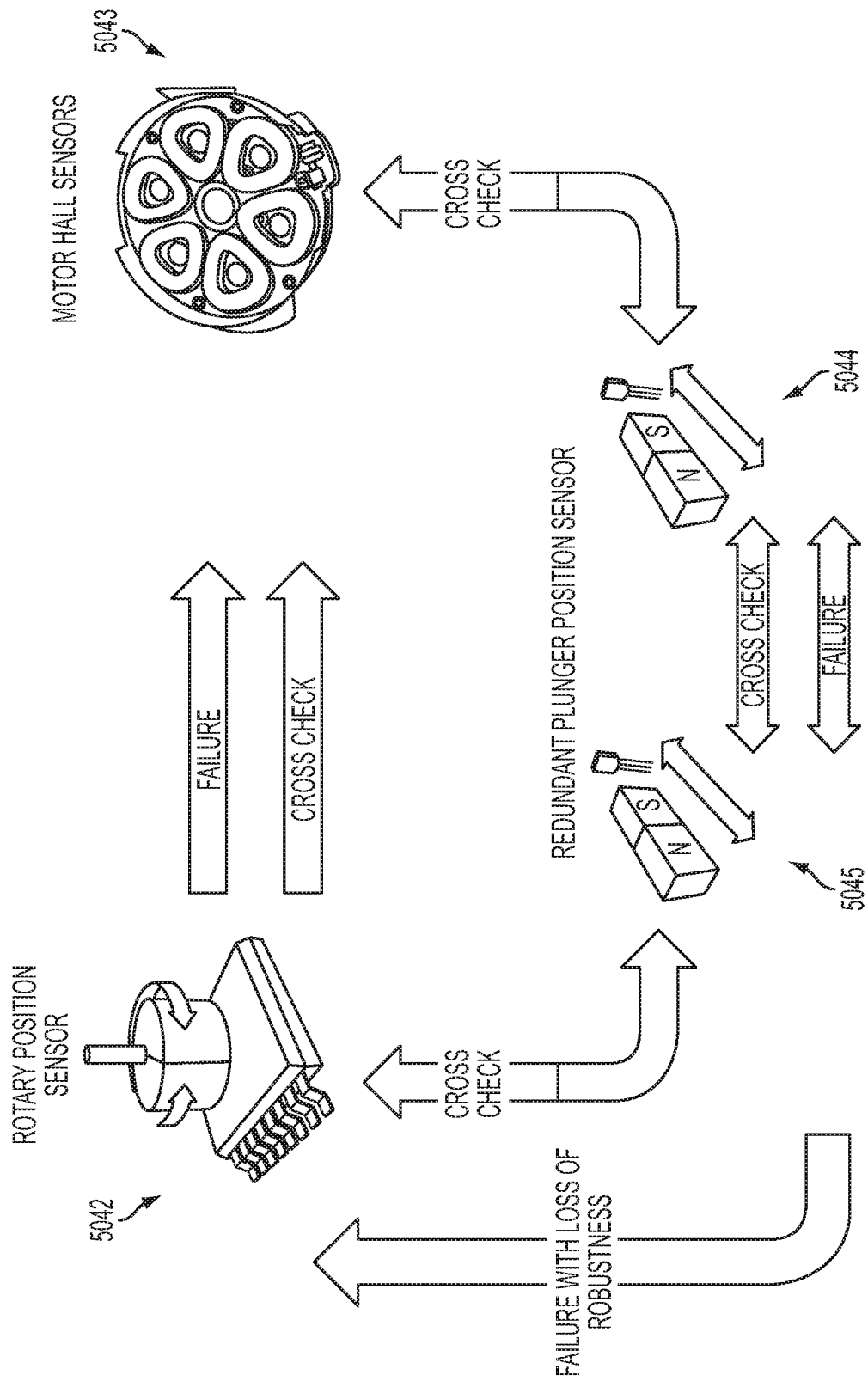
Figure 351:
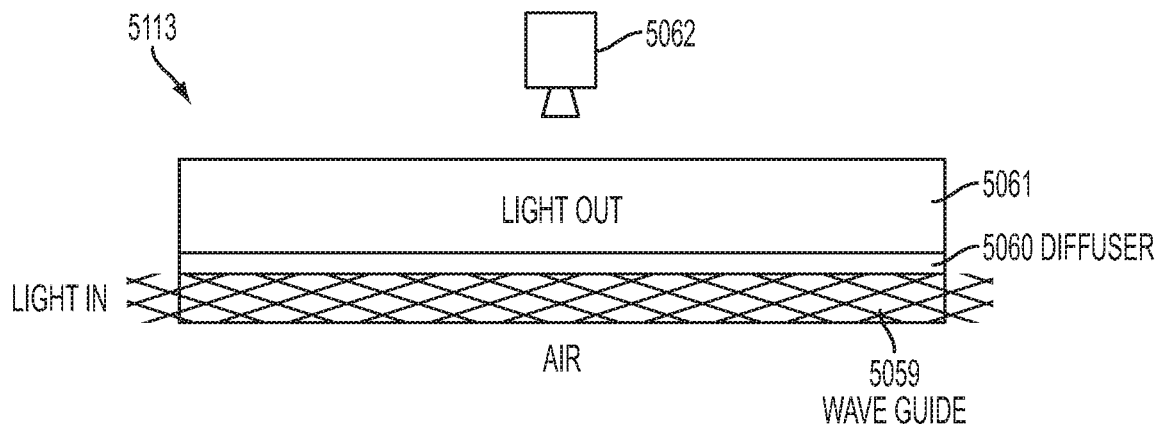
Figure 352:
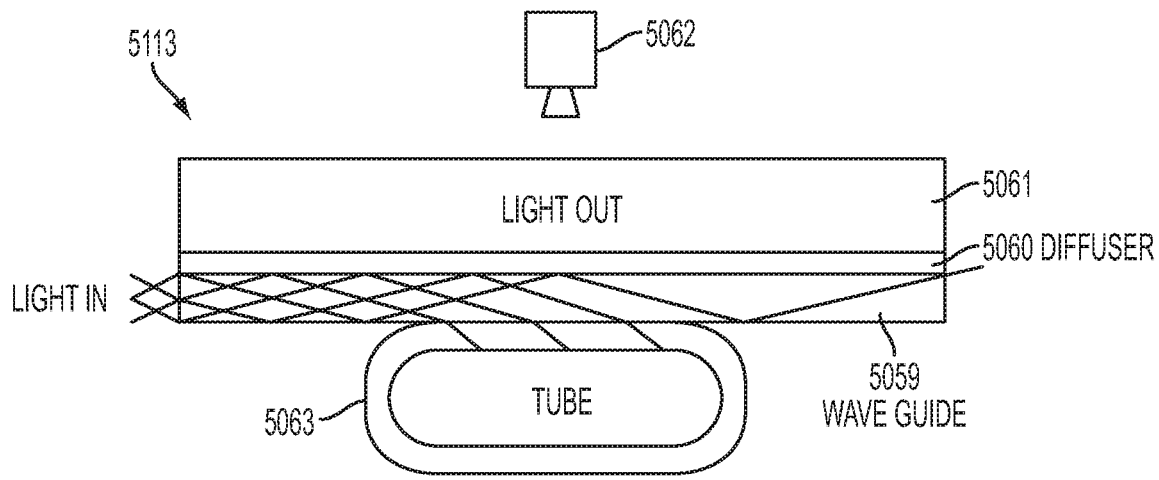
Figure 353:
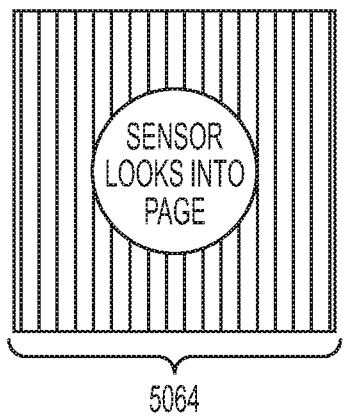
Figure 354:
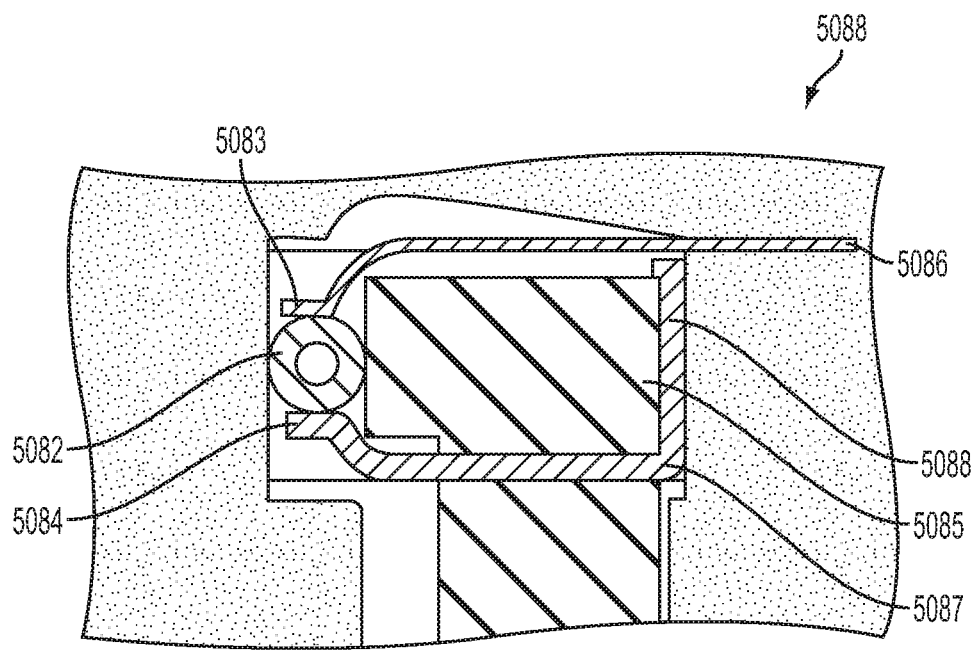
Figure 355:
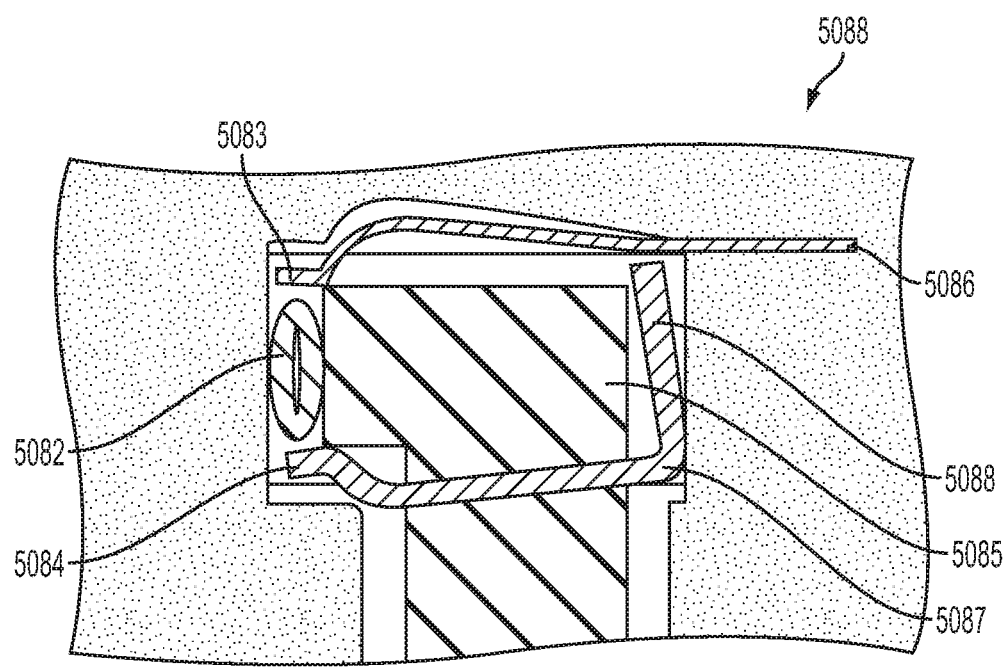
Figure 356:
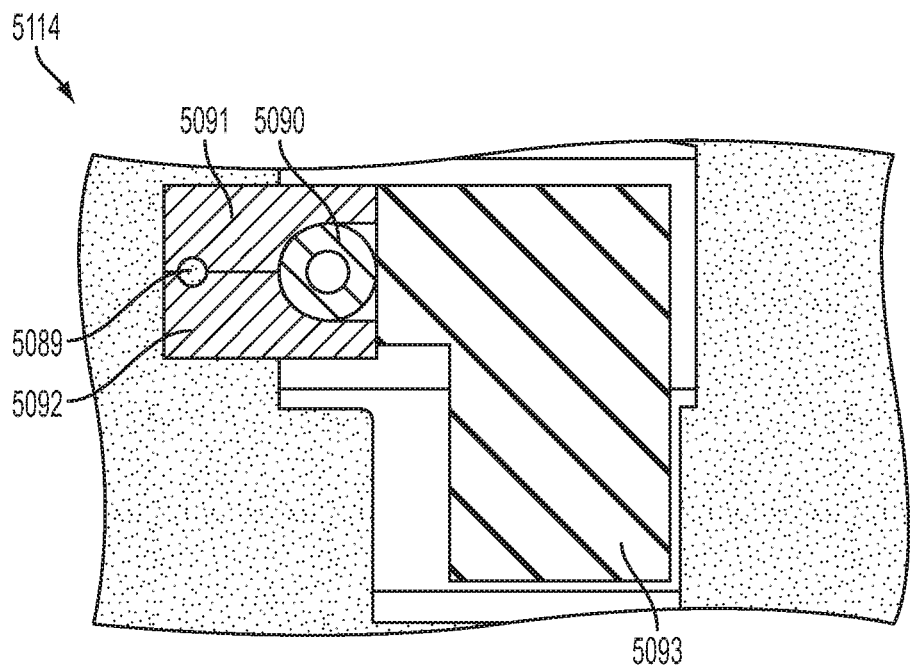
Figure 357:
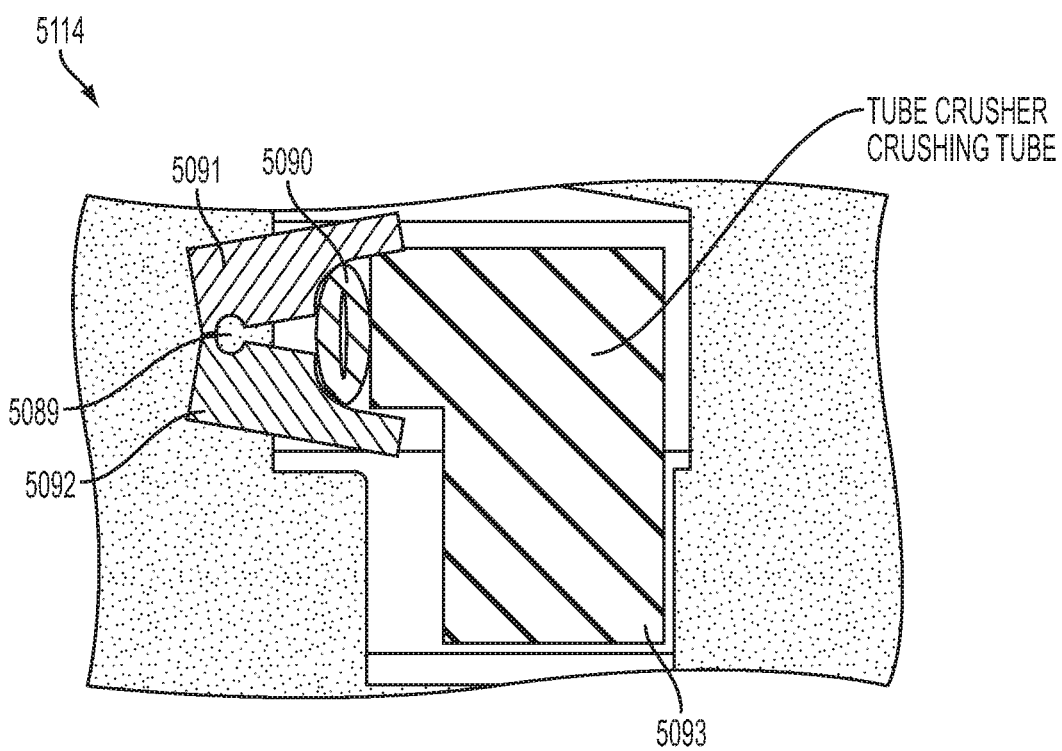
Figure 358:
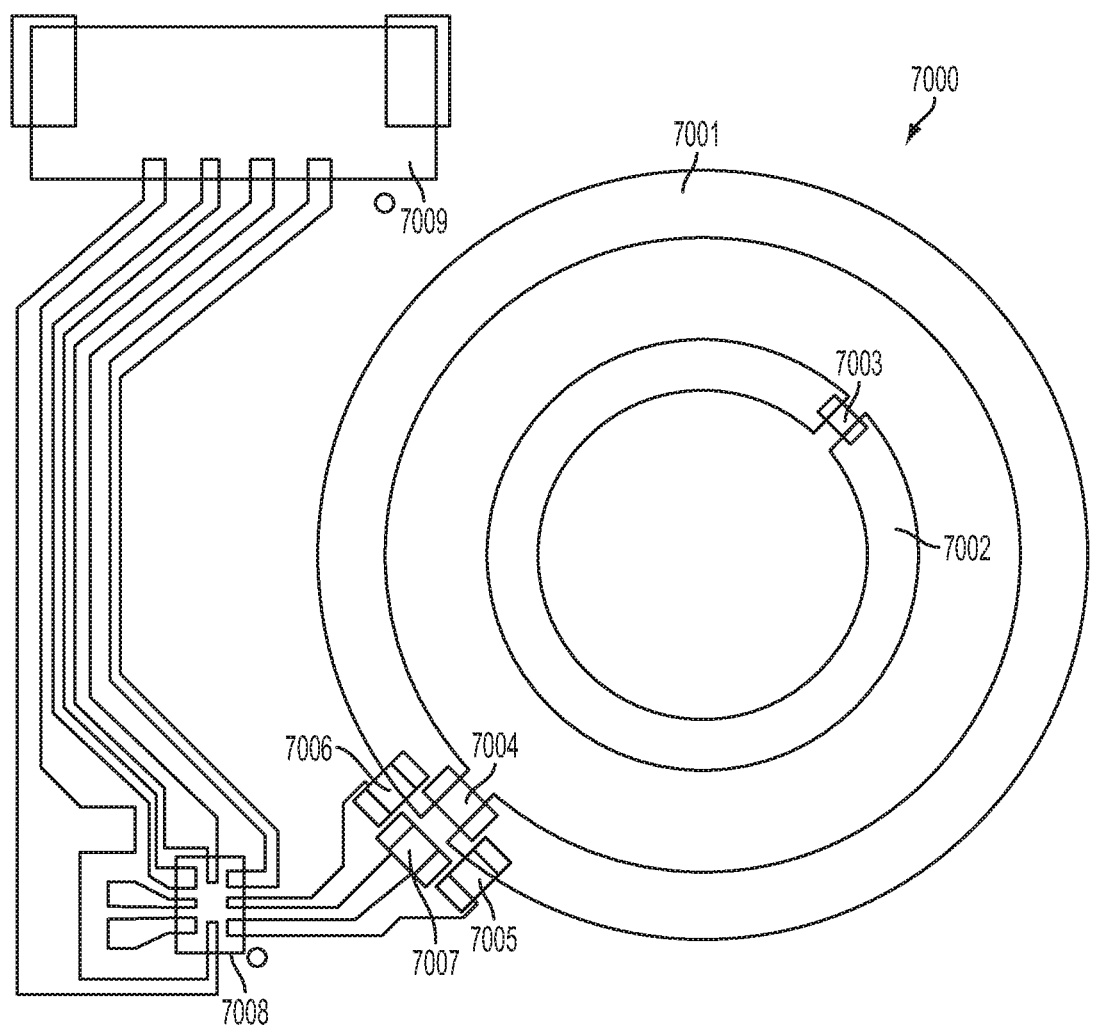
Figure 359:
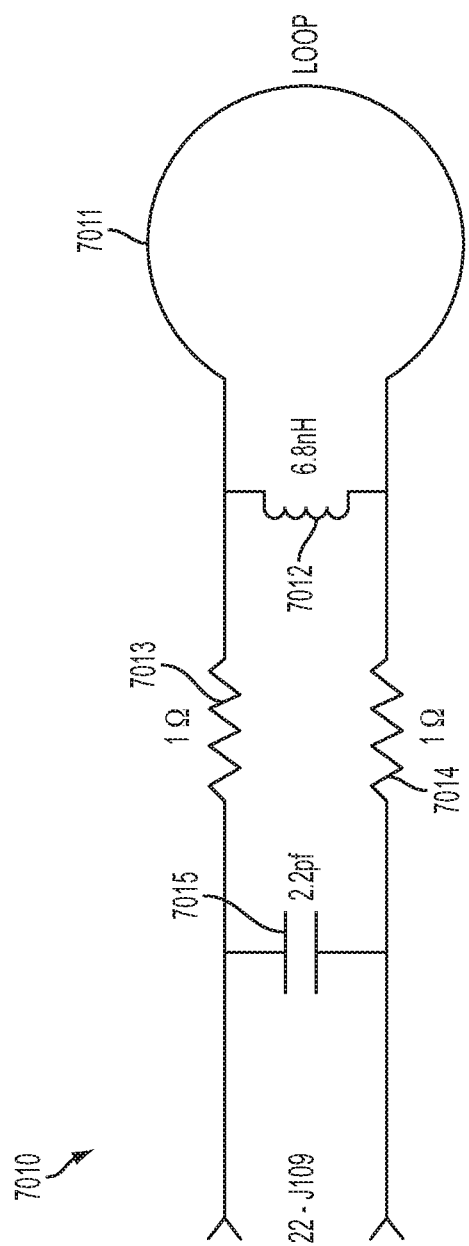
Figure 360:
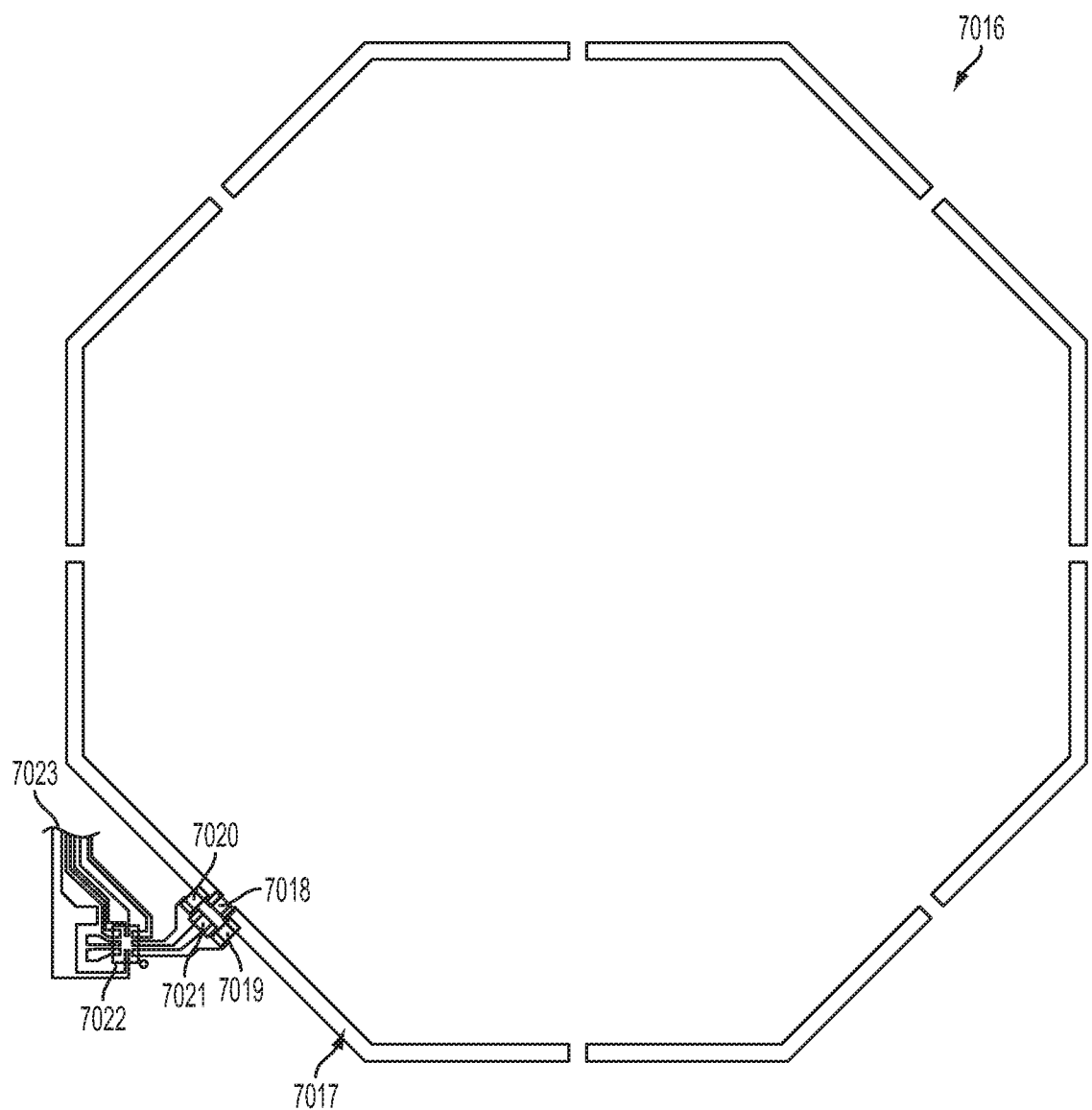
Figure 361:
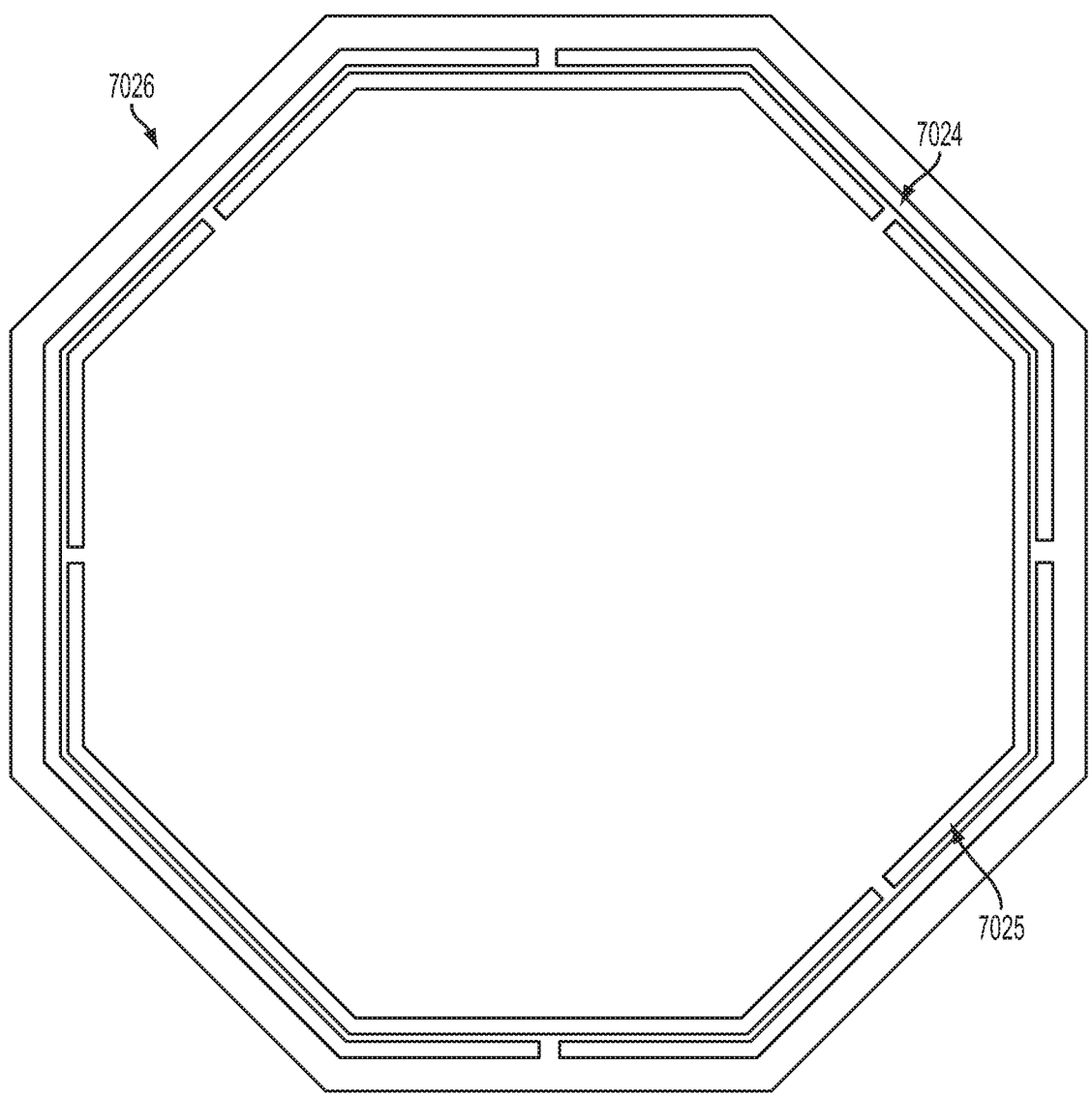

FIG. 164 illustrates several stages of operation of the peristaltic pump of FIG. 163 in accordance with an embodiment of the present disclosure;

FIG. 165 illustrates a peristaltic pump having two plungers external to an AVS chamber in accordance with an embodiment of the present disclosure;

FIG. 166 illustrate several stages of the peristaltic pump of FIG. 165 in accordance with an embodiment of the present disclosure;

FIG. 167 illustrates a peristaltic pump having a plunger with a linear sensor in accordance with an embodiment of the present disclosure;

FIG. 168 illustrates a graphic of data from the linear sensor of the peristaltic pump of FIG. 167 in accordance with an embodiment of the present disclosure;

FIG. 169 illustrates the stages of the peristaltic pump of FIG. 169 in accordance with an embodiment of the present disclosure;

FIG. 170 illustrates the detection of an occlusion condition vis-à-vis a non-occluded condition in accordance with an embodiment of the present disclosure;

FIG. 171 illustrates the detection of a valve leak vis-à-vis a full-valve-sealing condition in accordance with an embodiment of the present disclosure;

FIG. 172 illustrates the detection of a too much air in the tube or a valve fail vis-à-vis a proper operation in accordance with an embodiment of the present disclosure;

FIG. 173 shows a block diagram that illustrates the electronics of a peristaltic pump in accordance with another embodiment of the present disclosure;

FIG. 174 shows a block diagram that illustrates the electronics of a peristaltic pump in accordance with another embodiment of the present disclosure;

FIG. 175 shows a perspective view of peristaltic pump in accordance with an embodiment of the present disclosure;

FIGS. 176-180 show data from several AVS sweeps in accordance with an embodiment of the present disclosure;

FIG. 181 shows a side sectional view of a plunger in accordance with an embodiment of the present disclosure;

FIGS. 182A-182C show side sectional views of a plunger to illustrate the action of a peristaltic pump in accordance with an embodiment of the present disclosure;

FIGS. 183A-183C show side sectional views of a plunger to illustrate a scenario in which the resistance to flow of the liquid column within a tube segment is increased beyond the pre-determined functional range of the spring in accordance with an embodiment of the present disclosure;

FIG. 184 shows a sectional view of the pinch valves and plunger of the peristaltic pump of FIG. 175 in accordance with an embodiment of the present disclosure;

FIG. 185 show two views of a plunger with flexible fingers to grip a tube in accordance with an embodiment of the present disclosure;

FIG. 186 shows an embodiment of a cam mechanism of a peristaltic pump in accordance with an embodiment of the present disclosure;

FIG. 187 shows an embodiment of a cam mechanism of a peristaltic pump in accordance with an embodiment of the present disclosure;

FIGS. 188-189 and 190A-190C show several views of a peristaltic pump in accordance with an embodiment of the present disclosure;

FIGS. 191-195 show several views of a peristaltic pump in accordance with an additional embodiment of the present disclosure;

FIGS. 196A-196B illustrate torque on a cam shaft of a peristaltic pump in accordance with an embodiment of the present disclosure;

FIG. 197 illustrates a cam profile for several cams for a peristaltic pump in accordance with an embodiment of the present disclosure;

FIG. 198 shows various feedback modes of a peristaltic pumps in accordance with an embodiment of the present disclosure;

FIG. 199 shows a graph illustrating data of a linear sensor used to estimate fluid flow in accordance with an embodiment of the present disclosure;

FIGS. 200-206 show several perspective views of a peristaltic pump having a angular members interfacing into a cam in accordance with an embodiment of the present disclosure;

FIGS. 207-221 illustrate the operation of a slide occluder of the peristaltic pump of FIGS. 200-206 in accordance with an embodiment of the present disclosure;

FIGS. 222-223 show a two views of a peristaltic pump in accordance with an embodiment of the present disclosure;

FIGS. 224-238 show several views of the peristaltic pump of FIGS. 222-223 illustrating the operation of the slide occluder in accordance with an embodiment of the present disclosure;

FIGS. 239-245 show several view of the peristaltic pump of FIGS. 222-238 in accordance with an embodiment of the present disclosure;

FIGS. 246-250 show several views of an integrated cam and motor in for use in an peristaltic pump disclosed herein in accordance with another embodiment of the present disclosure;

FIGS. 251-254 illustrate a camera sensor for use for measuring the position of a plunger and pinch valves of a peristaltic pump in accordance with an embodiment of the present disclosure;

FIG. 255 illustrates a peristaltic pump having L-shaped cam followers in an exploded view of the mechanical elements from the top of the pump in accordance with an embodiment of the present disclosure;

FIGS. 256A-256B illustrates the peristaltic pump having L-shaped cam followers in two exploded views of the mechanical elements of the pump in accordance with an embodiment of the present disclosure;

FIG. 257 illustrates the peristaltic pump having L-shaped cam followers with a door open in an isometric view of the mechanical elements from the top of the pump in accordance with an embodiment of the present disclosure;

FIG. 258 illustrates the peristaltic pump having L-shaped cam followers in an exploded view showing the PCB, pump body, door, and a motor with a gear head in accordance with an embodiment of the present disclosure;

FIG. 259 illustrates the slide occluder inserted into the open door of the peristaltic pump having L-shaped cam followers in accordance with an embodiment of the present disclosure;

FIG. 260 illustrates the peristaltic pump having L-shaped cam followers with the door open and some elements removed to reveal the cam-shaft, pump and valves in accordance with an embodiment of the present disclosure;

FIG. 261 illustrates the insertion of the slide occluder into the open door of the peristaltic pump having L-shaped cam followers in accordance with an embodiment of the present disclosure;

FIGS. 262-263 show an alternative door with the door half of an alternative split carriage in accordance with an embodiment of the present disclosure;

FIG. 264 illustrates the door, a lever and a slide carriage of the peristaltic pump having L-shaped cam followers in an exploded view in accordance with an embodiment of the present disclosure;

FIG. 265 illustrates the peristaltic pump having L-shaped cam followers with the door open in an isometric view of the mechanical elements from the bottom of the pump in accordance with an embodiment of the present disclosure;

FIG. 266 illustrates a cam-shaft of the peristaltic pump having L-shaped cam followers in an isometric view in accordance with an embodiment of the present disclosure;

FIG. 267 illustrates the plunger cam follower of the peristaltic pump having L-shaped cam followers in an isometric view from the front in accordance with an embodiment of the present disclosure;

FIG. 268 illustrates the plunger cam follower of the peristaltic pump having L-shaped cam followers in an isometric view from the back in accordance with an embodiment of the present disclosure;

FIG. 269 illustrates the valve cam follower of the peristaltic pump having L-shaped cam followers in an isometric view from a first side in accordance with an embodiment of the present disclosure;

FIG. 270 illustrates the valve cam follower of the peristaltic pump having L-shaped cam followers in an isometric view from a second side in accordance with an embodiment of the present disclosure;

FIG. 271 illustrates a outlet cam of the peristaltic pump having L-shaped cam followers in an orthographic view in accordance with an embodiment of the present disclosure;

FIG. 272 illustrates a pump cam of the peristaltic pump having L-shaped cam followers in an orthographic view in accordance with an embodiment of the present disclosure;

FIG. 273 illustrates a intake cam of the peristaltic pump having L-shaped cam followers in an orthographic view in accordance with an embodiment of the present disclosure;

FIG. 274 illustrates the plunger and valve cam followers of the peristaltic pump having L-shaped cam followers in an exploded view in accordance with an embodiment of the present disclosure;

FIG. 275 illustrates retainers for the springs on the cam followers of the peristaltic pump having L-shaped cam followers in an isometric view in accordance with an embodiment of the present disclosure;

FIG. 276 shows a cross-section of the pump including sections of the cam, plunger and platen in accordance with an embodiment of the present disclosure;

FIG. 277 shows a cross-sectional view of the plunger compressing the infusion tube against the platen in accordance with an embodiment of the present disclosure;

FIG. 278 illustrates the housing, cam shaft and cam followers of the peristaltic pump having L-shaped cam followers in an exploded view in accordance with an embodiment of the present disclosure;

FIG. 279 illustrates the upper and lower housing of the peristaltic pump having L-shaped cam followers in an isometric view in accordance with an embodiment of the present disclosure;

FIG. 280 illustrates the assembled upper and lower housing of the peristaltic pump having L-shaped cam followers in isometric views in accordance with an embodiment of the present disclosure;

FIG. 281 illustrates the assembled upper and lower housing of the peristaltic pump having L-shaped cam followers in isometric views in accordance with an embodiment of the present disclosure;

FIG. 282 illustrates the peristaltic pump having L-shaped cam followers with PCB removed to reveal magnets on the plunger and corresponding sensors on PCB in accordance with an embodiment of the present disclosure;

FIG. 283 illustrates the insertion of the slide occluder into the open door of the peristaltic pump having L-shaped cam followers in accordance with an embodiment of the present disclosure;

FIG. 284 illustrates the slide occluder inserted into the open door of the peristaltic pump having L-shaped cam followers in accordance with an embodiment of the present disclosure;

FIG. 285 illustrates the split-carriage in the open position in accordance with an embodiment of the present disclosure;

FIG. 286 illustrates the split-carriage in the closed position in accordance with an embodiment of the present disclosure;

FIG. 287 illustrates the peristaltic pump having L-shaped cam followers with the door partially closed and some elements removed to reveal the slide occluder in the closed split-carriage in accordance with an embodiment of the present disclosure;

FIG. 288 illustrates the multi-part link between the split carriage and the lever in an isometric view in accordance with an embodiment of the present disclosure;

FIG. 289 illustrates the peristaltic pump having L-shaped cam followers with the door closed and some elements removed to reveal the slide occluder in the closed split-carriage in accordance with an embodiment of the present disclosure;

FIGS. 290-293 illustrate four steps of closing the door of the peristaltic pump having L-shaped cam followers in accordance with an embodiment of the present disclosure;

FIG. 294 illustrates a lever on the door engaging a pin on the body of the peristaltic pump having L-shaped cam followers in accordance with an embodiment of the present disclosure;

FIG. 295 illustrates a spring element in the door of the peristaltic pump having L-shaped cam followers in accordance with an embodiment of the present disclosure;

FIG. 296 illustrates two latch hooks of the lever on the door of the peristaltic pump having L-shaped cam followers in accordance with an embodiment of the present disclosure;

FIG. 297 shows a vertical cross-sectional view of the peristaltic pump with L-shaped cam followers in accordance with an embodiment of the present disclosure;

FIG. 298 shows a horizontal cross-sectional view of the peristaltic pump with L-shaped cam followers in accordance with an embodiment of the present disclosure;

FIG. 299 illustrates a spring-pin engaging a detent on the lever latch hook in the closed position within the door of the peristaltic pump having L-shaped cam followers in accordance with an embodiment of the present disclosure;

FIG. 300 illustrates a spring-pin engaging a detent on the lever latch hook in the open position within the door of the peristaltic pump having L-shaped cam followers in accordance with an embodiment of the present disclosure;

FIG. 301 illustrates a slide-occluder detection lever displaced by the slide occluder when the door is on the peristaltic pump having L-shaped cam followers in accordance with an embodiment of the present disclosure;

FIG. 302 illustrates a latch hook detection lever displaced by the latch hook when the door is on the peristaltic pump having L-shaped cam followers in accordance with an embodiment of the present disclosure;

FIGS. 303-306 show several views of a patient bedside system in accordance with an embodiment of the present disclosure;

FIG. 307 shows a close-up view of a portion of an interface of a clamp that is attachable to a pump shown in FIGS. 303-306 in accordance with an embodiment of the present disclosure;

FIG. 308 shows another close-up view of another portion of the interface shown in FIG. 301 in accordance with an embodiment of the present disclosure;

FIG. 309 shows a perspective view of a pump shown in FIGS. 303-306 in accordance with an embodiment of the present disclosure;

FIG. 310 shows a perspective view of a pump shown in FIGS. 303-306 in accordance with an embodiment of the present disclosure;

FIG. 311 shows a perspective view of a pump with the graphic user interface shown on the screen in accordance with an embodiment of the present disclosure;

FIG. 312 shows an example infusion programming screen of the graphic user interface in accordance with an embodiment of the present disclosure;

FIG. 313 shows an example infusion programming screen of the graphic user interface in accordance with an embodiment of the present disclosure;

FIG. 314 shows an example infusion programming screen of the graphic user interface in accordance with an embodiment of the present disclosure;

FIG. 315 shows an example infusion programming screen of the graphic user interface in accordance with an embodiment of the present disclosure;

FIG. 316 shows an example infusion programming screen of the graphic user interface in accordance with an embodiment of the present disclosure;

FIG. 317 shows an infusion rate over time graphical representation of an example infusion in accordance with an embodiment of the present disclosure;

FIG. 318 shows an infusion rate over time graphical representation of an example infusion in accordance with an embodiment of the present disclosure;

FIG. 319 shows an infusion rate over time graphical representation of an example infusion in accordance with an embodiment of the present disclosure;

FIG. 320 shows an infusion rate over time graphical representation of an example infusion in accordance with an embodiment of the present disclosure;

FIG. 321 shows an infusion rate over time graphical representation of an example infusion in accordance with an embodiment of the present disclosure;

FIG. 322 shows an example drug administration library screen of the graphic user interface in accordance with an embodiment of the present disclosure;

FIG. 323 shows a schematic of a battery powered draw speaker in accordance with an embodiment of the present disclosure;

FIG. 324 illustrates an electrical block diagram of peristaltic pump in accordance with an embodiment of the present disclosure;

FIG. 325 shows the electrical block diagram of FIG. 324 with reference boxes for use for the more detailed views of FIGS. 325A-325G in accordance with an embodiment of the present disclosure;

FIGS. 325A-325G illustrate a detailed electrical block diagram of peristaltic pump in accordance with an embodiment of the present disclosure;

FIG. 326 presents a linear encoder signal over cam angle graph in accordance with an embodiment of the present disclosure;

FIG. 327 illustrates a volume over time graph in accordance with an embodiment of the present disclosure;

FIG. 328 illustrates a cam shaft angle over volume graph in accordance with an embodiment of the present disclosure;

FIG. 329 illustrates a possible measured pressure vs. time trace of a delivery line downstream of peristaltic pump in accordance with an embodiment of the present disclosure;

FIG. 330 is a state diagram in accordance with an embodiment of the present disclosure;

FIG. 331 is a software block diagram in accordance with an embodiment of the present disclosure;

FIG. 332 is a software block diagram in accordance with an embodiment of the present disclosure;

FIG. 333 shows a feedback based control loop to control a motor of an infusion pump in accordance with an embodiment of the present disclosure;

FIG. 334 shows a process diagram to illustrate the software operation of an infusion pump in accordance with an embodiment of the present disclosure;

FIGS. 335-336 show two dual-band antennas for use with an infusion pump in accordance with an embodiment of the present disclosure;

FIG. 337 shows a state diagram illustrating a method of providing a watchdog functionality in accordance with an embodiment of the present disclosure;

FIGS. 338A-338F show a circuit diagram of a watchdog system that is one embodiment that implements the watchdog functionality of the state diagram of FIG. 337 in accordance with another embodiment of the present disclosure;

FIG. 339 shows another embodiment of peristaltic pump having an L-shaped plunger in accordance with an embodiment of the present disclosure;

FIG. 340 shows an exploded view of the peristaltic pump of FIG. 339 in accordance with an embodiment of the present disclosure;

FIG. 341 shows a close-up view of the upper housing, the lower housing, and the power supply of the peristaltic pump of FIG. 339 in accordance with an embodiment of the present disclosure;

FIG. 342A shows a front view of the display of the pump of FIG. 339 in accordance with an embodiment of the present disclosure;

FIG. 342B shows a back view of the display of the pump of FIG. 339 in accordance with an embodiment of the present disclosure;

FIG. 343 shows the back of the sensor portion of the touchscreen and a frame-based split-ring resonator of for use with a near-field antenna in accordance with an embodiment of the present disclosure;

FIG. 344 shows a close-up, side view of the pump of FIG. 339 showing a rotation sensor to measure rotation of the cam shaft in accordance with an embodiment of the present disclosure;

FIG. 345 shows a close-up, side view of the pump of FIG. 339 with a cut plane in accordance with an embodiment of the present disclosure;

FIG. 346 shows a diagram illustrating the use of the sensors of the pump of FIG. 399 when one or more of the sensors are unavailable in accordance with an embodiment of the present disclosure;

FIGS. 347-350 show the operation of the door latch of the pump of FIG. 399 in accordance with an embodiment of the present disclosure;

FIG. 351 shows an optical sensor for estimating parameters of a fluid line in accordance with an embodiment of the present disclosure;

FIG. 352 shows the optical sensor of FIG. 351 with a fluid line in accordance with an embodiment of the present disclosure;

FIG. 353 shows a layer optical sensor for estimating parameters of a fluid line in accordance with an embodiment of the present disclosure;

FIGS. 354-355 show the operation of a tube restoring apparatus in accordance with an embodiment of the present disclosure;

FIGS. 356-357 show the operation of a tube restoring apparatus in accordance with an embodiment of the present disclosure;

FIG. 358 shows a circuit for storing data within an RFID tag associated with an infusion pump in accordance with an embodiment of the present disclosure;

FIG. 359 shows an equivalent circuit for impedance as seen from the RFID tag of FIG. 358 in accordance with an embodiment of the present disclosure;

FIG. 360 shows another circuit for storing data within an RFID tag associated with an infusion pump in accordance with an embodiment of the present disclosure; and FIG. 361 shows a split-ring resonator used with the circuit of FIG. 360 in accordance with an embodiment of the present disclosure.

DETAILED DESCRIPTION

Figure 1:
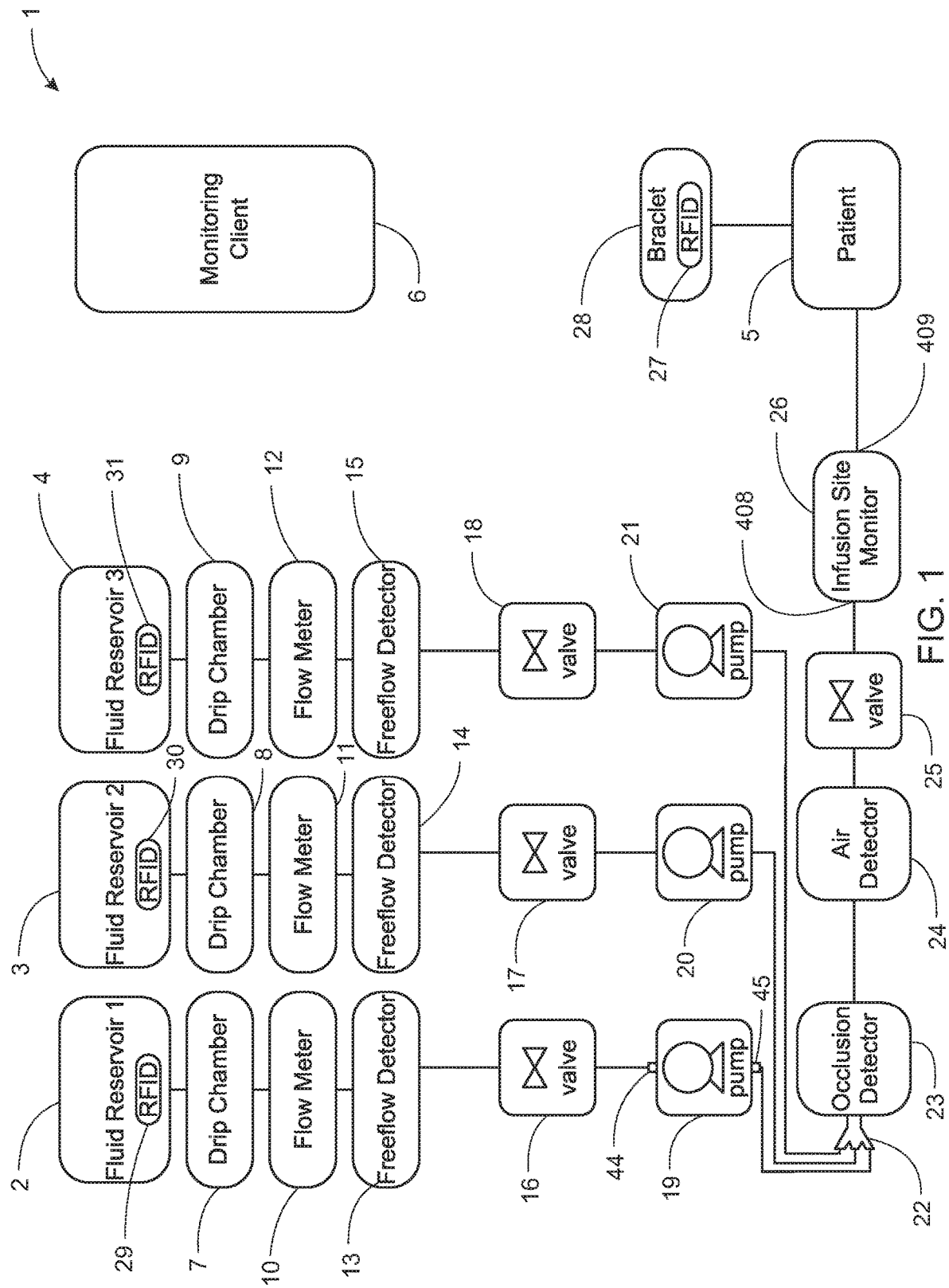
FIG. 1 shows block diagram of a system for infusing liquid in accordance with an embodiment of the present disclosure.

FIG. 1 shows a block diagram of a system 1 for infusing fluid. System 1 includes fluid reservoirs 2, 3, and 4 for infusing the fluid contained therein into a patient 5. The fluid reservoirs 2, 3, and 4 are gravity fed into drip chambers 7, 8, and 9, respectively. The drip chambers 7, 8, and 8 are respectively fed into flow meters 10, 11, and 12. From the flow meters 10, 11, and 12, the fluid is fed into free-flow detectors 13, 14, and 15, respectively.

System 1 also includes valves 16, 17, and 18 from a respective free-flow detector of the free-flow detectors 13, 14, and 15. Pumps 19, 20, and 21 receive fluid from valves 16, 17, and 18, and combine the fluid using a connector 22. The valves 16, 17, and 18 may be in wireless or wired communication with a respective pump 19, 20, and 21 to control the flow rate and/or discharge profile. For example, the pump 19 may communicate wirelessly with the valve 16 to adjust the opening and closing of the valve 16 to achieve a target flow rate, for example, when the pump 19 runs at a predetermined speed; the valves 16 may be downstream from the pump 19 in some embodiments.

Fluid from the connector 22 is fed into an occlusion detector 23 which is fed into an air detector 24. The occlusion detector 23 can detect when an occlusion exists within tubing of the system 1. The occlusion detector 23 may be a pressure sensor compressed against the tube such that increases beyond a predetermined threshold is indicative of an occlusion. The air detector 24 detects if air is present in the tubing, e.g., when flowing towards the patient 5. Prior to entering into an infusion site monitor 26, the fluid passes through a valve 25.

The monitoring client 6, in some embodiments, monitors operation of the system 1. For example, when an occlusion is detected by occlusion detector 23 and/or air is detected by the air detector 24, the monitoring client 6 may wirelessly communicate a signal to the valve 25 to shut-off fluid flow to the patient 5.

The monitoring client 6 may also remotely send a prescription to a pharmacy. The prescription may be a prescription for infusing a fluid using a fluid pump. The pharmacy may include one or more computers connected to a network (e.g., the internet) to receive the prescription and queue the prescription within the one or more computers. The pharmacy may use the prescription to compound the drug (e.g., using an automated compounding device coupled to the one or more computers or manually by a pharmacist viewing the queue of the one or more computers), pre-fill a fluid reservoir associated with an infusion pump, and/or program the infusion pump (e.g., a treatment regime is programmed into the infusion pump 19) at the pharmacy in accordance with the prescription. The fluid reservoir 2 may be automatically filled by the automated compounding device and/or the infusion pump 19 may be automatically programmed by the automated compounding device. The automated compounding device may generate a barcode, RFID tag 29 and/or data. The information within the barcode, RFID tag 29, and/or data may include the treatment regime, prescription, and/or patient information. The automated compounding device may: attach the barcode to the fluid reservoir 2 and/or the infusion pump 19; attach the RFID tag 29 to the fluid reservoir 2 and/or the infusion pump 19; and/or program the RFID tag 29 or memory within the fluid reservoir 2 or the infusion pump 19 with the information or data. The data or information may be sent to a database (e.g., electronic medical records) that associates the prescription with the fluid reservoir 2 and/or the infusion pump 19, e.g., using a serial number or other identifying information within the barcode, RFID tag 29, or memory.

The infusion pump 19 may have a scanner, e.g., an RFID interrogator that interrogates the RFID tag 29 or a barcode scanner that scans a barcode of the fluid reservoir 2, to determine that it is the correct fluid within the fluid reservoir 2, it is the correct fluid reservoir 2, the treatment programmed into the infusion pump 19 corresponds to the fluid within the fluid reservoir 2 and/or the fluid reservoir 2 and infusion pump 19 are correct for the particular patient (e.g., as determined from a patient's barcode, RFID 27, or other patient identification). For example, the infusion pump 19 may scan the RFID tag 29 of the fluid reservoir 2 and check if the serial number or fluid type encoded within the RFID tag 29 is the same as indicated by the programmed treatment within the infusion pump 19. Additionally or alternatively, the infusion pump 19 may interrogate the RFID tag 29 of the fluid reservoir 2 for a serial number and the RFID tag 27 of the patient 5 for a patient serial number, and also interrogate the electronic medical records to determine if the serial number of the fluid reservoir 19 within the RFID tag 29 matches a patient's serial number within the RFID tag 27 as indicated by the electronic medical records. Additionally or alternatively, the monitoring client 6 may scan the RFID tag 29 of the fluid reservoir 2 and an RFID tag of the infusion pump 19 to determine that it is the correct fluid within the fluid reservoir 2, it is the correct fluid reservoir 2, the treatment programmed into the infusion pump 19 corresponds to the fluid within the fluid reservoir 2, and/or the fluid reservoir 2 and infusion pump 19 are correct for the particular patient (e.g., as determined from a patient's barcode, RFID tag 27, electronic medical records, or other patient identification or information). Additionally or alternatively, the monitoring client 6 or the infusion pump 19 may interrogate an electronic medical records database and/or the pharmacy to verify the prescription or download the prescription, e.g., using a barcode serial number on the infusion pump 19 or fluid reservoir 2.

Additionally or alternatively, the flow from the pumps 19, 20, and 21 may be monitored and/or controlled by the monitoring client 6 to ensure safe drug delivery. The monitoring client 6 may scan a RFID tag 27 on a bracelet 28, and also RFID tags 29, 30, and 31 on the fluid reservoirs, 2, 3, and 4, respectively. The monitoring client 6 may download electronic medical records ("EMR") associated with the RFID tag 27 on the patient's 5 bracelet, and compare it to one or more prescriptions found in the EMR of the patient 5. If the EMR indicates that the fluid reservoirs 2, 3, and 4 contain the correct medication, a user can input into the monitoring client 6 a command to start pumping fluid through pumps 19, 20, and/or 21 into the patient 5.

Figure 2:
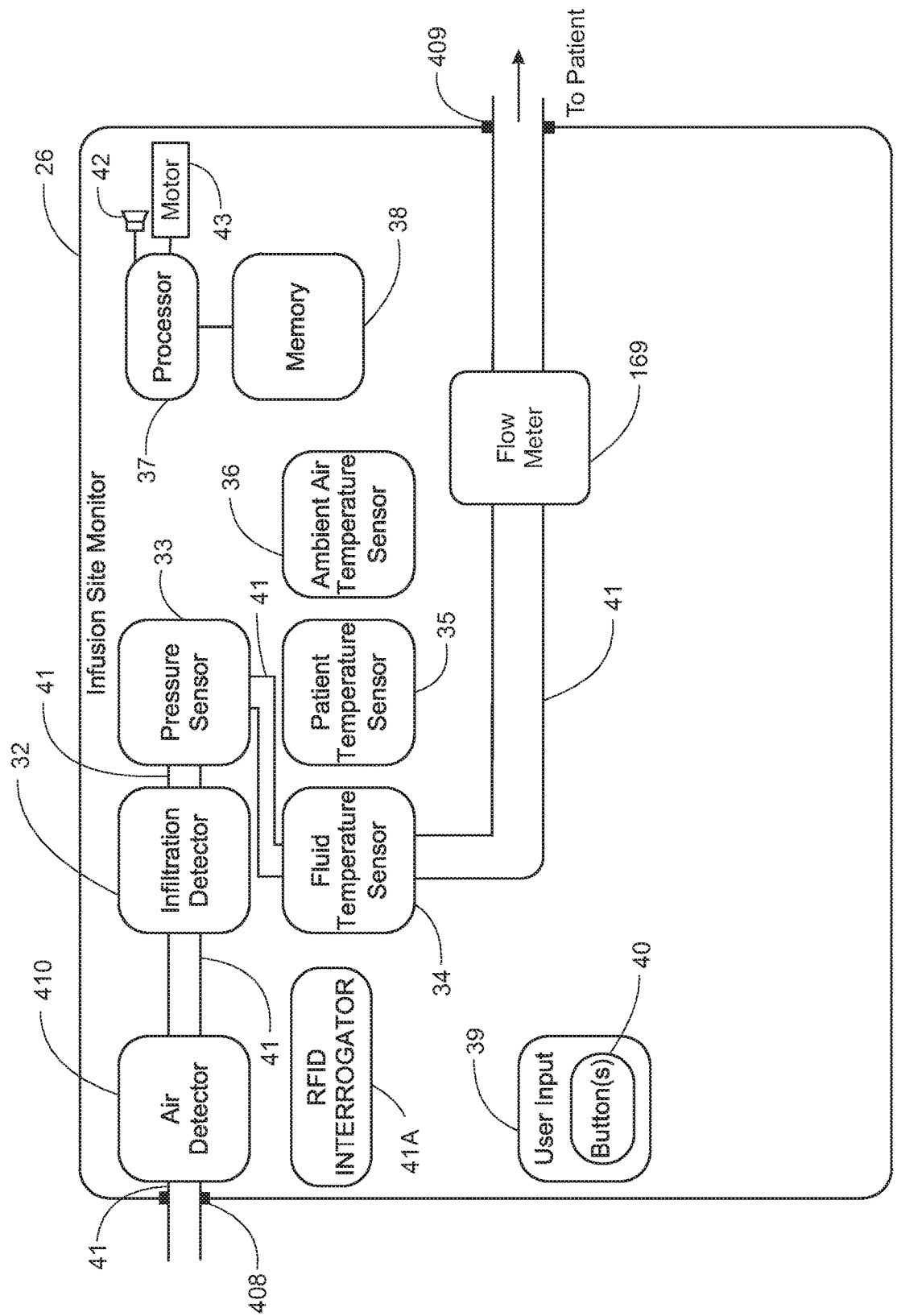
FIG. 2 shows a block diagram of an infusion site monitor of the system of FIG. 1 in accordance with an embodiment of the present disclosure.

The infusion site monitor 26 monitors the site at which the fluid is fed into the patient 5. The infusion site monitor 26 receives the fluid through an input port 408 and feeds the fluid to the patient 5 through an output port 409. As shown in FIG. 2, in some embodiments the infusion site monitor 5 optionally includes an air detector 410, an infiltration detector 32, a pressure sensor 33, a fluid-temperature sensor 34, and/or a patient temperature sensor 35. In some embodiments, the infusion site monitor 26 optionally includes an ambient air temperature sensor 35 and an RFID interrogator 41A.

The infusion site monitor 26 also includes a processor 37 and a memory 38. The memory 38 may include processor executable instructions configured for execution on the processor 37. The processor 37 is in operative communication with the air detector 410, the infiltration detector 32, the pressure sensor 33, the fluid-temperature sensor, the patient temperature sensor 35, the ambient air temperature sensor 36, the RFID interrogator 41A, the user input 39, and the buttons 40; for example, the processor 37 may be coupled to a bus, a parallel communication link, a serial communication link, a wireless communication link, and the like. Referring to FIGS. 1 and 2, information from the various circuitry of 410, 32, 33, 34, 35, 36, 39, 40, and/or 41 may be communicated to the monitoring client 6 via a wired or wireless communication link, e.g., WiFi, USB, serial, WiMax, Bluetooth, Zigbee, and the like.

In FIG. 1, in each of the pumps 19, 20, and 21, or the fluid reservoirs 2, 3, and 4 may include an upstream and/or downstream pressure generating source (e.g., an occluder, speaker, etc) to generate a pressure "signature" that would travel along the tube and into the other devices, e.g., pumping, monitoring, or metering devices. These pressure signatures may indicate the pressure in each of the tubes, may be used to identify each tube and coordinate the flow rates of the tubes, and/or may indicate what the measured flow rate of the tube should be. The pressure signature may be an ultrasonic signal generated by a piezoelectric ceramic that is modulated to encode information such as digital data or an analog signal, e.g., an acoustic carrier frequency with FM modulation, AM modulation, digital modulation, analog modulation, or the like.

For example, each of the pumps 19, 20, and 21 may transmit sound pressure down the IV tube to the infusion site monitor 26 (which may include a transducer to detect these pressure waves) indicating to the infusion site monitor 26 the expected total flow rate therethrough. A flow rate meter 169 (see FIG. 2) may measure the liquid flow rate, and if the measured liquid flow rate deviates by a predetermined amount, the infusion site monitor 26 may issue an alarm and/or alert, e.g., the alarm may signal the valves 16, 17, 18, and 25 to close, and/or the monitoring client 6 may use the information for logging purposes and/or to cause the valves 16, 17, 18, and 25 to close.

Referring again to FIG. 2 and as previously mentioned, the processor 37 is in operative communication with user input 39 and one or more buttons 40. The infusion site monitor 26 may receive various user input 39 to signal the processor 37 to start monitoring treatment of the patient 5. Additionally or alternatively, the infusion site monitor 26 may interrogate the RFID 27 of the patient's 5 bracelet (see FIG. 1) to determine if the infusion site monitor 26 is coupled to the correct patient 5.

The air detector 410 is in operative communication with the processor 37. The air detector 410 can measure, estimate, and/or determine the amount of air entering into the infusion site monitor 26 via the input port 29. In some embodiments, when the processor 37 determines that air within the tube exceeds a predetermined threshold, the processor 37 communicates an alarm or alert to the monitoring client 6 (see FIG. 1) which can signal valve 25 to shut off fluid flow to the patient 5. Additionally or alternatively, the processor 37 may communicate an alarm or an alert to the valve 25 or to one or more of the pumps 19, 20, and 21 to stop fluid flow when the air within the tube exceeds the predetermined threshold. The air detector 410 may be an ultrasonic air detector, an impedance-based air detector, and the like.

The infiltration detector 32 is in operative communication with the processor 37. The infiltration detector 32 can measure, estimate, and/or determine the amount of blood entering into the infusion site monitor 26 via the output port 30 during an infiltration test. In some embodiments, when the processor 37 determines that blood within the tube is less than a predetermined threshold during an infiltration test, the processor 37 communicates an alarm or alert to the monitoring client 6 (see FIG. 1) which can signal the valve 25 to shut off fluid flow to the patient 5. Additionally or alternatively, the processor 37 may communicate an alarm or an alert to the valve 25 or to one or more of the pumps 19, 20, and 21 to stop fluid flow when the infiltration tests determines that an infiltration has occurred. The infiltration test may include reversing one or more of the pumps 19, 20, and/or 21 to determine if blood does flow into the infusion site monitor 26. When an infiltration has occurred, blood will not easily flow into the infusion site monitor 26. Thus, when fluid is pulled from the patient 5, blood should enter into the tube 41 with a predetermined minimum amount of backward pumping when no infiltration has occurred. The infiltration detector 32 may be CCD based, camera based, optical based, and the like.

The pressure sensor 33 is in operative communication with the processor 37. The pressure sensor 33 can measure, estimate, and/or determine the amount of pressure entering, exiting and/or flowing through the infusion site monitor 26 via the ports 29 and 30. In some embodiments, when the processor 37 determines that pressure in the tube exceeds a predetermined threshold and/or is below a predetermined threshold, the processor 37 communicates an alarm or alert to the monitoring client 6 (see FIG. 1) which can signal valve 25 to shut off fluid flow to the patient 5. The pressure sensor 33 may be a resistive element that changes in resistance as a force is applied to the resistive element, the resistive element is stretched, and/or the resistive element is pulled. The resistive element may be wrapped around the tube 41 such that as the pressure of the fluid causes the tube 41 to expand, the resistance of the resistive element is measured and is associated with a pressure within the tube, e.g., the resistance may be measured and a look-up table may be used to look up an estimated pressure within the tube 41. In some embodiments, when the processor 37 determines that pressure within the tube is greater than a predetermined maximum value or less than predetermined minimum value, the processor 37 communicates an alarm or alert to the monitoring client 6 (see FIG. 1) which can signal the valve 25 to shut off fluid flow to the patient 5. Additionally or alternatively, the processor 37 may communicate an alarm or an alert to the valve 25 or to one or more of the pumps 19, 20, and 21 to stop fluid flow when the processor 37 receives from the pressure sensor 33 to a measured pressure within the fluid tube 41 greater than a predetermined maximum value or less than predetermined minimum value.

The fluid-temperature sensor 34 is in operative communication with the processor 37. The fluid-temperature sensor 34 can measure, estimate, and/or determine the temperature of the fluid within the tube 41. In some embodiments, when the processor 37 determines that temperature of the fluid within the tube 41 exceeds a predetermined threshold and/or is below a predetermined threshold, the processor 37 communicates an alarm or alert to the monitoring client 6 (see FIG. 1) which can signal valve 25 to shut off fluid flow to the patient 5. In some embodiments, a user may override the alarm or alert, e.g., using a touch screen of the monitoring client 6. Additionally or alternatively, the processor 37 may communicate an alarm or an alert to the valve 25 or to one or more of the pumps 19, 20, and 21 to stop fluid flow when the processor 37 receives a estimated temperature of the fluid within the tube 41 indicating the fluid is above a predetermined threshold and/or is below a predetermined threshold. The fluid-temperature sensor 34 may utilize a temperature sensitive material, a positive temperature-coefficient material, a negative temperature-coefficient material, or other temperature sensor technology.

The patient temperature sensor 35 is in operative communication with the processor 37. The patient temperature sensor 35 can measure, estimate, and/or determine the temperature of the patient 5 (see FIG. 1). The temperature of the patient 5 may be used to determine the condition of the patient, compliance with a temperature affecting medication, or effect of a temperature affecting medication. The temperature of the patient 5 (a patient-condition parameter) may be communicated to the monitoring client 6 (see FIG. 1). In some embodiments, when the processor 37 determines that the temperature of the patient 3 exceeds a predetermined threshold or is below a predetermined threshold, the processor 37 communicates an alarm or alert to the monitoring client 6 (see FIG. 1) which can signal valve 25 to shut off fluid flow to the patient 5, send an alert to a remote communicator, and/or notify a caregiver of the condition via an internal speaker 42 or vibration motor 43 within the infusion site monitor 26. Additionally or alternatively, the processor 37 may communicate an alarm or an alert to the valve 25 or to one or more of the pumps 19, 20, and 21 to stop fluid flow when the processor 37 receives an estimated temperature from the patient temperature sensor 35 that exceeds a predetermined threshold or is below a predetermined threshold. The patient temperature sensor 35 may utilize a temperature sensitive material, a positive temperature-coefficient material, a negative temperature-coefficient material, or other temperature sensor technology.

The ambient air temperature sensor 36 is in operative communication with the processor 37. The ambient air temperature sensor 36 can measure, estimate, and/or determine the temperature of the ambient air within the infusion site monitor 26, or in other embodiments, the temperate of the air outside of the infusion site monitor 26. An excessive ambient air temperature may be an indication of an electronic component failure, in some specific embodiments. In some embodiments, when the processor 37 determines that the temperature from the ambient air temperature sensor 36 exceeds a predetermined threshold or is below a predetermined threshold, the processor 37 communicates an alarm or alert to the monitoring client 6 (see FIG. 1) which can signal valve 25 to shut off fluid flow to the patient 5. Additionally or alternatively, the processor 37 may communicate an alarm or an alert to the valve 25 or to one or more of the pumps 19, 20, and 21 to stop fluid flow when the processor 37 receives an estimated temperature from the ambient temperature sensor 36 that exceeds a predetermined threshold or is below a predetermined threshold. The ambient air temperature sensor 36 may utilize a temperature sensitive material, a positive temperature-coefficient material, a negative temperature-coefficient material, or other temperature sensor technology.

Figure 3:
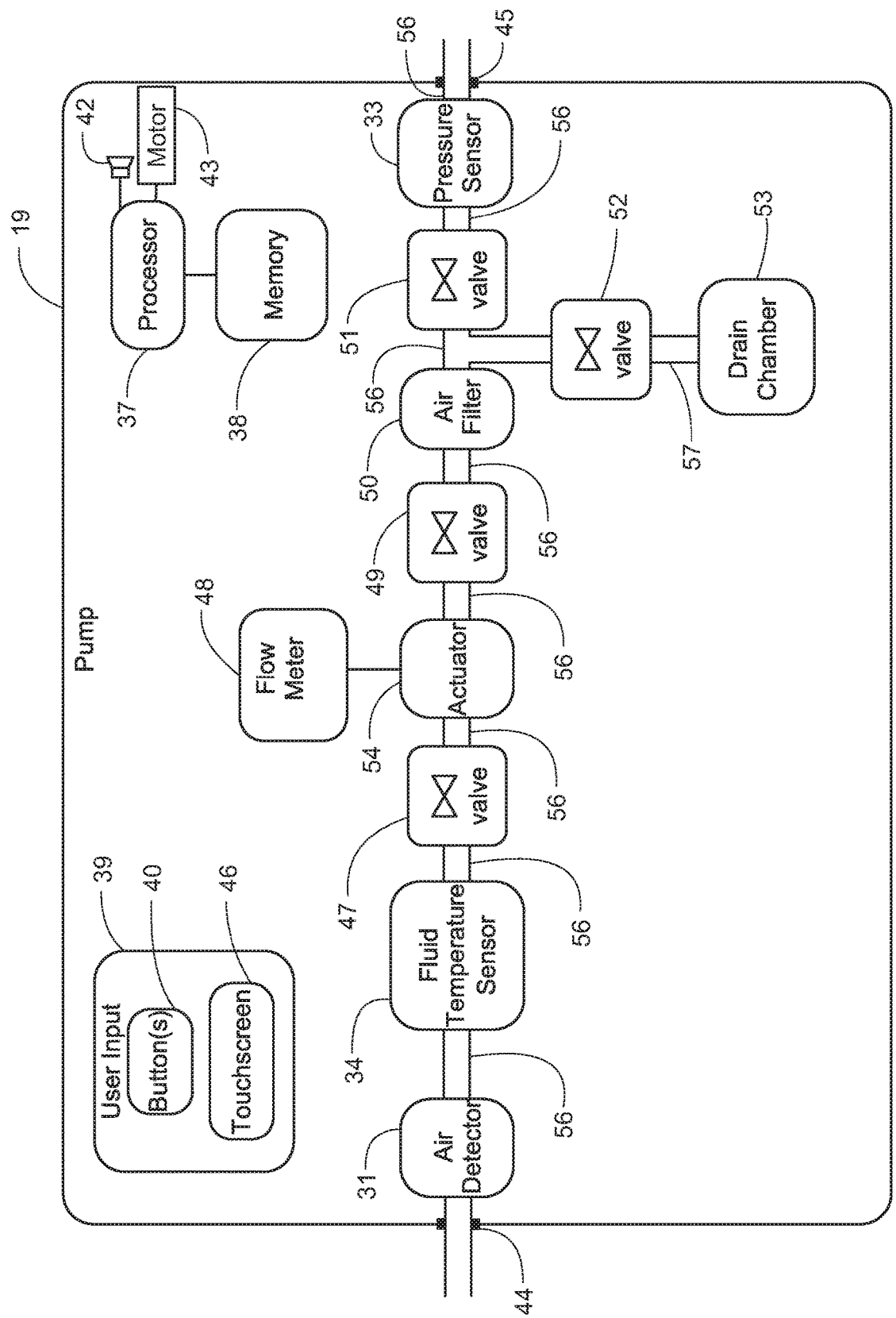
FIG. 3 shows a block diagram of a pump for infusing liquid of the system of FIG. 1 in accordance with an embodiment of the present disclosure.

Referring to the drawings, FIG. 3 shows a block diagram of a pump for infusing liquid of the system of FIG. 1 in accordance with an embodiment of the present disclosure. Although the pump 19 of FIG. 3 is described as being pump 19 of FIG. 1, the pump 19 of FIG. 3 may be one or more of the pumps 19, 20, and 21 of FIG. 1, or may be included within any sufficient pump disclosed herein.

Pump 19 includes a processor 37 coupled to a memory 38. The processor 37 is in operative communication with the memory 38 to receive processor executable instructions configured for execution on the processor 37. In some embodiments, the processor 37 is, optionally, in operative communication with the user input 39, the air detector 410, the fluid temperature sensor 34, valves 47, 49, 51 and 52, a flow meter 48, an actuator 54, an air filter 50, a drain chamber 53, and/or a pressure sensor 33.

The pump includes an actuator 54 which operates on fluid contained within tubing 56 flowing through the pump. The actuator 54 may directly operate on the tube 56, or may actuate against one or more membranes contained within the actuator 54. In some embodiments, the valves 47 and 49 cooperate with the actuator 54 to pump fluid, e.g., liquid, from the input port 44 to the output port 45 through the tube 56. In some embodiments of the present disclosure, the pump 19 contains no internal tubing and interfaces to external tubing.

The air filter 50 filters out air from the tube 56. In alternative embodiments, the air filter 50 is upstream from the air detector 410. Valve 52 can activate to allow air to enter in from the tube 56 into a drain chamber 53 via a diversion tube 57.

Figure 5:
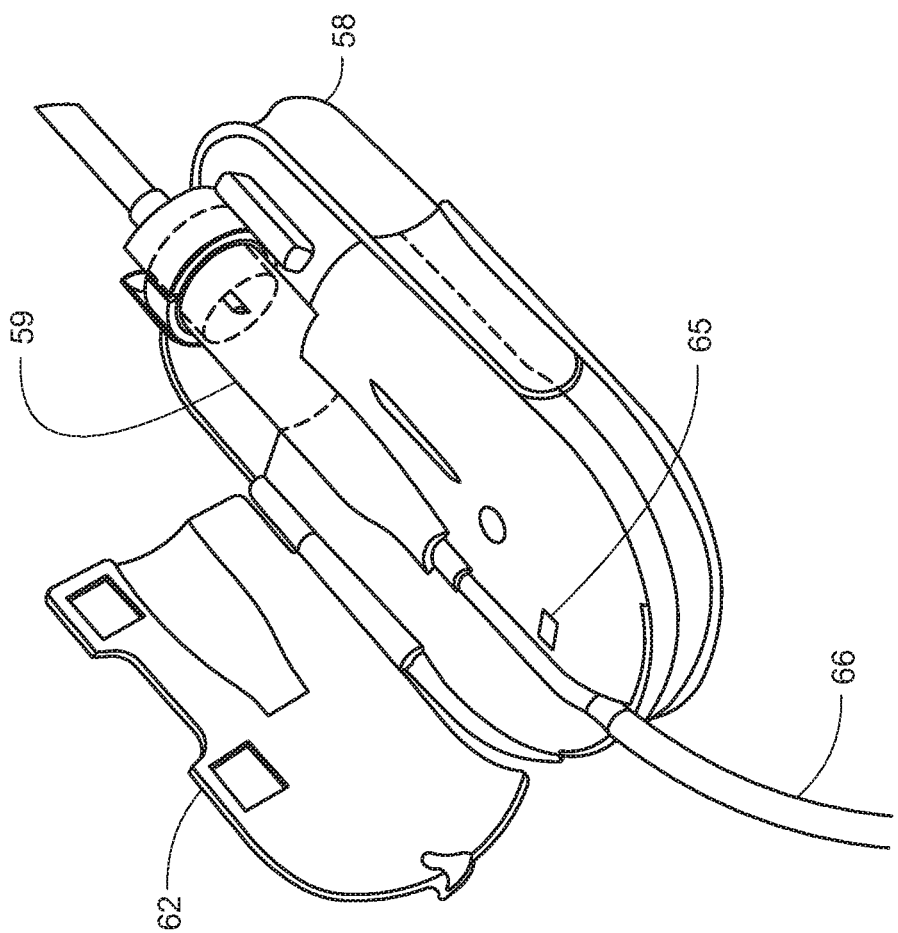
FIG. 5 shows the drip-chamber holder of FIG. 4 with the door open in accordance with an embodiment of the present disclosure.
Figure 4:
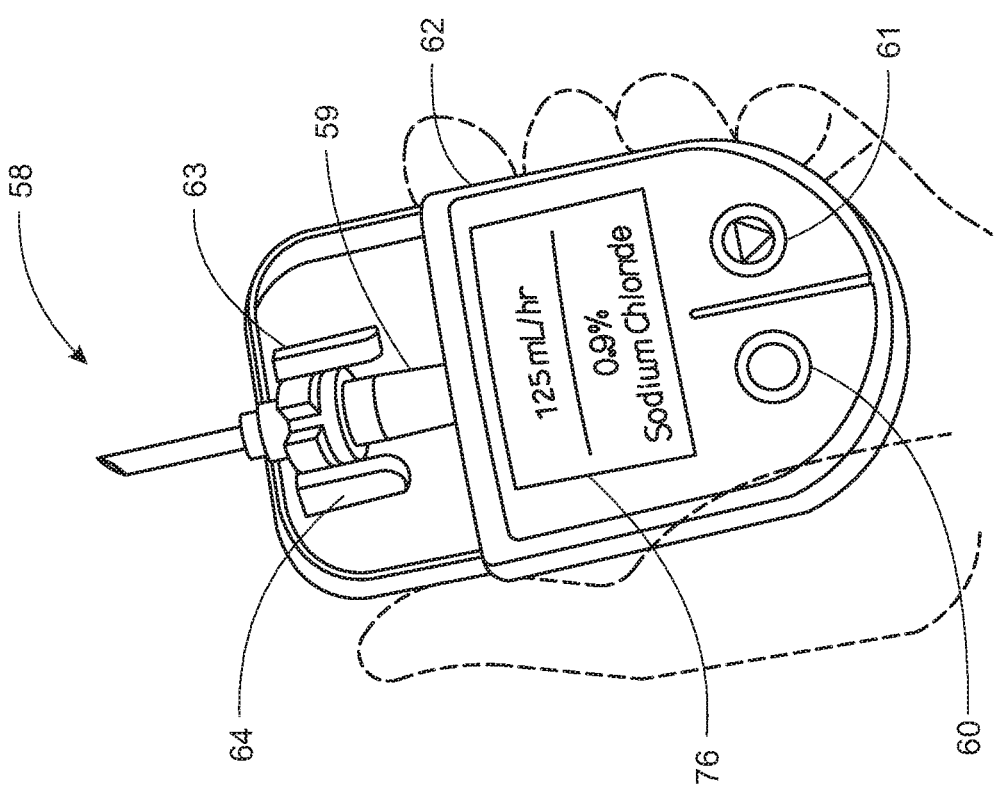
FIG. 4 shows a drip-chamber holder receiving a drip chamber, and the drip-chamber holder includes a flow meter and a free-flow detector in accordance with an embodiment of the present disclosure.

Referring to the drawings, FIGS. 4 and 5 show a drip-chamber holder 58 receiving a drip chamber 59. As described infra, the drip-chamber holder 58 includes a free-flow detector in accordance with an embodiment of the present disclosure. Additionally, alternatively, or optionally, the drip-chamber holder 58 may include a flow-rate meter in accordance with some embodiments of the present disclosure. FIG. 4 shows the drip chamber holder 58 with a shut door 62, and FIG. 5 shows the drip-chamber holder 58 with an open door 62. The drip chamber holder 58 may include the drip chamber 7, the flow meter 10, and the freeflow detector 13 of FIG. 1 integrated together, or some combination thereof. The drip chamber holder 58 includes a start button 60 and a stop button 61. The drip-chamber holder may include a valve to stop fluid from flowing therethrough or may signal another valve, e.g., valve 16 of FIG. 1, to stop the fluid from flowing.

The drip-chamber holder 58 optionally includes cameras 63 and 64 that can estimate fluid flow and/or detect free flow conditions. Although the drip-chamber holder 58 includes two cameras (e.g., 63 and 64), only one of the cameras 64 and 64 may be used in some embodiments. The cameras 63 and 64 can image a drop while being formed within the drip chamber 59 and estimate its size. The size of the drop may be used to estimate fluid flow through the drip chamber 59. For example, in some embodiments of the present disclosure, the cameras 63 and 64 use an edge detection algorithm to estimate the outline of the size of a drop formed within the drip chamber 59; a processor therein (see processor 90 of FIGS. 12 of 14, for example) may assume the outline is uniform from every angle of the drop and can estimate the drop's size from the outline. In the exemplary embodiment shown in FIGS. 4 and 5, the two cameras 63 and 64 may average together the two outlines to estimate the drop's size. The cameras 63 and 64 may use a reference background pattern to facilitate the recognition of the size of the drop as described herein.

In another embodiment of the present disclosure, the cameras 63 and 64 image the fluid to determine if a free flow condition exists. The cameras 63 and 64 may use a background pattern to determine if the fluid is freely flowing (i.e., drops are not forming and the fluid streams through the drip chamber 59). Although the drip-chamber holder 58 includes two cameras (e.g., 63 and 64), only one of the cameras 64 and 64 may be used in some embodiments to determine if a free flow condition exists Additionally or alternatively, in some embodiments of the present disclosure, another camera 65 monitors the fluid tube 66 to detect the presence of one or more bubbles within the fluid tube. In alternative embodiments, other bubble detectors may be used in place of the camera 65. In yet additional embodiments, no bubble detection is used in the drip-chamber holder 58.

Figure 6:
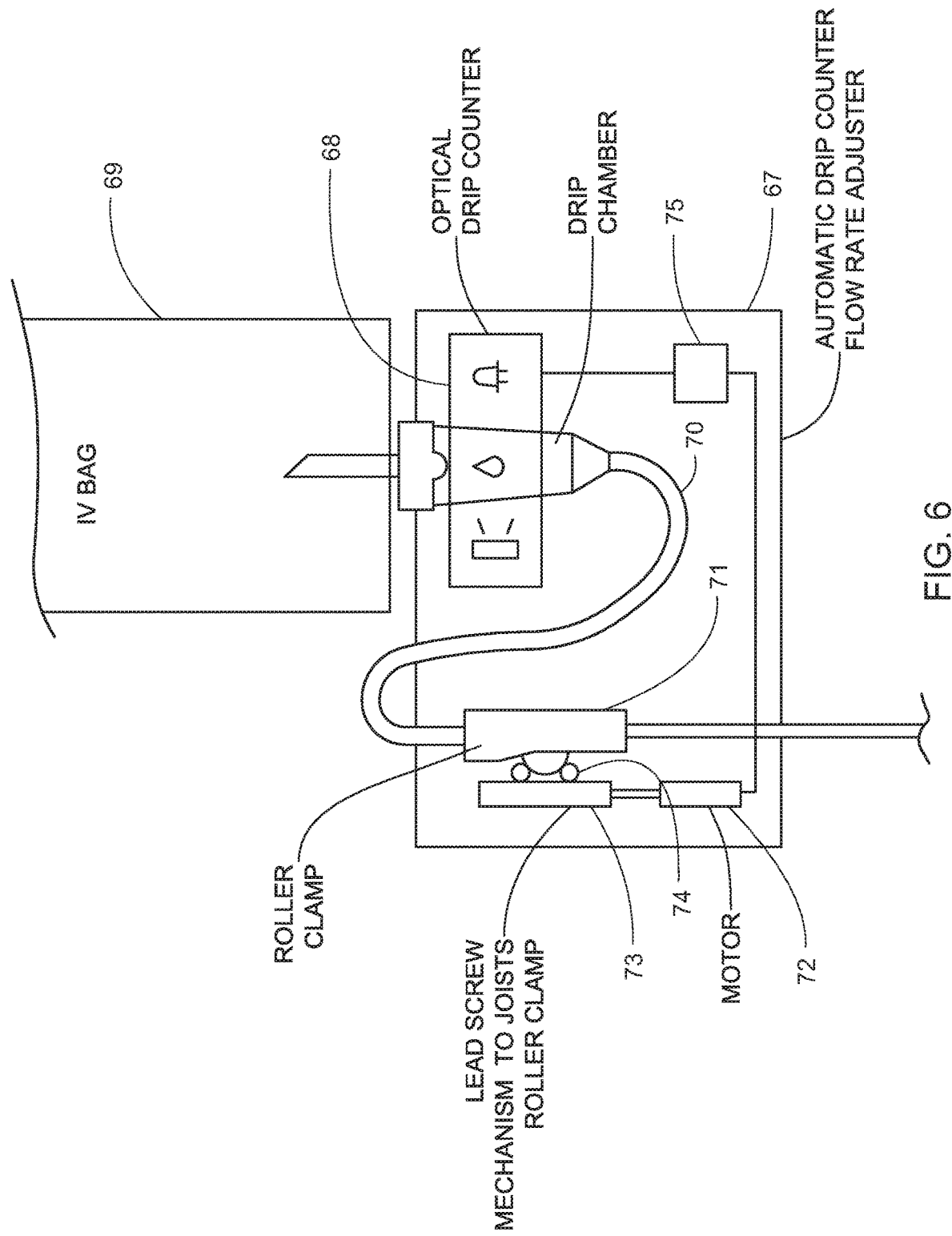
FIG. 6 shows a block diagram of another drip-chamber holder in accordance with another embodiment of the present disclosure.

FIG. 6 shows a block diagram of another drip-chamber holder 67 in accordance with another embodiment of the present disclosure. The drip-chamber holder 67 includes an optical drip counter 68 that receives fluid from an IV bag 69. In alternative embodiments, the optical drip counter 68 is a camera, is a pair of cameras, is a capacitive drip counter, and the like. The drip-chamber holder 67 is coupled to a tube 70 coupled to a holder clamp 71 that is controlled by a motor 72. The motor 72 may be coupled to a lead screw mechanism 73 to control a roller clamp 74.

The motor 72 may be a servo-motor and may be used to adjust the flow rate through the tube 70. That is, the drip-chamber holder 67 may also function as a flow meter and regulator. For example, a processor 75 within the drip-chamber holder 67 may adjust the motor 72 such that a desired flow rate is achieved as measured by the optical drip counter 68. The processor 75 may implement a control algorithm using the optical drip counter 68 as feedback, e.g., a proportional-integral-derivative ("PID") control loop with the output being to the motor 72 and the feedback being received from the optical drip counter 68.

In alternative embodiments, the motor 72, the lead screw mechanism 73, and the roller clamp 74 may be replaced and/or supplemented by an actuator that squeezes the tube 70 (e.g., using a cam mechanism or linkage driven by a motor) or may be replaced by any sufficient roller, screw, or slider driven by a motor.

The drip-chamber holder 67 may also include a display, e.g., the display 76 as shown on the drip-chamber holder 58 of FIGS. 4 and 5. The display may be used to set the target flow rate, display the current flow rate, and/or may provide a button, e.g., a touch screen button, to stop the flow rate (or a button 61 as shown in FIGS. 4 and 5 may be used to stop fluid flow).

Referring again to FIG. 4, in some specific embodiments of the present disclosure, the cameras 63 and/or 64 may be a camera cube manufactured by OmniVision of 4275 Burton Drive, Santa Clara, Calif. 95054; for example, the camera cube may be one manufactured for phone camera applications. In some embodiments of the present disclosure, the cameras 63 and/or 64 may use a fixed focus and have a depth of field ("DOF") from 15 centimeters to infinity.

The cameras 63 and 64 may each have the blur circle of a point imaged in the range of one of the cameras 63 and/or 64 entirely contained within the area of a single pixel. In an exemplary embodiment, the focal length of the camera lenses of cameras 63 and 64 may be 1.15 millimeters, the F # may be 3.0, and the aperture of the lenses of cameras 63 and 64 may be 0.3833 millimeter. A first order approximation to the optical system of one or more of the cameras 63 and 64 may be made using matrix equations, where every ray, r, is represented as the vector described in Equation (1) as follows:

$$r = \left\{ \begin{matrix} h \\ \theta \end{matrix} \right\}. \tag{1}$$

Figure 7:
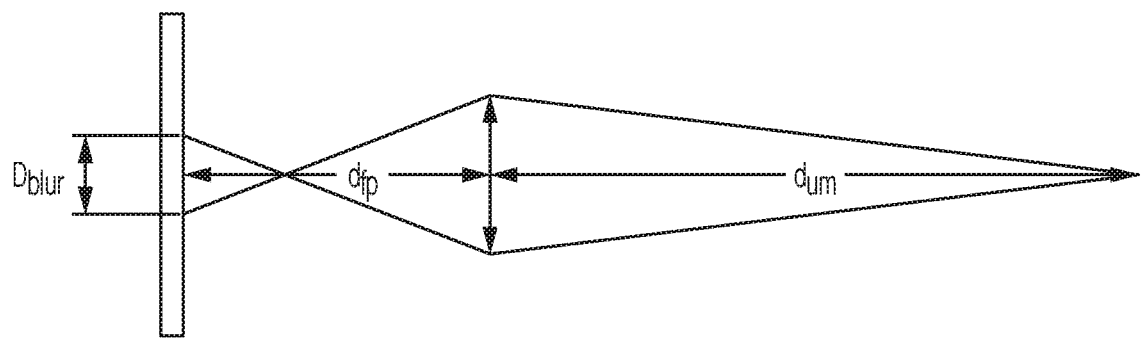
FIG. 7 shows a ray diagram illustrating the diameter of a blur circle to illustrate aspects of the cameras of the drip-chamber holder of FIGS. 4 and 5 in accordance with an embodiment of the present disclosure.

In Equation (1) above, h is the height of the ray at the entrance to the camera system of cameras 63 and/or 64, and $\theta$ is the angle of the ray. Referring to FIG. 7, when imaging a hypothetical point at a distance $d_{im}$ from the lens of one of the cameras 63 or 64 (which has focal length f) and the lens is a distance $d_{fp}$ from the focal plane, the corresponding matrix, $M_{cam}$, describing the camera (e.g., one or both of the cameras 63 and/or 64) is described by Equation (2) as follows:

$$M_{cam} = \begin{bmatrix} 1 & d_{fp} \\ 0 & 1 \end{bmatrix} \cdot \begin{bmatrix} 1 & 0 \\ -\frac{1}{f} & 1 \end{bmatrix} \cdot \begin{bmatrix} 1 & d_{im} \\ 0 & 1 \end{bmatrix}. \tag{2}$$

To find the place on the focal plane, fp, where the ray strikes, a matrix multiplication as described in Equation (3) as follows may be used:

$$\left\{ \begin{matrix} h_{fp} \\ \theta_{fp} \end{matrix} \right\} = M_{cam} \cdot \left\{ \begin{matrix} h_{im} \\ \theta_{im} \end{matrix} \right\}. \tag{3}$$

As illustrated in FIG. 7, the diameter of the blur circle, $D_{blur}$, is shown as approximately the distance between the two points illustrated in FIG. 7. This distance is found by tracing rays from the point $d_{im}$ away from the lens on the optical axis to the edges of the lens and then to the focal plane. These rays are given by the vectors shown in (4) as follows:

$$\left\{ \begin{matrix} 0 \\ \pm \tan^{-1} \frac{D_{lens}}{2 * d_{im}} \end{matrix} \right\}. \tag{4}$$

Figure 8:
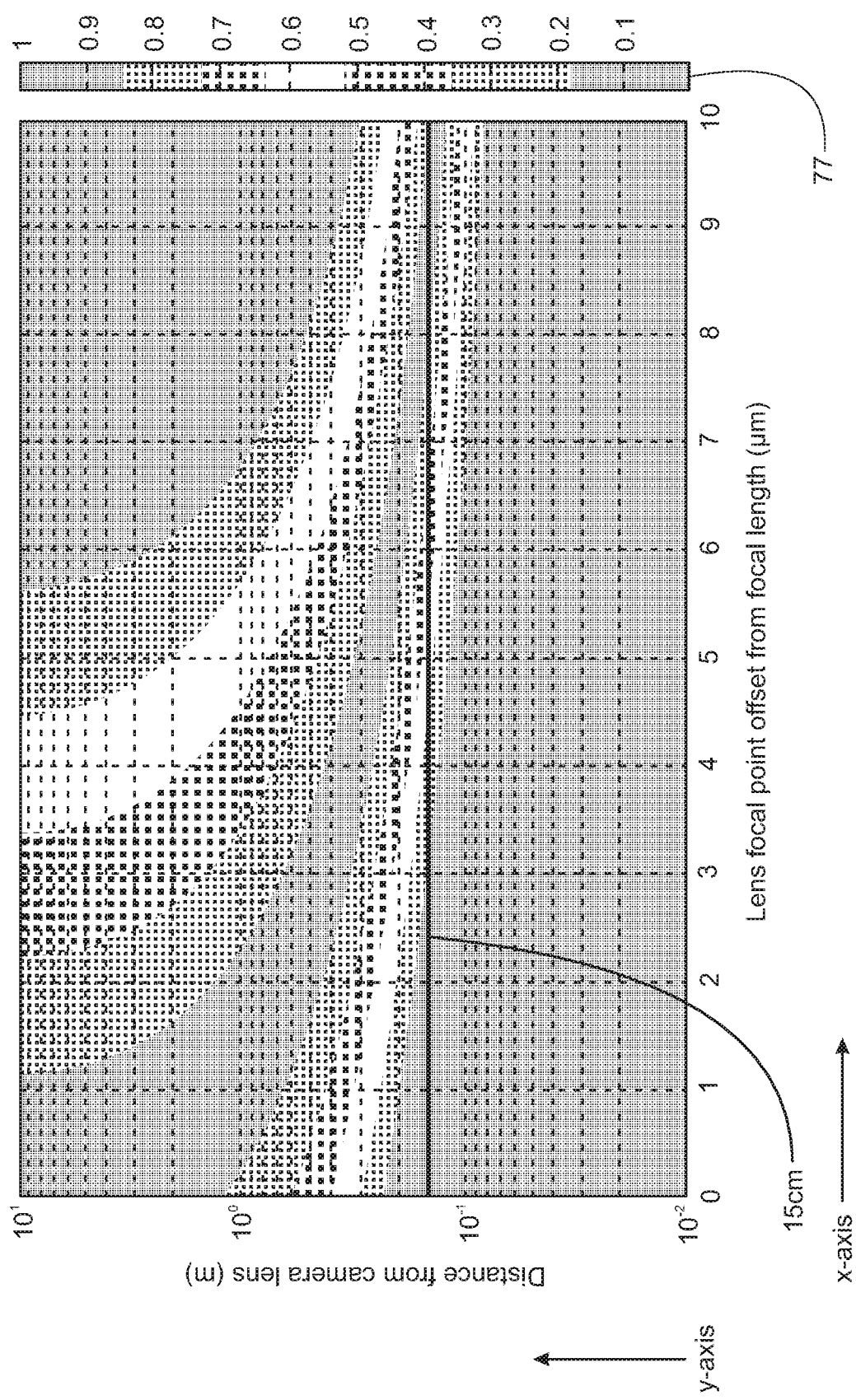
FIG. 8 is a graphic illustrating the blur circle as calculated for a variety of lens-to-focal plane separations and lens-to-image separations for the cameras of the drip-chamber holder of FIGS. 4 and 5 in accordance with an embodiment of the present disclosure.

As shown in FIG. 8, the blur circle, $D_{blur}$, is calculated and shown for a variety of lens-to-focal plane separations and lens-to-image separations. A contour map 77 is also shown in FIG. 8. The x-axis shows the distance in microns between the focal plane and a point located a focal length away from the lens of one of the cameras 63 and/or 64. The y-axis shows the distance in meters between the lens and the point being imaged. The values creating the contour map 77 is the blur size divided by the pixel size; therefore anything about 1 or less is sufficient for imaging. As shown in FIG. 8, the focal plane is located a focal length and an additional 5 micrometers away from the lens.

The cameras 63 and/or 64 may utilize a second lens. For example, one or more of the cameras 63 and/or 64 may utilize a second lens to create a relatively larger depth of field and a relatively larger field of view. The depth of field utilizing two lenses can be calculated using the same analysis as above, but with the optical matrix modified to accommodate for the second lens and the additional distances, which is shown in Equation (5) as follows:

$$M_{sys} = \begin{bmatrix} 1 & d_{fp} \\ 0 & 1 \end{bmatrix} \cdot \begin{bmatrix} 1 & 0 \\ -\frac{1}{f_{cam}} & 1 \end{bmatrix} \cdot \begin{bmatrix} 1 & d_{lens} \\ 0 & 1 \end{bmatrix} \cdot \begin{bmatrix} 1 & 0 \\ -\frac{1}{f_{lens}} & 1 \end{bmatrix} \cdot \begin{bmatrix} 1 & d_{im} \\ 0 & 1 \end{bmatrix}. \tag{5}$$

Figure 9:
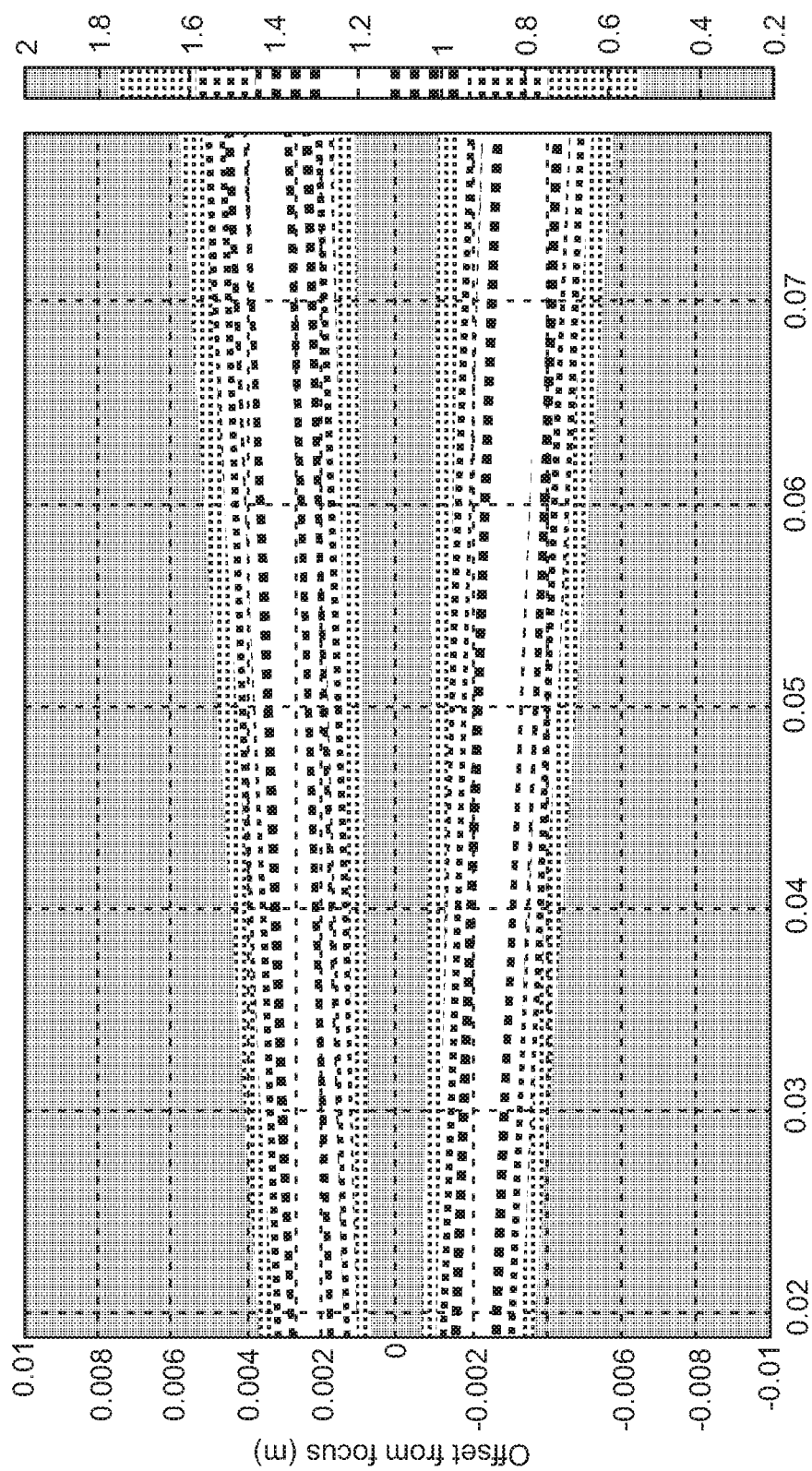
FIG. 9 is a graphic illustrating the blur circle divided by pixel size when a 20 millimeter focal length lens of the cameras of the drip-chamber holder of FIGS. 4 and 5 is used in accordance with an embodiment of the present disclosure.
Figure 10:
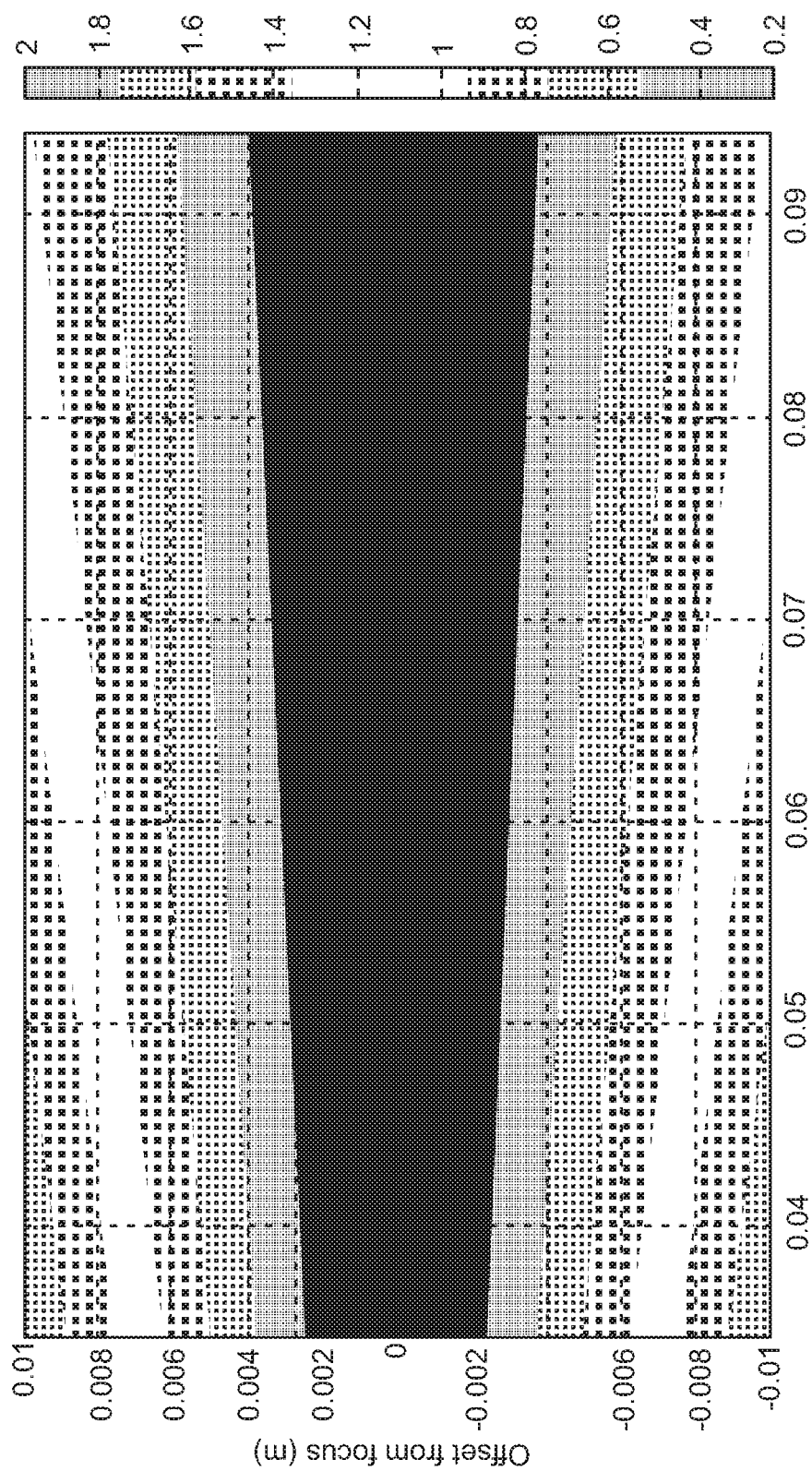
FIG. 10 is a graphic illustrating the blur circle divided by pixel size when a 40 millimeter focal length lens of the cameras of the drip-chamber holder of FIGS. 4 and 5 is used in accordance with an embodiment of the present disclosure.

FIGS. 9 and 10 illustrate the field changes with the separation between the lens and the camera and the corresponding change in the focus of the camera. FIGS. 9 and 10 show the blur circle divided by the pixel size. FIG. 9 shows the blur circle divided by pixel size when a 20 millimeter focal length lens is used. FIG. 10 shows the blur circle divided by pixel size when a 40 millimeter focal length lens is used. The corresponding fields of views about the optical axis for the corners of the two configurations of FIGS. 9 and 10 are shown in the table in FIG. 11.

As shown in FIG. 11, in some embodiments, the cameras 63 and 64 of FIGS. 4 and 5 may utilize a 40 mm to 60 mm focal length lens; this configuration may include placing one or more of the cameras 43 and 64 about 2 inches from the focus. In other embodiments of the present disclosure, other configurations may be used including those not shown in FIG. 11.

For example, the following analysis shows how the depth of field can be set for one or more of the cameras 63 and 65: using a lens of focal length, f, a distance, z, from the focal plane, and a distance, d, from a point in space; a matrix of the system is shown in Equation (6) as follows:

$$M = \begin{bmatrix} 1 & z \\ 0 & 1 \end{bmatrix} \cdot \begin{bmatrix} 1 & 0 \\ -\frac{1}{f} & 1 \end{bmatrix} \cdot \begin{bmatrix} 1 & d \\ 0 & 1 \end{bmatrix}. \quad (6)$$

Equation (6) reduces to Equation (7) as follows:

$$M = \begin{bmatrix} 1 & z \\ 0 & 1 \end{bmatrix} \cdot \begin{bmatrix} 1 & d \\ -\frac{1}{f} & 1 - \frac{d}{f} \end{bmatrix}. \quad (7)$$

Equation (7) reduces to Equation (8) as follows:

$$M = \begin{bmatrix} 1 - \frac{z}{f} & d + z - \frac{dz}{f} \\ -\frac{1}{f} & 1 - \frac{d}{f} \end{bmatrix}. \quad (8)$$

Considering the on-axis points, all of the heights will be zero. The point on the focal plane where different rays will strike is given by (9) as follows:

$$\left( d + z - \frac{dz}{f} \right) \theta. \quad (9)$$

As shown above in (9), θ is the angle of the ray. The point in perfect focus is given by the lens maker's equation given in Equation (10) as follows:

$$\frac{1}{f} = \frac{1}{z} + \frac{1}{d}. \quad (10)$$

Equation (10) may be rearranged to derive Equation (11) as follows:

$$d = \frac{1}{\frac{1}{f} - \frac{1}{z}} = \frac{fz}{z - f}. \quad (11)$$

Inserting d from Equation (11) into (9) to show the striking point results in Equation (12) as follows:

$$\left[ \frac{fz}{z-f} + z - \frac{\frac{fz}{z-f} z}{f} \right] \theta = \quad (12)$$

$$\theta = \frac{f^2 z + fz^2 - f^2 z - fz^2}{f(z-f)} \theta = 0.$$

All rays leaving this point strike the focal plane at the optical axis. As shown in Equation (13), the situation when the cameras 63 and/or 65 are shifted by a distance δ from the focus is described as follows:

$$\left[ \frac{fz}{z-f} + \delta + z - \frac{\left[\frac{fz}{z-f} + \delta\right] z}{f} \right] \theta = \quad (13)$$

$$\frac{f^2 z + fz\delta - f^2\delta + fz^2 - f^2 z - fz^2 - \delta z^2 + f\delta z}{f(z-f)} \theta =$$

$$\frac{fz - f^2 - z^2 + fz}{f(z-f)} \delta\theta = -\frac{(z-f)^2}{f(z-f)} \delta\theta = \frac{f-z}{f} \delta\theta.$$

Equation (13) shows that by properly positioning the lens of the cameras 63 and 64 with respect to the focal plane, we can change the depth of field. Additionally, the spot size depends upon the magnitude of the angle θ. This angle depends linearly on the aperture of the vision system created by the cameras 63 and/or 64.

Additionally or alternatively, in accordance with some embodiments of the present disclosure, cameras 63 and 64 may be implemented by adjusting for various parameters, including: the distance to the focus as it affects compactness, alignment, and sensitivity of the vision system to the environment; the field of view of the system; and the lens-focal plane separation as it affects the tolerances on alignment of the system and the sensitivity of the system to the environment.

Figure 12:
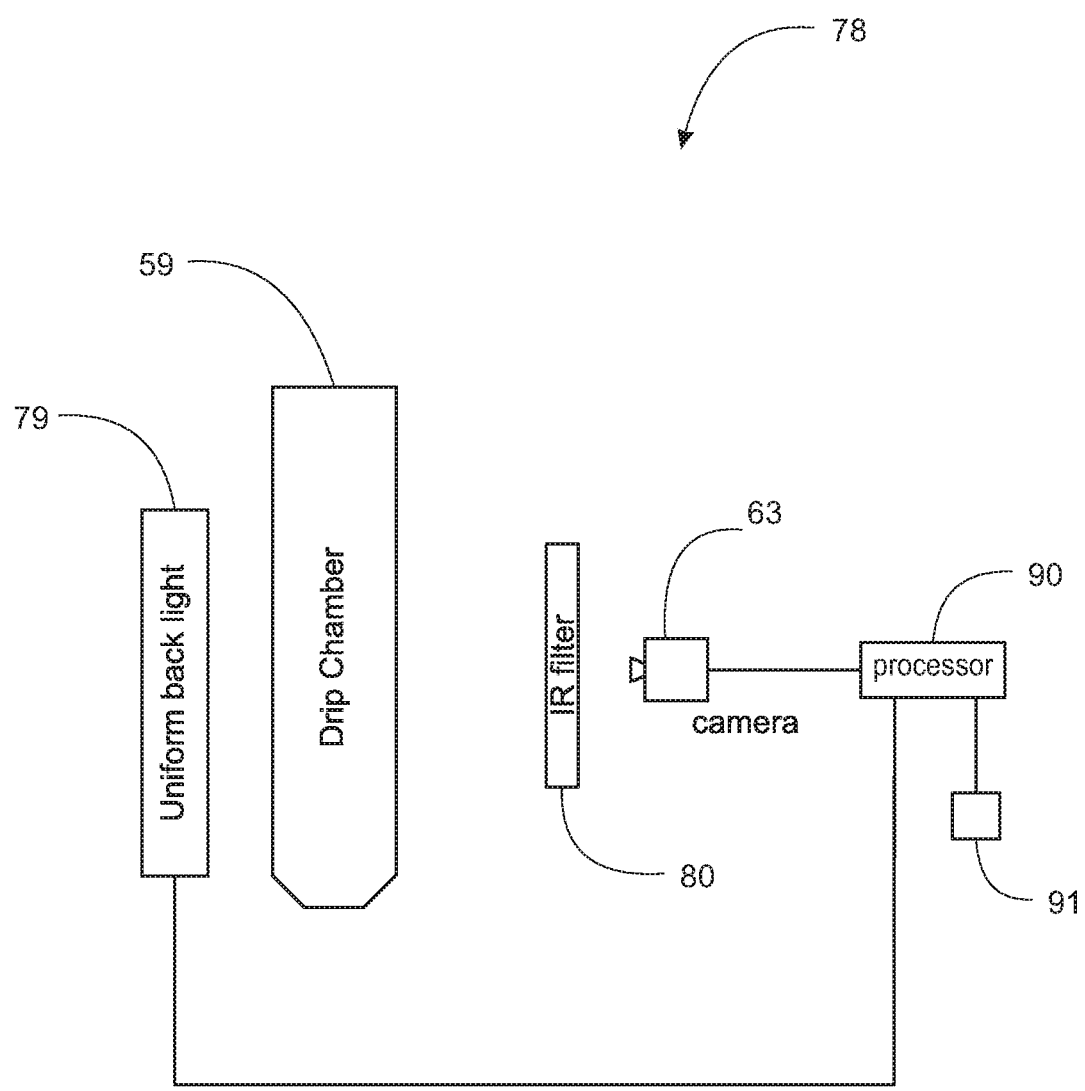
FIG. 12 is a block diagram of an imaging system of the cameras of the drip-chamber holder of FIGS. 4 and 5 in accordance with an embodiment of the present disclosure.

FIG. 12 is a block diagram of an imaging system 78 of the cameras of the drip-chamber holder of FIGS. 4 and 5 in accordance with an embodiment of the present disclosure. Although the camera 63 of FIGS. 4 and 5 will described with reference to FIG. 12, camera 64 may also utilize the configuration described in FIG. 12.

FIG. 12 shows an imaging system 78 including a camera 63, a uniform back light 70 to shine light at least partially through the drip chamber 59, and an infrared ("IR") filter 80 that receives the light from the uniform back light 79. System 78 also includes a processor 90 that may be operatively coupled to the camera 63 and/or the uniform back light 79.

The uniform back light 79 may be an array of light-emitting diodes ("LEDs") having the same or different colors, a light bulb, a window to receive ambient light, an incandescent light, and the like. In alternative embodiments, the uniform back light 79 may be replaced by one or more point-source lights.

The processor 90 may modulate the uniform back light 79 with the camera 63. For example, the processor 90 may activate the uniform back light 79 for a predetermined amount of time and signal the camera 63 to capture at least one image, and thereafter signal the uniform back light 79 to turn off. The one or more images from the camera 63 may be processed by the microprocessor to estimate the flow rate and/or detect free flow conditions. For example, in one embodiment of the present disclosure, system 78 monitors the size of the drops being formed within the drip chamber 59, and counts the number of drops that flow through the drip chamber 59 within a predetermined amount of time; the processor 90 may average the periodic flow from the individual drops over a period of time to estimate the flow rate. For example, if X drops each having a volume Y flow through the drip chamber in a time Z, the flow rate may be calculated as (X*Y)/Z.

Additionally or alternatively, the system 78 may determine when the IV fluid is streaming through the drip chamber 59 (i.e. during a free flow condition). The uniform back light 79 shines through the drip chamber 59 to provide an image of the drip chamber 59 to the camera 63. The camera 59 can capture one or more images of the drip chamber 59.

Other orientations of the system 78 may be used to account for the sensitivity and/or orientation of the uniform back light 79, the camera 63, the characteristics of the light from the uniform back light 79, and the ambient light. In some embodiments of the present disclosure, the processor 90 implements an algorithm that utilizes a uniformity of the images collected by the camera 63 facilitated by the uniform back light 79. For example, consistent uniform images may be captured by the camera 63 when a uniform back light 79 is utilized.

Ambient lighting may cause inconsistencies in the images received from the camera 63, such as that caused by direct solar illumination. Therefore, in some embodiments of the present disclosure, an IR filter 80 is optionally used to filter out some of the ambient light effects. For example, the IR filter 80 may be a narrow-band infrared light filter placed in front of the camera 63; and the uniform back light 79 may emit light that is about the same wavelength as the center frequency of the passband of the filter 80. The IR filter 80 and the uniform back light 79 may have a center frequency of about 850 nanometers. In alternative embodiments, other optical frequencies, bandwidths, center frequencies, or filter types may be utilized in the system 78.

Figure 13:
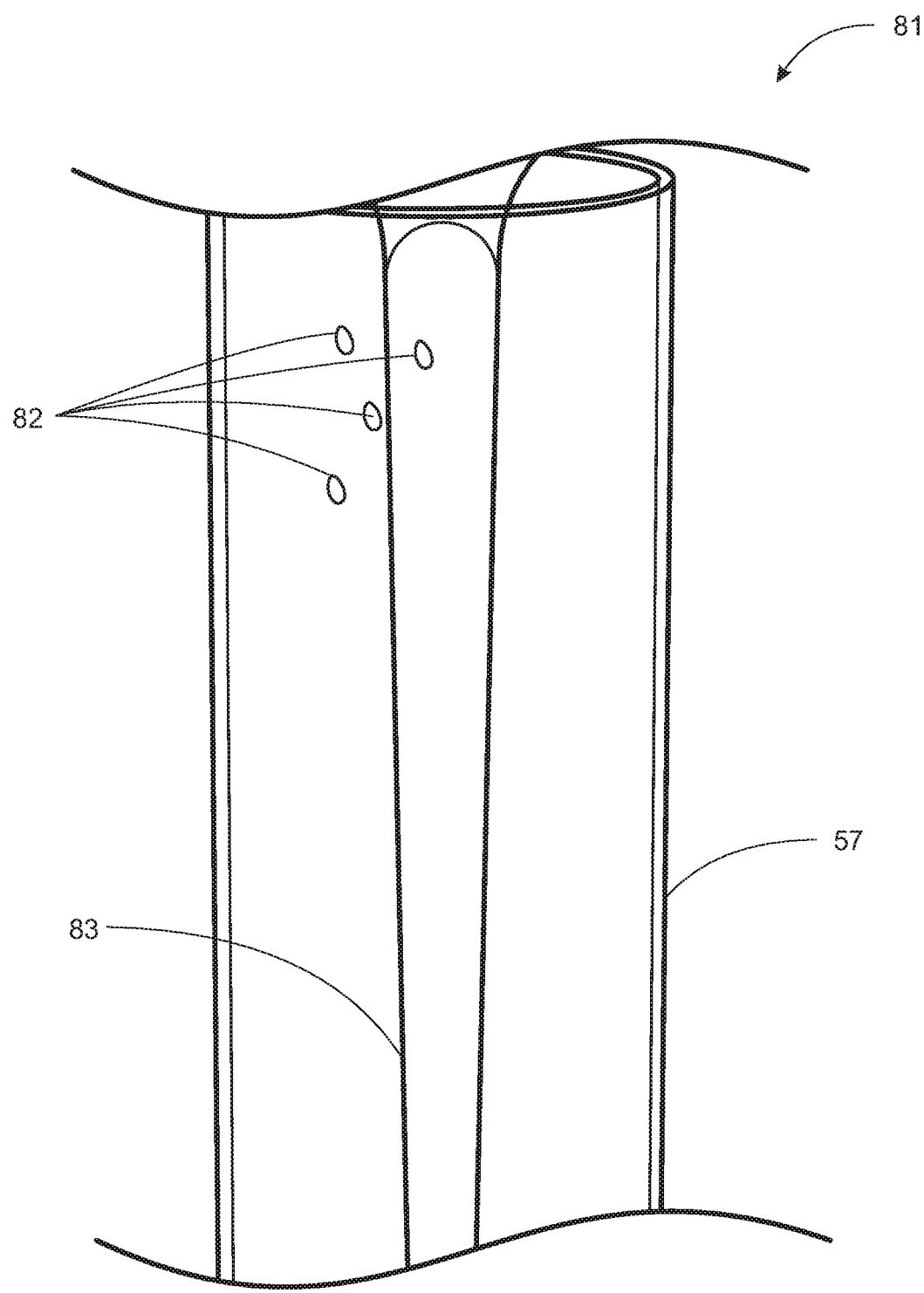
FIG. 13 is a graphic illustration of an image captured by the camera of the system of FIG. 12 in accordance with an embodiment of the present disclosure.

FIG. 13 is a graphic illustration of an image 81 captured by the camera 63 of the system of FIG. 12, in accordance with an embodiment of the present disclosure. The image 81 shows condensation 82 and a stream 83 caused by a free flow condition. Using edge detection may be used to determine the position of the stream 83 and/or the condensation 82, in some embodiments. Additionally or alternatively, a background image or pattern may be used as described infra.

Figure 14:
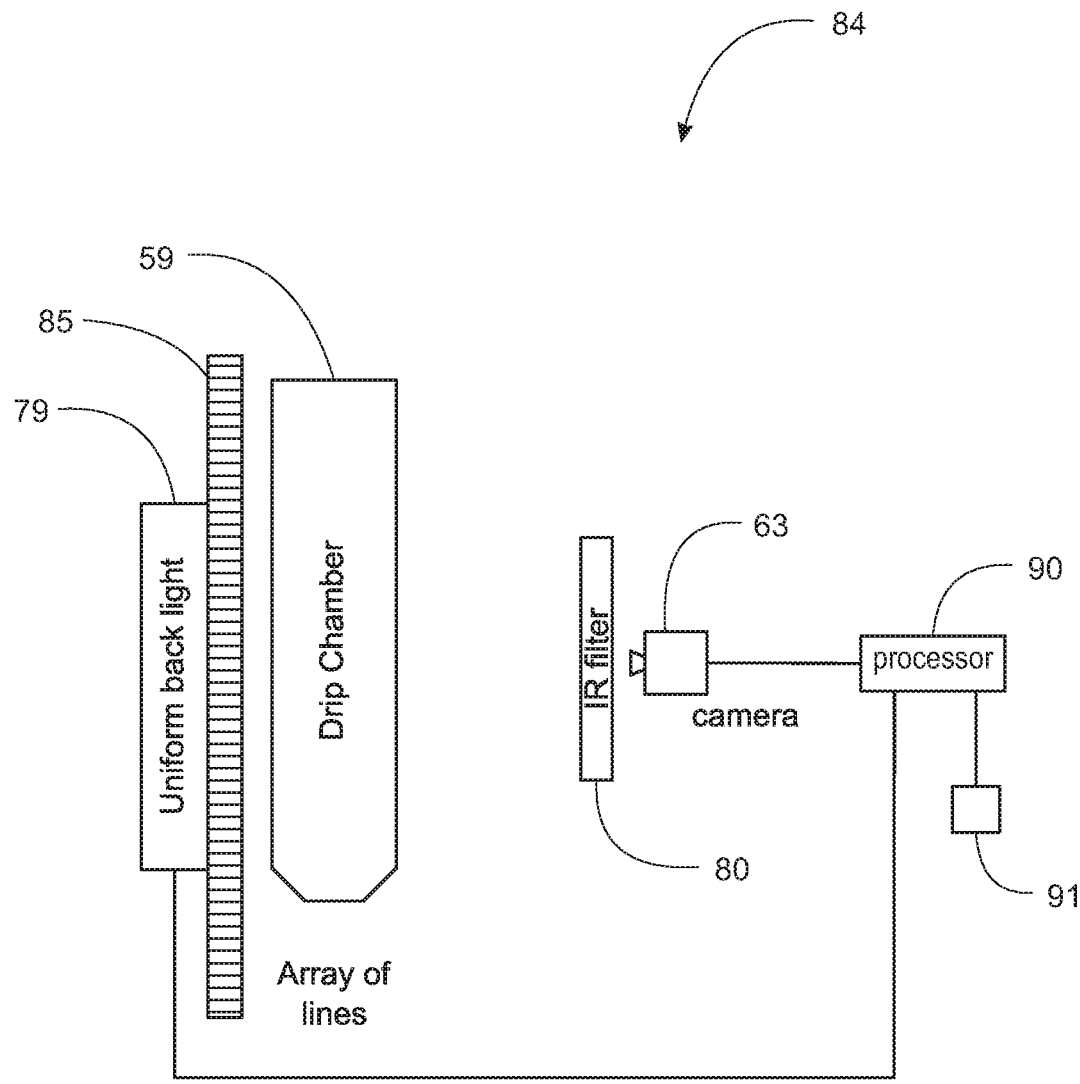
FIG. 14 is a block diagram of an imaging system of the cameras of the drip-chamber holder of FIGS. 4 and 5 in accordance with an embodiment of the present disclosure.

FIG. 14 is a block diagram of an imaging system 84 of the cameras of the drip-chamber holder of FIGS. 4 and 5 in accordance with an embodiment of the present disclosure. Although the camera 63 of FIGS. 4 and 5 will described with reference to FIG. 14, camera 64 may also utilize the configuration described in FIG. 14.

Figure 15:
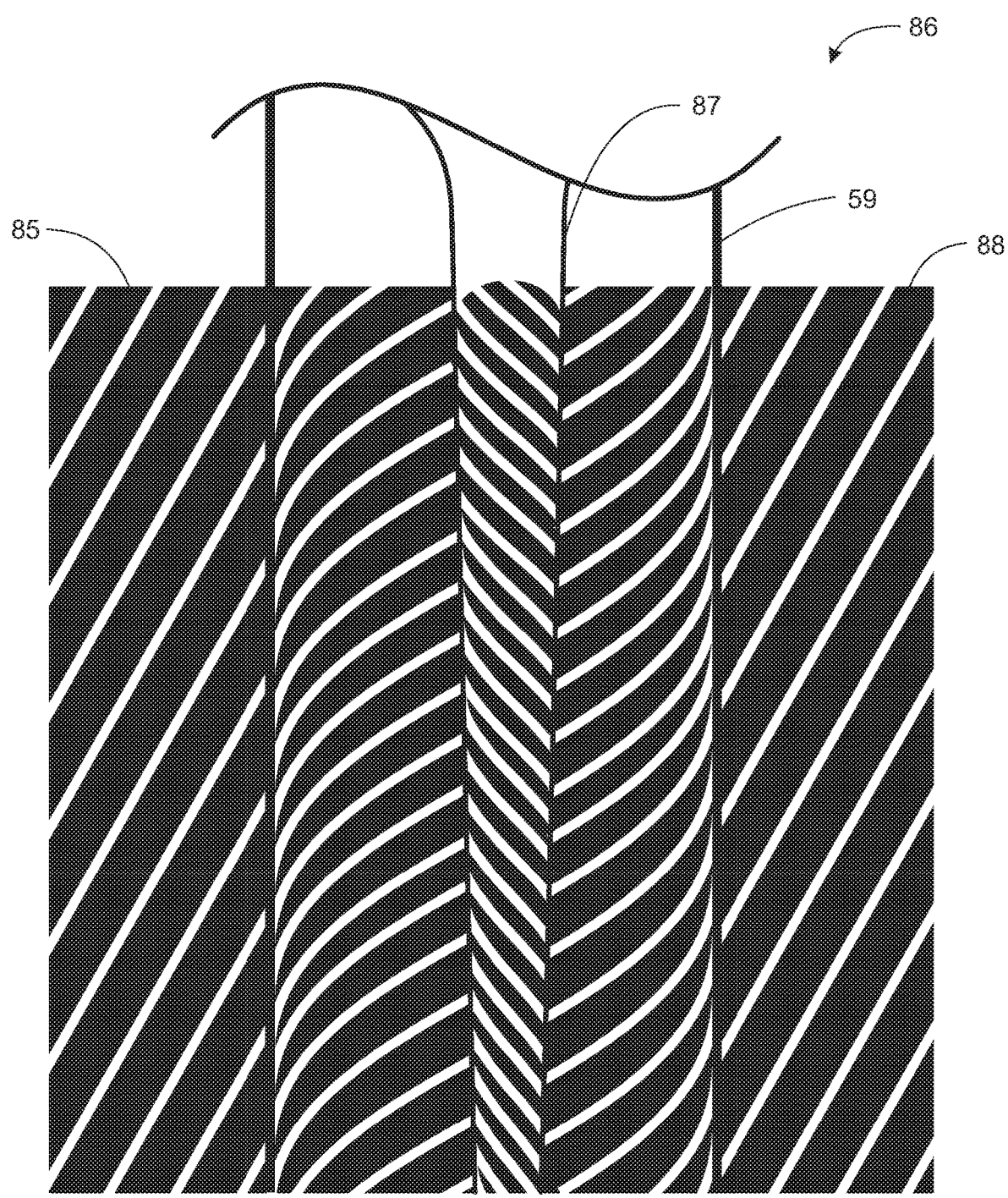
FIG. 15 is a graphic illustration of an image captured by the camera of FIG. 14 when a free flow condition exists in accordance with an embodiment of the present disclosure.

System 84 includes an array of lines 85 that are opaque behind the drip chamber 59. The array of lines 85 may be used in the detection of a free flow condition of the system 84. The free flow detection algorithm may use the presence or absence of drops for determining whether or not a streaming condition, (e.g., a free flow condition) exists. Referring now to FIG. 15, a graphic illustration of an image 86 is shown as captured by the camera 63 of FIG. 14 when a free flow condition exists in the drip chamber 59 in accordance with an embodiment of the present disclosure.

The image 86 illustrates the condition in which the drip chamber 59 experiences a free flow condition and shows that the stream of fluid 87 acts as a positive cylindrical lens. That is, as shown in FIG. 15, the array of lines 85 as captured in an image by the camera 63 show a reversed line pattern 88 from the array of lines 85 as compared to a non-free-flow condition.

In some embodiments of the present disclosure, an illumination of about 850 nanometers of optical wavelength may be used to create the image 86. Some materials may be opaque in the visible spectrum and transparent in the near IR at about 850 nanometers and therefore may be used to create the array of lines 85. The array of lines 85 may be created using various rapid prototyping plastics. For example, the array of lines 85 may be created using a rapid prototype structure printed with an infrared opaque ink or coated with a metal for making the array of lines 85. Additionally or alternatively, in some embodiments of the present disclosure, another method of creating the array of lines 85 is to create a circuit board with the lines laid down in copper. In another embodiment, the array of lines 85 is created by laying a piece of ribbon cable on the uniform back light 79; the wires in the ribbon cable are opaque to the infrared spectrum, but the insulation is transparent and the spacing of the wires may be used for the imagining by the camera 63 (see FIG. 14). In yet additional embodiments, a piece of thin electric discharge machined metal may be utilized. Metal is opaque and the spaces of the material may very finely controlled during manufacturer to allow the IR light to pass through the spaces.

The processor 90 implements an algorithm to determine when a free flow condition exists. The processor 90 may be in operative communication with a computer readable medium 91 (e.g., a non-transitory computer readable medium) to receive one or more instructions to implement the algorithm to determine if a free flow condition exists. The one or more instructions from the computer readable medium 91 are configured for execution by the processor 90.

Referring again to FIG. 14, blood may be used by the system 84. For example, system 84 may determine when a free flow condition of blood exists when utilizing the camera 63, the IR filter 80, and the uniform back light 79 configured, for example, for use using optical light having a wavelength of 850 nanometers or 780 nanometers, e.g., when using bovine blood. The blood may appear opaque compared to the imagery taken using water as the fluid.

The following algorithm implemented by the processor 90 and received from the computer readable medium 91 may be used to determine when a free flow condition exists: (1) establish a background image 89 (see FIG. 16); and (2) subtract the background image 89 from the current image. Additional processing may be performed on the resulting image.

Figure 16:
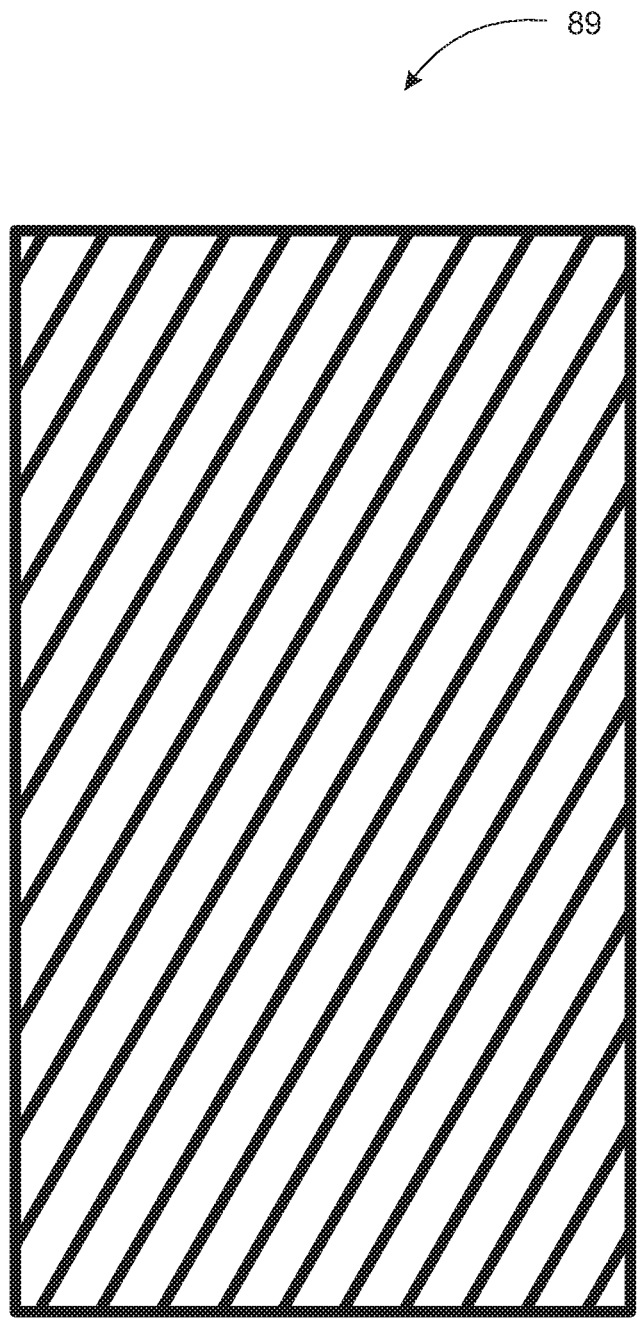
FIG. 16 is a graphic illustration of an image captured by the camera of FIG. 14 for use as a background image in accordance with an embodiment of the present disclosure.

In some embodiments of the present disclosure, the background image 89 of FIG. 16 may be dynamically generated by the processor 90. The dynamic background image may be used to account for changing conditions, e.g. condensation or splashes 82 on the surface of the drip chamber (see FIG. 13). For example, in one specific embodiment, for each new image captured by the camera (e.g., 63 of FIG. 14), the background image has each pixel multiplied by 0.96 and the current image (e.g., the most recently captured image) has a respective pixel multiplied by 0.04, after which the two values are added together to create a new value for a new background image for that respective pixel; this process may be repeated for all of the pixels. In yet another example, in one specific embodiment, if a pixel of the new image is at a row, x, and at a column, y, the new background image at row, x, and column, y, is the value of the previous background image at row, x, and column, y, multiplied by 0.96, which is added to the value of the pixel at row, x, and column, y of the new image multiplied by 0.04.

When the system 84 has no water flowing through the drip chamber 59 (see FIG. 14), the resulting subtraction should be almost completely black, i.e., low pixel magnitudes, thereby facilitating the algorithm to determine that the drip chamber 59 has no water flowing therethrough.

Figures 17, 18, 19:
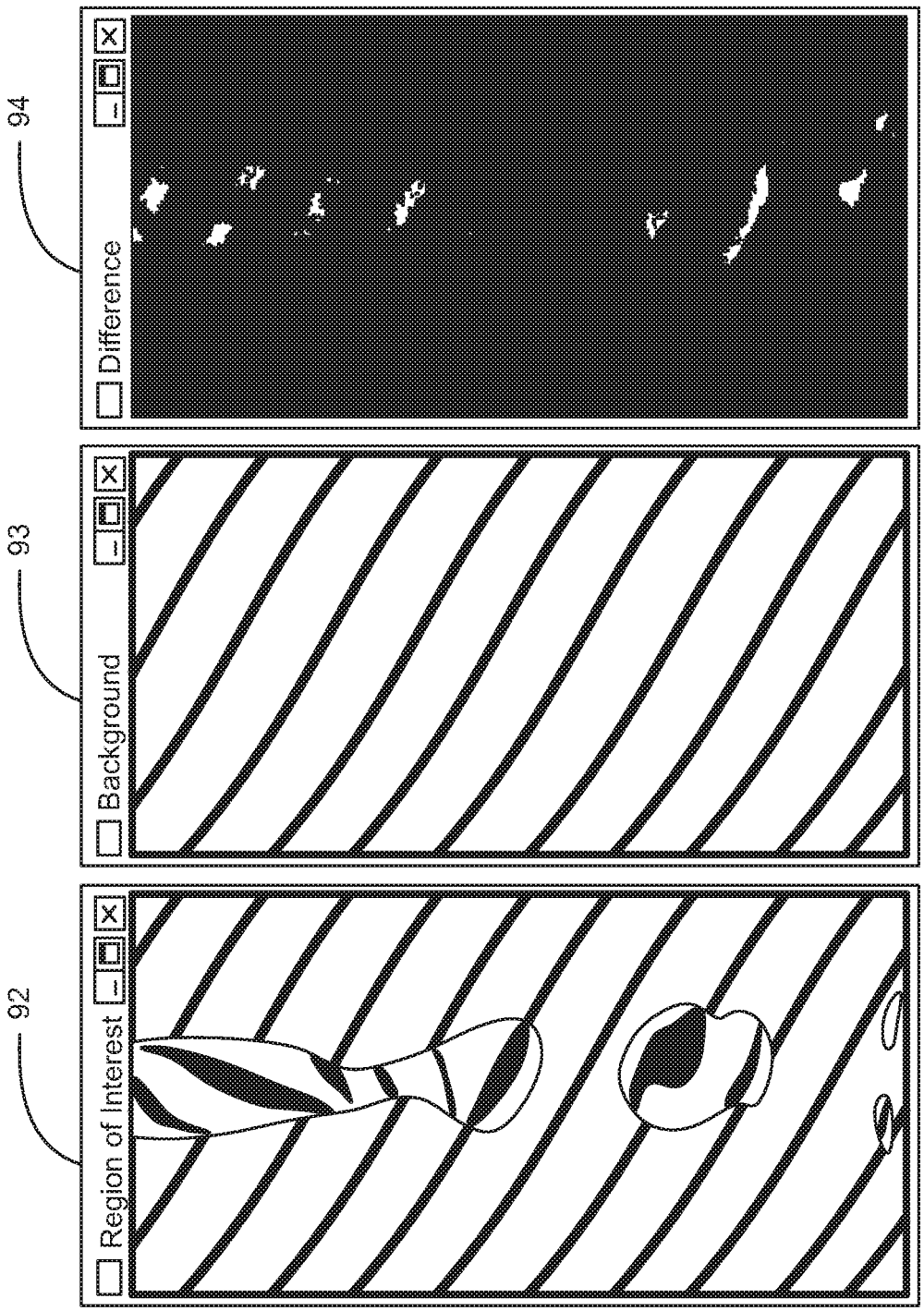
FIG. 17 is a graphic illustration of an image captured by the camera when drops are being formed within the drip chamber of FIG. 14 in accordance with an embodiment of the present disclosure.
FIG. 18 is a graphic illustration of an image captured by the camera of FIG. 14 for use as a background image in accordance with an embodiment of the present disclosure.
FIG. 19 is a graphic illustration of a difference between the images of FIGS. 17 and 18 with additional processing in accordance with an embodiment of the present disclosure.

FIG. 17 shows an image 92 from the camera 63 when there is a drop within the drip chamber 59 (see FIG. 14). FIG. 18 shows a background image 93 used by the system

84. When the system 83 has a drop as shown in image 92 of FIG. 17, the system 84 of FIG. 14 has a few high contrast-spots where the image of the array of lines is warped by the lensing of the droplet as illustrated by an image 94 of FIG. 19. Image 94 of FIG. 19 is generated by taking, for each respective pixel, the absolute value of the subtraction of the image 92 of FIG. 92 from image 93 of FIG. 18, and converting each respective pixel to a white pixel if the value is above a predetermined threshold or otherwise converts the pixel to a black pixel when the value is below the predetermined threshold. Each white pixel within the image 94 of FIG. 19 is a result of there being a difference for that pixel location between the images 92 and 93 that is greater than a predetermined threshold.

For example, consider three respective pixels of FIGS. 17, 18, and 19 having a location of row, x, and column, y. To determine the pixel of row x and column y for the image 94 of FIG. 19, the pixel at row x and column y of image 92 of FIG. 17 is subtracted from the pixel at row x and column y of image 92 of FIG. 18, then the absolute value of the result of the subtraction is taken; and if the absolute value of the result is above a predetermined threshold (e.g., above a grayscale value of 128, for example), the pixel at the location of row x and column y of image 94 of FIG. 19 is white, otherwise the pixel at the location of row x and column y of image 94 of FIG. 19 is black.

When it is determined that a few high contrast-spot exists within image 94 of FIG. 19, the processor 90 of system 84 (see FIG. 14) determines that drops are being formed within the drip chamber 59 and no free flow condition exists. The images of the drops may be utilized to determine their size to estimate a flow rate as described herein.

Figure 20:
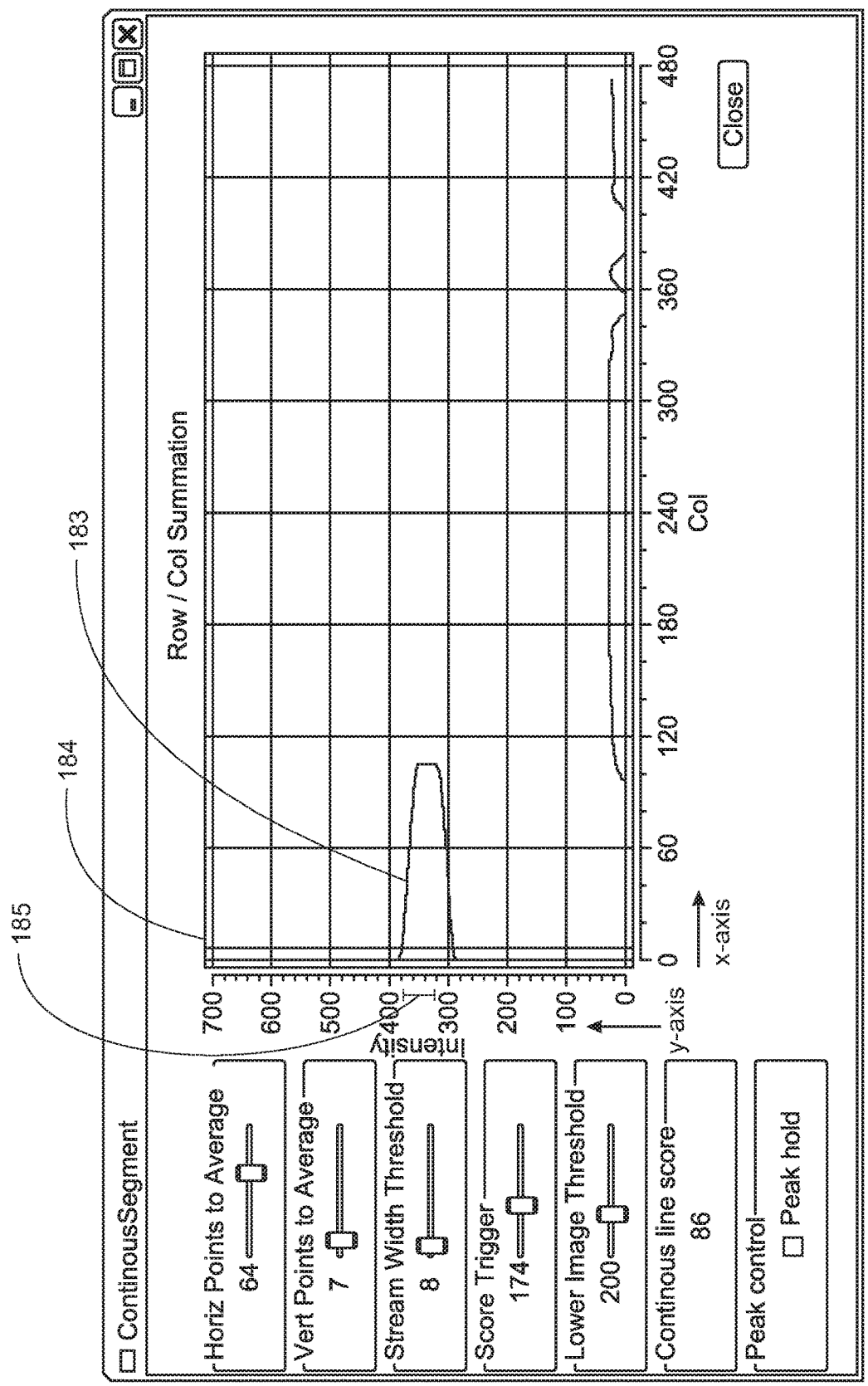
FIG. 20 is a graphic representation of the image processing performed using FIGS. 17-19 to determine if a free flow condition exists in accordance with an embodiment of the present disclosure.

FIG. 20 is a graphic representation of some image processing that may be performed using FIGS. 17-19 to determine if a free flow condition exists in accordance with an embodiment of the present disclosure. Referring to FIGS. 20 and 19, all of the white pixels for each row are summed together, and are illustrated in FIG. 20 as results 183. The y-axis represents the row number, and the x-axis represents the number of white pixels determined for each respective row.

Referring now to only FIG. 20, as previously mentioned, the number of white pixels for each row is summed together and is illustrated as results 183, which are used to determine if or when a free flow condition exists. In some specific embodiments, the processor 90 of system 84 (see FIG. 14) determines that a free flow condition exists when a predetermined number of contiguous values of the summed rows of the results 183 exist above a threshold 184. For example, within the results 183, a plurality of rows represented generally by 185 have a total value above the threshold 184. When greater than a predetermined number of contiguous summed rows are determined to exist within the results 183, a free flow condition is determined to exist by the processor 90 of FIG. 14. For example, as shown in FIG. 20, the plurality of contiguous rows 185 are below the predetermined number of contiguous summed rows and therefore a free flow condition is determined to not exist.

FIG. 21 shows an image 95 showing a stream as captured by the camera 63 of FIG. 14 when a free flow condition exists. FIG. 22 shows a background image 96. FIG. 23 shows an image 97 formed by the absolute value of the difference between the image 96 of FIG. 22 and the image 95 from FIG. 21 when the absolute value is converted either to a white pixel (when the absolute value of the difference is above a threshold) or to a black pixel (when the absolute value of the difference is below the threshold). As shown in FIG. 23, high-contrast spots caused by the reverse orientation of the lines in the stream run from top to bottom are detectable by the processor 90. The processor 90 of FIG. 14 can use the image 97 to determine if a free flow condition exists using the algorithm described above.

Figure 24:
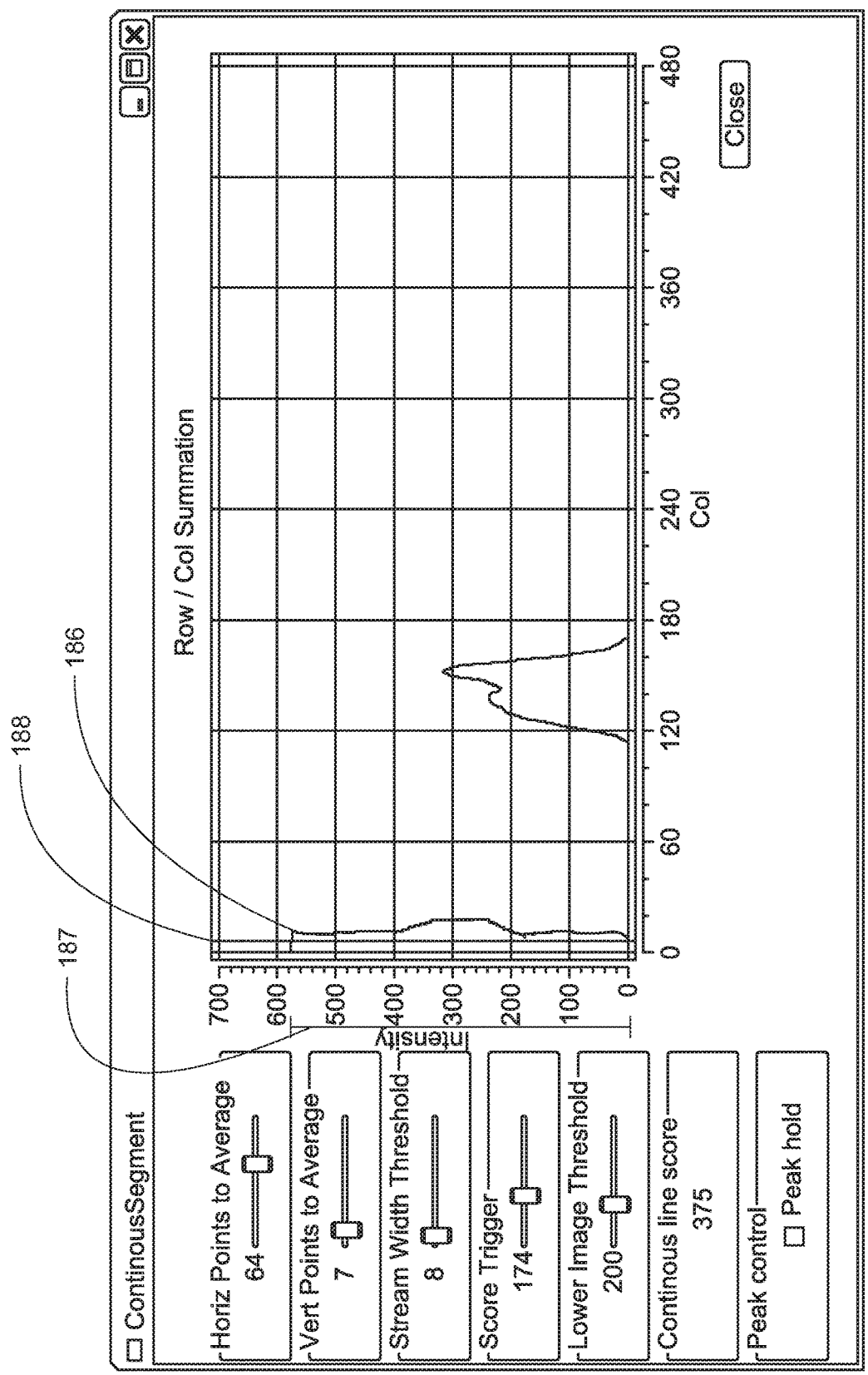
FIG. 24 is a graphic representation of the image processing performed using FIGS. 21-23 to determine if a free flow condition exists in accordance with an embodiment of the present disclosure.

That is, as shown in FIG. 24, results 186 are shown having a contiguous range 187 of the results 186 that are above a threshold 188. Because the contiguous range 187 of summed rows is greater than a predetermined threshold number of contiguous values above the threshold 188, a free flow condition is determined to exist by the processor 90 (see FIG. 14). That is, the contiguous range of the results 186 above the threshold 188 is greater than a predetermined threshold range of contiguous values; therefore, the processor 90 determines that a free flow condition exists when using the results 186 of FIG. 24.

In yet an additional embodiment of the present disclosure, the intensity, the intensity squared, or other function may be used to produce the results 183 and and/or 186. In yet an additional embodiment, one or more data smoothing functions may be used to smooth the results 183 and/or 186, such as a spline function, cubic spline function, B-spline function, Bezier spline function, polynomial interpolation, moving averages, or other data smoothing functions.

For example, an image of the camera 63 of FIG. 14, e.g., image 95 of FIG. 21, may be subtracted from a background image, e.g., the image 96 of FIG. 22, to obtain intensity values. For example, a pixel of row x and column y of FIG. 21 may be subtracted from a pixel of row x and column y of the image 96 of FIG. 22 to create an intensity value at row x and column y; this may be repeated for all pixel locations to obtain all of the intensity values. The intensity values of each row may be summed together to obtain the results 183 and/or 186, such that the processor 90 may determine that a free flow condition exists when the summed rows of the intensity values has a contiguous range of summed rows above a threshold. In some embodiments, the intensity values are converted to an absolute value of the intensity values, and the summed rows of the absolute values of the intensity values are used to determine if a contiguous range of summed rows of the absolute values is above a threshold range of contiguous values. Additionally or alternatively, the intensity may be squared and then the processor 90 may sum the squared intensity rows and determine if a contiguous range of summed rows of the intensity squared values exists beyond a threshold range of contiguous values to determine if a free flow condition exists. In some embodiments, a predetermined range of contiguous values above a threshold (e.g., min and max ranges) of the summed rows of intensity values or intensity squared values may be used by the processor 90 to determine if a drop of liquid is within the image. For the rows of the intensity values (or the intensity squared values) may be summed together and a range of the summed values may be above a threshold number; if the range of contiguous values is between a minimum range and a maximum range, the processor 90 may determine that the range of contiguous values above a predetermined threshold is from a drop within the field of view of the camera 63. In some embodiments of the present disclosure the summed rows of intensity values or intensity squared values may be normalized, e.g., normalized to have a value between 0 and 1.

The following describes a smoothing function similar to the cubic spline (i.e., the cubic-spline-type function) that may be used on the summed rows of intensity values or the summed rows of the intensity values square prior to the determination by the processor 90 to determine if a free flow condition exists. The cubic-spline-type function may be used to identify blocks as described below which may facilitate the processor's 90 identification of free flow conditions, in some specific embodiments.

The cubic-spline-type function is an analog to the cubic spline, but smoothes a data set rather than faithfully mimicking a given function. Having data sampled on the interval from [0,1] (e.g., the summation along a row of intensity squared or intensity that is normalized) the processor 90 may find the best fit set of cubic functions on the intervals $[x_0,x_1]$, $[x_1,x_2]$, . . . , $[x_{N-1},x_N]$ with $x_0=0$ and $x_N=$ where the total function is continuous with continuous derivatives and continuous curvature.

The standard cubic spline definition is illustrated in Equation (14) as follows:

$$\chi(x) = A_i(x)y_i + B_i(x)y_{i+1} + C_i(x)y''_i + D_i(x)y''_{i+1}, x_i \le x \le x_{i+1} \qquad (14),$$

with the functions $A_i$, $B_i$, $C_i$, $D_i$ defined as in the set of Equations (15):

$$A_i(x) = \frac{x_{i+1} - x}{x_{i+1} - x_i} = \frac{x_{i+1} - x}{\Delta_i}, \quad B_i = \frac{x - x_i}{x_{i+1} - x_i} = \frac{x - x_i}{\Delta_i} \qquad (15)$$

$$C_i(x) = \frac{\Delta_i^2}{6}(A_i^3(x) - A_i(x)), \quad D_i = \frac{\Delta_i^2}{6}(B_i^3(x) - B_i(x)).$$

Equations (14) and (15) guaranty continuity and curvature continuity. The only values which can be freely chosen are the $y_i$, $y''_0$ and $y''_N$. Please note that Equation (16) is chosen as follows:

$$y''_0 = y''_1 = 0 = 0 \qquad (16),$$

i.e., the function is flat at 0 and 1. The remaining $y''_i$ must satisfy the following set of Equations (17):

$$\frac{y_1 - y_0}{\Delta_0} + \frac{y''_1 \Delta_0}{3} = \frac{y_2 - y_1}{\Delta_1} - \frac{y''_1 \Delta_1}{3} - \frac{y''_2 \Delta_1}{6} \qquad (17)$$

$$\frac{y_2 - y_1}{\Delta_1} + \frac{y''_1 \Delta_1}{6} + \frac{y''_2 \Delta_1}{3} = \frac{y_3 - y_2}{\Delta_2} - \frac{y''_2 \Delta_2}{3} - \frac{y''_3 \Delta_2}{6}$$

$$\frac{y_3 - y_2}{\Delta_2} + \frac{y''_2 \Delta_2}{6} + \frac{y''_3 \Delta_2}{3} = \frac{y_4 - y_3}{\Delta_3} - \frac{y''_3 \Delta_3}{3} - \frac{y''_4 \Delta_3}{6}$$

$$\vdots$$

$$\frac{y_{N-2} - y_{N-3}}{\Delta_{N-3}} + \frac{y''_{N-3} \Delta_{N-3}}{6} + \frac{y''_{N-2} \Delta_{N-3}}{3} =$$

$$\frac{y_{N-1} - y_{N-2}}{\Delta_{N-2}} - \frac{y''_{N-2} \Delta_{N-2}}{3} - \frac{y''_{N-1} \Delta_{N-2}}{6}$$

$$\frac{y_{N-1} - y_{N-2}}{\Delta_{N-2}} + \frac{y''_{N-2} \Delta_{N-2}}{6} + \frac{y''_{N-1} \Delta_{N-2}}{3} =$$

$$\frac{y_N - y_{N-1}}{\Delta_{N-1}} - \frac{y''_{N-1} \Delta_{N-1}}{3}.$$

The set of Equations (17) can be rewritten as the set of Equations (18) as follows:

$$\frac{\Delta_0 - \Delta_1}{3} y''_1 + \frac{\Delta_1}{6} y''_2 = \frac{y_0}{\Delta_0} - \left[\frac{1}{\Delta_0} + \frac{1}{\Delta_1}\right] y_1 + \frac{y_2}{\Delta_1} \qquad (18)$$

$$\frac{\Delta_1}{6} y''_1 + \frac{\Delta_1 + \Delta_2}{3} y''_2 + \frac{\Delta_2}{6} y''_3 = \frac{y_1}{\Delta_1} - \left[\frac{1}{\Delta_1} + \frac{1}{\Delta_2}\right] y_2 + \frac{y_3}{\Delta_2}$$

$$\frac{\Delta_2}{6} y''_2 + \frac{\Delta_2 + \Delta_3}{3} y''_3 + \frac{\Delta_3}{6} y''_4 = \frac{y_2}{\Delta_2} - \left[\frac{1}{\Delta_2} + \frac{1}{\Delta_3}\right] y_3 + \frac{y_4}{\Delta_3}$$

$$\vdots$$

$$\frac{\Delta_{N-4}}{6} y''_{N-3} + \frac{\Delta_{N-3} + \Delta_{N-2}}{3} y''_{N-2} + \frac{\Delta_{N-2}}{6} y''_{N-1} =$$

$$\frac{y_{N-3}}{\Delta_{N-3}} - \left[\frac{1}{\Delta_{N-3}} + \frac{1}{\Delta_{N-2}}\right] y_{N-2} + \frac{y_{N-1}}{\Delta_{N-2}}$$

$$\frac{\Delta_{N-1}}{6} y''_{N-2} + \frac{\Delta_{N-2} + \Delta_{N-1}}{3} y''_{N-1} =$$

$$\frac{y_{N-2}}{\Delta_{N-2}} - \left[\frac{1}{\Delta_{N-2}} + \frac{1}{\Delta_{N-1}}\right] y_{N-1} + \frac{y_N}{\Delta_{N-1}}.$$

In turn, this becomes the matrix Equation (19):

$$\begin{bmatrix} \frac{\Delta_0 + \Delta_1}{3} & \frac{\Delta_1}{6} & 0 & 0 & 0 & 0 \\ \frac{\Delta_1}{6} & \frac{\Delta_1 + \Delta_2}{3} & \frac{\Delta_2}{6} & \cdots & 0 & 0 & 0 \\ 0 & \frac{\Delta_2}{6} & \frac{\Delta_2 + \Delta_3}{3} & & 0 & 0 & 0 \\ & & \vdots & \ddots & \vdots & & \\ 0 & 0 & 0 & \frac{\Delta_{N-4} + \Delta_{N-3}}{3} & \frac{\Delta_{N-3}}{6} & 0 \\ 0 & 0 & 0 & \cdots & \frac{\Delta_{N-3}}{6} & \frac{\Delta_{N-3} + \Delta_{N-2}}{3} & \frac{\Delta_{N-2}}{6} \\ 0 & 0 & 0 & 0 & \frac{\Delta_{N-2}}{6} & \frac{\Delta_{N-2} + \Delta_{N-1}}{3} \end{bmatrix} \begin{Bmatrix} y''_1 \\ y''_2 \\ y''_3 \\ \vdots \\ y''_{N-3} \\ y''_{N-2} \\ y''_{N-1} \end{Bmatrix} = \qquad (19)$$

$$\begin{bmatrix} \frac{1}{\Delta_0} & -\frac{1}{\Delta_0}-\frac{1}{\Delta_1} & \frac{1}{\Delta_1} & 0 & 0 & 0 \\ 0 & \frac{1}{\Delta_1} & -\frac{1}{\Delta_1}-\frac{1}{\Delta_2} & \cdots & 0 & 0 & 0 \\ 0 & 0 & \frac{1}{\Delta_2} & 0 & 0 & 0 \\ \vdots & & & \ddots & & \vdots \\ 0 & 0 & 0 & \frac{1}{\Delta_{N-3}} & 0 & 0 \\ 0 & 0 & 0 & \cdots & -\frac{1}{\Delta_{N-3}}-\frac{1}{\Delta_{N-2}} & \frac{1}{\Delta_{N-2}} & 0 \\ 0 & 0 & 0 & \frac{1}{\Delta_{N-2}} & -\frac{1}{\Delta_{N-2}}-\frac{1}{\Delta_{N-1}} & \frac{1}{\Delta_{N-1}} \end{bmatrix} \begin{Bmatrix} y_0 \\ y_1 \\ y_2 \\ y_3 \\ \vdots \\ y_{N-3} \\ y_{N-2} \\ y_{N-1} \\ y_N \end{Bmatrix}$$

The set of Equations (19) may be rewritten as the set of Equations (20):

$$Fy_{dd} = Gy$$

$$y_{dd} = F^{-1}Gy = Hy \quad (20).$$

Choosing the values in the vector y using a least squares criterion on the collected data is shown in Equation (21) as follows:

$$E = \Sigma[\psi_k - A_{i_k}(\xi_k)y_{i_k} - B_{i_k}(\xi_k)y_{i_k} - C_{i_k}(\xi_k)y''_{i_k} - D_{i_k}(\xi_k)y''_{i_k}]^2 \quad (21).$$

That is, Equation (21) is the minimum deviation between the data and the spline, i.e., an error function. The y values are chosen to minimize the error as defined in Equation 21; The vector of predicted values can be written as illustrated in Equation (22) as follows:

$$\begin{aligned}\hat{y} &= (A_{[k]} + B_{[k]})y + (C_{[k]} + D_{[k]})y_{dd} \quad (22)\\ &= (A_{[k]} + B_{[k]})y + (C_{[k]} + D_{[k]})Hy \\ &= [A_{[k]} + B_{[k]} + C_{[k]}+H + D_{[k]}H]y \\ &= Ay.\end{aligned}$$

The elements of the matrix in brackets of Equation (22) depend upon the x-value corresponding to each data point, but this is a fixed matrix. Thus the final equation can be determined using the pseudo-inverse. In turn, the pseudo-inverse only depends upon the x-locations of the data set and the locations where the breaks in the cubic spline are set. The implication of this is that once the geometry of the spline and the size of the image are selected, the best choice for the y given a set of measured values $y_m$ is illustrated in Equation (23) as follows:

$$y = (A^T A)^{-1} A \cdot y_m \quad (23).$$

The cubic spline through the sum intensity-squared function of the image will then be given by Equation (24):

$$y_{cs} = A \cdot y \quad (24).$$

Because we will want to find the maximum values of the cubic spline, we will also need the derivative of the spline. The cubic spline derivative is given by Equation (25) as follows:

$$\chi'(x_k) = A'_{i_k}(x_k)y_{i_k} + B'_{i_k}(x_k)y_{i_k+1} + C'_{i_k}(x_k)y''_{i_k} + D'_{i_k}(x_k)y''_{i_k+1} \quad (25)$$

$$= \frac{y_{i_k}}{\Delta_{i_k}} + \frac{y_{i_k+1}}{\Delta_{i_k}} - \frac{\Delta_{i_k} y''_{i_k}}{6}(3A^2_{i_k}(x_k) - 1) +$$

$$\frac{\Delta_{i_k} y''_{i_k+1}}{6}(3B^2_{i_k}(x_k) - 1).$$

Equation (25) can be written as Equation (26):

$$\begin{aligned}y'_{cs} &= (A'_{[k]} + B'_{[k]})y + (C'_{[k]} + D'_{[k]})y_{dd} \quad (26)\\ &= [A'_{[k]} + B'_{[k]} + C'_{[k]}H + D'_{[k]}H]y \\ &= A'y.\end{aligned}$$

Once the current values of y are found, the cubic spline, $y_{cs}$, and its derivative, $y'_{cs}$ can be calculated. The cubic spline data may include "blocks" of data that includes values above a predetermined threshold. A pipe block is formed by the liquid flowing out of the tube into the drip chamber 59 and a pool block is formed as the liquid collects at the gravity end of the drip chamber 59 (see FIG. 14).

The following algorithm may be applied to the cubic spline data: (1) determine the local maxima of the cubic spline data using the derivative information; (2) determine the block surrounding each local maxima by including all points where the cubic spline value is above a threshold value; (3) merge all blocks which intersect; (4) calculate information about the block of data including the center of mass (intensity), the second moment of the mass (intensity), the lower x-value of the block, the upper x-value of the block, the mean value of the original sum of intensity squared data in the block, the standard deviation of the original sum of intensity squared data in the block, and the mean intensity of a high-pass filtered image set in the block; and (5) interpret the collected data to obtain information about when drops occur and when the system is streaming.

The mean intensity of a high-pass filtered image set in the block is used to determine if the block created by each contiguous range of spline data is a result of a high frequency artifact (e.g., a drop) or a low frequency artifact. This will act as a second background filter which tends to remove artifacts such as condensation from the image. That is, all previous images in an image memory buffer (e.g., 30 previous frames, for example) are used to determine if the data is a result of high frequency movement between frames. If the block is a result of low frequency changes, the block is removed, or if it is a result high frequency changes, the block is kept for further analysis. A finite impulse response filter or an infinite impulse response filter may be used.

Each block is plotted over its physical extent with height equal to the mean value of the data within the block. If a block has a mean value of the high-pass filter image less than the threshold, it is an indication that it has been around for several images and thus may be removed.

Free flow conditions may be determined by the processor 90 to exist using the blocks when the pipe block extends nearly to the pool block, the pipe block and the pool block merge together, and/or the summed range of widths of the pool and pipe blocks (or all blocks) is greater than a predetermined threshold, e.g., the total extent of the blocks exceeds 380 pixels in width. The processor 90 may detect a drop when the transition of the pipe block from a larger width to a shorter width occurs as a result of a drop formation in the tube and as the drop leaves the pipe (i.e., tube) opening of the drip chamber 59. The processor 90 may detect this by looking at the ratio of the current pipe block width to the previous image's pipe block width, e.g., an image where the ratio is less than 0.9 while simultaneously is a local minima is may be considered by the processor 90 to be an image formed immediately after a drop has formed.

Various filtering algorithms may be used to detect condensation or other low frequency ratification, such as: If a block has a low mean value in the high-pass filter image, then it may be condensation. This artifact can be removed from consideration. Additionally or alternatively, long blocks (e.g., greater than a predetermined threshold) with a low high-pass mean value are possibly streams, since stream images tend to remain unchanging.

The processor 90 may, in some specific embodiments use the block data to count the drops thereby using the system 84 as a drop counter. The processor 90 may also use width changes in the pool block as a drop disturbs the water to determine if a bubble formed with the drop hit the pool. For example, the processor 90 may determines that a block forms below the pool block, then the processor 90 may determine that a bubble formed when a drop hit the water. The bubble may be filtered out by the processor 90 to determine if a predetermined value of total block ranges indicates that a free flow condition exists.

In some embodiments of the present disclosure, the depth of field of the system 84 may have a narrow depth of field to make the system 84 less sensitive to condensation and droplets on the chamber walls. In some embodiments, a near focus system may be used.

Figure 25:
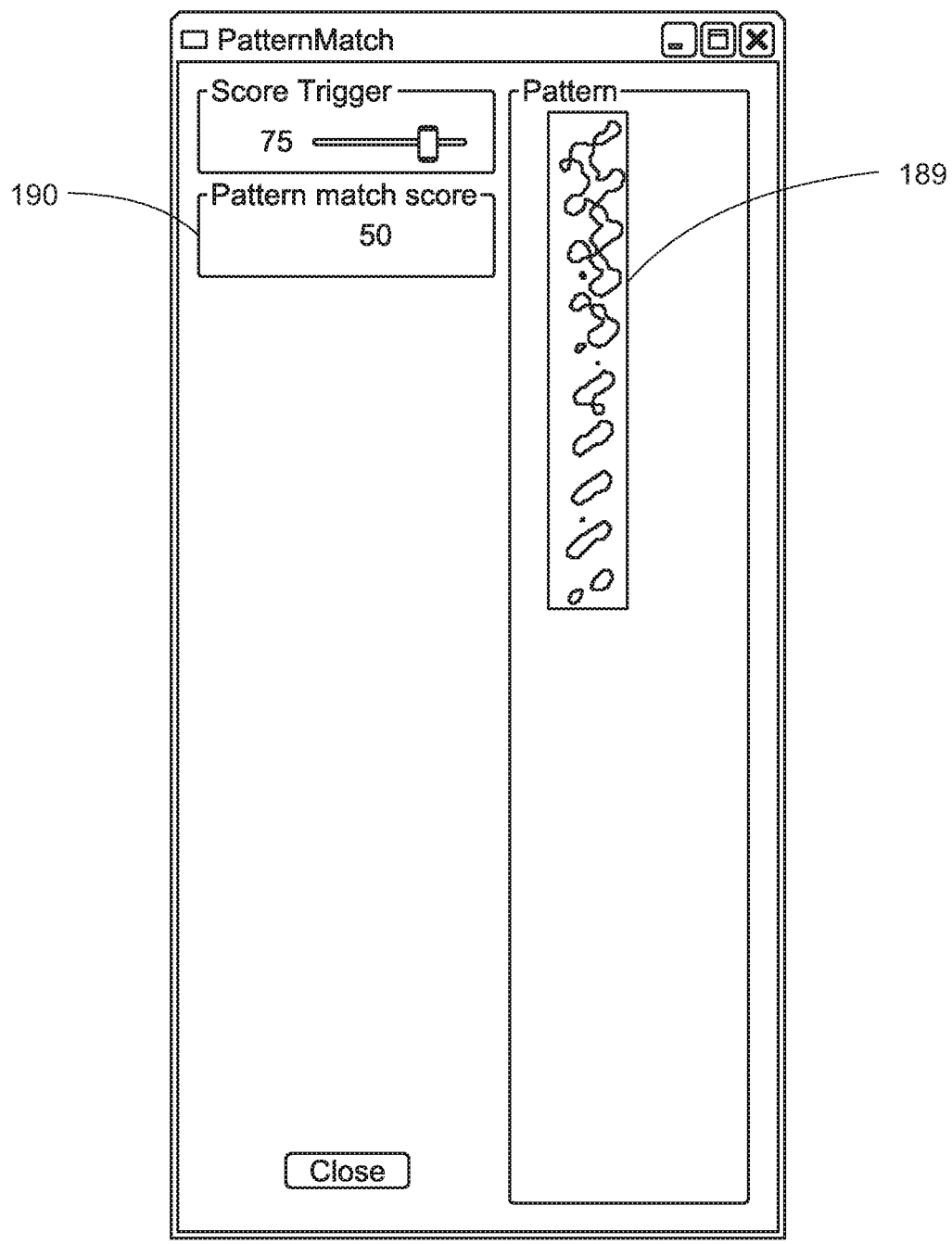
FIG. 25 illustrates a template for pattern matching to determine if a free flow condition exists using FIGS. 17-19 or FIGS. 21-23 in accordance with an embodiment of the present disclosure.

Referring now to FIG. 25, in another embodiment of the present disclosure a template 189 is used to determine if a free flow condition exists. The template 189 is used by the processor 90 of FIG. 14 to determine a pattern match score 190. The image 94 of FIG. 19 may be compared against the pattern 189 (e.g., a difference between a background image and an image captured by the camera 63 of FIG. 14 which is then converted to either a black pixel if the difference is below a threshold value or a white pixel if the difference is above a threshold value). If the pattern match score 190 is above a predetermined threshold, a free flow condition is determined to exist. The template matching may utilize a template matching algorithm as found in Open Source Computer Vision ("OpenCV") library. For example, the template 189 may be used with the matchTemplate function call of the OpenCV library using the CV_TM_CCOEFF method or the method of CV_TM_CCOEFF_NORMED.

The CV_TM_CCOEFF method uses the pattern matching algorithm illustrated in Equation (27) as follows:

$$R(x, y) = \sum_{x',y'} (T'(x', y') \cdot I'(x + x', y + y')), \quad (27)$$

where:

$$T'(x',y')=T(x',y')-1/(w \cdot h) \cdot \Sigma_{x'',y''} T''(x'',y'')$$

$$I'(x+x',y+y')=I(x+x',y+y')-1/(w \cdot h) \cdot \Sigma_{x'',y''} I(x+x'',y+y'');$$

The I denotes the image, the T denotes the template, and the R denotes the results. The summation is done over the template and/or the image patch, such that: x'=0 . . . w−1 and y'=0 . . . h−1.

The results R can be used to determine how much the template T is matched at a particular location within the image I as determined by the algorithm. The OpenCV template match method of CV_TM_CCOEFF_NORMED uses the pattern matching algorithm illustrated in Equation (28) as follows:

$$R(x, y) = \frac{\sum_{x',y'} (T'(x', y') \cdot I'(x + x', y + y'))}{\sqrt{\sum_{x',y'} T'(x', y')^2 \cdot \sum_{x',y'} I'(x + x', y + y')^2}}. \quad (28)$$

In another embodiment of the present disclosure, the template matching algorithm uses a Fast Fourier Transform ("FFT"). In some embodiments, any of the methods of the matchTemplate function of OpenCV may be used, e.g., CV_TM_SQDIFF, CV_TM_SQDIFF_NORMED, CV_TM_CCORR, and/or CV_TM_CCORR_NORMED.

The CV_TM_SQDIFF uses the pattern matching algorithm illustrated in Equation (29) as follows:

$$R(x, y) = \sum_{x',y'} (T'(x', y') - I'(x + x', y + y'))^2. \quad (29)$$

CV_TM_SQDIFF_NORMED uses the pattern matching algorithm illustrated in Equation (30) as follows:

$$R(x, y) = \frac{\sum_{x',y'} (T'(x', y') - I(x + x', y + y'))^2}{\sqrt{\sum_{x',y'} T(x', y')^2 \cdot \sum_{x',y'} I(x + x', y + y')^2}}. \quad (30)$$

CV_TM_CCORR uses the pattern matching algorithm illustrated in Equation (31) as follows:

$$R(x, y) = \sum_{x',y'} T(x', y') \cdot I(x + x', y + y')). \quad (31)$$

CV_TM_CCORR_NORMED uses the pattern matching algorithm illustrated in Equation (32) as follows:

$$R(x, y) = \frac{\sum_{x',y'} (T(x', y') \cdot I'(x + x', y + y'))}{\sqrt{\sum_{x',y'} T(x', y')^2 \cdot \sum_{x',y'} I(x + x', y + y')^2}}. \quad (32)$$

In yet another embodiment of the present disclosure, a template of a grayscale image of a free flow condition is compared to an image taken by the camera 63 of FIG. 14 to determine if a free flow condition exists. In some embodiments, the template matching function within the OpenCV library may be utilized.

Figures 26, 27:
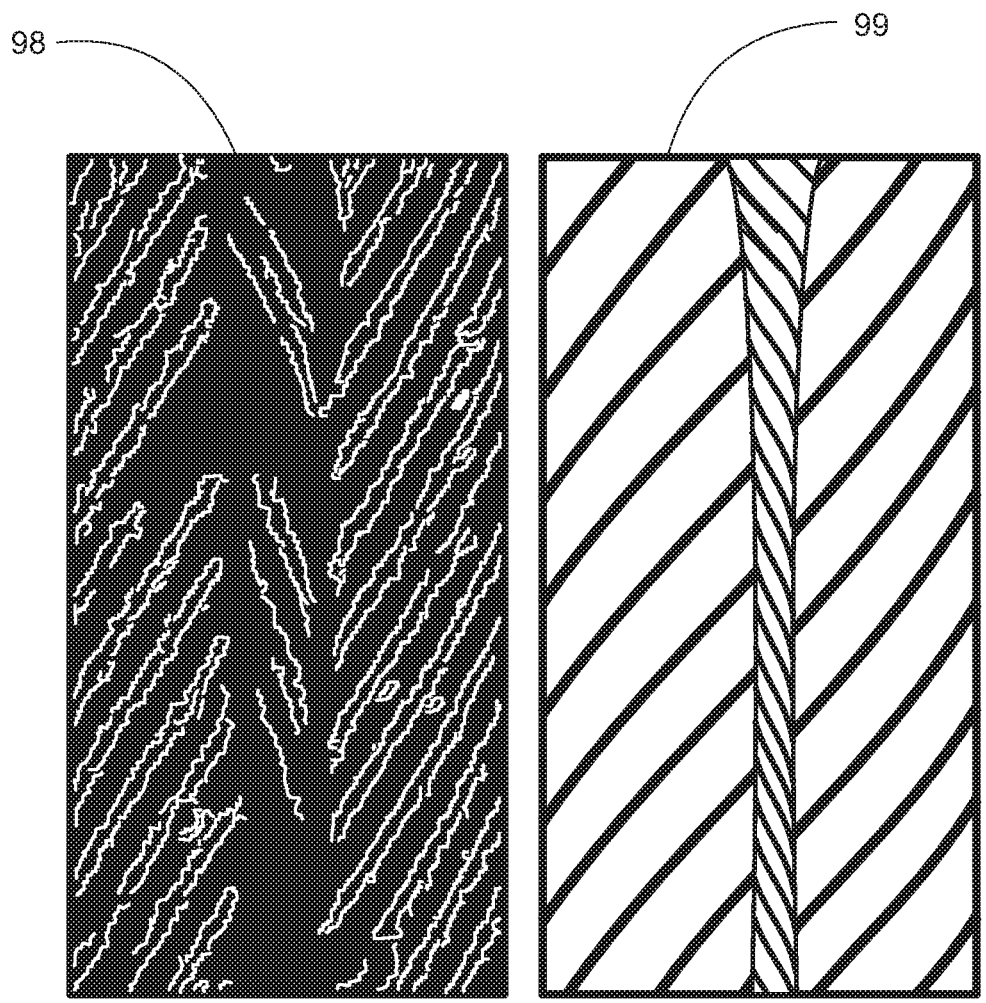
FIG. 26 is a graphic illustration of a difference between a reference image and an image containing a steam processed with edge detection and line detection for use in detecting a free flow condition in accordance with an embodiment of the present disclosure.
FIG. 27 is a graphic illustration of an image captured by the camera when a free flow condition exists thereby forming a stream within the drip chamber of FIG. 14 in accordance with an embodiment of the present disclosure.

Refer now to FIGS. 26 and 27; in yet an additional embodiment of the present disclosure, the algorithm to determine when a free flow condition exists being executed on the processor 90 of FIG. 14 may utilize an algorithm to determine if a template pattern matches an array of pixels utilizing edge detecting followed by line detection. As shown in FIG. 26, an image 98 is formed from an image 99 of FIG. 27, by using edge detected followed by line detection. The resulting lines may be utilized by the processor 90 to determine that a free flow condition exists. As shown in FIG. 26, the feature which shows up after this processing by the processor 90 are lines that have a different slope than the expected 45° slope of the background reference image. The lines having the angle of the background image may be filtered out of FIG. 26, in some embodiments. The lines may be detected as edges using a Canny algorithm as found in the OpenCV library with the Hough algorithm to determine the slope of the lines also found in the OpenCV library.

FIGS. 28-32 illustrate various background patterns that may be used to detect a free flow condition or estimate the size of a drop of liquid. When used with the back patterns of FIGS. 28-32, the cameras 102 mentioned for use in FIGS. 28-32 may be the cameras 63 or 64 of FIG. 4 or 5, the camera of FIG. 6, the camera 63 of FIG. 14 each of which may be coupled to a respective processor for processing the images from the camera, such as processor 75 of FIG. 6 or the processor 90 of FIG. 14.

Figure 28:
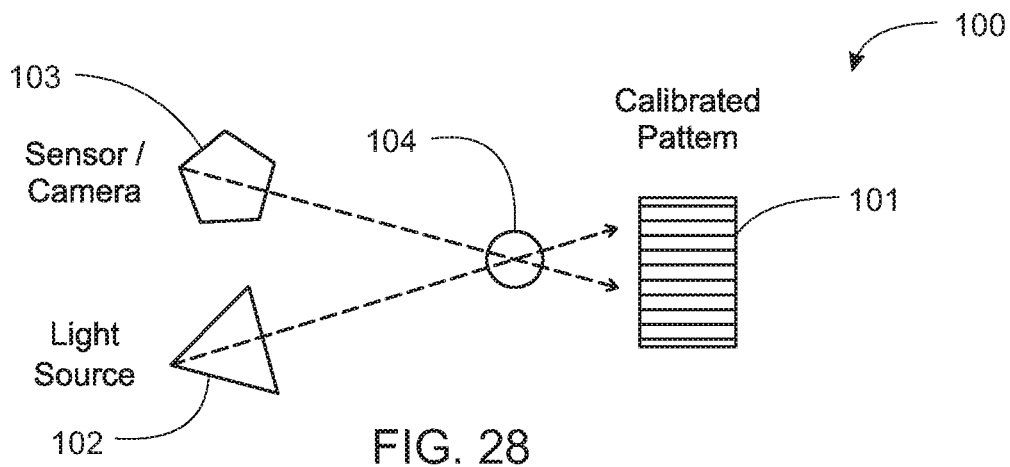
FIG. 28 is a block diagram of an imaging system for use with the drip-chamber holder of FIGS. 4-5 or FIG. 6 having a back pattern with stripes and a light source shining on the stripes from an adjacent location to a camera in accordance with an embodiment of the present disclosure.

FIG. 28 is a block diagram of an imaging system 100 for use with the drip-chamber 104 (e.g., a drip chamber as found in the drip-chamber holder of FIGS. 4-5 or FIG. 6) having a back pattern 101 with stripes and a light source 102 shining on the stripes from an adjacent location to a camera 103 in accordance with an embodiment of the present disclosure. Any drops or free flow streams within the drip chamber 104 distorts the image taken by the camera 103. A processor coupled to the camera 103 (e.g., processor 75 of FIG. 6) can use the distortions of the back pattern 101 as captured by the camera 103 to estimate flow rate and/or detect free flow conditions.

Figure 29:
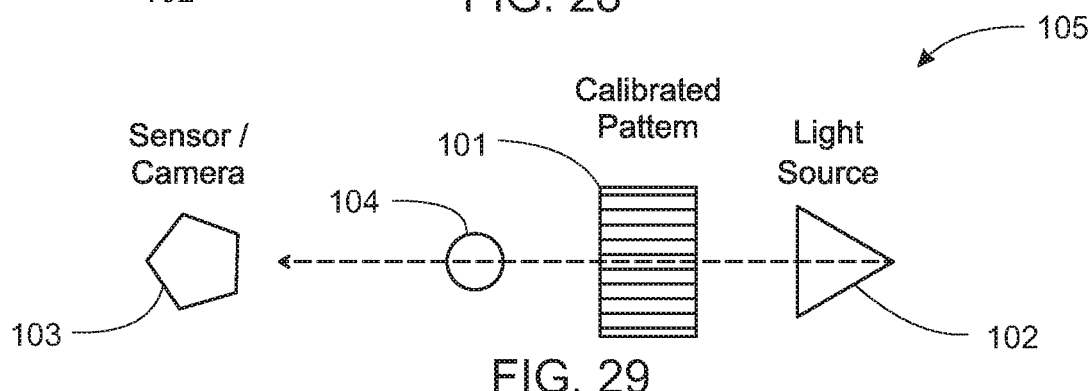
FIG. 29 is a block diagram of an imaging system for use with the drip-chamber holder of FIGS. 4-5 or FIG. 6 having a back pattern with stripes and a light source shining on the stripes from behind the back pattern relative to an opposite end to a camera in accordance with an embodiment of the present disclosure.
Figure 30:
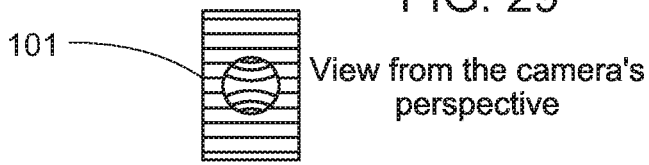
FIG. 30 shows an image from the camera of FIG. 29 when a drop distorts the back pattern of FIG. 26 in accordance with an embodiment of the present disclosure.

FIG. 29 is a block diagram of an imaging system 105 for use with the drip-chamber 104 having a back pattern 101 with stripes and a light source 102 shining on the stripes from behind the back pattern 101 relative to an opposite end to a camera 103 in accordance with an embodiment of the present disclosure. FIG. 30 shows an image from the camera 103 of FIG. 29 when a drop distorts the back pattern 101 of FIG. 29 in accordance with an embodiment of the present disclosure. Note that as shown in FIG. 30, the back pattern's 101 stripes are distorted by a drop (or will be distorted by a free flow stream) from the drip chamber 104 as captured in images by the camera 103. This distortion may be used to estimate the drop size, to calculate the flow rate through a fluid-chamber holder, or to determine if a free flow condition exists.

Figure 31:
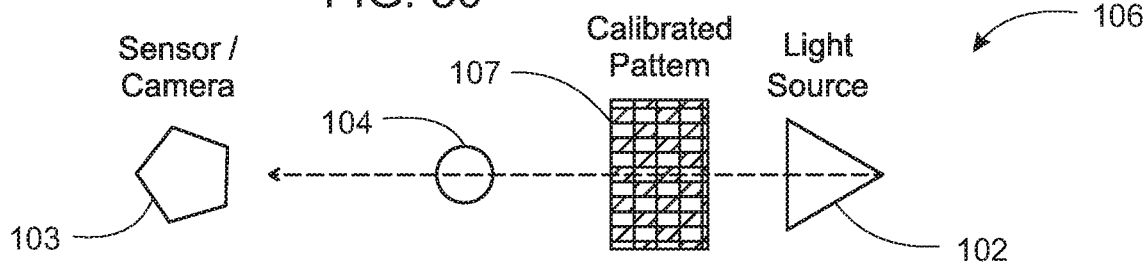
FIG. 31 is a block diagram of an imaging system for use with the drip-chamber holder of FIGS. 4-5 or FIG. 6 having a back pattern with a checkerboard pattern and a light source shining on the stripes from behind the back pattern relative to an opposite end to a camera in accordance with an embodiment of the present disclosure.
Figure 32:
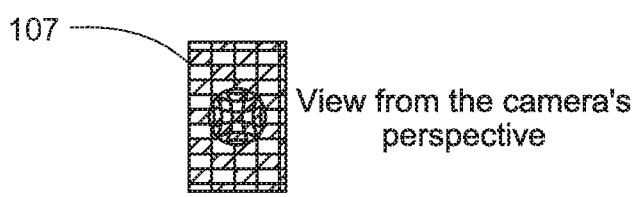
FIG. 32 shows an image from the camera of FIG. 31 when a drop distorts the back pattern of FIG. 26 in accordance with an embodiment of the present disclosure.

FIG. 31 is a block diagram of an imaging system for use with the drip-chamber holder of FIGS. 4-5 or FIG. 6 having a back pattern with a checkerboard pattern and a light source shining on the stripes from behind the back pattern relative to an opposite end to a camera in accordance with an embodiment of the present disclosure. FIG. 32 shows an image from the camera of FIG. 31 when a drop distorts the back pattern 107 of FIG. 26 in accordance with an embodiment of the present disclosure. In yet another embodiment, the background may be formed using a plurality of random dots and/or circles.

Referring to FIGS. 28-32, the Lensing of a drop (i.e., the distortion of the back pattern from the view of a camera) may be used to measure the radius of the drop. The radius of the drop is related to the effect it has on the light passing through it. By measuring the change to the calibration grid as seen through the drop, the radius and hence the volume of the drop can be calculated. For example, the magnification of a test grid of known size as seen through the drop could be measured optically and the radius inferred from this measurement. The relationship between the radius and the drop may be calculated and/or may be determined using a lookup table that has been generated empirically.

Figure 33:
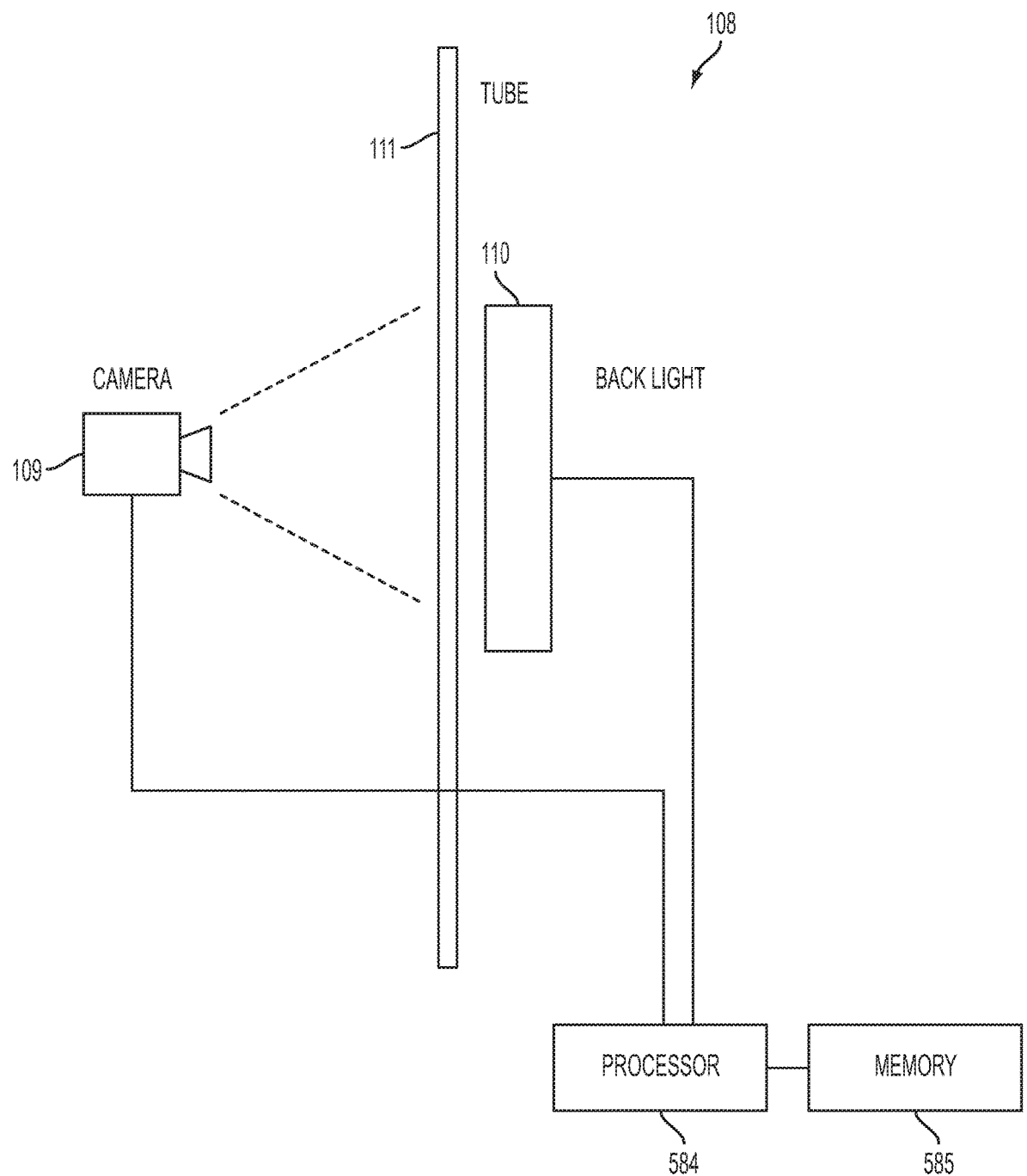
FIG. 33 shows a block diagram of an air detector using a camera in accordance with an embodiment of the present disclosure.

FIG. 33 shows a block diagram of an air detector 108 using a camera 109 in accordance with an embodiment of the present disclosure. The air detector 108 may be the air detector 24 of FIG. 1, the air detector 410 of FIG. 2 or FIG. 3, or the air detector 65 of FIG. 5. Additionally or alternatively, in some specific embodiments, the air detector 108 may be formed within the drip-chamber holder 58 and the camera 109 may be the camera 65 of the drip-chamber holder 58 (see FIGS. 4 and 5).

The air detector 108 includes the camera 109, a backlight 110, a processor 584, and a memory 585. The backlight 110 shines light through the tube 111. The camera may optionally include an IR filter on its lens and/or the backlight may be tuned to an infrared wavelength or bandwidth, e.g., to correspond to the IR filter.

The camera 109 may be operatively coupled to one or more processors 584 that are in operative communication with a computer readable memory 585, e.g., RAM, ROM, disk, hard disk, memory, etc. The computer readable memory 585 may include one or more operative instructions configuration for execution by the one or more processor. The one or more operative instructions may implement an algorithm to detect or determine the present of air within the tube 111; for example, by determining or detecting the presence of one or more bubbles within the tube 111.

Additionally or alternatively, the system 108 can be used to detect the status of the tube 111 designed to transport fluid, e.g., in this example IV tubing. The camera 109 may be a digital camera that captures images of the tube 111 that is back-lit with a diffuse light from a backlight 110. The backlight 110 may consist of a clear plastic material edge-lit with a set of LEDs (e.g., as is used on a liquid crystal display). The camera 109 may capture one or more images so that the one or more processors can detect or determine the following: (1) if the tube 111 has been installed in the device; (2) if the tube 111 has been primed (i.e., is full of liquid); (3) if there are bubbles in the tube; and/or (4) the color and opacity of the fluid in the tube.

Referring now to FIGS. 34, 35, and 36 for a description of an exemplary use of the system 108 of FIG. 33. The detection algorithm residing within the memory 585 and executed by the processor 584 (see FIG. 33) uses three template images: one representing no tube installed; another representing a tube installed with clear liquid therein; and another representing a thin vertical slice of a bubble as shown in FIG. 34. The algorithm quantifies how closely each section of the tube 111 matches the bubble template of FIG. 34, the no tube template, or the tube template with liquid therein. The matching algorithm may utilize the OpenCV pattern matching function, matchTemplate, described in Equation (14) or Equation (15) above, or an FFT pattern matching algorithm. In yet additional embodiment any of the methods for pattern matching of the matchTemplate of openCV may be used, such as, for example, CV_TM_SQDIFF, CV_TM_SQDIFF_NORMED, CV_TM_CCORR, and/or CV_TM_CCORR_NORMED.

The pattern matching algorithm may scan from one side to the other side, e.g., from left to right. As the processor 584 scans across the image, the pattern matching algorithm tries to match each template to one of the scanned section. If a template matches, and several scans later, no template is matched and finally another template is matched, the processor may interpolate that the later template is the most likely one that should have been matched. For example, when scanning from left to right, in region 191, the template of a tube with liquid therein matches. When transitioning from a side of the bubble 112 from the left, a region 194 on the left side of the bubble within the box 112 may not match any template, and finally, within the box 112, the bubble may match to the air template in region 193; the processor 584 may assume the reason the pattern matching algorithm could not match the intermediate region of 194 with a template is because the bubble's image started to change the camera's view. Therefore, in this example, the region 194 in which no template was determined to match, the processor 584 may assume that the bubble was present. Also note that interpolation may be used in region 195.

If there is a close match (including the interpolation as described above) a bubble can be identified as is shown in the box 112. The size of the bubble in the box 112 can be estimated based on the tube's 111 diameter (either known in advanced or measured by the camera 109 of FIG. 33) and the bubble length found in the template matching algorithm, e.g., as determined by the box 112. The box 112 may model the bubble as a cylinder having the diameter of the tube 111. The bubble information can be compared frame to frame to keep track of how many bubbles have moved through the field of view and their sizes (and thus the total amount of air delivered to a patient may be tracked). The processor 584 may issue an alert or alarm if any bubble exceeds a given size, if the total amount of air passing through the tube 111 exceeds a predetermined threshold, or if the total amount of air passing through the tube 111 exceeds a predetermined threshold within a predetermined amount of time. In some embodiments, the color of the fluid may be used to estimate and/or determine the amount of air dissolved within the liquid within the tube 111.

In some embodiments, the bubble of FIG. 36 may have its shape estimated. For example, edge detection may be used to identify the left and right edges of the bubble to estimate its volume, e.g., Canny edge detection, a first-order edge detection algorithm, a second-order edge detection algorithm, a phase congruency-based edge detection algorithm, and the like. The edge detection algorithm may utilize one found in OpenCV. Additionally or alternatively, the edge detection algorithm may average 5 previous pixels from a side (e.g., the left side) and compare that to an average of the next 5 pixels (e.g., the right side), and when the change exceeds a predetermined threshold, the edge of the bubble may be determined to be present.

Additionally or alternatively, the camera 109 can capture an image with a threshold amount of red liquid within the tube 111 such that the one or more processors 584 determines that blood is present within the tube 111. For example, the system 108 having the camera 109 of FIG. 33 may be used to form the infiltration detector 32 of FIG. 2. One or more of the pumps, e.g., pumps 19, 20, and 21, may be used to create a backpressure to determine if the catheter is properly in the vein. That is, if the catheter is properly within the vein, then a small amount of negative pressure within the tube should draw blood into the tube. As shown in FIG. 37, blood 113 may be captured within an image taken by the camera 109 of FIG. 33, which is then processed to determine that a threshold of red exists. FIG. 38 shows a region 114 determined by the one or more processors, e.g., processor 37 of FIG. 2, that a threshold amount of red color exists. The white pixels depicts that a threshold amount of red has been detected and a black pixel depicts that a threshold amount of red has not been detected for that pixel.

In another embodiment, the pixels are converted to grayscale and then a threshold amount of a dark color may be used to determine that blood exists at each individual pixel. For example, if the pixel is determined to be below a threshold (e.g., closer to black beyond a threshold), that pixel may be determined to be blood and is thereby converted to white while the remaining pixels are converted to black (or in other embodiments, vice versa). For example, the image taken may be in RGB format which is then converted to a grayscale image using the void cvtColor( ) function of the OpenCV library using the CV_RGB2GRAY color space conversion code. The threshold amount may be 50, 128, or may be dynamically adjusted.

The processor 37 may determine that infiltration has occurred when the infusion site monitor 26 of FIG. 2 receives no blood or less than a predetermined amount of blood within the tube when a predetermined amount of negative pressure is present within the tube, e.g., when running an infusion pump in reverse. The amount of blood may be determined by summing the white pixels within the region 114. The tube may include fiducials to help locate the tube and/or the tube's holder. Additionally or alternatively, fiducials may be used to indicate distance, e.g., the volume of blood in the tube may be correlated with the length of the blood within the tube using the fiducials, for example, to prevent drawing back too much blood during an infiltration test.

Figure 39:
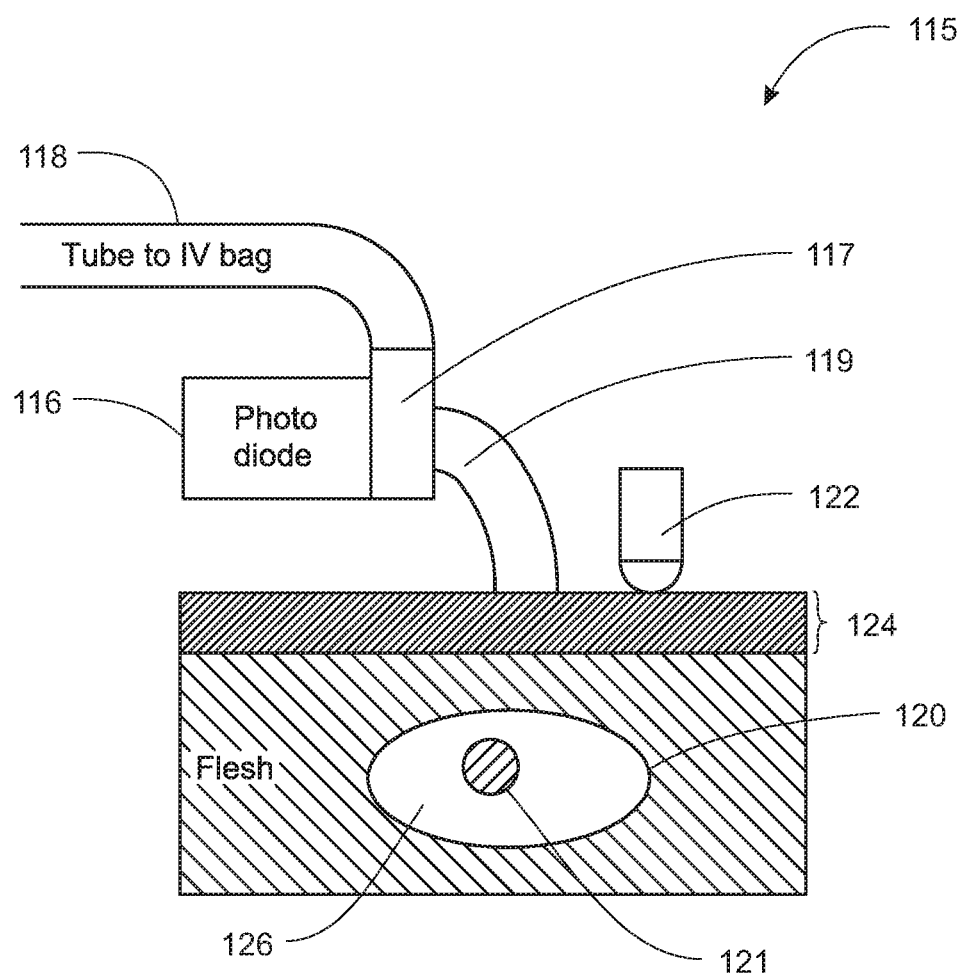
FIG. 39 shows an infiltration detector in accordance with an embodiment of the present disclosure.

FIG. 39 shows an infiltration detector 115 in accordance with an embodiment of the present disclosure. The infiltration detector 115 of FIG. 39 may be the infiltration detector 32 of FIG. 2. The infiltration detector 115 includes a photodiode coupled to a T-connector 117. The T-connector connects the tube 118 to the tube 119 that feeds liquid into the view 120 via an internal portion of the catheter 121. The infiltration detector 115 also includes an LED 122 that shines light into the skin 124. The photodiode 116 and the LED 122 may be coupled to a processor that implements an algorithm to determine when infiltration has occurred, e.g., processor 37 of the infusion site monitor 26 of FIG. 2. The algorithm may be implemented by an operative set of processor executable instructions (e.g., as stored on a memory 38) configured for execution by the processor (e.g., the processor 37).

Blood entering into the tube 119 and found around the catheter has significant light absorbing properties at specific wavelengths that would minimize the passage of light from the LED 122 through a light path that passes through soft tissue, the vein wall, venous blood, and the fluid in the IV catheter and tubing 119. When infiltration has occurred, fluid should surround the internal portion of the catheter 121 (e.g., 18 Gauge), and the amount of light from the LED 122 to the photodiode 116 is reduced from optical absorption caused by the blood. This is in contrast to an infiltrated state where IV fluid surrounding the catheter 121 minimally absorbs or attenuates the same light wavelength absorbed by venous blood and therefore allows a larger intensity of light to pass from the LED 122, through the soft tissue, extravasated fluid, and then into the catheter 121 and IV tubing 119 to the light detector, e.g., the photodiode 116.

The photodiode 116 may be disposed such that it could receive any light passing through a catheter 121 and the tube 119. The T-connector 117 is configured to allow fluid to simultaneously pass into the catheter 121 from tube 118 via tube 119, and allow light from the tube 119 to be diverted into the photodiode 116.

The LED 122 emits light at a wavelength that is attenuated by the hemoglobin in the blood and is positioned to illuminate the surface of the skin 124 near the open end of the catheter 121. When the catheter 121 is properly placed within the vein 126, the attenuation of the illumination from the LED 122 by blood reduces the amount of light that reaches the photodiode 116. Additionally, when the catheter 121 is no longer positioned within the vein 126 (e.g., which occurs when an infiltration occurs), the illumination from the LED 122 passes into the catheter 121 and through the tube 119 to be detected by the photodiode 116.

Figure 40:
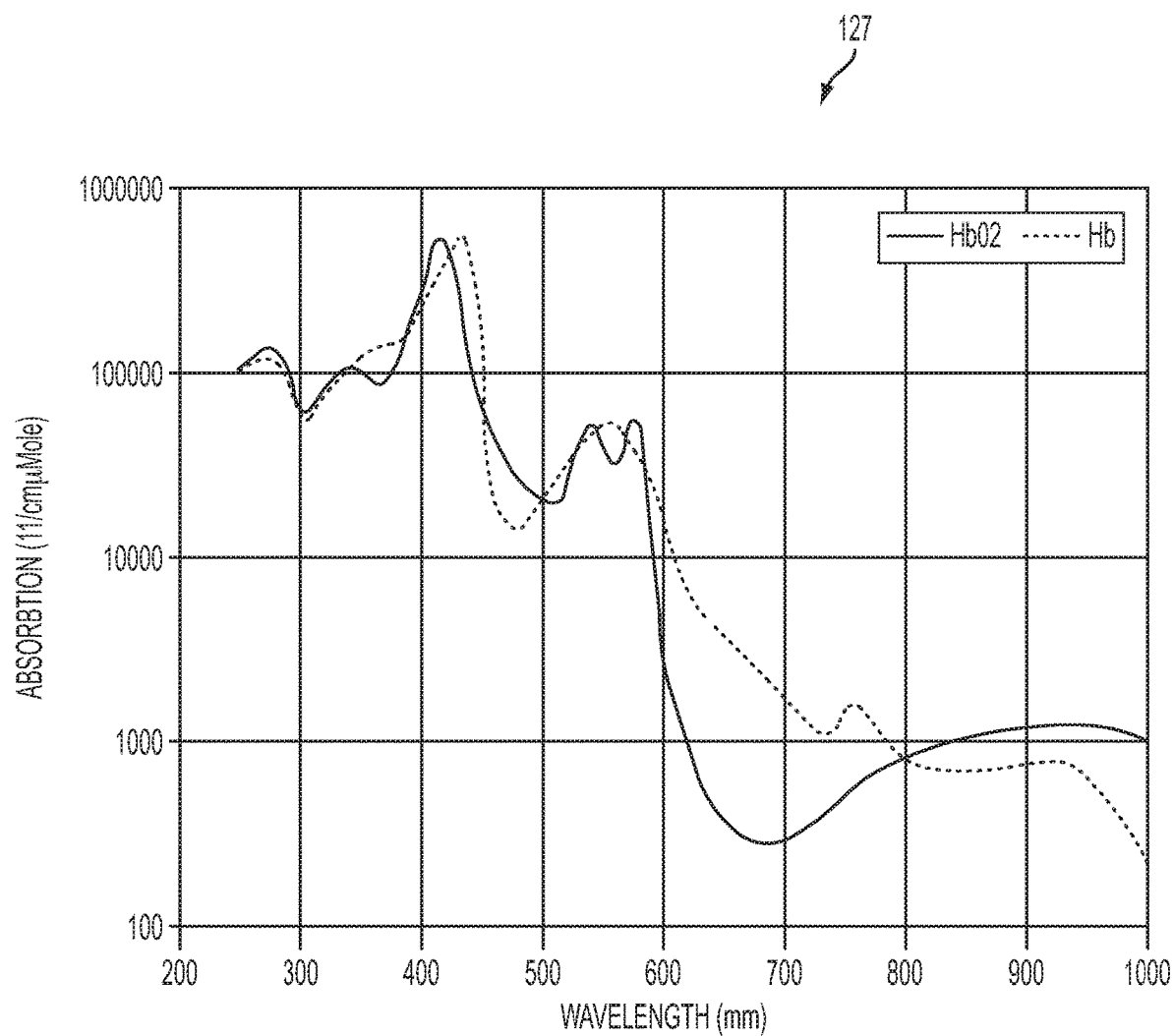
FIG. 40 shows a graphic illustrating the optical absorption of oxygenated and de-oxygenated hemoglobin in accordance with an embodiment of the present disclosure.

FIG. 40 shows a graphic 127 illustrating the optical absorption of oxygenated and de-oxygenated hemoglobin in accordance with an embodiment of the present disclosure. The graphic 127 shows that both oxygenated and de-oxygenated hemoglobin have strong absorption in the 530-590 nanometer range and the 400-450 nanometer range. Referring again to FIG. 39, in some embodiments of the present disclosure, the LED 122 and the photodiode 116 may be configured to emit and absorb, respectively, 405 nanometers, 470 nanometers, 530 nanometers, 590 nanometers and 625 nanometers optical wavelengths. In some embodiments, the photodiode 116 may be a silicon photo-detector with measurable response from 400 nanometers to 1000 nanometers.

Figure 41:
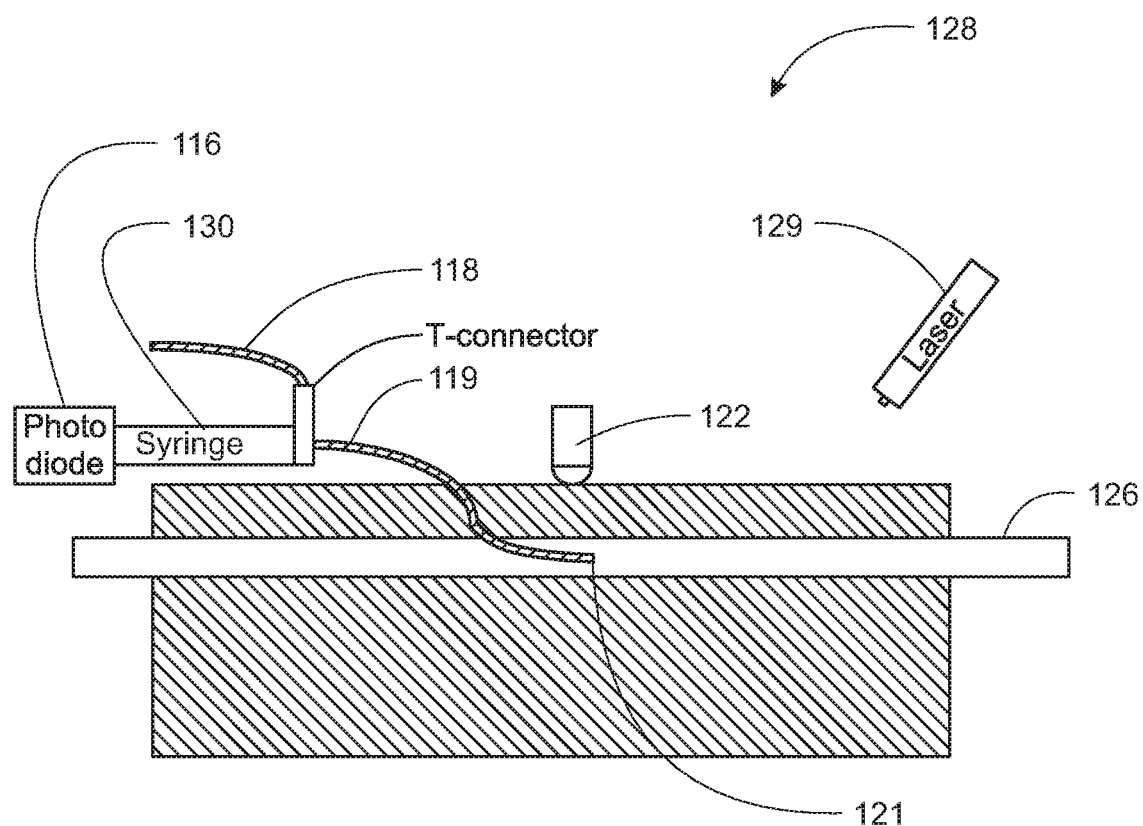
FIG. 41 shows another infiltration detector in accordance with another embodiment of the present disclosure.

Referring now to FIG. 41, another infiltration detector 128 in accordance with another embodiment of the present disclosure is shown. The infiltration detector 128 includes a laser 129 to further illuminate the vein 126. The photodiode 116 is placed at the end of a syringe 130, which includes a wrapping of copper tape to minimize stray light. The LED 122, the laser 129 (e.g., a laser pointer), or both may be used to illuminate the end of the catheter 121. The LED 122 may emit light having wavelengths about 625 nanometers, and the laser 129 may emit light red wavelengths.

In some embodiments of the present disclosure, the catheter 121 and/or the tube 119 includes a stainless steel needle (e.g., 18 gauge) having connectors wrapped in aluminum foil. In yet additional embodiments of the present disclosure, the LED 122 and/or the laser 129 may be modulated to enhance detection by the photodiode 116.

The syringe 130 may be used to apply a negative pressure to the tube 119. The processor 37 of FIG. 2 may be coupled to the photodiode 116 and a position sensor of the syringe 130 to determine if an infiltration has occurred. If, after the syringe 130 (either manually of via an automatic actuator) is pulled back as sufficient amount of distance and no blood is detected by the photodiode 116 (e.g., from spectral absorption by the blood), the processor 37 may issue an alert and/or alarm to indicate that an infiltration has occurred.

In another embodiment, a small fiber optic disposed through the catheter 121 or needle illuminates the area at the tip of the catheter 121, e.g., the LED 122 is coupled to the fiber optic cable to guide light into the vein 126. Additionally or alternatively, a pulse oximeter over the IV site may be used to automatically measure a baseline profile of absorption to detect changes caused by an infiltration, e.g., using the processor 37.

It yet additional embodiments, a fluorescent coating is optionally applied to the tip of the needle of the catheter 121 that is excitable by light in a wavelength significantly absorbed by venous blood. For example, colored light which is absorbed by hemoglobin would not be detectable when the catheter 121 is properly located in the vein. When the catheter 121 was located outside of the vein, this light would not be absorbed and would become detectable by the photodiode 116. The fluorescent coating will emit less when the exciting light is absorbed by the hemoglobin, and the emitted light may also be absorbed by the hemoglobin.

For example, the emitted light from the fluorescent coating may be different than the exciting light, e.g., from the LED 122, and the photodiode 116 may include a filter to filter out the exciting light from the LED 122 and to receive the light being emitted from the excited fluorescent coating. In some embodiments, the fluorescent coating may fluoresce when a black light is applied. Additionally or alternatively, the LED 122 may be modulated.

FIG. 42 shows a perspective view of an occluder 131 in accordance with an embodiment of the present disclosure. FIG. 43 shows a side view of the occluder 131, and FIG. 44 shows a side view of the occluder 131 in operation. Referring now to all of FIGS. 42, 43, and 44, the occluder 131 includes occluder edges 132 and a pivot 133. The occluder 131 may include a spring (not shown) to force the occlude edges 132 against a tube 135. Additionally or alternatively, the occluder 131 may include an actuator 134 to actuate the occluder 131 against the tube 134.

The occluder 131 may be used within a peristaltic pump such that when a door is opened for positioning the tube 135, the occluder 131 is opened for placing the tube 135 within the region of the occluder edges 132. When the door is opened again, the occluder 131 may transition from an open to a relaxed state by action of the actuator 134 to occlude the tube 135.

Figure 45:
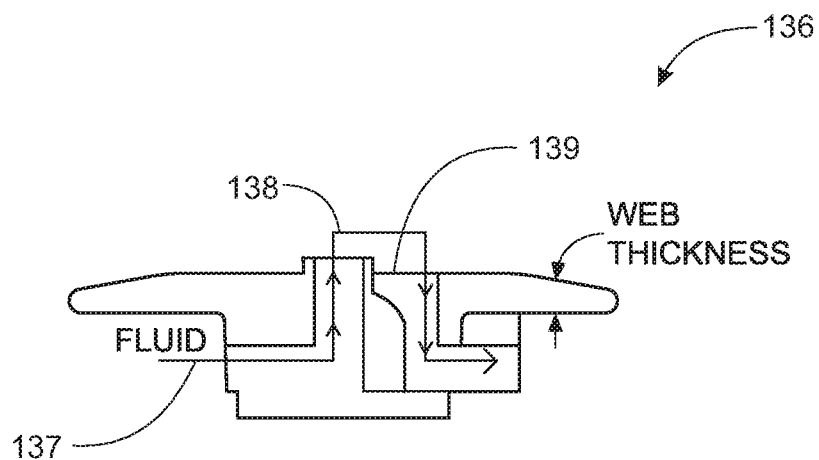
FIG. 45 shows a side-sectional view of a valve for use in a cassette in accordance with an embodiment of the present disclosure.
Figure 46:
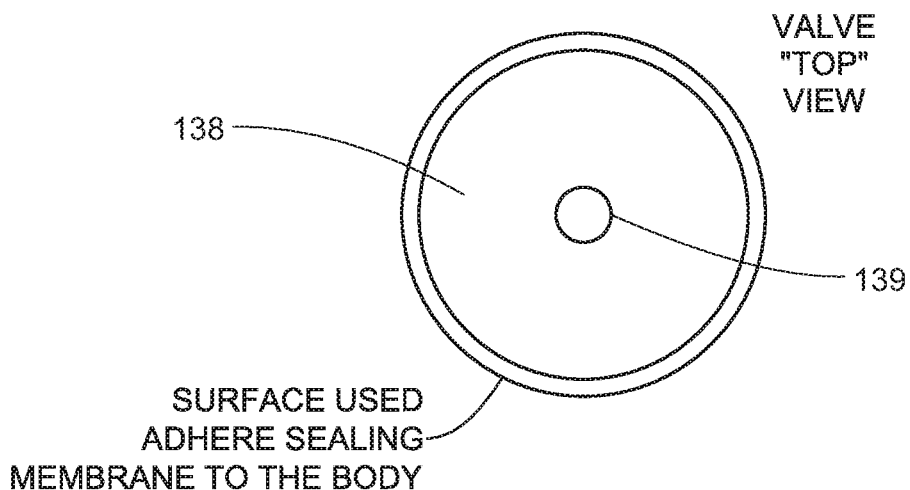
FIG. 46 shows a top view of the valve of FIG. 45 in accordance with an embodiment of the present disclosure.
Figure 47:
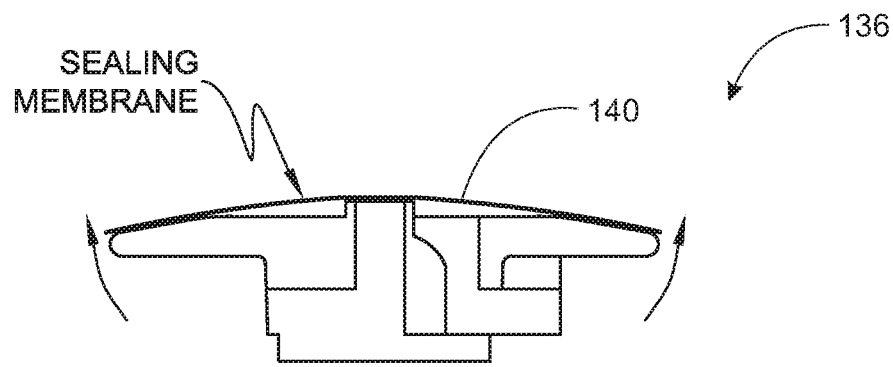
FIG. 47 shows another side-sectional view of the valve of FIG. 45 installed within a cassette in accordance with an embodiment of the present disclosure.

FIG. 45 shows a side view of a valve 136 for use in a cassette in accordance with an embodiment of the present disclosure; FIG. 46 shows a top view of the valve 136; and FIG. 47 shows another side view of the valve 136 installed within a cassette in accordance with an embodiment of the present disclosure. As is easily seen in FIG. 45, a path 137 illustrates the flow of fluid. In FIG. 46, the exit orifice 138 and reentry orifice 139 are visible. FIG. 47 shows a membrane 140 when the valve 136 is installed in a cassette. The membrane 140 may be set to compress again the valve 136 and may be 0.032 inches thick. The membrane 140 may use an UV-cured adhesive. The membrane 140 prevents the fluid from flowing in the wrong direction, e.g., opposite to that of the path 137 as shown in FIG. 45. When the fluid attempts to flow in the wrong direction, the suction force presses the membrane 140 against the exit orifice 138 preventing fluid from flowing from the reentry orifice 139 to the exit orifice 138. Additionally or alternatively, a plunger coupled to an actuator may be used to compress the membrane 140 to further close the valve 136. In yet an additional embodiment of the present disclosure, a positive or negative pressure may be applied to the top of the membrane 140 to control the valve 136.

Figure 48:
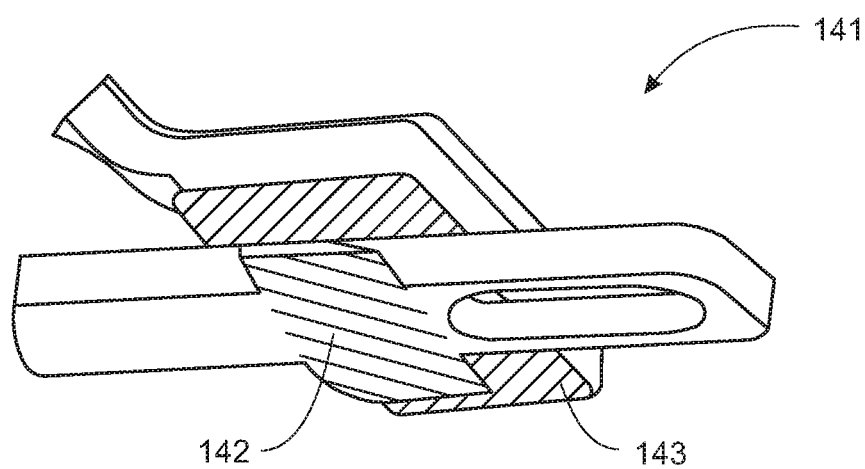
FIG. 48 shows a sliding valve having an inclined plane to provide sealing in accordance with an embodiment of the present disclosure.
Figure 49:
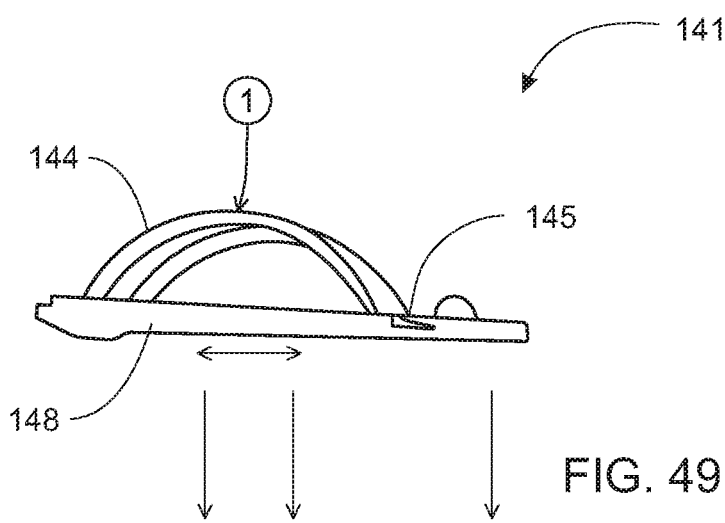
FIG. 49 shows a side view of the sliding valve of FIG. 48 in accordance with an embodiment of the present disclosure.
Figure 50:
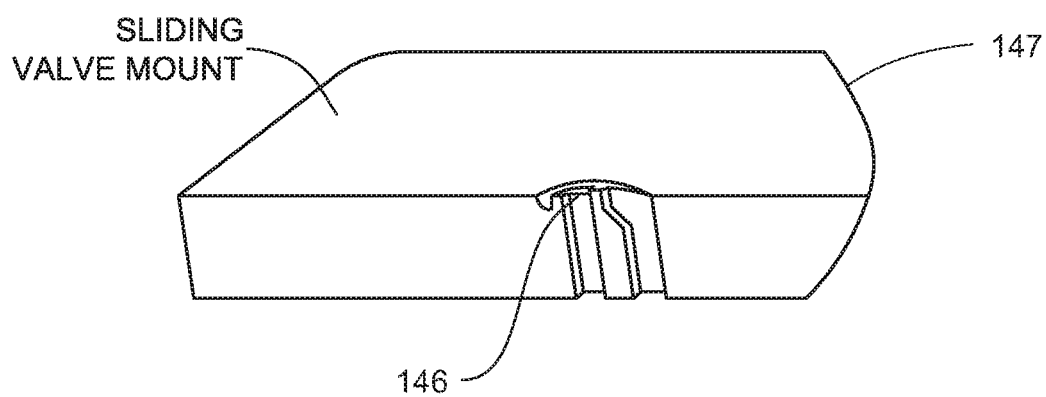
FIG. 50 shows the mount of the sliding valve of FIGS. 48-49 in accordance with an embodiment of the present disclosure.
Figure 51:
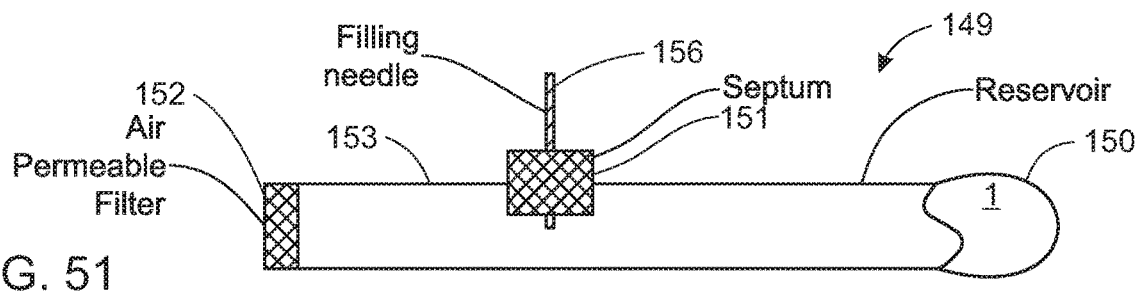
FIGS. 51-55 show a vent for a reservoir in accordance with an embodiment of the present disclosure.

FIG. 48 shows a sliding valve 141 having an inclined plane to provide sealing in accordance with an embodiment of the present disclosure. The sliding valve 141 includes a sealing surface 142 and a mounting surface 143. As seen from FIG. 49 which shows a side view of the sliding valve 141, the sliding valve 141 includes spring arches 144, and a wedge 145 to create a downward force to seal the port 146 of the mount 147 as shown in FIG. 50.

A downward force on the spring arches 144 causes the sliding valve 141 to slide away from the mounting surfaces 143 exposing the valve port 146. When released, the spring arches 144 force the sealing arm 148 towards the mounting surfaces 143, and the downward force wedges 145 make contact with a molded counterpart in the mount 147 and force the sealing surface 142 onto the valve sealing surface port 146.

FIGS. 51-55 show a vent 149 for a reservoir 150 in accordance with an embodiment of the present disclosure. The vent 149 may be used on the fluid reservoirs 2, 3, or 4 in FIG. 1, may be used on the air filter 50 or with the drain chamber 53 of the pump 19 as shown in FIG. 3. The vent includes a septum 151, an air permeable filter 151, and a tube 153. In some embodiments of the present disclosure, a reservoir 150 of an infusate is rigid, e.g., a rigid IV bag or other fluid reservoir for a fluid pumping device. The reservoir 150 may include a vent 149 to allow fluid flow out of a rigid reservoir 150 while venting the fluid reservoir 150 with an air permeable filter 152. In some embodiments, the vent 152 may not be impermeable to water vapor. However, by placing an oil plug 154 inline between the fluid reservoir 150 and the air filter 152, infusate 155 losses are reduced because the oil 154 prevents the infusate from evaporating through the oil plug 154.

Figure 52:
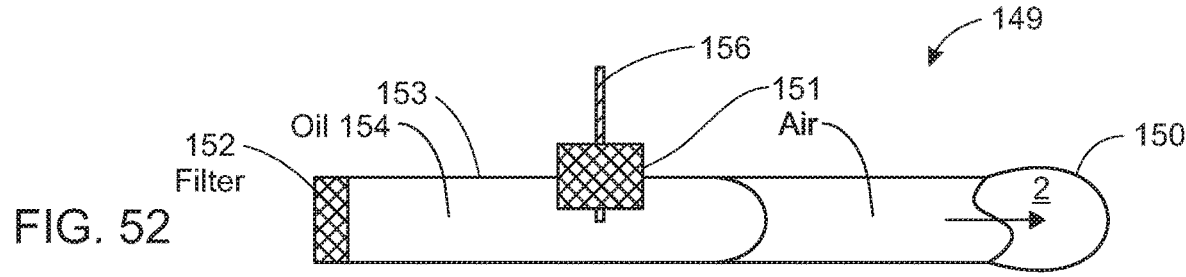
Figure 53:
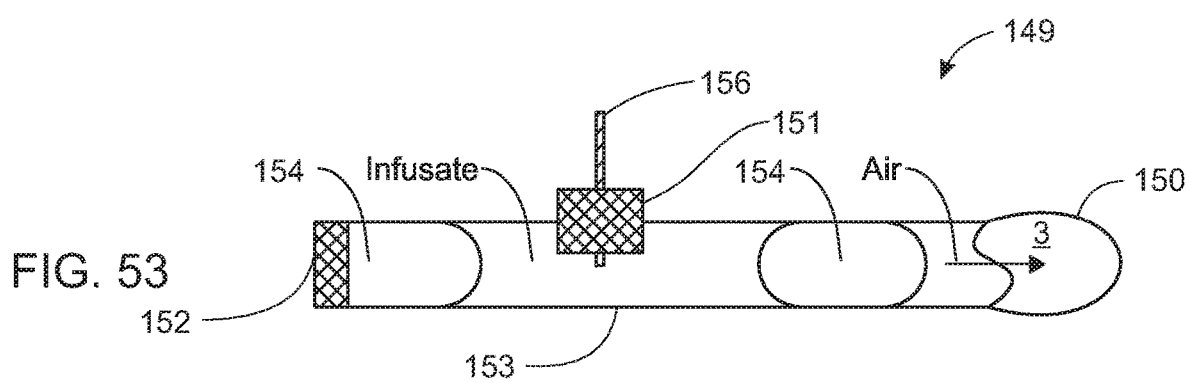
Figure 54:
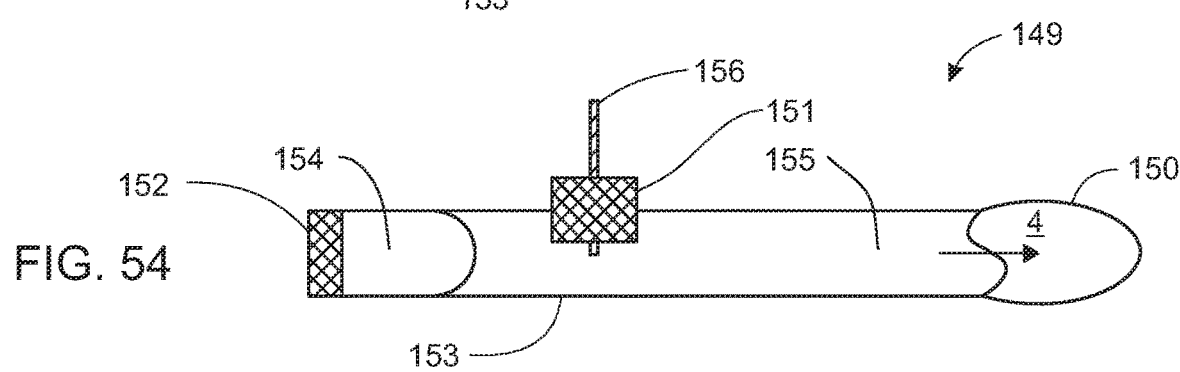
Figure 55:
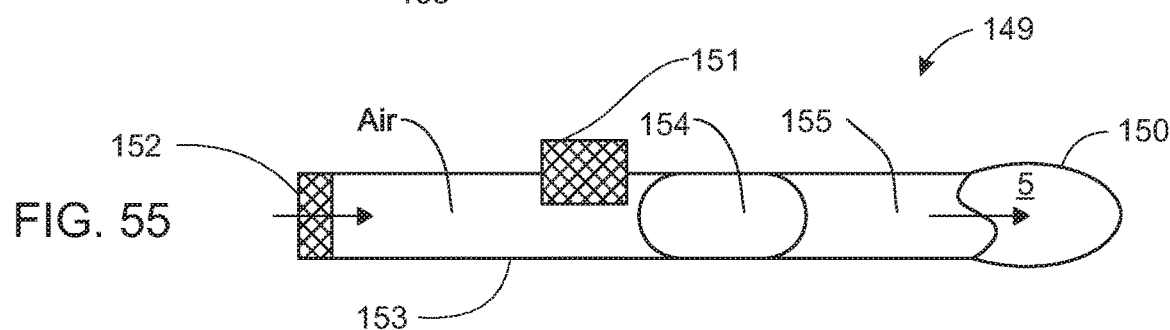

The oil plug 154 is created by placing the septum 151 upstream of the reservoir 150 in a relatively narrow cross-sectioned section of the reservoir 150 as shown in FIGS. 51, 52, 53, 54, and 55. As shown in FIG. 52, oil 154 is injected through the septum 151 through a filing needle 156 before injecting the infusate 155 (as shown sequentially in FIGS. 53 and 54). An amount of oil 154 is left in between the air filter 152 and the infusate 155 at the end of the fill. As air is drawn into the reservoir 150 through the air filter 152, as shown in FIG. 55, the oil 154 advances with the infusate 155 preventing evaporative losses.

Additionally or alternatively, in some embodiments, the oil plug 154 is pre-loaded into the tube 153 in between the septum 156 and the air filter 152; for example, as would be the case if the fill procedure began as shown in FIG. 52.

Figure 56:
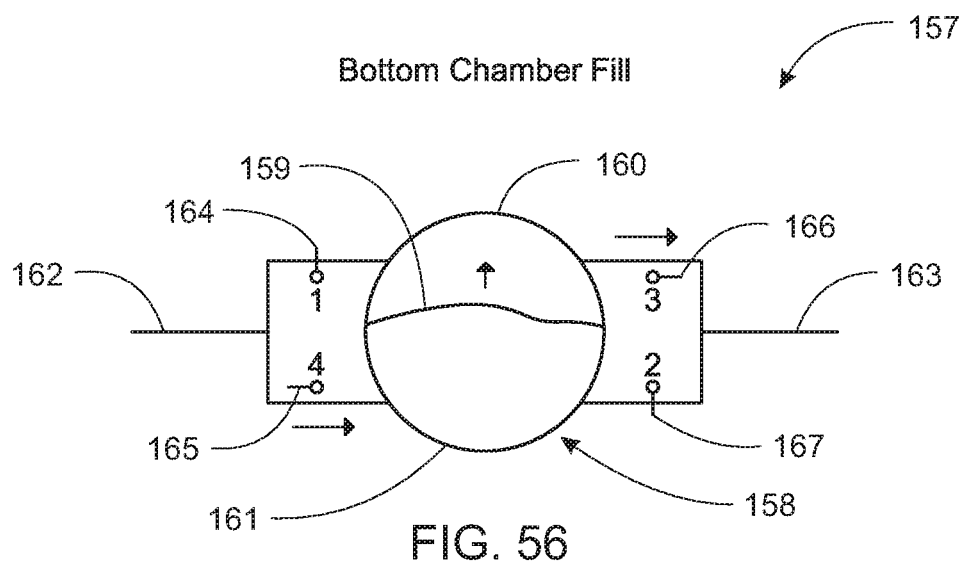
FIGS. 56-58 illustrate the stages of a flow meter in accordance with an embodiment of the present disclosure.
Figure 57:
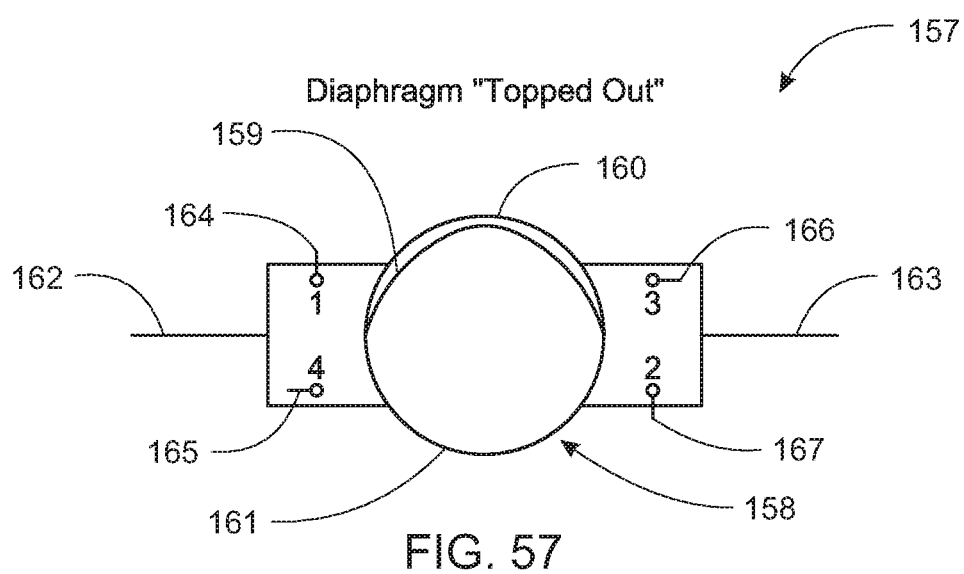
Figure 58:
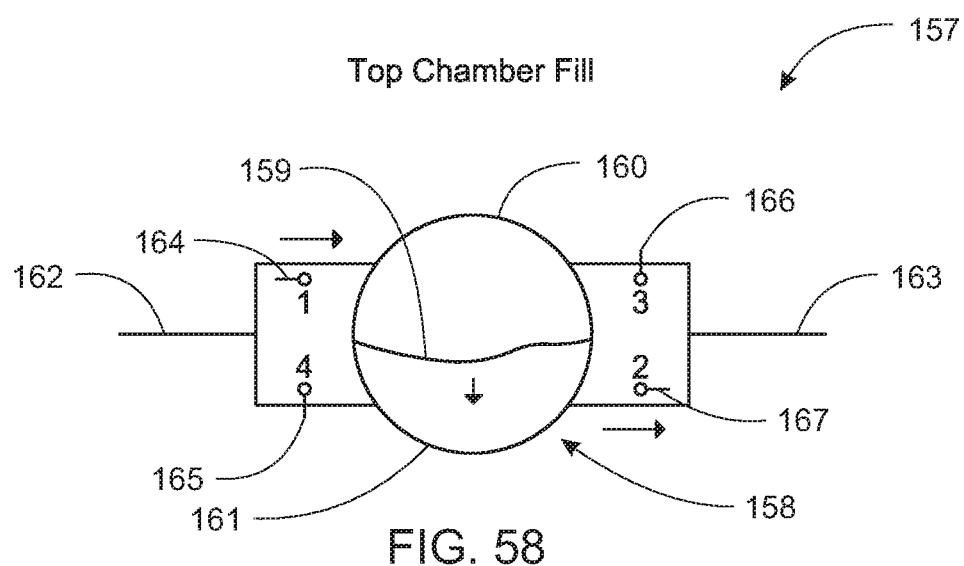

FIGS. 56-58 illustrate the stages of a flow meter 157 in accordance with an embodiment of the present disclosure. FIG. 56 illustrates a first stage, FIG. 57 illustrates a second stage, and FIG. 58 illustrates a third stage. The stages of FIGS. 56-58 may be implemented as a method in accordance with an embodiment of the present disclosure. A pump disclosed herein may be coupled upstream via the input port 162 and/or an infusion pump may be coupled to the output port 163 downstream to create a fluid from the input port 162 through the flow meter 157 to the output port 163.

The flow meter 157 includes a chamber 158 divided by a membrane 159. The membrane 159 divides the chamber 158 into a first section 160 and a second section 161. The flow meter 157 includes an input port 162 and an output port 163. The flow meter 157 includes first 164, second 167, third 166, and fourth 165 valves. The input port 162 is in fluid communication with the first section 160 via the first valve 164 and the second section 161 via the fourth valve 165. The output port 163 is in fluid communication with the first section 160 via the third valve 166 and the second section 161 via the second valve 167. The chamber 158 may be spherically shaped or cylindrically shaped. The chamber 158 may be rigid, e.g., the chamber 158 may be made out of a plastic, metal, or other rigid or semi-rigid material.

The flow from the input port 162 to the output port 163 may be monitored by use of the flexible membrane 159. The passage of fluid may be controlled via actuation of the first valve 164, the second valve 167, the third valve 166, and the fourth valve 165. To fill the second section 161 of the chamber 158 and empty the first section 160 of the chamber 158, the first valve 164 and the second valve 167 are closed while the third valve 166 and the fourth valve 165 are opened. This pushes the diaphragm or membrane 159 to the top side of the chamber 159 as shown in FIG. 57. As illustrated in FIG. 58, this process can be reversed to fill the first section 160 and empty the second section 161 by opening the first valve 164 and second valve 167 while closing the third valve 166 and fourth valve 165. Because the volume of the chamber 158 is known, the volume of fluid flowing through the input port 162 to the output port 163 can be estimated by the movement of the membrane because it is expected that the membrane 159 will become flush against the inner surface of the chamber 158.

To determine when the membrane 159 (i.e., diaphragm) has reached the top or bottom of the chamber 158, a pressure sensor could be added to the input valve 162. When the membrane 159 reaches the end of the travel, the flow from the input port 162 will be occluded and the pressure will increase. At this point, the valves can be switched (as shown in FIG. 58) and the process continued on the opposite chamber.

In some embodiments of the present disclosure, the valves 164, 165, 166, and 167 may be mechanically toggled. The input port 162 pressure could potentially be used to mechanically toggle a switch that alternately opens and closes the two pair of valves in each state as illustrated by FIGS. 56-57, or FIG. 58. For example, the inlet pressure could expand a spring-loaded diaphragm which pushes on a latching mechanism that controls the valves 164, 165, 166, and 167.

Additionally or alternatively, in some embodiments, the chamber 158 may be made of a clear material (polycarbonate, topaz, etc.) and the diaphragm 159 out of an opaque material, and a camera may be used to observe the chamber 158 and detect when the diaphragm 159 has reached the end of its travel. In yet another embodiment, a "target" image may be placed on the diaphragm 159 and a pair of stereo cameras (not shown) could detect when this target has reached the chamber 158 housing edge and is viewable. For example, there may be a camera to view the first section 160 from the outside and another camera to view the second section 161 from the outside.

Figure 59:
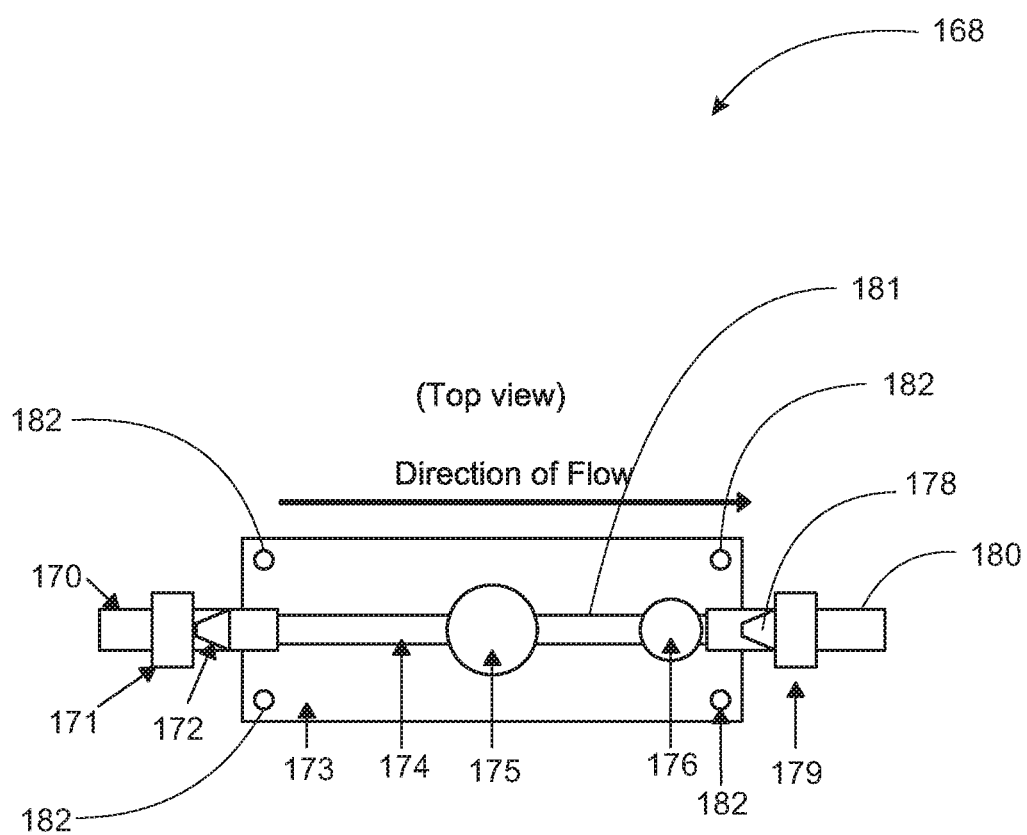
FIG. 59 shows a diagram of a disposable portion of a flow meter in accordance with an embodiment of the present disclosure.

FIG. 59 shows a diagram of a disposable portion 168 of a flow rate meter in accordance with an embodiment of the present disclosure. The disposable portion 168 may be part of the flow meter 10, 11, or 12 of FIG. 1, the flow meter 169 of FIG. 2 for use within the infusion site monitor 26, or may be the flow meter 48 of FIG. 3 for use with the pump 19 (in some embodiments, the flow meter 48 is coupled to the tube 56). In yet additional embodiments, the disposable portion 168 is part of an integrated flow rate meter and membrane pump. The disposable portion 168 may interface with an upper clam-shell Acoustic Volume Sensing (AVS) assembly and a lower clam-shell AVS assembly (e.g., the upper clam-shell AVS assembly 192 and the lower clam-shell AVS assembly 193 of FIG. 70 as described below). Acoustic volume sensing is described in greater depth in the section of the detailed description tilted "ACOUSTIC VOLUME SENSING"

The disposable portion 168 includes inlet tubing 170, an inlet occlude release collar 171, an inlet Duck-bill occluding valve 172, a disposable body 173, fluid tracks 174 and 181, an AVS chamber 175 (described below), an air purge and spectral analysis window 176, and an outlet assembly 177. The outlet assembly 177 includes an occluding valve 178, a release collar 179, and an outlet tubing 180.

The duck-bill valves 172 and 178 may be actuated open by deforming the duck-bill (pinching the slot) when AVS clam-shells (see FIG. 70) are closed over the AVS fluid chamber 175, and/or there may be separate components on the tubing set to open the valves 172 and 178 manually (e.g. sliding an oval ring over the duck bill to open it, etc.).

The AVS chamber 175 may be utilized to measure the fluid flowing through the disposable portion 168. That is, the AVS system described below can measured the volume of fluid within the AVS chamber 175. The flow rate may be communicated by a processor to the monitoring client 6, e.g., via a wired or wireless connection. The measurement taken from the AVS chamber 175 may be operatively communicated to a processor, e.g., the processor 37 of the infusion site monitor 26 of FIG. 2 or the processor 38 of the pump 19 of FIG. 3 to control the measurement of fluid flowing through the AVS chamber 175.

Referring to FIGS. 1 and 59, the disposable portion 168 may be used (with the full clam-shell AVS assembly described below) to control the flow of the pumps 19, 20, and/or 21 (directly or via a control system within the monitoring client 6) or may be used to indicate when a predetermined amount of fluid has been fed into the patient 5, in which case a signal is sent to the pumps 19, 20, and/or 21 to stop fluid flow (directly or via a control system within the monitoring client 6). In some embodiments, the disposable portion 168, when used as a flow meter with the full clam-shell AVS assembly, can be used to run a pump in a fixed volume mode with a variable fill and/or empty time, can be used to run in a variable volume with a fixed and/or variable fill or empty time, or can be run in a fixed measurement interval, etc. Additionally or alternatively, the disposable portion 168 may detect error conditions or runaway conditions (e.g., fluid is flowing beyond a predetermined threshold), which may cause the flow rate meter using the disposable portion 168 to issue an alarm or alert, e.g., directly or to the monitoring client 6. The alarm or alert may be used to cause one or more of the valves 16, 17, 18, and/or 25 to prevent additional fluid flow.

Referring again to FIG. 59, the disposable portion 168 may be formed by two or more sheets of barrier film or layers of barrier film and a rigid plastic sheet that are heat sealed together. The disposable portion 168 may be used with (or is part of) the disposable portion 194 of FIGS. 60-62, the disposable portion 201 of FIGS. 63-65, the disposable portion 208 of FIGS. 66-68, and the disposable portion 220 of FIG. 69. The fluid tracks may be incorporated into the film and/or the rigid plastic (e.g. they may be thermally formed or simply an area of the film that is not heat sealed). For example, the rigid portion may define the fluid tracks 174 and 181, and the AVS chamber 175; and a flexible layer may be placed over the rigid sheet such that the flexible layer is generally flat when in an unpressured state over the rigid layer.

For example, the disposable portion 168 may be formed from three layers using a rigid plastic sheet with a barrier film/membrane on either side that contains fluid tracks routed on one (or both) sides connected by through hole(s) in the rigid plastic sheet (e.g., a "via").

The AVS chamber 175 may be incorporated into the film and/or the rigid plastic (e.g. thermally formed or simply an area of the film that is not heat sealed; that is, the chamber expands with the elastomeric potential when filled). The fluid may be routed into the AVS chamber 175 via fluid tracks in the film/membrane, e.g., when using the three layer design. For example, the AVS chamber 175 may be fed by holes in the AVS chamber 175 with the fluid tracks 174 and 181 on the opposite side. In some embodiments, these holes are part of a valving system that works on the fluid tracks on the opposite side. The tubes 170 and 180 may interface into the fluid tracks 174. The tubes 170 and 180 include normally closed occluding valves 172 and 178, respectively. Additionally or alternatively, in some embodiments of the present disclosure, the occluding valves 172 and/or 178 may be one-way valves.

The air purge and spectral analysis window 176 may be transparent for spectral imaging and/or analysis of the composition of the fluid contained therein. For example, the spectral analysis window 176 may be used by a camera to detect blood therein or to determine the spectral absorption or reflection of the material therein which is compared to a database to determine the likely composition of the fluid and/or a concentration of a material.

The air purge 176 may include a micorporous hydrophobic membrane that has one side in contact with the infused fluid and the other side is exposed to atmosphere air. The micorporous hydrophobic membrane may be located, in some specific embodiments, in a pressurized section of the flow path. The air purge and spectral analysis window 176 may include an integral air bubble trap to prevent free flow of bubbles and/or pressure may drives trapped bubbles across the membrane while fluid passes past the trap, etc.

The disposable portion 168 may optionally include several alignment features 182, which may be ink markers, holes, indentations, or other alignment feature(s). The disposable portion 168 may be constructed using stamping, vacuum forming and heat sealing, and can use materials known to be compatible with infusion fluids (e.g. IV bag materials, polycarbonates, Topaz, etc.).

Figure 60:
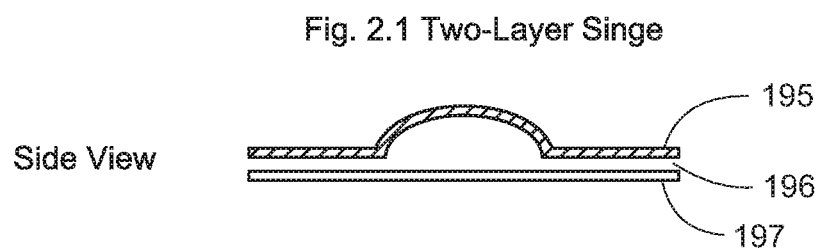
FIGS. 60-62 show several views of a single-sided disposable portion of a flow meter in accordance with an embodiment of the present disclosure.
Figure 61:
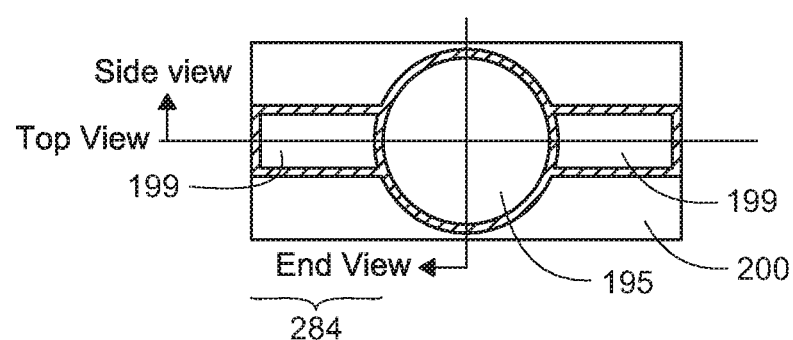
Figure 62:
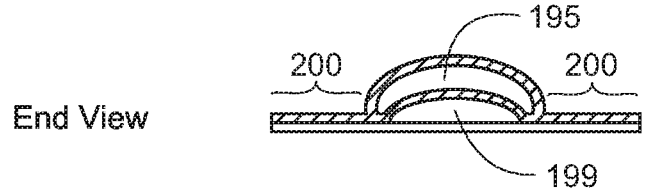

FIGS. 60-62 show several views of a single-sided disposable portion 194 of a flow meter in accordance with an embodiment of the present disclosure. FIG. 60 shows a side view of the disposable portion 194 of a flow meter, FIG. 61 shows a top view of the disposable portion 194 of the flow meter, and FIG. 62 shows an end view of the disposable portion 194 of the flow meter.

The disposable portion 194 includes a one or more film layers 195 that define a fluid space 196 with a bottom film 197 that may be rigid (in some embodiments the bottom film 197 is semi-rigid or flexible). As is easily seen in FIG. 61, the film 195 also forms an AVS chamber 198. As seen in FIG. 62, the AVS chamber 198 is positioned to measure the fluid flowing into and out of the AVS chamber 198 via the fluid track 199. The fluid track 199 interfaces with the AVS chamber 198 allowing it to expand as fluid enters into the AVS chamber 198 from the fluid track 199. The fluid track 199 may hold a volume of, in some specific embodiments, 0.025 cc allowing for 300 milliliters per hour maximum flow rate. The layers 195 are head bonded along length 200.

As shown in FIG. 62, the fluid track 199 formed by the layer 195 is visible and the AVS chamber 198 is also visible;

however, the layer 195, in some embodiments, transitions from the fluid track 199 to the AVS chamber 199 when transitioning from the left side of the disposable portion 194 to the right side as shown in FIG. 61. For example, in FIG. 62, the fluid track layer 199 is relatively proximal (along a length 284 of FIG. 61) to the AVS chamber 198 (which is along a length 285 of FIG. 62), which is distal in the view shown in FIG. 62.

Figure 63:
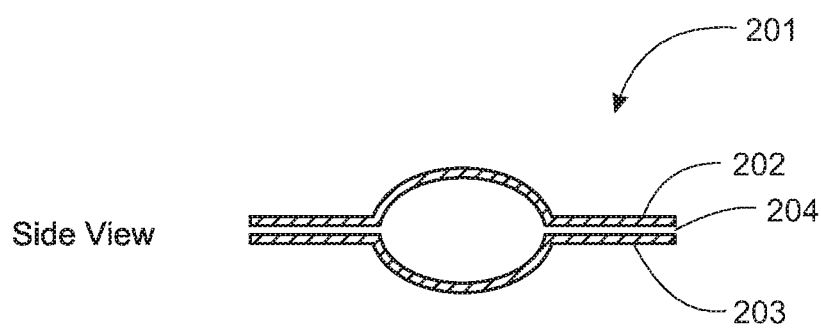
FIGS. 63-65 show several views of a double-sided disposable portion of a flow meter in accordance with an embodiment of the present disclosure.
Figure 64:
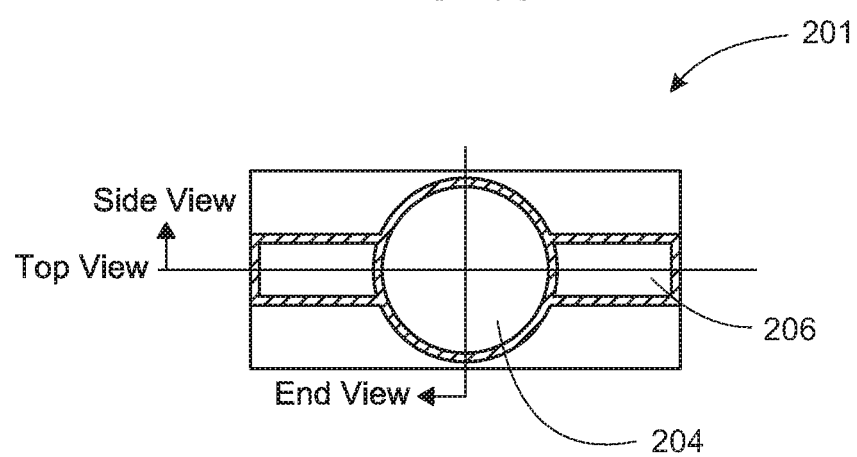
Figure 65:
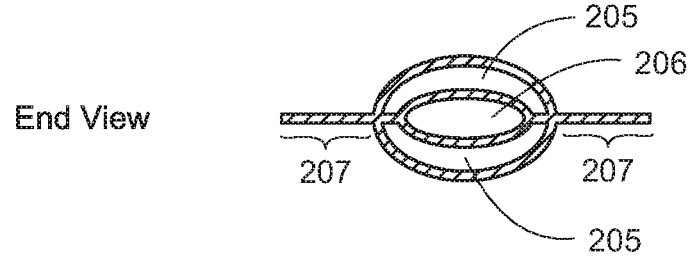

FIGS. 63-65 show several views of a double-sided disposable portion 201 of a flow meter in accordance with an embodiment of the present disclosure. The disposable portion 201 includes one or more top films 202 with one or more bottom films 203 that together define a fluid space 204. Either one of the films 202 and/or 203 may be rigid, semi-rigid, flexible, or elastic. In additional specific embodiments, a rigid, planar layer may be positioned between the layers 202 and 203 (not depicted) with the layers 202 and 203 being flexible.

As is easily seen in FIG. 64, the films 202 and 203 form an AVS chamber 205. As is easily seen FIG. 65, the AVS chamber 205 can measure fluid received from a fluid track 206. Also, fluid may leave the AVS chamber 205 via the fluid track 206. As also shown in FIG. 65, the heat sealed and/or bonded interface 207 is shown. As mentioned, in some embodiments, a rigid member (not shown) may be placed in the center of the layers 202 and 203 thereby defining two AVS chambers 205 and two fluid tracks 206; in this specific embodiment, a small hole may exists between the two fluid tracks 206 and/or the two AVS chambers 206 to provide pressure equalization therebetween. Any common mode compliance of the fluid track 206 would be accounted for by one of the AVS chambers 205 thereby providing a self balancing of the AVS measurements.

Figure 66:
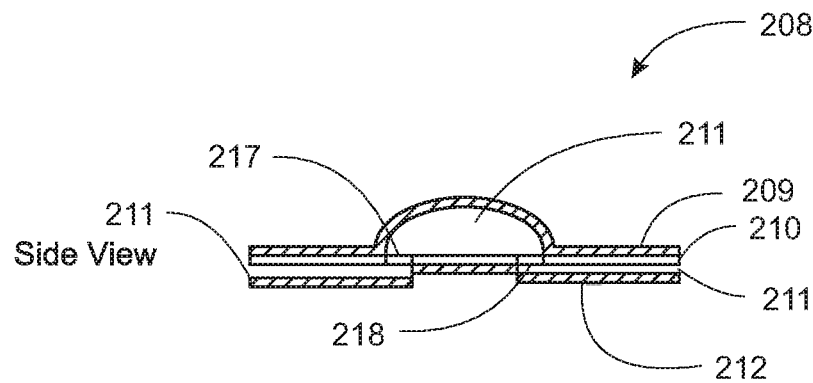
FIGS. 66-68 show several views of a three-layer, opposite-sided, disposable portion of a flow meter in accordance with an embodiment of the present disclosure.
Figure 67:
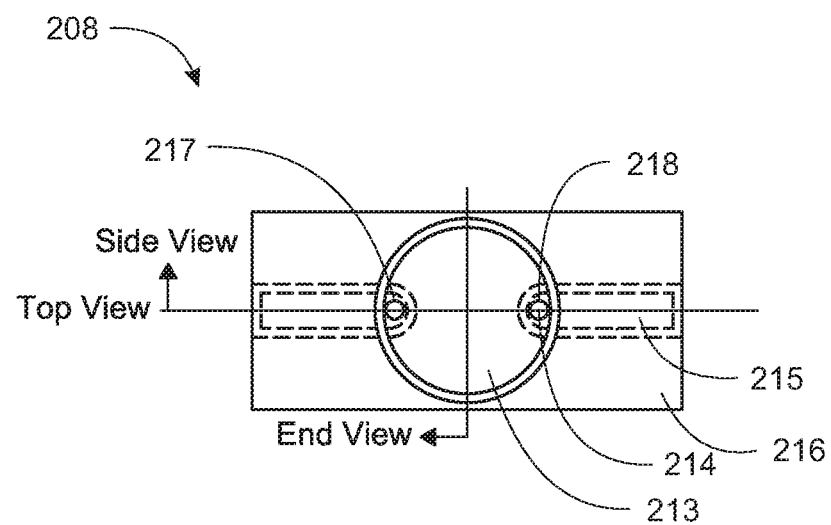
Figure 68:
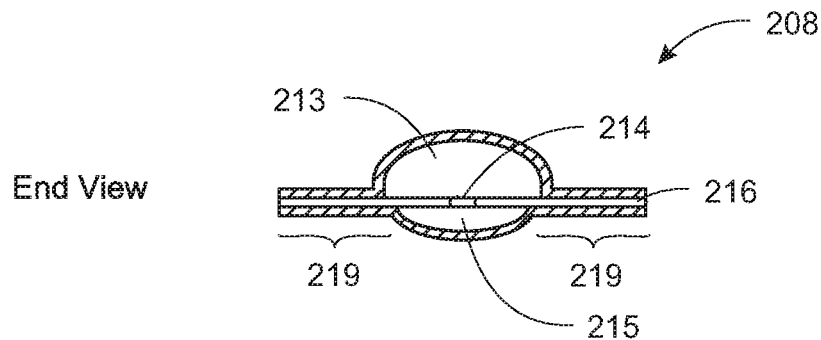

FIGS. 66-68 show several views of a three-layer, opposite-sided, disposable portion 208 of a flow meter in accordance with an embodiment of the present disclosure. The disposable portion 208 is formed by a top layer 209 and a bottom layer 212 having a rigid plastic layer 210 therebetween. The rigid plastic layer 210 has two holes 217 and 218 that allow fluid to pass between a fluid space 211 and the AVS chamber 213.

The fluid passes from the fluid track 215 through the holes 217 and 218 to transgress through the AVS chamber 213. Also, the disposable portion 208 includes a heat bonded portion 219.

Figure 69:
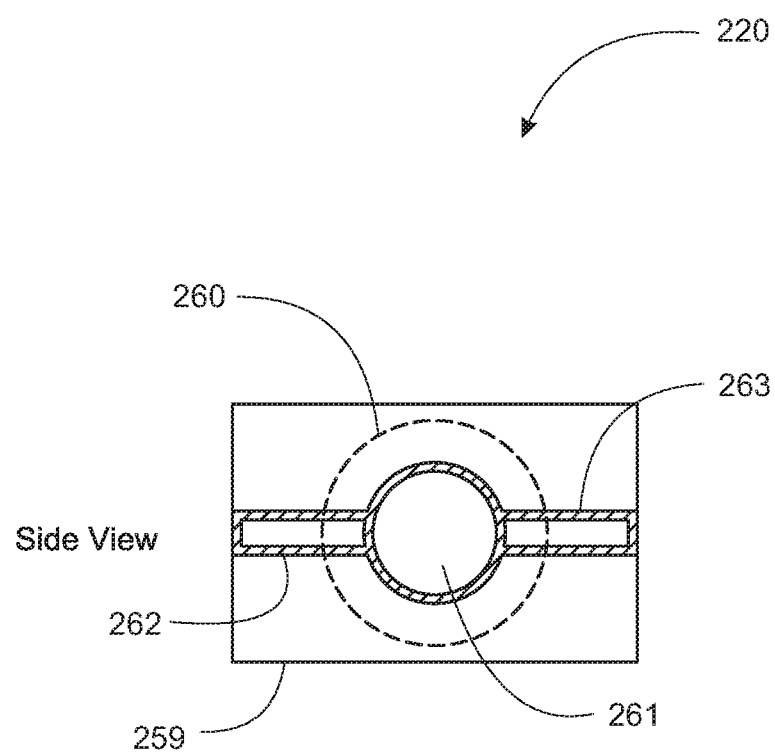
FIG. 69 shows a top view of another disposable portion of a flow meter in accordance with another embodiment of the present disclosure.

FIG. 69 shows a top view of another disposable portion 220 of a flow meter in accordance with another embodiment of the present disclosure. The disposable portion 220 includes one or more layers bonded to a rigid body 259. The rigid body 259 includes a cut-out portion 260. The AVS chamber 261 may protrude out of both side of the rigid body 259 allowing an AVS assembly (not shown) to surrounding the AVS chamber 261 to estimate the volume of the AVS chamber 261. Air may completely transgress through the cut-out portion 260 such that a variable volume may be positioned completely (or substantially) around the AVS chamber 261. The disposable portion 220 may be formed from one or more elastic layers sealed to the rigid body 259. The disposable portion 220 includes fluid tracks 262 and 263 enabling fluid to transgress and egress through the AVS chamber 261.

Figure 70:
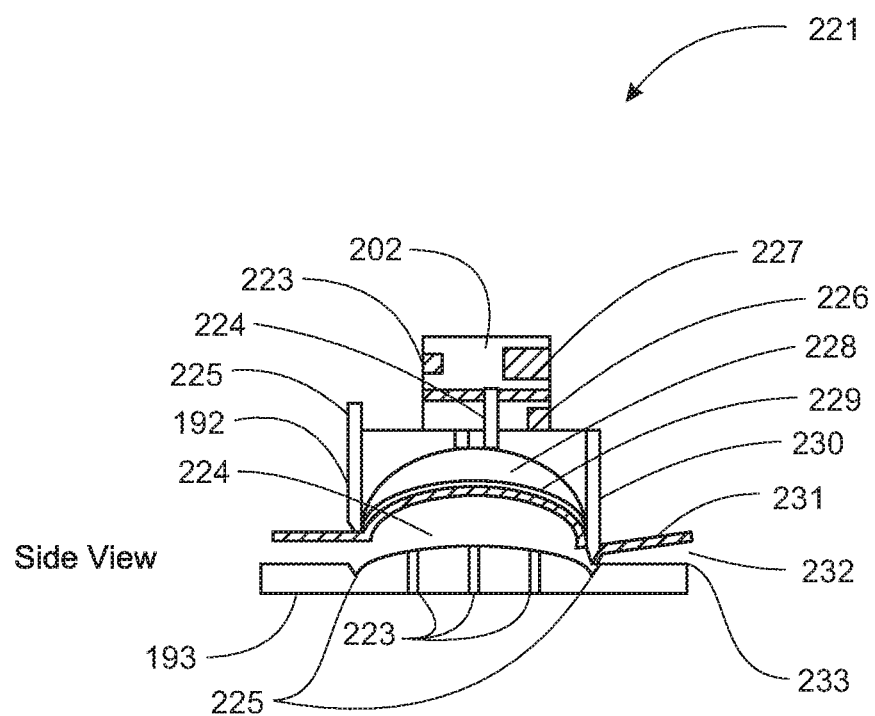
FIG. 70 shows a flow rate meter including a full acoustic volume sensing ("AVS") clam shell assembly and a single-sided disposable portion in accordance with an embodiment of the present disclosure.

FIG. 70 shows a flow meter 221 including a full AVS clam shell assembly and a single-sided disposable portion (e.g., the disposable portion 194 of FIG. 62) in accordance with an embodiment of the present disclosure. The flow meter 221 may fill 0.025 cc of liquid for up to 300 milliliters per hour.

The AVS clam shell assembly includes the upper clam-shell AVS assembly 192 and the lower clam-shell AVS assembly 193. The lower clam-shell AVS assembly 192 may be slightly biased for proper seating in the lower backing 233 and/or it may include a rigid plastic sheet or stiffener to compliment the vents 224. The upper and lower clam-shell AVS assemblies 192 and 193 may circumferentially surround the AVS fluid volume 224, e.g., just outside the heat seal using a trough/protrusion "pinch"; and an o-ring may optionally also be used to seal the AVS fluid volume 224. The flow meter 221 may optionally include an air sensor as described herein, e.g., ultrasonic- and/or camera-based air sensor, to determine if air beyond a threshold is being delivered to a patient; an alarm or alert may be issued in response to the air exceeding the threshold. Additionally or alternatively, the air may be subtracted from the volume of liquid estimated as flowing through the flow meter 221.

The flow meter 221 includes an AVS reference chamber 222, a reference microphone 223, a resonance port 224, an integral perimeter seal or valve 225 (shown in the open state), another integral perimeter seal or valve 230 (shown in the sealed state), a variable volume microphone 226, a speaker 227, and a variable volume 228. The flow meter 221 also includes a spring disk 229. The spring disk 229 may include a small hole for pressure equalization. The spring disk 229 may be formed, in some embodiments, out of an elastomeric film or layer. In some embodiments, the spring disk 229 is used to bring in fluid into the AVS fluid volume 224. The spring disk 229 may provide a spring via pre-forming and/or the variable volume 228 may have a negative or positive pressure relative to either the ambient air and/or the fluid flowing through the AVS fluid volume 224.

The valves 225 and 230 slide along the body of the upper clam-shell AVS assembly 192 to permit or occlude fluid from enter or leaving the AVS fluid volume 224. The valves 225 and 230 are coupled to an actuator (e.g., linear servo, linear stepper motor, a cam follower coupled to a rotating cam, etc.) to control the valve states of the valves 225 and 230. The valves 225 and/or 230 may: be normally closed; actuated open (e.g., using a solenoid and/or Nitinol); include a position sensor; cone-shaped (e.g., a cone shaped plunger from the fluid track side pushes through the elastomer into the AVS chamber inlet/outlet holes to form a seal); and may include an opposing pressure seal to determine if the valve is applying sufficient pressure. The actuators may be coupled to a processor disclosed herein (e.g., the processor 37 of FIG. 2 or 3). The valves 225 and/or 230 may both close in an error condition to prevent fluid from being sent to a patient, e.g., when the processor 37 of FIG. 2 or 3 and/or the monitoring client 6 determines that an error condition exists that requires the stoppage of the fluid flow to the patient. The processor may coordinate operation of the valve 225 and 230 such that the AVS volume 226 is filled when, for example, a pulsing pump pumps liquid downstream. The flow rate meter 221 may coordinate its operation with a pump, e.g., via wireless information received from the pump, such as a flow rate, pulse times, pulse durations, pulse volumes, pulse frequency, etc.

The speaker 227 emits one or more acoustic frequencies which are received by the reference microphone 223 and the variable volume microphone 226. The acoustic gain between the microphones 223 and 226 may be correlated with the volume of the variable volume 228 to determine the volume through the flow rate meter 221. Additionally or alternatively, the phase shift between the microphones 223 and 226 may be correlated with the volume of the variable volume 228. The speaker 227 and the microphones 223 and 226 may be in operative communication with one or more processors to implement an algorithm to determine the volume using AVS, e.g., the processor 37 of FIG. 2 or 3. Additional details related to the operation of AVS are described infra in the section entitled "ACOUSTIC VOLUME SENSING."

The films 231 and 233 define a fluid space 232. As the fluid varies within the AVS fluid volume 224 by entering and leaving via the fluid space 232, the difference in volume is calculated to determine the flow rate via the flow meter 221. That is, the variable volume 228 has an acoustic response that may be used to determine the AVS fluid volume 224. The flow meter 221 also includes ventilation paths 225 to prevent air from building up under the film 233 that defines the AVS fluid volume 224.

In yet an additional embodiment of the present disclosure, the flow rate meter 221 may be utilized as part of a membrane pump. For example, an actuator (not shown) may interface with the spring disk 229 (or the film 231) to providing a pumping action with the AVS fluid volume 224; the actuator may exists within the variable volume or may interface with the spring disk 229 via a shaft that transgresses through the upper clam shell assembly 192 (with an appropriate acoustic seal). The shaft's volume may be accounted for in the AVS measurement and/or the entire actuator may be in the variable volume.

Figure 71:
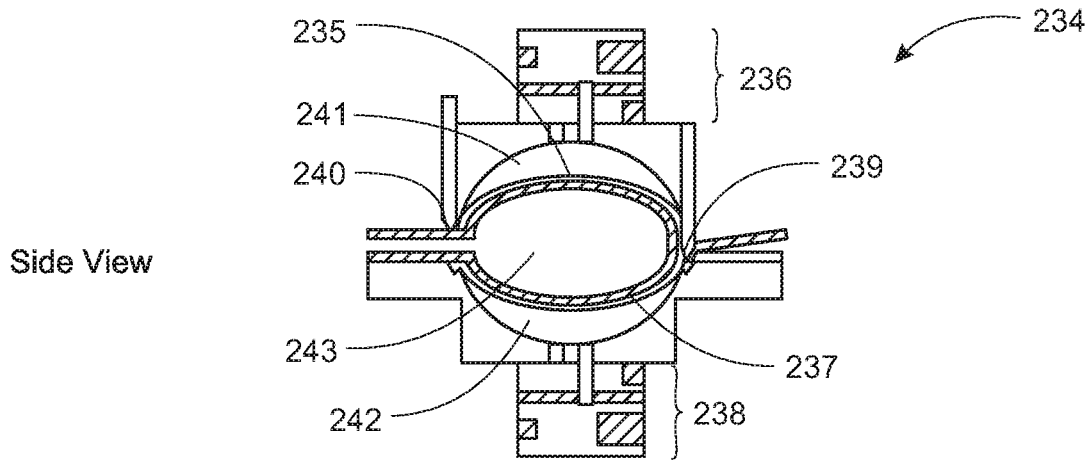
FIG. 71 shows a side view of flow rate meter including a double-sided AVS assembly with integral perimeter seal valves in accordance with an embodiment of the present disclosure.

FIG. 71 shows a side view of a flow rate meter 234 including a top AVS assembly 236 and bottom AVS assembly 238 with integral perimeter seal valves 239 and 340 in accordance with an embodiment of the present disclosure. The flow rate meter 234 may include the disposable portion 201 of FIGS. 63-65. The flow rate meter 234 may allow for flows of up to 0.25 cc per fill for up to 300 milliliters per hour, in some specific embodiments, e.g., 0.125 cc for each side for 150 millimeters per hour on each side.

The top AVS assembly 236 measures the acoustic response of the top variable volume 241 and the bottom AVS assembly 238 measures the acoustic response of the bottom variable volume 242. The measurements of the acoustic response of the top and bottom variable volumes 241 and 242 may be correlated to the top and bottom variable volumes 241 and 242. The volume of the AVS fluid chamber 243 may be estimated by subtracting a predetermined total volume from the volumes of the AVS chambers 241 and 242. A processor disclosed herein (e.g., processor 37 of FIG. 2 or 3) may estimate the volume of the AVS fluid chamber 243.

In yet an additional embodiment of the present disclosure, the flow rate meter 234 may be utilized as part of a membrane pump. For example, one or more actuator (not shown) may interface with the spring disks 235 and/or 237 (or the AVS fluid chamber 243) to provide a pumping action with the AVS fluid volume 243; the actuator may exists within the variable volumes 243 and/or 242 or may interface with the spring disks 235 and/or 237 via a shaft that transgresses through the AVS assemblies 236 and/or 238 (with an appropriate acoustic seal). The shaft's volume may be accounted for in the AVS measurement and/or the entire actuator may be in the variable volume.

Figure 72:
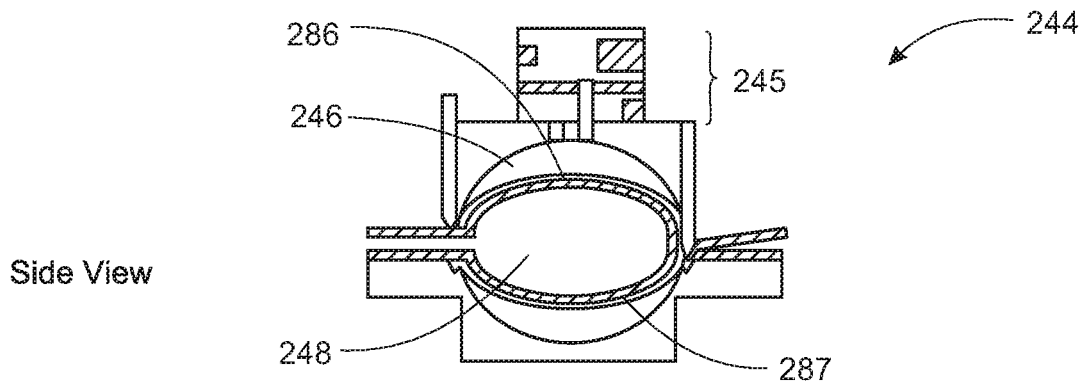
FIG. 72 shows a side view of another flow rate meter including a single-sided AVS assembly with surrounding AVS chambers in accordance with another embodiment of the present disclosure.

FIG. 72 shows a side view of another flow rate meter 244 including a single-sided AVS assembly 245 with surrounding variable volumes 246 and 247 in accordance with another embodiment of the present disclosure. The flow rate meter 244 may use the disposable portion 220 of FIG. 69. The variable volumes 246 and 247 may be in fluid communication with each other around the edges of the AVS fluid chamber 248. The AVS assembly 245 measures the acoustic response of the chambers 246 and 247 to correlate the volume of the AVS chambers 246 and 247. The total volume of the AVS chambers 246 and 247 is subtracted from the predetermined total volume to estimate the volume of the fluid within the AVS fluid volume 248.

In yet an additional embodiment of the present disclosure, the flow rate meter 244 may be utilized as part of a membrane pump. For example, one or more actuators (not shown) may interface with the spring disks 286 and/or 287 (or the AVS fluid chamber 248) to provide a pumping action with the AVS fluid volume 248; the actuator may exist within the variable volumes 246 and/or 247 or may interface with the spring disks 286 and/or 287 via a shaft that traverses through the AVS assembly 245 (with an appropriate acoustic seal). The shaft's volume may be accounted for in the AVS measurement and/or the entire actuator may be in the variable volume.

Figure 73:
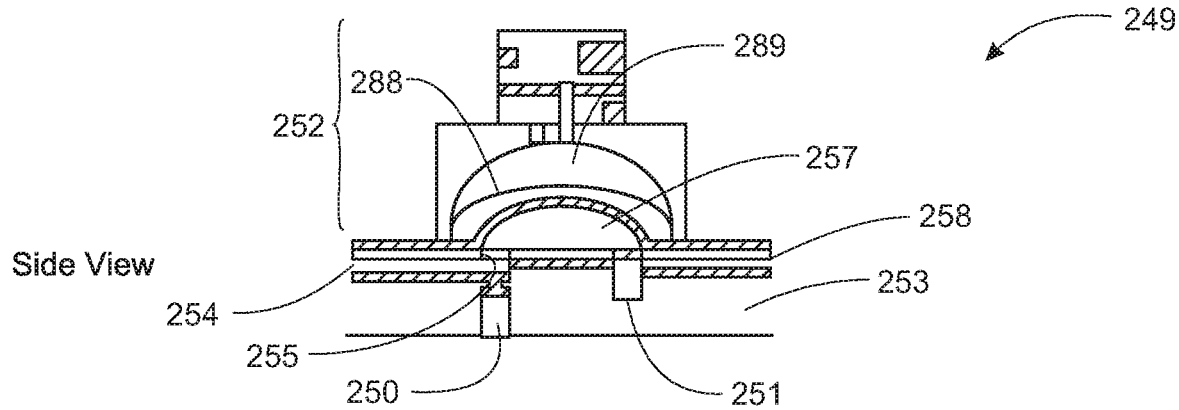
FIG. 73 shows a side view of yet another flow rate meter including two piston valves in accordance with another embodiment of the present disclosure.

FIG. 73 shows a side view of yet another flow rate meter 249 including two piston valves 250 and 251 in accordance with another embodiment of the present disclosure. The piston valves 250 and 251 may be coupled to actuators which are, in turn, coupled to a processor, e.g., the processor 37 of FIG. 2 or 3. The flow rate meter 249 includes a top AVS clam-shell assembly 252 and a bottom AVS claim-shell assembly 253. The fluid flows from the fluid track 254, through a hole 255 and into the AVS fluid chamber 256. Thereafter, the fluid can flow through the hole 257 (when the valve 251 is in the open state, through the fluid track 258) and finally out of the flow rate meter 249. The piston valves 250 and/or 251 may alternatively open and close such one of the piston valves is open while the other one is closed. The spring disk 229 may assist in the intake of the fluid or the expelling of the fluid out of the AVS fluid chamber 256.

In yet an additional embodiment of the present disclosure, the flow rate meter 249 may be utilized as part of a membrane pump. For example, one or more actuators (not shown) may interface with the spring disk 288 (or the AVS fluid chamber 257) to provide a pumping action with the AVS fluid volume 257; the actuator may exist within the variable volume 289 or may interface with the spring disk 289 via a shaft that transgresses through the AVS assembly 252 (with an appropriate acoustic seal). The shaft's volume may be accounted for in the AVS measurement and/or the entire actuator may be in the variable volume.

Figure 74:
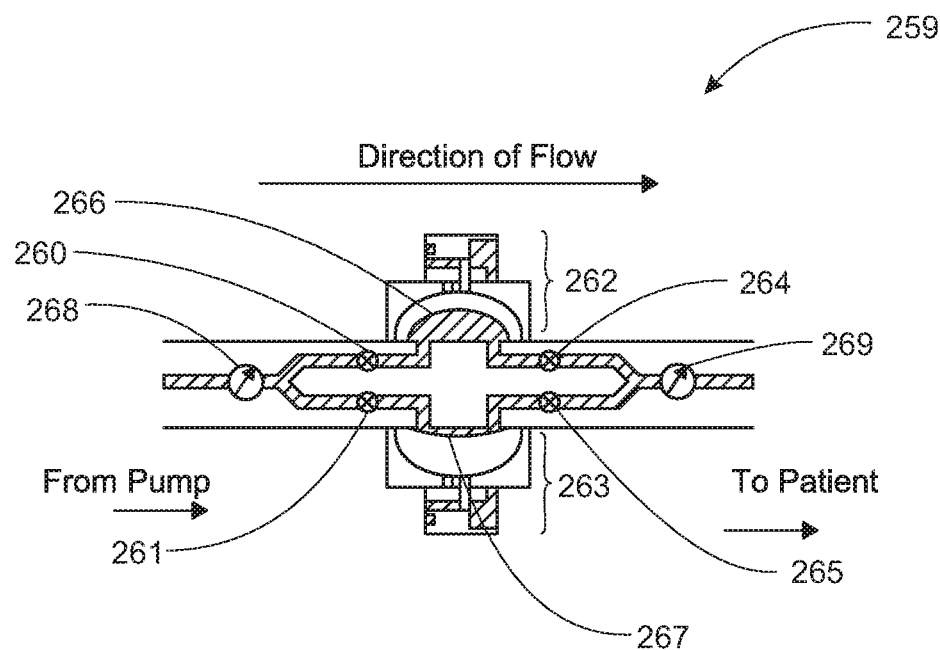
FIG. 74 shows a flow rate meter having top and bottom AVS assemblies which provide a semi-continuous flow in accordance with an embodiment of the present disclosure.

FIG. 74 shows a flow rate meter 259 having top and bottom AVS assemblies (262 and 263, respectively) which provide a semi-continuous flow in accordance with an embodiment of the present disclosure. The flow rate meter 259 includes valves 260, 261, 264, and 265. The valves 260, 261, 264, and 265 may operate together to fill an AVS fluid volume 266 and 267 in a sequential, but opposite, manner. For example, the valves 260, 261, 264, and 265 may operate to fill the AVS fluid volume 266 while discharging the other AVS fluid volume 267, and vice versa. That is, when an AVS fluid volume is being filled, the other AVS fluid volume may have an AVS measurement taken by the respective AVS assembly.

The flow rate meter 259 also includes a small reservoir 268 to buffer to fluid flowing from a pump and a variable occluder 269 that may be coupled to a processor. The variable occluder 269 may be varied such that the discharge of the AVS fluid volumes 266 and 267 are "smoothed" out to produce a semi-continuous flow to the patient (e.g., the AVS fluid volumes 266 and 267 may be spring loaded, such as with a disk spring, to force out the fluid). The processor may use the feedback from the AVS assemblies 262 and 263 to adjust the variable occlude 269 to achieve a target flow rate to a patient.

In one specific embodiment, the flow rate meter 259: measures flow over a range of 0.1 to 300 ml/hr; allows for non-metered flow rates of greater than 300 ml/hr to 2000 ml/hr; the flow resistance does not exceed 1 PSI across a flow range of 0.1 to 2000 ml/hr; the active volume accumulation does not exceed 2 millimeters; has a hold up volume of less than 0.5 ml; has a size of less than 1 inch, by 3 inches, by 1 inch for the disposable; may be battery or wired powered and may run at a rate of 100 ml/hr for 8 hours on the battery power; and may include a user interface that communicates with all of the valves, sensors, and component wirelessly.

Figure 75:
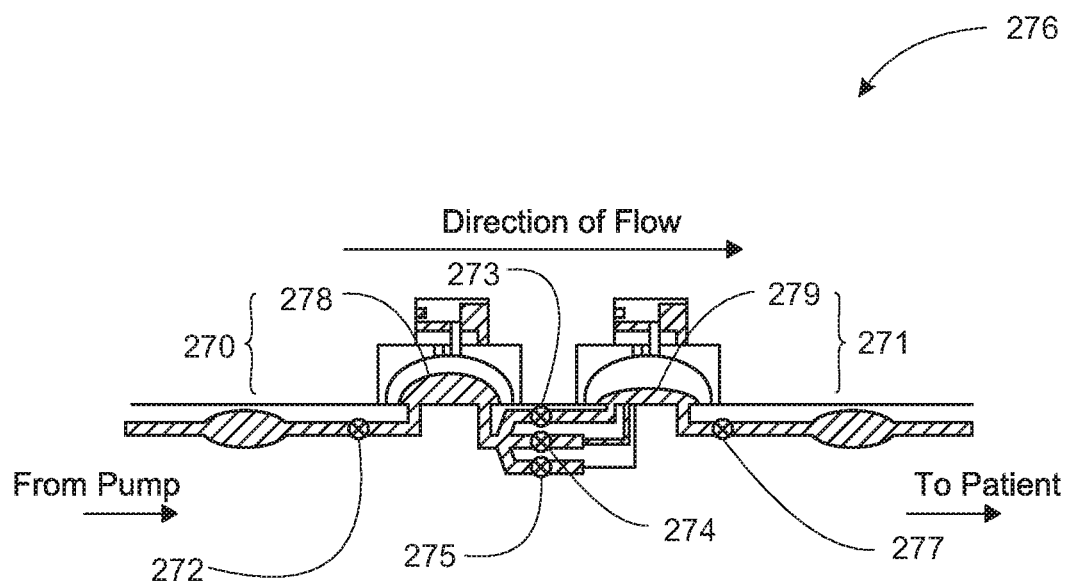
FIG. 75 shows a flow rate meter having two in-line AVS assemblies in accordance with an embodiment of the present disclosure.

FIG. 75 shows a flow rate meter 276 having two in-line AVS assemblies 270 and 271 with several valves 272, 273, 274, 275, and 277 to control to fluid flowing therethrough in accordance with an embodiment of the present disclosure. The valve 275 allows the least amount of fluid flow into the AVS volume 279 from the AVS volume 278, the valve 274 allows more fluid to flow into the AVS volume 279 from the AVS volume 278, and the valve 273 allow the most amount of fluid to flow into the AVS volume 279 from the AVS volume 278. The valves 273, 274, and 275 may be controlled to control the flow from the pump to the patient.

The two AVS assemblies 270 and 271 may each take measurements of the AVS fluid volumes 278 and 279, respectively. The AVS fluid volumes 278 and 279 may be different because of a pressure differences caused by the valves 273, 274, and 275 as the fluid flow from the pump to the patient. The continuous fluid flow causes a difference in pressure based upon the Bernoulli principle.

A continuous flow sensor may utilize the Bernoulli principle. For example, a fixed orifice or other restriction in a flow path of a fluid (e.g., one caused by an orifice plate) may be used to measure a pressure drop across the orifice to determine the flow rate based on the Bernoulli principle illustrated in Equation (33) as follows:

$$Q = C_d \sqrt{\frac{2\Delta p}{\rho}} \frac{A_2}{\sqrt{1 - \left(\frac{A_2}{A_1}\right)^2}}. \quad (33)$$

Where Q is the volumetric flow rate, $C_d$ is the discharge coefficient which relates to turbulence of flow, p is the density of the fluid, $A_1$ is the cross-sectional area just in front of the restriction, $A_2$ is the cross-sectional area of the restriction, and $\Delta p$ is the pressure drop across the restriction. Equation (33) may be simplified to Equation (34) as follows:

$$Q = C_f A_0 \sqrt{\frac{2\Delta p}{\rho}}. \quad (34)$$

Ao is the area of the orifice, and $C_f$ is a constant related to the turbulence and flow geometry specific to the restrictor design ($C_f$ typically has a value between 0.6 and 0.9 that is derived empirically). Therefore, the estimated flow rate is related to the area of the orifice and the square root of the measured pressure drop. The estimated flow rate is also related to the density of the fluid being measured and the orifice geometry.

Therefore, the valves 273, 274, and 275 of the flow meter 276 may be considered a restrictor (e.g., serving as an orifice plate in a continuous flow rate meter) to produce a measurable pressure difference between the AVS volumes 278 and 279. The AVS volumes 278 and 279 may be correlated with respective pressures because the respective membranes forming the AVS chambers 278 and 279 will stretch based upon the pressure therein.

For example, the valves 272 and 277 may be opened thereby allowing fluid to continuously flow from the pump to the patient. The AVS volumes 278 and 279 will have a difference in pressure caused by the total restriction from one or more of the valves 273, 274, and 275 (which may, in some embodiments, be modeled as an orifice).

The differential AVS volume measurements between the AVS chambers 278 and 279 are proportional to flow rate (the pressure difference may be correlated with flow rate empirically). Any common-mode, down-stream pressure change would result in a volume increase in both of the AVS chambers 278 and 279 thereby subtracting out the increase in the AVS chambers 278 and 279. Additionally, a predetermined positive change in the AVS volume measurements may be considered an indication of an occlusion, and a predetermined change in the flow rate may trigger an alarm and/or alert.

The valves 273, 274, and 275 allow a range of flow rates from the pump to the patient to be used and also change the measurement range of the flow rate meter 276. A processor can actuate one or more valves 273, 274, and 275 and can determine the total restriction of occlusion caused by the valves 273, 274, and 275. That is, the configuration of the valves 273, 274, and 275 may be correlated with a model, e.g., a cross-sectional area of a restriction using Equation (33) or (34), for determining the flow rate. The processor may vary the valves 273, 274, and 275 to determine the flow rate within a desired measurement flow rate range.

The AVS assemblies 270 and 271 perform a measurement within a predetermined amount of time by sweeping acoustic frequencies (as described herein), e.g., for one-half a second or 1/20 of a second. In some embodiments, the AVS assemblies 270 and 271 may perform two types of frequency sweeps, e.g., a shorter frequency sweep (e.g., performed in less time) and/or a full frequency sweep, e.g., to do other error checking such as, for example, to check for acoustic leak(s). The flow rate meter 276 may, in some embodiments, coordinate with a pump to introduce a periodic disturbance to calibrate the flow meter 276 and/or for error checking. Additionally or alternatively, small reservoirs 400 and 401 may provide fluid dampening to "smooth" the flow in some embodiments. The fluid reservoirs 400 and 401 may be formed from an elastic material that defines a bubble-type flexible bladder.

The valves 272 and 277 may have their operation coordinated to check for error conditions. For example, the valve 272 may be closed while the valve 277 remains open to determine if the fluid is being discharged to the patient for error checking (e.g., to check for occlusions, etc.).

In some embodiments, the valves 272, 273, 274, 275, and 277 are used so that the AVS volumes 278 and 279 are operated such that one of the AVS volumes is filled with a liquid while the other AVS volume is discharges the liquid thereby providing a piece-wise continuous flow measurements using the AVS volumes 278 and 270. Additionally or alternatively, the valves 272, 273, 274, 275, and 277 may also be used to do a "flow to zero" test to do a "flow zero" correction (e.g. correct for volume drift of the AVS volume measurements).

In one specific embodiment, the flow rate meter 276: may measure continuous flow over a range of 0.1 to 300 ml/hr (in some embodiments up to 2000 ml/hr); has an accuracy of measurement of +/−0.02 ml/hr from 0.1 to 2.5 ml/hr, or 5% otherwise; measures fast enough to be insensitive to flow disturbances of a 10% change in flow in 1 second; measures with head height pressure changes of +/−2 PSI; does not add flow resistance exceeding 1 PSI across a flow range of 0.1 to 2000 ml/hr; has a size of less than 1 inch, by 3 inches, by 1 inch for the disposable; may be battery or wired powered and may run at a rate of 100 ml/hr for 8 hours on battery power; and may include a user interface that communicates with all of the valves, sensors, and components wirelessly.

Figure 76:
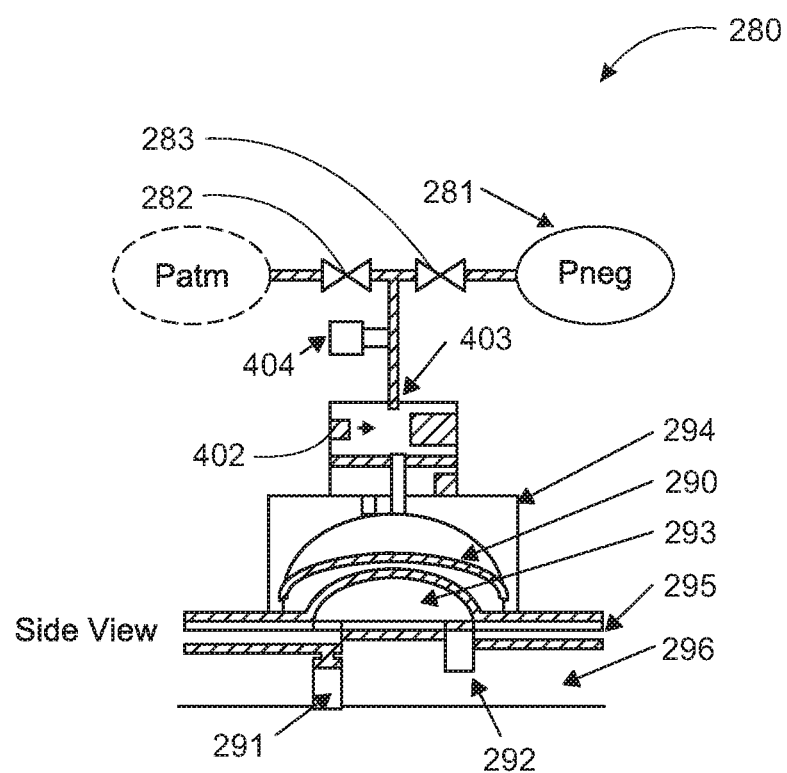
FIG. 76 shows a membrane pump having a negative pressure source in accordance with an embodiment of the present disclosure.

FIG. 76 shows a membrane pump 280 having a negative pressure source 281 in accordance with an embodiment of the present disclosure. The membrane pump 280 includes valves 282 and 283 that can alternate between applying a negative pressure to the variable volume 290 and apply atmospheric pressure to the variable volume 290. The valves 282 and 283 are fluidly connected to the AVS reference volume 402 via a port 403 that is of a sufficiently small size that does not introduce acoustic artifacts, e.g., 0.020 inches in some specific embodiments. A processor, e.g., processor 37 of FIG. 3, may control the valves 282 and/or 283 to achieve a target pressure within the reference volume 402 as measured by a pressure sensor 404. The processor, e.g., processor 37 of FIG. 37 of FIG. 3, may be in operative communication with the valves 282 and 283, and with the pressure sensor 404.

The valve 282 may be closed and the valve 283 may be opened thereby putting the variable volume 290 in fluid communication with the negative pressure source 281. Thereafter, the valve 283 may be closed and the valves 282 opened to put the variable volume 2190 in fluid communication with atmospheric air. This may be continually repeated to repeatedly oscillate the pressure within the variable volume 290. In some specific embodiments AVS measurements are made when the variable volume 402 is placed in a static pressure state (e.g., set to ambient pressure, the static negative pressure, or by closing the valves 282 and 283), and the AVS fluid volume 293 is placed in a static pressure state (e.g., the piston valves 291 and 292 are closed).

As previously mentioned, a negative source 281 may be applied to the variable volume 290 by opening the valve 283 and closing the valve 282. When the negative pressure is applied to the variable volume 290, the piston valve 291 may be opened and the piston valve 292 closed to draw fluid into the AVS fluid volume 293. Thereafter, the valve 283 and the piston valve 291 are closed so that an AVS measurement may be taken by the AVS assembly 249 (the AVS assembly 294 includes a lower AVS clam-shell assembly 296). Optionally, the piston valves 291 and 292 may be closed prior to or during the AVS measurement. Thereafter, the valve 282 and the piston valve 292 are opened to allow fluid to flow into the fluid channel 295 from the AVS chamber 293. Next, the piston valve 292 and the valve 282 are closed, and another AVS measurement is taken from the AVS chamber 293. The difference in these AVS measurements may be correlated to the amount of fluid pumped for each respective pumping cycle. That is, each pulse of liquid to the patient may be estimated by subtracting one AVS measurement from another AVS measurement. In some specific embodiments the AVS measurements are each taken at the same pressures of the AVS volume 290 (e.g., at atmospheric pressure or a static negative pressure, as may be determined by the pressure sensor 404) to account for the effects of positive and negative pressures on air-bubble volume thereby mitigating the effect that an air bubble has on the fluid volume flow measurements.

Figure 77:
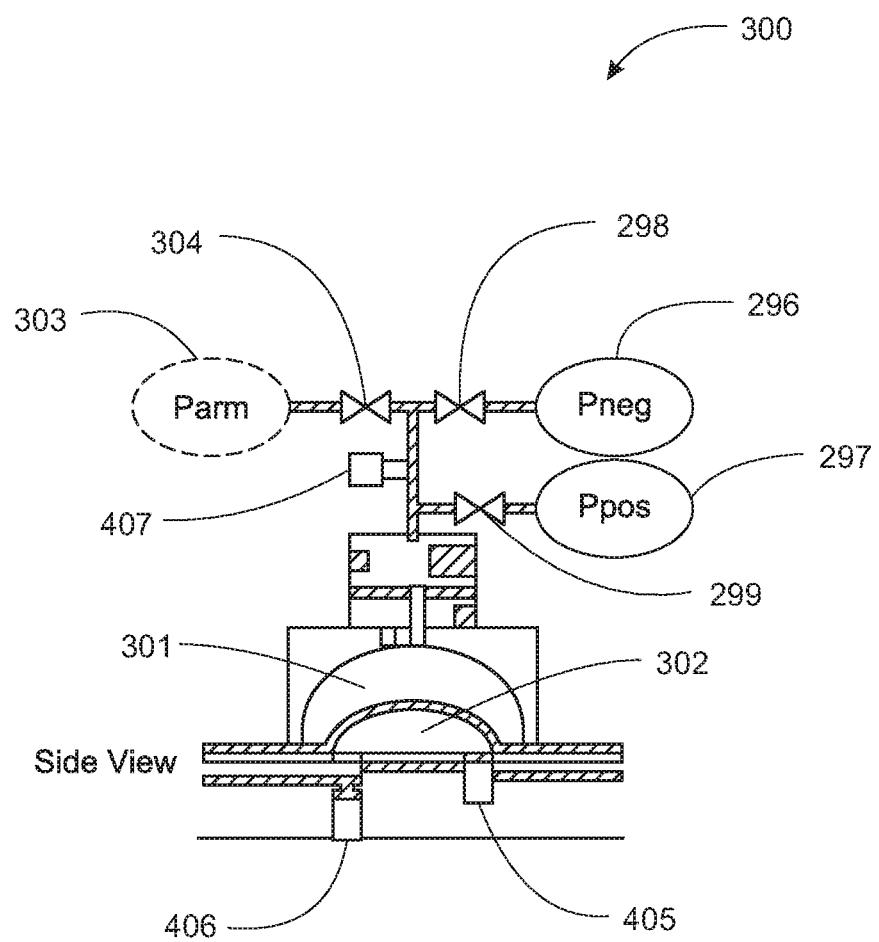
FIG. 77 shows a membrane pump having negative and positive pressure sources in accordance with an embodiment of the present disclosure.

FIG. 77 shows a membrane pump 300 having a negative-pressure source 296 and a positive-pressure source 297 coupled to valves 298 and 299, respectively, in accordance with an embodiment of the present disclosure. The negative-pressure source 296 may be in fluid communication with the variable volume 301 when drawing fluid into the AVS chamber 302. Likewise, the positive-pressure source 297 may be in fluid communication with the variable volume 301 when discharging fluid out of the AVS chamber 302. The variable volume may be coupled to atmospheric pressure 303 via a valve 304 when an AVS measurement is taken.

Note that no disk spring is used in the embodiment shown in FIG. 77. The AVS fluid volume 302 is formed by a flaccid material that generates little or no pressure within the variable volume 301. In some embodiments of the present disclosure, the pump 300 takes AVS measurements all at the same pressure to account for the pressure effects on bubble size; for example: the AVS volume measurement may be taken as follows: (1) close the piston valve 405, open the piston valve 406, open the valve 298, close the valve 299, and close the valve 304 thereby causing fluid to be drawn into the AVS chamber 302 with the negative pressure from the negative-pressure source 296; (2) close the piston valve 406 and close the valve 298; (3) open the valve 304 thereby causing the pressure of the variable volume 301 to reach atmospheric pressure 303; (4) close the valve 304; (5) take an AVS measurement; (6), open the valve 299 and open the piston valve 405 thereby discharging the fluid out of the AVS volume 302; (7) close the piston valve 405 and close the valve 299; (8) open the valve 304 to equalize the variable volume pressure to atmosphere 303; (9) close the valve 304; (10) take an AVS measurement; (11) and compare the AVS volumes measurements to determine the volume discharged, e.g., to estimate flow rate. The previous example may be modified to take one or more AVS measurements in positive pressure, negative pressure, atmospheric pressure, or in some combination thereof.

In yet an additional embodiment, the positive pressure source 297 is used to take AVS measurements when the variable volume 301 is under a positive pressure. For example, in some embodiments of the present disclosure, the pump 300 takes AVS measurements all at a positive pressure to account for the pressure effects on bubble size; for example: the AVS volume measurement may be taken as follows: (1) close the piston valve 405, open the piston valve 406, open the valve 298, close the valve 299, and close the valve 304 thereby causing fluid to be drawn into the AVS chamber 302 with the negative pressure from the negative-pressure source 296; (2) close the piston valve 406 and close the valve 298; (3) open the valve 299 thereby causing the pressure of the variable volume 301 to reach a predetermined positive pressure as indicated by the pressure sensor 407; (4) close the valve 299; (5) take an AVS measurement; (6) open the valve 304 and open the piston valve 405 thereby discharging the fluid out of the AVS volume 302; (7) close the piston valve 405 and close the valve 304; (8) open the valve 299 thereby causing the pressure of the variable volume 301 to reach a predetermined positive pressure as indicated by the pressure sensor 407; (9) close the valve 299; (10) take an AVS measurement; (11) and compare the AVS volumes measurements to determine the volume discharged, e.g., to estimate flow rate. The previous example may be modified to take one or more AVS measurements in positive pressure, negative pressure, atmospheric pressure, or some combination thereof.

The pump 300 may also, in some embodiments, determine if there is compliance in the system, such as compliance caused by air, by taking AVS volume measurements at two different pressures. For example, two AVS measurements may be taken during the fill phase at two different pressures (e.g., negative pressure and ambient pressure, or some other combination) and/or during the discharge phase at two difference pressures (e.g., negative pressure and ambient pressure, or some other combination). The change in volume at the two pressures may be correlated with compliance of the AVS volume 302, such as if there was an air bubble in the fluid. If a predetermined amount of AVS volume 302 variation is determined to exists, a processor may determine an error condition exists and issue an alarm or alert. In yet another embodiment, the flow rate measurement may be corrected for the air volume measurement taken; For example, a processor may determine the volume of air that was delivered to the patient instead of a drug, such as insulin, and compensate the delivery of the insulin to ensure that the prescribed does of insulin is delivered. For example, consider the following additional embodiments.

In some embodiments of the present disclosure, compliance may be estimated in the pump 300 by taking at least two AVS measurements at different pressures to account for air bubbles; for example: the AVS volume measurements may be taken as follows: (1) close the piston valve 405, open the piston valve 406, open the valve 298, close the valve 299, and close the valve 304 thereby causing fluid to be drawn into the AVS chamber 302 with the negative pressure from the negative-pressure source 296; (2) close the piston valve 406 and close the valve 298; (3) take an AVS measurement while the reference volume 301 remains under negative pressure; (3) open the valve 304 thereby causing the pressure of the variable volume 301 to reach atmospheric pressure 303; (4) close the valve 304; (5) take an AVS measurement while the reference volume 301 remains at atmospheric pressure; (6) compare the two AVS measurements from (3) and (5) to determine compliance of the AVS volume 302; (7) open the valve 299 and open the piston valve 405 thereby discharging the fluid out of the AVS volume 302; (8) close the piston valve 405 and close the valve 299; (9) take an AVS measurement while the variable volume 301 remains under positive pressure; (10) open the valve 304 to equalize the variable volume pressure to atmosphere 303; (11) close the valve 304; (12) take an AVS measurement while the variable volume 302 remains under atmospheric pressure; (13) compare the two AVS measurements from (9) and (12) to determine compliance of the AVS volume 302; (14) and compare at least two AVS volume measurements to determine the volume discharged, e.g., to estimate flow rate. The above example may be modified in various ways such that the two AVS measurements having two different pressures and may occur during the filling stage, the discharging stage, any other stage of the pumping, using one or more of a positive pressure measurement, a negative pressure measurement, an atmospheric pressure measurement, or some combination thereof.

Consider yet another embodiment: the AVS volume measurement and pumping action may occur as follows: (1) close the piston valve 405, open the piston valve 406, open the valve 298, close the valve 299, and close the valve 304 thereby causing fluid to be drawn into the AVS chamber 302 with the negative pressure from the negative-pressure source 296; (2) close the piston valve 406 and close the valve 299; (3) take an AVS measurement when the variable volume 301 remains at a negative pressure; (4) open the valve 299 thereby causing the pressure of the variable volume 301 to reach a predetermined positive pressure as indicated by the pressure sensor 407; (5) close the valve 299; (6) take an AVS measurement when the variable volume 301 is at a positive pressure; (7) compare the two AVS measurement from (3) and (6) to determine compliance of the AVS volume 302; (8) open the valve 304 and open the piston valve 405 thereby discharging the fluid out of the AVS volume 302; (9) close the piston valve 405 and close the valve 304; (10) take an AVS measurement while the variable volume 301 is at an atmospheric pressure (in another embodiment, the AVS volume measurement is taken at a negative pressure); (11) open the valve 299 thereby causing the pressure of the variable volume 301 to reach a predetermined positive pressure as indicated by the pressure sensor 407; (12) close the valve 299; (13) take an AVS measurement; (14) and compare at two AVS volume measurements to determine the volume discharged and/or the compliance of the variable volume, e.g., to estimate flow rate. The above example may be modified in various ways such that the two AVS measurements having two different pressures may occur during the filling stage, the discharging stage, any other stage of the pumping, using one or more of a positive pressure measurement, a negative pressure measurement, an atmospheric pressure measurement, or some combination thereof.

In one specific embodiment, the membrane pump 300: has a flow rate target of 0.1 to 2000 ml/hr; can generate at least a maximum of 3 PSI and up to 10 PSI; can draw fluid from a reservoir of a maximum of negative pressure of at least −2 PSI; may be battery powered; may be powered by a cable; and may have a user interface that wirelessly communicates with a processor coupled to all actuators, valves, pressure sensors, and other devices.

Figure 78:
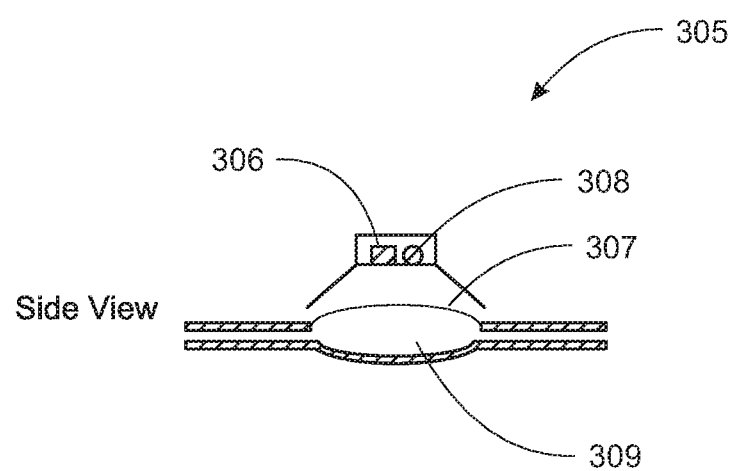
FIG. 78 shows a optical-sensor based flow rate meter in accordance with an embodiment of the present disclosure.

FIG. 78 shows an optical-sensor based flow rate meter 305 in accordance with an embodiment of the present disclosure. The flow rate meter 305 includes an IR source 306 that reflects light off a flexible membrane 307. The reflected IR light is received by a sensor 308. The sensor formed by the IR source 306 and the IR sensor 308 may be a sensor with the part number: GP2S60 manufactured by Sharp Corporation. The light reflected off of the membrane 307 may be correlated to a volume 309. With an upstream or downstream pump (not shown) used in conjunction with input and outlet valves (not shown) the flow rate me be calculated by measuring the light as it reflects off the membrane 307. Since a change in fluid pressure in the tube results in a displacement of the elastomer membrane 309, the distance between the sensor 308 varies as a function of the pressure in the fluid tube; therefore the output of the sensor is proportional to the pressure in the fluid tube and may be correlated with pressure and/or volume.

The flow rate meter 305 may be used by a membrane pump disclosed herein to facilitate positive and/or negative pressure measurements. The pressure sensitivity may be tuned by selecting the elastomeric properties of the membrane and the area of fluid contact with the membrane forming the AVS volume 309. The reflective property of the elastomeric membrane may be enhanced with metal, plastic, film, or other reflective material. A temperature sensor may be added to account for the thermal effects of the material that forms the AVS volume 309. A heat sink and/or thermal controller around the elastomer AVS chamber 309 may be used to mitigate thermal effects, in some specific embodiments.

The IR source 306 may be pulsed and/or multiplexing may be used with multiple IR sources 306 and multiple sensors 307 to inhibit cross-talk error. An initial reading may be used as an offset null, and the change in sensor output may be correlated with changes in pressure in the AVS volume 308. Focusing optics may be used with the disposable portion, e.g., the membranes, to facilitate the ranging and aligning of the IR source 306 and the IR sensor 308. In alternative embodiments, an ultrasonic proximity sensor is used instead of the IR source 306 and the IR sensor 308.

In one specific embodiment, the flow rate meter 305 may: have a sensitivity to tube pressure over a range of −2 to +10 PSI; may measure a tube pressure to within +/−20% over a range of 1 to 10 PSI; have a resolution of at least 10 bits; and may be low power.

Figure 79:
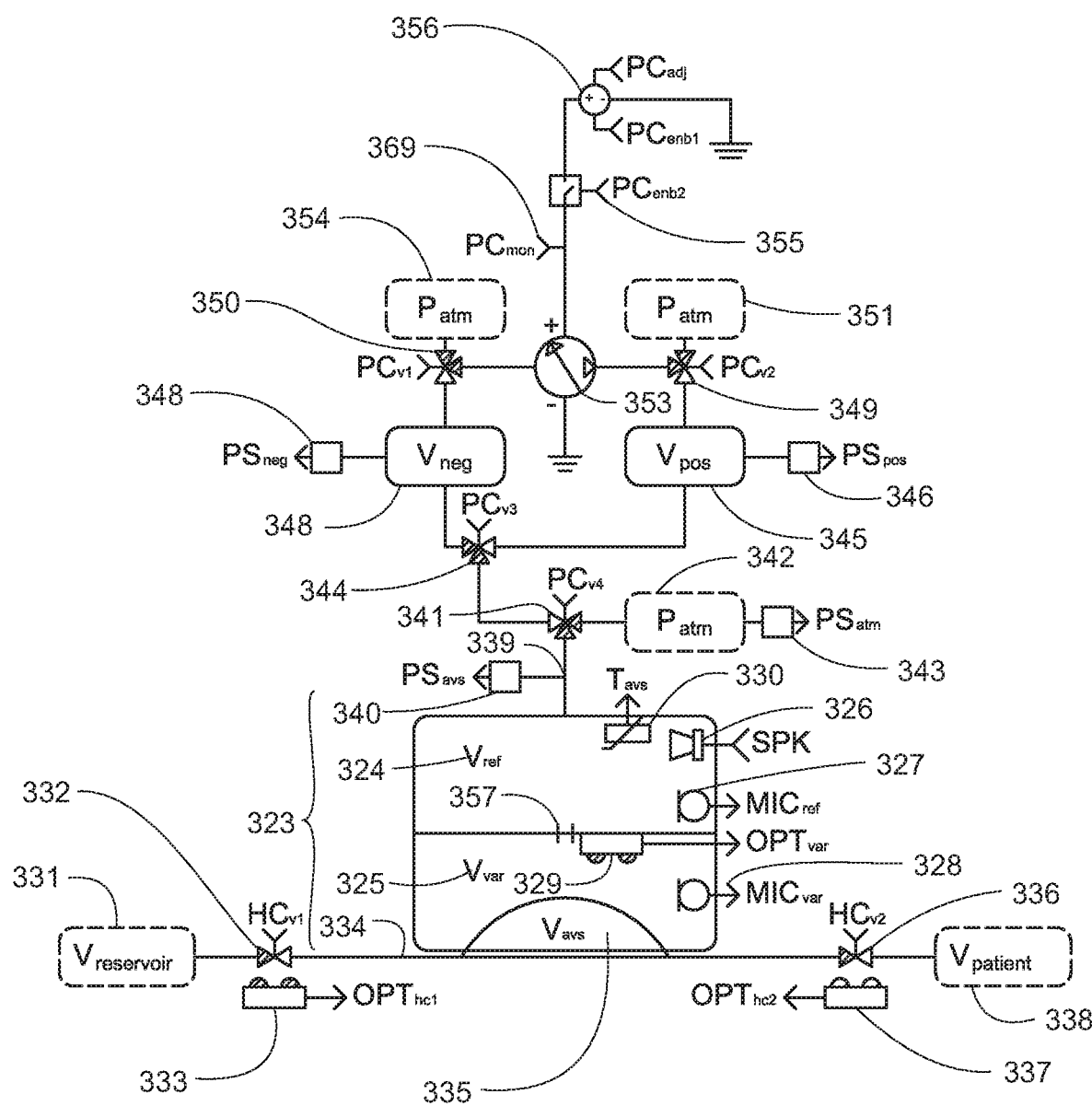
FIG. 79 shows a pressure-controlled membrane pump in accordance with an embodiment of the present disclosure.

FIG. 79 shows a pressure-controlled membrane pump 322 in accordance with an embodiment of the present disclosure. FIGS. 80-82 show a legend for reference herein; that is, refer to FIG. 80-82 for the legend of symbols for FIGS. 83, 85, 87, 88, 90, 91, 93, 95, and 97. Referring again to FIG. 79, the membrane pump 322 includes an AVS assembly 323 having a reference volume 324 and a variable volume 325. The reference volume 324 includes a speaker 326 for generating an acoustic signal in the reference chamber 324 which travels through a port 357 to the variable volume 325. The acoustic signal is received by a reference microphone 327 and a variable-volume microphone 328. The signals from the microphones 327 and 328 are compared to determine an acoustic response to measure the volume of the AVS chamber 335. An optional optical sensor 329 may be used to reflect light off of a membrane forming the AVS chamber 335. The optical sensor 329 may be used to facilitate the estimation of the volume of the AVS chamber 335. In some embodiments multiple optical sensors 329 may be used.

The pump 353 may be a diaphragm pump, such as one having the part number: T3CP-1HE-06-1SNB, manufactured by Parker Hannifin Corporation located at 6035 Parkland Boulevard, Cleveland, Ohio 44124-4141; additionally or alternatively, other pump types and/or pumps manufactured by any other manufacturer may be utilized.

A variable voltage applied to the pump 353 (see FIG. 79) may be adjusted in real time to reach a desired pressure as measured by the pressure sensor 340. The pump 353 can have a flow rate of several liters per minute. The variable volume 325 may have an air volume of 0.5 cc, and may be pressure limited to between 1-10 PSI. In some embodiments, the pump 353 has a fill and empty cycle time of 1 Hz and a fluid chamber of 0.5 cc resulting in a max flow rate of 1800 cc/hr, for example. In additional embodiments, variable pressure may be controlled in bursts that last in the tens of milliseconds and six aliquots may be delivered over an hour interval to achieve a flow rate of 0.1 cc/hr. In additional embodiments, an alternative pneumatic flow path (not shown) having a pneumatic flow restriction may be used to lower the working pressure on the variable volume 324 thereby facilitating low and high volumetric flow ranges.

A fluid reservoir 331 is coupled through a fluid path to a one-way valve 332. The valve 332 may be a pinch valve. An optical sensor 333 measures when the valve is closed, e.g., an optical beam may be broken when the pinch valve 332 is open or the optical beam is broken when the pinch valve 332 is closed.

The fluid travels into the AVS volume 335 through a fluid tube 334. The fluid may be discharged through a fluid path to a one-way valve 336 that is also measured using an optical sensor 337. Finally, the fluid enters into a patient 338.

The reference chamber 324 and the variable volume chamber 325 are in fluid communication with a tube 339. A pressure sensor 340 measures the pressure of the tube and hence the chambers 324 and 325. Additionally or alternatively, the pump 322 includes a temperature sensor 330. The pressure from the pressure sensor 340 and/or the temperature from the temperature sensor 330 may be used for to increase the accuracy of AVS measurements.

The valve 341 connects the tube 339 to the ambient pressure 342. A pressure sensor 343 measures ambient pressure. The valve 341 is also coupled to a valve 344 which, in turn, is connected to a negative pressure source 347 and a positive pressure source 345. The positive pressure source 345 is coupled to a pressure sensor 346, and the negative pressure source 347 is coupled to another pressure sensor 348. In some specific embodiments, the positive pressure source 345 and negative pressure source 347 may be accumulators where predetermined pressures are set therein and vented into the reference volume 324 (via the valves 344, 341, 350, and 349) to develop specific pressures.

A variable flow/pressure pump 353 is coupled to both of the valves 349 and 350 to keep the positive pressure reservoir 345 at a positive pressure and the negative pressure reservoir 347 at a sufficiently lower pressure. The valves 350 and 349 are also coupled to atmospheric vents 354 and 351, respectively. The variable flow/pressure pump 353 is fed a signal at 356, which may be fed back to an output pin for verification by a processor, e.g., processor 37 of FIG. 2. Also, a switch 355 may enable and/or disable the pump 353.

In some embodiments, the one or more optical sensors 329 may be used as part of an inner portion of a control loop that has a target aliquot volume to deliver. For example, the one or more optical sensors 320 may provide a controller within the processor 37 of FIG. 2 (e.g., a PID controller) with an estimate of fill or discharge volume based on the deflection of the AVS chamber's 335 membrane as measured by the one or more optical sensors 329. The feedback from the one or more optical sensors 329 may be used to control the pressure flow or the timing of the pneumatics in the AVS pump chamber, e.g., the valves 231, 344, 349, and 350.

Multiple optical sensors 329 may be used to triangulate the AVS chamber's 335 membrane position; additionally or alternatively, the membrane may have reflective features disposed surface of the membrane of the AVS chamber 335 to provide a reflective surface for the optical sensors 329. In some specific embodiments, an outer portion of the control loop can target the trajectory delivery volume delivered to the patient to tune the individual aliquot volume. For example, the optical volume sensing functionality performed by the one or more optical sensors 329 may provide an independent volume measurement that is used as a check on the AVS-based volume measurements and/or to calculate errors in volume estimation. In additional embodiments, only optical volume measurements are performed, i.e., in this specific exemplary embodiment, no AVS is used).

Figure 83:
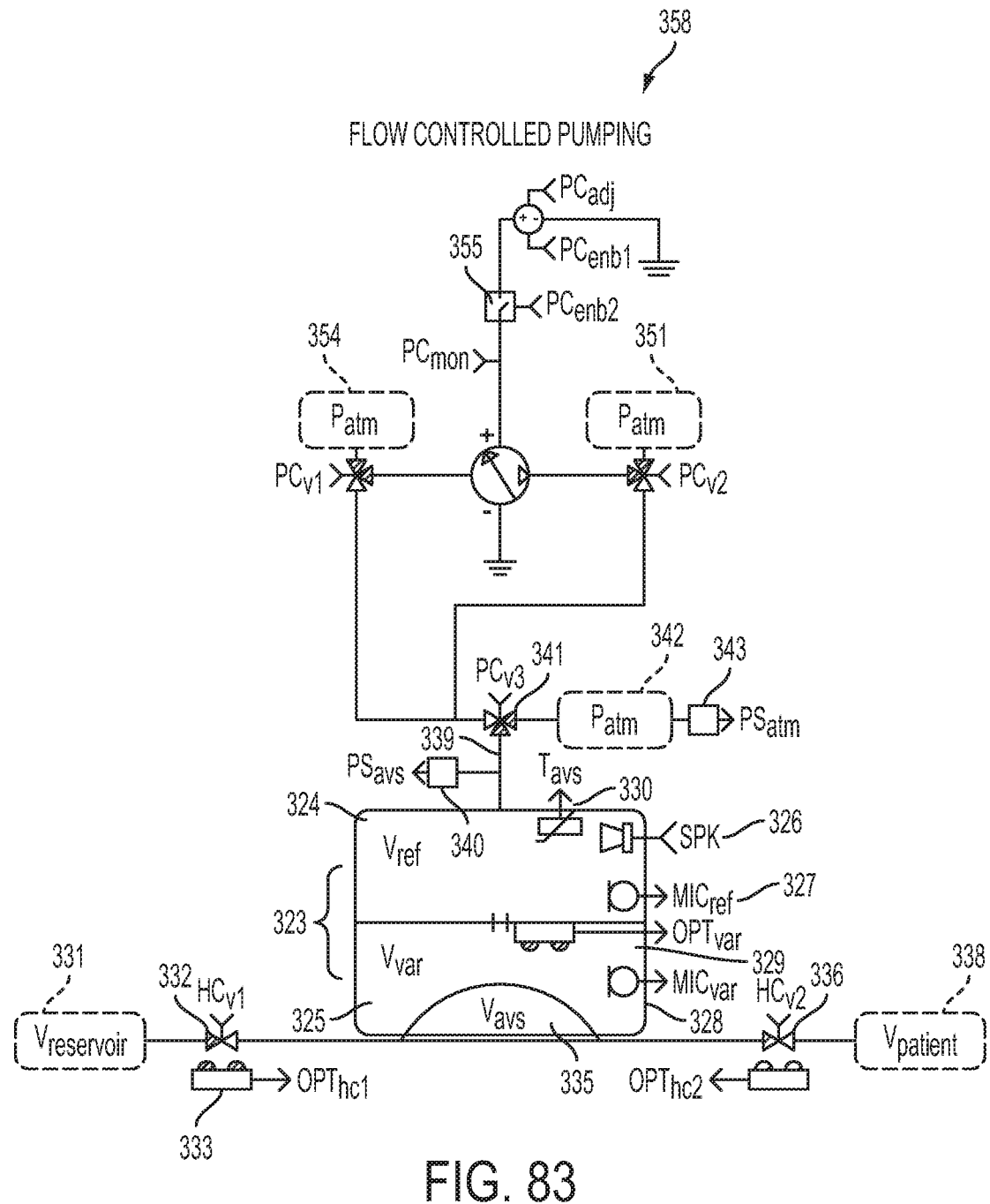
FIG. 83 shows a flow-controlled membrane pump in accordance with an embodiment of the present disclosure.

FIG. 83 shows a flow-controlled membrane pump 358 in accordance with an embodiment of the present disclosure. The flow-controlled membrane pump 358 is similar to the pressure controlled pump 322 of FIG. 79; however, the flow-controlled membrane pump 358 does not have the reservoirs 345 and 347 as shown in FIG. 79.

Figure 84:
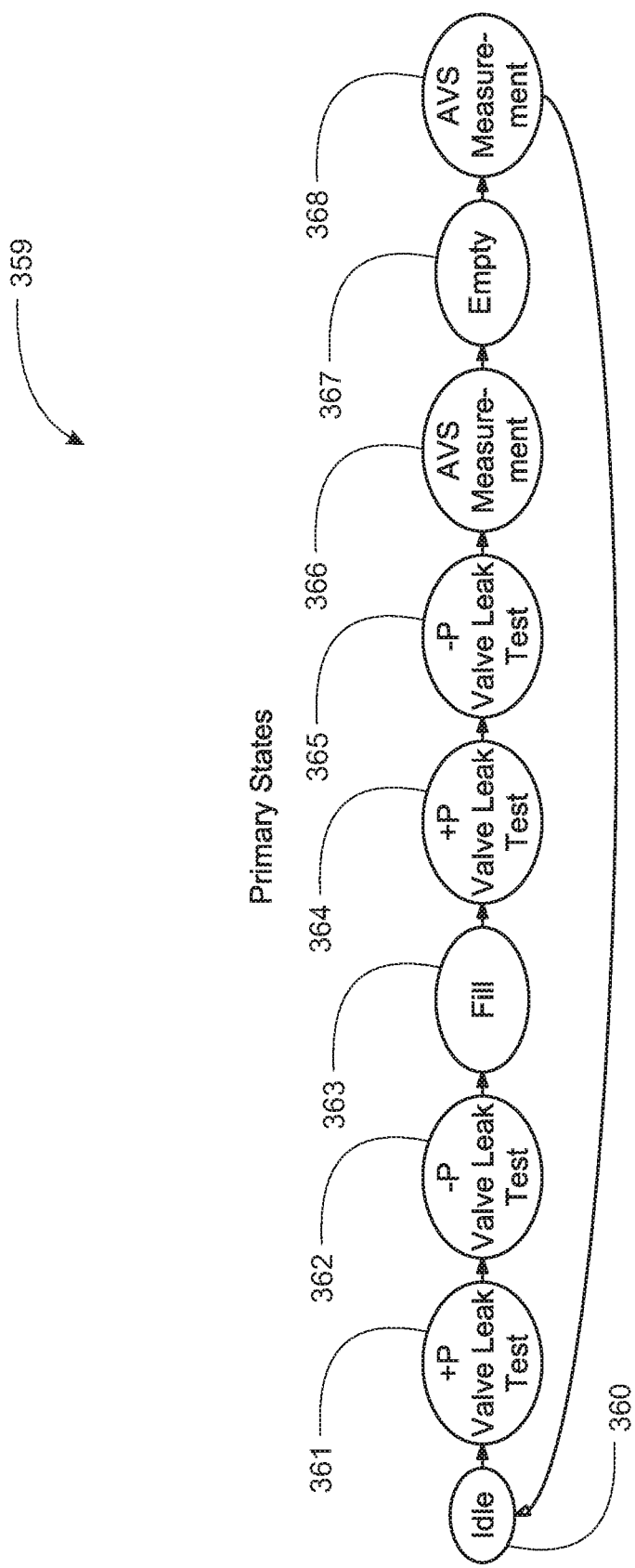
FIG. 84 shows a state diagram of the operation of the flow-controlled membrane pump of FIG. 83 in accordance with an embodiment of the present disclosure.

FIG. 84 shows a state diagram 359 of the operation of the flow-controlled membrane pump 358 of FIG. 83 in accordance with an embodiment of the present disclosure. The state diagram 359 includes states 360-368. The states 360-368 are illustrated by FIGS. 85-98.

Figure 85:
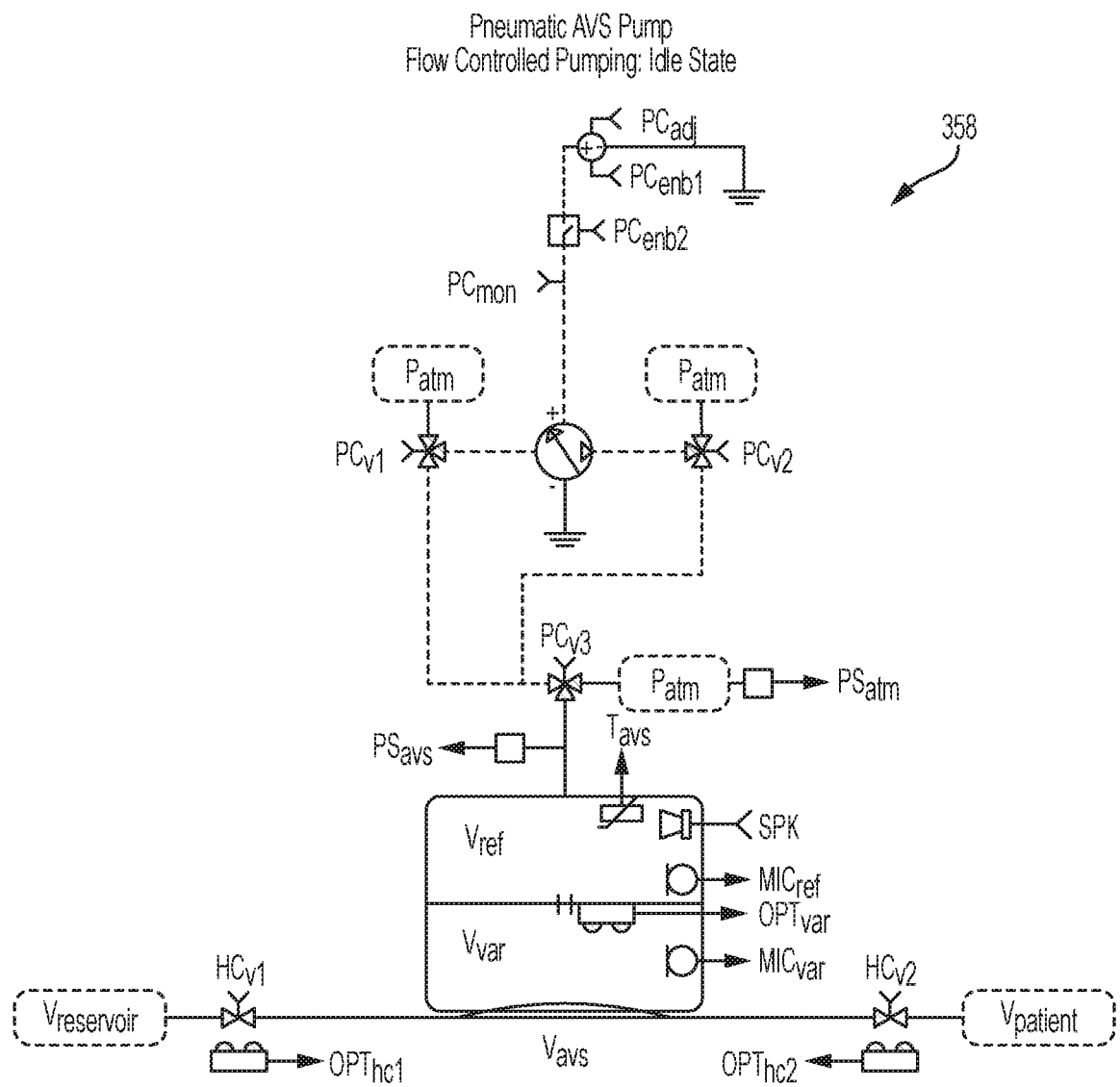
FIG. 85 shows the flow-controlled membrane pump of FIG. 83 illustrating the operation of the valves when in the Idle state of the state diagram of FIG. 84 in accordance with an embodiment of the present disclosure.
Figure 86:
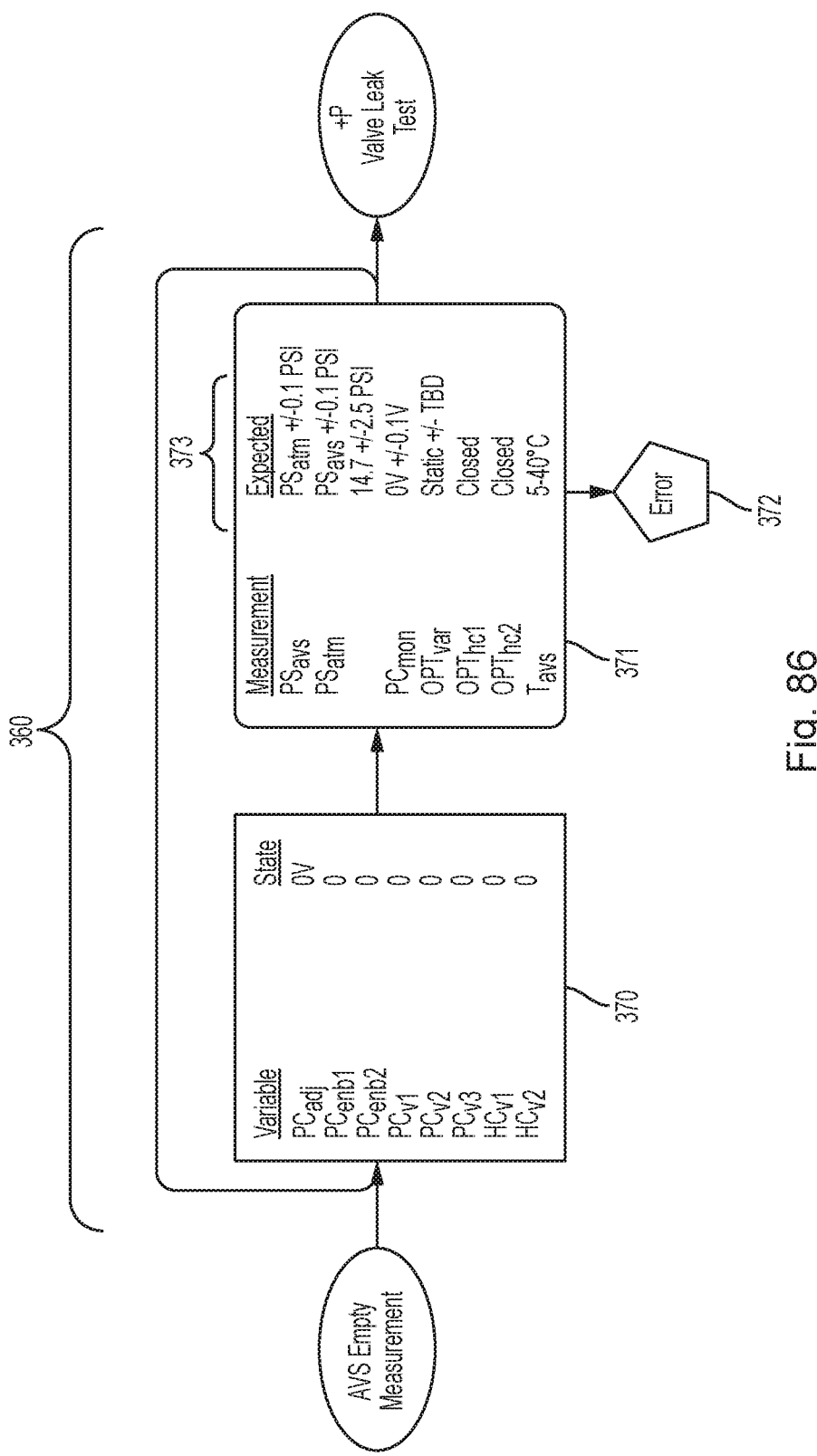
FIG. 86 shows a more detailed view of the idle state of the state diagram of FIG. 84 in accordance with an embodiment of the present disclosure.

Referring now to FIGS. 84, 85, and 86, an idle state 360 is depicted in FIGS. 84 and 86 with FIG. 86 showing more details. The idle state 360 includes substates 370-371. In substate 370, several variables are set. After a predetermined amount of time after substate 370 sets the variables, the substate 371 measures several values which are checked against predetermined ranges.

FIG. 85 shows the flow-controlled membrane pump 358 of FIG. 79 illustrating the operation of the valves when in the idle state 360 of the state diagram of FIG. 84 in accordance with an embodiment of the present disclosure. In the idle state 360, the valve 341 couples the reference volume 324 to the atmospheric pressure source 342. Note that, as shown in FIG. 85 which illustrates the idle state 360, the membrane forming the AVS volume 335 is deflated.

As shown in FIG. 86, the substate 370 sets the variables PCadj, PCenb1, PCenb2, PCv1, PCv2, PCv3, HCv1, and HCv2; e.g., via applying an input voltage into an appropriate input (see FIG. 83). Referring to FIGS. 85 and 86, the variable PCadj sets the pump 353, the variable PCenb1 enables the input to the pump 353, the variable PCenb2 enables the switch 355, the variable PCv1 controls the valve 350, the variable PCv2 controls the valve 349, the variable PCv3 controls the valve 341, the variable HCv1 controls the valve 332, and the variable HCv2 controls the valve 336.

Also as shown in FIG. 86, after the parameters are set in substate 370, the substate 371 takes several measurements. In substate 371, the PSavs, PSatm, PCmon, OPTvar, OPThv1, OPThc2, and Tavs values are taken and compared to predetermined ranges. If any of the measured values are outside a predetermined range, e.g., as shown in the expected column 373 in FIG. 86, an error condition 372 is determined to exist; in response to the error condition 372, an alert or alarm may be issued.

The PSavs is a value determined from the pressure sensor 340, PSatm is a value determined from the pressure sensor 343, PCmon is a value determined from the sensor 369 to determine if the pump is receiving the correct voltage from the input voltage 356, OPTvar is a measurement from the optical sensor 329, OPThv1 is the measurement from the optical sensor 333 to determine if the valve 332 is closed or open, OPThc2 is the measurement from the optical sensor 337 to determine if the valve 336 is open or closed, and Tavs is the measurement of the temperature from the temperature sensor 330.

Figure 87:
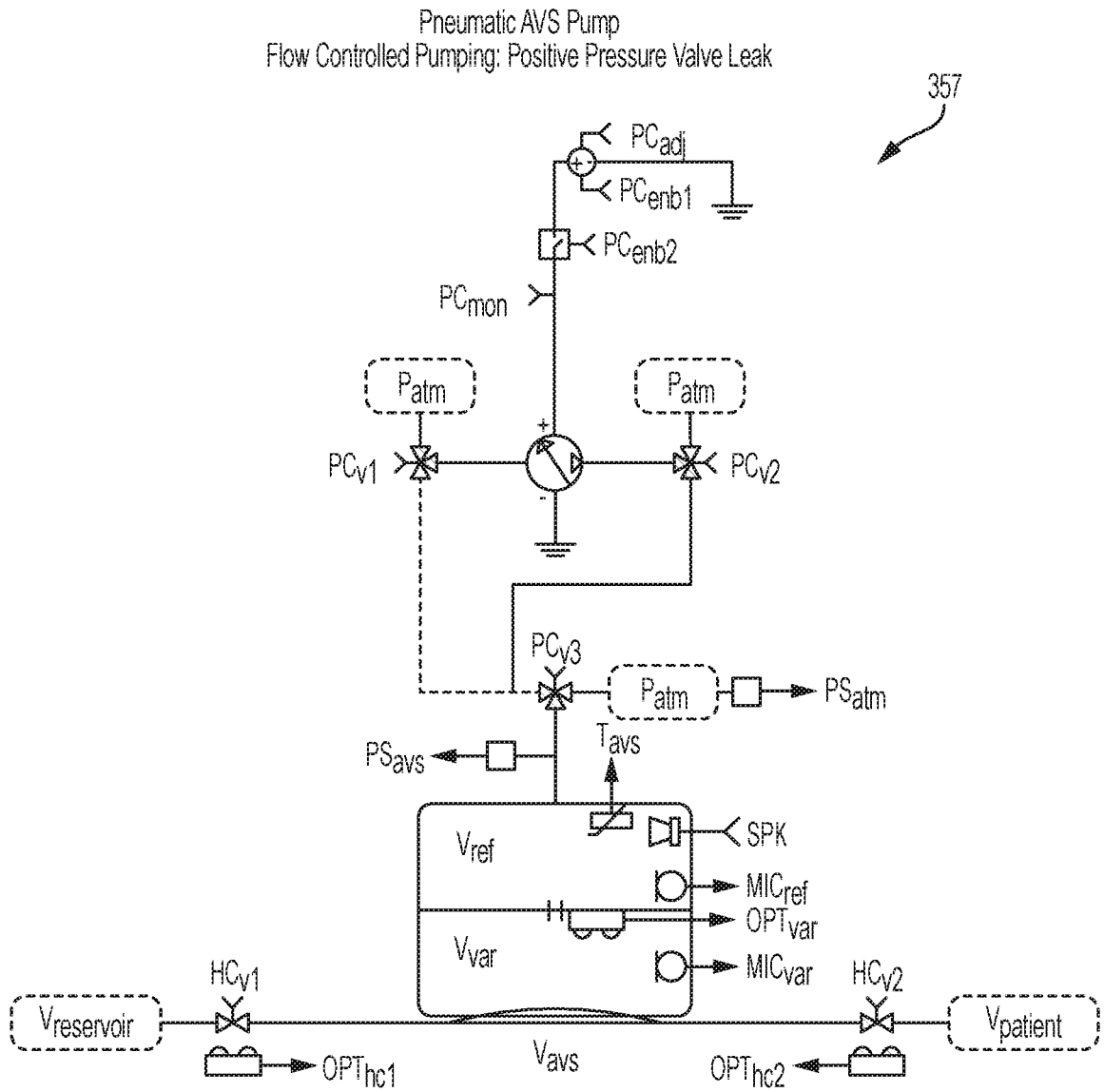
FIGS. 87-88 show the flow-controlled membrane pump of FIG. 83 in use during the positive pressure valve leak test state of FIG. 84 in accordance with an embodiment of the present disclosure.
Figure 88:
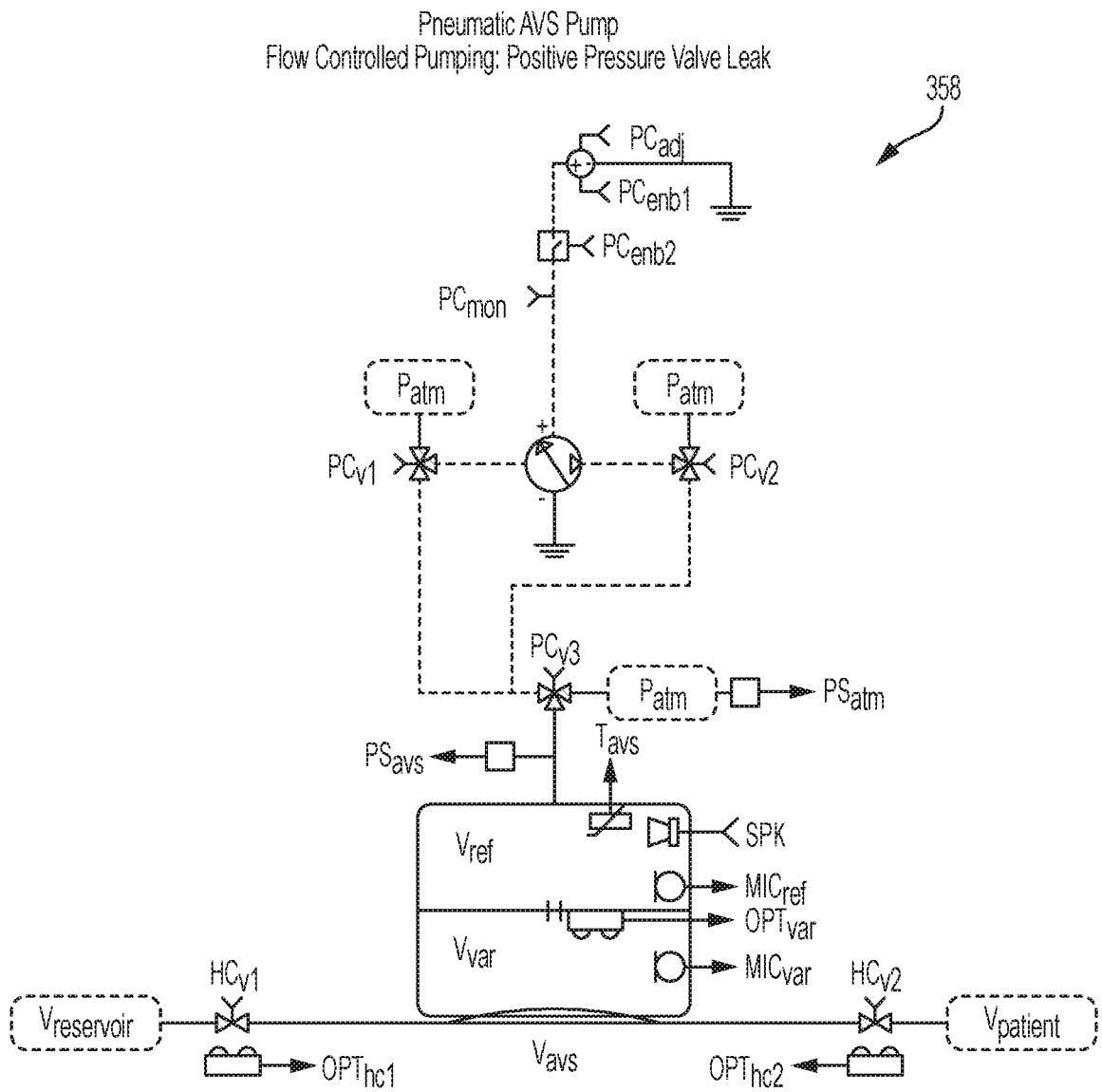

Referring again to FIG. 84, after the idle state 360, the state diagram 359 continues to the positive valve leak test state 361. FIGS. 87-88 show the flow-controlled membrane pump 358 of FIG. 83 in use during the positive pressure valve leak test state of FIG. 84 in accordance with an embodiment of the present disclosure. Note that there is a change in the valve 349 to allow the pumping of pressure into the reference volume 324 from as shown in FIG. 87. FIG. 88 shows where the valve 349 is switched again and the reference volume 324 is isolated from the fluid sources.

Figure 89:
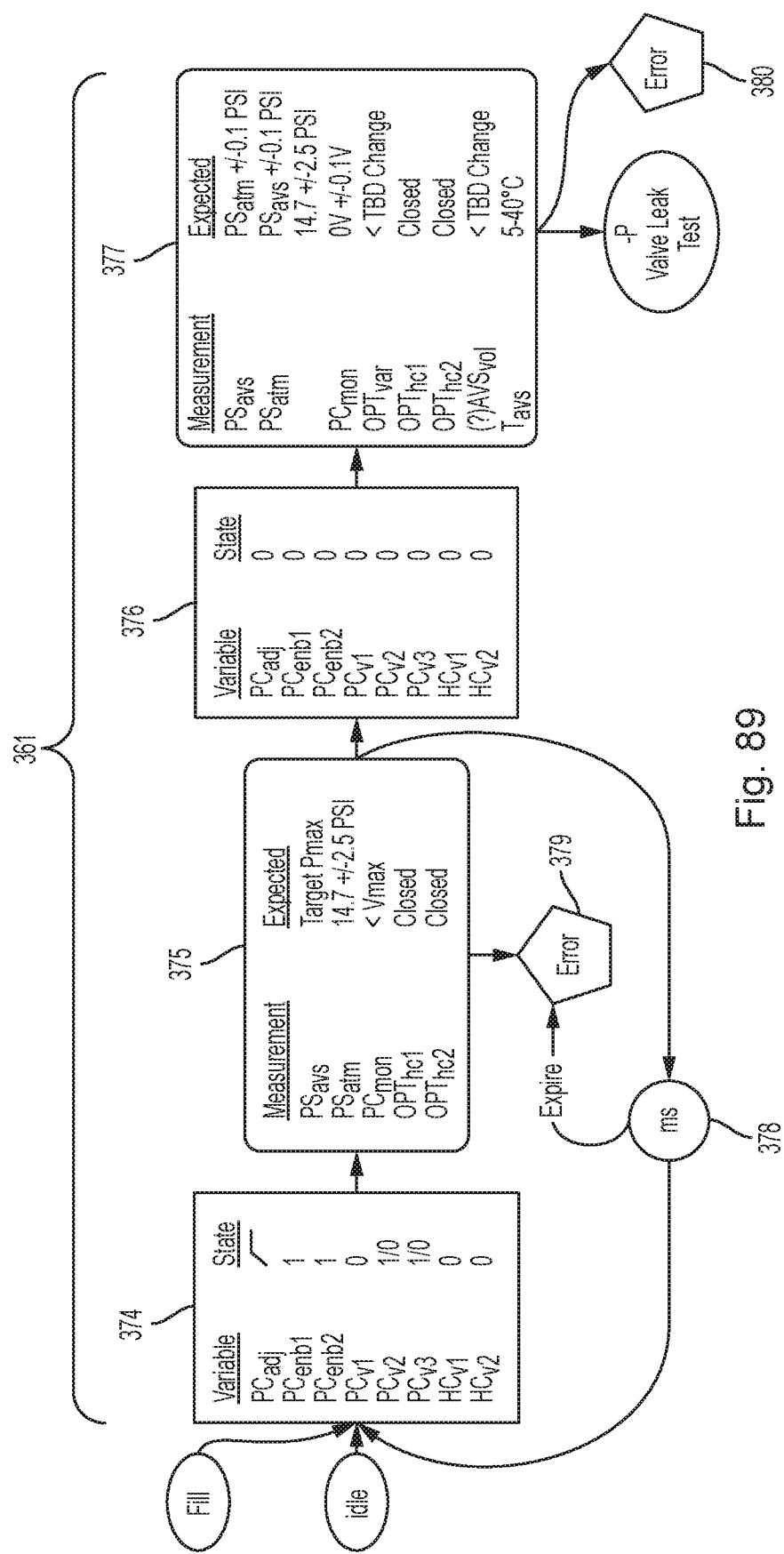
FIG. 89 shows a more detailed view of the positive pressure valve leak test state of FIG. 84 in accordance with an embodiment of the present disclosure.

FIG. 89 shows a more detailed view of the positive pressure valve leak test state 361 of FIG. 84 in accordance with an embodiment of the present disclosure. FIG. 89 may also represent state 364 of FIG. 84. The positive pressure valve leak test state 361 includes substates 374-380.

Substate 374 turns on the pump 353 and sets the valves 350, 249, and 341 such that positive pressure is applied to the reference volume 324. The valves 222 and 337 remain closed. In substate 374, measurements are taken. If the measured values are outside predetermined acceptable ranges, a substate 379 determines an error condition occurs. If the average pressure Target Pmax is not reached, state 361 continues to the substate 378 to wait for a predetermined amount of time. This process is depicted in FIG. 87. Substates 374, 375, and 378 may repeat until a predetermined number of substates 378 occurs or a predetermined amount of time is reached at which time an error 379 is substate determines an error condition exists.

State 361 may optionally wait a predetermined amount of time when transitioning from substate 375 to 376. In substate 376, the pump 353 is turned off and the valves 350 and 349 disconnect the variable volume 324 from the pump 353 (as depicted in FIG. 88). State 361 may optionally wait a predetermined amount of time when transitioning from substate 376 to 377. In substate 377, various measurements are taken, such as an AVS measurement using, for example, the AVS system having the speaker 326, and the microphones 327 and 328 which measure the volume of the variable volume 325 (using an acoustic response) to determine if the AVS volume 335 is changing thereby indicating a leak condition. Additionally or alternatively, the optical sensor 330 may detect if a predetermined movement of the membrane 335 occurs to determine if a leak condition exists. If these measurements are outside of a predetermined range and/or beyond a predetermined threshold, then an error condition is determined to exist in substate 280.

Figure 90:
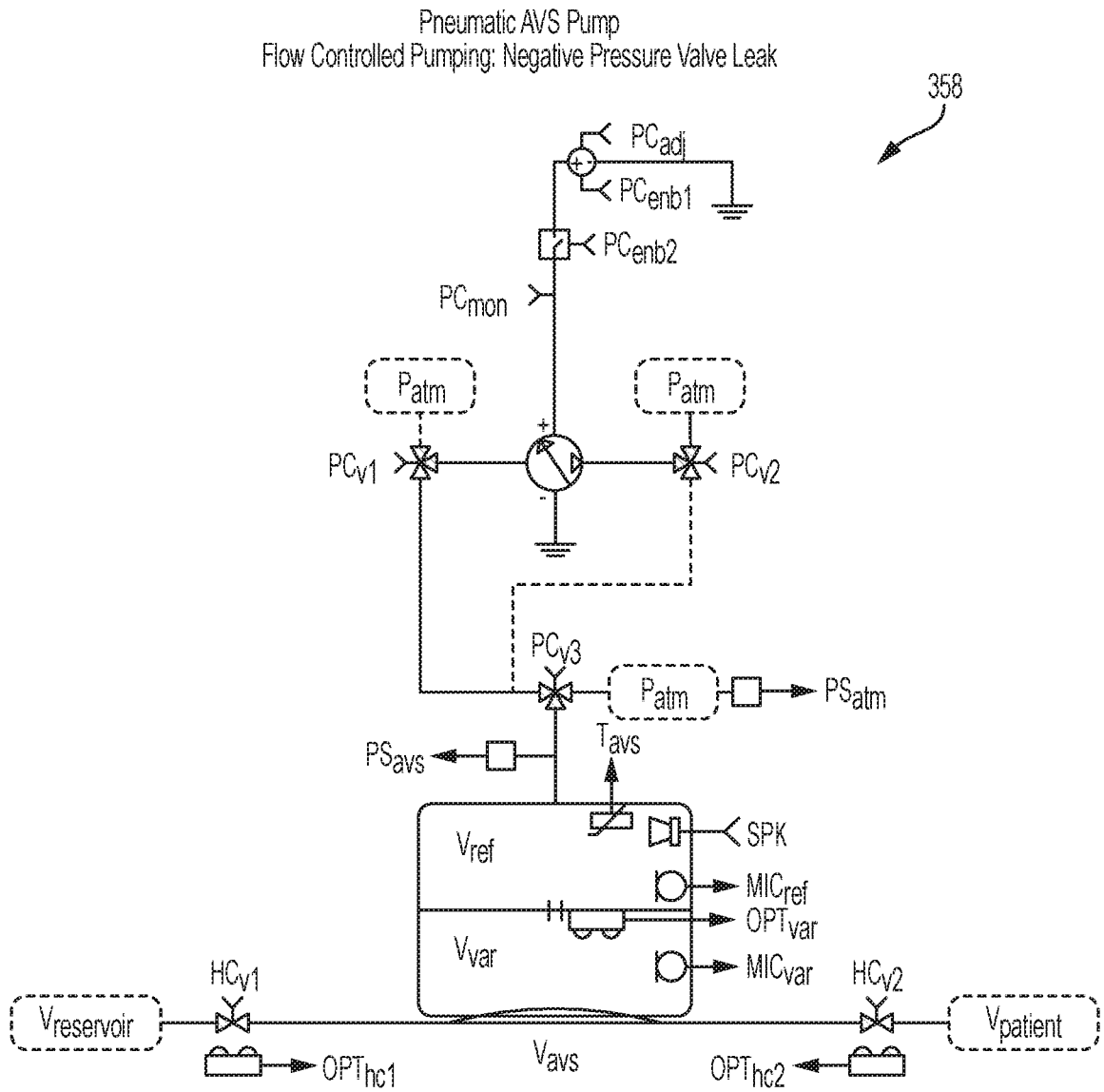
FIGS. 90-91 show the flow-controlled membrane pump of FIG. 83 in use during the negative pressure valve leak test state of FIG. 84 in accordance with an embodiment of the present disclosure.
Figure 91:
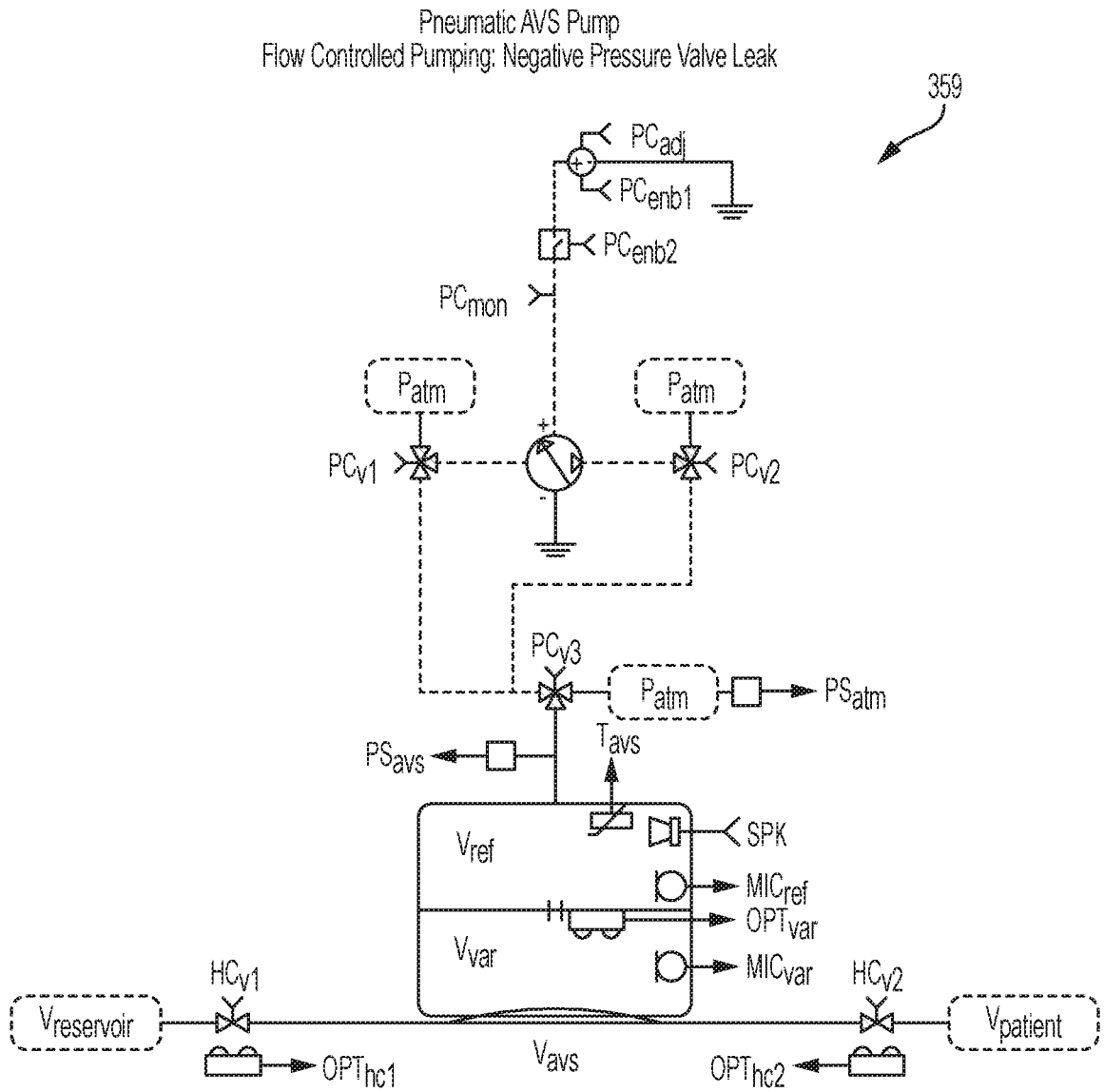
Figure 92:
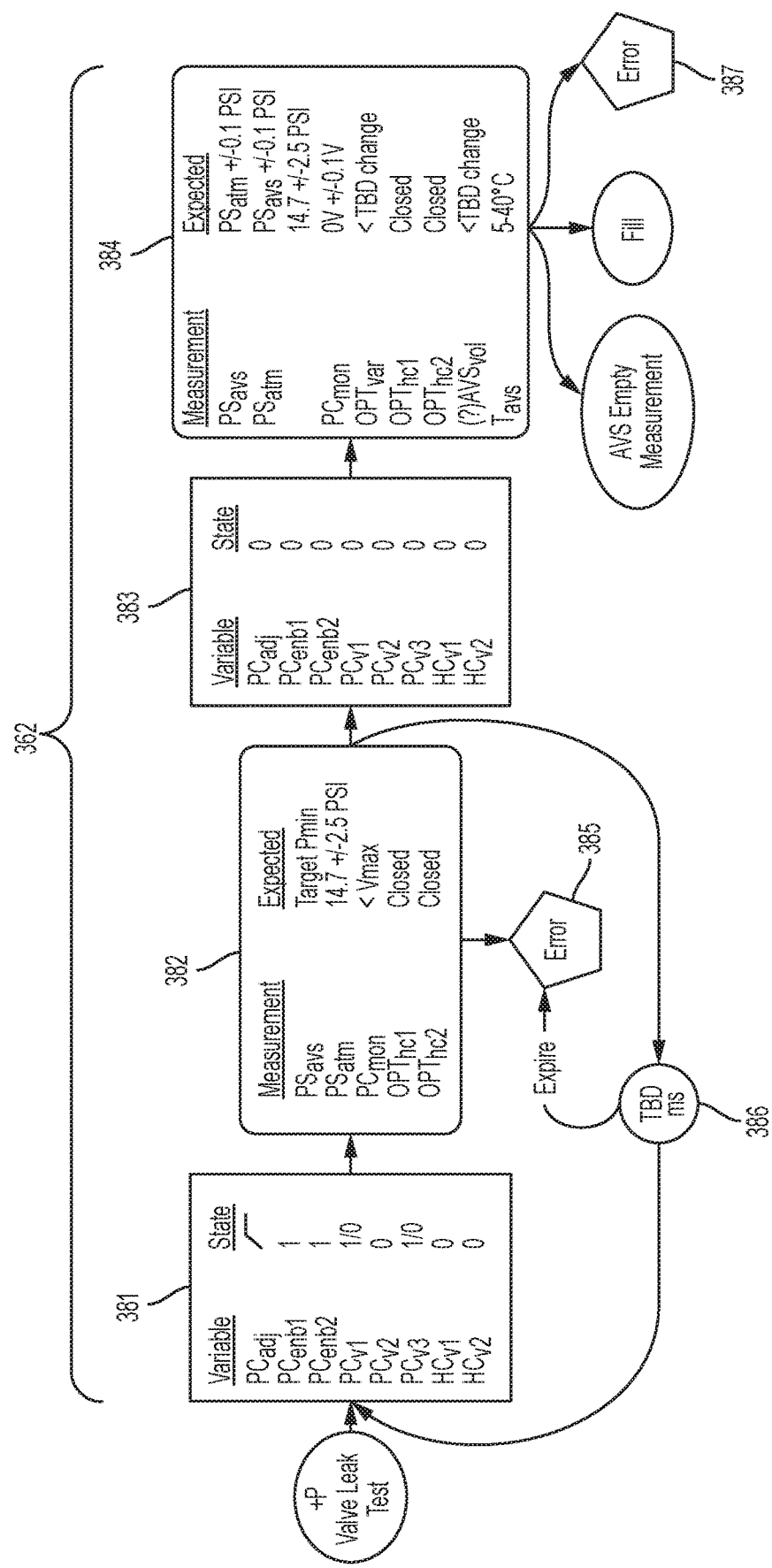
FIG. 92 shows a more detailed view of the negative pressure valve leak test state of FIG. 84 in accordance with an embodiment of the present disclosure.

Referring again to FIG. 84, after the positive leak valve test state 361 occurs, a negative leak valve test state 362 occurs. Refer to FIGS. 90, 91, and 92 for a description of the positive leak valve test state 362. FIGS. 90-91 show the flow-controlled membrane pump 358 of FIG. 83 in use during the negative pressure valve leak test state of FIG. 84, and FIG. 92 shows a more detailed view of the negative pressure valve leak test state 362 of FIG. 84 in accordance with an embodiment of the present disclosure. As shown in FIG. 92, state 362 includes substates 381-387. FIG. 92 may also be used to illustrate state 365 of FIG. 84.

Substate 381 turns on the pump 353 and sets the valves 350, 249, and 341 such that negative pressure is applied to the reference volume 324. The valves 222 and 337 remain closed. In substate 382, measurements are taken. If the measured values are outside predetermined acceptable ranges, a substate 382 determines an error condition occurs and continues to state 385. If the average pressure Target Pmin is not reached, state 382 continues to the substate 386 to wait for a predetermined amount of time. This process is depicted in FIG. 90. Substates 381, 382, and 386 may repeat until a predetermined number of substates 378 occurs or a predetermined amount of time is reached at which time substate 385 determines an error condition exists.

State 362 may optionally wait a predetermined amount of time when transitioning from substate 382 to 383. In substate 383, the pump 353 is turned off and the valves 350 and 349 disconnect the variable volume 324 from the pump 353 (as depicted in FIG. 91). State 362 may optionally wait a predetermined amount of time when transitioning from substate 383 to 384. In substate 383, various measurements are taken. For example, the AVS system using the speaker 326, and the microphones 327 and 328 to measure the volume of the variable volume 325 (using an acoustic response) to determine if the AVS volume 335 is changing thereby indicating a leak condition. Additionally or alternatively, the optical sensor 330 may detect if a predetermined movement of the membrane 335 occurs to determine if a leak condition exists. If these measurements are outside of a predetermined range and/or beyond a predetermined threshold, then an error condition is determined to exist in substate 387.

Figure 93:
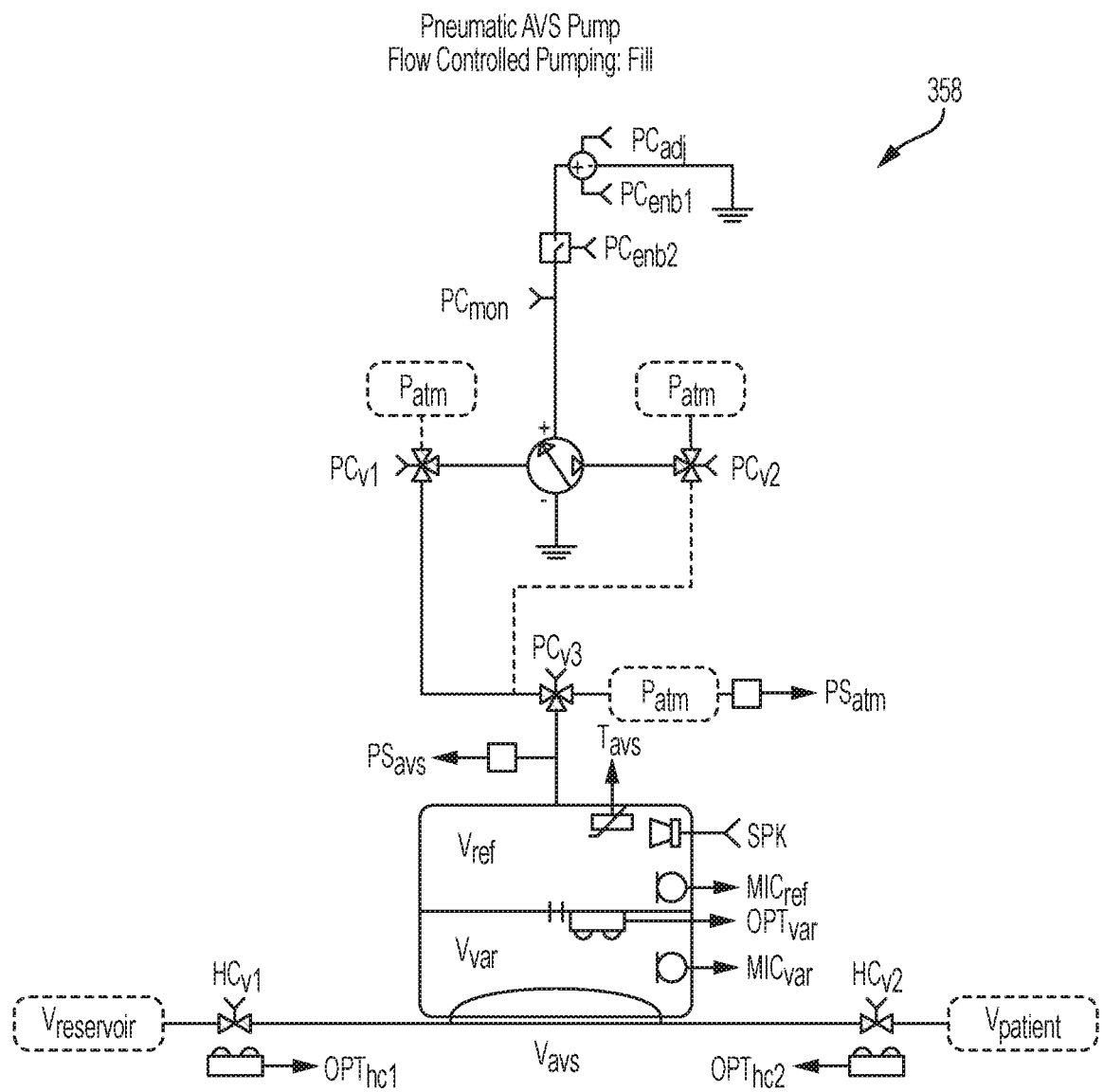
FIG. 93 shows the flow-controlled membrane pump of FIG. 83 in use during the fill state of FIG. 84 in accordance with an embodiment of the present disclosure.

FIG. 93 shows the flow-controlled membrane pump 358 of FIG. 83 in use during the fill state 363 of FIG. 84 in accordance with an embodiment of the present disclosure.

Figure 94:
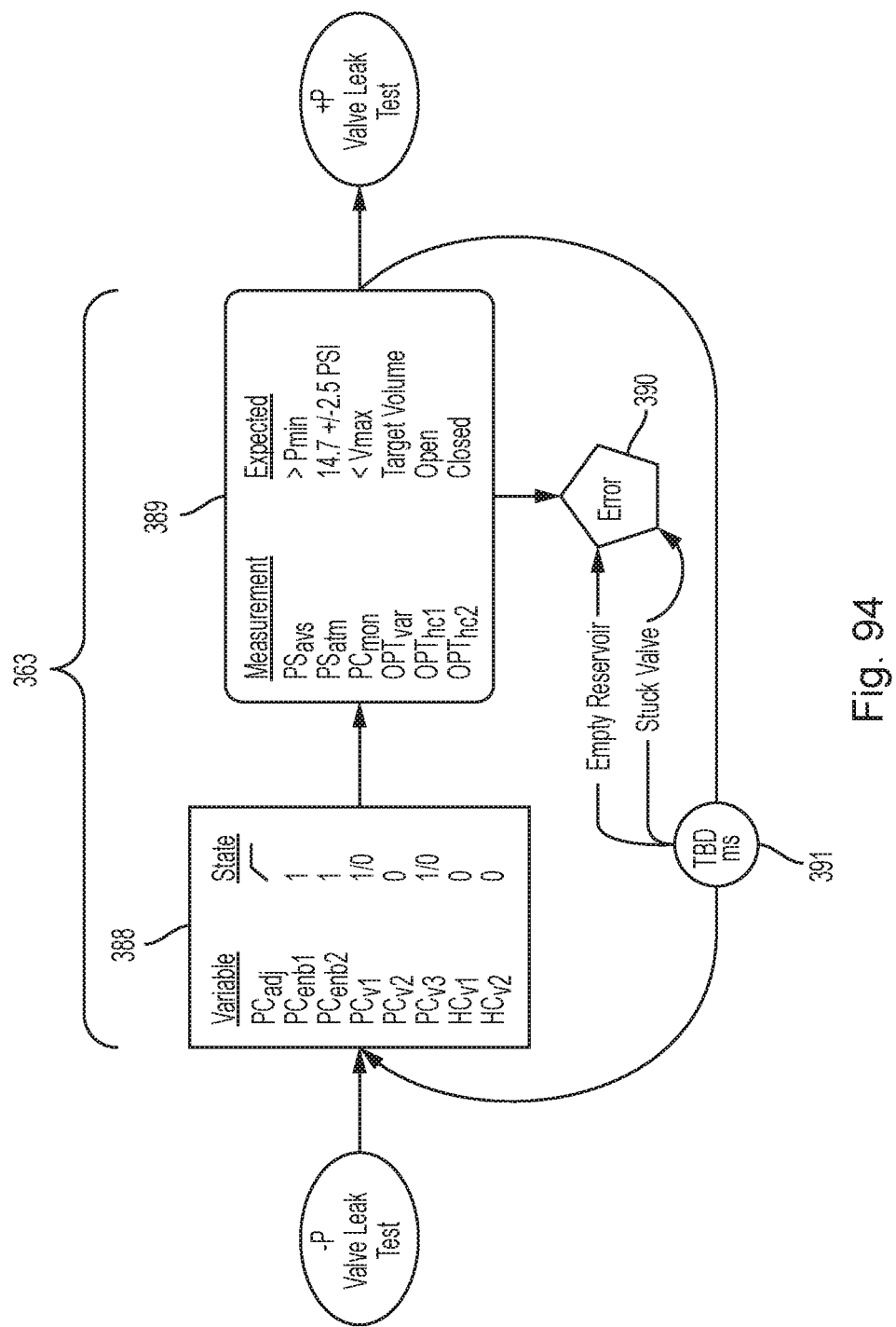
FIG. 94 shows a more detailed view of the fill state of FIG. 84 in accordance with an embodiment of the present disclosure.

FIG. 94 shows a more detailed view of the fill state 363 of FIG. 84 in accordance with an embodiment of the present disclosure.

State 363 includes substates 388-391. Substate 288 sets the valves 350 and 351, and the pump 353 to apply a negative pressure to the variable volume 324. The valve 332 is also opened and the AVS volume 335 fills with a fluid from the fluid reservoir 331. State 389 takes several measurements, including an optical measurement from the optical sensor 330, to determine if the membrane defining the AVS volume 335 is filling. If it hasn't filled, substate 391 waits a predetermined amount of time. Thereafter, substates 288, 289, and 391 may be repeated for at least a predetermined number of cycles and/or until a predetermined amount of time has passed, after which substate 390 determines that an error condition exists, e.g., because the reservoir 331 is empty and/or a valve is stuck, for example, valve 332 may be stuck closed, etc. Additionally or alternatively, if the measurement taken during the substate 389 is outside of a predetermined range and/or is beyond a predetermined threshold, the substate 390 may determine an error condition exists.

Referring again to FIG. 84, after state 363 is performed, another positive valve leak test is performed during state 364 and another negative valve leak test is performed in state 365.

Figure 95:
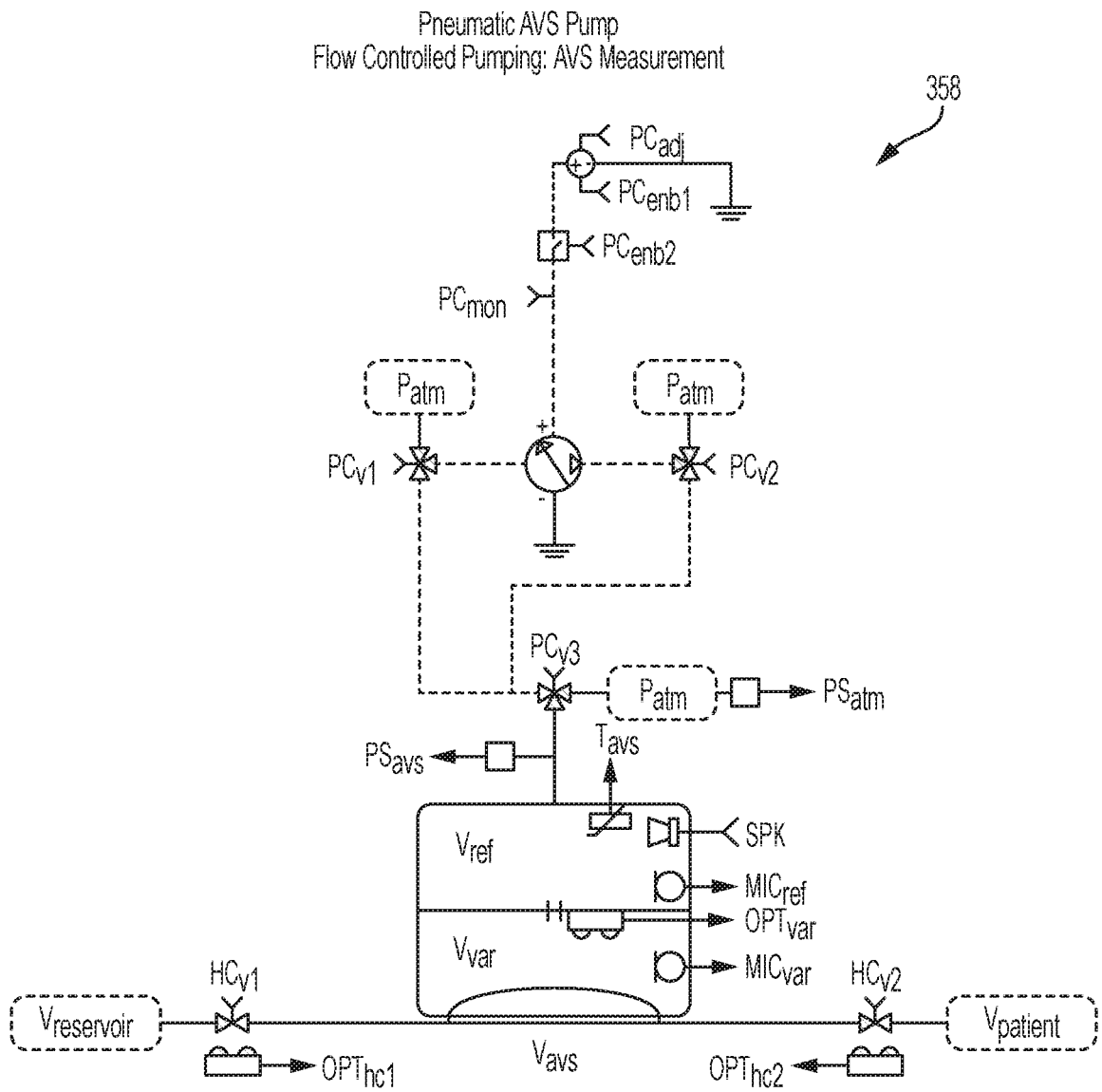
FIG. 95 shows the flow-controlled membrane pump of FIG. 83 in use during an AVS measurement in accordance with an embodiment of the present disclosure.
Figure 96:
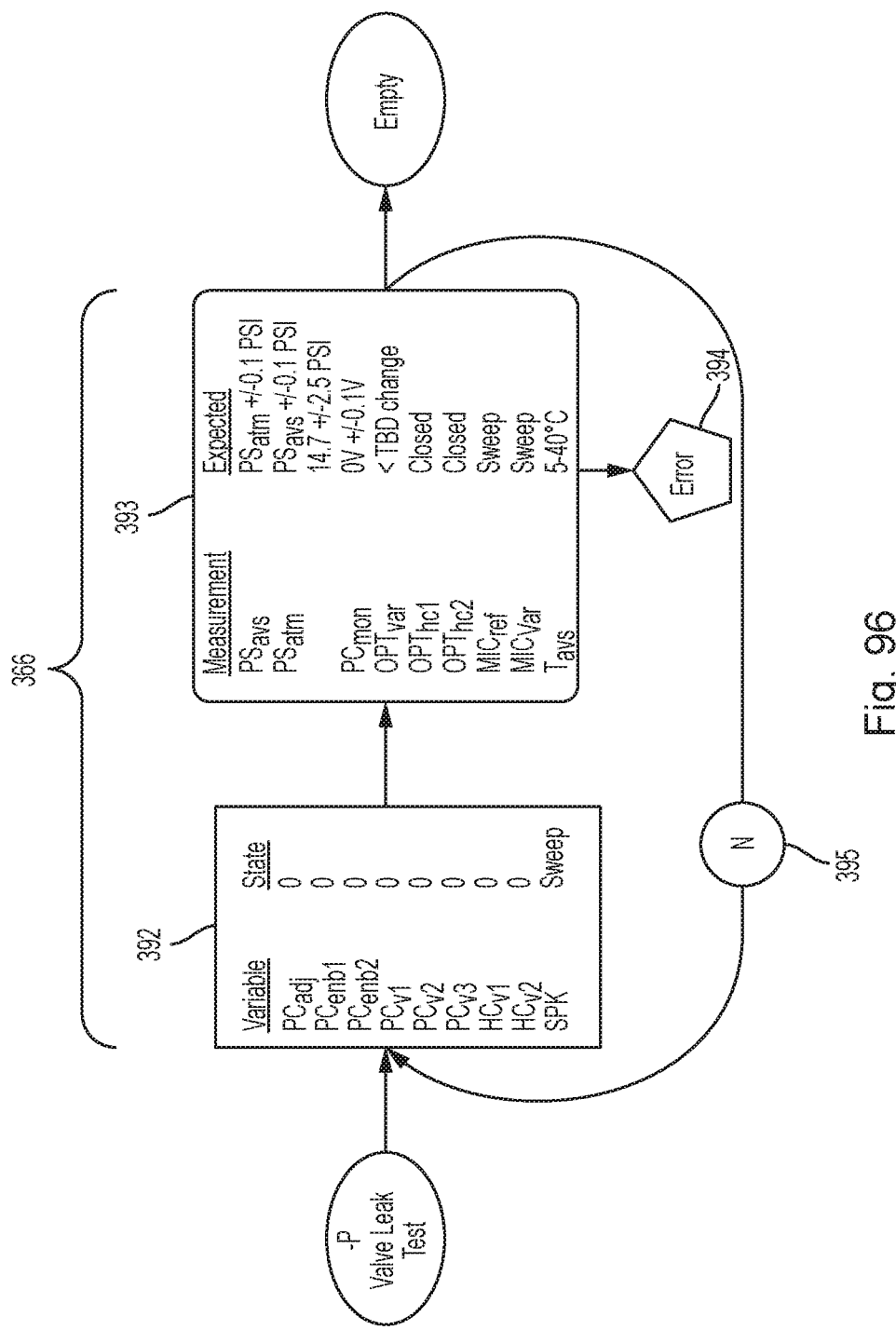
FIG. 96 shows a more detailed view of the AVS measurement state of FIG. 84 in accordance with an embodiment of the present disclosure.

State 366 takes an AVS measurement to determine the volume of the AVS chamber 355 (see FIG. 95). Referring now to FIGS. 95 and 96: FIG. 95 shows the flow-controlled membrane pump 358 of FIG. 83 in use during an AVS measurement state 366, and FIG. 96 shows a more detailed view of the AVS measurement state 366 of FIG. 84.

State 366 includes substates 392 and 395. Substate 392 causes the speaker 329 to emit one or more acoustic frequencies, and substate 393 takes measurements from the microphones 327 and 328 to determine an acoustic response. The acoustic response is correlated with a volume of the AVS chamber 335 and is thus also correlated with the fluid in the AVS chamber 335. The acoustic response and other measurements are taken during substate 393. Substates 392 and 393 may optionally repeated, e.g., shown as the substate 395. If one or more measurements from the substate 392 are outside of a predetermined range and/or is beyond a predetermined threshold, the substate 394 may determine that an error state exists.

Figure 97:
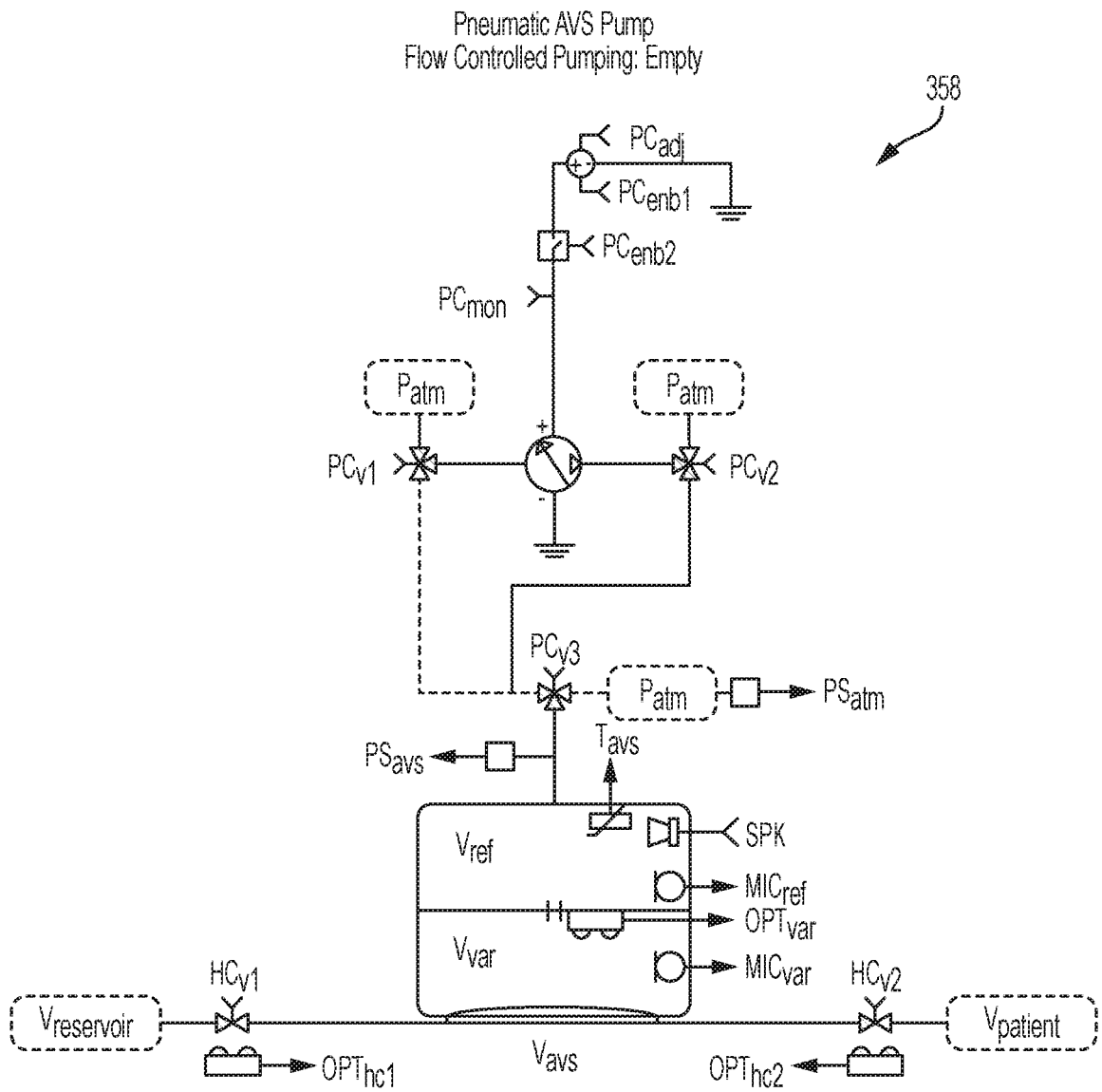
FIG. 97 shows the flow-controlled membrane pump of FIG. 83 in use during the emptying state of FIG. 84 in accordance with an embodiment of the present disclosure.

Referring again to FIG. 84, after the AVS measurements are taken in state 366, the emptying state 367 empties the AVS volume 335. FIG. 97 shows the flow-controlled membrane pump 358 of FIG. 83 in use during the emptying state 367 of FIG. 84, and FIG. 98 shows a more detailed view of the emptying state of FIG. 84.

Figure 98:
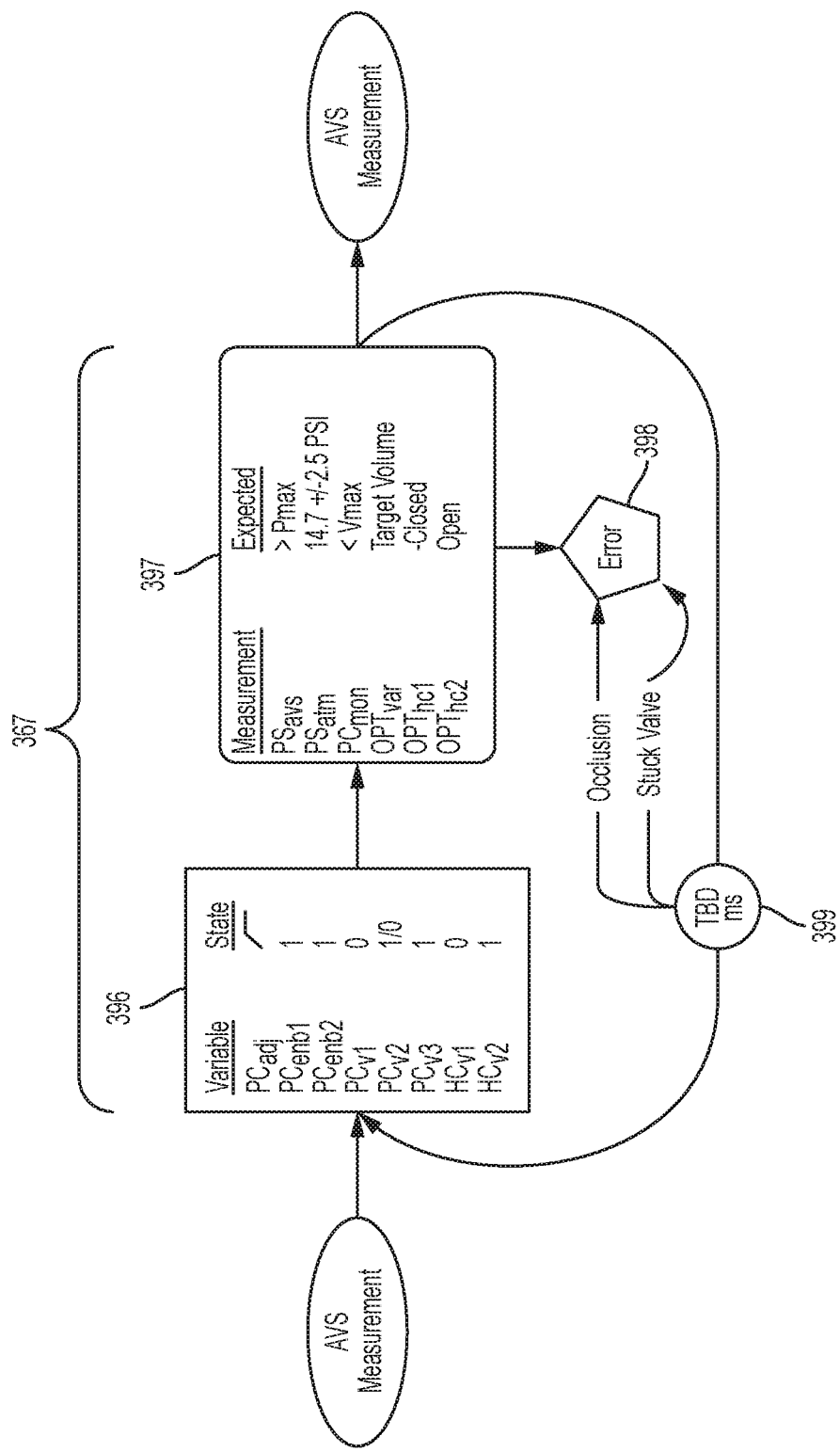
FIG. 98 shows a more detailed view of the emptying state of FIG. 84 in accordance with an embodiment of the present disclosure.

As shown in FIG. 98, the emptying state 367 includes substates 396-399. Substate 396 sets the valves 350 and 349, and the pump 353 to apply a positive pressure to the reference volume 324. Substate 396 also open the valve 336 to allow fluid to flow to the patient 338. During substate 387, several measurements are taken, and substate 397 continues to substate 399 to wait a predetermined amount of time. The substates 396, 397, and 399 repeat until the optical sensor 329 determines that the AVS volume is below a predetermined amount. If the measurements taken during substate 397 are outside of a predetermined range and/or a measurement exceeds a predetermined threshold (i.e., above or below the threshold) the substate 398 determines an error condition exists. If the substate 399 repeats a predetermined number of times and/or operates for a predetermined amount of time, the substate 398 may determine that an error condition exists, e.g., a stuck valve such as valve 336 and/or a downstream occlusion may be preventing the AVS volume from discharging the liquid to the patient 338, for example.

Referring again to FIG. 84, after state 367, state 368 takes an AVS measurement. The AVS measurement 368 may be compared to the AVS measurement 366 to determine an amount of fluid delivered to a patient 338. For example, in the emptying state 367, some of the fluid may remain in the AVS volume 335. By comparing the difference between the AVS measurements, the amount of fluid discharged down the tube to the patient 338 may be estimated.

Figure 99:
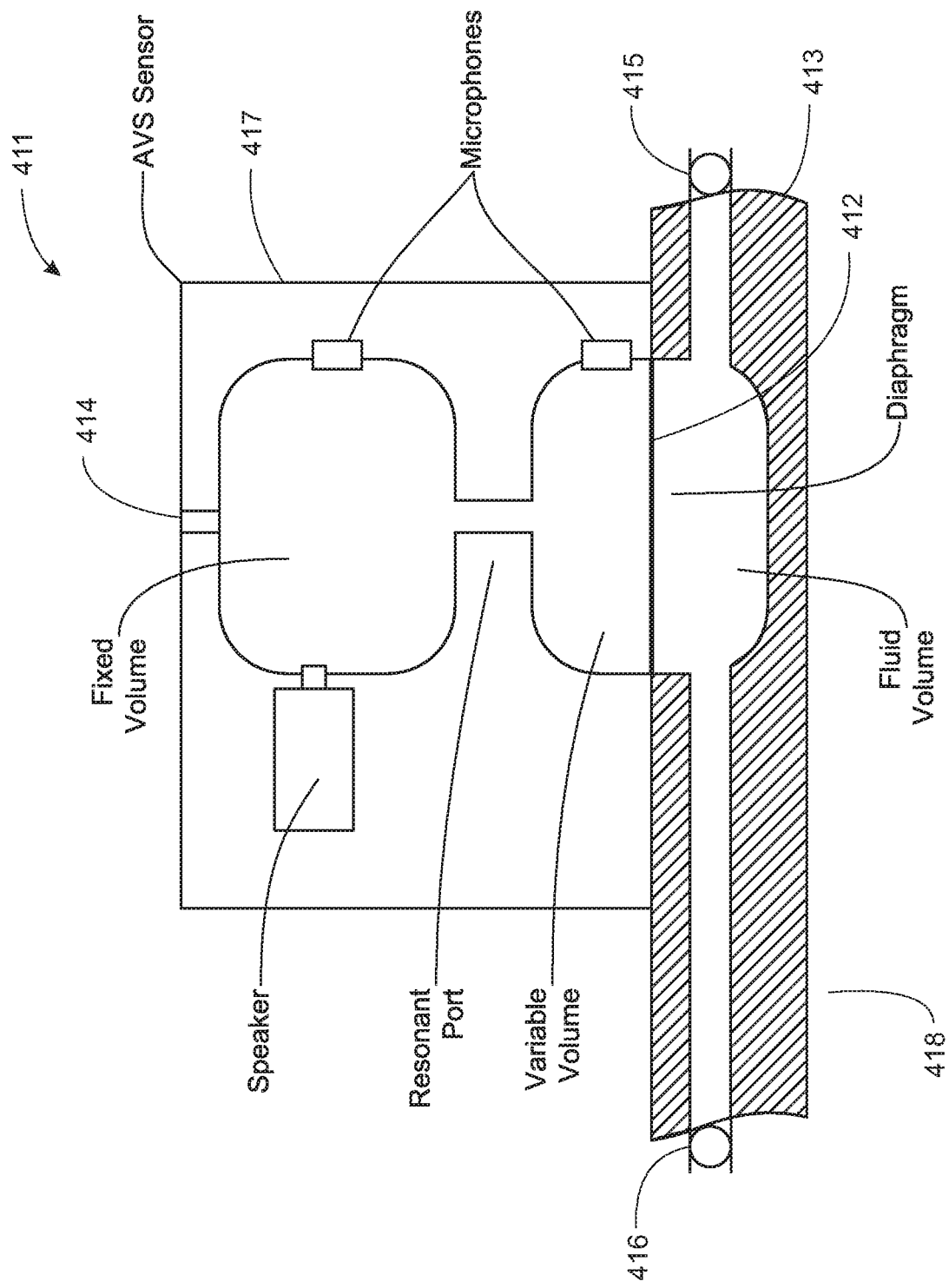
FIG. 99 shows a membrane pump having an elastic membrane that is flush with a disposable portion and applies a force to a liquid in accordance with an embodiment of the present disclosure.

FIG. 99 shows a membrane pump 411 having an elastic membrane 412 that is flush with a disposable portion 413 and applies force to a liquid in accordance with an embodiment of the present disclosure. That is, the action of the membrane 412 provides an actuation to move fluid through the membrane pump 411. The membrane pump 411 includes an AVS assembly 417 that couples to a disposable portion 418. The AVS assembly 417 may be snap-fitted, may screw onto, or may include latches to attach to the disposable portion 418. The membrane pump 411 includes a pneumatic fill port 414. The pneumatic fill port 414 may be connected to any air pump as described herein. In yet additional embodiments, the pneumatic fill port 414 may be connected to a liquid pump, e.g., a syringe pump, or other liquid pump. In some embodiments, alternative positive and negative pressures are applied to the pneumatic fill port 414, which is used in conjunction with valves 415 and 416 to pump fluid. In some embodiments, a negative pressure is applied to the pneumatic fill port 414 and the elastic property of the membrane 412 is used to suck in liquid through the valve 416. In some embodiments, a positive pressure is applied to the pneumatic fill port 414 and the elastic property of the membrane 412 is used to expel in liquid through the valve 415.

Figures 100, 101:
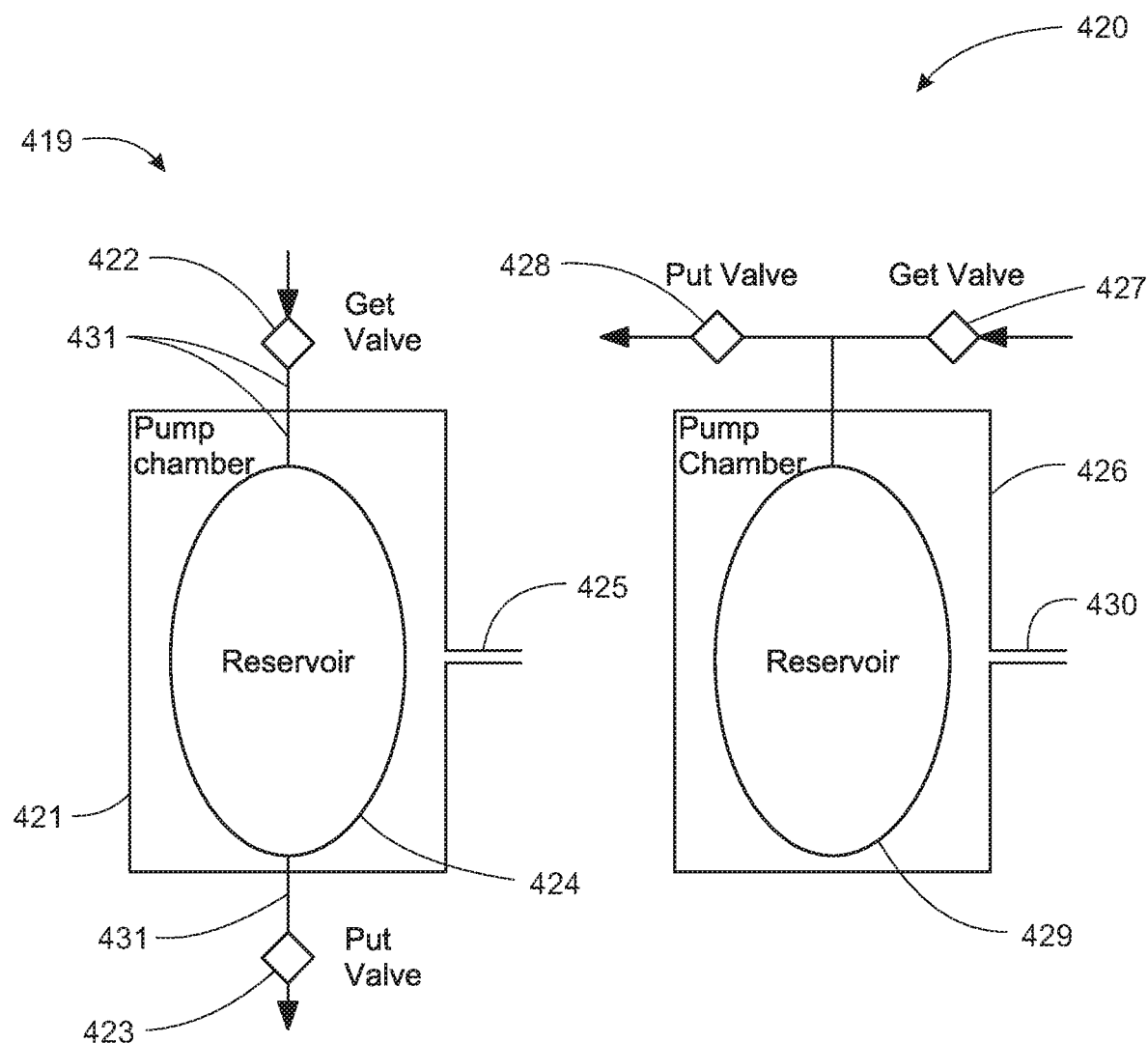
FIGS. 100-101 show two embodiments of lung pumps in accordance with embodiments of the present disclosure.

FIGS. 100-101 show two embodiments of lung pumps in accordance with embodiments of the present disclosure. FIG. 100 shows a lung pump 419, and FIG. 101 shows a lung pump 420.

The lung pump 419 of FIG. 100 includes a rigid body 421 having an AVS or FMS port 425 for measuring the volume of a reservoir 425 that is flexible. FMS is described in the U.S. Pat. Nos. 4,808,161; 4,826,482; 4,976,162; 5,088,515; 5,193,990; and 5,350,357. In some embodiments, positive and/or negative pressure is applied to the port 425 to facilitate the pumping action of the lung pump 419. The reservoir 424 is in fluid communication with the valves 422 and 423. The reservoir 424 may be molded or bonded to the tube 431, or is vacuum formed from the tube 431, e.g., a blister. The rigid body 421 may fully seal around the tube 431 as it passes through the rigid body and connects to the reservoir 424. By applying a positive or negative pressure via the port 425, the fluid may be drawn into and out of the reservoir 424. This positive and negative pressure may be supplied by a manifold which also contains a reference chamber allowing for FMS measurements via the port 425. Additionally or alternatively, the rigid body 421 may include hardware, such as, for example, a processor to control the valves 422 and 425, an AVS assembly coupled to the port 425, etc. The liquid is drawn from the valve 422 and leaves via the valve 423. The valves 422 and 423 may be pinch valves. The valves 422 and 423 may be alternatively closed and open, relative to each other and synchronized with any positive and/or negative pressure applied via the port 425. For example, a pumping sequence may occur as follows: (1) close the valve 413 and open the valve 422; (2) apply a negative pressure to the port 425; (3) close the valve 422; (4)

estimate the volume of fluid in the reservoir 425 (e.g., using AVS or FMS); (5) repeat steps (1)-(4) until a predetermined volume is within the reservoir; (6) open the valve 425; (7) apply a positive pressure to the valve 425; (8) close the valve 423; (9) estimate the volume of fluid in the reservoir; (10) compare the volumes measured during steps (9) and (4) to determine an amount of liquid discharged; (11) and repeat (1)-(10) until a predetermined amount of liquid has been pumped.

The lung pump 420 of FIG. 101 includes a rigid body 426 having an AVS or FMS port 430 for measuring the volume of a reservoir 429 that is flexible. In some embodiments, positive and/or negative pressure is applied to the port 430 for facilitating the pumping action of the lung pump 420. The reservoir 429 is in fluid communication with valves 427 and 428. The lung pump 420 may be similar to the lung pump 419 of FIG. 99; however, the valve 427 is opened and the valve 428 is closed to pump fluid into the reservoir; and the valve 428 is opened and the valve 427 is closed to pump fluid out of the reservoir.

Figure 102:
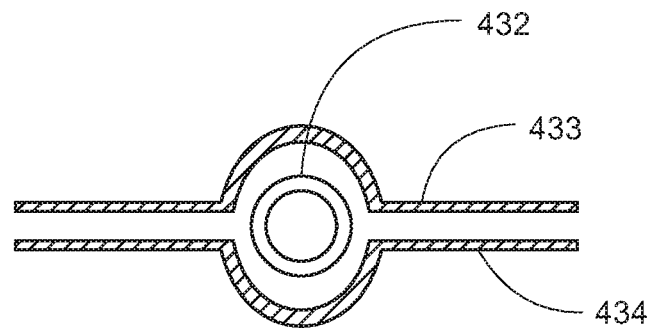
FIGS. 102-104 show several gaskets for sealing a lung pump in accordance with additional embodiments of the present disclosure.
Figure 103:
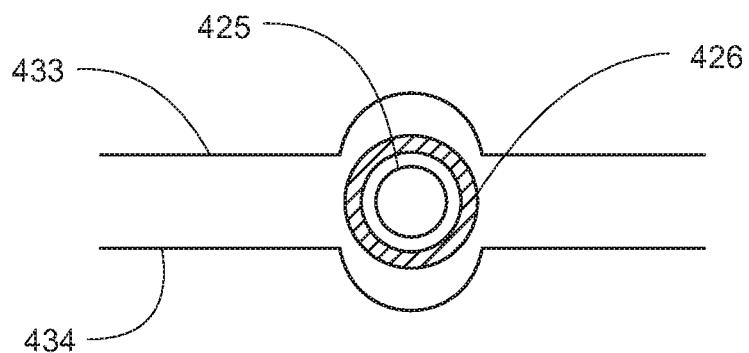
Figure 104:
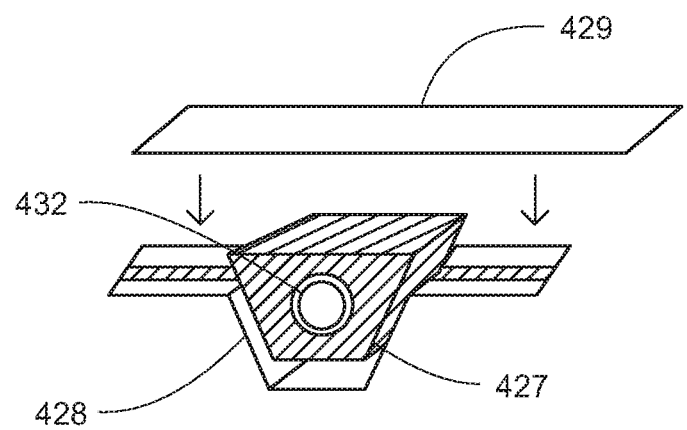

FIGS. 102-104 show several gaskets for sealing a lung pump in accordance with additional embodiments of the present disclosure. FIG. 102 shows a tube 432 that may be sealed by sections 433 and 434 of the rigid body of the lung pump (e.g., rigid body 421 of FIG. 99 or rigid body 426 of FIG. 100). In other embodiments, 422 and 424 may be part of a housing, latching, or dooring mechanisms. FIG. 103 shows a tube 425 that includes a gasket seal 426. The gasket seal 426 may push to the left and right causing a better seal where the two sides of the sealing surfaces meet (i.e., 422 and/or 424). FIG. 104 shows another way of sealing a tube 432 in including a gasket 427 that seals by being compressed in between a valley structure 427 and a compressing plate 429.

Figure 105:
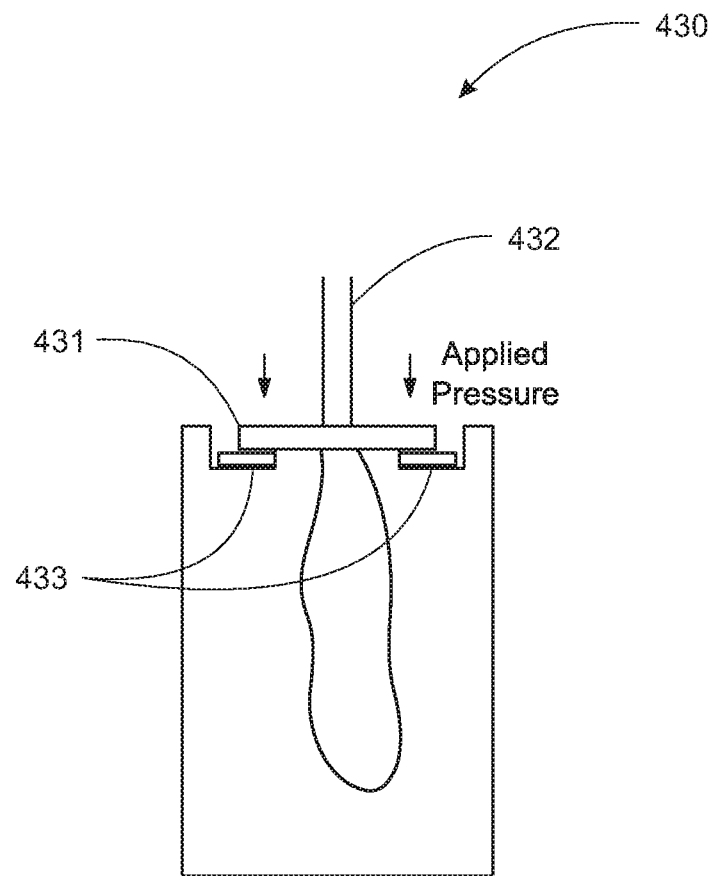
FIG. 105 shows another lung pump in accordance with another embodiment of the present disclosure.

FIG. 105 shows another lung pump 430 in accordance with another embodiment of the present disclosure. The lung pump 430 includes a rigid piece 431 bonded around a tube 432 that creates a face-sealing gasket that seals against a ring structure 433 when a pressure is applied to the rigid piece 431. The rigid piece 431 may be a circular structure, e.g., a ring structure similar to a washer.

Figure 106:
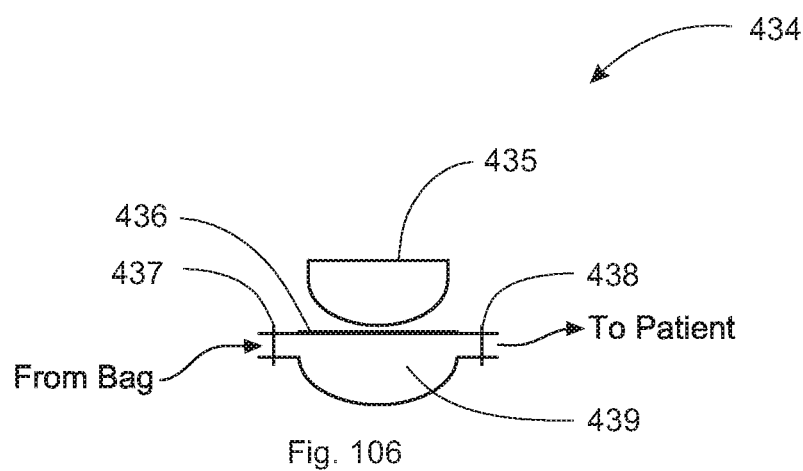
FIGS. 106-112 illustrate the operation of a piston pump while performing various checks in accordance with an embodiment of the present disclosure.

FIGS. 106-112 illustrate the operation of a piston pump while performing various checks in accordance with an embodiment of the present disclosure. The checks described in conjunction with the piston pump of FIGS. 106-112 may also be used with a peristaltic pump having a spring-biased plunger as described herein. FIG. 106 shows a pump 434 including a piston 435, a diaphragm 436, an inlet valve 437, an outlet valve 438, and a pump chamber 439. The piston 435 may be coupled to a linear actuator 54 (not shown in FIGS. 106-112) that is coupled to a processor 37 for control (see FIG. 3).

The opening of the valves 437 and 438 may be timed with the movement of the piston 435 to allow the integrity of the valves to be checked periodically during the pump operation. The piston 435 applies a pressure or vacuum to check the valves 437 and 438 to verify that one or both are not leaking before opening the other valve. This process may be used to safeguard against free-flow conditions; if one valve is not sealing properly the other valve is not opened. The same configuration can be used to check for air in the pumping chamber, upstream occlusions, and downstream occlusions.

In some embodiments, the piston 435 and valves 437 and 438 may be driven by a set of cams driven by a single motor. Additionally, in some embodiments, the piston 435 is spring loaded such that the cam lifts the piston 435 and the spring returns the piston 435 to the down position; this specific embodiment may have a relatively constant delivery pressure.

In some embodiments of the present disclosure, the position of the piston 435 and/or the position of the diaphragm 436 may be determined using a sensor. In some embodiments, the position of the piston 435 may be determined using an encoder, a magnetic sensor, a potentiometer, or rotational sensors on a camshaft, etc. In additional embodiments, the position of the piston 435 is measured directly by using an optical sensor, a LVDT (linear variable differential transformer) sensor, a hall-effect sensor, or other linear sensor. The position of the diaphragm 436 may be sensed using an AVS assembly as described elsewhere herein (e.g., the AVS assembly 417 of FIG. 98 may be used to determine the position of the diaphragm 436). In some additional embodiments, no piston is used and the diaphragm is moved using pneumatic pressure as described herein.

Figure 107:
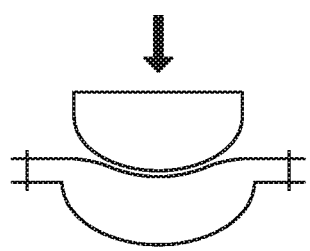

FIGS. 107-112 illustrate various stages of the piston pump of FIG. 106. FIG. 107 illustrates an air check and inlet valve 437 leak check. The piston 435 applies a downward force while the valves 437 and 438 are closed. If the piston 435 moves a predetermined distance and/or beyond a predetermined speed, the processor 37 may determine that excessive air exists within the pump chamber 439. If the piston 435 compresses an amount and slowly continues to move towards the bottom of the pump chamber 439, the processor may determine that one of the valves 437 and/or 438 is leaking. For example, if a valve 437 and/or 438 is leaking, the volume with the pump chamber 439 will continuously decrease. The movement (or speed) cause by excessive air in the pump chamber 439 may be at a different speed than the movement caused by a leak; and, in some specific embodiments, the processor 37 may distinguish between excessive air in the pump chamber 439 and/or a leak in one of the valves 437 and 438. For example, the piston 435 may move downwards at a first speed and quickly approaches a very slow speed; if the slow speed continues, then it may be determined that the continued slow movement after the abrupt negative acceleration is an indication of a leak in one of the valves 437 and 438.

Figure 108:
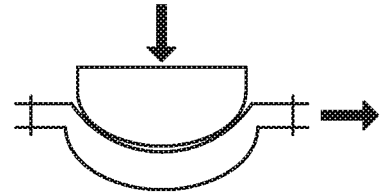

FIG. 108 shows a stage in which a downstream occlusion check is performed. The outlet valve 438 is opened and the fluid in the pump chamber 439 is delivered to the patient. If the volume does not change, there may be a downstream occlusion. Additionally or alternatively, if the piston 435 moves slower than a threshold and/or moves more slowly than the previous fluid discharge by a predetermined amount, the processor 37 (see FIG. 3) may determine that a downstream occlusion has occurred. Additionally or alternatively, if the piston 435 stops moving less than a predetermined amount of movement (e.g., with a predetermined force is applied to the piston 435) then the processor 37 may determine that a downstream occlusion has occurred.

Figure 109:
Figure 110:
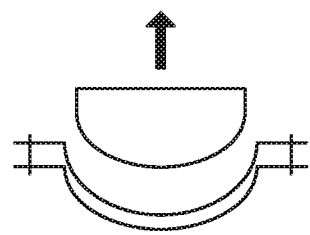

FIG. 109 illustrates the stages in which the outlet valve 438 is closed. FIG. 110 illustrates the stage in which the piston 435 is pulled up. The outlet valve 438 remains closed. The stretch of the diaphragm 436 results in vacuum in the pump chamber 439. If one of the valves 437 and 438 is leaking, the fluid in the pumping chamber 439 will increase. If the diaphragm 436 moves by a predetermined amount, the processor 37 may determine that a valve is leaking and issue an alert and/or alarm.

Figure 111:
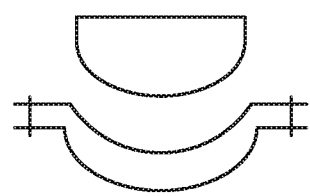
Figure 112:
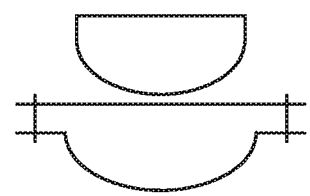

FIG. 111 illustrates a stage where the pump chamber 438 is filled, and an upstream occlusion check is performed. The inlet valve 437 is opened and the pump chamber fills 438 with liquid. If the pump chamber fails to fill by a predetermined amount, then the processor may determine that an upstream occlusion exists or the IV bag is empty. Additionally or alternatively, if the chamber fills 438 too slowly, or slower than the previous fill by a predetermined amount, the processor 37 may determine that an upstream occlusion exists. FIG. 112 illustrates the stage in which the inlet valve 437 is closed. The stages illustrated in FIGS. 107-112 may be repeated until a predetermined amount of fluid is delivered to a patient.

Figure 113:
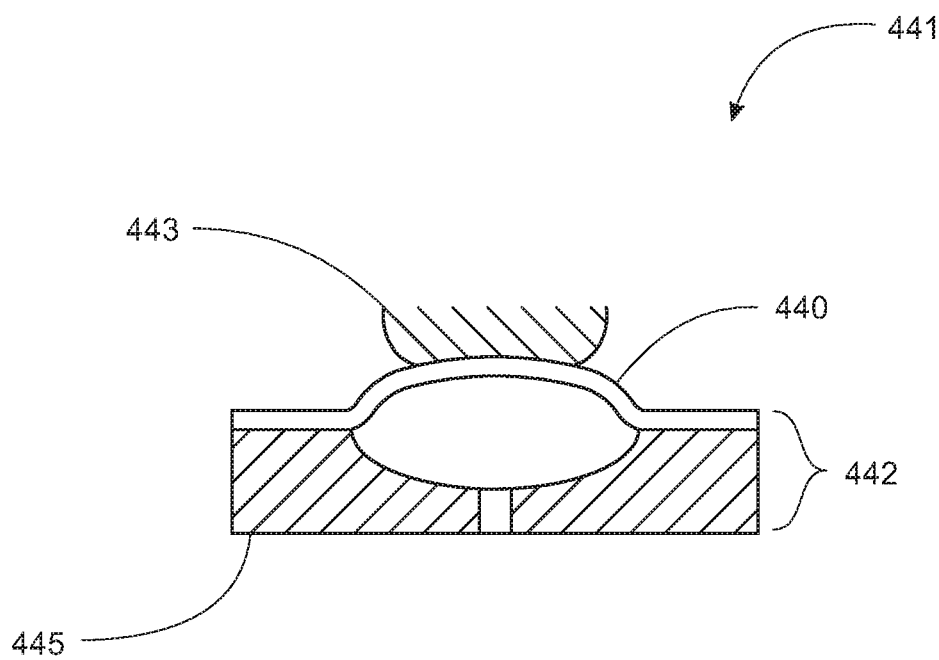
FIGS. 113 and 114 illustrate a piston pump in accordance with another embodiment of the present disclosure.
Figure 114:
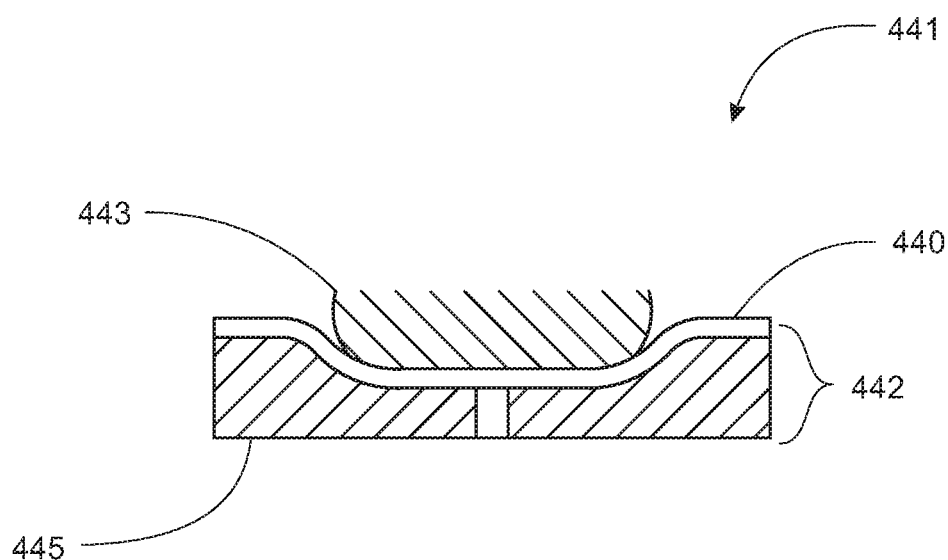
Figure 115:
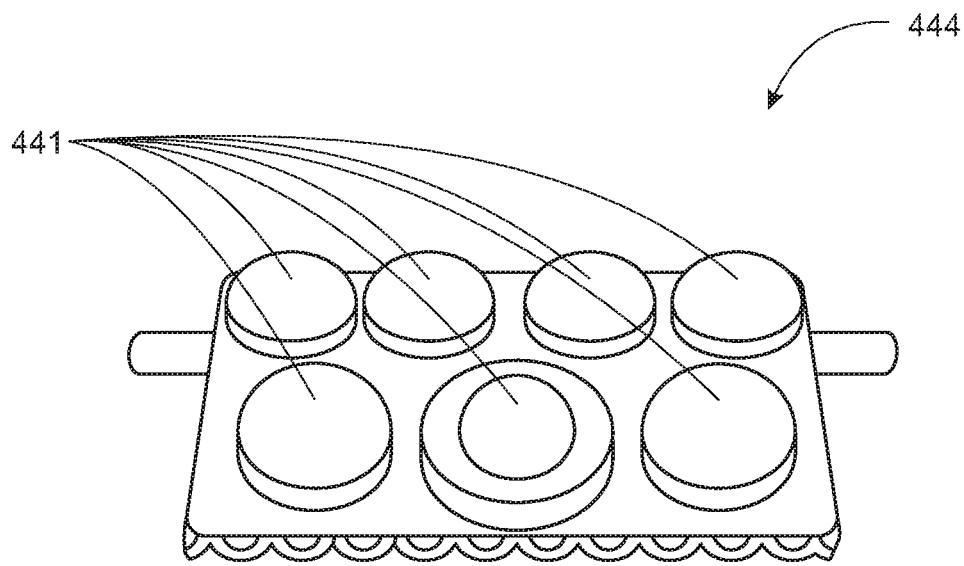
FIGS. 115 and 116 show two views of a cassette having several membrane pumps of FIGS. 113 and 114 in accordance with an embodiment of the present disclosure.
Figure 116:
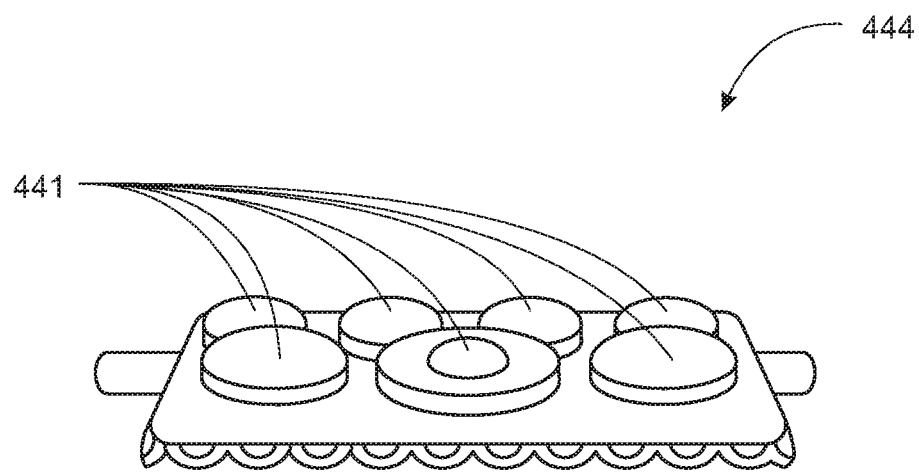

FIGS. 113 and 114 illustrate a piston pump 441 in accordance with another embodiment of the present disclosure. As shown in FIG. 113, piston pump 441 includes a disposable cassette 442 including a preformed membrane 440 and a cassette body 445. The preformed membrane 440 may be one or more of a PVC elastomeric such as, Sarlink, Pebax, Kraton, a Santoprene, etc. The preformed membrane 440 may be attached to the cassette body 445 using any method, including heat bonding, laser welding, using a solvent or adhesive bonding, ultrasonic welding or attachment, RF welding, or over molding. When the preformed membrane 440 is compressed, as shown in FIG. 114, the membrane will return to its original shape as shown in FIG. 113 after the piston 443 is withdrawn. FIGS. 115 and 116 show two views of a cassette 444 having several membrane pumps 441. The cassette 444 may be formed by a rigid body defining the cassette body with two elastic layers disposed around the rigid body. The rigid body may form the reservoir such that the elastic layer forms the preformed membrane as illustrated in FIGS. 113 and 114.

Figure 117:
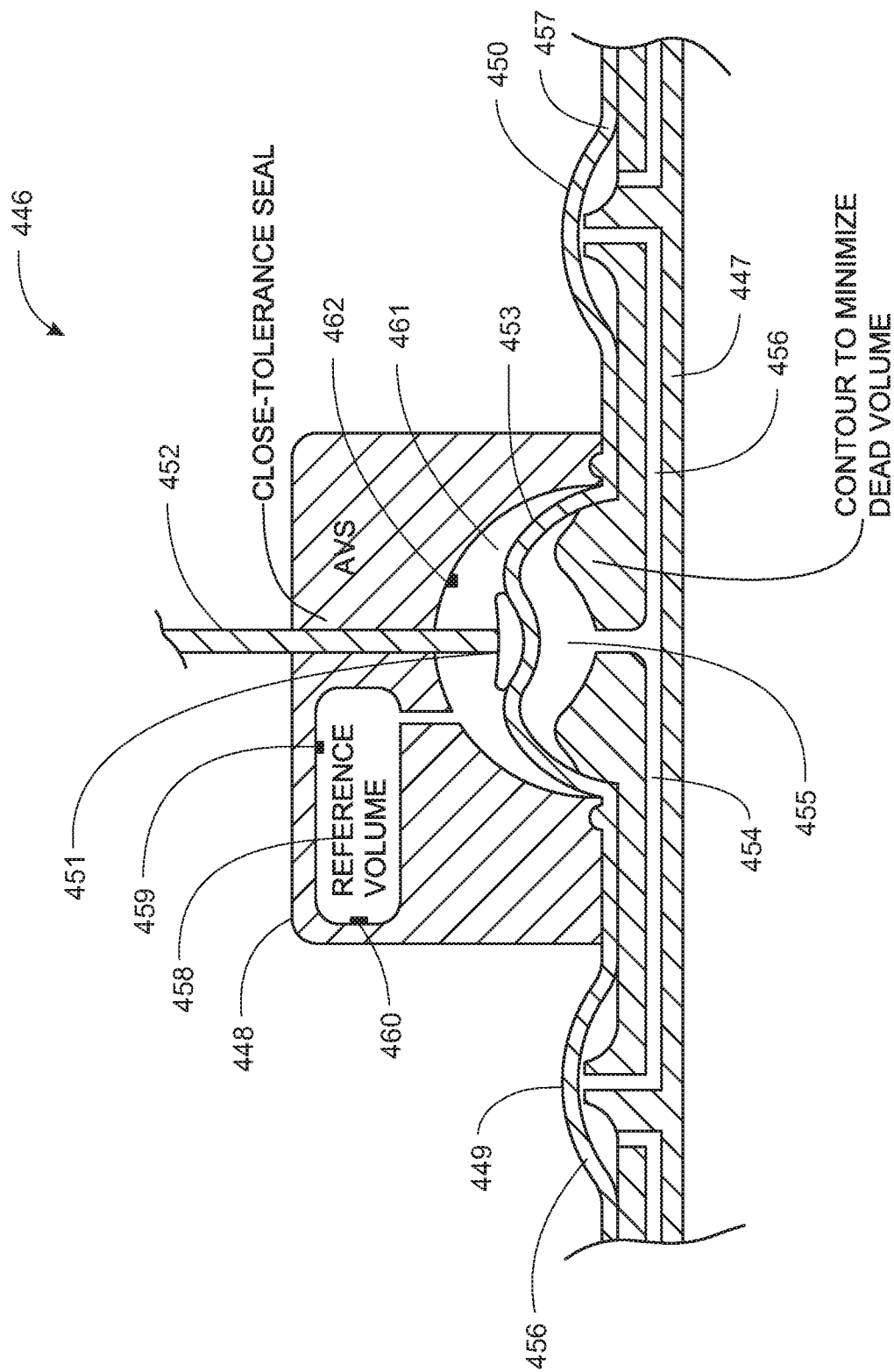
FIG. 117 shows a cassette having a membrane pump and volcano valves in accordance with an embodiment of the present disclosure.

FIG. 117 shows an assembly 446 having a cassette 447 that includes a membrane pump 451 and volcano valves 449 and 450 in accordance with an embodiment of the present disclosure. The membrane pump 451 includes a pump plunger 452 that interfaces with an membrane 451. As the plunger 451 reciprocates, fluid is draw from the fluid path 454 and out the fluid path 456. The volcano valve 449 is a one way valve that allows fluid into the fluid volume 455 from the volcano valve 449, but not in reverse. An actuator may press again the membrane 456 in some embodiments to help the one-way action of the volcano valve 449.

The volcano valve 450 is a one-way valve that allows fluid out of the fluid valve 455 through the fluid path 455 and the volcano valve 450 (but not in reverse). An actuator may press again the membrane 457 in some embodiments to help the one-way action of the volcano valve 450.

The assembly 446 also includes an AVS assembly 448. The AVS assembly includes a reference volume 458 having a speaker 459 and a microphone 460. The variable volume 461 includes a microphone 462. The speaker 459 and the microphones 460 and 462 are coupled to a processor 37 to measure the volume of the fluid volume 455 and coordinate the operation of the plunger 452 as described herein.

The plunger 452 may interface with one or more acoustic seals coupled to the AVS assembly 448. The processor 37 may be in operative communication with a position sensor (e.g., one coupled to a linear actuator of the plunger) to determine the position of the plunger 452. The processor 37 may account for the amount of volume the plunger 37 displaces as it reciprocates in and out of the variable volume 461; this volume correction may be done by directly measuring the plunger's (452) displacement or by measuring the a drive shaft angle coupled to a cam that moves the plunger 452.

Figure 118:
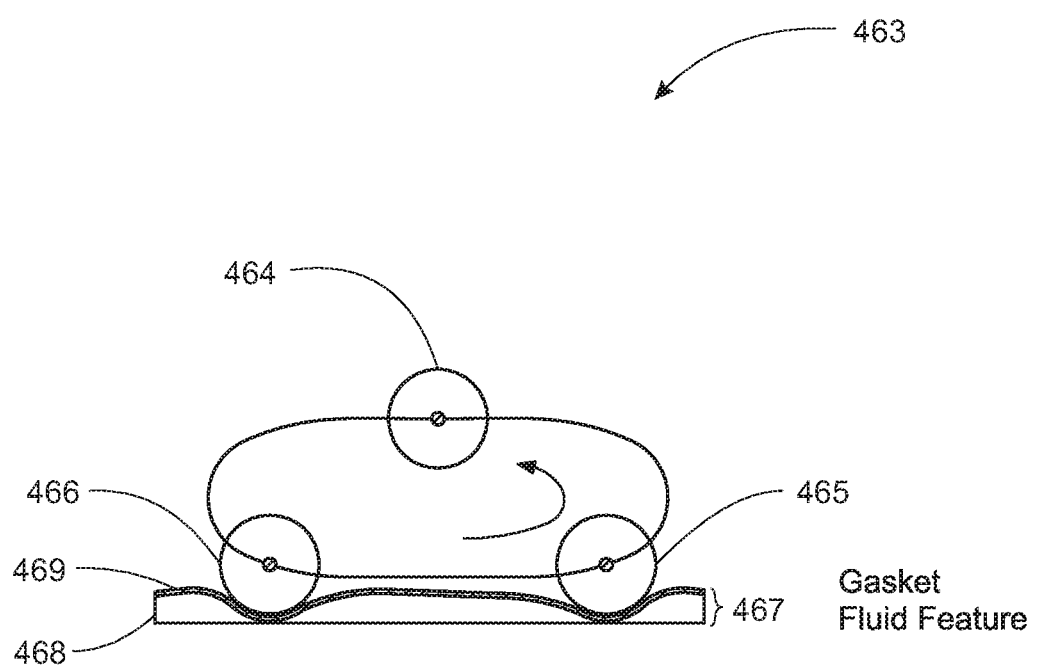
FIG. 118 shows a roller mechanism of a cassette-based pump in accordance with an embodiment of the present disclosure.

FIG. 118 shows a roller mechanism 463 of a cassette-based pump in accordance with an embodiment of the present disclosure. The roller mechanism 463 includes rollers 464, 465, and 466. The rollers 464, 465, and 466 move in a circular direction and apply a downward pressure again a cassette 467 having a cassette body 468 and a membrane 469. The rollers 464, 465, and 466 may be on a rail and may be spaced such that at least one roller engages the cassette 467. The roller mechanism 463 may be controlled by a stepper motor. The roller mechanism 463 may help pump liquid at a rat of, for example, 0.1 ml/hr.

The roller mechanism 463 may be used to estimate fluid flow based upon the speed of its movement, for example. The rollers 464, 465, and 466 may be disengaged from the cassette 467 to facilitate non-occluded flow and/or to create a desired free-flow condition.

Figure 119:
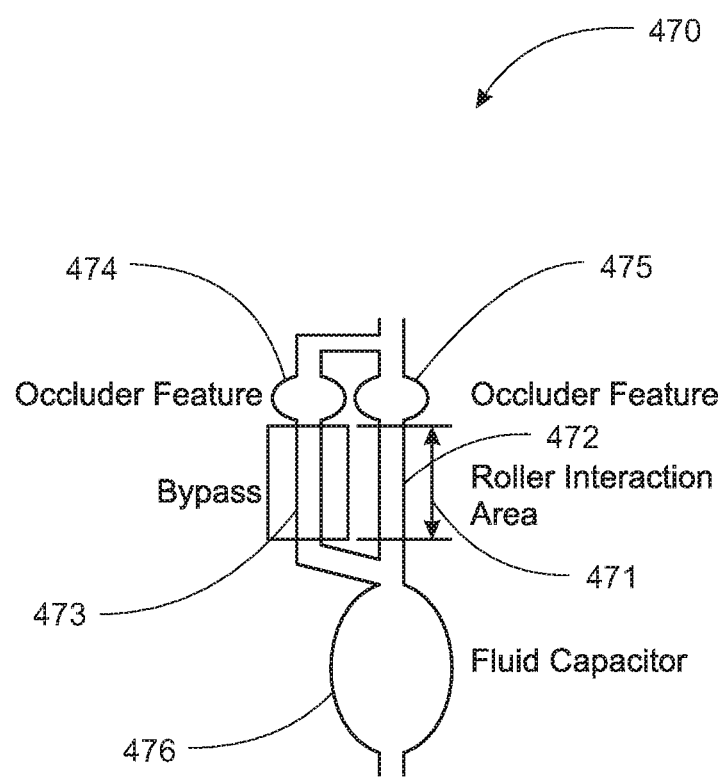
FIG. 119 shows the fluid paths of a cassette-based pump for use with the roller mechanism of FIG. 118 in accordance with an embodiment of the present disclosure.

FIG. 119 shows the fluid paths 470 of a cassette-based pump for use with the roller mechanism of FIG. 118 in accordance with an embodiment of the present disclosure. The fluid paths 470 include a roller interaction area 471 having a path 472 and a bypass path 473. The fluid paths 470 may included a vacuum formed film bonded to a ridged back to form raised flexible features. The path 470 includes occluders 474 and 475. The occluders 474 and 475 may be independently occluded. The paths 472 and 473 may have the same or different cross-sectional areas. The roller mechanism 463 may interact with the roller interaction area 472 to create different flow rates based on the rate of movement of the roller mechanism 463 and the total cross sectional area of all channels that are un-occluded (e.g., which of the occlude features 474 and 475 are engaged. The occluder features 474 and 475 may be volcano valves with a plunger that may be applied on the membrane of the volcano valve to stop fluid from flowing in any direction. In other embodiments, the occluders 474 and 475 may be a pinch valves coupled to an actuator, such as a solenoid.

The fluid paths 470 may include a fluid capacitor 476 to buffer the flow of liquid (e.g., smooth the liquid). Additionally or alternatively, an AVS assembly may be coupled to the fluid capacitor 476 to measure fluid flowing therethrough.

In another embodiment, one or more of the fluid paths 472 or 473 include a flat flexible film boded to a ridged back with the features molded into the rigid backing (cassette body). In this embodiment, the roller 463 has a feature that recesses into the channel 478 in order to pinch off the channel 478. This embodiment may also have molded-in features that allows a ball-head piston to variably restrict the flow through the channel 478 (e.g., the occlude features 474 and 475). The geometry of the features that recess into the channels and the piston head may be adjusted to allow different flow profiles based on the linear engagement of the piston. In one embodiment, the disposable has one channel 472 for the roller mechanism 463 and a second channel 473 that acts as a bypass from the roller area. The two channels 472 and 473 in conjunction with the occluders 474 and 475 allow the cassette (which may be disposable) to be used in a bypass mode or a pump mode. In some embodiments, the roller mechanism 463 of FIG. 119 is always engaged above the channel 478 but not over the bypass channel 473.

In one embodiment, the roller mechanism 463 may be used for high flow rates and the bypass 474 may be used for low flow rates. For example, in some specific embodiments, when the fluid paths 472 and 473 have a cross sectional area of 0.4 $cm^2$, the flow rates may be from 100 ml/hr to 1000 ml/hr by using a stepper motor to actuate the linear travel of the rollers from 250 cm/hr to 2500 cm/hr; the bypass 473 is used to achieve flow rates under 100 cm/hour.

Figure 120:
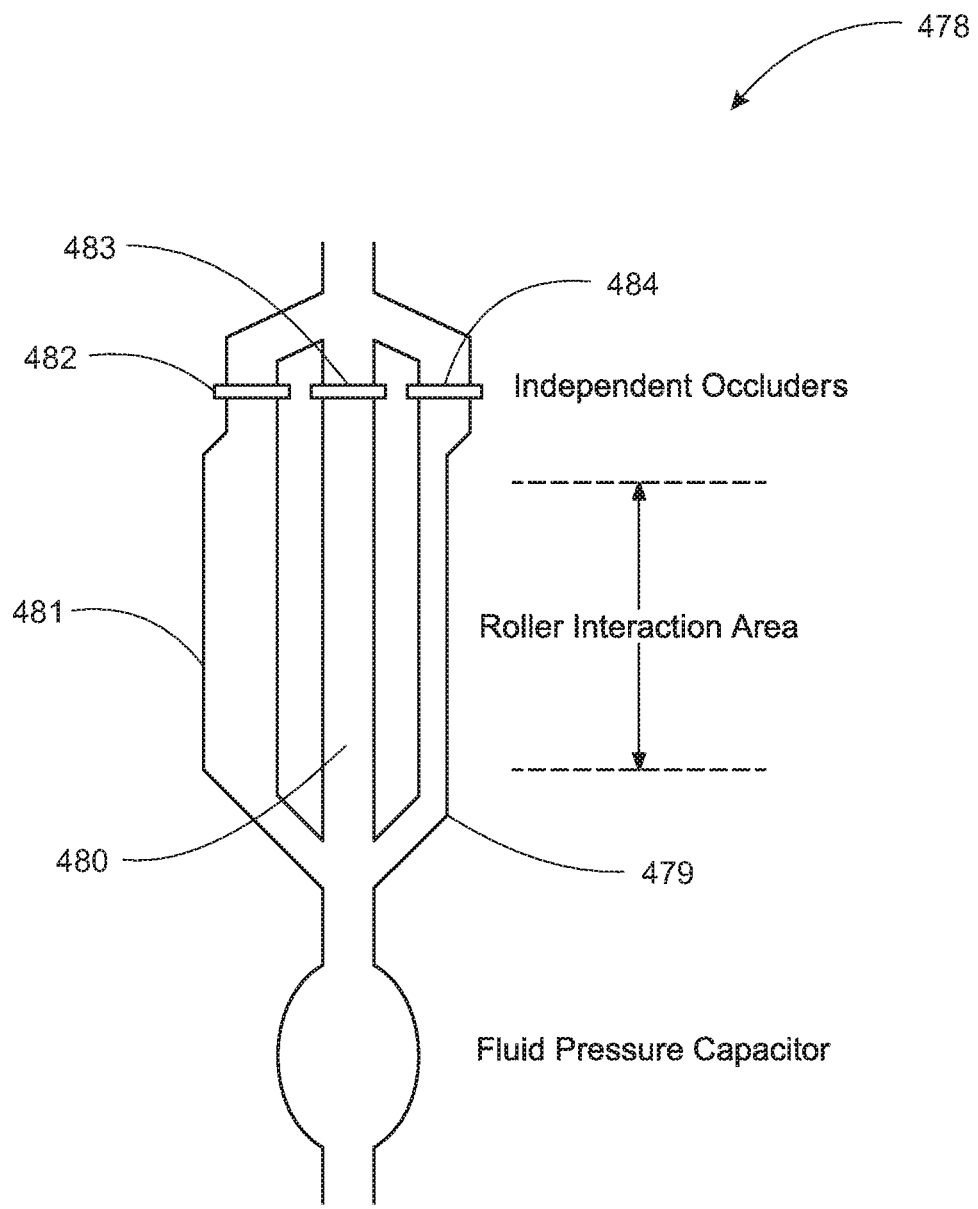
FIG. 120 shows the fluid paths of a cassette-based pump for use with the roller mechanism of FIG. 118 in accordance with an embodiment of the present disclosure.

FIG. 120 shows the fluid paths 478 of a cassette-based pump for use with the roller mechanism of FIG. 118 in accordance with an embodiment of the present disclosure. The fluid paths 478 include two paths 479 and 480, and a bypass path 481 The roller mechanism 470 of FIG. 118 interfaces with the fluid paths 470 and 480. The fluid paths 478 are also coupled to occluders 482, 483, and 484.

Figure 121:
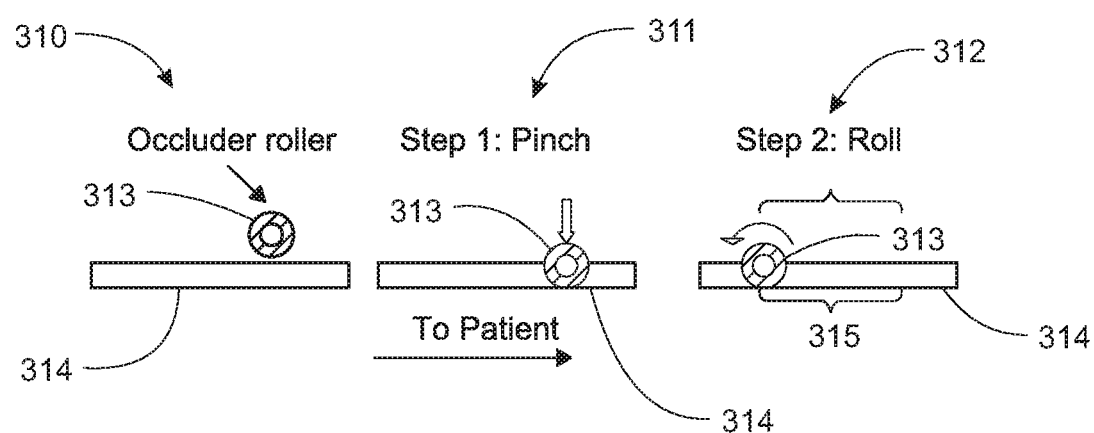
FIG. 121 shows the stages of an infiltration test using a roller in accordance with an embodiment of the present disclosure.

FIG. 121 shows the stages 310, 311, and 312 of an infiltration test in accordance with an embodiment of the present disclosure. The infiltration test illustrated by FIG. 121 includes an occluder roller 313 that is pressed against a tube 314 (as shown in stage 311) which is then drawn back through a rolling motion (shown in stage 314). The occluder roller 313 may be in the pumps 19, 20, and/or 21 (see FIG. 1) or in the infusion site monitor 26 (See FIG. 2). The monitoring client 6 can instruct the occluder roller 313 to perform an infiltration test. For example, the monitoring client 6 may instruct a stepper motor coupled to the roller occluder 313 to pull liquid out of the patient 5 (See FIG. 1). The monitoring client 6 may then receive an estimate of the amount of blood that enters into the infusion site monitor 26 (see FIG. 1) from the infiltration detector 32 (see FIG. 2). The infiltration detector 32 determines if the proper amount of blood is pulled into the infusion site monitor 26 during the stages of the infiltration test, or alternatively, the monitoring client 6 may receive raw data from the infiltration detector 32 to determine if the proper amount of blood is pulled into the infusion site monitor 26 (See FIGS. 1 and 2).

As previously mentioned, the infiltration detector 32 of FIG. 2 may be a camera-based infiltration detector 32 as described above in relation to the system 108 of FIG. 33 when used to capture images illustrated by FIGS. 37 and 38. FIGS. 37 and 38 illustrate the images taken by the camera 109 of the system 108 of FIG. 33 for estimating blood that enters into the infusion site monitor 26 of FIG. 2 during an infiltration test. That is, the system 108 of FIG. 33 may be within the infiltration detector 32 of the infusion site monitor 26 (see FIG. 2) for detecting blood when the roller occluder 313 of FIG. 121 actuates to draw blood into the infusion site monitor 26 of FIG. 2.

During stage 312, a drawback volume 315 thereby is pulled from a patient 5. A camera 109 of FIG. 33 at an infusion site monitor 26 (e.g., within the infiltration detector 32) may determine if blood is drawn back from the patient as shown in FIGS. 37 and 38. If no blood is pulled into the tube within the infusion site monitor 26 (see FIG. 2), it may be an indication that an infiltration has occurred. Additionally or alternatively, the camera 109 of FIG. 33, in conjunction with a pressure sensor 33 and/or volume sensor 169, may be used to determine what amount of pressure causes the blood to be pulled back into the tube 41.

In some embodiments, the fluid is returned to the patient 5 by actuating the rolling occluder 313 in the opposite direction, or by lifting the occluder 313 off of the tube 314. In an additional embodiment, a compliant upstream reservoir may be included which holds the drawback fluid (valves may direct the reverse fluid into the complaint upstream reservoir). The upstream reservoir may be coupled to an AVS chamber as described herein or is a separate chamber. The AVS chamber may have the drawback fluid volume measured by a processor coupled thereto and/or communicated to the monitoring client 6. Additionally or alternatively, the pumps 19, 20, and 21 are stopped during an infiltration test or may assist in draw back fluid, in conjunction with the rolling occluder 313 or in lieu of the rolling occluder 313.

In additional embodiments, a compliant chamber is used between the roller occluder 313 and the patient 5. The displacement volume of the chamber membrane during the drawback is monitored using, for example, AVS or an optical sensor. The deflection of the chamber membrane is proportional to the pressure in the fluid tube 314, the amount of the deflection of the membrane is proportional to the effort to draw blood into the tubing. A threshold amount of drawback pressure needed to draw blood out of the patient 5 is used to determine if an infiltration exists. In addition, if a threshold amount of time is required to drawback, this may be used as an indication that a downstream occlusion exists or an infiltration exists. Therefore, the chamber membrane could be monitored over time and detect a rate in pressure change that is an indication of the drawback effort (as determined by the processor 37 of FIG. 2).

Figure 122:
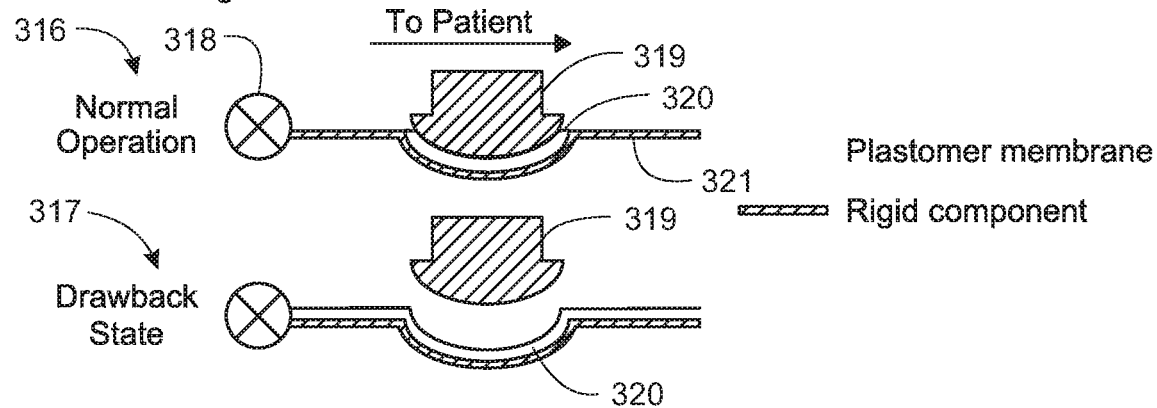
FIG. 122 shows the stages of an infiltration test using a piston in accordance with an embodiment of the present disclosure.

FIG. 122 shows stages of an infiltration test 316 and 318 in accordance with an embodiment of the present disclosure. A piston 319 may be disposed anywhere along the fluid tube or in a pump 19, 20 or 21 of FIG. 2, or the piston 319 may be disposed in the infusion site monitor 26 of FIG. 2. In stage 316, a valve 318 remains open and the piston 319 is press against a membrane 320, but fluid continues to flow to the patient. In stage 317, the valve 318 is closed, and the piston 319 is lifted up, after which the resiliency of the membrane 320 pulls back and draws fluid backwards. The drawn back fluid returns to the patient when the piston actuates back to the resting state as shown in stage 316. A camera 109 of FIG. 33 at an infusion site monitor 26 in the infiltration detector 32 (see FIG. 2) may determine if blood is drawn back from the patient 5 as described above. If no blood is pulled into the tube within the infusion site monitor 26 (see FIG. 2), it may be an indication that an infiltration has occurred.

In some embodiments, the elastomer surface area and elastomer properties are selected in combination with the chamber volume such that there is a maximum determined fluid pressure that is applied during the drawback, e.g., the properties may be chosen such that there is sufficient drawback pressure to draw back blood into the monitoring area, however, there would be insufficient pressure to draw back the blood into the monitoring when an infiltration has occurred. Additionally or alternatively, the blood must be drawn back within a predetermined amount of time; otherwise, an infiltration condition may be determined to exist. The amount of time allowed for the drawback can be used with predetermined criteria to determine if an infiltration has occurred (i.e., allow the drawback chamber to persist with drawback for a predetermined amount of time while looking for the indication of blood using the camera 109, and determining that an infiltration has occurred if no blood is detected by the infiltration sensor 32 (see FIGS. 2 and 33), e.g., a camera 109, before the predetermined amount of time has passed).

Figures 123, 124:
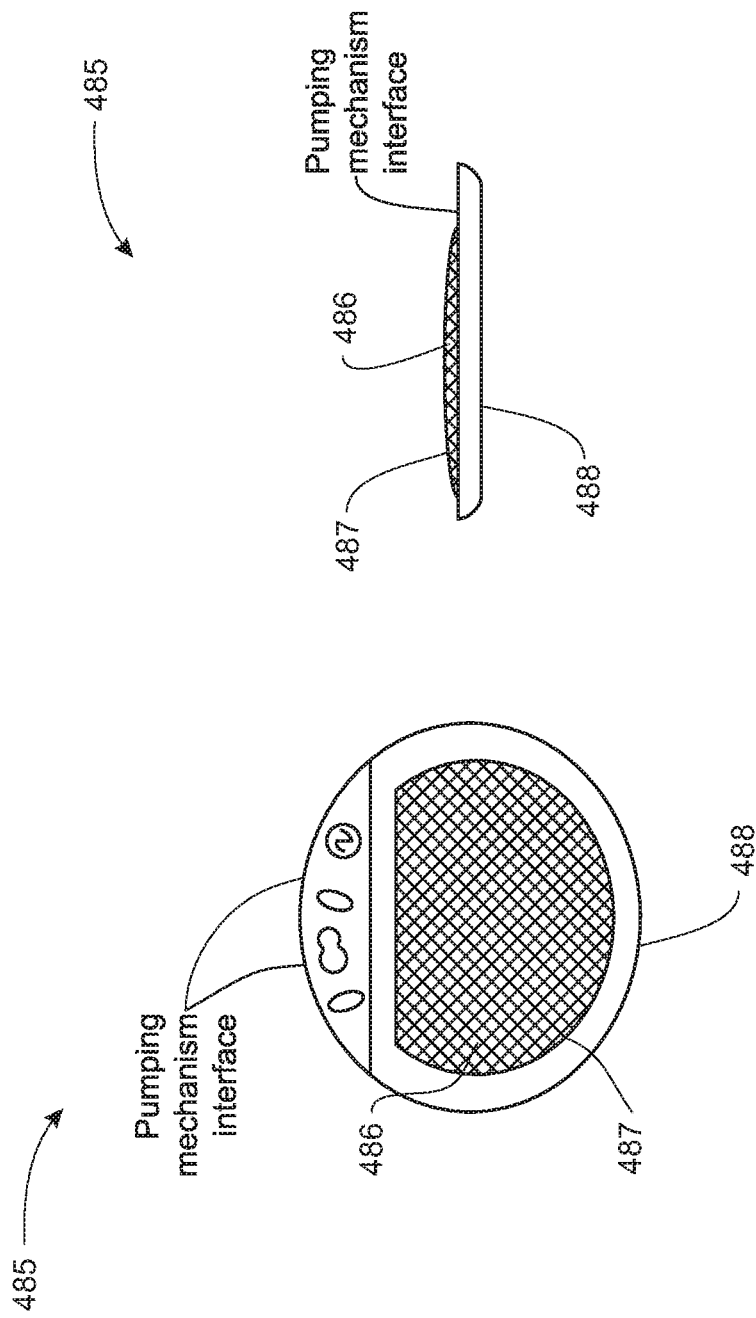
FIGS. 123 and 124 show a cell-base reservoir in accordance with an embodiment of the present disclosure.

FIGS. 123 and 124 show a cell-based reservoir 485 in accordance with an embodiment of the present disclosure. The cell-based reservoir 485 may be the reservoirs 2, 3, or 4 of FIG. 1. The cell-based reservoir 485 includes cell foam 486 capable of absorbing liquid constructed of a compatible material to dampen the motion of an infusate. The cell foam 486 may include a membrane 487. The reservoir base 488 may be constructed using a in a rigid, semi-rigid, or non-rigid fluid reservoir to increase infusate stability in the presence of fluid shear.

For example, when using a semi-rigid base 488, the cell foam 486 may include an open-cell silicone foam to fill the normally empty reservoir cavity. The cell foam 486 may help prevent sloshing of the reservoir contents to help preserve the stability of the infusate in some embodiments. By choosing a foam with a high degree of compressibility relative to both the collapsible membrane's 487 spring rate and the pumping mechanism, the residual volume of the cell foam 486 may be minimal in some embodiments.

FIGS. 125 and 126 show a tube-based reservoir 489 in accordance with an embodiment of the present disclosure. The cell-based reservoir 489 may be the reservoirs 2, 3, or 4 of FIG. 1. The tube-based reservoir 489 includes a tubing reservoir 490 that can house a liquid. The tube-based reservoir 489 may be vented through a filter 491. The filter 491 may be part of the vent of FIGS. 51-55. For example, a pumping mechanism (e.g., a pump as described herein but not shown in FIGS. 125 and 126) may draw fluid from the tubing reservoir 490 stored in a rigid reservoir cavity 492 (the base 492 may be flexible, rigid, semi-rigid, and/or part of a cassette in some embodiments). The tubing reservoir 490 can help prevent sloshing of the reservoir contents thereby helping preserve infusate stability in some embodiments.

Figure 127:
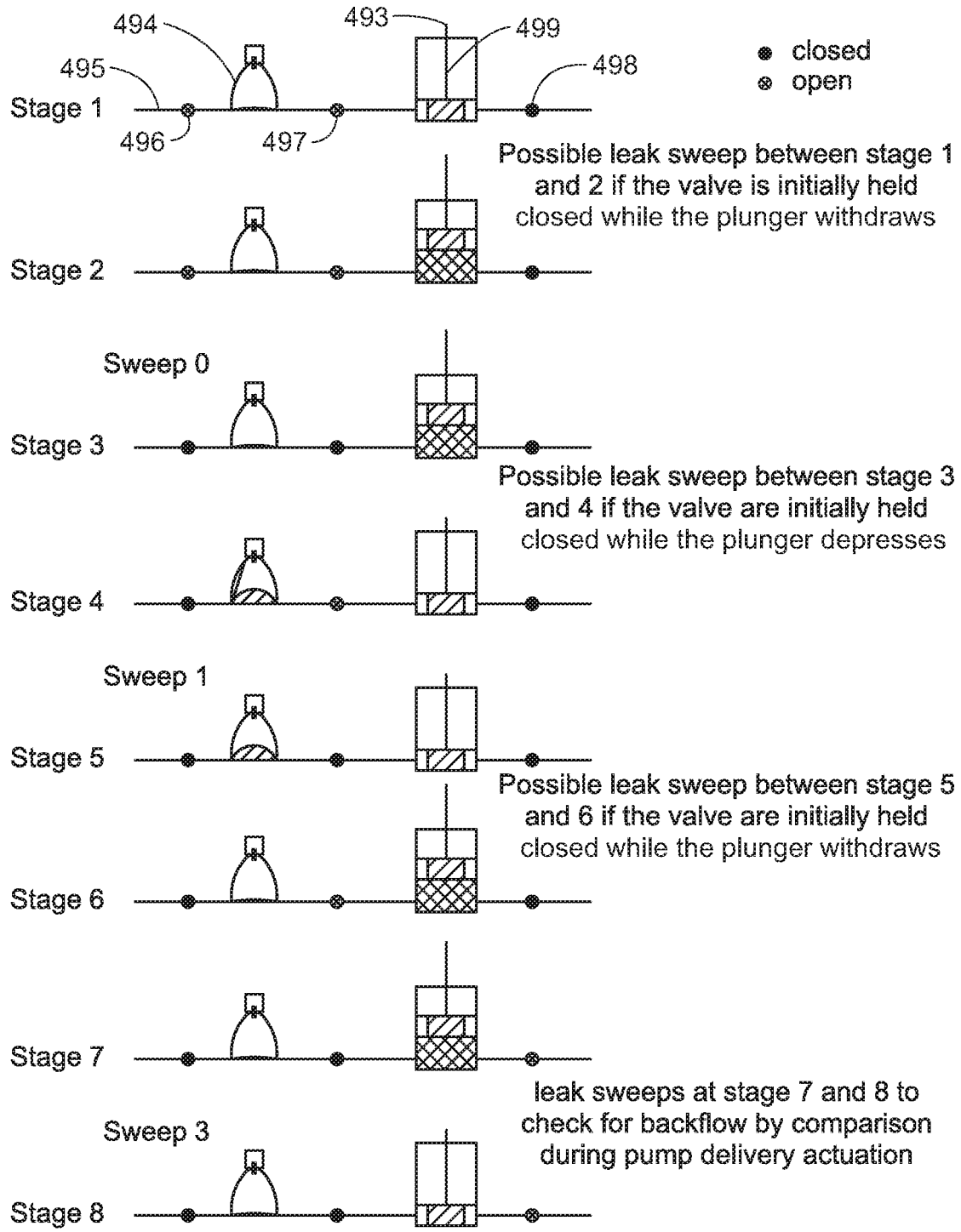
FIG. 127 shows several stages illustrating a method for operating a plunger pump in conjunction with an AVS assembly in accordance with an embodiment of the present disclosure.

FIG. 127 shows stages 1-8 illustrating a method for operating a plunger pump 493 in conjunction with an AVS assembly 494 in accordance with an embodiment of the present disclosure. A fluid path 495 includes valves 496, 497, and 498.

Stage 1 shows the valve 498 closed with valves 496 and 497 open. The valve 497 may be closed while the plunger 499 withdraws to check if the valves 498 and 497 are leaking. For example, a constant force may be applied to the plunger 499 drawing the plunger up (e.g., from a spring) and either valves 496 and/or 497 may be closed. If the plunger 499 moves upwards beyond a predetermined amount or more quickly than predetermined speed, the processor 37 (see FIG. 2) may determine that a leak has occurred. Additionally or alternatively, the valve 496 may be closed, and the plunger 499 applies an upwards force by a predetermined amount of time and then applies a downward force. The AVS assembly 494 may then perform an AVS sweep. If the fluid within the AVS assembly (e.g., measured by the volume of the fluid volume) is beyond a predetermined amount) then the processor may determine that one of the valves 496 and 498 may be leaking.

Stage 2 shows the fluid being drawn into the plunger pump 493. Stage 3 performs an AVS sweep. Between stages 3 and 4, a leak check may be performed, e.g., the valves 497 and 498 may remain closed while the plunger 493 applies a downwards force. If there is movement beyond a predetermined amount, the one or both of the valves 497 and 498 may be determined to be leaking by the processor. In Stage 4, the volume of fluid from the plunger pump 493 is transferred to the membrane of the AVS assembly 494. Stage 5 there is an AVS sweep to determine the fluid in the AVS assembly 494. In stage 6, the valve 497 is opened, and the volume of fluid is transferred from the AVS assembly 494 to the plunger pump 493. Between stages 5 and 6, the valve 497 may temporarily be left closed to perform another valve leak check.

In stage 7, the valve 497 is closed. In stage 8, the fluid in the plunger pump 493 is discharged. Between stages 7 and 8, the valve 498 may initially remain closed to determine if one or both of the valves 497 and 498 is leaking.

Figure 128:
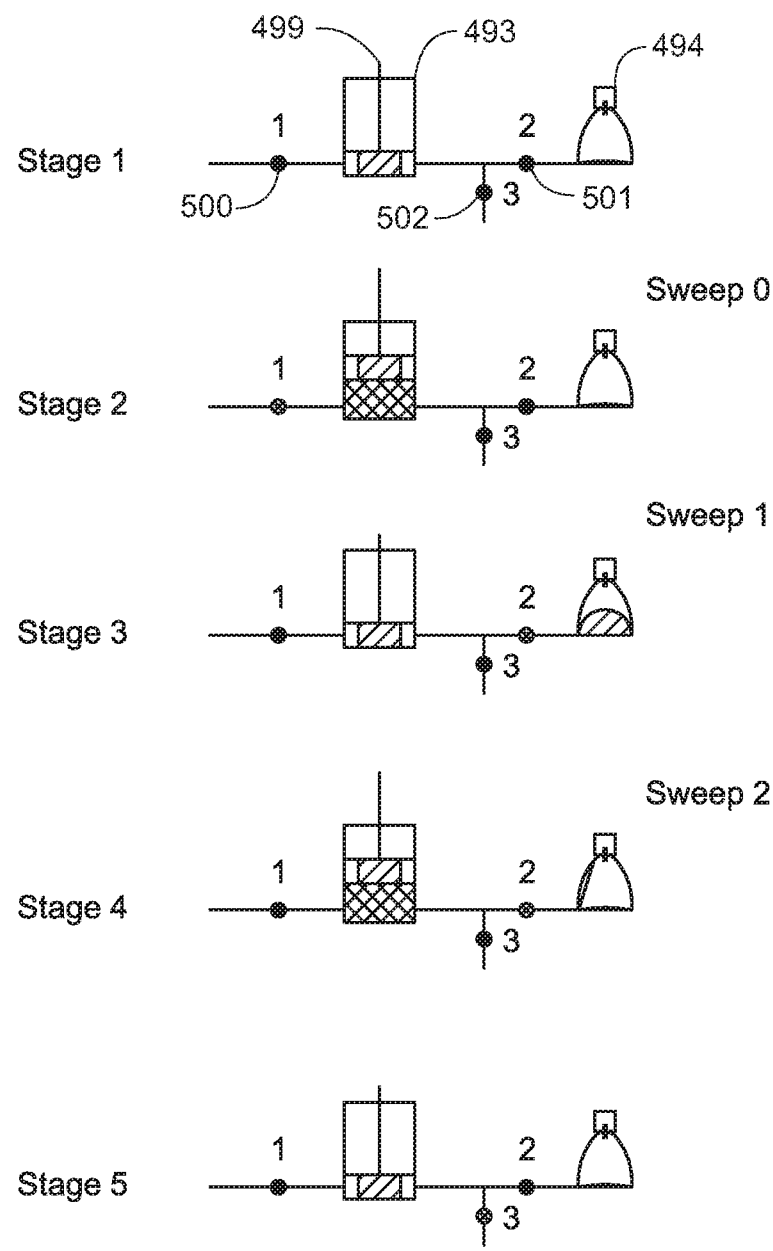
FIG. 128 shows several stages illustrating a method for operating a plunger pump in conjunction with an AVS assembly in accordance with another embodiment of the present disclosure.

FIG. 128 shows several stages illustrating a method for operating a plunger pump in conjunction with an AVS assembly in accordance with another embodiment of the present disclosure. Between stages 1 and 2, a leak test may be performed by keeping the valve 500 temporarily closed while an upwards force is applied to the plunger 499. In stage 2, fluid is drawn into the plunger pump 493. Also during stage 2 an AVS sweep may be performed by the AVS assembly 494. In stage 3, the fluid is transferred to the AVS assembly 494. Also during stage 2 an AVS sweep may be performed by the AVS assembly 494. A leak test may be performed between stages 2 and 3 (e.g., by keeping the valve 501 closed while applying a downward force on the plunger 499. In stage 4, the fluid is drawn from the AVS assembly 494 into the plunger 493. Also during stage 2 an AVS sweep may be performed by the AVS assembly 494. Between stages 3 and 4, a leak test may be performed by keeping the valve 501 temporarily closed while an upwards force is applied to the plunger 499. In stage 5, the fluid is discharged from the plunger 493 to the patient (i.e., past the AVS assembly 494). A leak test may be performed between stages 4 and 5, by keeping the valve 501 temporarily closed and/or to check for backflow. A leak test may also be performed during stage 5 to check for backflow.

Figure 129:
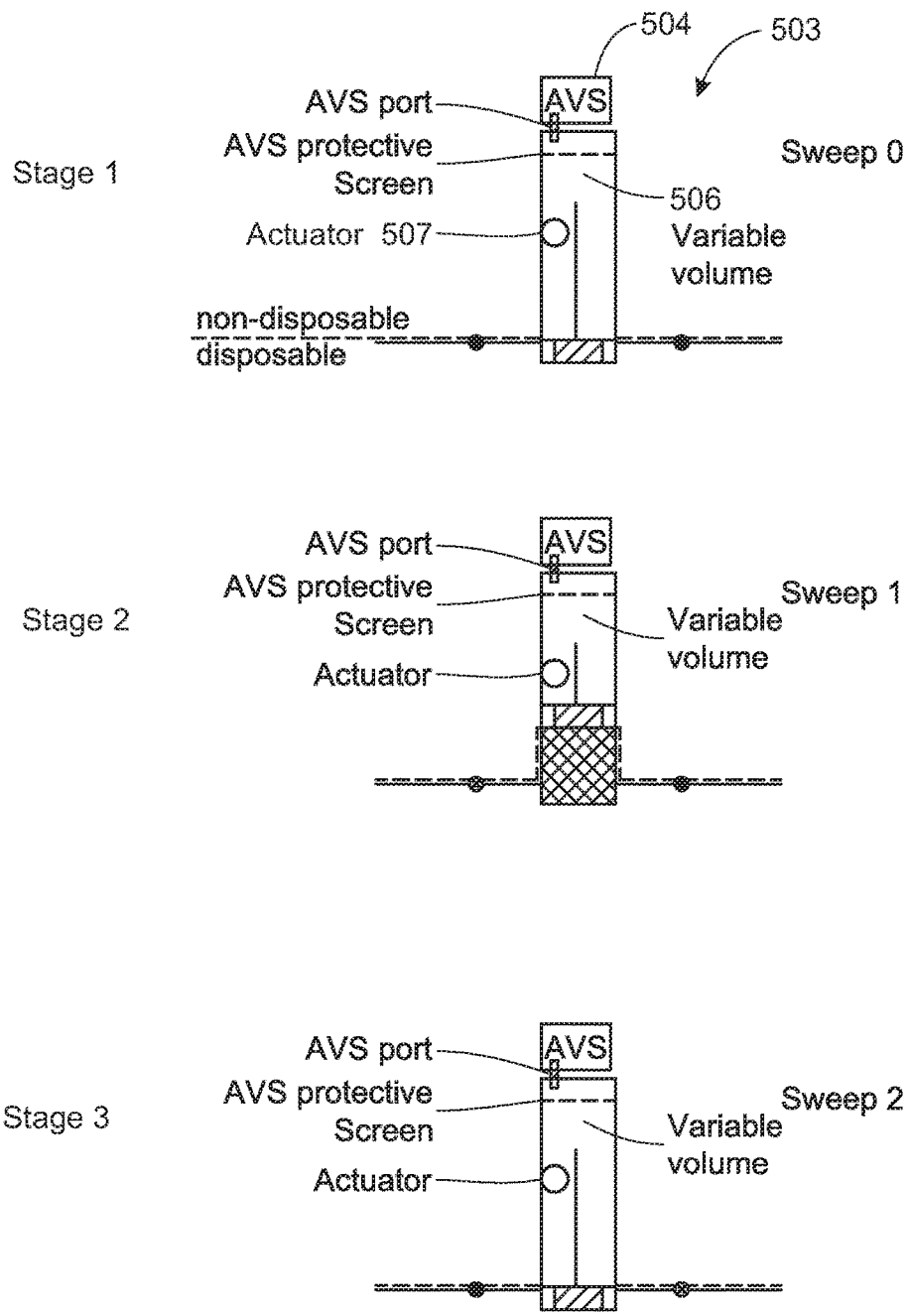
FIG. 129 shows several stages illustrating a method for using a plunger pump having an AVS assembly in accordance with an embodiment of the present disclosure.

FIG. 129 shows several stages illustrating a method for using a plunger pump 503 having an AVS assembly 504 in accordance with an embodiment of the present disclosure. In stage 1, an AVS sweep is performed. In stage 2, fluid is drawn into the variable volume 506. In stage 2, after fluid is drawn into the variable volume 453, another AVS sweep is performed. In stage 3, the fluid is discharged. In stage 3, after the fluid has discharged, an AVS sweep may be performed. Note that the actuator 507 is within the variable volume 506. Therefore, the movement of the actuator 507 does not affect the volume of the variable volume 506.

Figure 130:
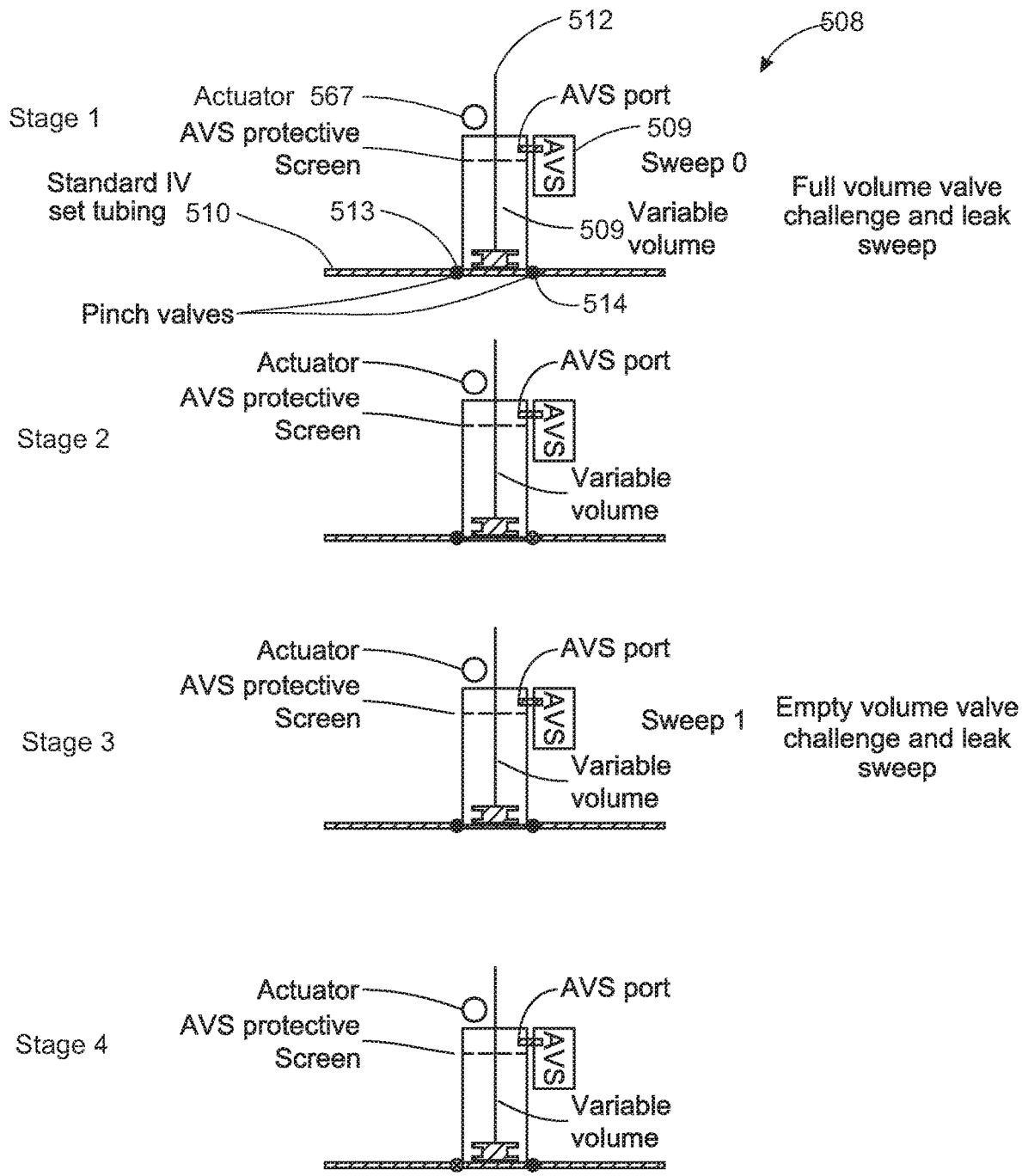
FIG. 130 shows several stages illustrating a method for using a plunger pump having an AVS assembly in accordance with an embodiment of the present disclosure.

FIG. 130 shows several stages illustrating a method for using a plunger pump 508 having an AVS assembly 509 in accordance with an embodiment of the present disclosure. The actuator 507 is located outside of the variable volume 509. The plunger pump 508 uses a standard IV set 510 such that the compliance of the tubing 510 draws liquid in during stage 4. Stage 2 discharges the liquid. The stages 1-4 may be repeated.

Stage 1, an AVS sweep is performed by the AVS assembly 509 and a downward force may be applied to the plunger 512 with both of the pinch valves 513 and 514. In stage 2, the fluid volume is discharged. In stage 3, the plunger 512 is retracted, after which an AVS sweep may be performed to determine if the valves 513 and 514 are leaking (e.g., the compliance of the tubing 455 may provide a negative pressure within the tubing 510.

Figure 131:
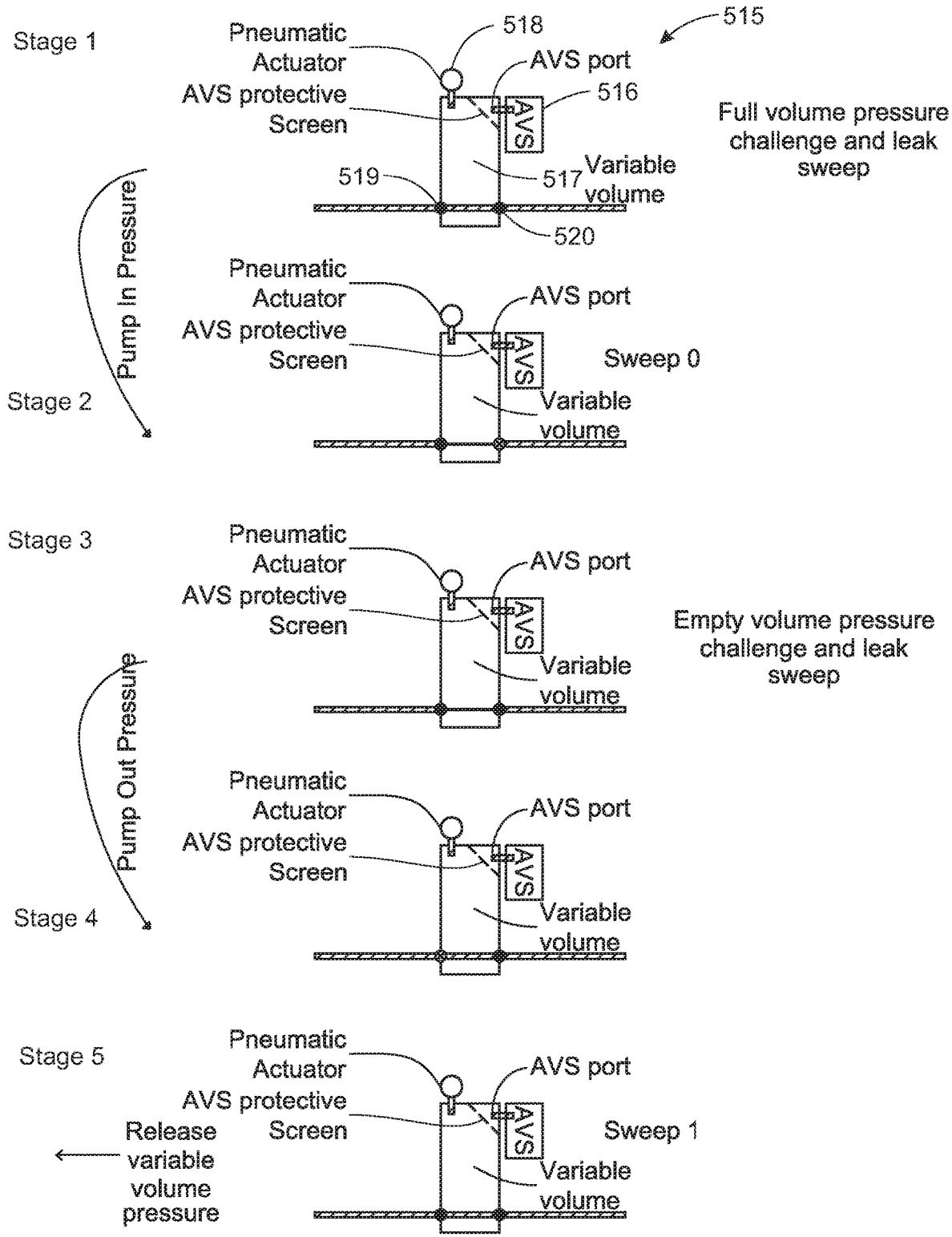
FIG. 131 shows several stages illustrating a method for using a plunger pump having an AVS assembly in accordance with an embodiment of the present disclosure.

FIG. 131 shows several stages 1-5 illustrating a method for using a plunger pump 515 having an AVS assembly 516 in accordance with an embodiment of the present disclosure. The plunger pump 515 draws fluid into and out of the variable volume 517 via a pneumatic actuator 518. During stage 1, a positive and/or negative pressure may be applied to the variable volume 518 with both of the valves 519 and 520 closed. During stage one, one or more AVS sweeps may be performed by the AVS assembly 516. If the volume estimated by the AVS assembly 516 changes when both of the valves 519 and/or 520, then the processor 37 may determine that a leak in one or both of the valves 519 and/or 520 exists.

During stage 3, a positive and/or negative pressure may be applied to the variable volume 518 with both of the valves 519 and 520 closed. During stage one, one or more AVS sweeps may be performed by the AVS assembly 516. If the volume estimated by the AVS assembly 516 changes when both of the valves 519 and/or 520, then the processor 37 may determine that a leak in one or both of the valves 519 and/or 520 exists.

Figure 132:
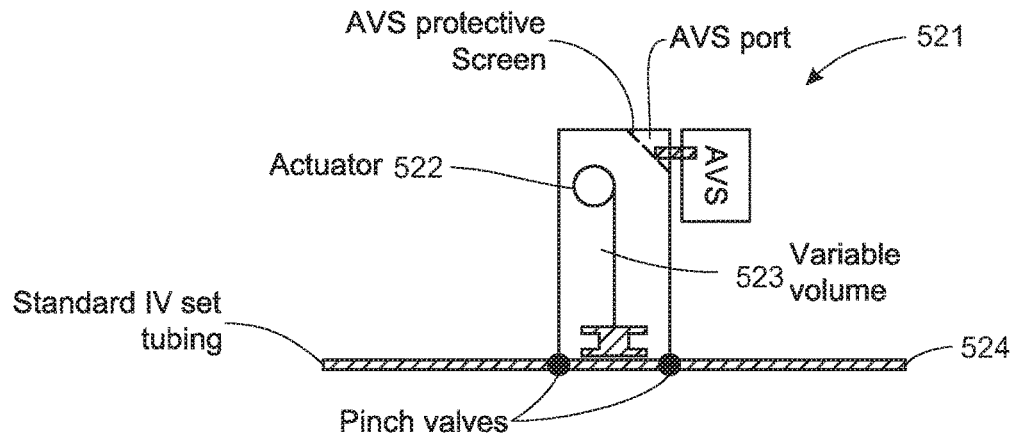
FIG. 132 shows a plunger pump with an actuator inside the variable volume for use with a standard IV set tubing in accordance with an embodiment of the present disclosure.

FIG. 132 shows a plunger pump 521 with an actuator 522 inside the variable volume 523 for use with a standard IV set tubing 524 in accordance with an embodiment of the present disclosure.

Figure 133:
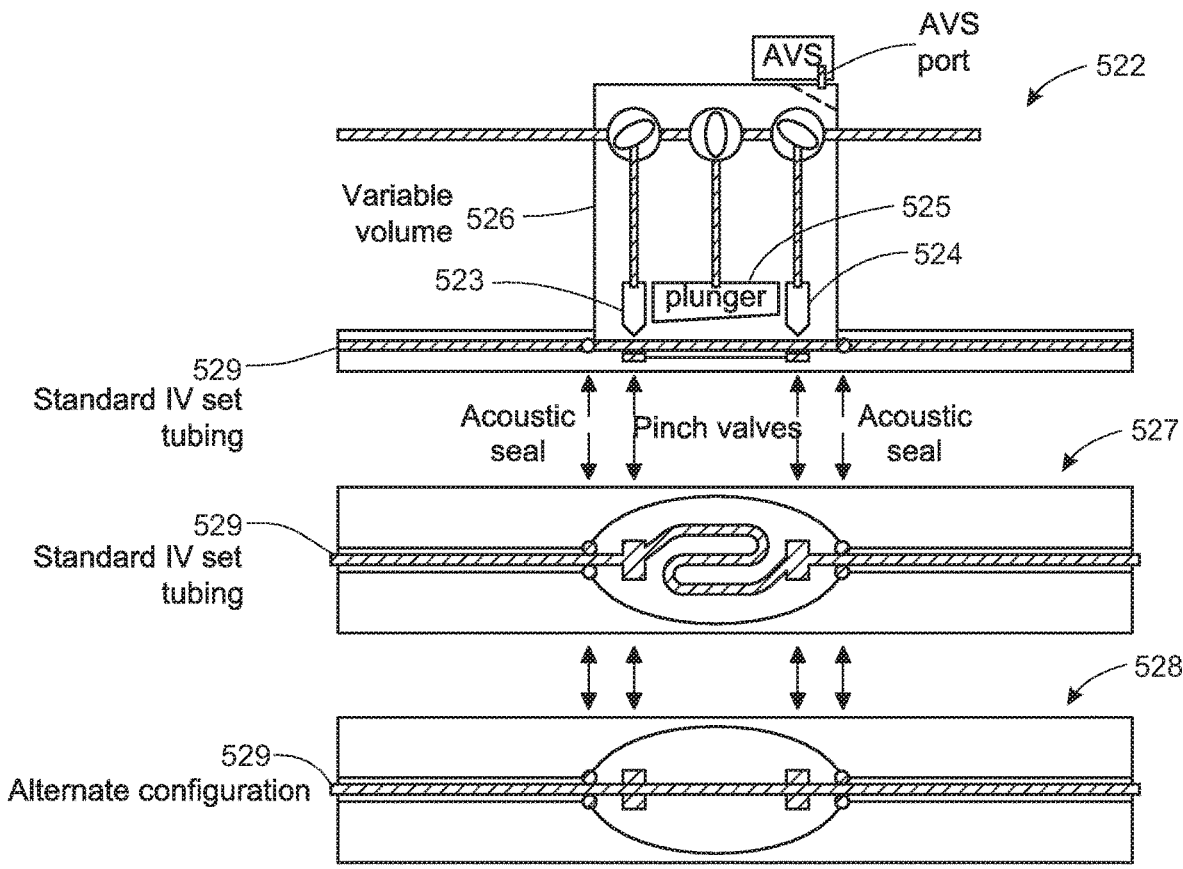
FIG. 133 shows several views of a cam-driven linear peristaltic pump having pinch valves and a plunger inside a variable volume in accordance with an embodiment of the present disclosure.

FIG. 133 shows several views of a cam-driven linear peristaltic pump 522 having pinch valves 523 and 524 and a plunger 525 inside a variable volume 536 in accordance with an embodiment of the present disclosure. The cross-sectional views 527 and 528 show two different standard IV set tubing 529 configurations below the plunger 525.

Figure 134:
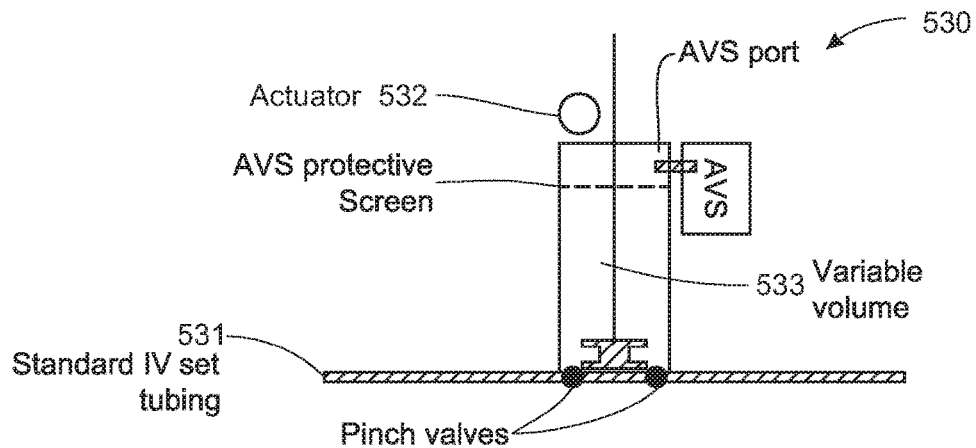
FIG. 134 shows a plunger pump for use within a standard IV set tubing with an actuator outside of the variable volume in accordance with an embodiment of the present disclosure.
Figure 135:
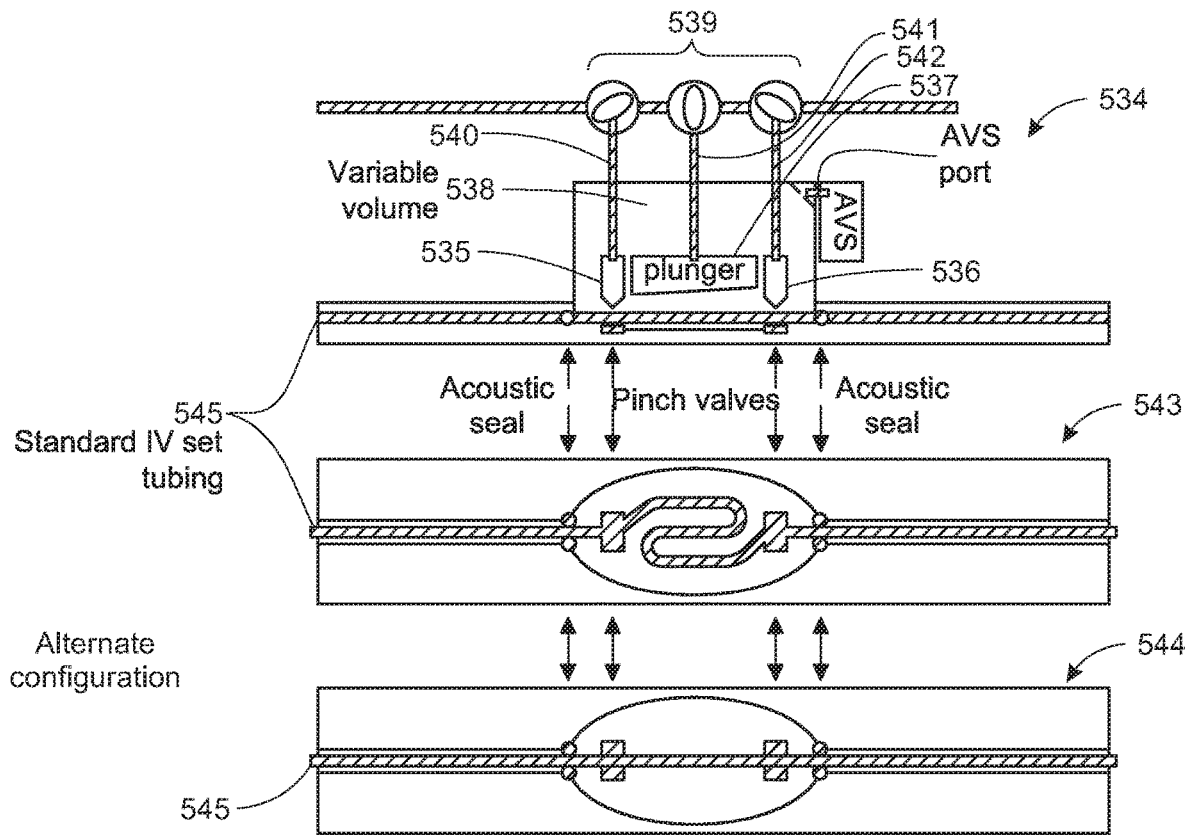
FIG. 135 shows several views of a cam-driven linear peristaltic pump having pinch valves and a plunger inside a variable volume with a corresponding cam mechanism outside of the variable volume in accordance with an embodiment of the present disclosure.

FIG. 134 shows a plunger pump 530 for use within a standard IV 531 set tubing with an actuator 532 outside of the variable volume 533 in accordance with an embodiment of the present disclosure. FIG. 135 shows several views of a cam-driven linear peristaltic pump 534 having pinch valves 535 and 536 a plunger 537 inside a variable volume 538 with a corresponding cam mechanism 539 outside of the variable volume 538 in accordance with an embodiment of the present disclosure. As the cam followers 540, 541, and 542 move in and out of the variable volume 535, the processor 37 of FIG. 2 may adjust the measured volume to account for the changes in volume the cam followers 540, 541, and 542 affect the variable volume. Cross-section views 543 and 544 show two different configuration of the standard IV set tubing 545 for the plunger 537 to interface with.

Figure 136:
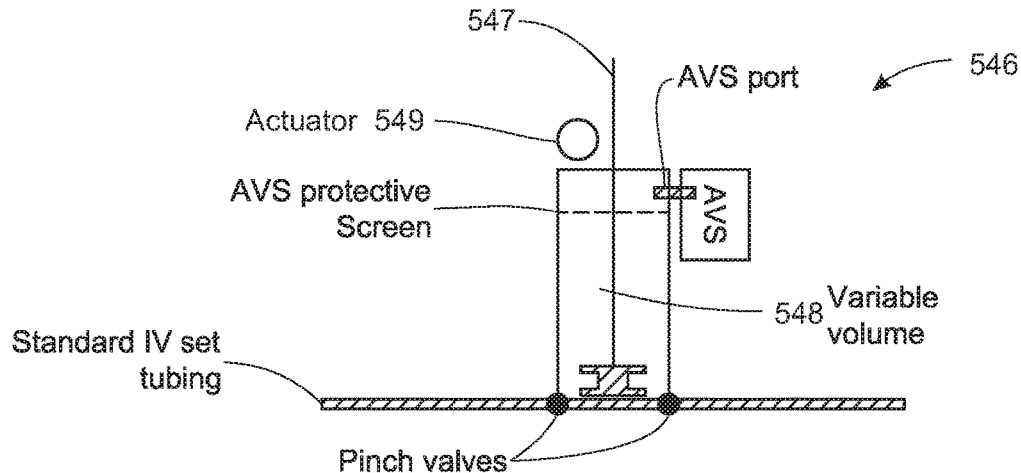
FIG. 136 shows a plunger pump having a plunger inside a variable volume with an actuator outside of the variable volume in accordance with an embodiment of the present disclosure.

FIG. 136 shows a plunger pump 546 having a plunger 547 inside a variable volume 548 with an actuator 549 outside of the variable volume 548 in accordance with an embodiment of the present disclosure. The processor 37 is coupled to a position sensor of FIG. 2 to account for the volume of the shaft of the plunger 547 as it moves in and out of the variable volume 548.

Figure 137:
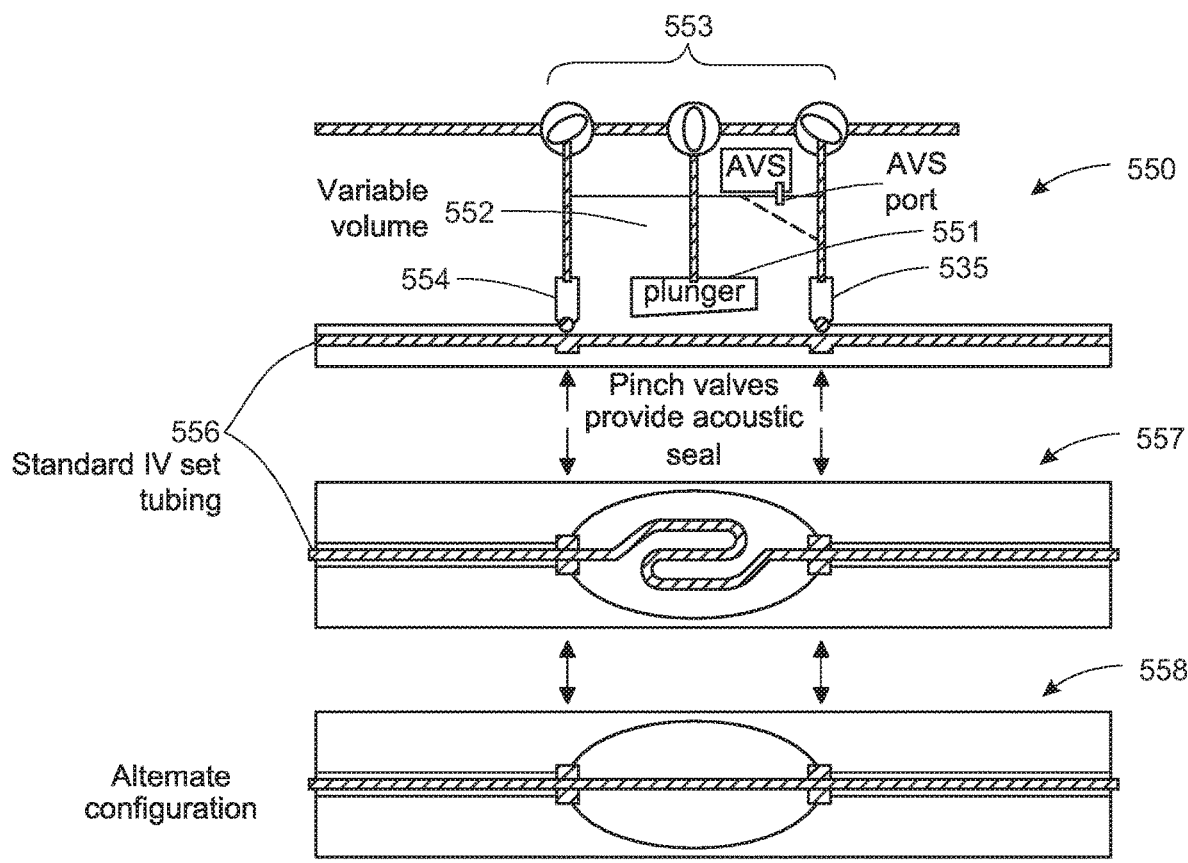
FIG. 137 shows a cam-driven linear peristaltic pump having a plunger inside a variable volume with a corresponding cam mechanism outside of the variable volume and pinch valves on the housing of the variable volume in accordance with an embodiment of the present disclosure.

FIG. 137 shows a cam-driven linear peristaltic pump 550 having a plunger 551 inside a variable volume 552 with a corresponding cam mechanism 553 outside of the variable volume 552 and pinch valves 554 and 555 on the housing of the variable volume 552 in accordance with an embodiment of the present disclosure. The pinch valves 554 and 555 may also form the acoustic seal for interface of the variable volume 552 and the standard IV set tubing 556. Two cross-sectional views 557 and 558 are shown to illustrate the configuration of the interface of the plunger 551 with the standard IV set tubing 556.

Figure 138:
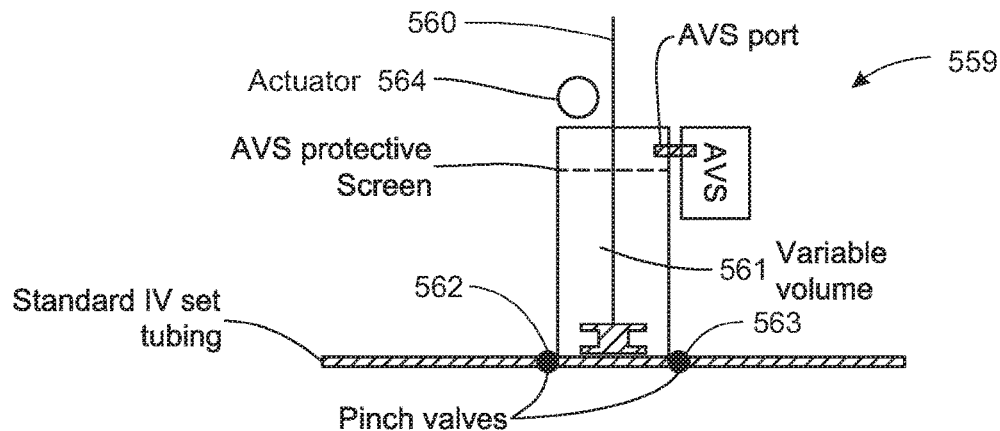
FIG. 138 shows a plunger pump having a plunger inside a variable volume and pinch valves outside of the variable volume in accordance with an embodiment of the present disclosure.

FIG. 138 shows a plunger pump 559 having a plunger 560 inside a variable volume 561 and pinch valves 562 and 563 outside of the variable volume 561 in accordance with an embodiment of the present disclosure. The actuator 564 (e.g., a cam mechanism, linear motor, linear actuator, etc.) is located outside of the variable volume 561. The processor 37 of FIG. 2 can compensate for the shaft of the plunger 560 as it enters and exits the variable volume 561.

Figure 139:
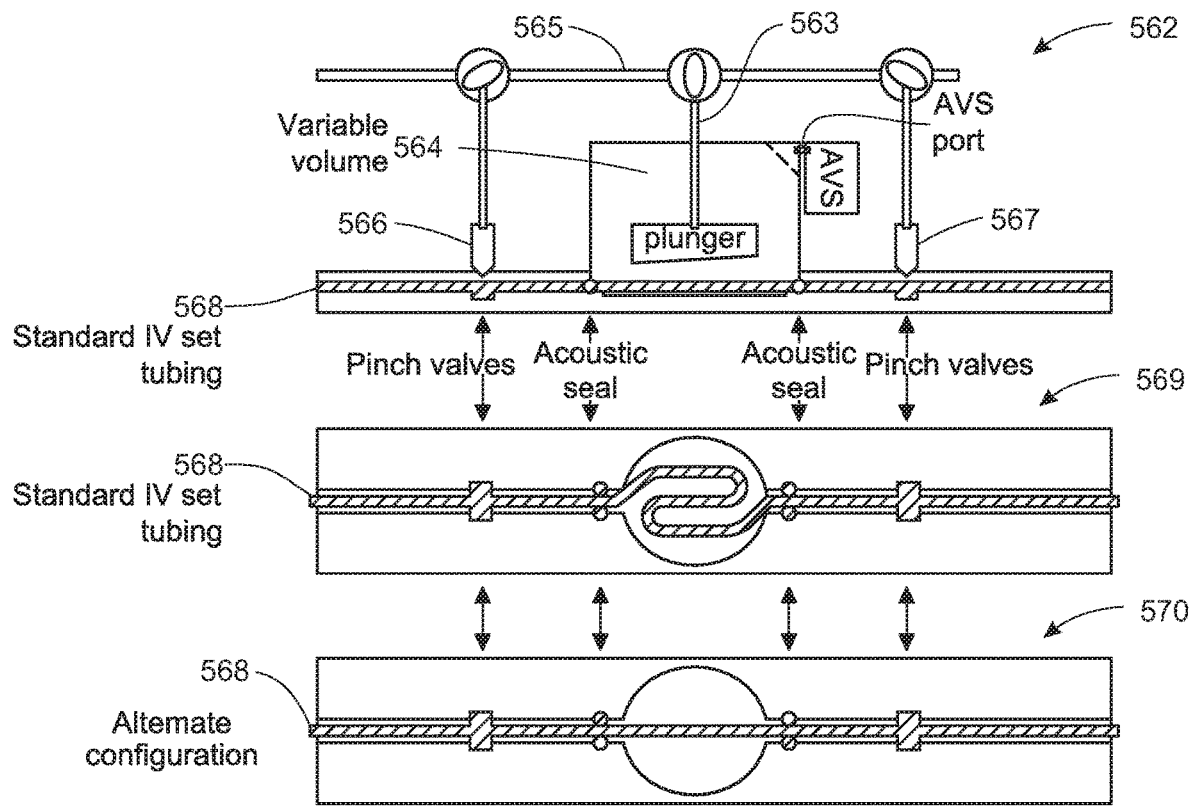
FIG. 139 shows several views of a cam-driven linear peristaltic pump having a plunger inside a variable volume with a corresponding cam mechanism and pinch valves outside of the variable volume in accordance with an embodiment of the present disclosure.

FIG. 139 shows several views of a cam-driven linear peristaltic pump 562 having a plunger 563 inside a variable volume 564 with a corresponding cam mechanism 565 and pinch valves 566 and 567 outside of the variable volume 564 in accordance with an embodiment of the present disclosure. Views 569 and 570 shows two different configuration of the standard IV set tubing 568. The standard IV set tubing 568 may be positioned by a raceway (e.g., defined below, above, and/or around the tubing 568).

Figure 140:
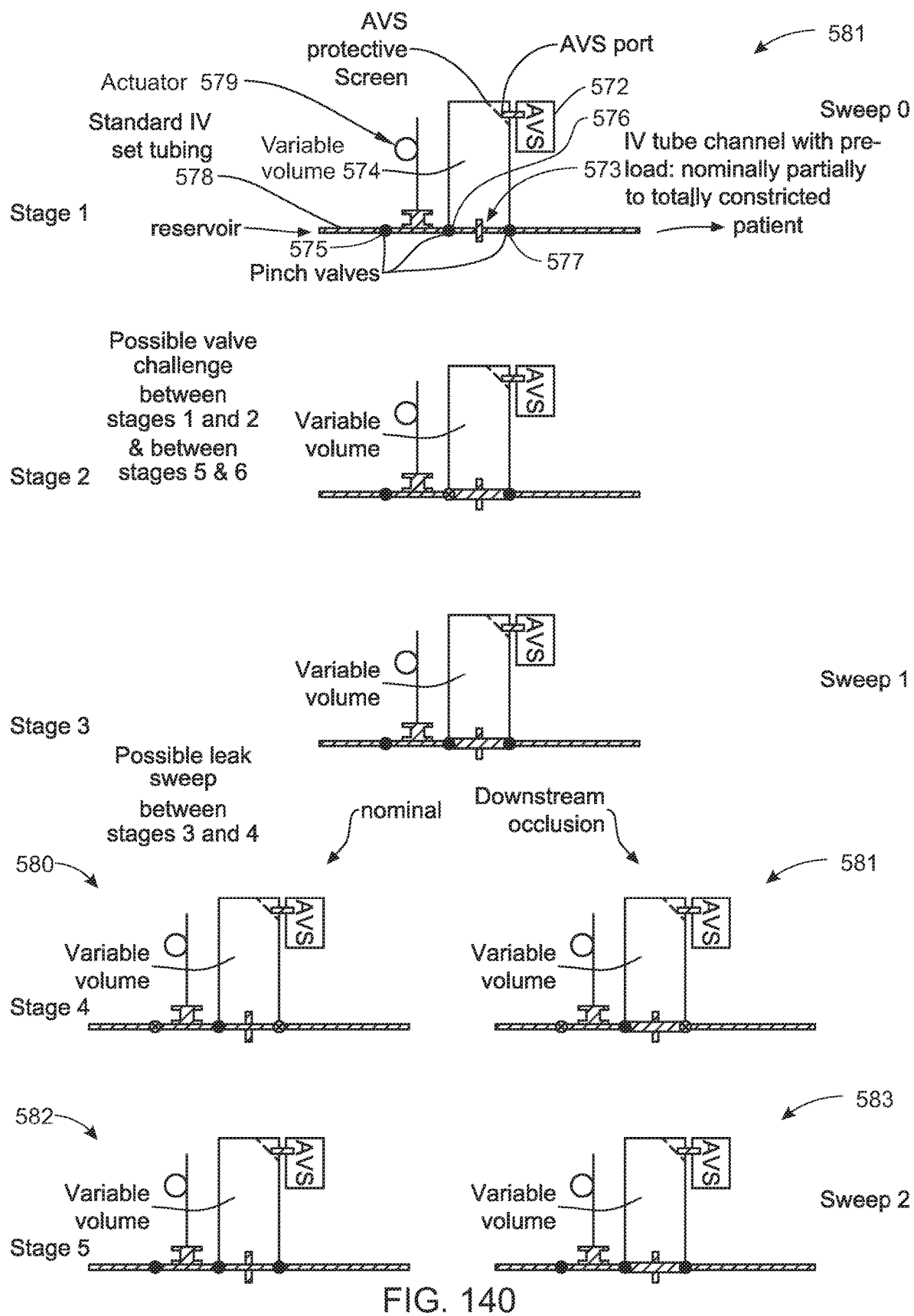
FIG. 140 illustrates occlusion detection using a plunger pump having an AVS assembly and a spring-biased pinching mechanism inside the variable volume in accordance with an embodiment of the present disclosure.

FIG. 140 illustrates the stages 1-5 of occlusion detection using a plunger pump 571 having an AVS assembly 572 and a spring-biased pinching mechanism 573 inside the variable volume 574 in accordance with an embodiment of the present disclosure. The plunger pump 571 includes pinch valves 575, 576, and 577.

In stage 1, the pinch valves 575, 576, and 577 are closed. The variable volume 574 may be measured as the spring-biased pinching mechanism 573 compresses the tube 578. If the volume of the variable volume increases (e.g., the tube diameter within the variable volume 574 decreases) then the processor 37 of FIG. 2 may determine that one or both of the valves 576 and 577 are leaking. Additionally or alternatively, the spring-biased pinching mechanism 573 may include a sensor to estimate the volume of the liquid within the tube 573 within the variable volume 574. The sensor may be, for example, a linear hall effect sensor. If the sensor indicates that the pinching mechanism 573 is slowly closing despite that the pinch valves 575, 576, and 577 are closed, the processor 37 may determine that an error condition exists (see FIG. 2).

In stage 2, the valve 576 is opened and the actuator 579 compresses against the tube 573 thereby filling the tube within the variable volume with a liquid. In stage 3, the valve 576 is closed. In stage 4, the valve 577 is opened. If there is no occlusion the liquid within the spring-biased pinching mechanism 573 will discharge the liquid. In FIG. 137, the stage 4 shows a view 580 where there is no occlusion and the spring-biased pinching mechanism 573 discharges the liquid, and stage 4 also shows a view 581 where the spring-biased pinching mechanism 573 does not discharge (or does not fully discharge) the liquid. In some embodiments of the present disclosure, the position of then spring-biased pinching mechanism 573 during stage 4 is used to determine if an occlusion condition downstream exists (e.g., the processor 37 may determine that an occlusion exists). Stage 5 shows two views 582 and 583. View 582 of stage 5 shows when no downstream occlusion exists and view 583 shows stage 5 when a downstream occlusion exists) note the difference volumes of the spring-biased pinching mechanism 573 in the two views 582 and 583). An AVS sweep and/or the position sensor of the spring-biased pinching mechanism 573 may be used in stage 5 to determine if the volume of the liquid within the variable volume 573 exceeds a predetermined threshold such that the processor 37 of FIG. 2 determines that a downstream occlusion exists.

Figure 141:
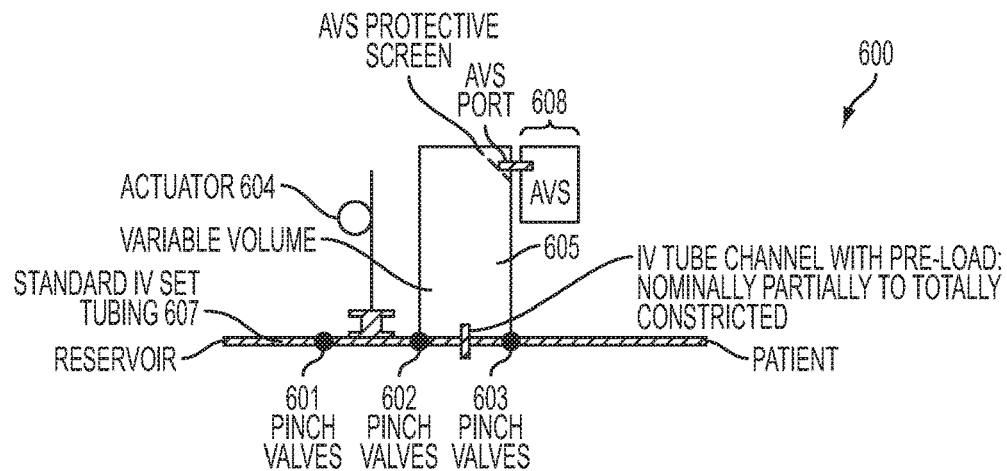
FIG. 141 shows a pump with a spring-loaded plunger within a variable volume of an AVS assembly with an actuated plunger outside of the variable volume in accordance with an embodiment of the present disclosure.

FIG. 141 shows a pump 600 with a spring-loaded plunger 604 within a variable volume 605 of an AVS assembly 606 with actuated plunger 604 outside of the variable volume 605 in accordance with an embodiment of the present disclosure. The valve 602 may be closed and the valve 601 opened with the plunger 604 retracted to allow the tube 607 to pull fluid in under the plunger 604.

The valves 601 and 603 are closed and the valve 602 opened while the plunger 604 presses against the tube 607 to force fluid into the tube 607 region disposed within the variable volume 605; this causes the spring-loaded (or spring-biased) plunger 604 actuate to increase the amount of energy stored in its spring. The valve 602 is closed and an AVS measurement is taken. Thereafter, the pinch valve 603 is opened which forces fluid within the variable volume 605 out of the tube 607 and towards the patient. Thereafter, the valve 602 is closed and another AVS sweep is performed. The AVS volume measurements are compared to determine the amount of fluid discharged through the pump 600. The spring biased plunger 604 may be a single plunger with a spring attached to a shaft to apply a downward force on the tube 607.

Figure 142:
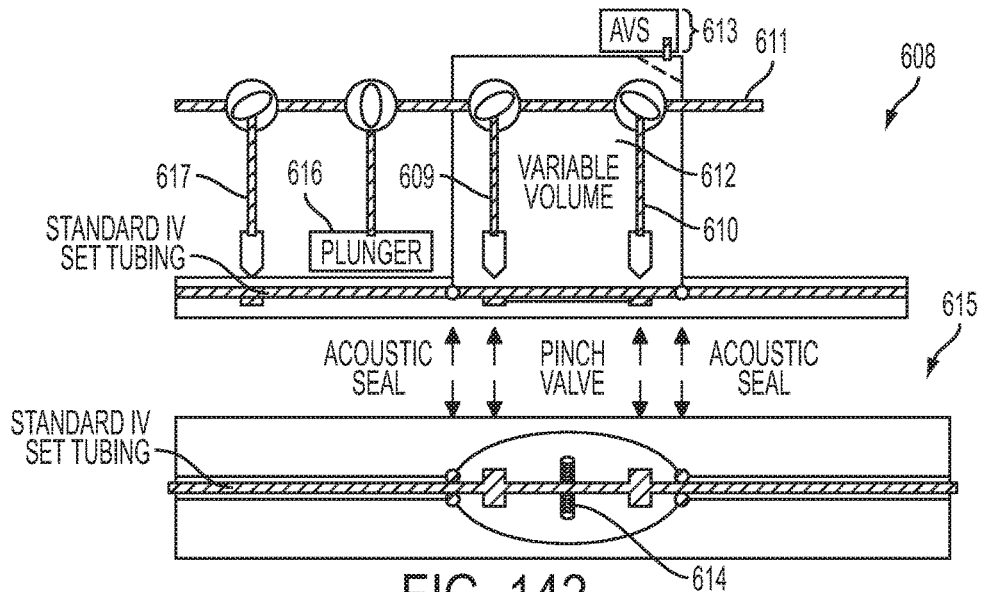
FIG. 142 shows a linear peristaltic pump with pinch valves and a cam shaft disposed within a variable volume of an AVS assembly having spring-biased pinching mechanism disposed therein, and a plunger and a pinch valve outside of the variable volume in accordance with an embodiment of the present disclosure.

FIG. 142 shows a linear peristaltic pump 608 with pinch valves 609 and 610 and a cam shaft 611 disposed within a variable volume 612 of an AVS assembly 613 having spring-biased pinching mechanism 614 (see view 615) disposed therein, and a plunger 616 and a pinch valve 617 outside of the variable volume 612 in accordance with an embodiment of the present disclosure. The manner of operation may be the same as the pump 600 of FIG. 141 (e.g., the plunger 616 force fluid to expand the pinching-mechanism 614 and load the associated springs).

Figure 143:
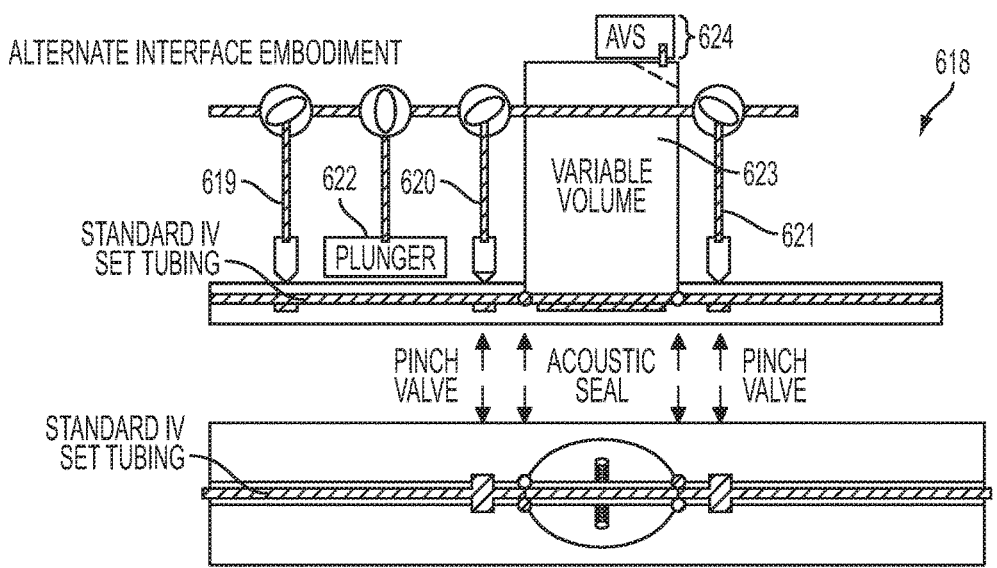
FIG. 143 shows a linear peristaltic pump with pinch valves and a plunger disposed outside of a variable volume of an AVS assembly in accordance with an embodiment of the present disclosure.

FIG. 143 shows a linear peristaltic pump 618 with pinch valves 619, 620, and 621 and a plunger 622 disposed outside of a variable volume 623 of an AVS assembly 624 in accordance with an embodiment of the present disclosure. The manner of operation may be the same as in pump 600 of FIG. 141.

Figure 144:
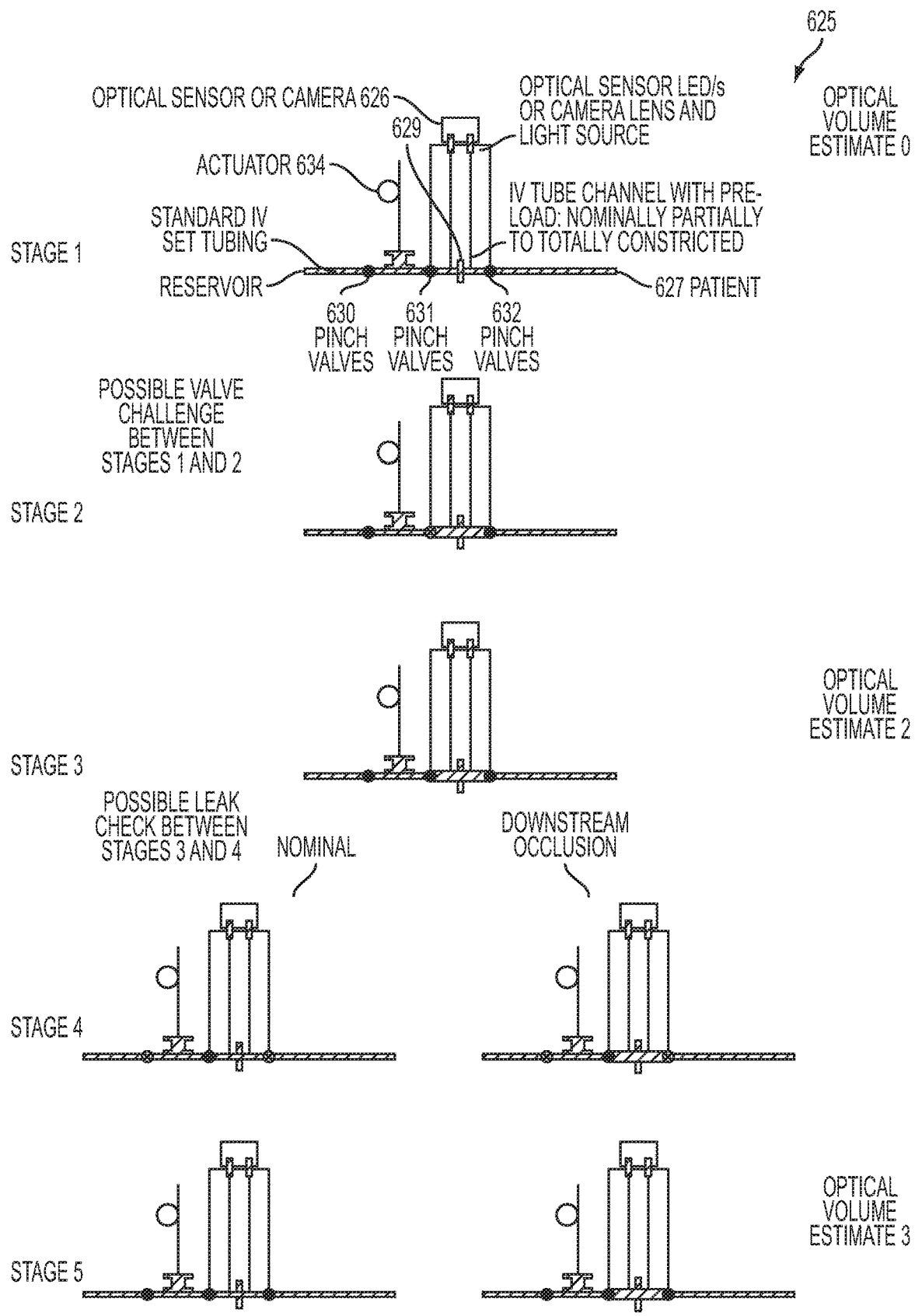
FIG. 144 shows a the stages of a plunger pump having a an optical sensor or camera to measure the volume within a tube residing within a chamber in accordance with an embodiment of the present disclosure.

FIG. 144 shows a the stages 1-5 of a plunger pump 625 having an optical sensor or camera 626 to measure the volume within a tube 627 residing within a chamber 628 in accordance with an embodiment of the present disclosure. The plunger pump 625 includes a spring-biased pinching mechanism 629. An actuator 634 applies a pumping force to force fluid into the region of the tube 627 within the chamber 628 in the manner similar to the pump 600 of FIG. 141.

In stage 1, the valves 630, 631, and 632 are closed. The optical sensor or camera 626 estimates the volume within the region of the tube 627 disposed within the chamber 628. The plunger 633 may compress the tube 627 to determine if the plunger 633 moves beyond a predetermined amount to perform a check of the valves 630 and 631. That is, if the plunger 633 moved beyond a threshold amount, a processor 37 may determine that one of the valves 630 and 631 is leaking.

Figure 145:
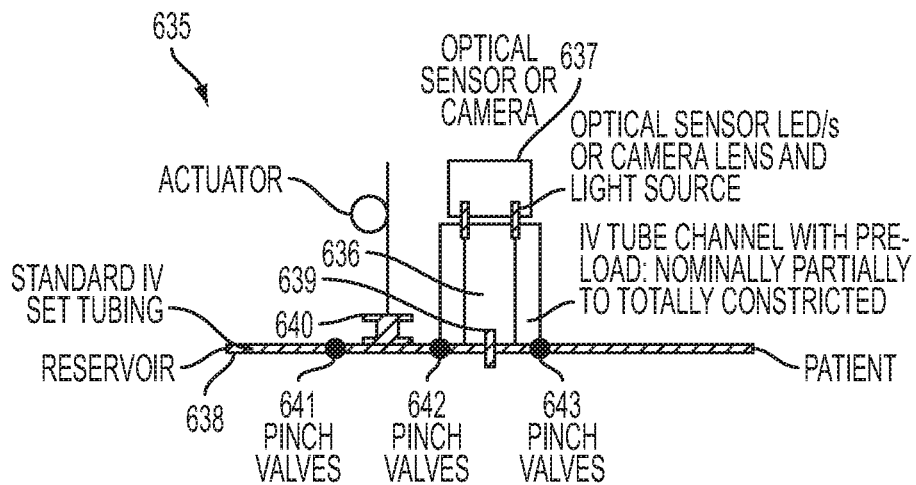
FIG. 145 shows a plunger pump having a chamber having an optical sensor to estimate fluid volume of a tube having a spring-biased pinch mechanism around the tube and a plunger and pinch valves in accordance with an embodiment of the present disclosure.

In stage 2, the valve 631 is opened, and fluid is forced into the chamber 628 by actuation of the plunger 633. In stage 3, another optical volume estimate is made after both valves 631 and 632 are closed. In stage 4, the valves 632 is opened. If an occlusion exists, the spring-biased pinching mechanism 629 cannot discharge all of the fluid out of the tube 627 within the chamber 628. If no occlusion exists, then the spring-biased pinching mechanism 629 can discharge the fluid out. During stage 5 a volume measurement is made to determine if the fluid has been discharged beyond a threshold. If fluid has not been discharged beyond a threshold, the processor 37 of FIG. 3 determines that an occlusion exists FIG. 145 shows a plunger pump 635 having a chamber 636 having an optical sensor 637 to estimate fluid volume of a tube 638 having a spring-biased pinch mechanism 639 around the tube 638 and a plunger 640 and pinch valves 641, 642, and 643 in accordance with an embodiment of the present disclosure. The optical sensor 637 may be an LED time-of-flight device or a camera. The manner of operation of the plunger pump 635 may be the same as the plunger pump 625 of FIG. 144.

Figure 146:
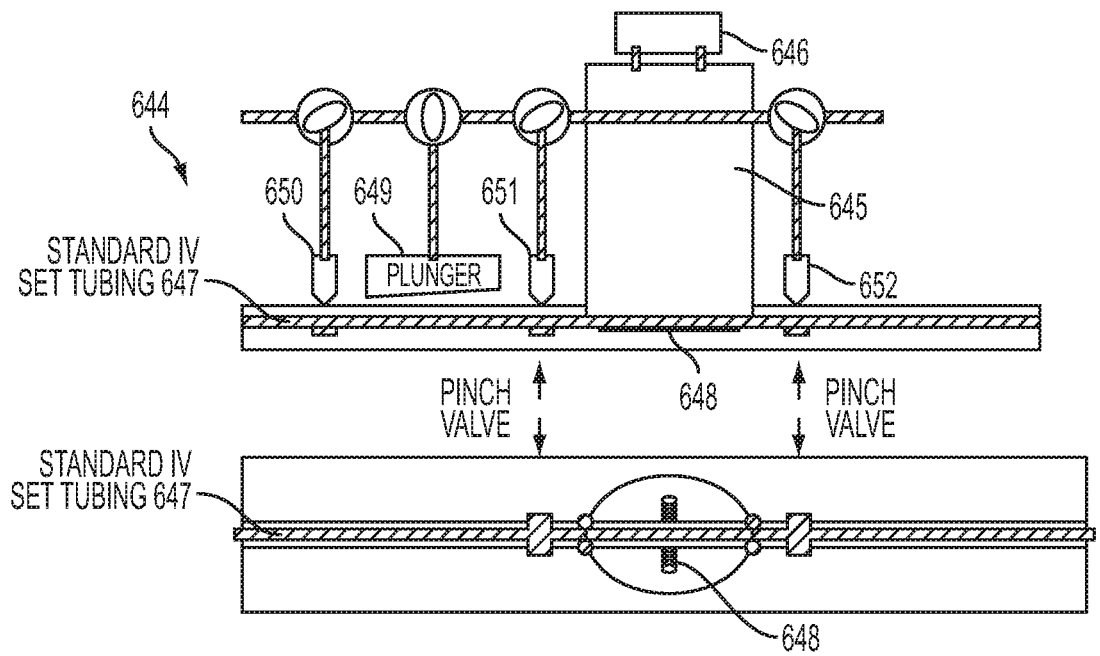
FIG. 146 shows a plunger pump having a chamber with an optical sensor to estimate fluid volume of a tube having a spring-biased pinch mechanism around the tube and a plunger and pinch valves outside the chamber in accordance with an embodiment of the present disclosure.

FIG. 146 shows a plunger pump 644 having a chamber 645 with an optical sensor 646 to estimate fluid volume of a tube 647 having a spring-biased pinch mechanism 648 around the tube 647 and a plunger 649 and pinch valves 650, 651, and 652 outside the chamber 645 in accordance with an embodiment of the present disclosure. The plunger pump 644 may operate in the same manner of operation of the pump 625 of FIG. 144.

FIG. 147 show several views of a plunger pump 653 having an AVS assembly 655 with pinch valve disposed 656 and 657 within the variable volume 658 of the AVS assembly 659, and a plunger 660 and pinch valve 661 disposed outside the variable volume 658 in accordance with an embodiment of the present disclosure. Note that the pinch valves 656 and 657 wholly traverse through the variable volume 658. FIG. 148 shows an two cross-sectional views of the plunger pump of FIG. 147 in accordance with an embodiment of the present disclosure. FIG. 149 shows an alternative two cross-sectional views of the plunger pump of FIG. 147 in accordance with an embodiment of the present disclosure. Note in the two views of FIG. 148, the pinch valve is disposed around the tube and in FIG. 149 the pinch valve is disposed on one side of the tube.

Figure 150:
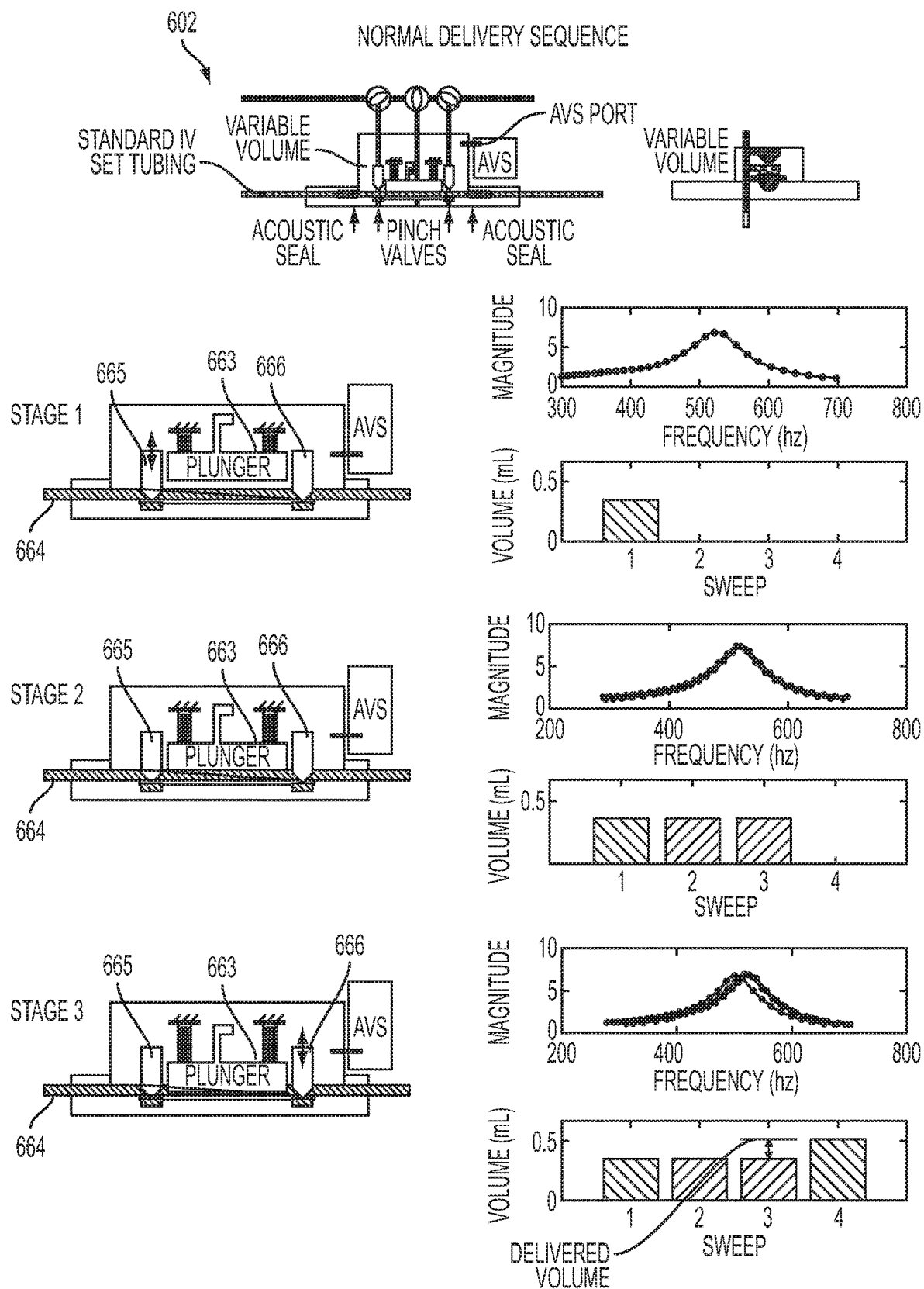

FIG. 150 illustrates the stages 1-4 during normal operation of a plunger pump 662 having a spring-biased plunger 663 in accordance with an embodiment of the present disclosure. In stage 1, the plunger 663 is pulled away from the tube 664 and the pinch valve 665 is opened. An AVS measurement is taken. In stage 2, the pinch valves 665 is closed and the plunger 663 compresses the tube 664. Another AVS measurement is taken. In stage 3, the pinch valve 666 is opened and the plunger 663 pushes fluid out of the tube 664. An AVS sweep is performed to estimate the volume of fluid delivered. In some embodiments, the plunger 663 includes a linear hall effect sensor which correlates the movement of the plunger between stages 2 and 3 to estimate the amount of fluid discharged.

Figure 151:
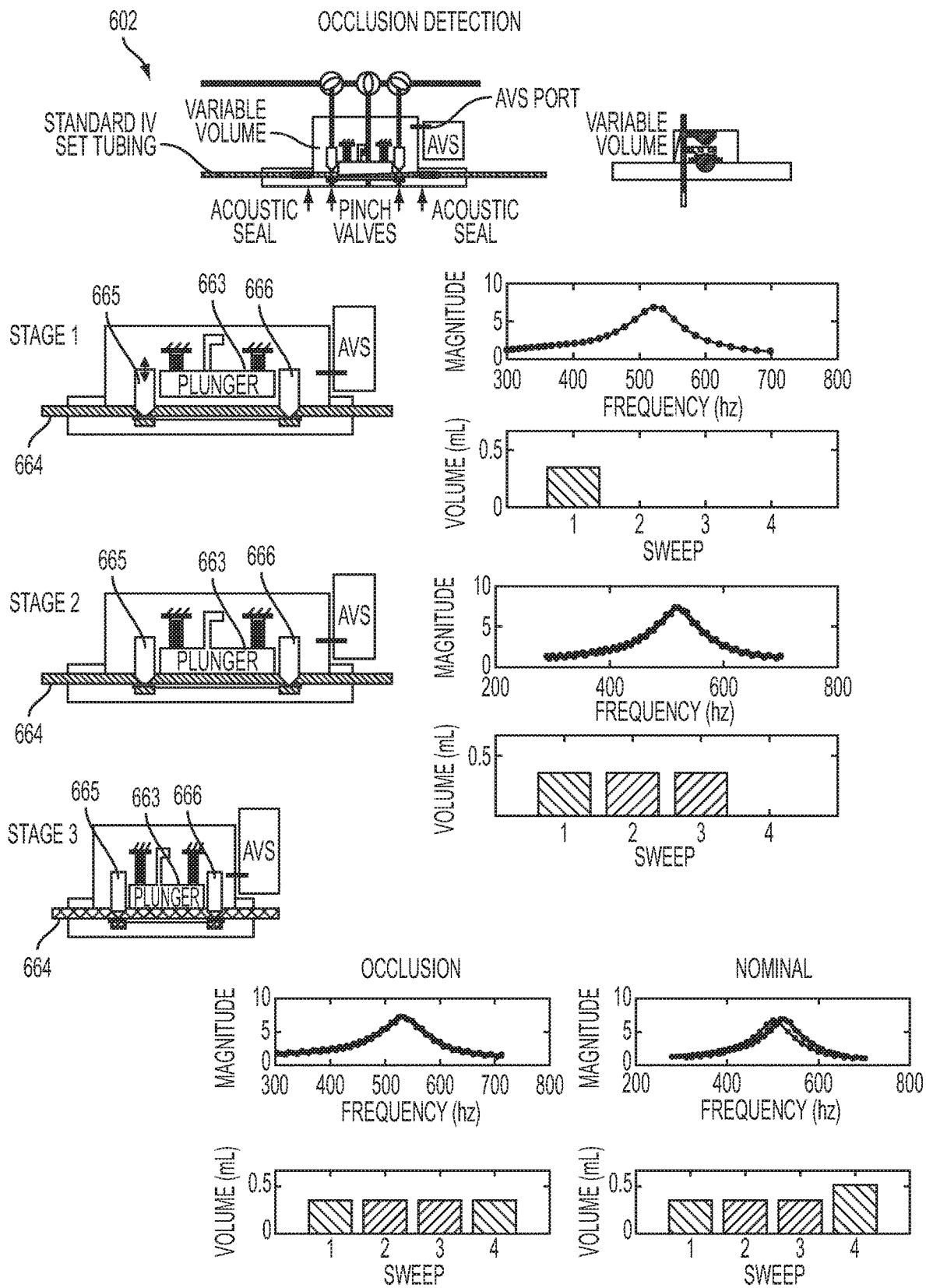

FIG. 151 illustrates the stages for detecting an occlusion for the plunger pump 622 of FIG. 150 in accordance with an embodiment of the present disclosure. Stage 3 compares the AVS measurements when an occlusion occurs vs. a normal fluid delivery. The processor 37 of FIG. 3 can detect when not enough fluid is delivered thereby indicating to the processor than an occlusion has occurred.

Figure 152:
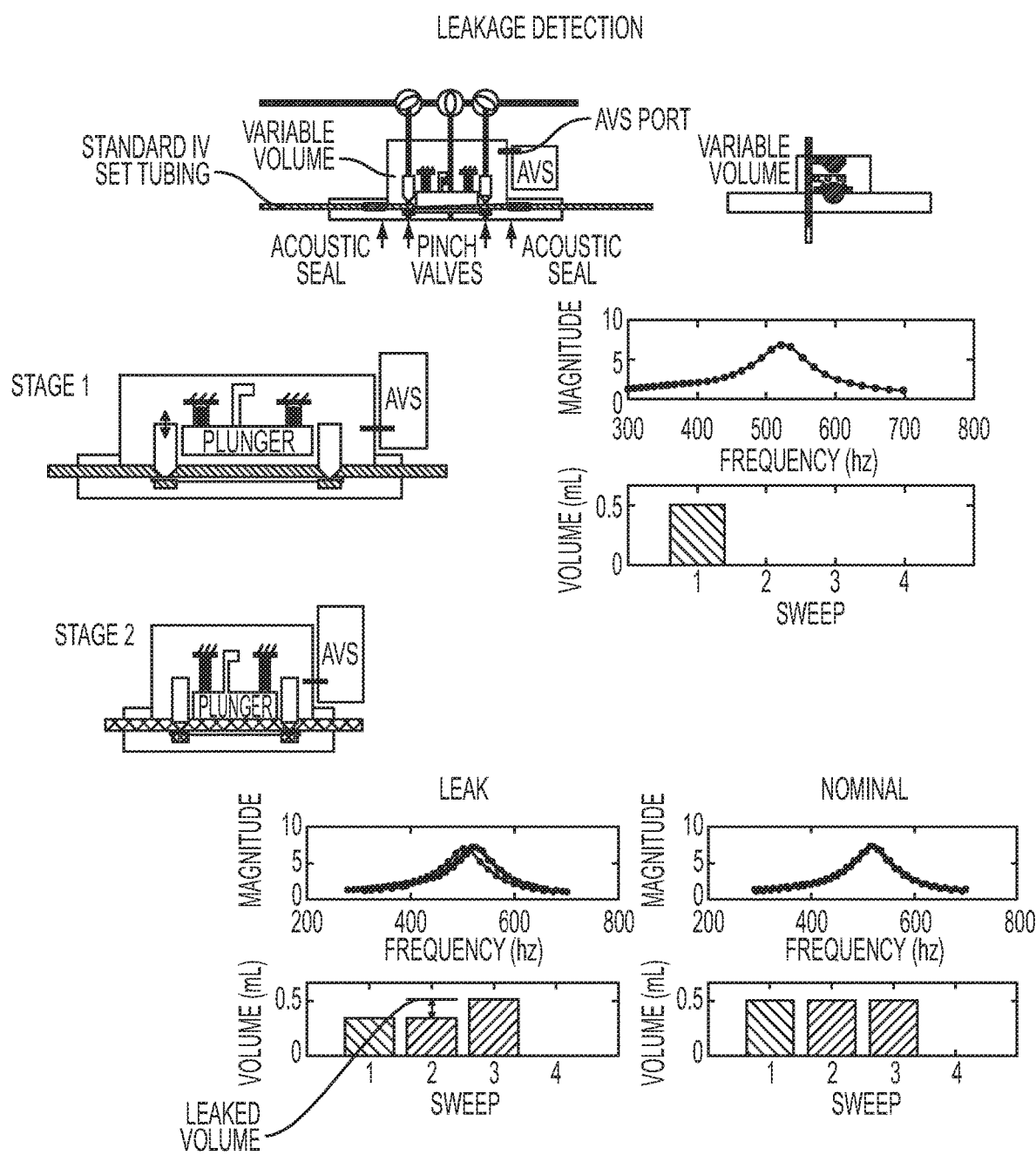

FIG. 152 illustrates stages 1-2 for leakage detection for the plunger pump 622 of FIG. 150 in accordance with an embodiment of the present disclosure. In stage 1, the pinch valve 665 is opened and the plunger 663 is opened thereby drawing fluid into the tube 664. In stage 2, after the pinch valve 665 is compressed against the tube 664, the plunger applies a force against the tube 664. If one of the valves 665 and 666 is leaking, in stage 2, the AVS measurement would indicate a leakage of fluid (i.e., the variable volume would increase.

Figure 153:
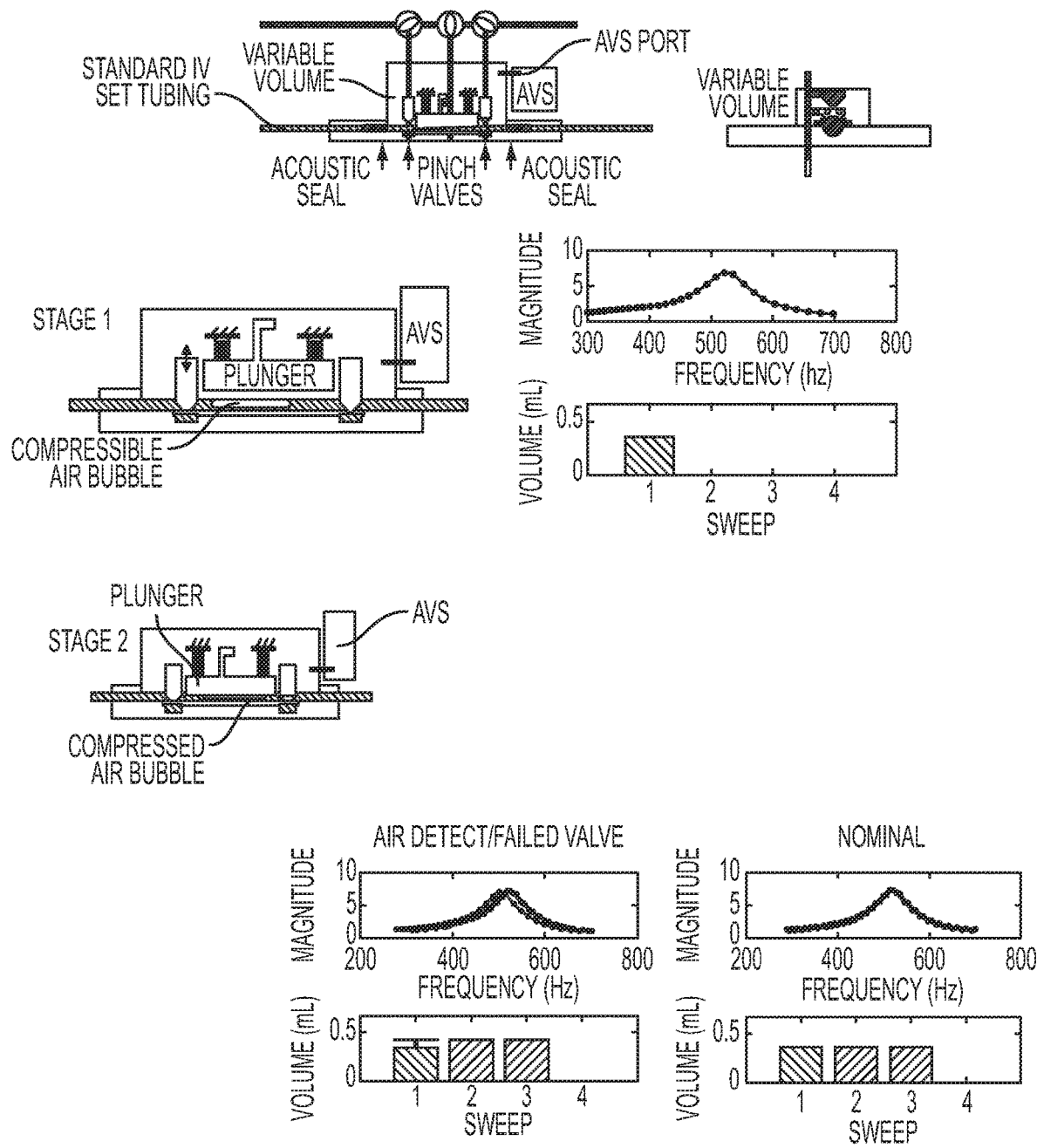

FIG. 153 illustrates the stages 1-2 for detecting a failed valve and/or bubble detection for the plunger pump 602 in accordance with an embodiment of the present disclosure. As shown in stage 2, if the variable volume increases beyond a predetermined threshold and does not continue to decrease, the processor 37 of FIG. 3 may determine that a bubble exists in the tube 664.

FIG. 154 illustrates the stages for empty reservoir detection and/or upstream occlusion detection for a plunger pump 662 in accordance with an embodiment of the present disclosure. As shown in stage 2, if the AVS sweeps indicate that fluid is not being drawn into the tube 664, then the processor 37 of FIG. 3 may determine that the upstream reservoir is empty.

Figure 155:
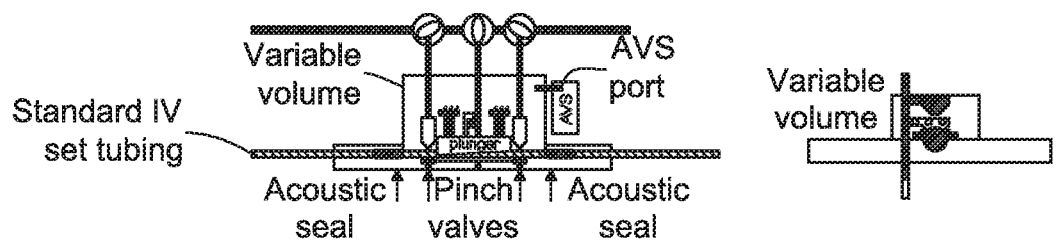

FIG. 155 illustrates the stage for free flow prevention for a plunger pump 662 in accordance with an embodiment of the present disclosure. That is, when a free flow condition is detected, the plunger 663 may compress against the tube 664 to stop the free flow.

Figure 156:
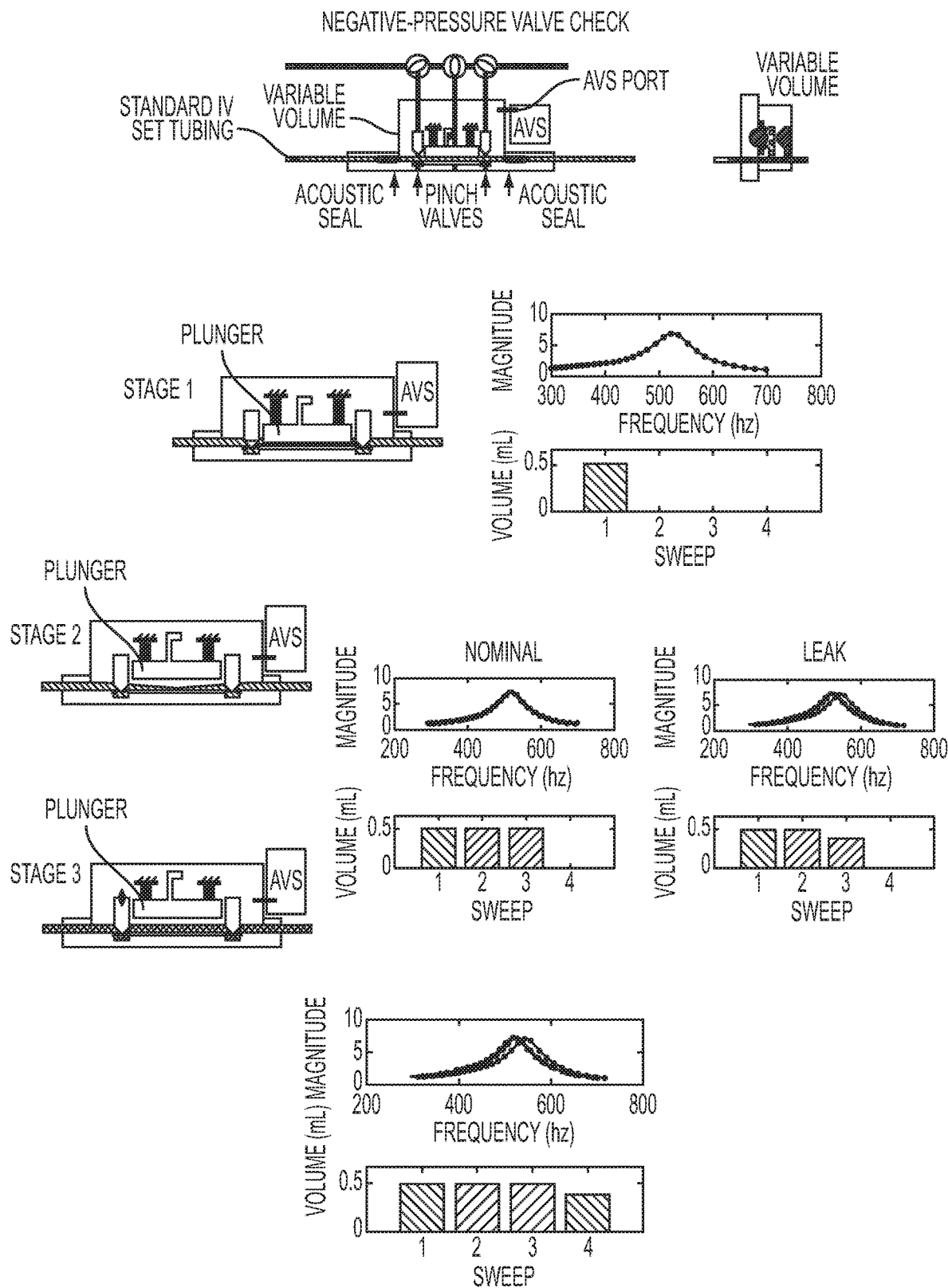

FIG. 156 illustrates the stages for a negative pressure valve check for the plunger pump 662 in accordance with an embodiment of the present disclosure. Stage 1, the plunger 663 is compressed against the tube 664, and both valves 665 and 665 are closed. In stage 2, the plunger 663 is lifted from the tube 665. If there is a leak, the compliance of the tube 664 will pull in fluid which is detected by the AVS sweeps. As shown in Stage 3, the valves 665 and 665 are opened.

FIGS. 157-158 show views of a plunger pump 670 having a cam shaft 671 that traverses the variable volume 672 of an AVS assembly 673 in accordance with an embodiment of the present disclosure;

FIGS. 159-162 illustrate several cam profiles in accordance with several embodiments of the present disclosure. The cam profiles of FIGS. 159-162 may be used with the peristaltic pump 662 of FIGS. 150-158, or any sufficient pump disclosed herein.

Figure 159:
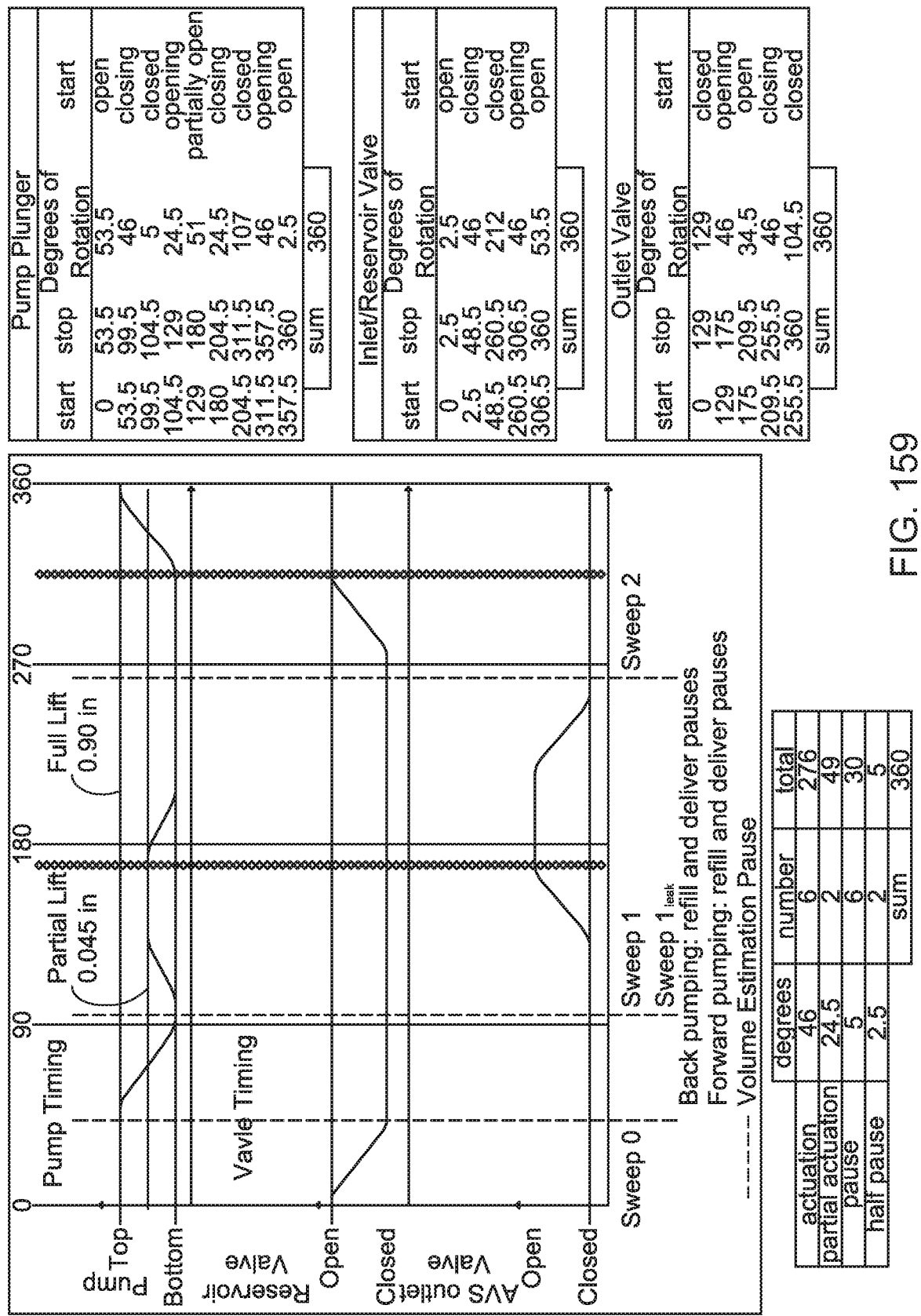
Figure 160:
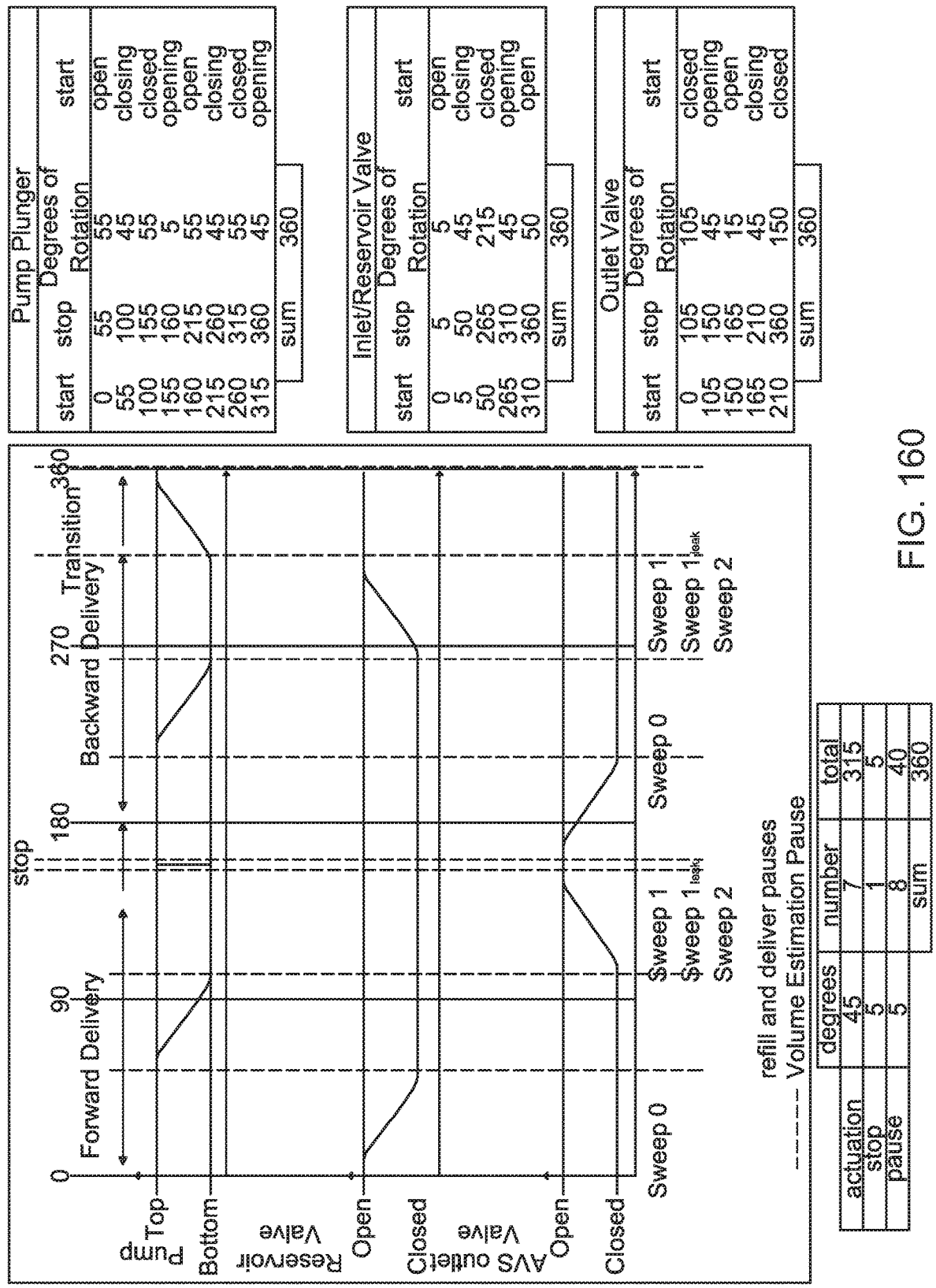
Figure 161:
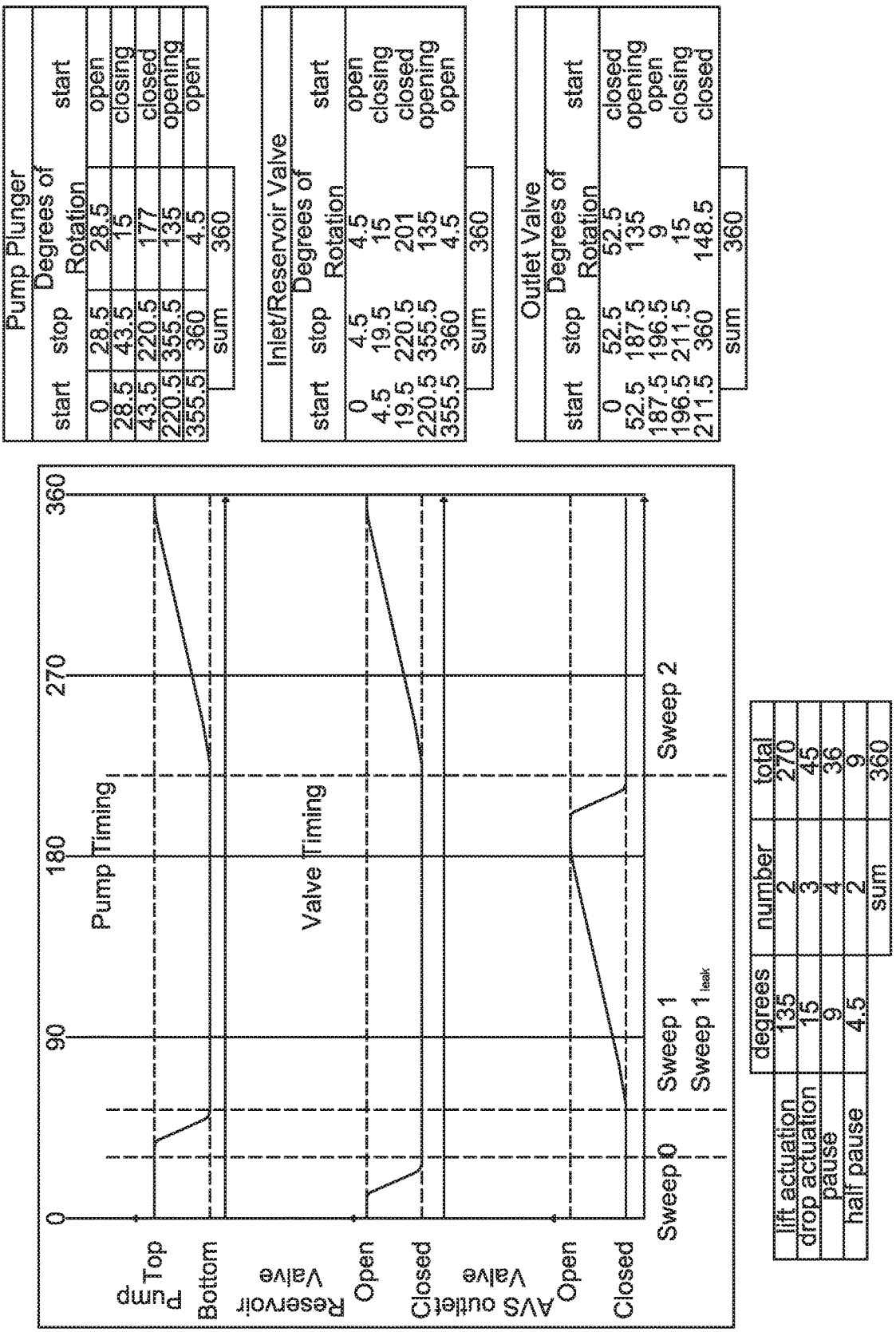
Figure 162:
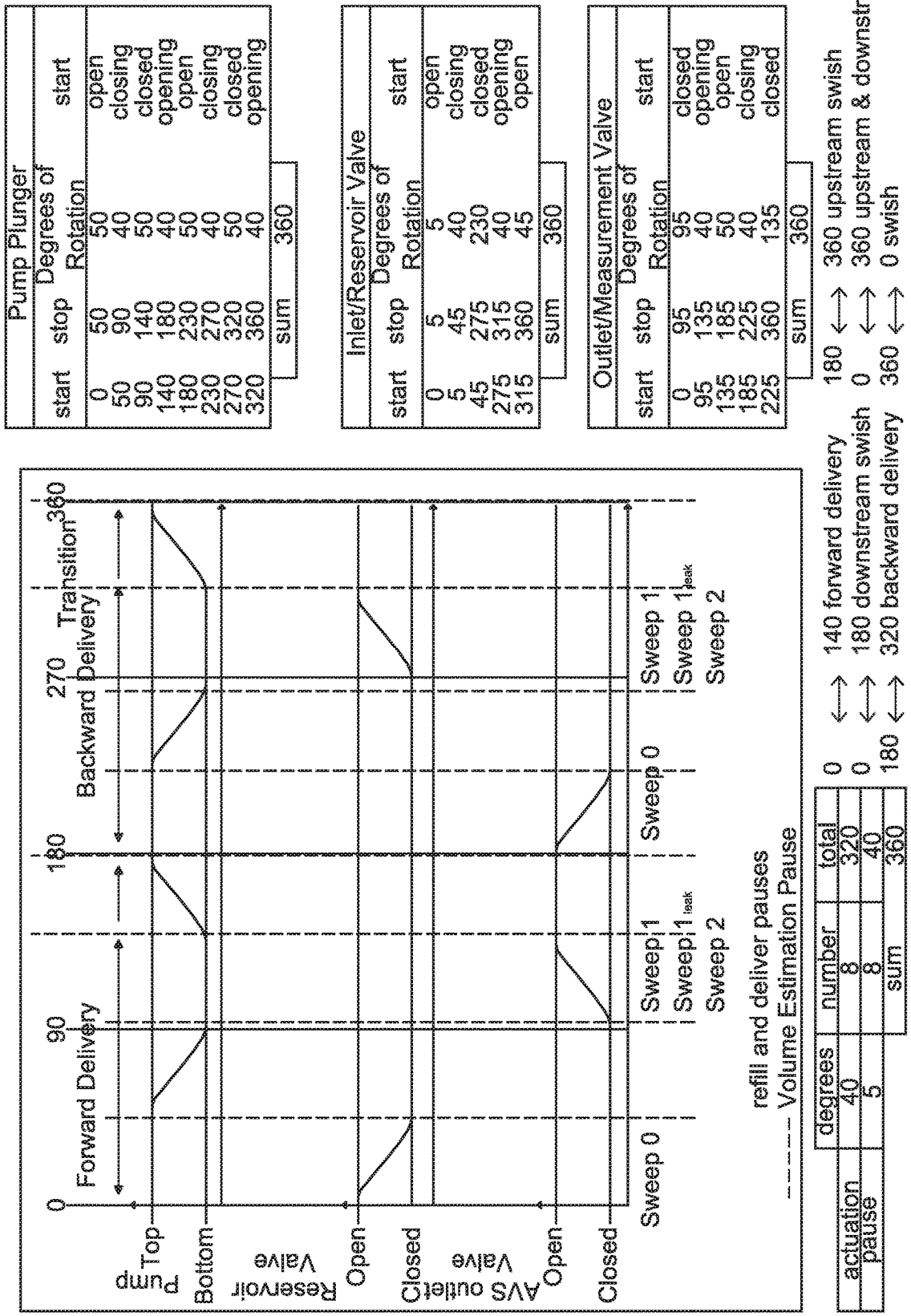

FIG. 159 shows a cam profile that uses the integrity check described in FIGS. 150-158 except for a negative pressure valve check, and can be used for forward pumping and backward pumping. The backward pumping may be used during an infiltration test as described herein. FIG. 160 shows a cam profile which uses the integrity checks described in FIGS. 150-158 without the negative pressure check. Rotation of the cam in a back and forth manner causes fluid flow in the cam profile of FIG. 160 when the cam is rocked from 0 to 155 degrees. Back pumping is accomplished in the cam profile of FIG. 160 by rotating the cam shaft back and forth from 315 degrees to 160 degrees. In FIG. 161 a cam profile is shown that uses the integrity check described in FIGS. 150-158 except for a negative pressure valve check. The cam profile in FIG. 161 can be used to provide forward fluid flow of the pump. FIG. 161 shows a cam profile that pulses fluid when rotated continuously in one direction with a zero total fluid flow. The chart in the bottom right hand corner of FIG. 162 shows the movement to achieve forward, backwards, and swishing fluid movement.

FIG. 163 illustrates a peristaltic pump 675 having a plunger 676 and a pinch valve 677 outside of an AVS variable volume 678 with two pinch valves 679 and 680 on the interface of the AVS variable volume 678 in accordance with an embodiment of the present disclosure. FIG. 164 illustrates stages 1-5 of operation of the peristaltic pump of FIG. 163 (in simplified version) in accordance with an embodiment of the present disclosure.

FIG. 165 illustrates a peristaltic pump 681 having two plungers 682 and 683 external to an AVS variable volume 684 in accordance with an embodiment of the present disclosure. FIG. 166 illustrates several stages 1-6 of the peristaltic pump 681 of FIG. 165 in accordance with an embodiment of the present disclosure;

FIG. 167 illustrates a peristaltic pump 685 having a plunger 686 with a linear sensor 687 in accordance with an embodiment of the present disclosure. FIG. 168 illustrates a graphic of data from the linear sensor 687 of the peristaltic pump 685 of FIG. 167 in accordance with an embodiment of the present disclosure. As shown in FIG. 168, the amount of movement of the plunger 686 between the pressurized stage (e.g., both pinch valves closed 688 and 689 and the plunger's 686 spring applying a force again the tube 690) and the delivery stage (e.g., the outlet pinch valve 689 is opened) is correlated with the amount of fluid discharged. The correlation between the amounts of fluid discharged with the delta output from the sensor 687 may be determined empirically. The plunger 686 may be spring loaded against the tube 690 such that the cam only comes into contact with a cam follower coupled to the plunger 686 in order to lift the plunger 686 away from the tube 690.

FIG. 169 illustrates the stages of the peristaltic pump of FIG. 167 in accordance with an embodiment of the present disclosure. FIG. 170 illustrates the detection of an occlusion condition vis-à-vis a non-occluded condition in accordance with an embodiment of the present disclosure. That is, the plunger position data is shown for the normal vs. occluded conditions. Note that when there is an occlusion, fluid does not discharge and thus the plunger position does not move as much. This may be detected by the processor 37 of FIG. 3. FIG. 171 illustrates the detection of a valve leak vis-à-vis a full-valve-sealing condition. FIG. 172 illustrates the detection of a too much air in the tube or a valve fail vis-à-vis a proper operation.

FIG. 173 shows a block diagram that illustrates the electronics of a peristaltic pump in accordance with another embodiment of the present disclosure. That is, FIG. 173 shows the electronics of one of pumps 16, 17, and 18 of FIG. 1 in one specific embodiment. FIG. 174 shows a block diagram that illustrates the electronics of another embodiment of the peristaltic pump of one of the pumps 16, 17, and 18 in FIG. 1.

FIG. 175 shows a perspective view of peristaltic pump 700 in accordance with an embodiment of the present disclosure. The peristaltic pump includes an AVS chamber (see the AVS chamber 714 of FIG. 184). The peristaltic pump 700 includes cams 701, 702, and 703 that rotate along with a cam shaft 704 coupled to a motor via a gear 705. The cam 702 control an inlet pinch valve, the cam 702 controls a plunger, and the cam 703 controls an outlet pinch valve.

The cams 701-703 may be shaped to provide a peristaltic-pumping action along the tube 707. The cams 701-703 may be shaped to provide a three stage pumping action or a four stage pumping action.

The three stage pumping action includes stages 1, 2, and 3. In stage 1, the outlet valve is closed, the inlet valve is opened, and the plunger is lifted off of the tube. In one embodiment, the outlet valve is substantially closed before the inlet valve is substantially open. In stage 2, the inlet valve is closed, and the spring-biased plunger is allowed by the cam to apply a compression force against the tube 707. In stage 3, the outlet valve is opened such that the compressive force of the spring's plunger compresses out the fluid towards the patient. A linear sensor (e.g., optical or hall-effect) measures the position of the plunger. A processor coupled to a motor to control the cam shaft 704 and coupled to the linear sensor may compare the difference of the plunger's position in stage 2 when the plunger stops movement and fully compresses against the tube 707 and at the end of stage 3 (all fluid has been forced out towards the patient and the plunger stops moving because no additional fluid may be compressed out of the tube). In another embodiment, the processor, coupled to the processor coupled to a motor to control the cam shaft 704 and coupled to the linear sensor, may compare the difference of the plunger's position in stage 2 when the plunger rate of movement drops below a defined threshold and during stage 3 when the plunger rate of movement drops below a given threshold or the plunger position drops below a defined value. The thresholds for the rate of movement and position of the plunger are determined by calibration experiments. The processor uses the measured differences between the displacements between these two positions to correlate the difference to a volume of fluid pumped (e.g., by comparing the delta value (the difference between the two measurements) to values in a look-up table). Optionally, in stage 3, the opening of the outlet valve is controlled by the rotation of the cam 704 to achieve a target fluid discharge-rate profile, e.g., the delta is used between the measurement of stage 2 and in real-time as the outlet valve is opened in stage 3 (e.g., the delta is continuously calculated).

During stage 2, if the plunger moves beyond a predetermined threshold and/or beyond a predetermined slope, one of the inlet valve and the outlet valve may be leaking. For example, if the plunger quickly moves to compress the tube and continues to move (e.g., beyond a predetermined slope), the processor may determine that one of the inlet and outlet valves are leaking. The processor (the processor 37 of FIG. 3) is coupled to the linear sensor may issue an alarm and/or alert.

During stage 2, if the plunger moves beyond a predetermined threshold when the cams allows the compression of the spring to compress the tube or the movement slows as the plunger hits the tube and then moves more beyond a predetermined threshold (as the bubble is compressed), it may indicate that a bubble exists within the tube. For example, if the plunger moves as the cam follower moves the spring-biased plunger towards the tube, then momentarily stops, and then moves again, the processor may determine that air within the tube has been compressed. In some embodiments, movement beyond a predetermined threshold may suggest that air exists within the tube. The processor coupled to the linear sensor may issue an alarm and/or alert. In some embodiments, to distinguish between a leaking valve and a bubble, a downstream bubble sensor (not shown) may be used by the processor to distinguish between the two error conditions.

In some embodiments, if the spring-biased plunger in stage 2 moves towards the tube and does not engage the tube until after a predetermined threshold has been crossed, the processor may determine that an upstream occlusion exists and the tube did not fill up with fluid during stage 1.

In some embodiments, if the spring-biased plunger in stage 3 does not move beyond a predetermined threshold, the processor may determine that a downstream occlusion exists (e.g., the tube cannot discharge fluid downstream). Additionally or alternatively, the processor may determine that a downstream occlusion exists when each cycles of the stages 1-3, less and less fluid is discharged to a patient (i.e., the compliance is increasing taking in fluid downstream).

In some embodiments of the present disclosure, the cams 701, 702, and 703 may be shaped to have a four stage pumping action.

In stage 1, the outlet valve is closed, the inlet valve is opened, and the plunger is lifted off of the tube. In stage 2, the inlet valve is closed, and the spring-biased plunger is allowed by the cam to apply a compression force against the tube 707. In stage 3, the plunger is lifted off of the tube and the outlet valve is opened. In stage 4, the cam 702 allows the plunger to apply the compressive force of the spring's plunger to compress out the fluid towards the patient. A linear sensor (e.g., optical or hall-effect) measures the position of the plunger. A processor coupled to a motor to control the cam shaft 704 and coupled to the linear sensor may compare the difference of the plunger's position in stage 2 when the plunger stops movement and fully compresses against the tube 707 and at the end of stage 4 (all fluid has been forced out towards the patient and the plunger stops moving because no additional fluid may be compressed out of the tube). The processor uses the measured differences between the displacements between these two positions to correlate the difference to a volume of fluid pumped (e.g., by comparing the delta value (the difference between the two measurements) to values in a look-up table). Optionally, in stage 4, the movement of the plunger to compress the tube using the plunger's compressive force (as allowed by the cam 702) is controlled by the rotation of the cam 704 to achieve a target fluid discharge-rate profile, e.g., the delta is used between the measurement of stage 2 when the plunger fully compresses the tube and the movement of the plunger in real-time as the plunger is allowed to compress the tube 707 (e.g., the delta is continuously calculated).

In some embodiments, a downstream occluder may be adjusted to smooth the flowing of the fluid to the patient.

In some embodiments AVS may be used instead of the linear position sensor. In some embodiments, only the linear position sensor is used. In yet additional embodiments, both of the AVS and the linear position sensor are used.

FIGS. 176-180 show data from several AVS sweeps in accordance with an embodiment of the present disclosure. The AVS sweeps of FIGS. 176-180 are for the peristaltic pump 700 of FIG. 175.

Figure 176:
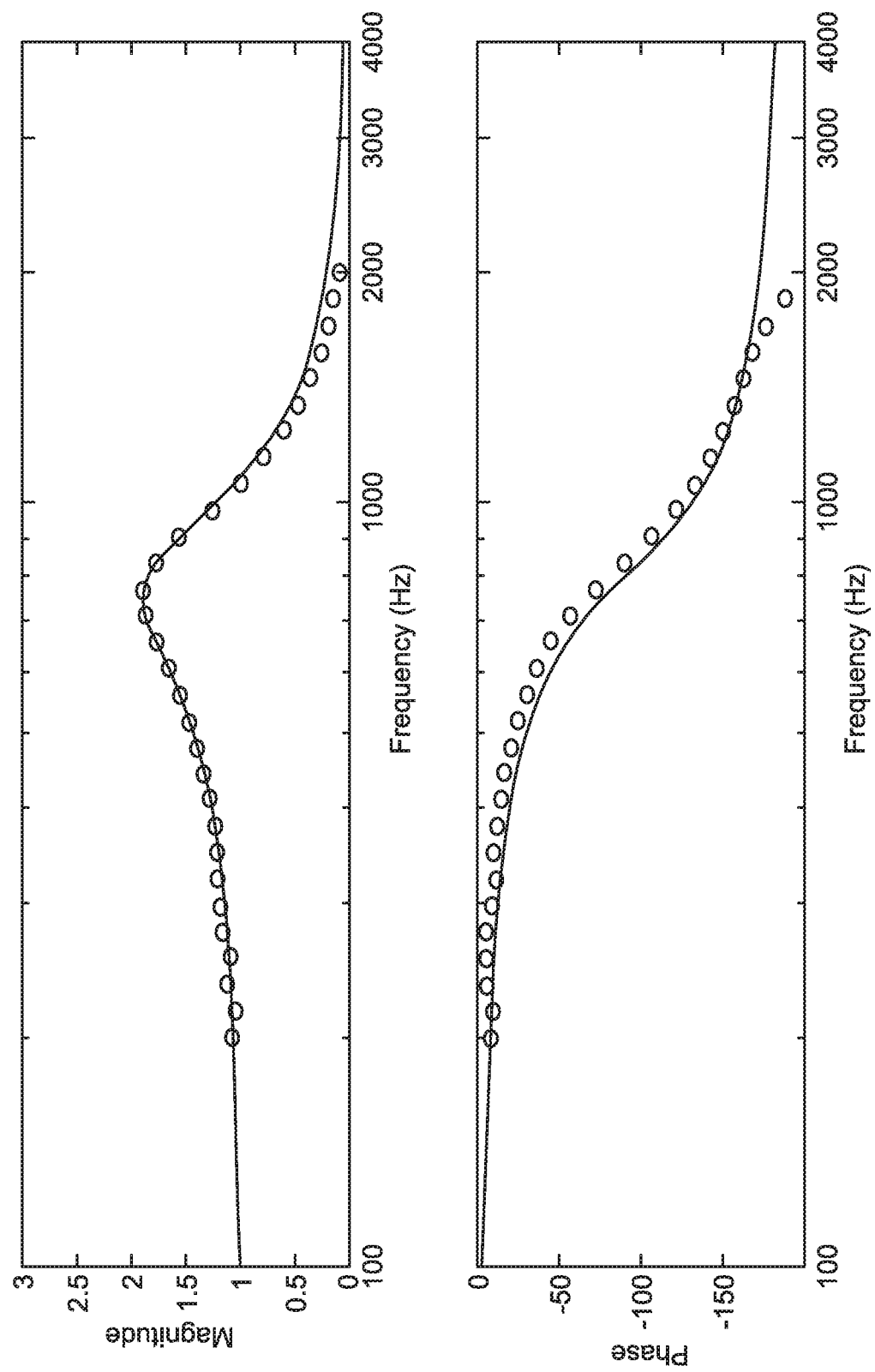

FIG. 176 shows data, including a magnitude and phase response, of a variable volume around the tube 707 of the peristaltic pump 700 of FIG. 175 relative to a reference volume. That is, the data as shown in FIG. 176 is correlated to the volume of air around the tube 707 (see FIG. 175) within an acoustically sealed region as shown in FIG. 184 (i.e., a variable volume chamber).

Figure 177:
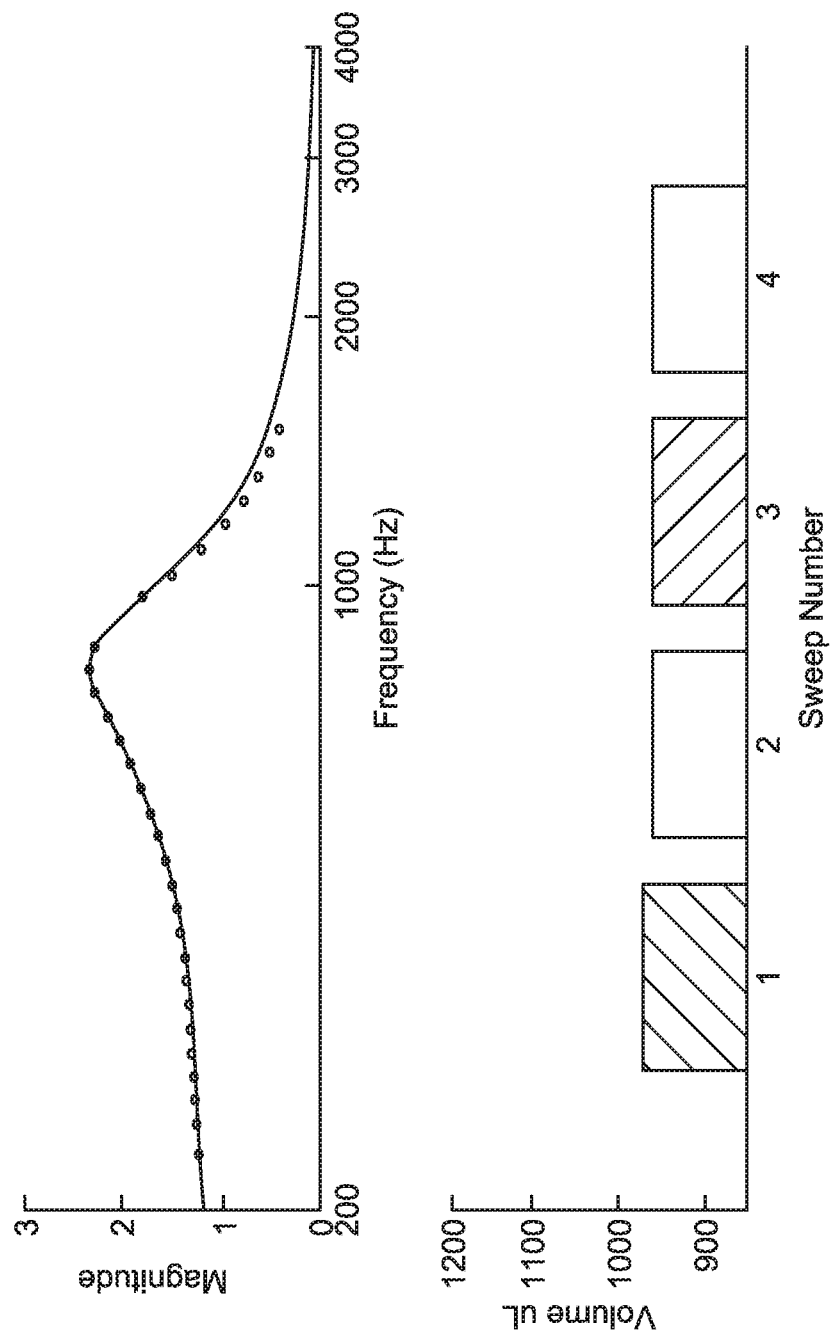

FIG. 177 illustrates several AVS sweeps performed using the peristaltic pump 700 of FIG. 175. Note that, although the plunger is spring-loaded against the tube 707 in Sweep 3 and the outlet valve is opened by the cam 703, the fluid is not discharged downstream towards the patient. The processor 37 of FIG. 3 may determine that a downstream occlusion exists in this circumstance.

Figure 178:
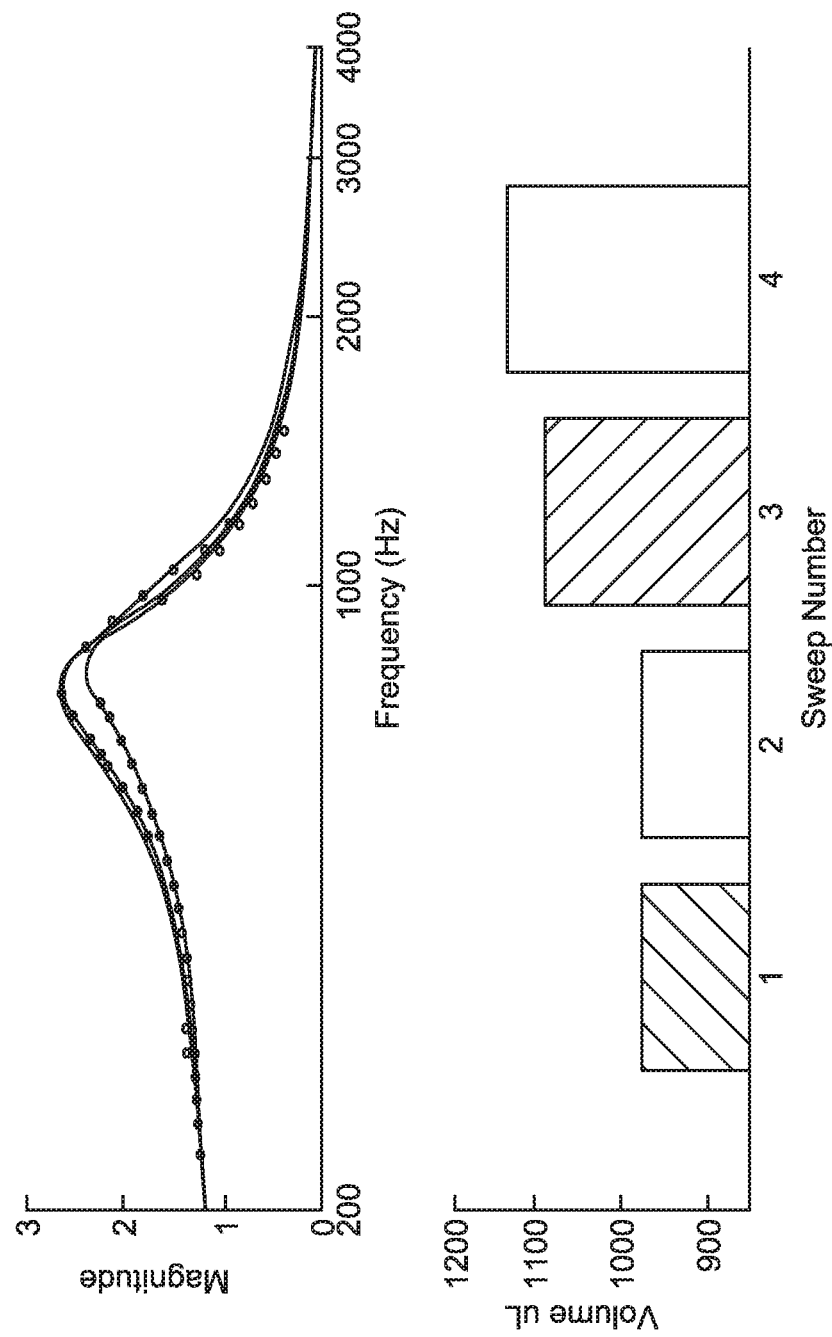

FIG. 178 shows several AVS sweeps using the pump 700 of FIG. 175. In sweeps 2 and 3 of FIG. 178, the cam 702 allows the plunger's spring to compress against the tube 707, but the cams 701 and 703 force the pinch valves closed. In sweep 3, the inlet and outlet valves have remained closed, however, the variable volume is increasing which thereby indicates that the fluid is being discharged out of one of the inlet and outlet valves. The processor 37 of FIG. 3 may determine that one of the inlet and outlet valves are leaking when the sweeps data appears as in sweeps 2 and 3 despite that the inlet and outlet valves have remained closed.

Figure 179:
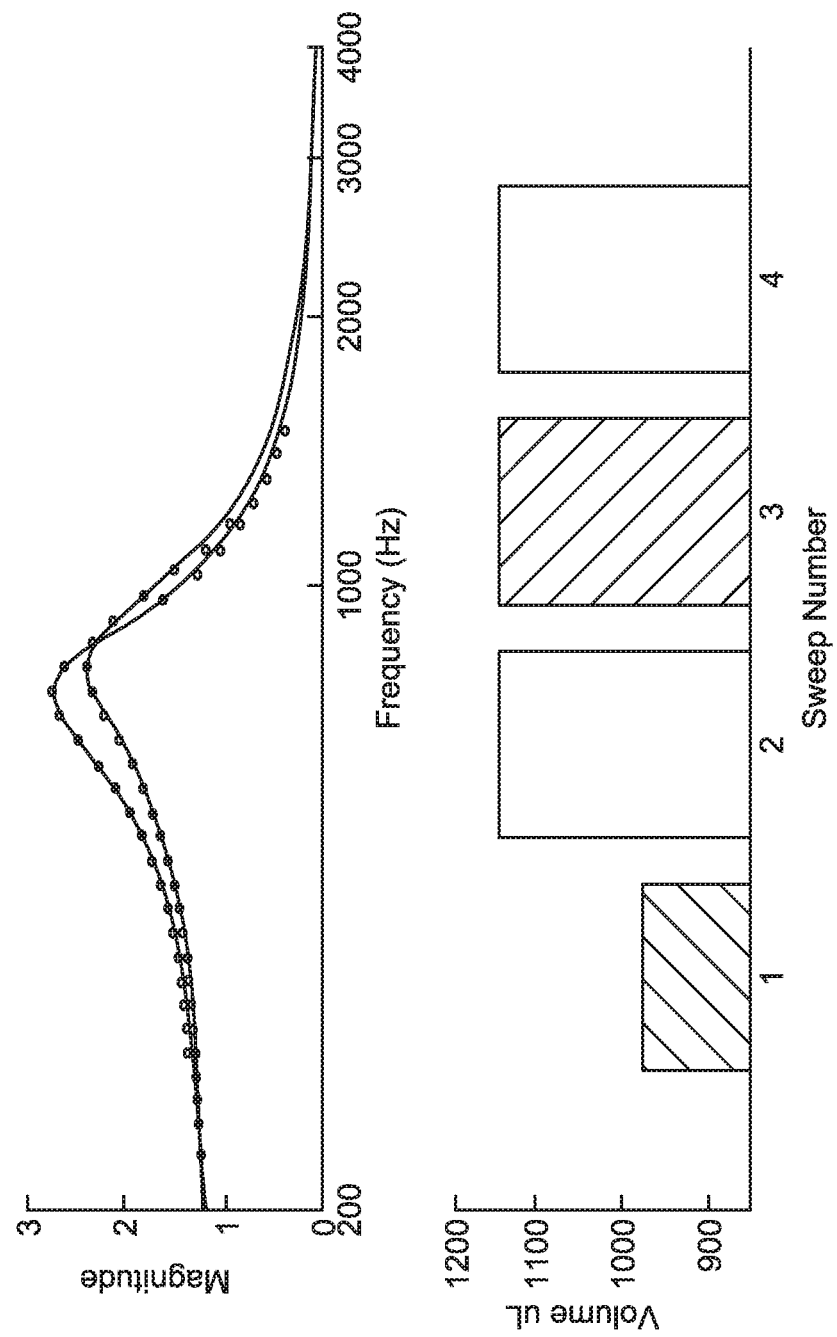

FIG. 179 shows several AVS sweeps using the pump 700 of FIG. 175. In sweep 1, the cams 701 and 703 close the valves, and the cam 702 allow the plunger's spring the compress against the tube 707. In sweep 2, the cams 701 and 703 have kept the valves closed, however, the plunger's spring has moved the plunger beyond an predetermined amount. The processor 37 may determine that the movement of the plunger is because air is within the tube under the plunger. A downstream air detector 24 (see FIG. 1) may be used to distinguish between movements caused by the compressibility of air when air is within the tube 707 below the plunger vs. a leaking inlet or outlet pinch valve.

Figure 180:
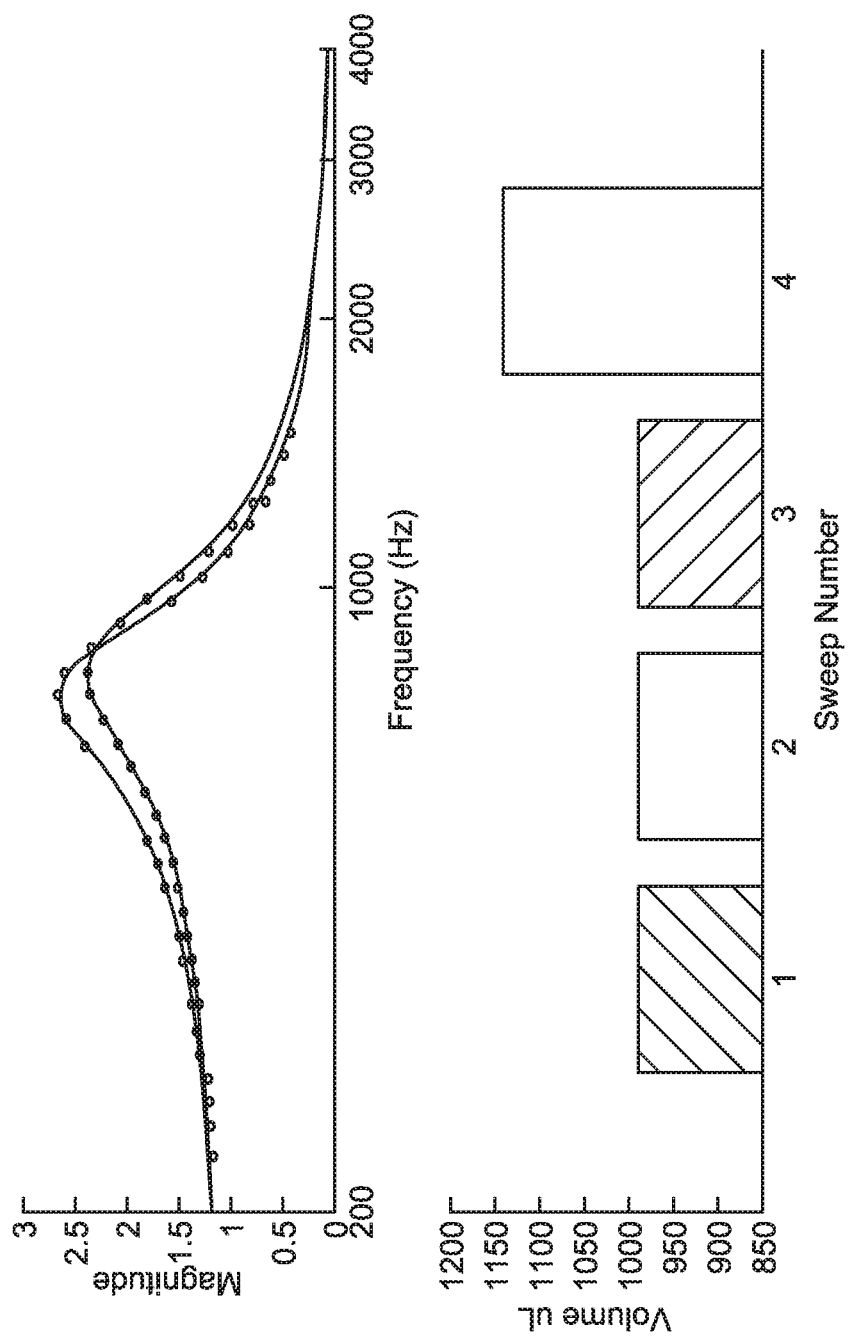

FIG. 180 illustrates the AVS sweep performed during multiple (full cycles) of fluid discharge towards the patient using the pump 700 of FIG. 175 when there is a downstream occlusion. That is, each sweep may be performed after the plunger is expected to discharge fluid towards the patient. As shown in sweep 4, the pump 700 is not discharging the fluid. For example, the pump 700 may slowly fill the downstream compliance of the tube 707 until the tube can no longer expand, in which case, the pump 700 has difficultly pumping additional liquid downstream because the spring of the plunger cannot apply sufficient force to pump additional liquid downstream. The processor 37 (see FIG. 3) may determine that the decreased liquid delivery during each cycle of the pump 700 indicates that a downstream occlusion exists.

FIGS. 181-183 show several side views of a cam mechanism of the peristaltic pump of FIG. 175 in accordance with an embodiment of the present disclosure. FIG. 181 shows a side sectional-view of the plunger 706. The movement of the plunger 706 and cam follower 709 is monitored by an optical cam follower position sensor 711.

There are various devices that may be used to sense the position of the pump plunger 706 and pinch valves of the pump of FIG. 175. These include, but are not limited to one or more of the following: ultrasonic, optical (reflective, laser interferometer, camera, etc), linear caliper, magnetic, mechanical contact switch, infrared light measurement, etc. In one embodiment, a small reflective optical sensor assembly (hereinafter "optical sensor") that fits into the exemplary embodiments of the peristaltic pump 175, as shown and described, for example, herein, may be used. The optical sensor in the various embodiments has a sensing range that accommodates the components for which the optical sensor may be sensing, e.g., in some embodiments, the plunger 706. In the exemplary embodiment any optical sensor may be used, including, but not limited to a Sharp GP2S60, manufactured by Sharp Electronics Corporation, which is a US subsidiary of Sharp Corporation of Osaka, Japan.

In various embodiments, the pumping apparatus may be based on the principle of indirect compression of a flexible tube segment through the application of a restoring force against the tubing segment by a spring-based apparatus. As shown in FIG. 181, a cam lobe or element 702 may be eccentrically disposed on a shaft 705 to cause cam follower 709 to move in a reciprocating fashion as the cam element 702 rotates. Plunger spring 710 in this illustration is biased to urge a plunger 706 to compress the flexible tube segment 707 situated within the peristaltic pump 700. Thus, in this arrangement, a spring constant may be selected for spring 710 to cause the plunger to compress flexible tube segment 707 to the extent necessary to deform the wall of the tube segment when liquid having a pre-selected range of viscosities is present within it, and for a pre-determined flow resistance of the fluid column to the end of a catheter or cannula attached to the terminal end of the flexible tube. In this way, the distance and speed with which plunger 706 moves to compress tubing segment 707 can provide information about the state of the tubing distal to tubing segment 707, such as whether there is a complete or partial occlusion involving the tube or an attached catheter, or whether the catheter has been dislodged out of a blood vessel or body cavity and into an extravascular tissue space. The movement of the spring or attached elements (such as the plunger) may be monitored by one or more sensors, the data being transmitted to a controller (e.g., the processor 37 of FIG. 3) for analysis of the rate and pattern of movement as the tube segment is compressed. Examples of suitable sensors for this purpose may include, for example, Hall Effect sensors, potentiometers, or optical sensors including LED-based, laser-based or camera-based sensing systems that are capable of transmitting data to a controller employing various forms of pattern-recognition software.

The action of peristaltic pump 700 of FIG. 175 is illustrated in FIGS. 182A-182C. FIG. 182a shows the cam lobe or element 704 contacting cam follower 709, compressing spring 710, and moving the plunger 706 away from tube segment 707. FIG. 182b shows cam lobe 704 having rotated about cam shaft 705 away from cam follower 709, allowing spring 710 to extend, and the plunger 706 to begin compressing tube segment 707. In FIG. 182c, cam lobe 704 has rotated sufficiently to completely release cam follower 709 to allow spring 710 to extend sufficiently to allow the plunger 706 to completely compress tube segment 707. Assuming that an inlet valve acting on tube segment 707 entering pump 700 is closed, and an outlet valve acting on tube segment 707 leaving pump 700 is open, a volume of liquid within tube segment 707 will be propelled distally out of the tube segment 707. Although the side-view shown in FIG. 182 is of a plunger, the operation of the inlet and outlet valve may be similar and/or the same.

FIGS. 183A-183C illustrate a scenario in which the resistance to flow of the liquid column within tube segment 707 is increased beyond the pre-determined functional range of the spring selected for pump 700. As cam lobe 704 moves from a spring compressing position in FIG. 183a to a spring de-compressing position in FIG. 183b, the spring force is insufficient to compress tube segment 707 quickly, and may only be able to compress tube segment 707 partially, as shown in FIG. 183c. The rate of movement and end position of a component the plunger-spring-cam follower assembly may be detected by one more sensors appropriate for this task (e.g., camera-based sensor), which may, for example, be mounted near or adjacent to plunger 706. This information may be transmitted to a controller, which can be programmed to interpret the signal pattern in light of stored data that has previously been determined empirically. The pattern of volume-change vs. time of a compressed tube segment such as that shown in FIG. 180 may in some cases mirror the pattern to be expected of movement vs. time when the relative position of a component of the plunger-spring-cam follower assembly is tracked.

FIG. 184 shows a sectional view of the pinch valves 715 and 716 and plunger 718 of the peristaltic pump of FIG. 175 in accordance with an embodiment of the present disclosure. In various embodiments, the tube segment within the pumping apparatus is held against an anvil plate during compression by a plunger. The tube segment may be held in position by being secured in a form-following raceway having sufficient space to allow for the lateral displacement of the tube segment walls as it is being compressed. However, this may allow for some lateral movement of the tube segment in an uncompressed state. FIG. 185 shows an alternative arrangement in which the tube segment may be held in position by flexible side arms or fingers that can elastically spread apart to accommodate the spreading sides of the tube segment as it is compressed. FIG. 185 shows a plunger comprising flexible side arms or fingers to grip a tube segment to keep it relatively immobilized in both a non-compressed and compressed state. In an uncompressed or 'unpinched' state, the flexible fingers fit snugly against the sides of the tube segment, preventing lateral movement of the tube within the pumping apparatus. In a compressed or 'pinched' state, the flexible fingers elastically spread apart to accommodate the lateral displacement of the tube segment walls as it is compressed, maintaining the overall position of the tube segment within the pumping apparatus.

FIG. 186 shows an embodiment of a cam mechanism of a peristaltic pump 719 in accordance with an embodiment of the present disclosure. A cam 720 controls a pinch valve 721. A Cam 722 controls plungers 723, 724, and 725. A cam 726 controls another pinch valve 727. A latching mechanism (e.g., a magnetic latch) may prevent the plungers 723 and 725 from moving to compress the tube 728 as shown in FIG. 187.

Figure 188:
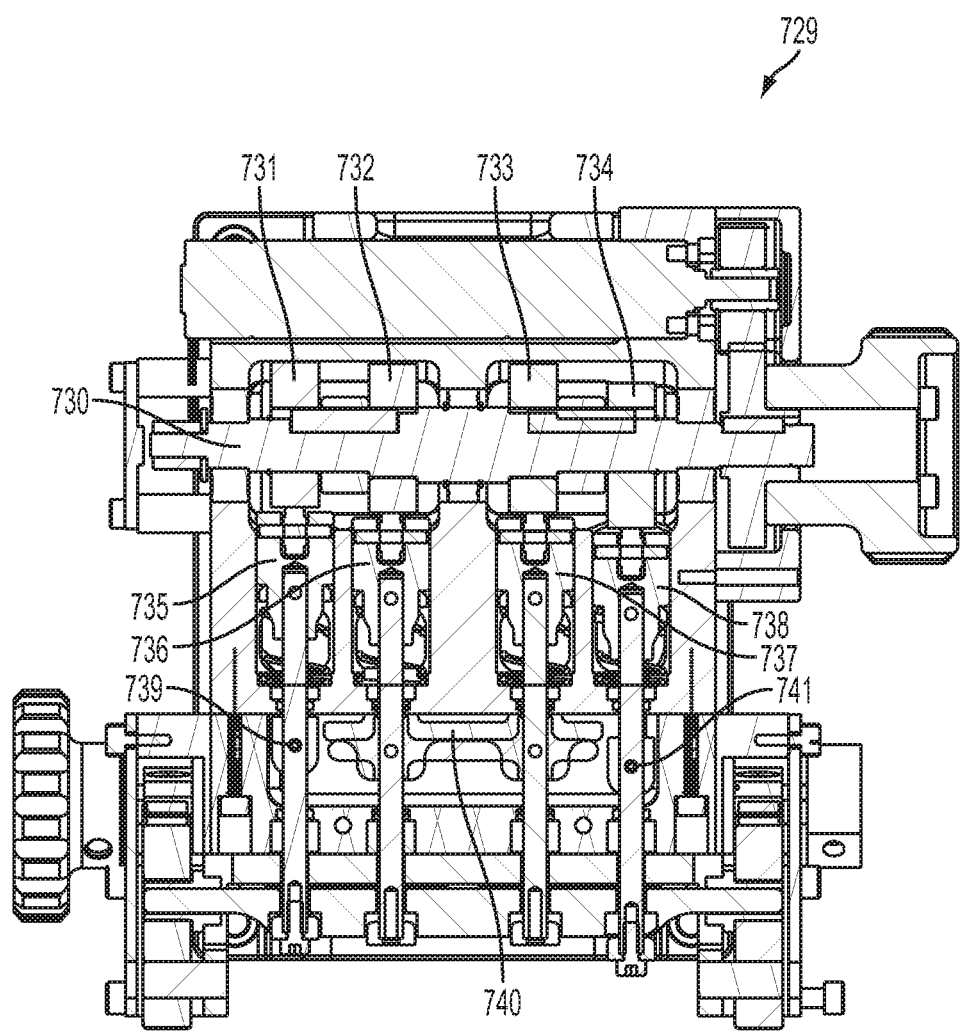
Figure 189:
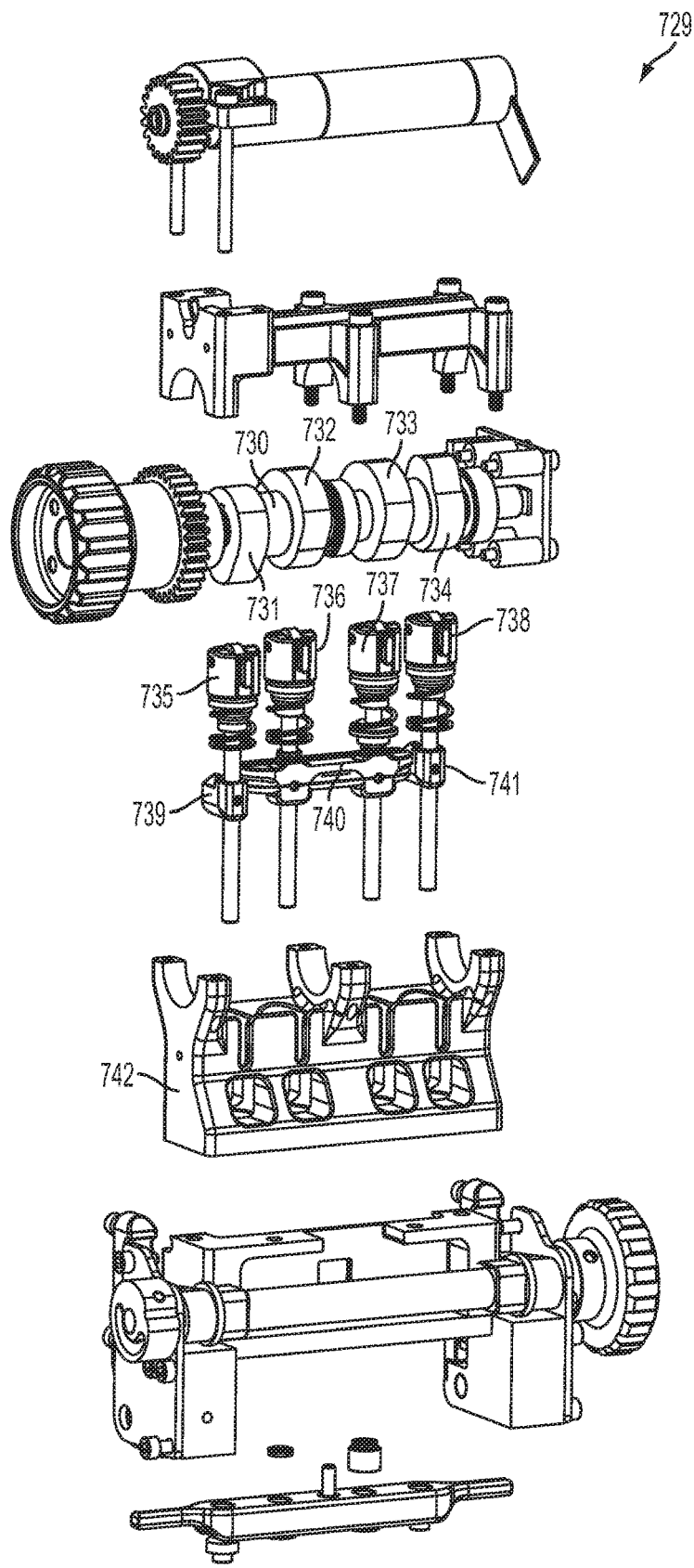
Figure 190A:
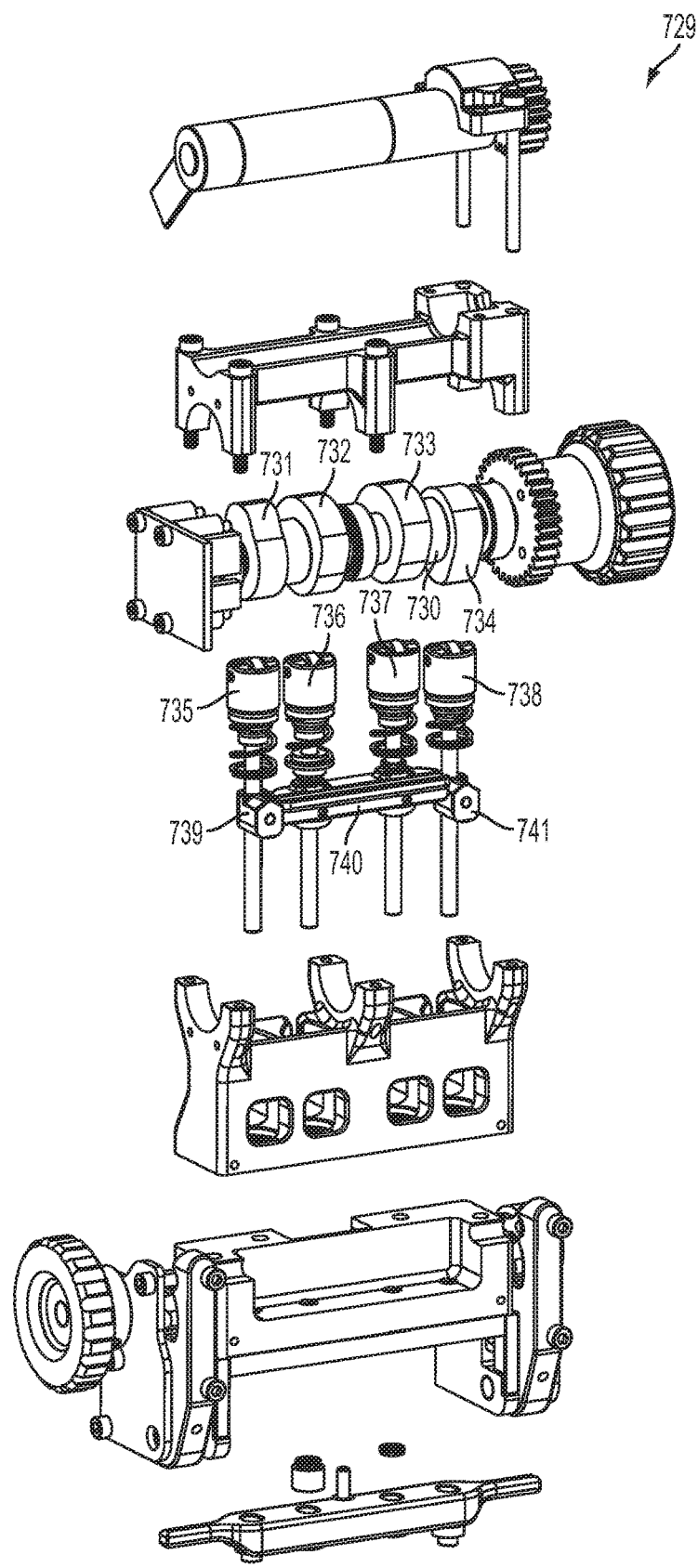
Figure 190B:
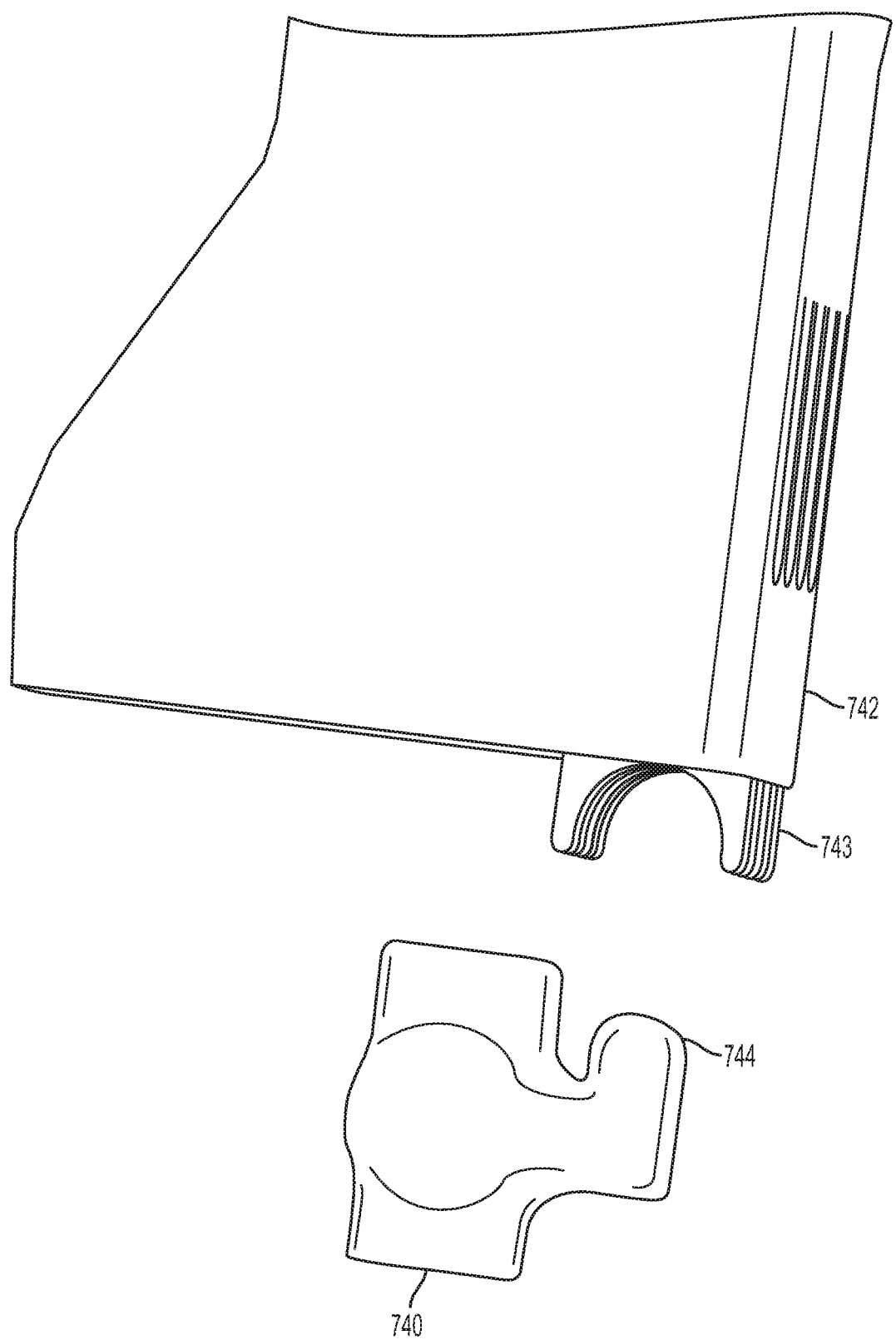
Figure 190C:
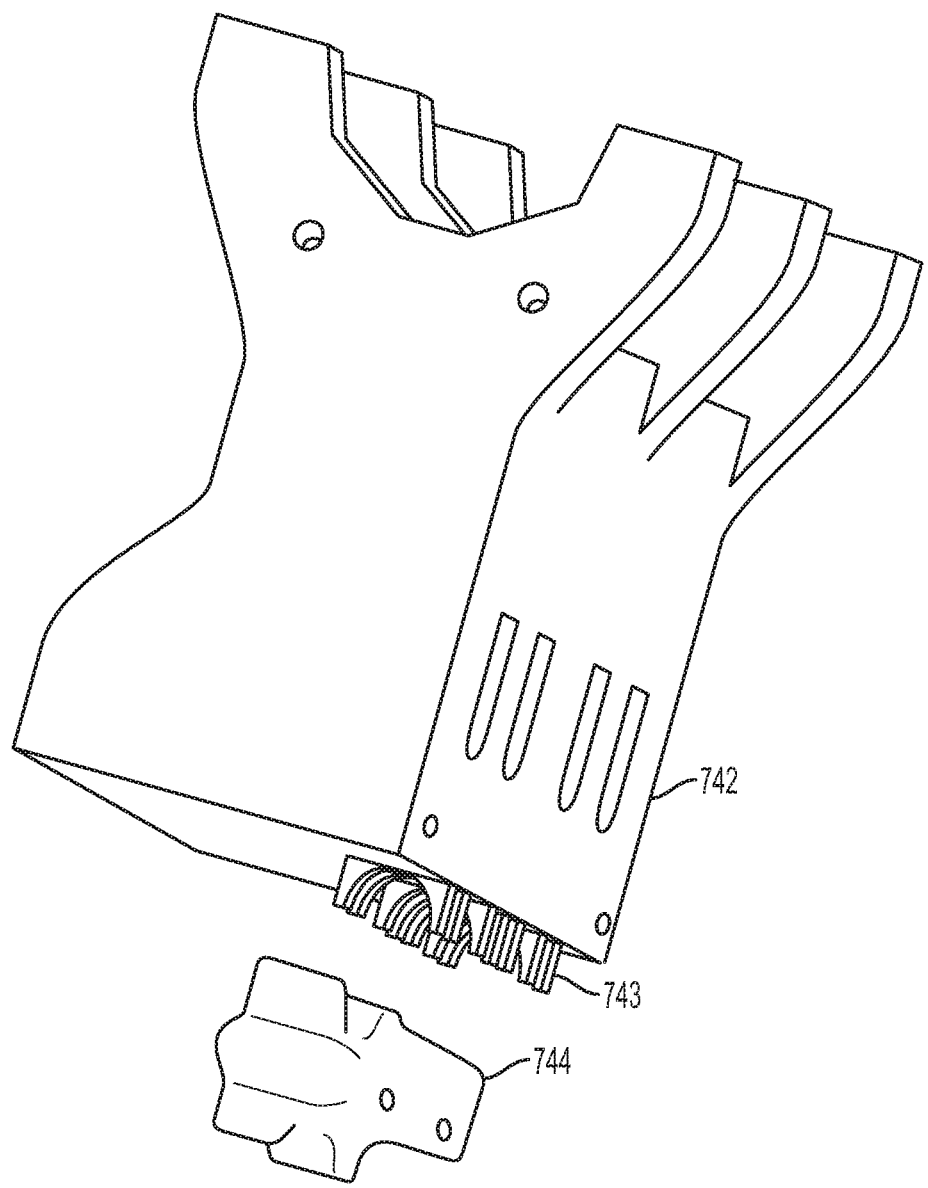
Figure 192:
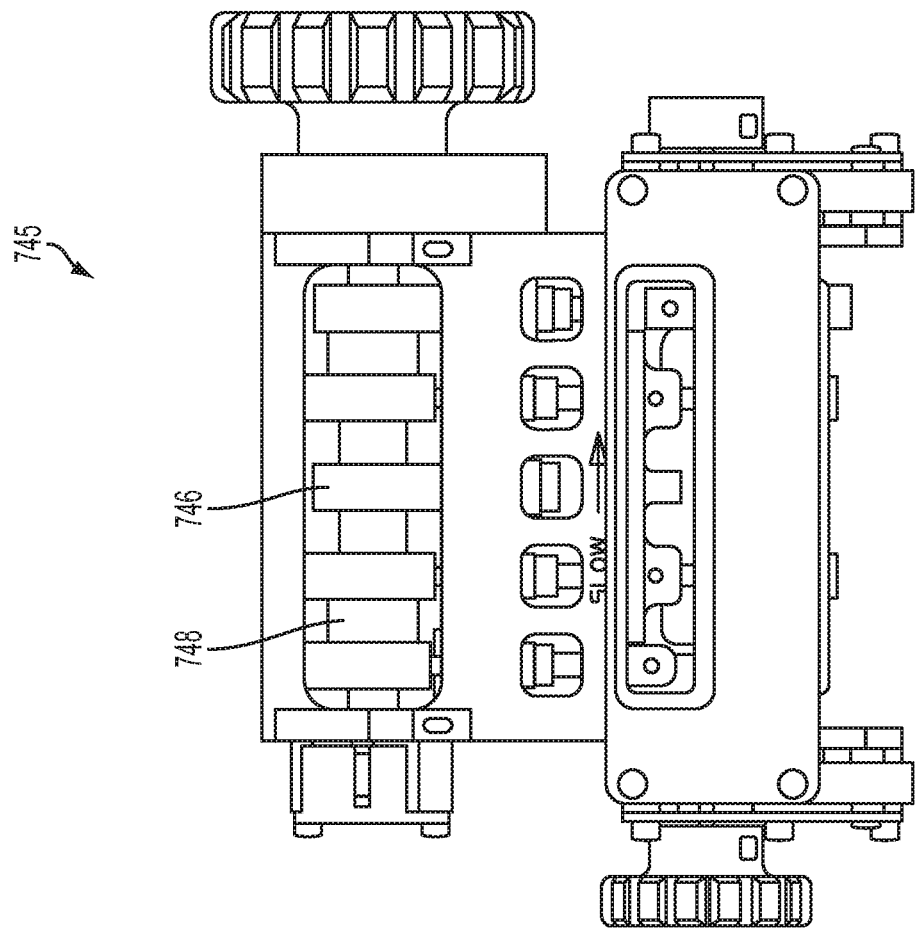
Figure 191:
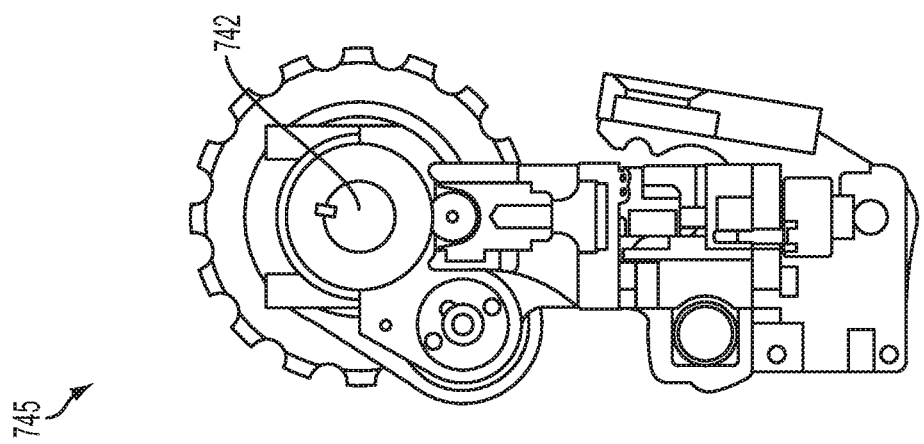
Figure 193:
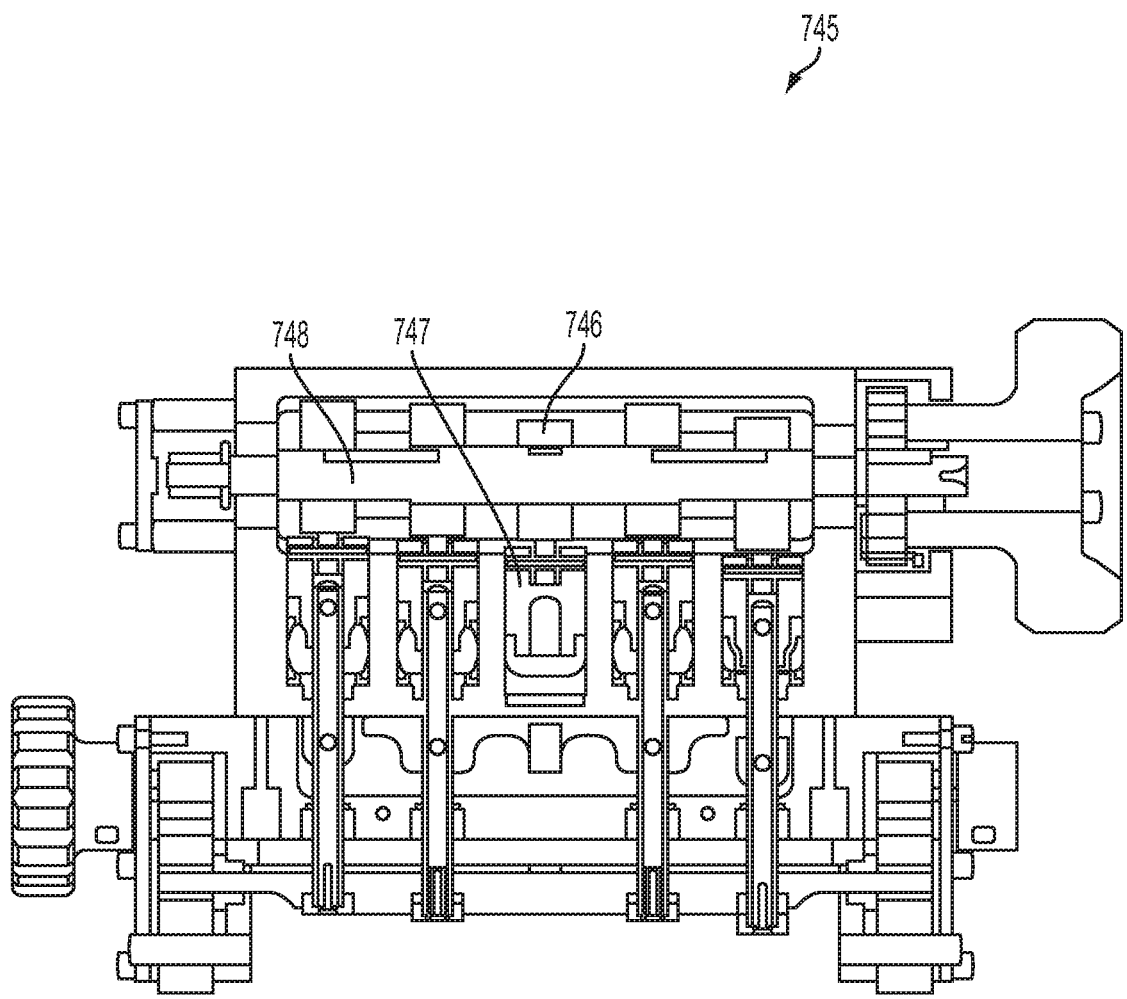
Figure 194:
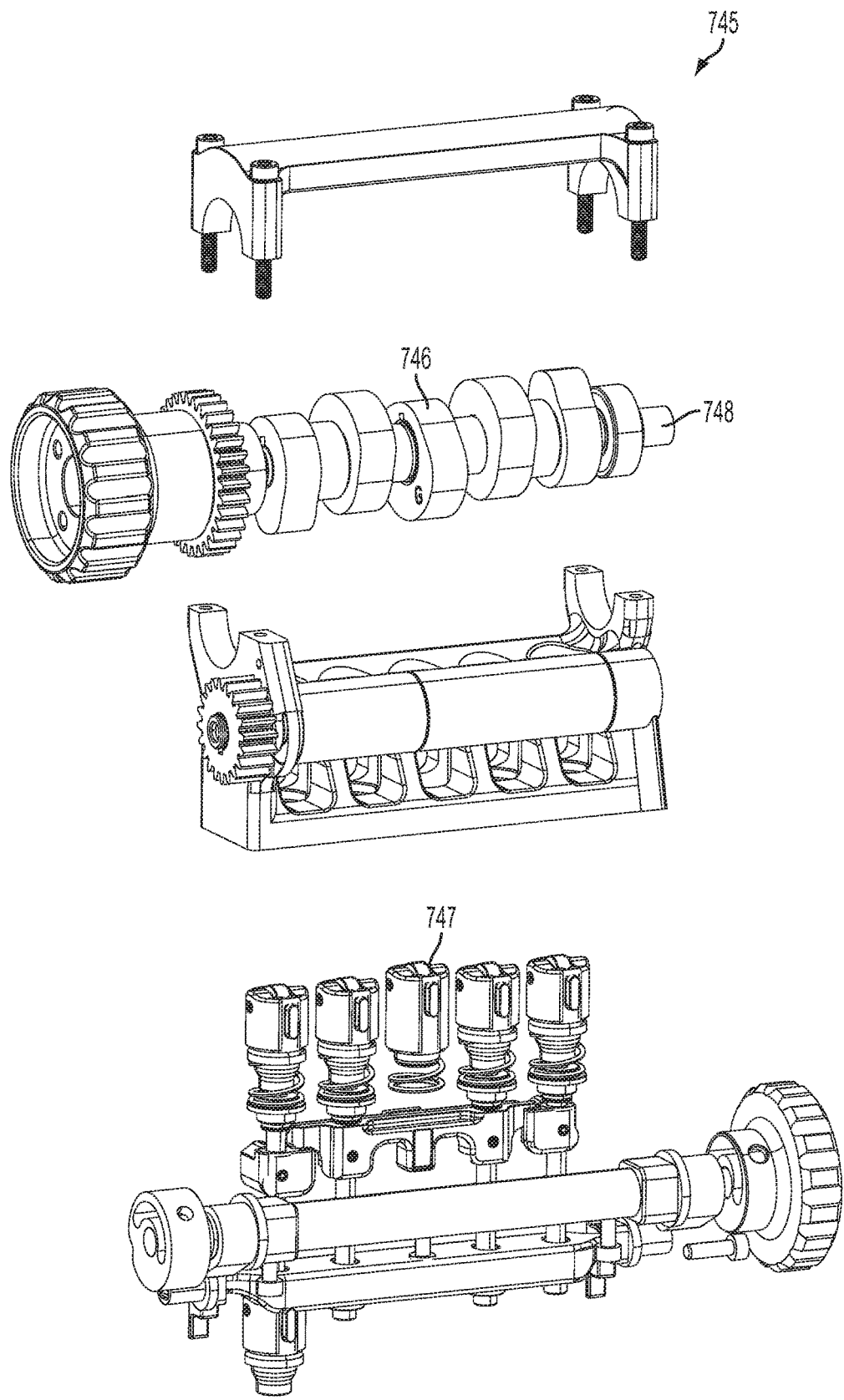
Figure 195:
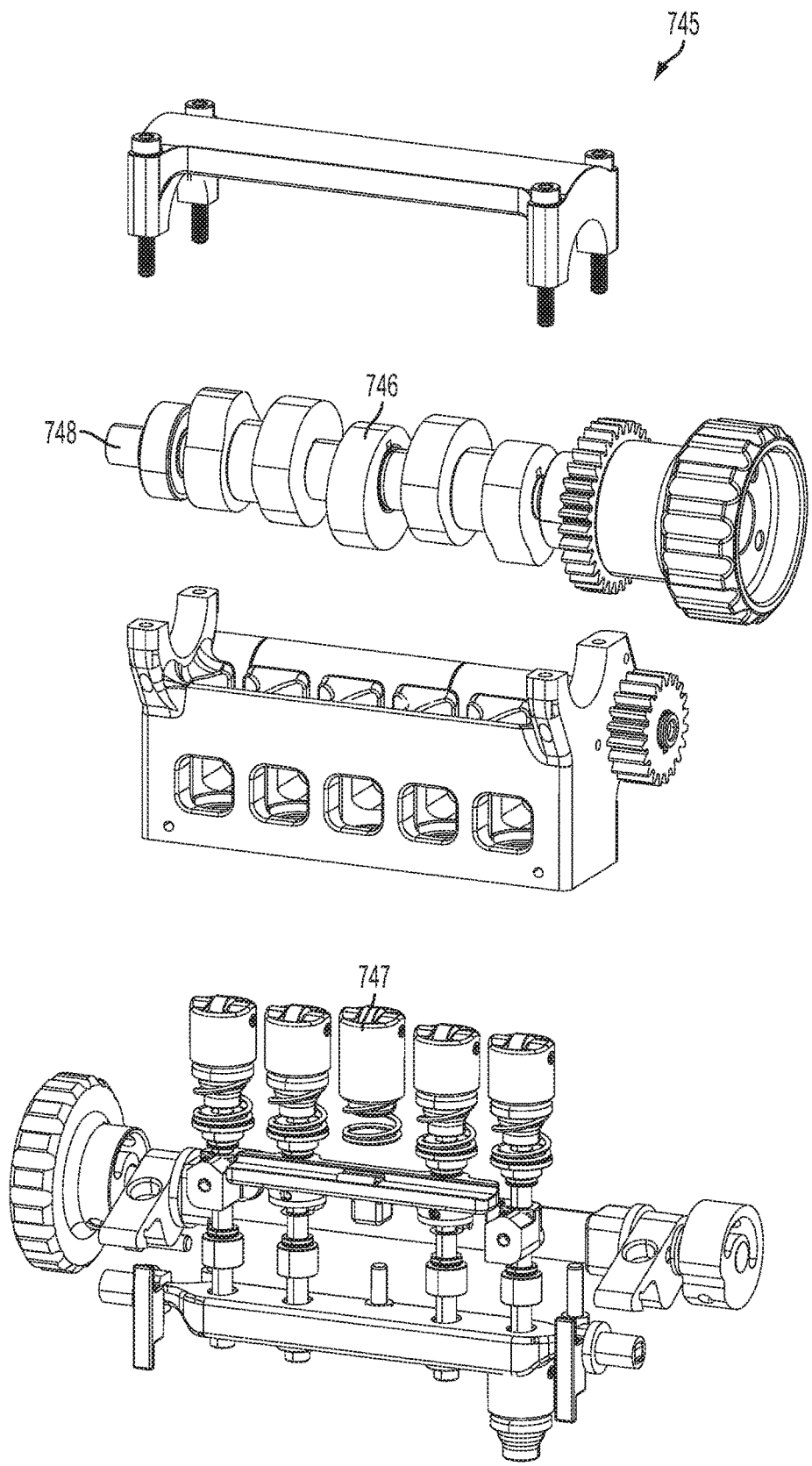

FIGS. 188, 189, and 190A show several views of a peristaltic pump 729 in accordance with the present disclosure. The peristaltic pump 729 includes a cam shaft 730 coupled to cams 731, 732, 733, and 734 that engage the cam followers 735, 736, 737, and 738, respectively. The cam follower 735 is coupled to a first pinch valve 739, the cam followers 736 and 737 are coupled to a plunger 740, and the cam follower 738 is coupled to another pinch valve 741. As shown in FIGS. 190B-190C, the plunger 740 includes a pincher 744 that engages fingers 743 forming a raceway.

FIGS. 191-195 show several views of a peristaltic pump 745 in accordance with an additional embodiment of the present disclosure. The peristaltic pump 745 of FIGS. 190-195 is similar to the peristaltic pump 729 of FIGS. 188-190C, except that the peristaltic pump 745 of FIGS. 190-195 includes a torque balancing cam 746 coupled to a cam follower 747 that operate together to smooth the rotational torque of the camshaft 748.

FIG. 196A illustrates the torque profile of a rotating cam shaft of the peristaltic pumps of FIGS. 188-190C and of FIGS. 191-195 in accordance with an embodiment of the present disclosure. The torque profile 749 shows the torque of the peristaltic pumps of FIGS. 188-190C. torque 750 shows the torque produced by the torque balancing cam 746 of the peristaltic pump of FIGS. 191-195. The torque profile 751 shows the resulting net torque on the camshaft 748 caused by the smoothing operation of the torque balancing cam 746 (also see FIG. 196B).

FIG. 197 illustrates a cam profile for several cams for a peristaltic pump in accordance with an embodiment of the present disclosure. The cam profile describes the four stage pumping action described above. The solid lines describe the linear position of the cams. The dashed lines plot the position of the plunger and valves. The Pump cam and plunger position over time are plotted in 1300. The inlet valve cam and inlet valve position are plotted in 1302. The outlet valve cam and outlet valve position are plotted in 1304. In stage 1, the outlet valve closes at 1306. The inlet valve opens at 1308. The plunger is lifted off the tube at 1310, which allows fluid to enter the tube under the plunger. In stage 2, the inlet valve closes at 1312, while the plunger remains lifted off the tube. In stage 3, the plunger is allowed to compress the tube. The position of the plunger 1314 departs from the cam position due to the presence of fluid in the tube. The controller may execute a number of diagnostic tests including but not limited to leak tests, air in the line, occlusions based on the measured position and movement of the plunger during stage 3. In stage 4, the outlet valve is opened at 1316 first. After the outlet valve is opened, the plunger is allowed to compress the tube forcing liquid out of the pump. The plunger force is supplied by springs acting on the plunger or springs acting on the plunger cam followers. The cam may be formed to limit the descent of the plunger during stage 4. The actual position of the plunger may be further limited by the fluid flow out of the tube. The processor on the pump may actively control the plunger position by controlling the cam rotation based on the measured location of the plunger. This closed loop control of the motor may provide low flow rates (FIG. 198). In other embodiments at higher flows, the cam and/or motor will be controlled in an open loop.

FIG. 198 shows various feedback modes of a peristaltic pump in accordance with an embodiment of the present disclosure. In a closed loop mode, feedback from the AVS measurements and/or the linear sensor is used to control the speed of the camshaft. In open loop mode, the speed of rotation is selected by reference to a lookup table in response to a target fluid flow rate.

FIG. 199 shows a graph illustrating data of a linear sensor used to estimate fluid flow in accordance with an embodiment of the present disclosure; The delta value from the plateau 752 caused by both inlet and outlet valves being closed in a peristaltic pump with the plunger fully compressing against a fluid filled tube and the plateau 753 cause after the outlet valve is opened and all of the fluid is expelled out of the peristaltic pump and the plunger is fully compressing against the tube by the force from its spring.

FIGS. 200-206 show an alternate embodiment of a peristaltic pump 1200 wherein a motor 1204 may drive a cam shaft 1206 via a gear train 1208. The cams may actuate one or more valves 1226, 1228 and a plunger 1222 via levers that rotate about a common axis. The tube 1202 is held in place by a door 1212. The peristaltic pump 1200 may include a receptacle for a slide occluder 1200 and mechanisms that prevent a free-flow condition on the tube during installation of the tube in the peristaltic pump 1200.

The cam shaft 1206 may include several cams 1232A-E. The cams 1232A-E may control the position of several items that may include but are not limited to the following: inlet pinch valve 1224, plunger 1222, outlet pinch valve 1226, and a torque balancer. The cams 1232A-E may be contacted by wheels 1214A-E on the cam followers 1216A-E. The cam followers 1214A-E may include magnets 1218A-E. The position of each magnet may be detected by an array of sensors 1220. The pump controller may calculate the position of a pump plunger 1222 and valves 1226, 1228 from the sensor signals generated by the magnets 1218A-E. The peristaltic pump 1200 may include an ultrasonic sensor 1228 to detect the presence of the air bubbles in the fluid exiting the pump. The ultrasonic sensor 1228 may communicate with the pump controller.

The cam followers 1214A-E may have an L shape and may pivot about a central axis at 1230. The cam followers are held against the cams 1232A-E by springs 1234A-E. Spring 1234C may provide a torque balancing load. The springs 1234B and 1234D may provide the force to urge the plunger toward the anvil plate 1236. The springs 1234A and 1234E may provide the force to close the pinch valves 1226, 1228 against the anvil plate 1236.

Figure 207:
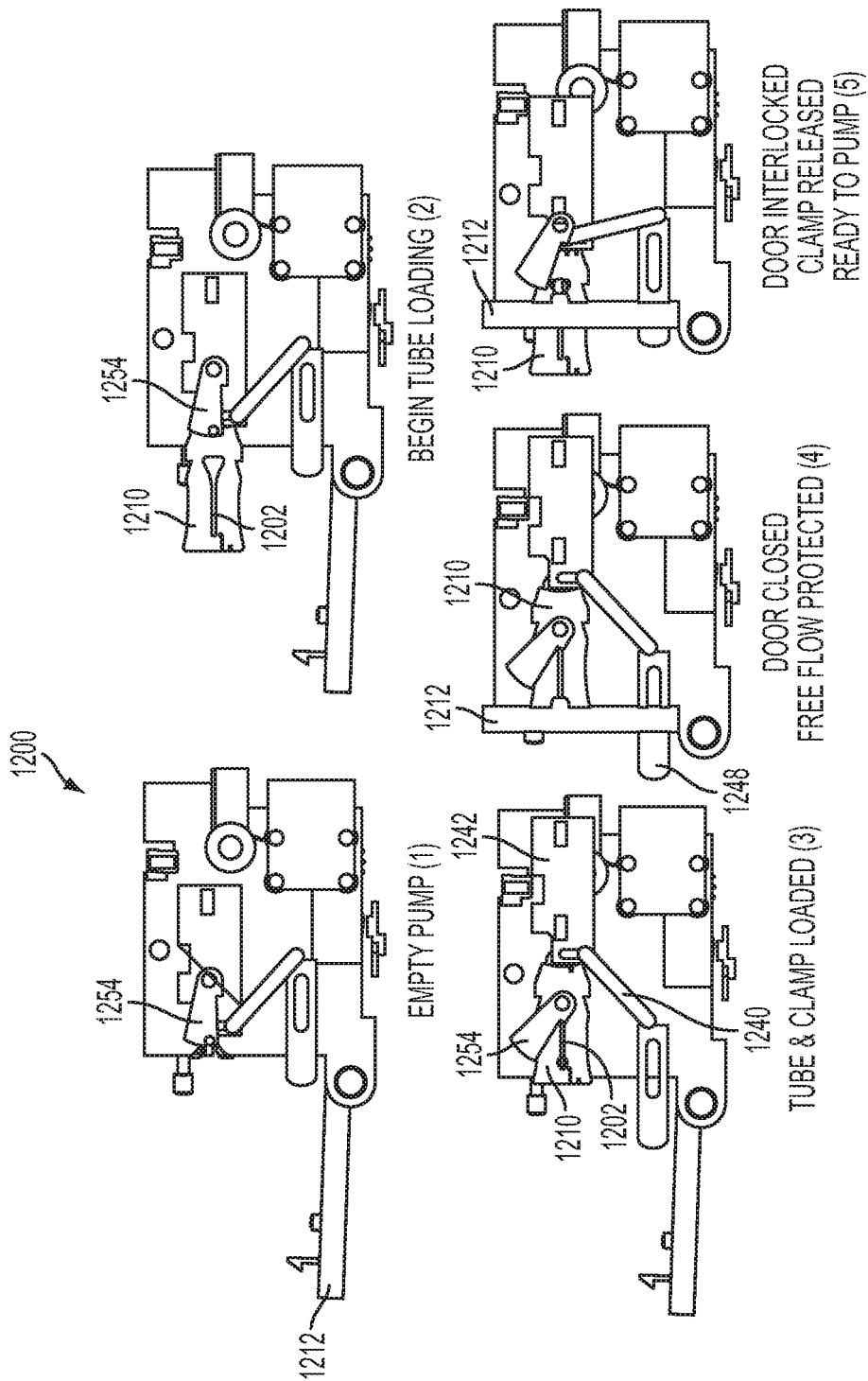
Figure 209:
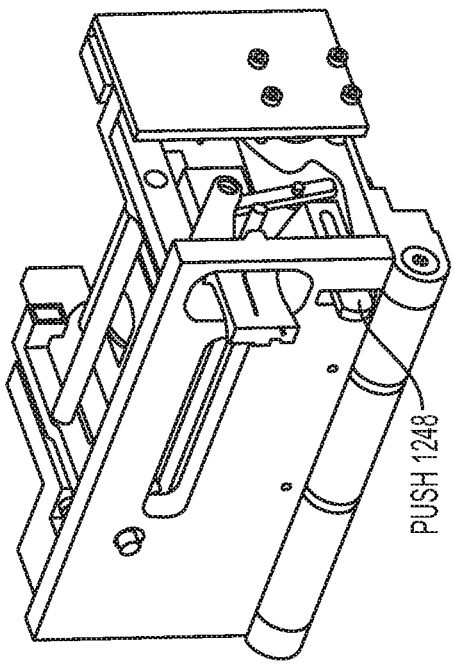
Figure 208:
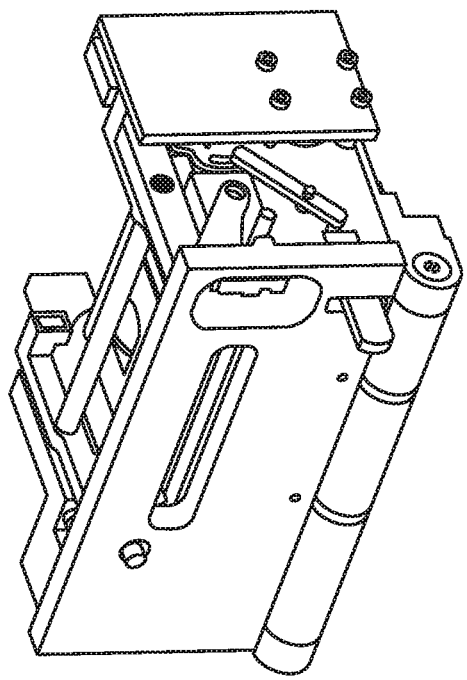

FIG. 207 illustrates the installing tube with the slide occluder in the peristaltic pump 1200. In step 1, the door 1212 is open. In step 2, the tube 1202 and slide occluder 1210 are placed in position in the peristaltic pump 1200. In step 3, the slide occluder 1210 is slid into the peristaltic pump 1200 and displaces slide 1242 and lever 1240 away from the door and displaces button 1248 forward. The tube 1202 is held near the front peristaltic pump 1200 as the slide occluder 1210 so that the tube 1202 is in the narrow part of the slot and pinched closed. In step 4 the door is closed. In step 5, the slide occluder 1210 pushed out by the movement of button 1248 toward the back of the peristaltic pump 1200. The button 1248 moves lever 1240, which draws slide 1242 forward. The forward movement of the slide occluder 1210 releases the pinch on the tube 1202 by the slide occluder 1202.

Figure 210:
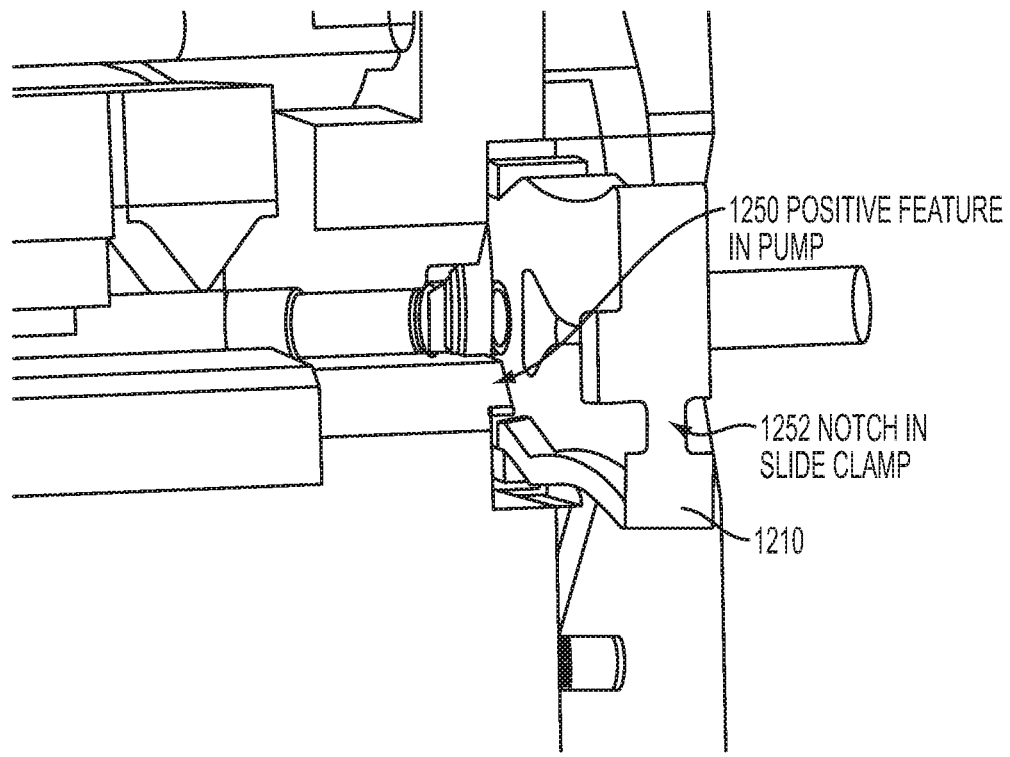
Figure 218:
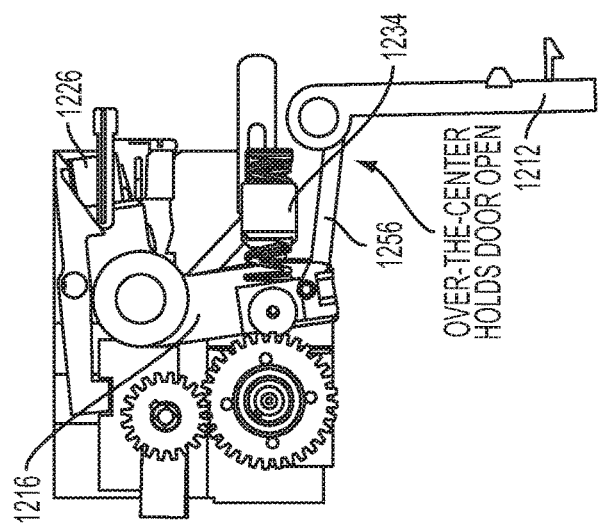
Figure 217:
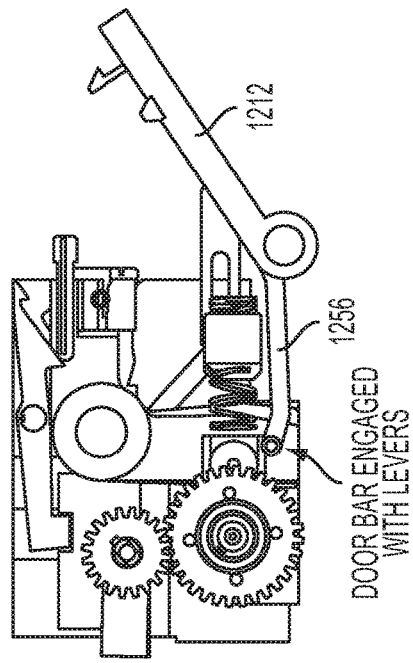
Figure 216:
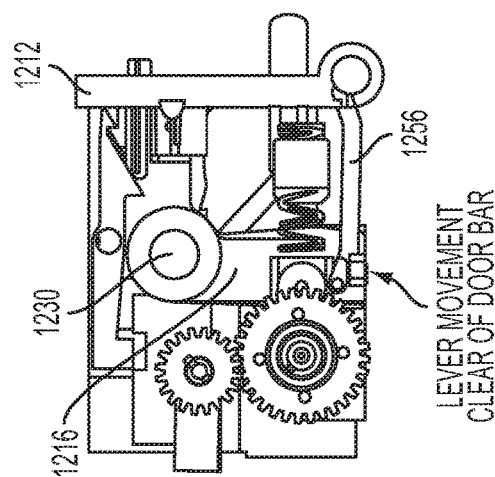
Figure 220:
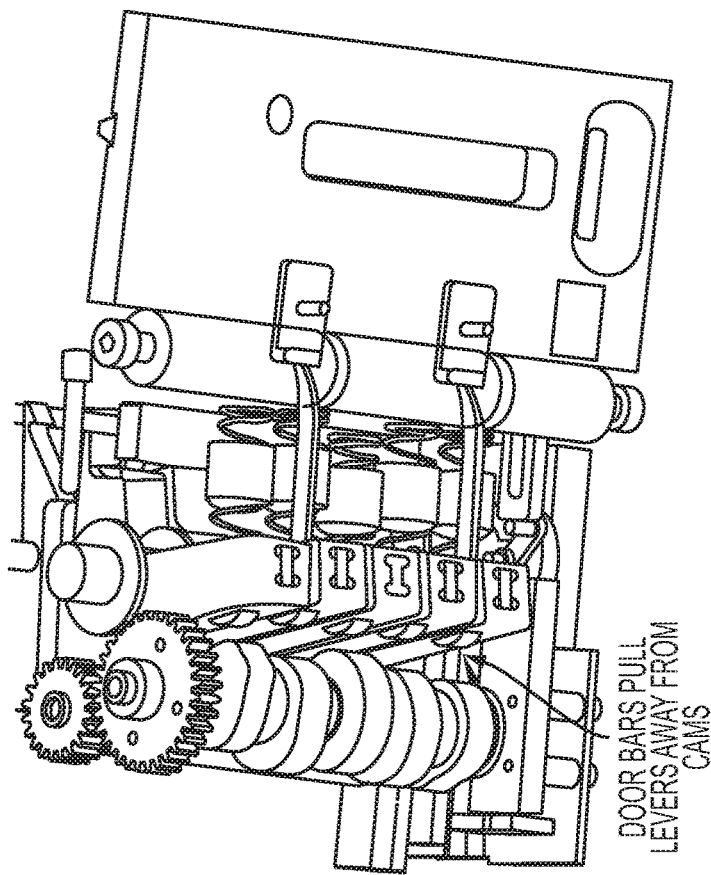
Figure 219:
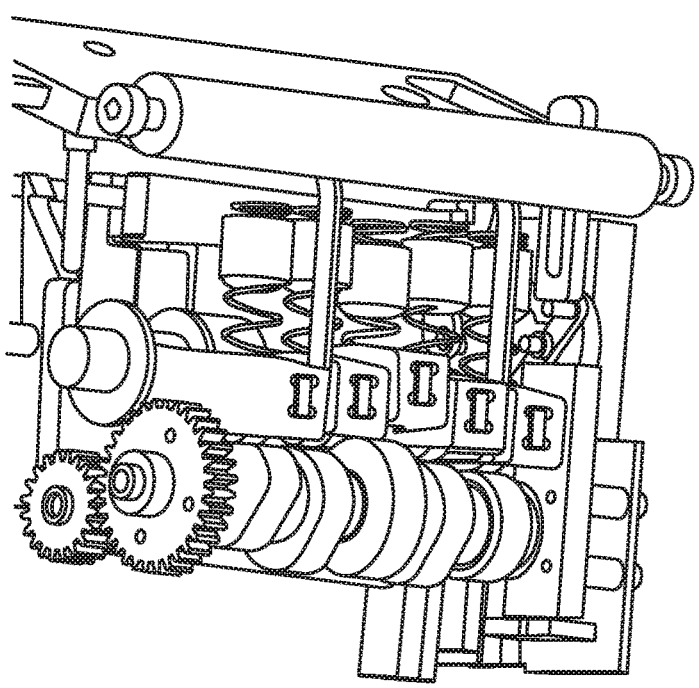

FIGS. 210-212 illustrates features to prevent the user from installing a tube without the correct slide occluder. A tab 1250 prevents a slide occluder 1210 from being installed that does not have a matching slot 1252. A shutter 1254 prevents the door 1212 from closing. The shutter 1254 is displaced by the slide occluder 1210 in step 3 of FIG. 207.

FIGS. 213-220 illustrate how the peristaltic pump 1200 prevents a free flow condition when the tube 1202 is loaded and/or removed. The door 1212 easily opens to an angular position 90° from the front of the peristaltic pump 1200. A small force may be applied to further rotate the door 1212, which forces the plunger 1222 and the pinch valves 1224, 1226 into the open position. The movement of the door 1212 pulls the L shaped cam followers 1218A-E toward the front and thereby lifts the plunger 1222 and the pinch valves 1224, 1226 off the tube 1202.

Figure 221:
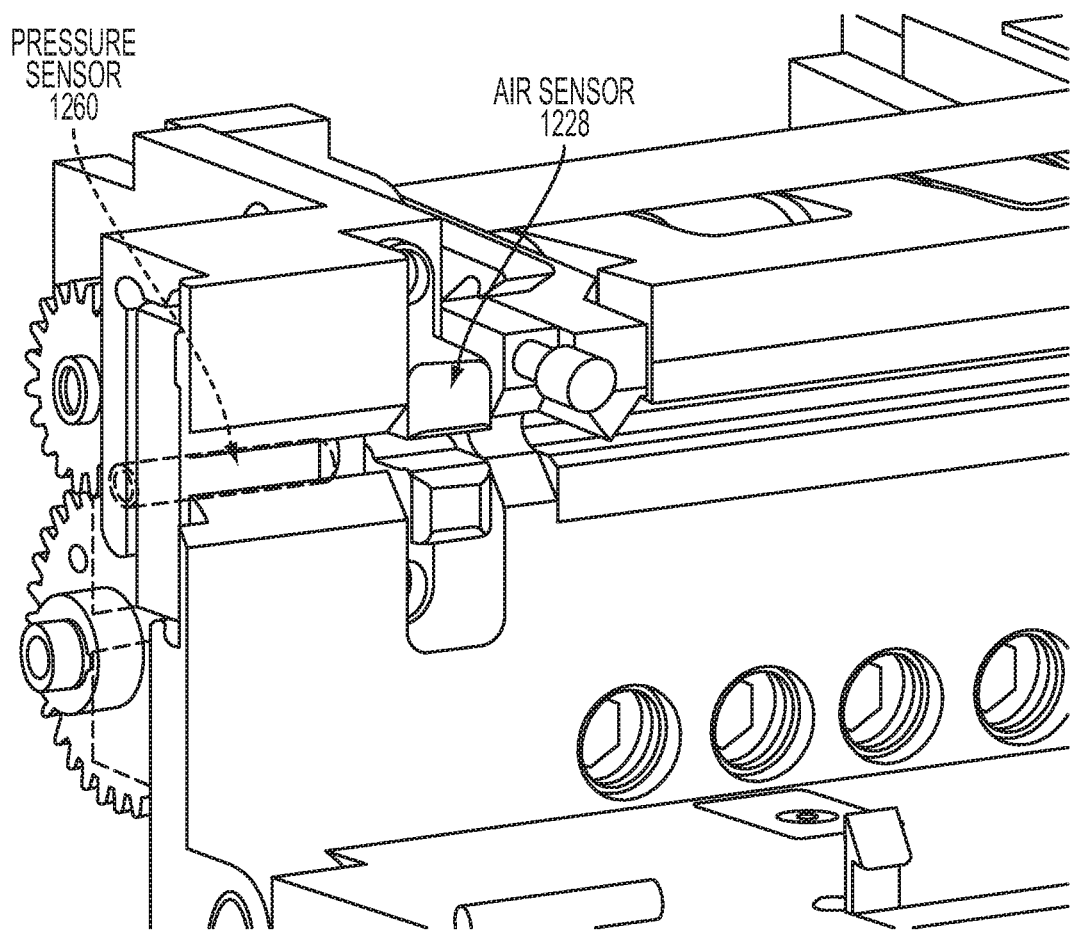

FIG. 221 illustrates the ultrasonic air sensor 1228 that may detect air bubbles of a certain size in the fluid downstream of the pinch valve 1266 pump. The pressure sensor 1260 may measure the static pressure in the fluid downstream of the pump. The pressure sensor 1260 and air sensor 1228 may communicate with the pump controller.

FIG. 222-223 shows two views of a peristaltic pump 754 in accordance with an embodiment of the present disclosure.

Figure 225:
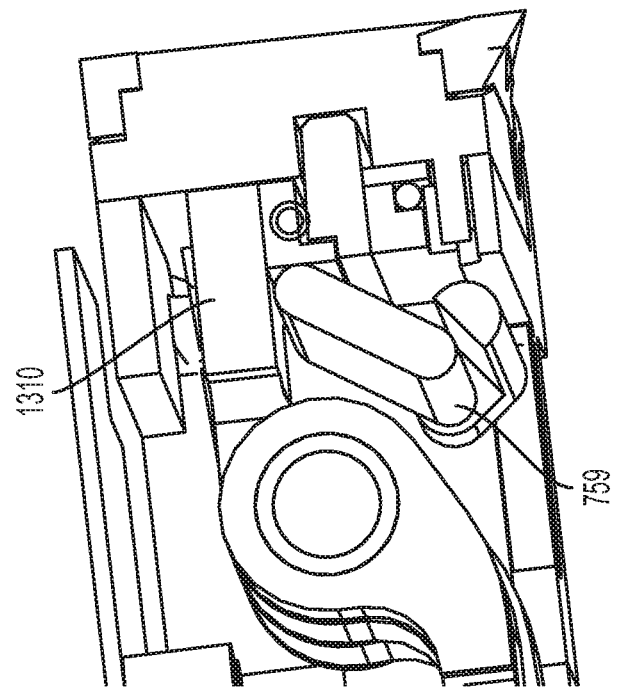
Figure 224:
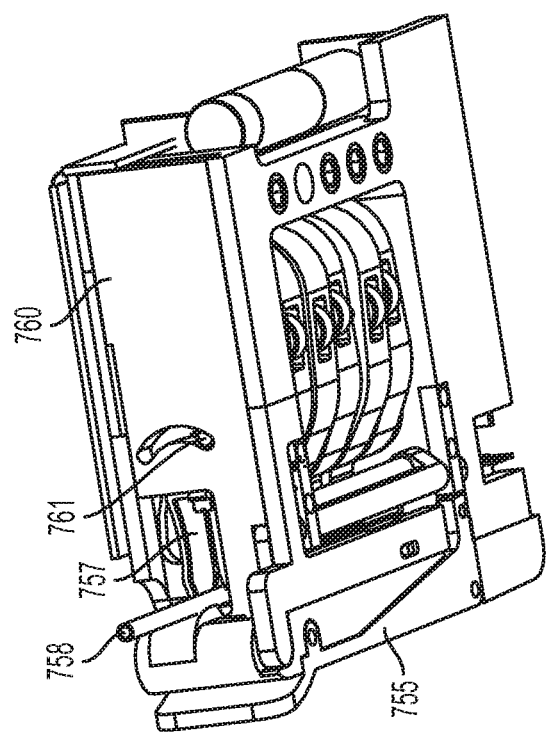
Figure 228:
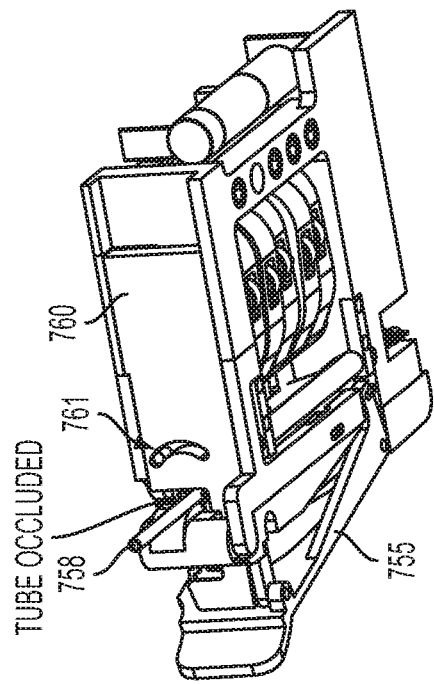
Figure 229:
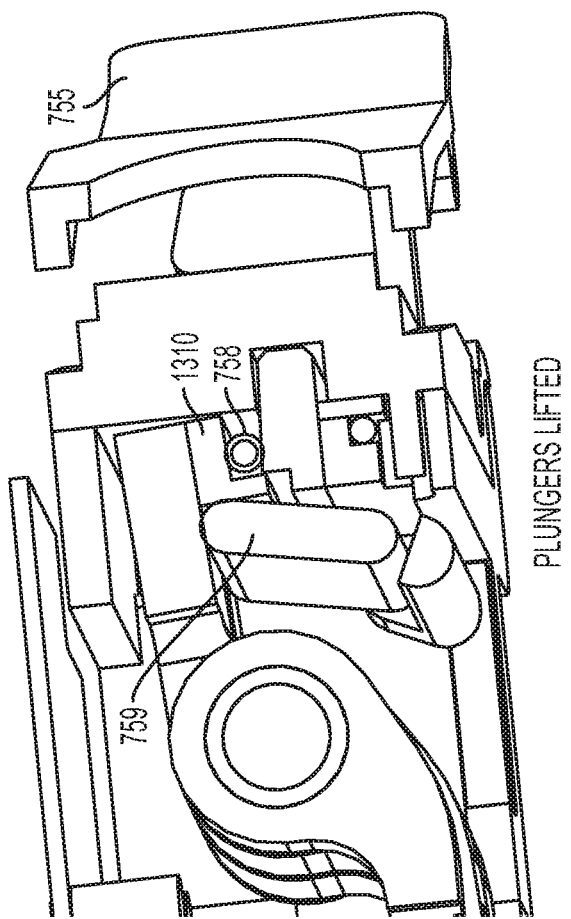

The peristaltic pump 754 includes a door lever 755 and a door 756. FIG. 224 shows the slide occluder 757 in an open position against the tube 758. The slide occluder 754 is carried in the slide occluder carriage 1312. The slide occluder carriage 760 engages a pin 761 that is in mechanical communication with the plunger lift lever 759 in FIG. 225. FIG. 225 illustrates that as the door lever 755 is opened (see FIG. 244), a plunger lift lever 759 is not lifting the plunger 1310 and pinch valves. FIG. 226 shows how as the door lever 755 is opened, the carriage 760 moves forward toward the door and moves the slide occluder 757 passed the tube 758 so that the tube 758 is closed as it passes into the narrow section of the slide occluder 757. At approximately the same time that the tube 758 is pinched closed by the slide occluder 757 the forward motion of the carriage 760 rotates the pin 761 which moves the plunger lift level 759 to lift the plungers 1310 and pinch valve off the tube 758 as shown in FIG. 227. In FIG. 228, the door lever 755 is fully opened and the carriage 760 stops moving. As shown in FIG. 229, the plunger lift lever 759 is in a stable over center position that will keep the plunger 1310 off the tube 758 when the door lever 755 is fully opened.

Figure 230:
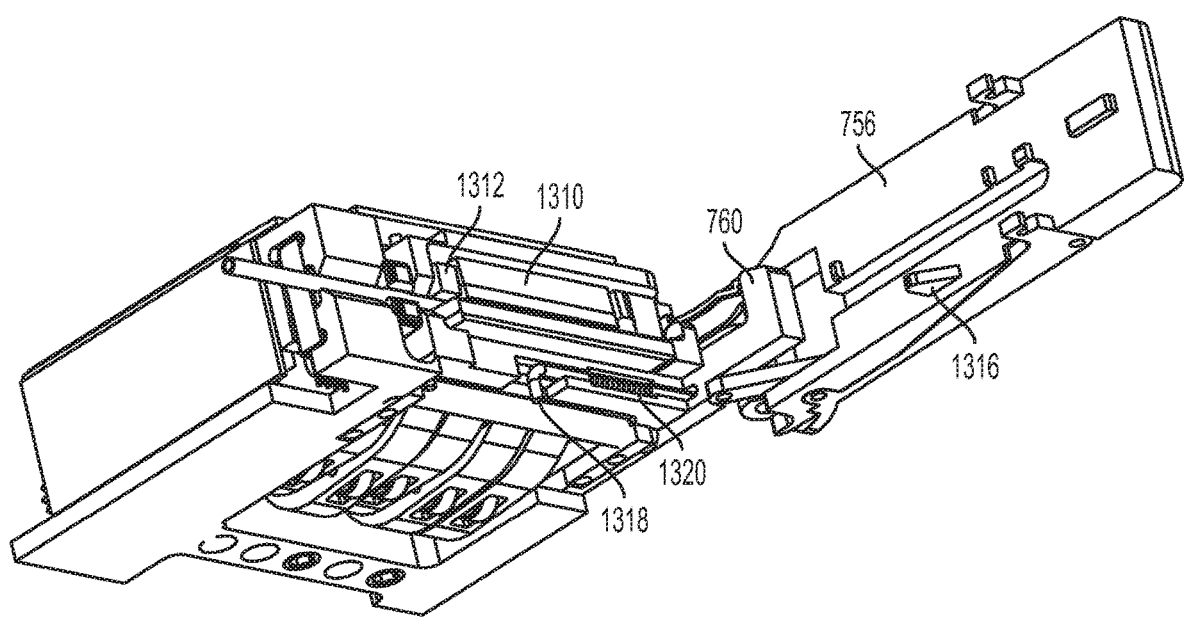

FIGS. 230-233 illustrate an interlock that may prevent the slide occluder carriage 760 from moving and closing the plungers 1310 and valves 1312 without the door 756 being closed first. FIG. 230 shows the door 756 open and the release tab 1316 exposed. The interlock pin 1318 is shown in the interlocked position that prevents the slide occluder carriage 760 from moving. A spring 1320 pushes the interlock pin 1318 toward the slid occluder carriage 760 and engages the interlock pin in a matching hole when the slide occluder carriage 760 is in position.

Figure 231:
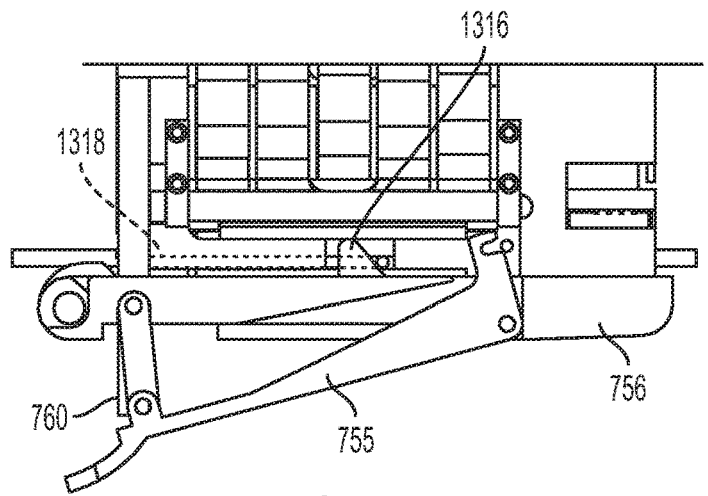
Figure 232:
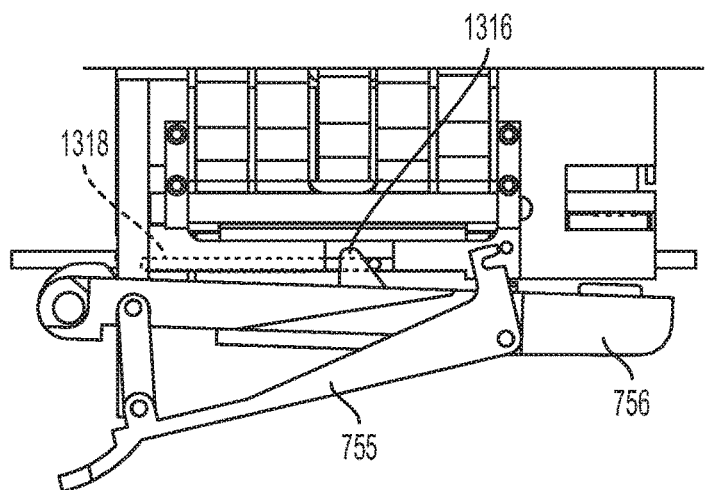
Figure 233:
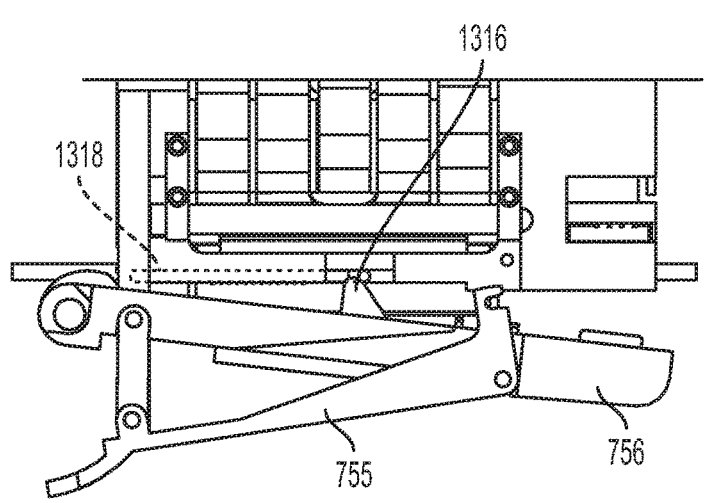

FIGS. 231-233 show the sequence of the door 756 opening and releasing the interlock pin 1316 by withdrawing the release tab 1316. As the tab is withdrawn the interlock pin 1318 is pushed toward the slide occluder carriage 760.

Figure 234:
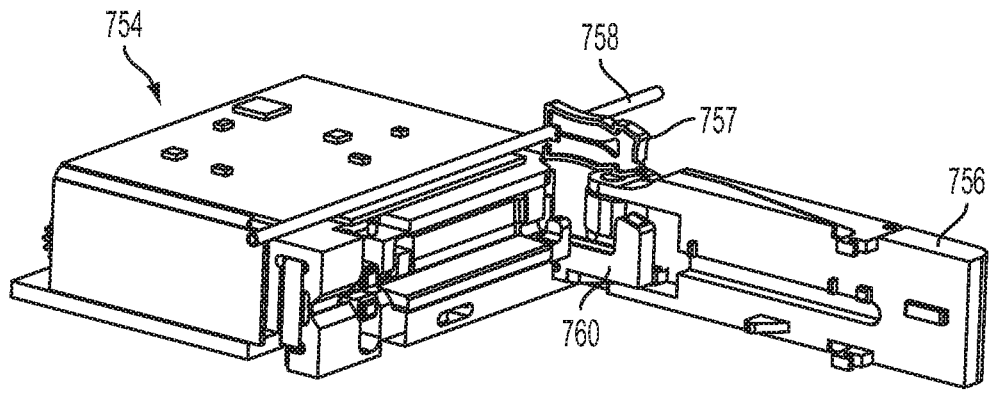
Figure 235:
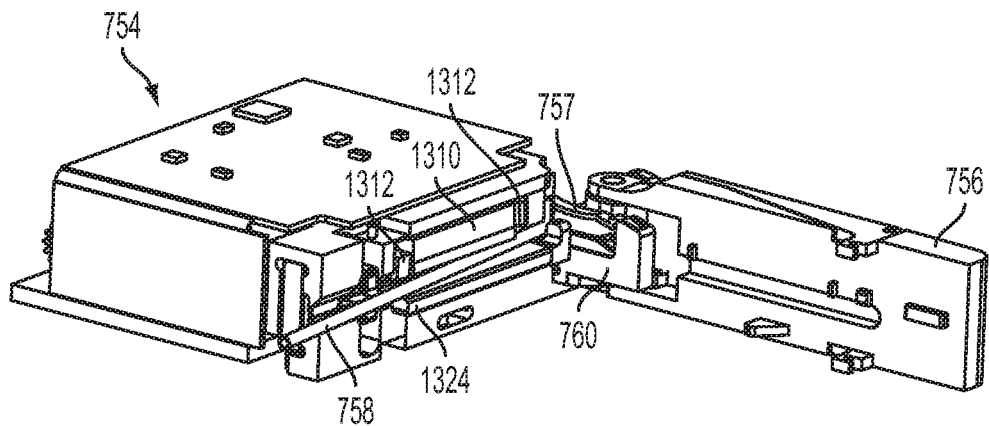
Figure 236:
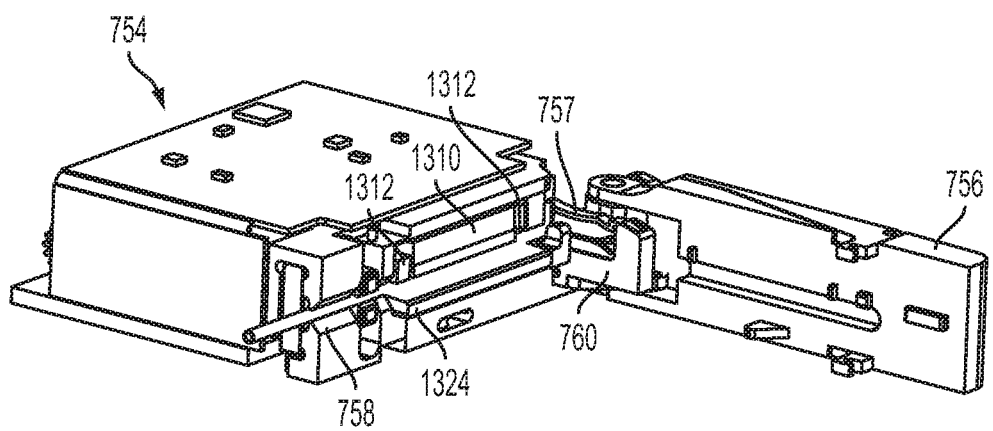
Figure 238:
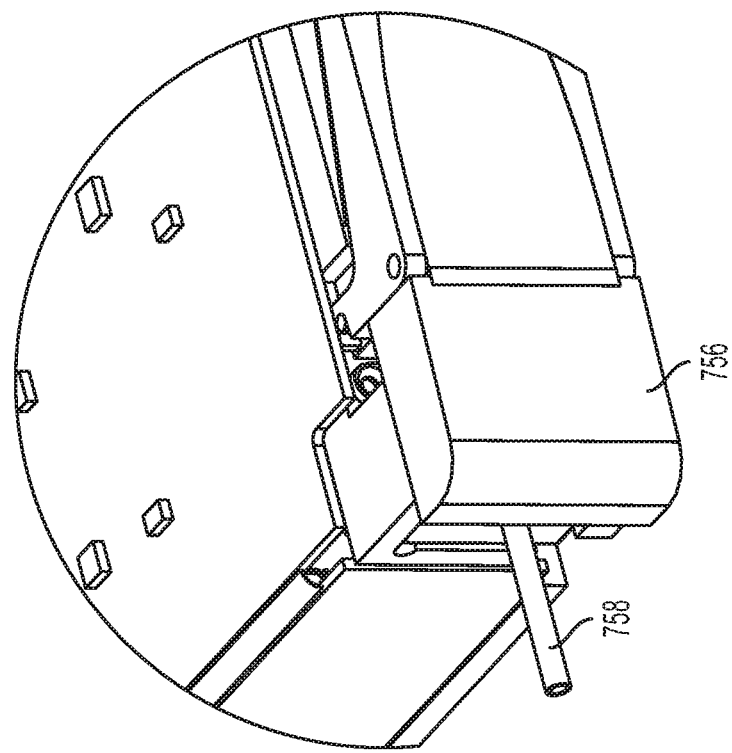
Figure 237:
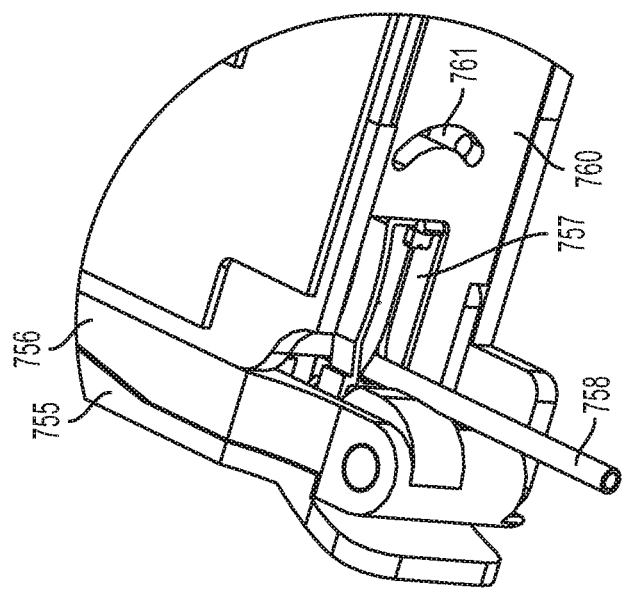
Figure 239:
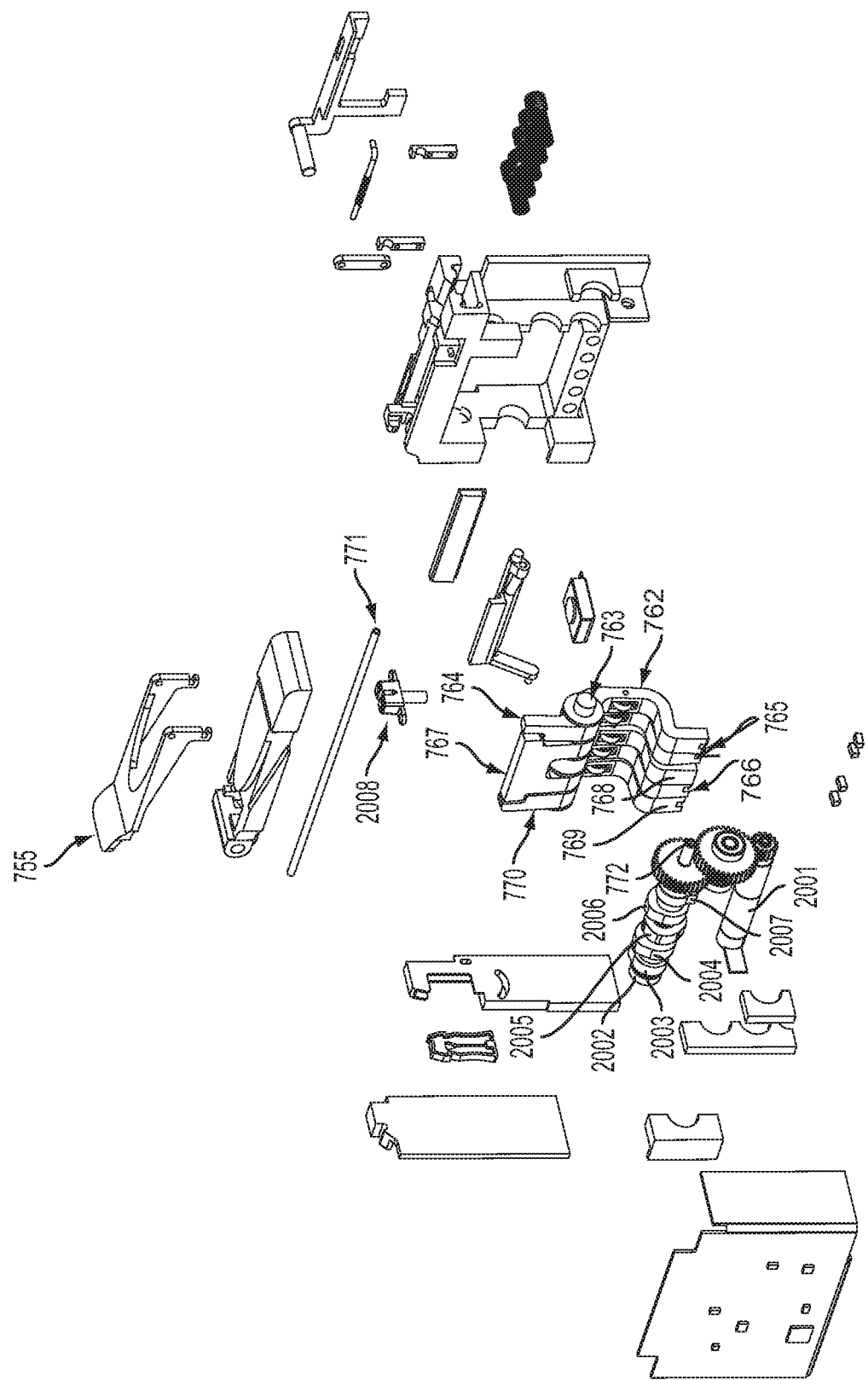
Figure 240:
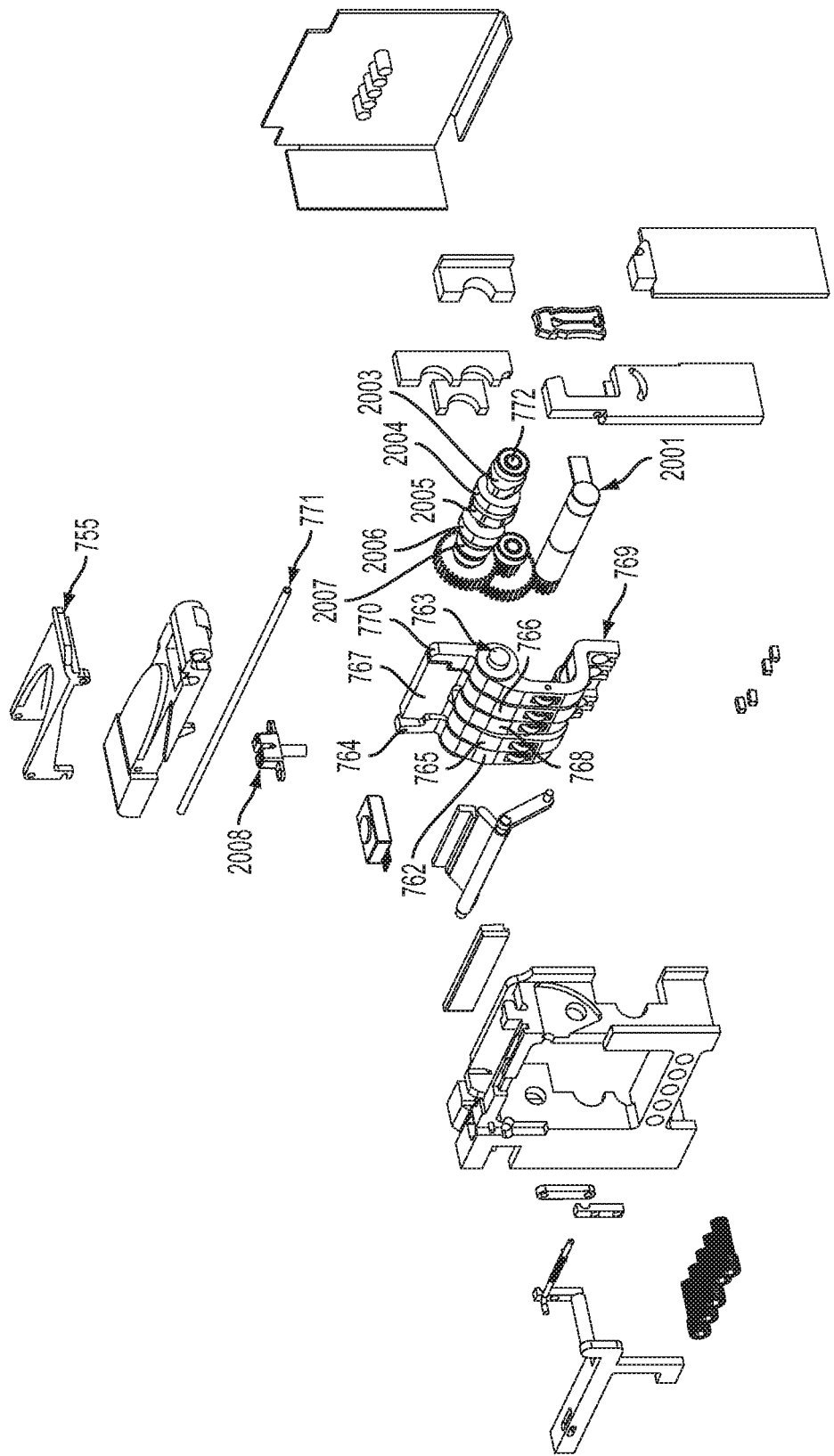

FIG. 234 shows the door 756 open and the slide occluder 757 being lifted out of the slide occluder carriage 760. The tube 758 is in the narrow section of the slide occluder 757 that pinches the tube 758 closed. FIG. 235 illustrates placing the tube 758 into the pump between the anvil plate 1324 and the plunger 1310 and valves 1312. FIG. 236 shows the slide occluder 757 and tube 758 fully installed in the pump 754, where the slide occluder 757 is pinching the tube 758 closed. FIG. 237 shows the door 756 and the door lever 755 being shut which slid the slide occluder carriage 760 toward the rear of the pump 754. The movement of the slide occluder carriage 760 pushed the slide occluder 757 past the tube 758 so that the tube is open and rotated the pin 761 that in turn rotated the plunger lift lever 759 that released the plungers 1310 and valves 1312 to descend and close the tube 758. FIG. 238 shows a front view of the door 756 being shut.

FIGS. 239-245 show several views of the peristaltic pump of FIGS. 222-238 in accordance with an embodiment of the present disclosure. A motor 2001 rotates gears which in turn rotates a camshaft 772. As the camshaft 772 rotates, the cams 2003, 2004, 2005, 2006, and 2007 rotate with the camshaft 772. The cam 2003 engages a cam follower 769, which pivots along a pivot 763 to move a pinch valve 770. The cams 2004 and 2006 engage cam follows 766 and 765, which pivot along the pivot 763 to move a plunger 767. The cam 2007 engages the cam follower 762 to move the pinch valve 764. Additionally, the cam 2005 engages a cam follower 768. The cam 2005 is shaped such that the engagement with the cam follower 768 at least partially balances the torque (e.g., to reduce the peak toque). In some embodiments, the cam 2005 and the cam follower 768 are optional.

The inlet valve 770 (which is a pinch valve), the plunger 767, and the outlet valve 764 (which is a pinch valve) may engage the tube 771 using the three or four stages of pumping action as described above. A bubble sensor 2008 may be used to distinguish between a bubble and a leaking valve 764 or 770 (e.g., pinch valves) as described above.

The rotation of the cam shaft 772 may be controlled by the motor 2001 such that while fluid is compressed by the plunger 767, the outlet valve 764 is opened by a PID control loop to achieve a target discharge rate profile (e.g., smoothed out discharge rate) as measured by the plunger position sensor. In some embodiments, a range of angles only moves the outlet valve (e.g., outlet pinch valve). In yet additional embodiments, in the four stage pumping action described above, the movement of the plunger 767 is closed after the outlet valve 764 opens to achieve a target discharge rate profile (e.g., smoothed out discharge rate) as measured by the plunger's 767 position sensor.

Figure 241:
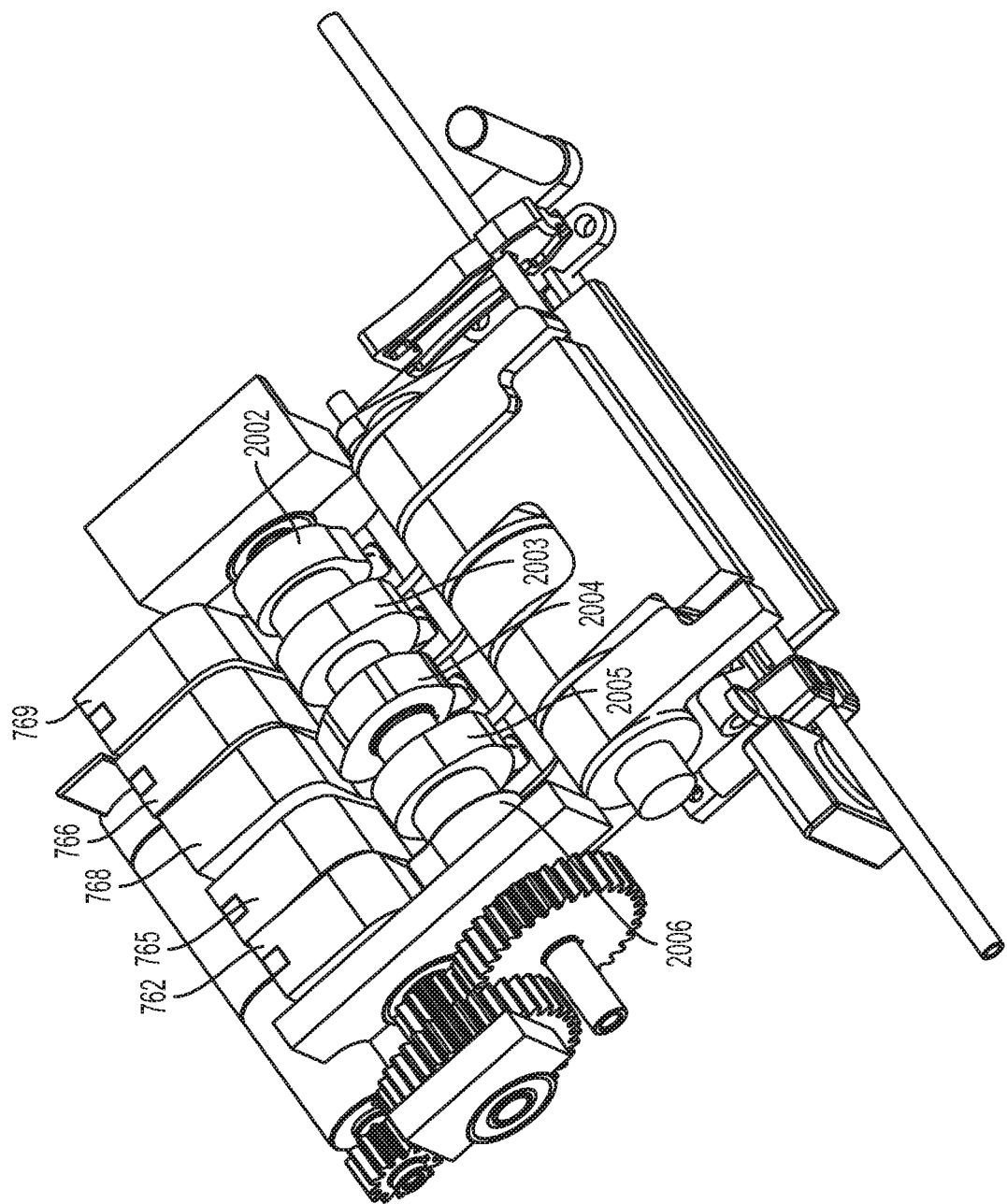
Figure 242:
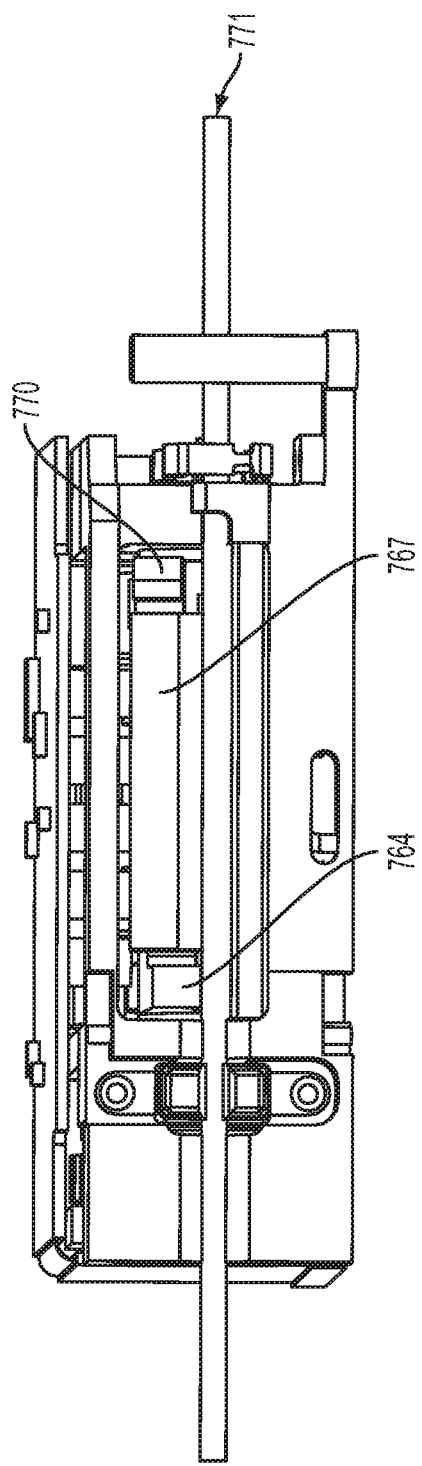
Figure 243:
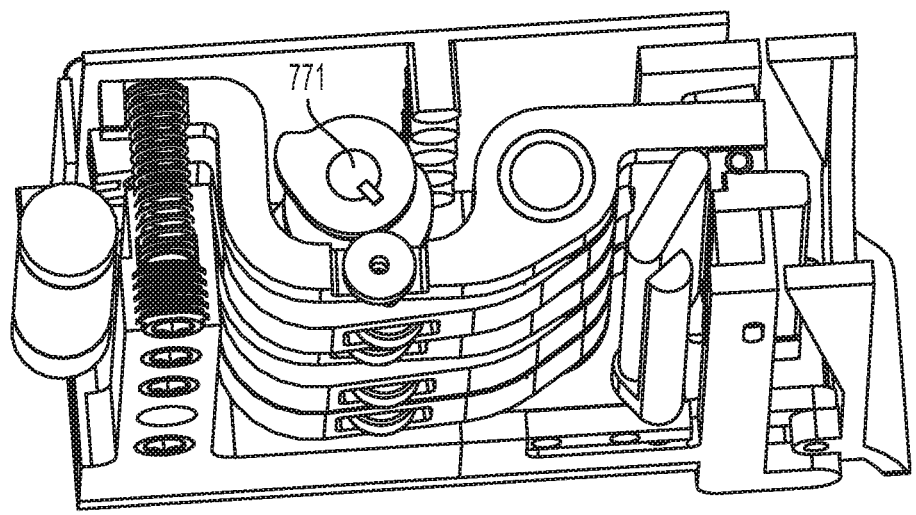
Figure 244:
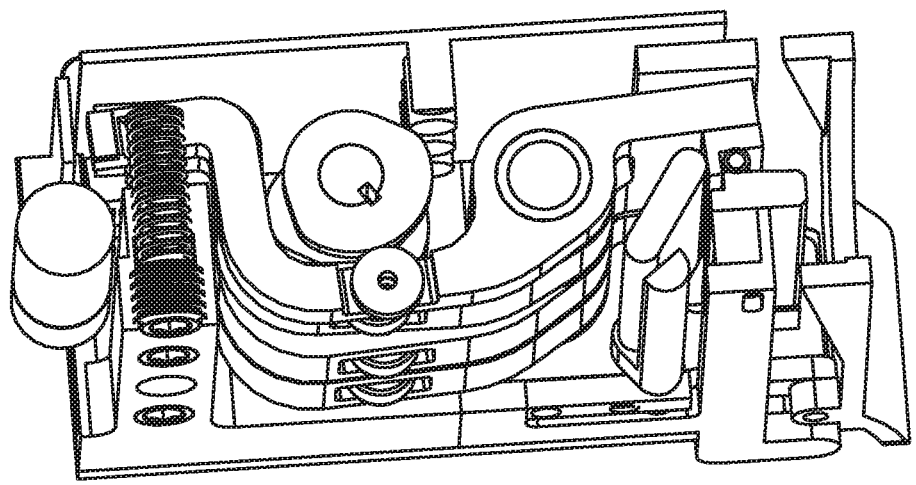
Figure 245:
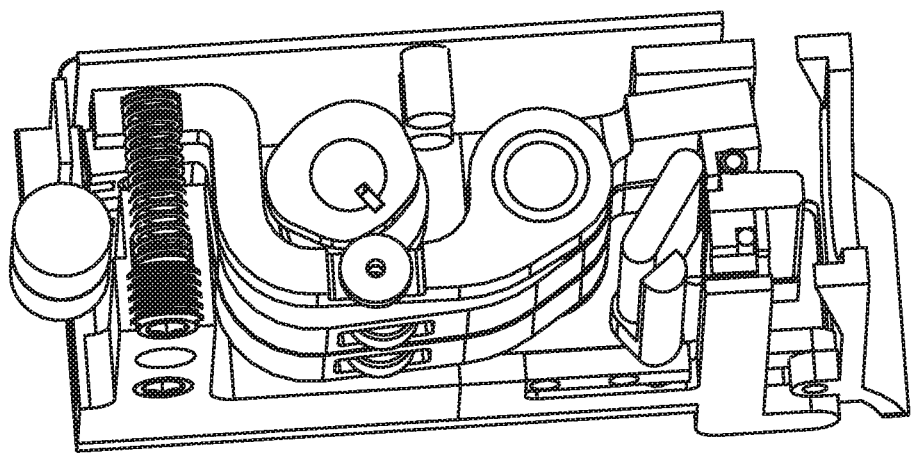
Figure 246:
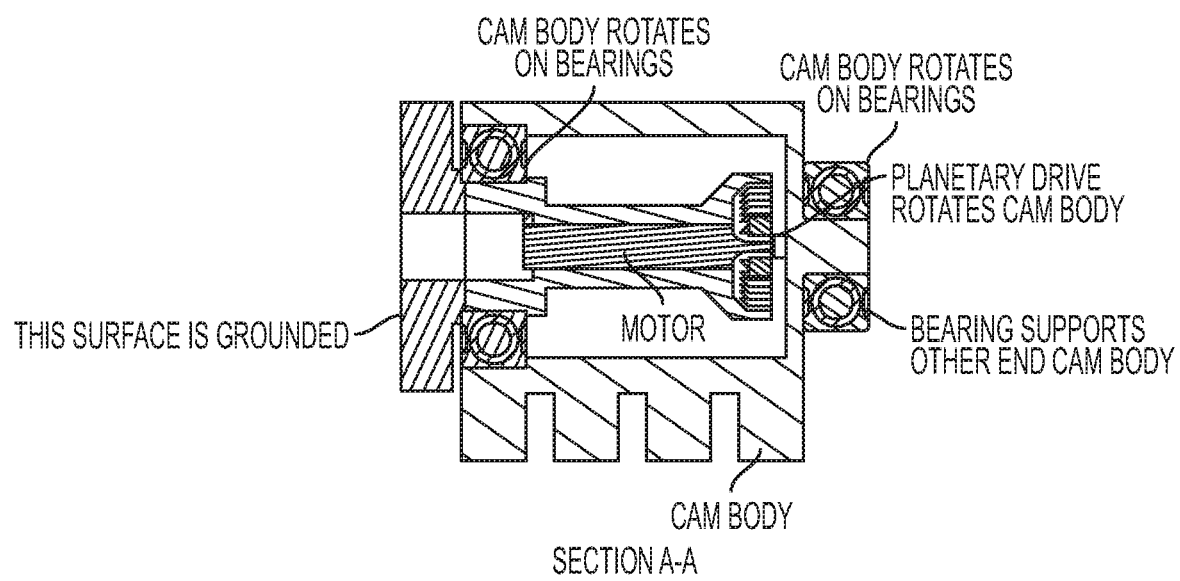
Figure 247:
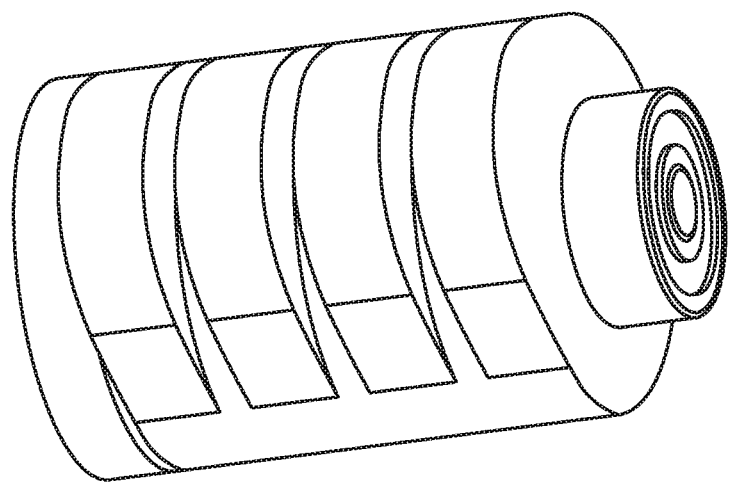
Figure 250:
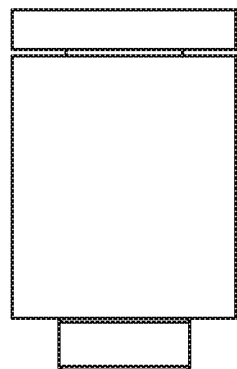
Figure 249:
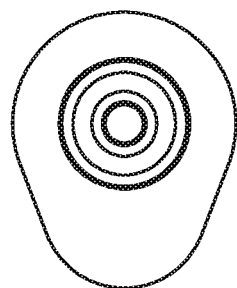
Figure 248:
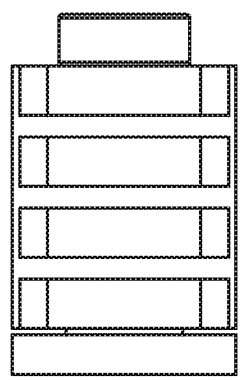

As is easily seen in FIG. 241, the cams 2002, 2003, 2004, 2005, and 2006 are shows as engaging the cam followers 769, 766, 768, 765, and 762, respectively. FIG. 242 shows a front view of the peristaltic pump including the plunger 767, and the pinch valves 764 and 770 positioned to engage the tube 771.

Figure 251:
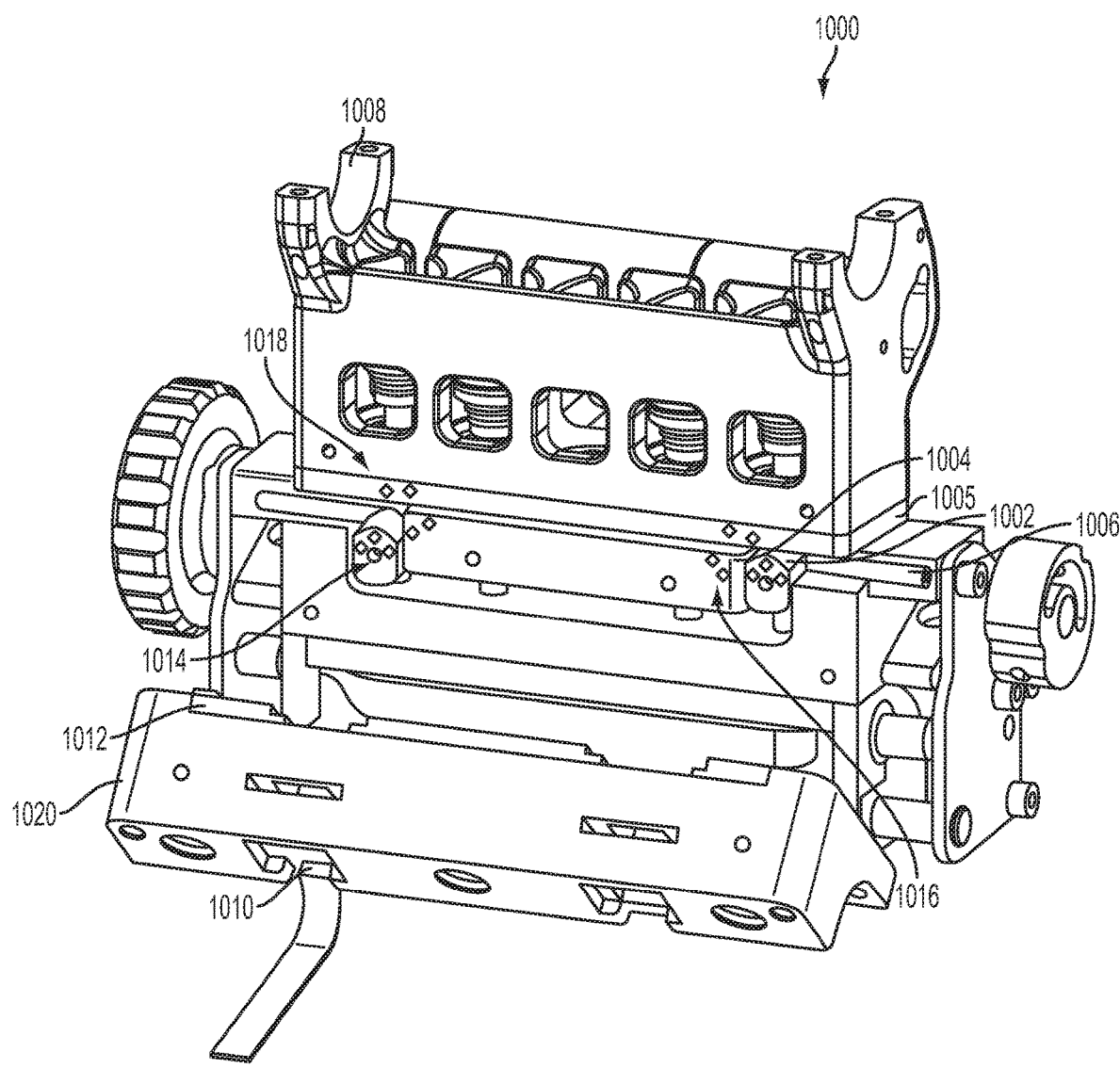
Figure 252:
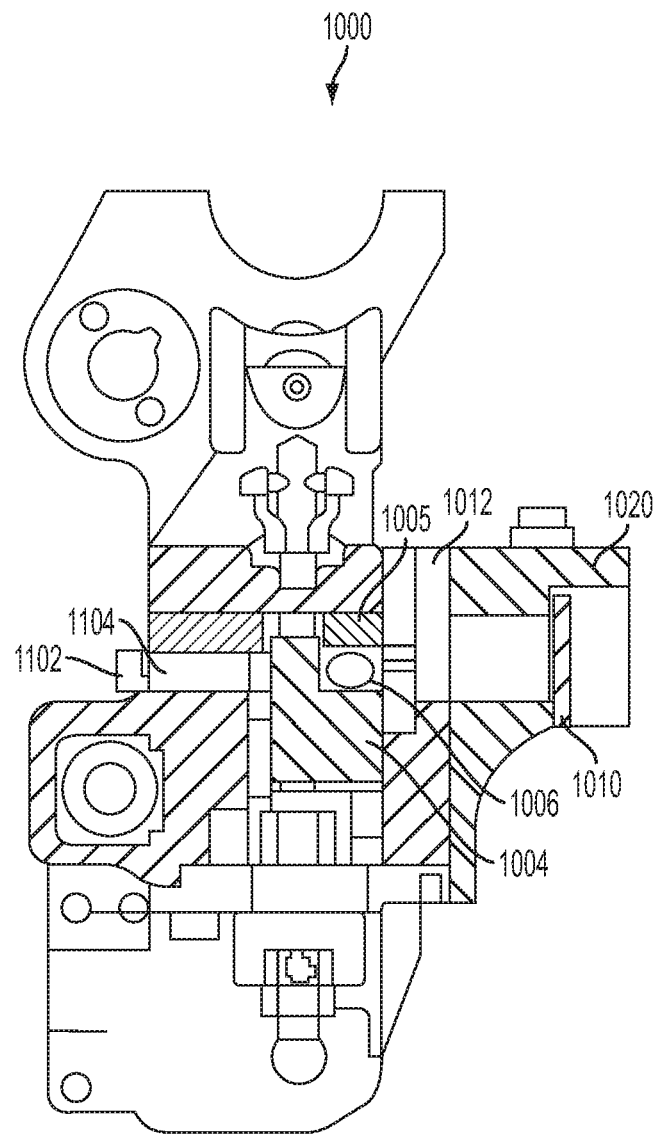

A standard tubing pump 1000 with an optical monitoring system is shown in FIGS. 251 and 252. The optical monitoring system is comprised of a camera 1010 with a field of view that may include part or all of the plunger 1004, one pinch valve 1002, a portion of the tube 1006, fiducial marks on the pinch valve 1014, fiducial marks on the plunger 1016, fiducial marks on the backstop 1018, a light source (not shown) and a light guide 1012 to illuminate the surfaces facing the camera 1010. The optical monitoring system may further additional cameras 1010 with fields of view that include or all of the plunger 1004, additional pinch valves 1002, a portion of the tube 1006, fiducial marks on the pinch valve 1014, fiducial marks on the plunger 1016, fiducial marks on the backstop 1018, a light source (not shown) and a light guide 1012 to illuminate the surfaces facing the camera 1010. The optical monitoring system may further comprising one or more rear light sources 1102, rear light guides 1104 and a transparent plunger 1006 to illuminate the back side of the tube 1006 relative to the camera 1010. The camera 1010 and lights may operate in a range of spectrums from ultraviolet to infrared.

The optical system may further be comprised of a processor, memory and software that may allow the images to be interpreted to provide a range of information on the status of the pump, tubing and flow that includes but is not limited to plunger position relative to the backstop 1005, the pinch valve position relative to the backstop 1005, the speed and direction of the plunger 1004 and pinch valve 1002, the presence of the tube 1006, the presence of liquid or gas in the tube 1006, the presence of gas bubbles in the tube 1006, the presence deformations in the tube 1006. The processor may further interpret the information on plunger and valve position to determine fluid flow rate, presence of an occlusion in the tube, presence of a leak in the tubing, The optical monitoring system recognizes and measures the positions of the plunger 1004 and valves 1002 relative to the anvil plate 1005. The anvil plate 1005 is the stationary part of the pump and elsewhere may be referred to as the counter surface or occlusion bed. The pump controller may command the optical monitoring system may take an image using the camera 1010 and front or rear light sources. A processor located in the camera or elsewhere may process the image using software to identify the relative distance and orientation of the plunger 1004 and valves 1002 relative to the anvil plate 1005. In one embodiment, the machine vision software may identify the elements 1002, 1004 and 1005 and their location within its field of view through an edge detection algorithm as described above. The detected edges may be e assigned to each element 1002, 1004 and 1005 based the edge location within the field of view. By way of an example, an edge detected in the up third of the field of view may be assigned as the anvil plate 1005, while an edge detected in the lower left quadrant may be assigned as the pinch valve 1002 if the camera 1010 is the on the left hand side as shown in FIG. 251.

In another embodiment, the machine vision software may identify the pinch valve 1002, plunger 1004 and anvil plate 1005 and their location within its field of view with fiducial marks located on each of the elements 1002, 1004 and 1005. Each element may include one or more fiducial marks that are located within the field of view of the camera 1010. Fiducial marks will be assigned to each element 1002, 1004, 1005 based on the region in the field of view that it is detected. Considering the left hand camera 1010 in FIG. 251 by way of example, fiducial marks in the lower left region may be assigned as the pinch valve 1002, while fiducial marks in the lower right region may be assigned as the plunger 1004 and fiducial marks in the upper region may be assigned to as the anvil plate 1005. A single fiducial mark may allow the optical monitoring system to measure the relative movement of the pinch valve 1002, and plunger 1004 to the anvil plate 1006. More than one fiducial mark on a single element may allow the optical monitoring system to identify elements that rotated in their plane of motion. The processor may signal a warning or an alarm if one or more of the elements 1002, 1004 and/or 1005 have rotated beyond an allowed amount. A significant rotation may indicate a mechanical break in the pinch valve 1002 or plunger 1004 or that the camera has rotated within its mounting on the camera door 1020.

The machine vision software may identify the fiducial elements by matching a stored template to the image. The vision software may be an off-the-shelf product such as Open Source Computer Vision referred to as OpenCV and available for download from the internet. The vision software may use the function or module TemplateMatching to identify the fiducial marks from a stored template.

The machine vision software may then calculate the relative position and orientation of elements 1002, 1004 and 1005 from observed location within the camera's field of view and stored geometric data of the pinch valve 1002, plunger 1004 and anvil plate 1005. The locations and orientations determined by the machine vision software may then be passed to algorithms to identify specific conditions which include, but are not limited to the following: pinch valve opening, pinch valve closing, plunger at maximum stroke, plunger at minimum stroke. Other algorithms may process the machine vision determined locations and orientation data to determine parameters that include but are not limited to the following, plunger speed, fluid flow rate, occlusion in the tube, air in the tube, external leaks. These conditions and parameters are determined in the same way as they are determined from hall effect sensors measuring the location of the plunger 1004 and pinch valves 1002, which is described above.

In other embodiments, the machine vision software may identify the conditions and determine the parameters described above. In other embodiments, the relative position and orientation of the pinch valve 1002, plunger 1004 and anvil plate 1006 may be calculated by algorithms outside the machine vision software.

The machine vision software or algorithms that process the output of the machine vision software may recognize a number of conditions including but not limited to the following: tubing is not present, tubing is not correctly placed, tubing is empty of fluid, tubing is full of fluid, tubing is deformed, and a gas bubble is present in the liquid.

The optical monitoring system may calculate the volume of the tube with fewer assumptions with data from an additional camera 1011 mounted at a substantial angle to camera 1010 as shown in FIG. 252. The back light 1102, light guide 1104 may supply infrared illumination to the back of the plunger 1004. The plunger 1004 may be nylon or similar material that is transparent to infrared radiation. The plunger is uncoated in the field of view of camera 1011 to provide a clear view of the tube through the plunger 1004 in the infrared spectrum. A machine vision software package may determine the profiles of the tube 1006 from camera 1010 and the profile from camera 1011. An algorithm may calculate a first thickness of the tube as seen by camera 1010 and a second distance as seen by camera 1011. The volume of the tube may then be calculated from the two distances and the known circumference of the tube. A comparison of the two distances and the tube circumference may identify buckling in the tube shape that would significantly change the volume of liquid in the tube.

The volume of fluid in the tube 1006 may depend on the shape taken by the filled-tube when the pinch valves 1002 are closed. The shape of the tube 1006 near the pinch valves 1002 may change after the pump is calibrated due to a number of factors including but not limited to changes in the tubing materials, changes in manufacturing, changes in humidity and temperature. The camera 1010 may observe the shape of the tube 1006 near the pinch valve 1002. The tube may be illuminated with visible or infrared light from the front or back. In a preferred embodiment, the tube may be illuminated from behind with infrared light. Here illuminating from behind refers to placing the source of the illumination on the opposite side of the tube 1006 from the camera 1010.

In one embodiment, the machine vision software may detect the tube shape using edge detection. An algorithm may compare the observed tube shape to a shape stored in the memory. In one embodiment the algorithm may correct the volume of fluid per stroke to account for the changed tube shape. In another embodiment, the algorithm evaluating the tube shape may signal a warning or alarm to a higher level algorithm. In another embodiment, the machine vision software may confirm an acceptable tube shape by attempting to match a template of the accepted tube shape to the image. The machine vision software or the next higher level of software control may signal a warning or alarm if an acceptable tube shape is not identified.

The cameras 1010, 1011 may include either CCD (charge coupled device) or CMOS (Complementary Metal Oxide Semiconductor) chips to convert light into electrical signals that can be processes to generate an image. One example of a camera is HM0357-ATC-00MA31 by Himax Imaging, Inc. of Irvine Calif. USA. The cameras 1010, 1011 and lights 1012 may be powered on only when taking measurements in order to reduce power consumption.

Figure 253:
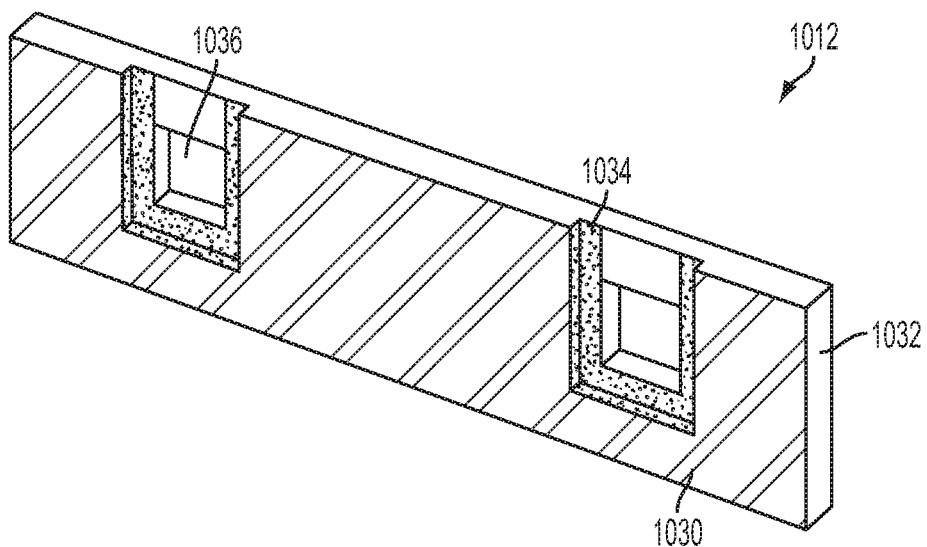
Figure 254:
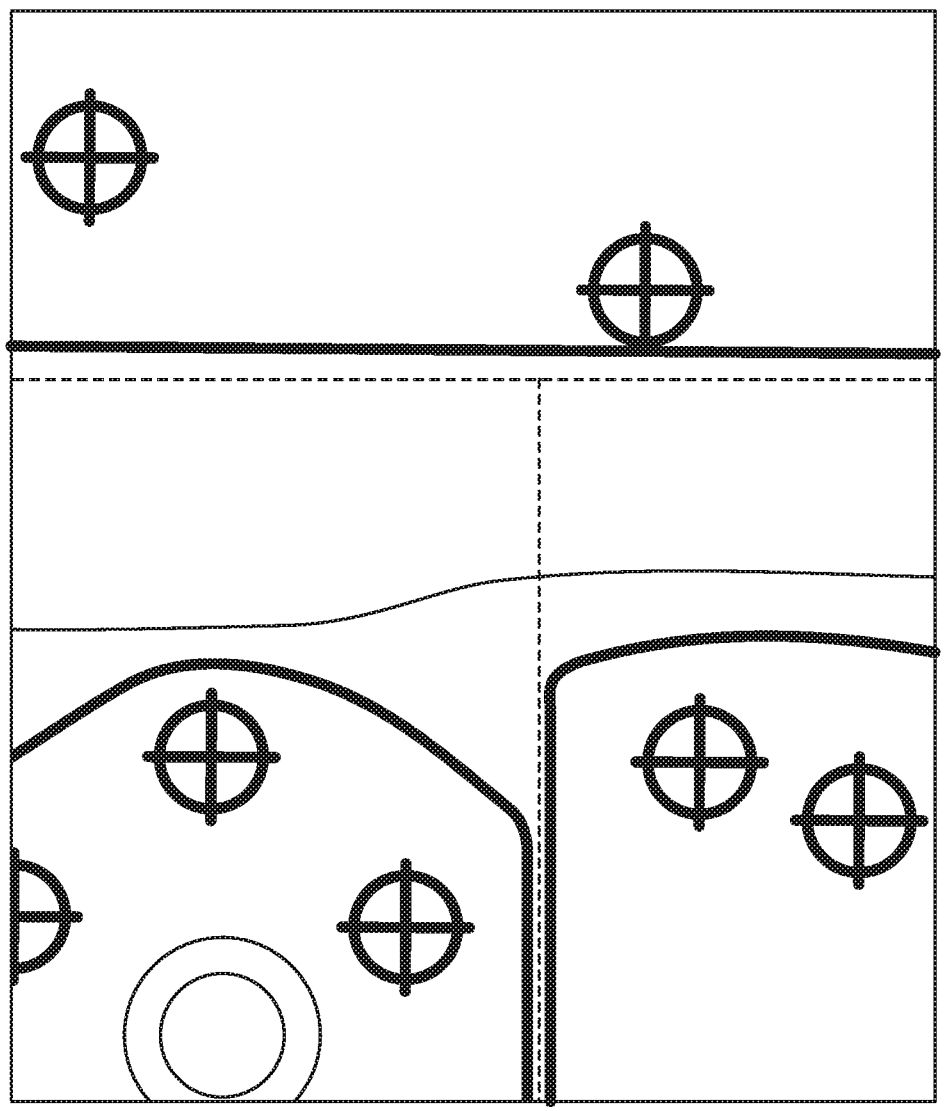

The pinch valve 1002, plunger 1004, tube 1006 and anvil plate 1005 may be illuminated from the front. Front illumination refers to a light source that is on the same side of the object of interest as the camera 1010 and supplies illumination to the camera 1010 by reflection from the object of interest. One embodiment to supply front illumination is comprised of a light bar 1012 that transmits light from LED's mounted in the camera door 1020. One embodiment of the light bar 1012 is shown in FIG. 253. Light is supplied to the end surfaces 1032 of the light bar from LED's or other light sources mounted in the camera door 1020. The front surface 1030 and back surface (not shown) are covered with a material that reflects the supplied light. In one embodiment, the front and back surfaces are covered with an aluminized tape. Holes 1036 provide a clear field of view for the cameras 1010. The light bar may include a surface around each hole 1036 that is roughened to provide a diffuse light that illuminates the front of the pinch valve 1002, plunger 1004, tube 1006 and anvil plate 1005. The area around the holes 1036 may be recessed and then roughened to provide more diffuse light.

It may be advantageous to provide backlighting or illumination from the opposite side of the tube 1006 relative to the camera 1010. Backlighting may allow clearer visualization of the tube shape and or the shape of the volume inside the tube 1006. One embodiment places the rear light source on the back of the pump 1000. The rear light source 1102 may be an LED or other light providing illumination in the ultraviolet, visible and or infrared range. A light guide 1104 may direct the light to the back of the plunger 1004. The plunger may be made from a material that is transparent to the spectrum of light emitted by the light source 1102. In one embodiment, the plunger is made from nylon and the light source 1102 provides infrared illumination, which the camera 1010 can sense. In some embodiments, the backlight may be a plurality of light sources. The plurality of light sources may be controlled and/or modulated such that only specific lights are on that are necessary to illuminate a pixel being exposed. For example, the camera may have a region of interest, and only the lights needed to illuminate the region of interest are turned on during the exposure time of pixels within the region of interest. In some embodiments, the lights may be rows and/or columns of lights and/or pixels of lights (e.g., an array of LED lights).

The spectrum of the rear light source 1102 and camera 1010 may be selected to maximize the visibility of the fluid in the tube. In one embodiment, the spectrum may be broad to provide the maximum light to visualize the tube. In another embodiment, a set of filters in front of the rear light source 1102 emits a narrow range of the infrared spectrum that passes through the light guide 1104, plunger 1004 and tube 1006, but is absorbed by the liquid in the tube. The light source 1102 may also emit a narrow range of the infrared spectrum that passes through the light guide 1104. In another embodiment, the filters to allow only the desired band of infrared are in front of the camera 1010.

Acoustic Volume Sensing

The follow discussion describes acoustic volume sensing that may be performed by a processor disclosed herein with a speaker and two microphones (e.g., a reference microphone and a variable-volume microphone) of a peristaltic pump, e.g., a peristaltic pump disclosed herein; AVS may be used to estimate liquid within a reservoir disclosed herein, to estimate an amount of liquid discharged from a reservoir disclosed herein, and/or to estimate a liquid discharge rate of a reservoir disclosed herein. Table 1 shows the definition of various terms as follows:

TABLE 1

| Term | Definition |
|---|---|
| Symbols | |
| P | Pressure |
| p | Pressure Perturbation |
| V | Volume |
| v | Volume Perturbation |
| γ | Specific Heat Ratio |
| R | Specific Gas Constant |
| ρ | Density |
| Z | Impedance |
| f | Flow friction |
| A | Cross sectional Area |
| L | Length |
| ω | Frequency |
| ζ | Damping ratio |
| α | Volume Ratio |
| Subscripts | |
| 0 | Speaker Volume |
| 1 | Reference Volume |
| 2 | Variable Volume |
| k | Speaker |
| r | Resonant Port |
| z | Zero |
| p | Pole |

The acoustic volume sensor ("AVS") measures the fluid volume displaced by the non-liquid side of a reservoir in the AVS chamber, e.g., an acoustic housing or within a reservoir, etc. The sensor does not directly measure the fluid volume, but instead measures the variable volume of air, V2, within the AVS chamber; if the total volume of AVS chamber remains constant, the change in the V2 will be the direct opposite of the change in the fluid volume. The AVS chamber is the volume of air in fluid communication with a variable-volume microphone beyond the acoustic port.

The volume of air, V2, is measured using an acoustic resonance. A time-varying pressure is established in the fixed volume of the reference chamber, V1, using a speaker. This pressure perturbation causes cyclic airflow in the acoustic port connecting the two volumes, which in turn causes a pressure perturbation in the variable volume. The system dynamics are similar to those of a Helmholtz oscillator; the two volumes act together as a "spring" and the air in the port connecting the volumes as a resonant mass. The natural frequency of this resonance is a function of the port geometry, the speed of sound, and the variable volume. The port geometry is fixed and the speed of sound can be found by measuring the temperature; therefore, given these two parameters, the variable volume can be found from the natural frequency. In some embodiments of the present disclosure, a temperature sensor is used within the acoustic housing and/or within the non-liquid side of a reservoir. In some embodiments, the temperature is considered to be a predetermined fixed value, e.g., is assumed to be room temperature, etc.

The natural frequency of the system is estimated by measuring the relative response of the pressures in the two volumes to different frequency perturbations created by the speaker. A typical AVS measurement will consist of taking an initial measurement. The liquid is then released from the liquid side of one or more reservoirs and delivered to the patient (after which a second volume measurement is taken). The difference between these measurements will be the volume of liquid delivered to the patient. In some embodiments a measurement will be taken before filling the liquid side of the one or more reservoirs and/or prior to discharging the liquid, e.g., when the syringe pump is preloaded, to detect any failures of the fluidic system.

An AVS measurement may occur in accordance with the following acts: (1) the processor will turn on power to the AVS electronics, enable the ADC of the processor, and initialize an AVS algorithm; (2) an AVS measurement consists of collecting data at a number of different frequencies; (3) optionally measuring the temperature; and (4) then running an estimation routine based on the collected data to estimate the volume of liquid in the liquid side of a reservoir.

To collect data at each frequency, the speaker is driven sinusoidally at the target frequency and measurements are taken from the two microphones over an integer number of wavelengths, e.g., the reference microphone and the variable volume microphone (as described above). Once the data has been collected, the processor disclosed herein performs a discrete Fourier transform algorithm on the data to turn the time-series data from the microphones into a single complex amplitude. Integrity checks are run on the data from the microphones to determine if the data is valid, e.g., the response is within a predetermined phase and/or amplitude range of the acoustic frequency.

The frequency measurements are taken at a number of different frequencies. This sine-sweep is then used by the estimation routine to estimate the variable volume. After the estimation is complete, other integrity checks is may be performed on the whole sine sweep, including a secondary check by a processor disclosed herein.

In some embodiments, after the a processor disclosed herein verifies the measurement integrity, the volume estimates are finalized and the sensor is powered off.

AVS Resonance Model

The governing equations for the AVS system can be found from first-principles given a few simplifying assumptions. The system is modeled as two linearized acoustic volumes connected by an idealized acoustic port.

Modeling the Acoustic Volumes

The pressure and volume of an ideal adiabatic gas can be related by Equation (35) as follows:

$$PV^\gamma = K \quad (35),$$

where K is a constant defined by the initial conditions of the system. Equation 1 can be written in terms of a mean pressure, P, and volume, V, and a small time-dependent perturbation on top of those pressures, p(t), v(t) as illustrated in Equation (36) as follows:

$$(P+P(t))(V+v(t))^\gamma = K \quad (36).$$

Differentiating Equation (36) results in Equation (37) as follows:

$$\dot{p}(t)(V+v(t))^\gamma + \gamma(V+v(t))^{\gamma-1}(P+p(t))\dot{v}(t) = 0 \quad (37).$$

Equation (37) simplifies to Equation (38) as follows:

$$\dot{p}(t) + \gamma \frac{P+p(t)}{V+v(t)} \dot{v}(t) = 0 \quad (38)$$

If the acoustic pressure levels are much less than the ambient pressure the Equation (38) can be further simplified to Equation (39) as follows:

$$\dot{p}(t) + \frac{\gamma P}{V} \dot{v}(t) = 0 \quad (39)$$

Using the adiabatic relation, Equation (40) can be shown as follows:

$$\frac{P}{V} = \left(\frac{P+p(t)}{V+v(t)}\right)\left(\frac{P+p(t)}{P}\right)^{\frac{\gamma+1}{\gamma}}. \quad (40)$$

Thus, the error assumption is shown in Equation 41 as follows:

$$\text{error} = 1 - \left(\frac{P+p(t)}{P}\right)^{\frac{\gamma+1}{\gamma}}. \quad (41)$$

A very loud acoustic signal (e.g., 120 dB) would correspond to pressure sine wave with amplitude of roughly 20 Pascal. Assuming air at atmospheric conditions has the parameters of $\gamma=1.4$ and P=101325 Pa, the resulting error is 0.03%. The conversion from dB to Pa is shown in Equation (42) as follows:

$$\lambda = 20\log_{10}\left(\frac{p_{rms}}{p_{ref}}\right) \text{ or } p_{rms} = p_{ref} 10^{\frac{\lambda}{20}}, \quad (42)$$

where $p_{ref}=20 \cdot \mu$Pa

Applying the ideal gas law, $P=\rho RT$, and substituting in for pressure gives the result as shown in Equation (43) as follows:

$$\dot{p}(t) + \frac{\gamma RT\rho}{V} \dot{v}(t) = 0. \quad (43)$$

This can be written in terms of the speed of sound in Equation (44) as follows:

$$a = \sqrt{\gamma RT} \quad (44).$$

And, substituting in Equation (44) in Equation (43) results in Equation (45) as follows:

$$\dot{p}(t) + \frac{\rho a^2}{V} \dot{v}(t) = 0. \quad (45)$$

Acoustic impedance for a volume is defined in Equation 46 as follows:

$$Z_v = \frac{p(t)}{\dot{v}(t)} = -\frac{1}{\left(\frac{V}{\rho a^2}\right)s}. \quad (46)$$

Modeling the Acoustic Port

The acoustic port is modeled assuming that all of the fluid in the port essentially moves as a rigid cylinder reciprocating in the axial direction. All of the fluid in the channel is assumed to travel at the same velocity, the channel is assumed to be of constant cross section, and the end effects resulting from the fluid entering and leaving the channel are neglected.

If we assume laminar flow friction of the form $\Delta p = f \rho \dot{v}$, the friction force acting on the mass of fluid in the channel can be written: $F=f\rho A^2 \dot{x}$. A second order differential equation can then be written for the dynamics of the fluid in the channel as shown in Equation (47) as follows:

$$\rho L \ddot{x} = \Delta p A - f\rho A^2 \dot{x} \quad (47),$$

or, in terms of volume flow rate as shown in Equation (48) as follows:

$$\dot{v} = -\frac{fA}{L}v + \Delta p \frac{A}{\rho L}. \quad (48)$$

The acoustic impedance of the channel can then be written as shown in Equation (49):

$$Z_p = \frac{\Delta p}{\dot{v}} = \frac{\rho L}{A}\left(s + \frac{fA}{L}\right). \quad (49)$$

System Transfer Functions

Using the volume and port dynamics define above, the AVS system can be described by the following system of Equations 50-53:

$$\dot{p}_0 - \frac{\rho a^2}{V_0}\dot{v}_k = 0, \quad (50)$$

$$\dot{p}_1 + \frac{\rho a^2}{V_1}(\dot{v}_k - \dot{v}_r) = 0, \quad (51)$$

$$\dot{p}_2 + \frac{\rho a^2}{V_2}\dot{v}_r = 0, \text{ and} \quad (52)$$

$$\ddot{v}_r = -\frac{fA}{L}\dot{v}_r + \frac{A}{\rho L}(p_2 - p_1). \quad (53)$$

One equation can be eliminated if $p_0$ is treated as the input substituting in $$\dot{v}_k = \frac{V_0}{\rho a^2}\dot{p}_0$$

as shown in Equations 54-56:

$$\dot{p}_1 + \frac{V_0}{V_1}\dot{p}_0 - \frac{\rho a^2}{V_1}\dot{v}_r = 0, \quad (54)$$

$$\dot{p}_2 + \frac{\rho a^2}{V_2}\dot{v}_r = 0, \text{ and} \quad (55)$$

$$\ddot{v}_r = -\frac{fA}{L}\dot{v}_r + \frac{A}{\rho L}p_2 - \frac{A}{\rho L}p_1. \quad (56)$$

The relationship between the two volumes on each side of the acoustic port is referred to as the Cross Port transfer function. This relationship is illustrated in Equation (57) as follows:

$$\frac{p_2}{p_1} = \frac{\omega_n^2}{s^2 + 2\zeta\omega_n s + \omega_n^2}, \quad (57)$$

-continued where $\omega_n^2 = \frac{a^2 A}{L}\frac{1}{V_2}$ and $\zeta = \frac{fA}{2L\omega}$.

This relationship has the advantage that the poles are only dependent on the variable volume and not on the reference volume. Note that the resonant peak is actually due to the inversion of the zero in the response of the reference volume pressure. This means that that pressure measurement in the reference chamber will have a low amplitude in the vicinity of the resonance which may influence the noise in the measurement.

Resonance Q Factor and Peak Response

The quality of the resonance is the ratio of the energy stored to the power loss multiplied by the resonant frequency. For a pure second-order system the quality factor can be expressed as a function of the damping ratio illustrated in Equation (58):

$$Q = \frac{1}{2\zeta}. \quad (58)$$

The ratio of the peak response to the low-frequency response can also be written as a function of the damping ratio shown in Equation (59):

$$|G|_{\omega_d} = \frac{1}{\zeta\sqrt{5-4\zeta}}. \quad (60)$$

This will occur at the damped natural frequency $\omega_d = \omega_n\sqrt{1-\zeta}$.

Electrical and Mechanical Analogies

The acoustic resonator is analogous to either a spring-mass-damper system or a LRC circuit, e.g., a resistor, inductor and capacitor coupled together in series, for example.

Computing the Complex Response

To implement AVS, the system must get the relative response of the two microphones to the acoustic wave set up by the speaker. This is accomplished by driving the speaker with a sinusoidal output at a known frequency; the complex response of each microphone is then found at that driving frequency. Finally, the relative responses of the two microphones are found and corrected for alternating sampling of the analog-to-digital converter coupled to the a processor disclosed herein.

In addition, the total signal variance is computed and compared to the variance of pure tone extracted using the discrete Fourier transform ("DFT"). This gives a measure of how much of the signal power comes from noise sources or distortion. In some embodiments of the present disclosure, this value can be used to reject and repeat bad measurements.

Computing the Discrete Fourier Transform

The signal from each microphone is sampled synchronously with the output to the speaker such that a fixed number of points, N, are taken per wavelength. The measured signal at each point in the wavelength is summed over an integer number of wavelengths, M, and stored in an array x by an interrupt service routine ("ISR") in the a processor disclosed herein after all the data for that frequency has been collected.

A discrete Fourier transform is done on the data at the integer value corresponding to the driven frequency of the speaker. The general expression for the first harmonic of a DFT is as follows in Equation (61):

$$x_k = \frac{2}{MN} \sum_{n=0}^{N-1} x_n e^{-\frac{2\pi i}{N}kn}. \tag{61}$$

The product MN is the total number of points and the factor of 2 is added such that the resulting real and imaginary portions of the answer match the amplitude of the sine wave illustrated in Equation (62):

$$x_n = \mathrm{re}(x_k)\cos\left(\frac{2\pi}{N}kn\right) + \mathrm{im}(x_k)\sin\left(\frac{2\pi}{N}kn\right). \tag{62}$$

This real part of this expression is illustrated in Equation (63):

$$\mathrm{re}(x) = \frac{2}{MN} \sum_{n=0}^{N-1} x_n \cos\left(\frac{2\pi}{N}n\right). \tag{63}$$

We can take advantage of the symmetry of the cosine function to reduce the number of computations needed to compute the DFT. The expression above is equivalent to Equation (64) as follows:

$$\mathrm{re}(x) = \frac{2}{MN}\left[\left(x_0 - x_{\frac{1}{2}N}\right) + \sum_{n=1}^{\frac{1}{4}N-1} \sin\left(\frac{\pi}{2} - \frac{2\pi}{N}n\right)\left[\left(x_n - x_{\frac{1}{2}N+n}\right) - \left(x_{\frac{1}{2}N-n} - x_{N-n}\right)\right]\right]. \tag{64}$$

Similarly, the imaginary portion of the equation is illustrated in Equation (65) as follows:

$$\mathrm{im}(x) = -\frac{2}{MN} \sum_{n=0}^{N-1} x_n \sin\left(\frac{2\pi}{N}n\right), \tag{65}$$

which may be expressed as Equation (66):

$$\mathrm{im}(x) = -\frac{2}{MN}\left[\left(x_{\frac{1}{4}N} - x_{\frac{3}{4}N}\right) + \sum_{n=1}^{\frac{1}{4}N-1} \sin\left(\frac{2\pi}{N}n\right)\left[\left(x_n - x_{\frac{1}{2}N+n}\right) + \left(x_{\frac{1}{2}N-n} - x_{N-n}\right)\right]\right]. \tag{66}$$

The variance of the signal at that driven frequency is illustrated in Equation (67) as follows:

$$\sigma_{tone}^2 = \tfrac{1}{2}(\mathrm{re}(x)^2 + \mathrm{im}(x)^2) \tag{67}$$

The tone variance is proportional to the acoustic power at the driven frequency. The maximum possible value of the real and imaginary portions of x is $2^{11}$; this corresponds to half the A/D range. The maximum value of the tone variance is $2^{21}$; half the square of the AD range.

Computing the Total Signal Variance

A good measure of the integrity of a measurement is the ratio of the acoustic power at the driven frequency relative to the total acoustic power at all frequencies. The total signal variance is given by the expression in Equation (68):

$$\sigma_{total}^2 = \frac{1}{NM}\sum_{n=0}^{MN-1} p_n^2 - \overline{p}^2 = \frac{1}{NM}\sum_{n=0}^{MN-1} p_n^2 - \left(\frac{1}{NM}\sum_{n=0}^{MN-1} p_n\right)^2. \tag{68}$$

However, in some specific embodiments, the summations are performed in the A/D interrupt service routine (ISR) where there are time constraints and/or all of the microphone data must be stored for post-processing. In some embodiments, to increase efficiency, a pseudo-variance is calculated based on a single averaged wavelength. The pseudo-variance of the signal is calculated using the following relation illustrated in Equation (69) as follows:

$$\sigma_{total}^2 = \frac{1}{NM^2}\sum_{n=0}^{N-1} x_n^2 - \frac{1}{N^2 M^2}\left(\sum_{n=0}^{N-1} x_n\right)^2. \tag{69}$$

The result is in the units of AD counts squared. The summation will be on the order of $$\sum_{n=0}^{N-1} x_n^2 = O(NM^2 2^{24})$$

for a 12-bit ADC. If $N<2^7=128$ and $M<2^6=64$ then the summation will be less than $2^{43}$ and can be stored in a 64-bit integer. The maximum possible value of the variance would result if the ADC oscillated between a value of 0 and $2^{12}$ on each consecutive sample. This would result in a peak variance of $\tfrac{1}{4}(2^{12})^2 = 2^{22}$ so the result can be stored at a Maximum of a Q9 Resolution in a Signed 32-Bit Integer.

Computing the Relative Microphone Response

The relative response of the two microphones, G, is then computed from the complex response of the individual microphones illustrated in Equations 70-72:

$$G = \frac{x_{var}}{x_{ref}} = \frac{x_{var}}{x_{ref}} \frac{x_{ref}^*}{x_{ref}^*}. \tag{70}$$

$$\mathrm{Re}(G) = \frac{\mathrm{Re}(x_{var})\mathrm{Re}(x_{ref}) + \mathrm{Im}(x_{var})\mathrm{Im}(x_{ref})}{\mathrm{Re}(x_{ref})^2 + \mathrm{Im}(x_{ref})^2}. \tag{71}$$

$$\mathrm{Im}(G) = \frac{\mathrm{Re}(x_{ref})\mathrm{Im}(x_{var}) - \mathrm{Re}(x_{var})\mathrm{Im}(x_{ref})}{\mathrm{Re}(x_{ref})^2 + \mathrm{Im}(x_{ref})^2}. \tag{72}$$

The denominator of either expression can be expressed in terms of the reference tone variance computed in the previous section, illustrated as follows in Equation 73:

$$\mathrm{Re}(x_{ref})^2 + \mathrm{Im}(x_{ref})^2 = 2\sigma_{ref}^2 \tag{73}$$

Correcting for A/D Skew

The speaker output may be updated at a fixed 32 times per sample. For example, as the driving frequency is changed, the speaker output frequency is also updated to maintain the fixed 32 cycles. The two microphones are sampled synchronous with the speaker output so the sampling frequency remains at a fixed interval of the driving frequency. The microphone A/D measurements, however, are not sampled simultaneously; the A/D ISR alternates between the two microphones, taking a total of N samples per wavelength for each microphone. The result will be a phase offset between the two microphones of $$\frac{\pi}{N}.$$

To correct for this phase offset, a complex rotation is applied to the relative frequency response computed in the previous section.

To rotate a complex number an angle $$\frac{\pi}{N}$$

it is multiplied by $$e^{i\frac{\pi}{N}} = \cos\left(\frac{\pi}{N}\right) + i\sin\left(\frac{\pi}{N}\right).$$

The result is illustrated in Equation (74) as follows:

$$G_{rotated} = \left(\text{Re}(G)\cos\left(\frac{\pi}{N}\right) - \text{Im}(G)\sin\left(\frac{\pi}{N}\right)\right) + \left(\text{Im}(G)\cos\left(\frac{\pi}{N}\right) + \text{Re}(G)\sin\left(\frac{\pi}{N}\right)\right)i. \quad (74)$$

Time Delays

In some embodiments, one of the assumptions when deriving the AVS equations is that the pressure is uniform in the acoustic volumes. This assumption is true if the acoustic wavelength is large compared to the dimensions of the AVS chamber. The wavelength of a sound wave at a given frequency can be computed with the following Equation (75):

$$\lambda = \frac{a}{f}. \quad (75)$$

For example, the wavelength at 1 kHz is roughly 246 mm and at 5 kHz is roughly 49.2 mm. The AVS chamber may have a diameter such that the time delay associated with acoustic waves traveling through the volumes has a small but measurable effect. The effect can be modeled as a time delay (or time advance, depending on microphone orientation). The Laplace transform of a pure time delay, d, is illustrated in Equation (76) as follows:

$$G = e^{ds} \quad (76).$$

The phase is influenced by the time delay, but not the magnitude of system response. To correct for the time delays, the frequency response data may be corrected in advance by applying a model fit algorithm. The complex amplitude may be rotated as a function of frequency according the time delay equation above. The time delay may be assumed to be fixed, so the rotation is only a function of frequency.

The time delay may be determined by running an optimization routine to find the time delay to minimize the model fit error. Additionally or alternatively, there may be an apparent "time advance" in the data. For example, the reference microphone may experience a pressure perturbation slightly in advance of the acoustic port and the variable microphone may experience a pressure perturbation slightly behind the acoustic port. These "advances" and "delays" may be the effects of the propagation of the pressure waves and are in addition to "resonant" dynamics of the system, e.g., these effects may be accounted for.

Amplitude Leveling

The amplitude of the pressure measurements for a given speaker drive signal may vary from device-to-device and also as a function of the driven frequency. The device-to-device variations result from part-to-part differences in microphone and speaker sensitivities (e.g., roughly on the order of +/−3 dB). The frequency-based dependencies result from variations in speaker sensitivity over frequency as well as from the expected dynamics of the acoustic resonance.

To compensate, in some embodiments, the speaker gain is automatically tuned during the AVS measurement. The speaker gains are stored in an array with one entry for each of the sine-sweep frequencies, e.g., within the memory 22 of FIG. 2. The amplitude of the microphone signal (from either the variable or reference microphone) may be checked against the target amplitude. If it is either too large or too small a binary search routine may be employed to update the speaker gain at that frequency.

Checking Individual Measurement Integrity

It is possible for component errors, failures, or external disturbances to result in an erroneous measurement. Component failures might include a distorted speaker output or failed microphone. External disturbances might include mechanical shock to the pump housing or an extremely loud external noise. These types of failures can be detected using two different integrity checks: microphone saturation and out-of-band variance.

The microphone saturation check looks at the maximum and minimum values of the wavelength averaged signal for each microphone. If these values are close to the limits of the A/D then a flag within the a processor disclosed herein is set indicating that the measurement amplitude was out of range.

The out-of-band variance check compares the tone variance to the total signal variance for each microphone. In the ideal case the ratio of these signals will be 1—all of the acoustic power will be at the driven frequency. In the event of shock or an extremely loud external acoustic noise, more power will be present at other frequencies and this value will be lower than unity. In some embodiments, normal operation may be considered to have a ratio greater than 0.99.

In some embodiments, if an individual data point fails either of these integrity checks, it may be repeated or excluded without having to repeat the entire sine-sweep to help facilitate AVS robustness. Other integrity checks may be done based on the complete sine-sweep and are described later.

Volume Estimation Using Swept Sine-Generalized Solution

The resonant frequency of the system may be estimated using swept-sine system identification. In this method the response of the system to a sinusoidal pressure variation may be found at a number of different frequencies. This frequency response data may be then used to estimate the system transfer function using linear regression.

The transfer function for the system can be expressed as a rational function of s. The general case is expressed below for a transfer function with an $n^{th}$ order numerator and an $m^{th}$ order denominator. N and D are the coefficients for the numerator and denominator respectively. The equation has been normalized such that the leading coefficient in the denominator is 1, as illustrated in Equations (77) and (78):

$$G(s) = \frac{N_n s^n + N_{n-1} s^{n-1} + \ldots + N_0}{s^m + D_{m-1} s^{m-1} + D_{m-2} s^{m-2} + \ldots + D_0} \tag{77}$$

or $$G(s) = \frac{\sum_{k=0}^{n} N_k s^k}{s^m + \sum_{k=0}^{m-1} D_k s^k}. \tag{78}$$

This equation can be re-written in the form of Equation 79 as follows:

$$G s^m = \sum_{k=0}^{n} N_k s^k - G \sum_{k=0}^{m-1} D_k s^k. \tag{79}$$

Equation (80) shows this summation in matrix notation:

$$\begin{bmatrix} G_1 s_1^m \\ \vdots \\ G_k s_k^m \end{bmatrix} = \begin{bmatrix} s_1^n & \ldots & s_1^0 & -G_1 s_1^{m-1} & \ldots & -G_1 s_1^0 \\ \vdots & & \vdots & \vdots & & \vdots \\ s_k^n & \ldots & s_k^0 & -G_k s_k^{m-1} & \ldots & -G_k s_k^0 \end{bmatrix} \begin{bmatrix} N_n \\ \vdots \\ N_0 \\ D_{m-1} \\ \vdots \\ D_0 \end{bmatrix}. \tag{80}$$

Where k is the number of data points collected in the swept sine. To simplify the notation this equation can be summarized using the vectors y illustrated in Equation (81).

$$y = Xc \tag{81}$$

Where y is k by 1, x is k by (m+n−1) and c is (m+n−1) by 1. The coefficients can then be found using a least square approach. The error function can be written as shown in Equation (82):

$$e = y - Xc \tag{82}$$

The function to be minimized is the weighted square of the error function; W is a k×k diagonal matrix, as illustrated in Equations 83-84.

$$e^T W e = (y - Xc)^T W (y - Xc) \tag{83}$$

$$e^T W e = y^T W y - (y^T W X c)^T - y^T W X c + c^T X^T W X c \tag{84}$$

The center two terms are scalars so the transpose can be neglected, as illustrated in Equations 85-87:

$$e^T W e = y^T W y - 2 y^T W X c + c^T X^T W X c \tag{85}$$

$$\frac{\partial e^T W e}{\partial c} = -2 X^T W y + 2 X^T W X c = 0, \tag{86}$$

and $$c = (X^T W X)^{-1} X^T W y \tag{87}$$

In some embodiments, the complex transpose in all of these cases is utilized. This approach can result in complex coefficients, but the process can be modified to ensure that all the coefficients are real. The least-square minimization can be modified to give only real coefficients if the error function is changed to Equation (88).

$$e^T W e = \text{Re}(y - Xc)^T W \text{Re}(y - Xc) + \text{Im}(y - Xc)^T W \text{Im}(y - Xc) \tag{88}$$

Then the coefficients can be found with the Equation (89):

$$c = (\text{Re}(X)^T W \text{Re}(X) + \text{Im}(X)^T W \text{Im}(X))^{-1} (\text{Re}(X)^T W \text{Re}(y) + \text{Im}(X)^T W \text{Im}(y)) \tag{89}$$

Volume Estimation Using Swept Sine-Solution for a $2^{nd}$ Order System

For a system with a $0^{th}$ order numerator and a second order denominator as shown in the transfer function illustrated in Equation (90).

$$G(s) = \frac{N_0}{s^2 + D_1 s + D_0}. \tag{91}$$

The coefficients in this transfer function can be found based on the expression found in the previous section as follows Equation (92):

$$c = (\text{Re}(X)^T W \text{Re}(X) + \text{Im}(X)^T W \text{Im}(X))^{-1} (\text{Re}(X)^T W \text{Re}(y) + \text{Im}(X)^T W \text{Im}(y)) \tag{92}$$

Where Equation (93) is as follows:

$$y = \begin{bmatrix} G_1 s_1^2 \\ \vdots \\ G_k s_k^2 \end{bmatrix}, X = \begin{bmatrix} 1 & -G_1 s_1 & -G_1 \\ \vdots & \vdots & \vdots \\ 1 & -G_k s_k & -G_k \end{bmatrix}, \text{ and } c = \begin{bmatrix} N_0 \\ D_1 \\ D_0 \end{bmatrix}. \tag{93}$$

To simplify the algorithm we can combine some of terms as illustrated in Equations 94-96:

$$c = D^{-1} b \tag{94},$$

where $$D = \text{Re}(X)^T W \text{Re}(X) + \text{Im}(X)^T W \text{Im}(X) \tag{95, and}$$

$$b = \text{Re}(X)^T W \text{Re}(y) + \text{Im}(X)^T W \text{Im}(y) \tag{96}.$$

To find an expression for D in terms of the complex response vector G and the natural frequency s=jω we first split X into its real and imaginary parts as illustrated in Equations (97) and (98), respectively, as follows:

$$\text{Re}(X) = \begin{bmatrix} 1 & \omega_1 \text{Im}(G_1) & -\text{Re}(G_1) \\ \vdots & \vdots & \vdots \\ 1 & \omega_k \text{Im}(G_k) & -\text{Re}(G_k) \end{bmatrix}, \text{ and} \tag{97}$$

$$\text{Im}(X) = \begin{bmatrix} 0 & -\omega_1 \text{Re}(G_1) & -\text{Im}(G_1) \\ \vdots & \vdots & \vdots \\ 0 & -\omega_k \text{Re}(G_k) & -\text{Im}(G_k) \end{bmatrix}. \tag{98}$$

The real and imaginary portions of the expression for D above then become Equations (99) and (100), respectively:

$$\operatorname{Re}(X)^T W \operatorname{Re}(X) = \begin{bmatrix} \sum_{i=1}^{k} w_i & \sum_{i=1}^{k} w_i \operatorname{Im}(G_i)\omega_i & -\sum_{i=1}^{k} w_i \operatorname{Re}(G_i) \\ \sum_{i=1}^{k} w_i \operatorname{Im}(G_i)\omega_i & \sum_{i=1}^{k} w_i \operatorname{Im}(G_i)^2 \omega_i^2 & -\sum_{i=1}^{k} w_i \operatorname{Im}(G_i)\operatorname{Re}(G_i)\omega_i \\ -\sum_{i=1}^{k} w_i \operatorname{Re}(G_i) & -\sum_{i=1}^{k} w_i \operatorname{Im}(G_i)\operatorname{Re}(G_i)\omega_i & \sum_{i=1}^{k} w_i \operatorname{Re}(G_i)^2 \end{bmatrix}, \text{ and} \quad (99)$$

$$\operatorname{Im}(X)^T W \operatorname{Im}(X) = \begin{bmatrix} 0 & 0 & 0 \\ 0 & \sum_{i=1}^{k} w_i \operatorname{Re}(G_i)^2 \omega_i^2 & \sum_{i=1}^{k} w_i \operatorname{Im}(G_i)\operatorname{Re}(G_i)\omega_i \\ 0 & \sum_{i=1}^{k} w_i \operatorname{Im}(G_i)\operatorname{Re}(G_i)\omega_i & \sum_{i=1}^{k} w_i \operatorname{Im}(G_i)^2 \end{bmatrix}. \quad (100)$$

Combining these terms gives the final expression for the D matrix. This matrix will contain only real values, as shown in Equation (101) as follows:

$$D = \begin{bmatrix} \sum_{i=1}^{k} w_i & \sum_{i=1}^{k} w_i \operatorname{Im}(G_i)\omega_i & -\sum_{i=1}^{k} w_i \operatorname{Re}(G_i) \\ \sum_{i=1}^{k} w_i \operatorname{Im}(G_i)\omega_i & \sum_{i=1}^{k} w_i(\operatorname{Re}(G_i)^2 + \operatorname{Im}(G_i)^2)\omega_i^2 & 0 \\ -\sum_{i=1}^{k} w_i \operatorname{Re}(G_i) & 0 & \sum_{i=1}^{k} w_i(\operatorname{Re}(G_i)^2 + \operatorname{Im}(G_i)^2) \end{bmatrix}. \quad (101)$$

The same approach can be taken to find an expression for the b vector in terms of G and ω. The real and imaginary parts of y are illustrated in Equation 102-103.

$$\operatorname{Re}(y) = \begin{bmatrix} -\operatorname{Re}(G_1)\omega_1^2 \\ \vdots \\ -\operatorname{Re}(G_k)\omega_k^2 \end{bmatrix}, \text{ and} \quad (102)$$

$$\operatorname{Im}(y) = \begin{bmatrix} -\operatorname{Im}(G_1)\omega_1^2 \\ \vdots \\ -\operatorname{Im}(G_k)\omega_k^2 \end{bmatrix}. \quad (103)$$

Combining these two gives the expression for the b vector illustrated in Equation 104 as follows:

$$b = \operatorname{Re}(X)^T W \operatorname{Re}(y) + \quad (104)$$

$$\operatorname{Im}(X)^T W \operatorname{Im}(y) = \begin{bmatrix} -\sum_{i=1}^{k} w_i \operatorname{Re}(G_i)\omega_i^2 \\ 0 \\ \sum_{i=1}^{k} w_i(\operatorname{Re}(G_i)^2 + \operatorname{Im}(G_i)^2)\omega_i^2 \end{bmatrix}.$$

The next step is to invert the D matrix. The matrix is symmetric and positive-definite so the number of computations needed to find the inverse will be reduced from the general 3×3 case. The general expression for a matrix inverse is shown in Equation (105) as:

$$D^{-1} = \frac{1}{\det(D)} \operatorname{adj}(D). \quad (105)$$

If D is expressed as in Equation (106):

$$D = \begin{bmatrix} d_{11} & d_{12} & d_{13} \\ d_{12} & d_{22} & 0 \\ d_{13} & 0 & d_{33} \end{bmatrix}, \quad (106)$$

then the adjugate matrix can be written as in Equation (107) as follows:

$$\operatorname{adj}(D) = \begin{bmatrix} \begin{vmatrix} d_{22} & 0 \\ 0 & d_{33} \end{vmatrix} & -\begin{vmatrix} d_{12} & 0 \\ d_{13} & d_{33} \end{vmatrix} & \begin{vmatrix} d_{12} & d_{22} \\ d_{13} & 0 \end{vmatrix} \\ -\begin{vmatrix} d_{12} & d_{13} \\ 0 & d_{33} \end{vmatrix} & \begin{vmatrix} d_{11} & d_{13} \\ d_{13} & d_{33} \end{vmatrix} & -\begin{vmatrix} d_{11} & d_{12} \\ d_{13} & 0 \end{vmatrix} \\ \begin{vmatrix} d_{12} & d_{13} \\ d_{22} & 0 \end{vmatrix} & -\begin{vmatrix} d_{11} & d_{13} \\ d_{12} & 0 \end{vmatrix} & \begin{vmatrix} d_{11} & d_{12} \\ d_{12} & d_{22} \end{vmatrix} \end{bmatrix} = \begin{bmatrix} a_{11} & a_{12} & a_{13} \\ a_{12} & a_{22} & a_{23} \\ a_{13} & a_{32} & a_{22} \end{bmatrix}. \quad (107)$$

Due to symmetry, only the upper diagonal matrix needs to be calculated. The Determinant can then be computed in terms of the adjugate matrix values, taking advantage of the zero elements in the original array as illustrated in Equation (108) as follows:

$$\det(D) = a_{12}d_{12} + a_{22}d_{22} \quad (108).$$

Finally, the inverse of D can be written in the form shown in Equation (109):

$$D^{-1} = \frac{1}{det(D)} adj(D). \tag{109}$$

In some embodiments, we may solve the value in Equation (110):

$$c = D^{-1}b = \frac{1}{det(D)} adj(D)b; \tag{110}$$

So that Equation (111) is used:

$$c = \frac{1}{det(D)} \begin{bmatrix} a_{11} & a_{12} & a_{13} \\ a_{12} & a_{22} & a_{23} \\ a_{13} & a_{32} & a_{22} \end{bmatrix} \begin{bmatrix} b_1 \\ 0 \\ b_3 \end{bmatrix} = \frac{1}{det(D)} \begin{bmatrix} a_{11}b_1 + a_{13}b_3 \\ a_{12}b_1 + a_{23}b_3 \\ a_{13}b_1 + a_{33}b_3 \end{bmatrix}, \tag{111}$$

To get a quantitative assessment of how well the data fits the model, the original expression for the error as shown in Equation (112) is utilized:

$$e^T W e = \text{Re}(y-Xc)^T W \text{Re}(y-Xc) + \text{Im}(y-Xc)^T W \text{Im}(y-Xc) \tag{112}$$

This can be expressed in terms of the D matrix and the b and c vectors illustrated in Equation (113):

$$e^T W e = h - 2c^T b + c^T D c \tag{113},$$

where:

$$h = \text{Re}(y^T) W \text{Re}(y) + \text{Im}(y^T) W \text{Im}(y) \tag{114}, \text{ and}$$

$$h = \sum_{i=1}^{k} w_i (\text{Re}(G_i)^2 + \text{Im}(G_i)^2) \omega_i^4. \tag{115}$$

In some embodiments, to compare the errors from different sine sweeps, the fit error is normalized by the square of the weighted by matrix as follows in Equation (116), where h is a scalar:

$$e^T W e h^{-1} = (h - 2c^T b + c^T D c) h^{-1} \tag{116}.$$

Volume Estimation Using Swept Sine-Estimating Volume

The model fit may be used such that the resonant frequency of the port may be extracted from the sine sweep data. The delivered volume may be related to this value. The ideal relationship between the two can be expressed by the relation illustrated in Equation (117):

$$\omega_n^2 = \frac{a^2 A}{L} \frac{1}{V_2}. \tag{117}$$

The speed of sound will vary with the temperature, so it is useful to split out the temperature effects as shown in Equation (118):

$$\omega_n^2 = \frac{\gamma R A}{L} \frac{T}{V_2}. \tag{118}$$

The volume can then be expressed as a function of the measured resonant frequency and the temperature, illustrated in Equation (119) as follows:

$$V_2 = C \frac{T}{\omega_n^2}. \tag{119}$$

Where C is the calibration constant illustrated in Equation (120) as follows:

$$C = \frac{\gamma R A}{L}. \tag{120}$$

Volume Estimation Using Swept Sine-Volume Estimation Integrity Checks

In some embodiments, a second set of integrity check can be performed out of the output of the mode fit and volume estimation routines (the first set of checks is done at the FFT level). Checks may be done either through redundancy or through range checking for several values, such as: (1) model fit error, (2) estimated damping ratio, (3) estimated transfer function gain, (4) estimated natural frequency, (5) estimated variable volume, and (6) AVS sensor temperature.

In addition, portions of the AVS calculations may be done redundantly on the a processor disclosed herein using an independent temperature sensor and an independent copy of the calibration parameters to guard against RAM failures, in some specific embodiments.

Volume Estimation Using Swept Sine-Disposable Detection

The presence of the disposable, e.g., cartridges or reservoirs that are attachable, may be detected using a magnetic switch and mechanical interlock, in some specific embodiments. However, a second detection method may be used to 1) differentiate between the pump being attached to a disposable and a charger, and 2) provide a backup to the primary detection methods.

If the disposable is not present, the variable volume, $V_2$, is effectively very large. As a result, there will be a normal signal from the reference microphone, but there will be very little signal on the variable microphones. If the mean amplitude of the reference microphone during a sine sweep is normal (this verifies that the speaker is working) and the mean amplitude of the variable microphone is small, a flag is set in the a processor disclosed herein indicating that the disposable is not present.

Implementation Details-Sizing V1 Relative to V2

Sizing $V_1$ may include trading off acoustic volume with the relative position of the poles and zeros in the transfer function. The transfer function for both $V_1$ and $V_2$ are shown below relative to the volume displacement of the speaker as illustrated in Equations 121-124, as follows:

$$\frac{p_2}{v_k} = -\frac{\rho a^2}{V_1} \frac{\omega_n^2}{s^2 + 2\zeta\omega_n s + \alpha\omega_n^2}, \text{ and} \tag{121}$$

$$\frac{p_1}{v_k} = -\frac{\rho a^2}{V_1} \frac{s^2 + 2\zeta\omega_n s + \alpha\omega_n^2}{s^2 + 2\zeta\omega_n s + \omega_n^2} \tag{122}$$

where $$\omega_n^2 = \frac{a^2 A}{L} \frac{1}{V_2}, \quad \zeta = \frac{fA}{2L\omega_n} \text{ and} \tag{123}$$

-continued $$\alpha = \left(1 + \frac{V_2}{V_1}\right). \quad (124)$$

As $V_1$ is increased the gain decreases and the speaker must be driven at a higher amplitude to get the same sound pressure level. However, increasing $V_1$ has the benefit of moving the complex zeros in the $p_1$ transfer function toward the complex poles. In the limiting case where $V_1 \rightarrow \infty$ then $\alpha \rightarrow 1$ and you have pole-zero cancellation and a flat response. Increasing $V_1$, therefore, has the reduces both the resonance and the notch in the $p_1$ transfer function, and moves the $p_2$ poles toward $\omega_n$; the result is a lower sensitivity to measurement error when calculating the $p_2/p_1$ transfer function.

Implementation Details-Aliasing

Higher frequencies can alias down to the frequency of interest. The aliased frequency can be expressed in Equation (125) as follows:

$$f = |f_n - nf_s| \quad (125).$$

Where $f_s$ is the sampling frequency, $f_n$ is the frequency of the noise source, n is a positive integer, and f is the aliased frequency of the noise source.

The demodulation routine may filter out noise except at the specific frequency of the demodulation. If the sample frequency is set dynamically to be a fixed multiple of the demodulation frequency, then the frequency of the noise that can alias down to the demodulation frequency will be a fixed set of harmonics of that fundamental frequency.

For example, if the sampling frequency is 8 times the demodulation frequency then the noise frequencies that can alias down to that frequency are $$\frac{f_n}{f} = \left\{\frac{1}{n\beta+1}, \frac{1}{n\beta-1}\right\} = \left\{\frac{1}{7}, \frac{1}{9}, \frac{1}{15}, \frac{1}{17}, \frac{1}{23}, \frac{1}{25}, \dots\right\} \quad (126)$$

where $$\beta = \frac{f_s}{f} = 8. \quad (127)$$

For $\beta=16$ we would have the series $$\frac{f_n}{f} = \left\{\frac{1}{15}, \frac{1}{17}, \frac{1}{31}, \frac{1}{33}, \dots\right\}. \quad (127)$$

Sources of Avs Measurement Error-Avs Chamber Movement

In some embodiments, one of the assumptions of the AVS measurement is that the total AVS volume ($V_2$ plus the volume taken up the by the other components) is constant. However, if the AVS housing flexes the total volume of the AVS chamber may change slightly and affect the differential volume measurement. In some embodiments, to keep the contribution of the volume error is kept to be less than 1.0% of the fluid delivery.

Sources of Avs Measurement Error-External Noise

In some embodiments, external noise sources may be filtered out.

Sources of Avs Measurement Error-Mechanical Shock

Mechanical shock to the pump housing during an AVS measurement will affect the microphone measurements and may result in an error in the frequency response data. This error, however, is detectable using the out-of-band variance check in the demodulation routine by the a processor disclosed herein. If such an error is detected, the data point can be repeated (e.g., another sample is taken) resulting in little or no effect on the resulting AVS measurement.

Sources of Avs Measurement Error-Air in the AVS Chamber

A mechanism for an air bubble to affect the AVS measurement is through a secondary resonance. This secondary resonance will make the system $4^{th}$ order and, depending on the frequency and magnitude of the secondary resonance, can cause some error if the estimation is using a $2^{nd}$ order model.

Sources of Avs Measurement Error-Electrical Component Failure

In general, failure an electrical component will result in no signal or in increased harmonic distortion. In either case the fault would be detected by AVS integrity checks and the measurement invalidated.

An exception that has been identified is a failure of the oscillator used to control the DAC and ADC. If this oscillator were to drift out of tolerance it would introduce a measurement error that may not be detected by the low-level integrity check (it would be detected in an extreme case by the volume integrity checks described above). To guard against these failures, in some embodiments, the oscillator is checked against an independent clock whenever an AVS measurement is initiated.

L-Shaped Cam Follower Peristaltic Pump

FIGS. 255-302 show another embodiment of a peristaltic pump 2990.

FIG. 255 illustrates a peristaltic pump 2990 comprising a pumping mechanism 3000, display 2994, buttons 2996, chassis 2992, and clamp 2998. The chassis 2992 includes an extension 2992A above the pumping mechanism 3000 that deflects liquid away from the inside of the mechanism.

FIGS. 256A-B illustrate a peristaltic pumping mechanism 3000 having L-shaped cam followers 3090, 3100, 3110 (see FIG. 274) in an exploded view. A housing, composed optionally of two halves, 3005, 3010 provides a attachment points for a cam shaft 3080, a main PCB 3002, a cam-follower shaft 3120, a gear head assembly 3070, and hinge points 3010A to mount a door 3020. The two halves 3005, 3010 may be an upper half 3010 and a lower half 3005. The sensor housing 3015 may mount to the housing halves 3005, 3010 and provide an attachment point for a sensor mount 3060 and a rotation sensor board 3130 (FIG. 257). An air-in-line detector 3066 (see FIG. 257) and a pressure sensor 3068 (FIG. 257) may be attached to the sensor mount 3060.

FIG. 257 illustrates the pumping mechanism 3000 having L-shaped cam followers 3090, 3100, 3110 (see FIG. 274) with the door assembly 3021 fully open and the infusion tube 3210 and slide occluder 3200 mounted in the door 3020. The door assembly 3021 is mounted to the housing halves 3010, 3005 (FIG. 256A) via two hinges 3010A and a hinge pin 3012 (FIG. 258). In the open position, the door assembly 3021 may provide convenient receiving elements, which may serve to locate an infusion tube 3210 on the door assembly 3021. The receiving elements may locate the infusion tube 3210 so that it properly interfaces or lines up with the sensors and active elements of the peristaltic pump 2990. The sensors may, for example, include a pressure sensor 3068 (FIG. 257) and/or an air-in-line sensor 3066 (FIG. 257). The active elements may include, for example, the plunger 3091, inlet valve 3101 and outlet valve 3111 (FIG. 260). The plunger 3091, inlet valve 3101, and outlet valve 3111 may be referred to herein collectively simply as active elements 3091, 3101, 3111. The inlet valve 3101 and outlet valve 3111 may be referred to herein collectively as simply valves 3101, 3111. The active elements 3091, 3101, 3111 may be included respectively on a portion of the L-shaped cam followers 3090, 3100, 3110. The receiving elements in the door 3020 may include one or more of the following: grooves in the door 3020K (see FIG. 259), clips 3062A (FIG. 257), clip inserts 3024 (FIG. 257), platen 3022 (FIG. 257). The platen 3022 may be a tube platen (i.e., a platen 3022 configured to receive a tube, such as an intravenous infusion tube). In some embodiments, the platen 3022 is an infusion-tube platen (i.e., a platen 3022 configured to receive an infusion tube). The platen 3022 may define a well or deep groove to receive an infusion tube 3210. The clips 3062A (FIG. 257) and 3024 (FIG. 257) may be fabricated out of any suitable, non-deformable, non or minimally compliant material. The clips 3062A are preferably molded from plastic such as nylon, but many other materials including ABS plastic, aluminum, steel or ceramics may be used.

The door assembly 3021 (FIG. 257) may include a receiving element for the slide occluder 3200. The slide occluder 3200 receiving elements in the door assembly 3021 may hold the slide occluder 3200 in position so that the slide occluder 3200 enters a receiving opening in the pump body 3001 (FIG. 265). Some of the slide occluder 3200 receiving elements may include features that prevent the infusion set from being loaded incorrectly. In some embodiments, a door split carriage 3040 includes a slot to receive the slide occluder 3200 and hold it perpendicular to the infusion tube 3210 as the door assembly 3021 is closed against the pump body 3001. The door split carriage 3040 may include tabs 3040C (FIG. 259) that allow the slide occluder 3200 to only be inserted such that cutouts 3200A (FIG. 261) line up with the tabs 3040C (as best shown in FIG. 259). In another embodiment, the door 3020 may include tabs 3020F (FIG. 262, 263) that allow the slide occluder 3200 to only be inserted such that cutouts 3200A (FIG. 261) line up with tabs 3020F (FIG. 262). The door 3020 (FIG. 259) may include tabs 3020D (FIG. 259) that prevent the slide occluder 3200 (FIG. 259) from being inserted with the tab 3200B (FIG. 259) at an undesired orientation. The combination of tab 3020D and either the tabs 3020F (FIG. 262) located on the door 3020 and/or the tabs 3040C on the door-split-carriage 3040 (FIG. 259) may allow the slide occluder 3200 (FIG. 261) to be inserted in only one orientation and thereby force the correct orientation between the infusion set and the pumping mechanism 3000. The platen 3022 (FIG. 257) may receive the infusion tube 3210 and provides a general "U" shape to constrain the infusion tube 3210 as a plunger 3091 deforms the infusion tube 3210 during pumping.

Figure 292:
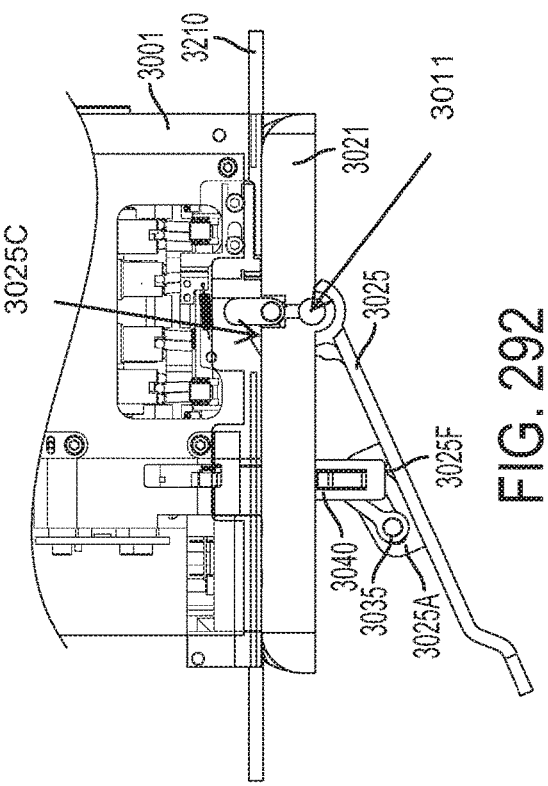

FIG. 264 illustrates, in an exploded view, the door assembly 3021 including a lever 3025 (i.e., a lever handle 305) and a split carriage 3041 (i.e., a carrier 3041) comprised of two parts, a door split carriage 3040 and a body split carriage 3045. Infusion tube 3210 receiving elements 3062, 3022 (FIG. 260), 3024 (FIG. 257) may be mounted respectively in recesses 3020A, 3020B, 3020E (FIG. 264) of the door 3020. The door assembly 3021 may include a door split carriage 3040 that is connected to the lever 3025 via a link 3035 (FIG. 292). The door assembly 3021 may also include a door spring 3032 (FIG. 264). The door spring 3032 may be a substantially flat sheet of resilient material such as spring-steel. The door spring 3032 may be pressed against the door 3020 by a latch pin 3034 as the lever 3025 grips the body pins 3011 (FIG. 297) on the pump body 3001 and draws the latch pin 3034 toward the pump body 3001. Referring to FIG. 297, the latch pin 3034 may move along a slot 3020C in the door 3020 as the latch hooks 3025C engage the body pins 3011.

In FIG. 265 the door assembly 3021 is open and the lever 3025 is retracted. The main PCB 3002, which includes the control processors and some sensors is shown attached to the top of the upper housing 3010. A motor 3072 and gear head 3070 are shown in position at one end of the upper housing 3010. The rotation sensor assembly 3130 may be mounted on the lower housing half 3005. The pump body 3001 may comprise housing halves 3005, 3010, the rotating, and reciprocating mechanisms inside the housing halves 3005, 3010, the motor 3072 and gearbox 3070, the sensors and the structure in which the above mount.

FIG. 260 illustrates a part of the peristaltic pump 2990 (FIG. 255) having L-shaped cam followers 3090, 3100, 3110 (see FIG. 274) with the door 3020 open and with some elements removed to reveal the cam-shaft 3080, the plunger 3091 and valves 3101, 3111. The motor 3072 may drive the cam shaft 3080 through the gearbox 3070. The motor 3072 may have a drive shaft. In such embodiments, the speed and/or position of the drive shaft may be controlled. In some embodiments, the motor 3072 is a brushless DC servo-motor 3072 controlled by a motor controller 3430 (see FIG. 325B) that may be mounted on the main PCB 3002. In alternative embodiments, the motor 3072 may be a stepper motor 3072, a DC brushed motor 3072 or an AC motor 3072 with the appropriate controller.

The motor 3072 may be fixedly coupled to the gearbox 3070 allowing the motor/gearbox unit to be attached as a unit to the cam shaft 3080 and upper housing 3010. The gear reduction of the gearbox 3070 may increase the torque, while also increasing the number of motor 3072 rotations per rotation of the cam shaft 3080 (FIG. 260). In one embodiment, the gearbox 3070 has a reduction ratio of 19:1. The gear reduction allows reasonable resolution on the cam shaft 3080 (FIG. 260) position with a relatively small number of hall sensors in the motor 3072. In some embodiments, three hall sensors and eight windings produce twenty-four crossings per revolution. The twenty-four crossings combined with a 19:1 gear ratio provides better than 0.8° angular resolution on the cam shaft 3080 (FIG. 260) orientation.

The orientation of the cam shaft 3080 (FIG. 260) may be directly measured with a rotation sensor 3130 (FIG. 257) that detects the position of the magnet 3125 (FIG. 260) on the end of the cam shaft 3080 (FIG. 260). In one embodiment, the sensor 3130 is a single-chip magnetic rotary encoder IC that employs 4 integrated Hall elements that detect the position of the magnet 3125 (FIG. 260), a high resolution analog to digital converter and a smart power management controller. The angular position, alarm bits and magnetic field information may be transmitted over a standard 3-wire or 4-wire SPI interface to a host controller. One example of a rotary encoder is model AS5055 manufactured by Austriamicrosystems of Austria that provides 4096 increments per rotation.

The movements of the valves 3101, 3111, and the plunger 3091 are controlled by the rotation of the cam shaft 3080. As best shown in FIG. 266, rotation of the cam shaft 3080 causes rotation of individual cams 3083, 3084, 3082, which in turn deflects a roller end 3092, 3102, 3112 (FIG. 274) of the L-shaped followers 3090, 3100, 3110 (FIG. 274) downward.

The plunger 3091 is spring biased such that the cam 3083 lifts the plunger 3091 away from the tube 3210 (when the door 3020 is closed). The springs 3091 urge the plunger 3091 toward the tube 3210 and the cam 3083 leave the cam follower of the 3091 to define a pressurization period. The position of the plunger 3091 during the pressurization period is used as a baseline to estimate how much fluid is in the tube 3210 so the process can estimate how much fluid is discharged when the outlet valve 3111 is opened. This process is shown in FIG. 197.

FIG. 266 shows an actuator mechanism 3081 that includes a cam shaft 3080, an outlet-valve cam 3084, a plunger cam 3083, and an inlet-valve cam 3082. The outlet-valve cam 3084, plunger cam 3083, and inlet-valve cam 3082 may be referred to collectively herein as simply cams 3084, 3083, 3082. FIG. 271 shows a profile of the outlet-valve cam 3084, FIG. 272 shows a profile of the plunger cam 3083, and FIG. 273 shows a profile of the outlet-valve cam 3082.

Referring now to FIG. 274, the L-shaped cam followers 3090, 3100, 3110 rotate about a cam-follower shaft 3120, so downward movement of the roller end 3092, 3102, 3112 may cause the active elements 3091, 3101, 3111 to pull away from an infusion tube 3210 (FIG. 276). Bias members 3094, 3104, 3114 on each of their respective L-shaped cam followers 3090, 3100, 3110 may urge the rollers 3092, 3102, 3112 on each of their respective L-shaped cam followers 3090, 3100, 3110 upward against the cams 3083, 3082, 3084 for each of their respective L-shaped cam followers 3090, 3100 3110 (FIG. 260). The bias members 3094, 3104, and 3114 may also urge the active ends 3091, 3101, 3111 toward an infusion tube 3210 (FIG. 276). The bias members 3094, 3104, 3114 may be torsional springs.

FIG. 276 shows a cross-sectional view where the bias member 3094 for the plunger L-shaped cam follower 3090 is a torsional spring and is urging the roller 3092 of the plunger L-shaped cam follower 3090 against the cam 3083. The bias member 3094 is also urging the plunger 3091 of the plunger L-shaped cam follower 3090 toward the infusion tube 3210.

As mentioned above, the profiles of the outlet valve cam 3084, plunger cam 3083, and inlet valve cam 3082 are pictured in FIGS. 271-273. These profiles produce a valve sequence similar to that plotted in FIG. 197. The cams 3084, 3083, 3082 may be connected to the cam shaft 3080 in any of the standard methods including adhesive, press fit, keyed shaft. In some embodiments, the cams 3084, 3083, 3082 may be physically integrated into the cam shaft 3080 as a single piece. In some embodiments, the cams 3084, 3083, 3082 have a key slot 3082A, 3083A, 3084A and are pressed onto the cam shaft 3080 against a shoulder (not shown) with a key (not shown) to fixedly lock the cams 3084, 3083, 3082 from rotation about the cam shaft 3080 surface. A circle clip 3085 to hold the cams 3084, 3083, 3082 in position along the axis of the cam shaft 3080 may also be included. The cam shaft 3080 may be mounted in the upper and lower housings 3005, 3010 by bearings 3086 (FIG. 278). In one embodiment, the bearings 3086 are sealed roller bearings.

FIG. 274 illustrates the plunger L-shaped cam follower 3090, valve L-shaped cam followers 3100, 3110 and cam-follower shaft 3120 in an exploded view. The plunger L-shaped cam follower 3090 and outlet valve L-shaped cam follower 3110 are shown by themselves respectively in FIGS. 267-268 and FIGS. 269-270. The L-shaped cam followers 3090, 3100, 3110 mount on the cam-follower shaft 3120 and may rotate freely on the cam-follower shaft 3120. The rotation of the L-shaped cam followers 3090, 3100, 3110 on the cam-follower shaft 3120 may be facilitated by bearings. In some embodiments, the bearings may be solid flanged bushings 3095, 3105, 3115 pressed into the L-shaped structures 3093, 3103, 3113 of the L-shaped cam followers 3090, 3100, 3110. The bearings may be any low friction bushing including but not limited to bronze, brass, plastic, nylon, polyacetal, polytetrafluoroethylene (PTFE), ultra-high-molecular-weight polyethylene (UHMWPE), rulon, PEEK, urethane, and vespel. The flanges on the bushings 3095, 3105, 3115 may serve as axial bearing surfaces between adjacent L-shaped cam followers 3090, 3100, 3110 and between the valve L-shaped cam followers 3100, 3110 and the housing halves 3005, 3010 (FIG. 278). The flanges on the bushings 3095, 3105, 3115 (FIG. 274) may also serve to properly space the active ends 3091, 3100, 3111 (FIG. 274) of the L-shaped cam followers 3090, 3100, 3110 (FIG. 274) relative to platen 3022 (FIG. 257) on the door assembly 3021 (FIG. 257).

The cam-follower shaft 3120 (FIG. 274) may include end sections 3120A (FIG. 274) that are eccentric relative to the center section 3120B (FIG. 274) of the cam-follower shaft 3120 (FIG. 274). The position of the cam-follower shaft 3120 (FIG. 274) relative to the cam-shaft 3080 (FIG. 260) and/or platen 3022 (FIG. 260) may be finely adjusted by turning the eccentric end 3120A (FIG. 274). Turning the eccentric end 3120A (FIG. 274) may allow adjustment of the lash between rollers 3092, 3102, 3112 (FIG. 274) and the cams 3084, 3083, 3082 (FIGS. 271-273) on the cam shaft 3080 (FIG. 260).

The end section 3120A of the cam-follower shaft 3120 (FIG. 274) may include a feature 3120C to receive a tool such as a screw driver, hex key or other tool capable of applying a torque to the cam-follower shaft 3120 (FIG. 274). In some embodiments, the feature 3120C may be a slot sized to accept a flat-headed screw driver. The eccentric ends 3120A fit in holes formed by cut-outs 3005D, 3010D (see FIG. 278) in the housing halves 3005, 3010 respectively. In one embodiment, the holes formed by cutouts 3005D, 3010D (FIG. 278) do not bind the cam-follower shaft 3120 (FIG. 274) in order to allow adjustment. A clamping element may be added to secure the rotary position of the cam-follower shaft 3120 (FIG. 274). In some embodiments, the clamping element is a set screw threaded into a threaded hole in the end section 3120A.

The L-shaped cam followers 3090, 3100, 3110 (FIG. 274) or actuators each may comprise contacting elements which in the example embodiment are rollers 3092, 3102, 3112 that touch the cams 3084, 3083, 3082 (FIGS. 271-273). The L-shaped cam followers 3090, 3100, 3110 may each also comprise a bias member 3094, 3104, 3114 that urges the contacting element toward the surface of the cams 3084, 3083, 3082. The L-shaped cam followers 3090, 3100, 3110 may each also comprise an L-shaped structure 3093, 3103, 3113 that includes a bore, which mounts on a cam-follower shaft 3120. The structures 3093, 3103, 3113 may connect the rollers 3092, 3102, 3112 to the active elements 3091, 3101, 3111. The active elements 3091, 3101, 3111 may in turn touch the infusion tube 3210 (FIG. 276). The L-shaped cam followers 3090, 3100, 3110 (FIG. 274) may additionally include flanged bushings 3095, 3105, 3115 mounted in the bore of the respective structures 3093, 3103, 3113 (FIG. 274).

In some embodiments, and referring now to FIG. 274, the rollers 3092, 3102, 3112 may rotate about a shaft 3096, 3106, 3116 that is mounted in the structures 3093, 3103, 3113. In other embodiments any different type of suitable contacting element may be used.

In some embodiments, the active elements 3091, 3101, 3111, or inlet valve 3101, plunger 3091, an outlet valve 3111, may be formed as part of the L-shaped cam followers 3090, 3100, 3110 (FIG. 274). In some embodiments, the active elements, 3091, 3101, 3111 may be removably attached to the structures 3093, 3103, 3113 of each L-shaped cam follower 3090, 3100, 3110 (FIG. 274). In some embodiments, the active elements 3091, 3101, 3111 (FIG. 274) may be mechanically attached with screws or any other suitable fastener. In other embodiments, the active elements 3091, 3101, 3111 (FIG. 274) may include studs that pass through holes in the structures 3093, 3103, 3113 (FIG. 274) and are held in place with nuts. In other embodiments, the active elements 3091, 3101, 3111 (FIG. 274) may include plastic studs that snap into receiving elements in the structures 3093, 3103, 3113 (FIG. 274). In some embodiments, the active elements 3091, 3101, 3111 may be fixedly coupled to the structures 3093, 3103, 3113 by another other suitable or obvious coupling method.

The bias members 3094, 3104, 3114 (FIG. 274) may urge the L-shaped cam followers 3090, 3100, 3110 (FIG. 274) against the cam surfaces of the cams 3084, 3083, 3082 (FIGS. 271-273) and toward the platen 3022 (FIG. 260) and infusion tube 3210 (FIG. 276). In some embodiments, the bias members 3094, 3104, 3114 (FIG. 274) are coiled torsion springs that wrap around the section of the structures 3093, 3103, 3113 (FIG. 274) that includes the bore. In such embodiments, one portion of the torsion springs may press against the part of the structures 3093, 3103, 3113 of the L-shaped cam followers 3090, 3100, 3110 (FIG. 274) between the bore and the rollers 3092, 3102 and 3112. The another portion of each torsion spring may contact a fixed structure of the peristaltic pump 2990 (FIG. 255). In some such embodiments the fixed structure may be a spring or bias member retainer 3140 (FIGS. 275, 276) that may include a slot 3140A to capture the portion of the torsion spring. A retainer set screw 3142 (FIG. 275) can be turned to move the spring or bias member retainer 3140 within the upper housing 3010 and apply a load against the bias members 3094, 3104, 3114. At some cam 3084, 3083, 3082 (FIGS. 271-273) rotary positions, the load applied to a bias member 3094, 3104, 3114 may in turn be applied through the active ends 3091, 3101, 3111 to the infusion tube 3210. The compressive load of each active ends 3091, 3101, 3111 (FIG. 274) on the infusion tube 3210 may be adjusted by turning the corresponding retainer set screw 3142.

In other embodiments, the bias members 3094, 3104, 3114 (FIG. 274) may be helical springs that are located between the L-shaped cam followers 3090, 3100, 3110 (FIG. 274) and the structure of the pump body 3001. The helical springs may located such that they urge the an end of the L-shaped cam followers 3090, 3100, 3110 (FIG. 274) toward the cams 3082, 3083, 3084 (FIG. 271-273). The helical springs may also urge the active elements 3091, 3101, 3111 of the L-shaped cam followers 3090, 3100, 3110 (FIG. 274) toward the platen 3022 (FIG. 260). One arrangement of helical springs and L-shaped cam followers 3090, 3100, 3110 is shown in FIGS. 205, 206, 219, 220.

FIG. 276 shows a cross-section of the pump mechanism 3000 including sections of the plunger cam 3083, plunger 3091 and platen 3022. The cam shaft 3080 turns the plunger cam 3083 which is keyed to the shaft at 3084A. The cam 3083 displaces the cam contacting element or cam roller 3092, which is part of the plunger L-shaped cam follower 3090. The plunger L-shaped cam follower 3090 rotates about the cam-follower shaft 3120. The plunger 3091 L-shaped cam follower 3090 is held against the plunger cam 3083 by a bias member 3094. One end portion 3094A of the bias member 3094 contacts the structure 3093, while the free end of the bias member 3094B contacts the spring or bias member retainer 3140. As shown in FIG. 276, the plunger 3091 may compress the infusion tube 3210 against the platen 3022. The plunger 3091 may retract from the platen 3022, when the plunger cam 3083 depresses the cam-roller 3092.

FIG. 277 presents a cross-section of the plunger 3091, platen 3022 and infusion tube 3210 at the bottom of the plunger 3091 stroke. At the top of the plunger 3091 stroke, the infusion tube 3210 may be substantially non-compressed and may have a nominally round cross section that contains a maximum volume. Referring now also to FIG. 276, the pumping mechanism 3000 maximizes pumping per stroke by allowing the infusion tube 3210 to substantially completely fill at the top of the plunger 3091 stroke and minimize the volume inside the infusion tube 3210 at the bottom of the plunger 3091 stroke. The amount of volume pumped may be impacted by the shape of the plunger 3091, the length of the plunger 3091 stroke and the shape of the platen 3022. The design of the plunger 3091 and platen 3022 may be selected to balance increased volume against higher loads on the plunger 3091. In some embodiments, the plunger 3091 and platen 3022 are designed to avoid crushing infusion tube 3210 walls by providing a gap between the plunger 3091 and the platen 3022 that is slightly larger than two times the infusion tube 3210 wall thickness.

In some embodiments, the plunger cam 3083 and plunger L-shaped cam follower 3090 may be designed to provide a minimum clearance 3022G between the tip of the plunger 3091B (e.g., a rounded tip) and the bottom of the platen 3022D. In one example, the clearance 3022G is 2 to 3 times the infusion tube 3210 wall thickness and sufficient such that the infusion tube 3210 walls do not touch between the plunger tip 3091B and platen bottom 3022D. In one example, the clearance 3022G between the plunger tip 3091B and the bottom of the platen 3022D is approximately 0.048", which is 9% larger than twice the wall thickness of an example infusion tube 3210. In another example, the clearance 3022G may be as small as 2% larger than twice the wall thickness of an example infusion tube 3210. In another example the clearance 3022G may be as large as 50% larger than twice the wall thickness of an infusion tube 3210.

In some embodiments, the dimensions of the platen 3022 and plunger tip 3091B are selected to provide a clearance 3022G that is 2 to 3 times the wall thickness of a single wall of the infusion tube 3210. In one example, the clearance 3022G between the plunger tip 3091B and the platen 3022 is 8% to 35% larger than twice the wall thickness of an example infusion tube 3210. The clearance 3022G may allow the sides of the infusion tube 3210 to fold without pinching the fold shut. In some embodiments, the plunger tip 3091B has a radius of 0.05" and sides 3091C that diverge from each other at an angle of 35°. The sides 3091C may meet the plunger tip 3091B radius at a tangent. The length of the plunger tip 3091B may be 0.116". The platen bottom 3022D may be flat and have a curved portion 3022C on each side. The platen bottom 3022D forms a well such that it is a tube platen 3022. The length of the platen bottom 3022D and radii of the curved portions 3022C are selected to maintain a clearance 3022G between the plunger tip 3091B and the platen 3022 that is more than twice the infusion tube 3210 wall thickness. In one example, the platen bottom 3022D is 0.05 long and each radius the curved portions 3022C is 0.06". Side 3022B is angled away from the plunger 3091. The shorter side 3022E is nearly vertical. Side 3022F is at a shallower angle than the plunger walls 3091C to allow the plunger tip 3091B to enter the platen 3022 as the door assembly 3021 is closed.

The plunger 3091 and platen 3022 may include two substantially flat sections 3091A and 3022A which provide a mechanical stop (i.e., 3091A and 3022A may be contacting sections). The flat sections 3091A and 3022A may also be referred to herein as stops 3091A and 3022A. The mechanical stops 3091A, 3022A ensure that tube 3210 is deformed by about the same amount every actuation of the plunger 3091. As described elsewhere, the volume is determined from the change in plunger 3091 position from the beginning of the displacement stroke to the end of stroke. The profile of the plunger cam 3083 may be designed to lift off the roller 3092, when the flat section 3091A contacts the platen 3022 at 3022A when discharging fluid.

The plunger 3091 and platen 3022 may be formed of or with a surface that easily slides on an infusion tube 3210 material of PVC or Non-DEHP. In some embodiments, the plunger 3091 and platen 3022 may be formed of nylon. In another embodiment, the plunger 3091 and platen 3022 may be metal (e.g. aluminum) that is coated with PTFE. In other embodiments, other plastic may be used or other coatings may be applied to a metal plunger 3091 and/or platen 3022 that provide a low friction coefficient with a PVC or Non-DEHP infusion tube 3210.

The cam shaft 3080 (FIG. 276) and the cam-follower shaft 3120 (FIG. 276) are mounted in cut-outs 3005C, 3005D, 3010C in the lower and upper housing 3005, 3010 as shown in FIG. 278. The accuracy of the movements of the valves 3101, 3111 and the plunger 3091 as well as the usage life of the roller elements 3092, 3102, 3112 and cams 3082, 3083, 3084 are improved by better parallel alignment and correct spacing of the two shafts 3080, 3120 (FIG. 276). The parallel alignment and spacing of the two shafts 3080, 3120 (FIG. 276) are controlled in part by the parallel alignment and spacing of the cutouts 3005C, 3005D, 3010C. In some embodiments, the two parts of the housing 3005, 3010 are initially formed without the cutouts 3005C, 3005D, 3010C. The two parts of the housing 3005, 3010 are then mechanically joined as shown in the progression of FIG. 279 to FIG. 280. The holes 3006, 3007 may then be drilled or bored by the same machine in the same setup at the same time. The two parts of the housing 3005, 3010 are shown in FIG. 281 after the two holes 3006, 3007 have be created by such a process. In some embodiments, the two housing parts 3005, 3010 include features to hold them in a fixed alignment with one another when assembled. In one example embodiment, alignment features of the housing parts 3005, 3010 are pins pressed in one of the housing parts 3005, 3010 and matching holes in the other. In another example, features on one part extend across the split line 3008 to engage features on the other part. The operation of accurately boring holes is sometimes referred to as line boring. Line boring may improve the parallel alignment of the cutouts 3005C, 3005D, 3010C. The line boring of the cutouts 3005C, 3005D, 3010C in the joined parts of the housing 3005, 3010 inexpensively creates cutouts 3005C, 3005D, 3010C, that combine to form more accurately circular holes 3006, 3007 and holes 3006, 3007 that are more parallel to one another.

The measurement of pumped volume is based on the measured position of the plunger 3091. In one embodiment as shown in FIG. 282 the plunger 3091 position is measured remotely without contacting the plunger L-shaped cam follower 3090. In some embodiments, the plunger 3091 position is measured with a linear hall effect encoder IC 6001 (and/or 6002) and a simple two-pole magnet 3196 (or 3197). The linear encoder 6001 (FIG. 282) is located on the main PCB 3002 (shown in FIG. 282 as transparent) and reports the position of the magnet 3196 located on the plunger L-shaped cam follower 3090 to the controller. The linear encoder IC 6001 is advantageously mechanically disconnected from the moving components, so the sensor will not wear, degrade or break with use. In some embodiments, the linear encoder IC 6001 may be part AS5410 manufactured by Austriamicrosystems of Austria. The AS5410 allows the conversion of a wide range of geometries including curved movements, non-linear scales, and tilted chip/magnet geometries into a linear output signal. The flexibility of the linear encoder IC 6001 allows larger tolerances in the placement of the main PCB 3002 relative to the plunger magnet 3196. Alternatively, the position of the plunger 3091 may be measured with a vision system that uses edges or datums located on the plunger L-shaped cam follower 3090. Alternatively, the plunger 3091 position may be measured with any of several other sensors well known in the art including one or more of the following: a linear potentiometer, a rotary potentiometer, rotary encoder, linear encoder, or LVDT. Methods to mechanically connect one of these sensors to the plunger L-shaped cam follower 3090 may be those apparent to one skilled in the art. Additionally or alternatively, the linear encoder 6002 may be used to measure the plunger 3091 position using the magnet 3197. The results from the two linear encoders 6001, 6002 may be used by averaging their results together and/or one may be a backup for the other, in some specific embodiments. For example, the redundancy of the two linear encoders 6001, 6002 may allow operation in a fail operative mode in the event that one of the two linear encoders 6001, 6002 fails or is otherwise compromised. This redundancy may also be used to cross check results from one of the two linear encoders 6001, 6002 with the other of the two linear encoders 6001, 6002 to ensure that both of the two linear encoders 6001, 6002 are functioning properly. Upon identification of an inoperative encoder one of the two linear encoders 6001, 6002, the RTP 3500 (see FIG. 324) may disregard the inoperative encoder. The two linear encoders 6001, 6002 may be compared to the motor hall sensors 5043 and/or the rotary position sensor 5042 to determine inoperative one (refer to FIG. 346).

The slide occluder 3200 can be seen in FIG. 261. The slide occluder 3200 serves to pinch the infusion tube 3210 closed, blocking flow, when the infusion tube 3210 is in the narrow part of the opening 3200D. Flow is allowed through the infusion tube 3210 when it is located in the wide end of the opening 3200C at the front of the slide occluder 3200. The open position on the slide occluder 3200 refers to the infusion tube 3210 being located in the wide end of the opening 3200C. The closed position of the slide occluder 3200 refers to the infusion tube 3210 being located in the narrow part of the opening 3200D. The slide occluder 3200 includes at least one opening 3200A on the front end of the slide occluder 3200 in a raised wall 3200E running along the perimeter of the slide occlude 3200. A tab 3200B is located at the back end of the slide occluder 3200.

The process of closing the door 3020 and inserting the slide carriage 3041 to release the slide occluder 3200 is described with reference to FIGS. 283 to 293. FIG. 283 illustrates the slide occluder 3200 fully inserted into the door split carriage 3040 and the infusion tube 3210 clipped into the clips 3062A, 3024 (FIG. 257). The door assembly 3021 may close by rotating about the hinges 3010A. The initial position of the body split carriage 3045 in the pump body 3001 can be seen in FIG. 284. The slot 3045E in the body split carriage 3045 receives the slide occluder 3200 when the door assembly 3021 is closed against the pump body 3001. The opening 3045B in the body split carriage 3045 accommodates the tab 3200B of the slide occluder 3200 allowing the back end of the slide occluder 3200 to enter the body split carriage 3045 and allowing the door assembly 3021 to close. The body split carriage 3045 and/or upper housing 3010 may prevent the door assembly 3021 from closing when the slide occluder 3200 has been incorrectly oriented. The side of the body split carriage 3045 opposite the opening 3045B does not provide an opening or slot that could accommodate the tab 3200B on the slide occluder 3200. In some embodiments, the upper housing 3010 includes a rail 3010E (FIG. 287) that blocks the tab 3200B.

FIG. 285 illustrates an example two part split-carriage assembly 3041 in the open position. Such a position may be reached when the door assembly 3021 is open. FIG. 286 illustrates the two part split-carriage assembly 3041 in the closed position. Such a position may be reached when the door assembly 3021 is closed against the pump body 3001. The axis of the hinge 3040B is approximately in line with the axis of the upper housing 3010 hinge 3010A when the door assembly 3021 is open. A hinge pin 30410 which extends along the axis of the hinge 3040B may be included to hinged couple the body split carriage 3045 and door split carriage 3040 together. The two part split-carriage assembly 3041 (a carrier) includes a first portion 3045 (e.g., a body split carriage 3045) a second portion 3040 (a door split carriage 3040). The door split carriage 3040 includes at least one slot 3040D that allows it to accommodate at least one tab 3020D on the door 3020 and rail 3010E (FIG. 287) in the upper housing 3010. In an alternative embodiment shown in FIGS. 262-263, the slot 3040D may accommodate or be guided on tabs 3020D, 3020F (as is easily seen FIG. 285). The body split carriage 3045 includes at least one slot 3045D to accommodate rail 3010E (FIG. 287) on the upper housing 3010 and/or rail 3015E (FIG. 256A) on the sensor housing 3015. The slots 3040D and 3045D allow the split carriage 3041 to slide within the pump body 3001 and door 3020 when the door 3020 is closed against the body 3001.

FIG. 287 illustrates part of the pump body 3001 with the door 3020 partially closed and some elements removed to reveal the slide occluder 3200 in the closed split-carriage 3041. The door assembly 3021 is closed and the lever 3025 has not begun to engage the body pins 3011. The position of the split carriage 3041 comprising parts 3045 and 3040 is controlled by the position of the lever 3025. The split carriage 3041 is pushed into the pump body 3001 by a rib 3025F as the lever 3025 is closed or rotated toward the pump body 3001. The split carriage 3041 is pulled partially out of the pump body 3001 by the lever link 3035 (best shown in FIGS. 290-293) as the lever 3025 is opened or rotated away from the pump body 3001. The door split carriage 3040 is connected to the lever 3025 via the closed end of the lever link 3035C (FIG. 264) that fits over the carriage pin 3040A and the open end 3035B (FIG. 264) holds a pin 3026 that slides in a slotted rib 3025A (FIG. 264) on the lever 3025. The travel of the split carriage 3041 may be limited to accommodate the slide occluder openings 3200C, 3200D (best shown in FIG. 261). In such embodiments, the limited travel of the slide carriage 3041 may not create an optimal amount of mechanical advantage during rotation of the lever 3025 to allow the lever 3025 to engage the body pins 3011 and compress the infusion tube 3210 against the inlet and/or outlet valves 3101, 3111. One solution is to allow the lever 3025 to rotate through some portion of its full movement without moving the split carriage 3041. In one embodiment, the lever 3025 may be mounted rotatably to the door assembly 3021. Upon closing the door assembly 3021, the door assembly 3021 contacts the split carriage 3041 to push the split carriage 3041 into a recess included in the pump body 3001. The door assembly 3021 may be connected to the spilt carriage 3041 by a member. The member may be configured to pull the split carriage 3041 out of the recess when the lever 3025 is opened. Upon opening the lever 3025 at least one portion of the connecting member may be caused to move a pre-determined amount or distance before the connecting member pulls the split carriage 3041 out of the recess. In this embodiment, the connecting member may have several forms that are discussed in detail in the following paragraphs. In FIG. 287, the connecting member is a link 3035 that mounts on a post of the door split carriage 3040 and is connected to the lever 3025 via a slot 3025A. In FIG. 288, the connecting member comprises two hinged links 3036, 3037, that connect to the post 3040A on the door split carriage 3040 and is rotatably pinned to the lever 3025 at 3025G. Alternatively, the two hinged links 3036, 3037, could be replaced with a flexible cable, or stretchable member that attaches to door split carriage or lever 3025.

The lever 3025, split carriage 3041 and door assembly 3021 are designed to maintain occlusion of the infusion tube 3210 at all times during the door 3020 opening and closing processes. The infusion tube 3210 is occluded by pressing the door 3020 against the body 3001, before the slide occluder 3200 is moved by the split carriage 3041 during closing. In the opening process, the slide occluder 3200 is moved first to occlude the infusion tube 3210 before the door 3020 is disengaged from the body 3001 thus maintaining occlusion of the infusion tube 3210 as mentioned above.

Referring now specifically to FIG. 287, the slotted rib 3025A and lever link 3035 allow the lever 3025 to rotate several degrees and begin engaging the body pins 3011 with the latch hooks 3025C without moving the split carriage 3041 when closing the lever 3025. Upon opening, the slotted rib 3025A and lever link 3035 allow the lever 3025 to retract the split carriage 3041 and occlude the infusion tube 3201 before disengaging the body pins 3011 and releasing the infusion tube 3210 from the valves 3101, 3111. The lever link 3035 may mechanically connect the lever 3025 to the door split carriage 3041 such that the lever 3025 only applies a tension force on the lever link 3035. Limiting the force on the lever link 3035 to tension force removes the need to ensure the lever link 3035 is buckle resistant, allowing the lever link 3035 to be lighter and smaller.

The rotation of the lever 3025 toward the door 3020 and body 3001 compresses the infusion tube 3210 between the platen 3022 and the valves 3101, 3111 and plunger 3091, latches the door 3020 shut, and moves the slide occluder 3200 to an open position. The lever link 3035, the slotted rib 3025A, and the geometry of the latch hook 3025C assure that the infusion tube 3210 is occluded by at least one of the valves 3101, 3111 before the slide occluder 3200 is moved to the open position when the lever 3025 is closed. The lever link 3035, the slotted rib 3025A, and the geometry of the latch hook 3025C also assure that the slide occluder 3200 is moved into the occluding position before the infusion tube 3210 is unoccluded by the valves 3101, 3111 when the lever 3025 is opened. This sequence of occluding flow through the infusion tube 3210 with one element before releasing the second element assures that the infusion tube 3210 is never in a free-flow state during the loading of the infusion tube 3210 in the peristaltic pump 2990.

Alternatively, the door split carriage 3040 may be pulled out of the pump body 3001 by the lever 3025 that is connected to the door split carriage 3040 by two links 3036, 3037 as shown in FIG. 288. The first link 3036 fits over the split carriage pin 3040A and connects to the second link 3037 at hinge 3036A. The second link connects the first link 3036 to the lever 3025 at pivot point 3025G. The two links 3036, 3037 each have a flat 3036B, 3037B that limits the relative rotation of the links 3036, 3037 so that they never cross a center point and always fold toward each other in the same direction. In the pictured embodiment, the links 3036, 3037 can only fold so that their mutual pivot point 3036A moves away from the lever pivot 3025B as the lever 3025 closes. The two links 3036, 3037 allows the lever 3025 to rotate several degrees and begin engaging the body pins 3011 with the latch hooks 3025C and occlude the infusion tube 3210 against at least one of the valves 3101, 3111 without moving the split carriage 3041. Once the two links 3036, 3037 have folded closed, the rib 3025F contacts the door split carriage 3040. The rib 3025F pushes the split carriage 3041 into the pump body 3001 as the lever 3025 completes its rotation toward the door assembly 3021.

Upon opening the lever 3025, or rotating the lever 3025 away from the door assembly 3021, the two links 3036, 3037 unfold and only begin to retract the split carriage 3041 after an initial amount of lever 3025 rotation. During the second part of the lever 3025 rotation, the split carriage 3041 withdraws from the pump body 3001 and moves slide occluder 3200, which occludes the infusion tube 3210 before disengaging the body pins 3011 and releasing the infusion tube 3210 from the valves 3101, 3111. The infusion tube 3210 is unoccluded by the valves 3101, 3111, but is occluded by the slide occlude 3200 during the third portion of the lever 3025 rotation.

Alternatively, the two links 3036, 3037 could be replaced with a flexible cable or wire, which pulls the split carriage 3041 out of the pump body 3001. The flexible cable may be attached to the door split carriage 3040 and to a fixed point on the lever 3025. The split carriage 3041 is pushed into the pump body 3001 by the rib 3025F as the lever 3025 rotates toward the pump body 3001.

Figure 293:
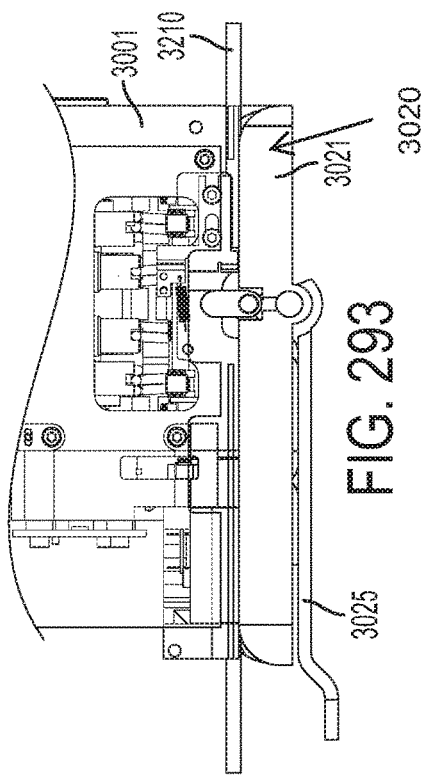

In FIG. 293, the door 3020 is closed and the lever 3025 latched. The split carriage 3041 has been slid through the door 3020 and into the body 3001. The movement of the split carriage 3041 moves the slide occluder 3200 into the pump body 3001, while the infusion tube 3210 is held in position. The movement of the slide occluder 3200 relative to the infusion tube 3210 moves the infusion tube 3210 into the wide end 3200C of the slide occluder 3200 allowing flow through the infusion tube 3210.

Figure 290:
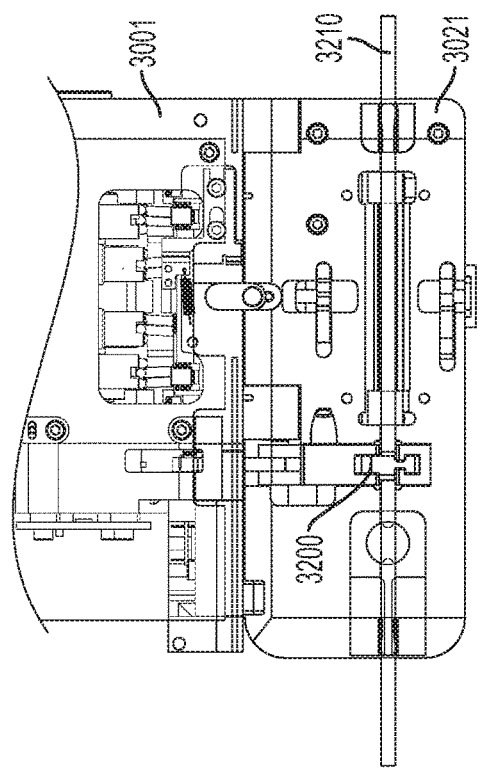
Figure 291:
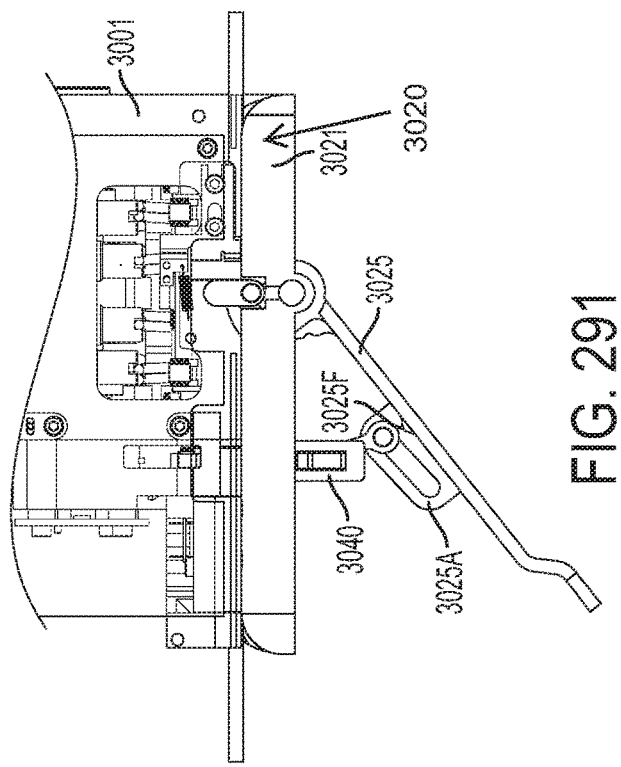

FIGS. 290-293 illustrate four steps of closing the door 3020. In FIG. 290, the door assembly 3021 is open and the infusion tube 3210 and slide occluder 3200 are installed. In FIG. 291, the door assembly 3021 is closed, the lever 3025 is open and the split carriage 3041 is fully retracted, so the infusion tube 3210 is occluded by the slide occluder 3200. In FIG. 292, the lever 3025 is partially rotated toward the body 3001 to a point where the split carriage 3041 has not moved and the slide occluder 3200 still occludes the infusion tube 3210, but the latch hooks 3025C have engaged the body pins 3011 and also occluded the infusion tube 3210 between the door assembly 3021 and at least one of the valves 3101, 3111. In FIG. 293, the lever 3025 is fully rotated toward the pump body 3001 or closed. In FIG. 293, the slide carriage 3041 is fully inserted into the pump body 3001, so that the infusion tube 3210 is no longer occluded by the slide occluder 3200 and the door 3021 is fully preloaded against the pump body 3001. At least one of the valves 3101, 3111 is still occluding the infusion tube 3210 as it is in FIG. 292. In some embodiments, actuation of the lever handle 3025 to latch the door assembly 3021 to the pump body 3001 may also actuate the inlet valve 3101 or the outlet valve 3111 (see FIG. 274) to occlude the infusion tube 3210 (e.g., by pulling the door assembly 3021 closer to the pump body and/or by the RTP 3500 (see FIG. 324) controlling the motor 3072 (see FIG. 324) to rotate the cam shaft 3080 (see FIG. 266) so that one or both of the inlet valve 3101 and the outlet valve 3111 are occluding the infusion tube 3210).

FIGS. 294-298 illustrate the elements of the door assembly 3021, pump body 3001, and lever 3025 that together latch the door 3020 closed, position the door assembly 3021 parallel to the face of the upper-housing 3010, and occlude the infusion tube 3210 between the platen 3022 and at least one of the valves 3101, 3111 and/or plunger 3091. The door assembly 3021 is positioned and pressed against the upper housing 3010 without placing a load on the hinge pin 3012 or requiring close tolerance on hinge pin 3012 and pivot holes 3020J, 3010F (FIG. 258).

As described above and pictured in FIG. 287 the two latch hooks 3025C engage the body pins 3011, which are mounted in the upper housing 3010 tabs 3010B, when the door assembly 3021 has been rotated to contact the upper housing 3010 and the lever 3025 is rotated toward the door 3020. The latch hooks 3025C have tapered openings to assure engagement for a broader range of initial positions between the door assembly 3021 (FIG. 257) and the upper housing 3010 (FIG. 258). The opening in the latch hook 3025C is shaped to pull the latch pin 3034 (FIG. 295) closer to the body pin 3011 as the lever 3025 (FIG. 296) is rotated. The latch pin 3034 (FIG. 295) is free to move within the door 3020 along slots 3020C as the latch pin 3034 moves toward the body pin 3011 (FIG. 294). The slot structure 3020C on the top of the door 3020 in FIG. 294 is repeated toward the bottom of the door 3020 in FIG. 295, where the second latch 3025C engages the pin 3034 (e.g., a latch pin 3034).

In FIG. 298, the movement of the latch pin 3034 toward the upper housing 3010 deflects the door spring 3032 that is supported by the door 3020 at each end 3032A of the door spring 3032. The deflection of the door spring 3032 generates a force that is applied to the door 3020 and directed toward the upper housing 3010 and the pump body 3001. As shown in FIG. 296, the door 3020 may include protrusions or standoffs 3020H that contact the face of the upper housing 3010 in three or more places distributed around the valves 3101, 3111 and plunger 3091 (FIG. 260). In some embodiments, the standoffs 3020H are configured so that the spring force is equally distributed to each standoff 3020H. In some embodiments, as shown for example in FIG. 296, four standoffs 3020H are located around the platen 3022, near where the valves 3101, 3111 (FIG. 260) contact the infusion tube 3210. The pivot holes 3020J in the door 3020 are slightly oversized for the hinge pin 3012 (FIG. 295), which allows the door 3020 to rest on the standoffs 3025H without being constrained by the hinge pin 3012.

FIG. 297 shows a cross-section through the latch pin 3034 and includes the latches 3025C fully engaging body pins 3011. In some embodiments, the body pins 3011 include a plain bearing 3011A to reduce wear and friction. The plain bearing 3011A may be a tube of hard material that can rotate on the body pin 3011 to reduce wear on the latch hooks 3025C. The latch pin 3034 passes through the lever pivot holes 3025B and is free to move in the slots 3020C and deflect the door spring 3032. In FIG. 297, the plunger 3091 is in a position to compress the infusion tube 3210 against the platen 3022. The force of the deflected door spring 3032 supplies the force to compress the infusion tube 3210 from the platen 3022 side, while the plunger bias member 3094 (FIG. 267) supplies the force on the plunger 3091 side.

FIG. 298 shows a cross section across the midline of the door spring 3032 and perpendicular to the latch pin 3034. The deflection of the door spring 3032 is evident between the latch pin 3034 and an edge 3020F at each end of the door spring 3032 and of the spring cutout 3020G. FIG. 296 presents an embodiment where the standoffs 3020H are located between and equal distant to the locations where the door spring 3032 contacts the door 3020.

As shown in the embodiment in FIGS. 299-300, one of the latch hooks 3025C may comprise detents 3025G, 3025J and a spring pin 3027 or ball to engage the detents 3025G, 3025J. FIG. 299 illustrates the lever 3025 fully closed against the door 3020. The latch hook 3025C includes a first detent 3025G that is engaged by a spring pin 3027. The spring pin 3027 is mounted in the door 3020 at such a position that it engages the first detent 3025G when lever 3025 is closed.

FIG. 300 illustrates the lever 3025 fully opened relative to door 3020 and the door split carriage 3040 retracted. The spring pin 3027 engages a second detent 3025J when the door 3020 is in the fully open position. In some embodiments, the detents 3025G, 3025J in the latch hooks 3025C may allow the lever 3025 to hold one or more positions relative to the door 3020.

FIG. 301 illustrates a detection lever 3150 displaced by the slide occluder 3200, when the door assembly 3021 and the lever 3025 (FIG. 265) are fully are closed. The detection lever 3150 rotates on a pin 3151 that is attached to the upper housing 3010 and swings through a slot 3045F in the body split carriage 3045. If a slide occluder 3200 is present in the split carriage 3041 when the door 3020 is closed, the slide occluder 3200 will deflect the detection lever 3150 upward toward the main PCB 3002. A sensor 3152 on the main PCB 3002 will detect the nearness of a magnet 3150A on the detection lever 3150. The detection lever 3150, magnet 3150A and sensor 3152 may be designed to only detect a specific slide occluder 3200 geometry. Other slide occluders 3200 or slide occluder 3200 shapes may not deflect the detection lever 3150 enough for the sensor 3152 to detect the magnet 3150A or cause the detection lever 3150 to contact the main PCB 3002 and prevent the full insertion of the split carriage 3041 and closing of the lever 3025. A controller may only allow operation when the sensor 3152 detects the displaced detection lever 3150 indicating that the appropriate slide occluder 3200 is present.

FIG. 302 illustrates a latch hook detection slide 3160 displaced by the latch hook 3025C, when the door assembly 3021 and the lever 3025 are fully closed. The latch hook detection slide 3160 may include one or more slots 3160A that guide it past screws or posts on mounted in the upper housing 3010. A spring 3164 returns latch hook detection slide 3160 to a non-displaced position, when the latch hook 3025C is not engaging the body pin 3011. The latch hook detection slide 3160 may include at least one magnet 3161 that is located so that a sensor 3163 mounted on the main PCB 3001 may detect its presence only when the detection slide 3160 is fully displaced. In some embodiments, the latch hook detection slide 3160 may include a second at least one magnet 3162 that is detected by the sensor 3163 only when the latch hook detection slide 3160 is fully retracted. A controller may only allow operation when the sensor 3163 detects the displaced latch hook detection slide 3160 indicating that the lever 3025 is fully closed.

Figure 303:
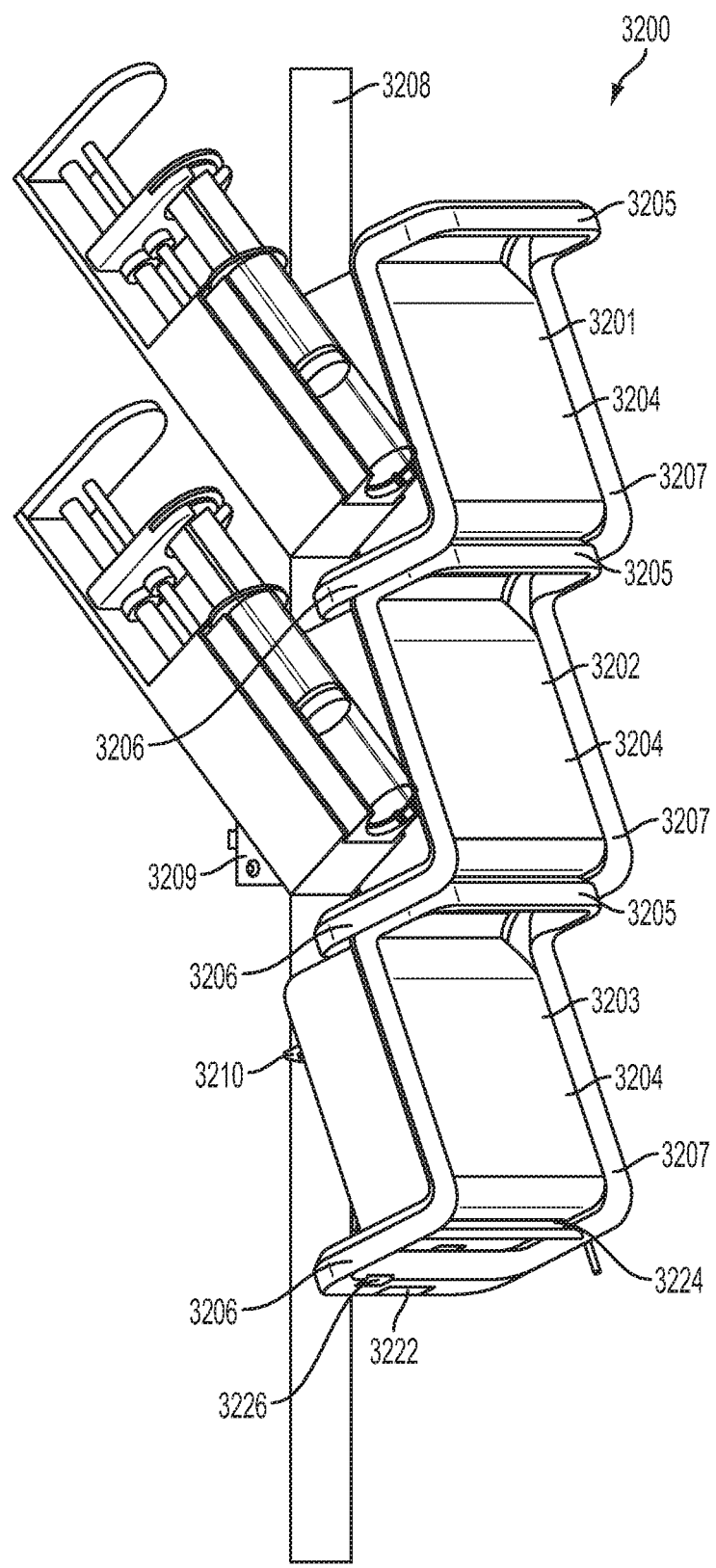

FIGS. 303-310 show various views related to a system 3200. FIG. 303 shows a system 3200 that includes several pumps 3201, 3202, and 3203. The pumps 3201, 3202, 3203 can be coupled together to form a group of pumps that are connectable to a pole 3208. The system 3200 includes two syringe pumps 3201, 3202 and a peristaltic pump 3203; however, other combinations of various medical devices may be employed.

Each of the pumps 3201, 3202, 3203 includes a touch screen 3204 which may be used to control the pumps 3201, 3202, 3203. One of the pumps' (e.g., 3201, 3202, 3203) touch screens 3204 may also be used to coordinate operation of all of the pumps 3201, 3202, 3203 and/or to control the one or more of the other pumps 3201, 3202, 3203.

The pumps 3201, 3202, and 3203 are daisy chained together such that they are in electrical communication with each other. Additionally or alternatively, the pumps 3201, 3202, and/or 3203 may share power with each other or among each other. For example, one of the pumps 3201, 3202, and/or 3203 may include an AC/DC converter that converts AC electrical power to DC power suitable to power the other pumps 3201, 3202, 3203.

Within the system 3200, the pumps 3201, 3202, and 3203 are stacked together using respective Z-frames 3207. Each of the Z-frames 3207 includes a lower portion 3206 and an upper portion 3205. A lower portion 3206 of one Z-frame 3207 (e.g., the lower portion 3206 of the pump 3201) can engage an upper portion 3205 of another Z-frame 3207 (e.g., the upper portion 3205 of the Z-frame 3207 of the pump 3202).

Figure 304:
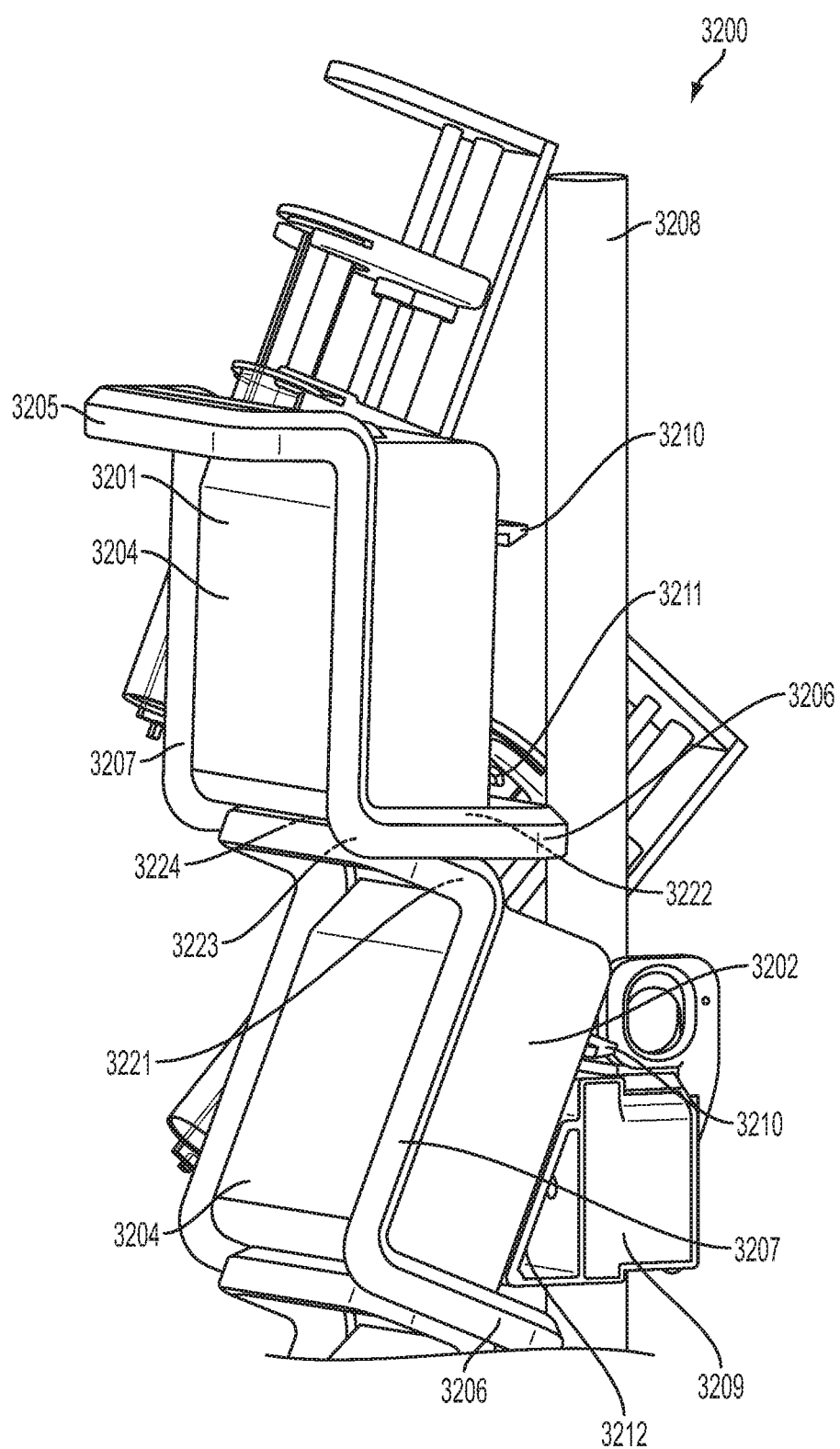

A clamp 3209 may be coupled to one of the pumps 3201, 3202, 3203 (e.g., the pump 3202 as shown in FIG. 304). That is, the clamp 3209 may be coupled to any one of the pumps 3201, 3202, and/or 3203. The clamp 3209 is attachable to the back of any one of the pumps 3201, 3202, and/or 3203. As is easily seen in FIG. 306, each of the pumps 3201, 3202, 3203 includes an upper attachment member 3210 and a lower attachment member 3211. A clamp adapter 3212 facilitates the attachment of the clamp 3209 to the pump 3202 via a respective pump's (e.g., 3201, 3202, or 3203) upper attachment member 3210 and lower attachment member 3211. In some embodiments, the clamp adapter 3212 may be integral with the clamp 3209.

FIG. 307 shows a close-up view of a portion of an interface of a clamp (i.e., the clamp adapter 3212) that is attachable to the pump 3202 (or to pumps 3201 or 3203) shown in FIGS. 304-306 in accordance with an embodiment of the present disclosure. The clamp adapter 3212 includes a hole 3213 in which a lower attachment member 3211 (see FIG. 306) may be attached. That is, the lower attachment member 3211, a curved hook-like protrusion, may be inserted into the hole 3213 and thereafter rotated to secure the lower attachment member 3211 therein.

As is easily seen in FIG. 308, the clamp adapter 3212 also includes a latch 3214. The latch 3214 is pivotally mounted to the clamp adapter 3212 via pivots 3216. The latch 3214 may be spring biased via springs 3218 that are coupled to the hooks 3220. The stop members 3219 prevent the latch 3214 from pivoting beyond a predetermined amount. After the hole 3213 is positioned on the lower attachment member 3211, the clamp adapter 3212 may be rotated to bring the latch 3214 towards the upper attachment member 3210 such that the latch 3214 is compressed down by the upper attachment member 3210 until the protrusion 3215 snaps into a complementary space of the upper attachment member 3210. The hooks 3220 help secure the clamp adapter 3212 to the pump 3202.

Each of the Z-frames 3207 for each of the pumps 3201, 3202, 3203 includes a recessed portion 3223 on its upper portion 3205 (see FIG. 306) and each pump 3201, 3202, 3203 includes a protrusion 3224 (see FIG. 309). A protrusion 3224 of one pumps (e.g., pumps 3201, 3202, or 3203) may engage a recessed portion 3223 of another Z-frame to enable the pumps 3201, 3202, 3203 to be stacked on top of each other. Each of the pumps 3201, 3202, 3203 includes a latch engagement member 3221 that allows another one of the pumps 3201, 3202, 3203 to be attached thereto via a latch 3222 (see FIG. 309). The latch 3222 may include a small spring loaded flange that can "snap" into the space formed under the latch engagement member 3221. The latch 3222 may be pivotally coupled to the lower portion 3206 of the Z-frame 3207.

As is seen in FIG. 304, the latch 3222 of the Z-frame of pump 3201 may be pulled to withdraw a portion of the latch 3222 out of the space under the latch engagement member 3221 of the pump 3202. Thereafter, the pump 3201 may be rotated to pull the protrusion 3224 of the pump 3201 out of the recessed portion 3223 of the Z-frame of pump 3202 such that the pump 3201 may be removed from the stack of pumps 3202, 3203 (see FIG. 305).

Each of the pumps 3201, 3202, 3203 includes a top connector 3225 (see FIG. 310) and a bottom connector 3226 (see FIG. 309). The connectors 3225 and 3226 allow the stacked pumps 3201, 3202, and 3203 to communication between each other and/or to provide power to each other. For example, if the battery of the middle pump 3202 (see FIG. 303) fails, then the top pump 3201 and/or the bottom pump 3203 may provide power to the middle pump 3202 as a reserve while one or more of the pumps 3201, 3202, 3203 is audibly alarming.

An example embodiment of the graphic user interface (hereafter GUI) 3300 is shown in FIG. 311. The GUI 3300 enables a user to modify the way that an agent may be infused by customizing various programming options. For purposes of example, the GUI 3300 detailed as follows uses a screen 3204 which is a touch screen as a means of interaction with a user. In other embodiments, the means of interaction with a user may be different. For instance, alternate embodiments may comprise user depressible buttons or rotatable dials, audible commands, etc. In other embodiments, the screen 3204 may be any electronic visual display such as a, liquid crystal display, L.E.D. display, plasma display, etc.

As detailed in the preceding paragraph, the GUI 3300 is displayed on the screen of the pumps 3203. All of the pumps 3201, 3202, 3203 may have their own individual screen 3204 as shown in FIGS. 303-305. In arrangements where one of the pumps 3201, 3202, 3203 is being used to control all of the pumps 3201, 3202, 3203, only the master pump may require a screen 3204. As shown, the pump is seated in a Z-frame 3207. As shown, the GUI 3300 may display a number of interface fields 3250. The interface fields 3250 may display various information about the pump or infusion status, the medication, etc. In some embodiments, the interface fields 3250 on the GUI 3300 may be touched, tapped, etc. to navigate to different menus, expand an interface field 3250, input data, and the like. The interface fields 3250 displayed on the GUI 3300 may change from menu to menu.

The GUI 3300 may also have a number of virtual buttons. In the non-limiting example embodiment in FIG. 311 the display has a virtual power button 3260, a virtual start button 3262, and a virtual stop button 3264. The virtual power button 3260 may turn the pump 3201, 3202, 3203 on or off. The virtual start button 3262 may start an infusion. The virtual stop button 3264 may pause or stop an infusion. The virtual buttons may be activated by a user's touch, tap, double tap, or the like. Different menus of the GUI 3300 may comprise other virtual buttons. The virtual buttons may be skeuomorphic to make their functions more immediately understandable or recognizable. For example, the virtual stop button 3264 may resemble a stop sign as shown in FIG. 305. In alternate embodiments, the names, shapes, functions, number, etc. of the virtual buttons may differ.

As shown in the example embodiment in FIG. 312, the interface fields 3250 of the GUI 3300 (see FIG. 311) may display a number of different programming parameter input fields. For the GUI 3300 to display the parameter input fields, a user may be required to navigate through one or a number of menus. Additionally, it may be necessary for the user to enter a password before the user may manipulate any of the parameter input fields.

In FIG. 312, a medication parameter input field 3302, in container drug amount parameter input field 3304, total volume in container parameter input field 3306, concentration parameter input field 3308, dose parameter input field 3310, volume flow rate (hereafter abbreviated as rate) parameter input field 3312, volume to be infused (hereafter VTBI) parameter input field 3314, and time parameter input field 3316 are displayed. The parameters, number of parameters, names of the parameters, etc. may differ in alternate embodiments. In the example embodiment, the parameter input fields are graphically displayed boxes which are substantially rectangular with rounded corners. In other embodiments, the shape and size of the parameter input fields may differ.

In the example embodiment, the GUI 3300 is designed to be intuitive and flexible. A user may choose to populate a combination of parameter input fields which are simplest or most convenient for the user. In some embodiments, the parameter input fields left vacant by the user may be calculated automatically and displayed by the GUI 3300 as long as the vacant fields do not operate independent of populated parameter input fields and enough information can be gleaned from the populated fields to calculate the vacant field or fields. Throughout FIGS. 312-316 fields dependent upon on another are tied together by curved double-tipped arrows.

The medication parameter input field 3302 may be the parameter input field in which a user sets the type of infusate agent to be infused. In the example embodiment, the medication parameter input field 3302 has been populated and the infusate agent has been defined as "0.9% NORMAL SALINE". As shown, after the specific infusate has been set, the GUI 3300 may populate the medication parameter input field 3302 by displaying the name of the specific infusate in the medication parameter input field 3302.

To set the specific infusate agent to be infused, a user may touch the medication parameter input field 3302 on the GUI 3300. In some embodiments, this may cull up a list of different possible infusates. The user may browse through the list until the desired infusate is located. In other embodiments, touching the in medication parameter input field 3302 may cull up a virtual keyboard. The user may then type the correct infusate on the virtual keyboard. In some embodiments, the user may only need to type only a few letters of the infusate on the virtual keyboard before the GUI 3300 displays a number of suggestions. For example, after typing "NORE" the GUI 3300 may suggest "NOREPINEPHRINE". After locating the correct infusate, the user may be required to perform an action such as, but not limited to, tapping, double tapping, or touching and dragging the infusate. After the required action has been completed by the user, the infusate may be displayed by the GUI 3300 in the medication parameter input field 3302. For another detailed description of another example means of infusate selection see FIG. 322.

In the example embodiment in FIG. 312, the parameter input fields have been arranged by a user to perform a volume based infusion (for instance mL, mL/hr, etc.). Consequentially, the in container drug amount parameter input field 3304 and total volume in container parameter input field 3306 have been left unpopulated. The concentration parameter input field 3308 and dose parameter input field 3310 have also been left unpopulated. In some embodiments, the in container drug amount parameter input field 3304, total volume in container parameter input field 3306, concentration parameter input field 3308, and dose parameter input field 3310 may be locked, grayed out, or not displayed on the GUI 3300 when such an infusion has been selected. The in container drug amount parameter input field 3304, total volume in container parameter input field 3306, concentration parameter input field 3308, and dose parameter input field 3310 will be further elaborated upon in subsequent paragraphs.

When the GUI 3300 is being used to program a volume base infusion, the rate parameter input field 3312, VTBI parameter input field 3314, and time parameter input field 3316 do not operate independent of one another. A user may only be required to define any two of the rate parameter input field 3312, VTBI parameter input field 3314, and time parameter input field 3316. The two parameters defined by a user may be the most convenient parameters for a user to set. The parameter left vacant by the user may be calculated automatically and displayed by the GUI 3300. For instance, if a user populates the rate parameter input field 3312 with a value of 125 mL/hr (as shown), and populates the VTBI parameter input field 3314 with a value of 1000 mL (as shown) the time parameter input field 3316 value may be calculated by dividing the value in the VTBI parameter input field 3314 by the value in the rate parameter input field 3312. In the example embodiment shown in FIG. 312, the quotient of the above calculation, 8 hrs and 0 min, is correctly populated by the GUI 3300 into the time parameter input field 3316.

For a user to populate the rate parameter input field 3312, VTBI parameter input field 3314, and time parameter input field 3316 the user may touch or tap the desired parameter input field on the GUI 3300. In some embodiments, this may cull up a number pad with a range or number, such as 0-9 displayed as individual selectable virtual buttons. A user may be required to input the parameter by individually tapping, double tapping, touching and dragging, etc. the desired numbers. Once the desired value has been input by a user, a user may be required to tap, double tap, etc. a virtual "confirm", "enter", etc. button to populate the field. For another detailed description of another example way of defining numerical values see FIG. 322.

FIG. 313 shows a scenario in which the infusion parameters being programmed are not those of a volume based infusion. In FIG. 313, the infusion profile is that of a continuous volume/time dose rate. In the example embodiment shown in FIG. 313, all of the parameter input fields have been populated. As shown, the medication parameter input field 3302 on the GUI 3300 has been populated with "HEPARIN" as the defined infusate. As shown, the in container drug amount parameter input field 3304, total volume in container input field 3306, and concentration parameter input field 3308 are populated in FIG. 313.

Additionally, since a volume/time infusion is being programmed the dose parameter input field 3310 shown in FIG. 312 has been replaced with a dose rate parameter input field 3318.

The in container drug amount parameter input field 3304 is a two part field in the example embodiment shown in FIG. 313. In the example embodiment in FIG. 313 the left field of the in container drug amount parameter input field 3304 is a field which may be populated with a numeric value. The numeric value may defined by the user in the same manner as a user may define values in the rate parameter input field 3312, VTBI parameter input field 3314, and time parameter input field 3316. In the example embodiment shown in FIG. 313, the numeric value displayed by the GUI 3300 in the in left field of the in container drug amount parameter input field 3304 is "25,000".

The parameter defined by the right field of the in container drug amount parameter input field 3304 is the unit of measure. To define the right of the in container drug amount parameter input field 3304, a user may touch the in container drug amount parameter input field 3304 on the GUI 3300. In some embodiments, this may cull up a list of acceptable possible units of measure. In such embodiments, the desired unit of measure may be defined by a user in the same manner as a user may define the correct infusate. In other embodiments, touching the in container drug amount parameter input field 3304 may cull up a virtual keyboard. The user may then type the correct unit of measure on the virtual keyboard. In some embodiments the user may be required to tap, double tap, etc. a virtual "confirm", "enter", etc. button to populate the left field of the in container drug amount parameter input field 3304.

In some embodiments, including the embodiment shown in FIG. 313, the right field of the in container drug amount parameter input field 3304 may have one or more acceptable values with may be dependent on the parameter input into one or more other parameter input fields. In the example embodiment, the meaning of the unit of measure "UNITS" may differ depending on the infusate set in the medication parameter input field. The GUI 3300 may also automatically convert the value and unit of measure in respectively the left field and right field of the in container drug amount parameter input field 3304 to a metric equivalent if a user inputs a non-metric unit of measure in the right field of the in container drug amount parameter input field 3304.

The total volume in container parameter input field 3306 may be populated by a numeric value which defines the total volume of a container. In some embodiments, the GUI 3300 may automatically populate the total volume in container parameter input field 3306 based on data generated by one or more sensors. In other embodiments, the total volume in container parameter input field 3306 may be manually input by a user. The numeric value may defined by the user in the same manner as a user may define values in the rate parameter input field 3312, VTBI parameter input field 3314, and time parameter input field 3316. In the example embodiment shown in FIG. 313 the total volume in container parameter input field 3306 has been populated with the value "250" mL. The total volume in container parameter input field 3306 may be restricted to a unit of measure such as mL as shown.

The concentration parameter input field 3308 is a two part field similar to the in container drug amount parameter input field 3304. In the example embodiment in FIG. 313 the left field of the concentration parameter input field 3308 is a field which may be populated with a numeric value. The numeric value may defined by the user in the same manner as a user may define values in the rate parameter input field 3312, VTBI parameter input field 3314, and time parameter input field 3316. In the example embodiment shown in FIG. 313, the numeric value displayed by the GUI 3300 in the in left field of the concentration parameter input field 3308 is "100".

The parameter defined by the right field of the concentration parameter input field 3308 is a unit of measure/volume. To define the right field of the concentration parameter input field 3308, a user may touch the concentration parameter input field 3308 on the GUI 3300. In some embodiments, this may cull up a list of acceptable possible units of measure. In such embodiments, the desired unit of measure may be defined by a user in the same manner as a user may define the correct infusate. In other embodiments, touching the concentration parameter input field 3308 may cull up a virtual keyboard. The user may then type the correct unit of measure on the virtual keyboard. In some embodiments the user may be required to tap, double tap, etc. a virtual "confirm", "enter", etc. button to store the selection and move on to a list of acceptable volume measurements. The desired volume measurement may be defined by a user in the same manner as a user may define the correct infusate. In the example embodiment shown in FIG. 313 the right field of the concentration parameter input field 3308 is populated with the unit of measure/volume "UNITS/mL".

The in container drug amount parameter input field 3304, total volume in container input field 3306, and concentration parameter input field 3308 are not independent of one another. As such, a user may only be required to define any two of the in container drug amount parameter input field 3304, total volume in container input field 3306, and concentration parameter input field 3308. For instance, if a user were to populate the concentration parameter input field 3308 and the total volume in container parameter input field 3306, the in container drug amount parameter input field may be automatically calculated and populated on the GUI 3300.

Since the GUI 3300 in FIG. 313 is being programmed for a continuous volume/time dose, the dose rate parameter input field 3318 has been populated. The user may define the rate at which the infusate is infused by populating the dose rate parameter input field 3318. In the example embodiment in FIG. 313, the dose rate parameter input field 3318 is a two part field similar to the in container drug amount parameter input field 3304 and concentration parameter input field 3308 described above. A numeric value may defined in the left field of the dose rate parameter input field 3318 by the user in the same manner as a user may define values in the rate parameter input field 3312. In the example embodiment in FIG. 313, the left field of the dose rate parameter input field 3318 has been populated with the value "1000".

The right field of the dose rate parameter input field 3318 may define a unit of measure/time. To define the right field of the dose rate parameter input field 3318, a user may touch the dose rate parameter input field 3318 on the GUI 3300. In some embodiments, this may cull up a list of acceptable possible units of measure. In such embodiments, the desired unit of measure may be defined by a user in the same manner as a user may define the correct infusate. In other embodiments, touching the dose rate parameter input field 3304 may cull up a virtual keyboard. The user may then type the correct unit of measure on the virtual keyboard. In some embodiments the user may be required to tap, double tap, etc. a virtual "confirm", "enter", etc. button to store the selection and move on to a list of acceptable time measurements. The desired time measurement may be defined by a user in the same manner as a user may define the correct infusate. In the example embodiment shown in FIG. 313 the right field of the dose rate parameter input field 3318 is populated with the unit of measure/time "UNITS/hr".

In the example embodiment, the dose rate parameter input field 3318 and the rate parameter input field 3312 are not independent of one another. After a user populates the dose rate parameter input field 3318 or the rate parameter input field 3312, the parameter input field left vacant by the user may be calculated automatically and displayed by the GUI 3300 as long as the concentration parameter input field 3308 has been defined. In the example embodiment shown in FIG. 313, the rate parameter input field 3312 has been populated with an infusate flow rate of "10 mL/hr". The dose rate parameter input field 3318 has been populated with "1000" "UNITS/hr".

In the example embodiment shown in FIG. 313 the VTBI parameter input field 3314 and time parameter input field 3316 have also been populated. The VTBI parameter input field 3314 and time parameter input field 3316 may be populated by a user in the same manner described in relation to FIG. 306. When the GUI 3300 is being programmed to a continuous volume/time dose rate infusion, the VTBI parameter input field 3314 and the time parameter input field 3316 are dependent on one another. A user may only need to populate one of the VTBI parameter input field 3314 or the time parameter input field 3316. The field left vacant by the user may be calculated automatically and displayed on the GUI 3300.

FIG. 314 shows a scenario in which the infusion parameters being programmed are those of a drug amount based infusion herein referred to as an intermittent infusion. In the example embodiment shown in FIG. 314, all of the parameter input fields have been populated. As shown, the medication parameter input field 3302 on the GUI 3300 has been populated with the antiboitic "VANCOMYCIN" as the defined infusate.

As shown, the in container drug amount parameter input field 3304, total volume in container input field 3306, and concentration parameter input field 3308 are laid out the same as in FIG. 314. In the example embodiment in FIG. 308, the left field of the in container drug amount parameter input field 3304 has been populated with "1". The right field of the in container drug amount parameter input field 3304 has been populated with "g". Thus the total amount of Vancomycin in the container has been defined as one gram. The total volume in container parameter input field 3306 has been populated with "250" ml. The left field of the concentration parameter input field 3308 has been populated with "4.0". The right field of the concentration parameter input field has been populated with "mg/mL".

As mentioned in relation to other possible types of infusions which a user may be capable of programming through the GUI 3300, the in container drug amount parameter input field 3304, total volume in container input field 3306, and concentration parameter input field 3308 are dependent upon each other. As above, this is indicated by the curved double arrows connecting the parameter input field names. By populating any two of these parameters, the third parameter may be automatically calculated and displayed on the correct parameter input field on the GUI 3300.

In the example embodiment in FIG. 314, the dose parameter input field 3310 has been populated. As shown, the dose parameter input field 3310 comprises a right and left field. A numeric value may defined in the right field of the dose parameter input field 3310 by the user in the same manner as a user may define values for other parameter input fields which define numeric values. In the example embodiment in FIG. 314, the left field of the dose parameter input field 3310 has been populated with the value "1000".

The right field of the dose parameter input field 3310 may define a unit of mass measurement. To define the right field of the dose parameter input field 3310, a user may touch the dose parameter input field 3310 on the GUI 3300. In some embodiments, this may cull up a list of acceptable possible units of measure. In such embodiments, the desired unit of measure may be defined by a user in the same manner as a user may define the correct infusate. In other embodiments, touching the dose parameter input field 3310 may cull up a virtual keyboard. The user may then type the correct unit of measure on the virtual keyboard. In some embodiments the user may be required to tap, double tap, slide, etc. a virtual "confirm", "enter", etc. button to store the selection and move on to a list of acceptable mass measurements. The desired mass measurement may be defined by a user in the same manner as a user may define the correct infusate. In the example embodiment shown in FIG. 314 the right field of the dose parameter input field 3310 is populated with the unit of measurement "mg".

As shown, the rate parameter input field 3312, VTBI parameter input field 3314, and the time parameter input field 3316 have been populated. As shown, the rate parameter input field 3312 has been populated with "125" mL/hr. The VTBI parameter input field 3314 has been defined as "250" mL. The time parameter input field 3316 has been defined as "2" hrs "00" min.

The user may not need to individually define each of the dose parameter input field 3310, rate parameter input field 3312, VTBI parameter input field 3314, and the time parameter input field 3316. As indicated by the curved double arrows, the dose parameter input field 3310 and the VTBI parameter input field 3314 are dependent upon each other. Input of one value may allow the other value to be automatically calculated and displayed by the GUI 3300. The rate parameter input field 3312 and the time parameter input field 3316 are also dependent upon each other. The user may need to only define one value and then allow the non-defined value to be automatically calculated and displayed on the GUI 3300. In some embodiments, the rate parameter input field 3312, VTBI parameter input field 3314, and the time parameter input field 3316 may be locked on the GUI 3300 until the in container drug amount parameter input field 3304, total volume in container parameter input field 3306 and concentration parameter input field 3308 have been defined. These fields may be locked because automatic calculation of the rate parameter input field 3312, VTBI parameter input field 3314, and the time parameter input field 3316 is dependent upon values in the in container drug amount parameter input field 3304, total volume in container parameter input field 3306 and concentration parameter input field 3308.

In scenarios where an infusate may require a body weight based dosage, a weight parameter input field 3320 may also be displayed on the GUI 3300. The example GUI 3300 shown on FIG. 315 has been arranged such that a user may program a body weight based dosage. The parameter input fields may be defined by a user as detailed in the above discussion. In the example embodiment, the infusate in the medication parameter input field 3302 has been defined as "DOPAMINE". The left field of the in container drug amount parameter input field 3304 has been defined as "400". The right field of the in container drug amount parameter input field 3304 has been defined as "mg". The total volume in container parameter input field 3306 has been defined as "250" ml. The left field of the concentration parameter input field 3308 has been defined as "1.6". The right field of the concentration parameter input field 3308 has been defined as "mg/mL". The weight parameter input field 3320 has been defined as "90" kg. The left field of the dose rater parameter input field 3318 has been defined as "5.0". The right field of the dose rate parameter input field 3318 has been defined as "mcg/kg/min". The rate parameter input field 3312 has been defined as "16.9" mL/hr. The VTBI parameter input field 3314 has been defined as "250" mL. The time parameter input field 3316 has been defined as "14" hrs "48" min.

To define the weight parameter input field 3320, a user may touch or tap the weight parameter input field 3320 on the GUI 3300. In some embodiments, this may cull up a number pad with a range of numbers, such as 0-9 displayed as individual selectable virtual buttons. A user may be required to input the parameter by individually tapping, double tapping, touching and dragging, etc. the desired numbers. Once the desired value has been input by a user, a user may be required to tap, double tap, etc. a virtual "confirm", "enter", etc. button to populate the field.

As indicated by the curved double arrows, some parameter input fields displayed on the GUI 3300 may be dependent upon each other. As in previous examples, the in container drug amount parameter input field 3304, total volume in container parameter input field 3306, and concentration parameter input field 3308 may be dependent upon each other. In FIG. 315, the weight parameter input field 3320, dose rater parameter input field 3318, rate parameter input field 3312, VTBI parameter input field 3314, and the time parameter input field 3316 are all dependent upon each other. When enough information has been defined by the user in these parameter input fields, the parameter input fields not populated by the user may be automatically calculated and displayed on the GUI 3300.

In some embodiments, a user may be required to define a specific parameter input field even if enough information has been defined to automatically calculate the field. This may improve safety of use by presenting more opportunities for user input errors to be caught. If a value entered by a user is not compatible with already defined values, the GUI 3300 may display an alert or alarm message soliciting the user to double check values that the user has entered.

In some scenarios the delivery of infusate may be informed by the body surface area (BSA) of a patient. In FIG. 316, the GUI 3300 has been set up for a body surface area based infusion. As shown, a BSA parameter input field 3322 may be displayed on the GUI 3300. The parameter input fields may be defined by a user as detailed in the above discussion. In the example embodiment, the infusate in the medication parameter input field 3302 has been defined as "FLUOROURACIL". The left field of the in container drug amount parameter input field 3304 has been defined as "1700". The right field of the in container drug amount parameter input field 3304 has been defined as "mg". The total volume in container parameter input field 3306 has been defined as "500" ml. The left field of the concentration parameter input field 3308 has been defined as "3.4". The right field of the concentration parameter input field 3308 has been defined as "mg/mL". The BSA parameter input field 3320 has been defined as "1.7" m$^2$. The left field of the dose rate parameter input field 3318 has been defined as "1000". The right field of the dose rate parameter input field 3318 has been defined as "mg/m2/day". The rate parameter input field 3312 has been defined as "20.8" mL/hr. The VTBI parameter input field 3314 has been defined as "500" mL. The time parameter input field 3316 has been defined as "24" hrs "00" min. The dependent parameter input fields are the same as in FIG. 309 with the exception that the BSA parameter input field 3322 has taken the place of the weight parameter input field 3320.

To populate the BSA parameter input field 3322, the user may touch or tap the BSA parameter input field 3322 on the GUI 3300. In some embodiments, this may cull up a number pad with a range of numbers, such as 0-9 displayed as individual selectable virtual buttons. In some embodiments, the number pad and any of the number pads detailed above may also feature symbols such as a decimal point. A user may be required to input the parameter by individually tapping, double tapping, touching and dragging, etc. the desired numbers. Once the desired value has been input by a user, a user may be required to tap, double tap, etc. a virtual "confirm", "enter", etc. button to populate the field.

In some embodiments, a patient's BSA may be automatically calculated and displayed on the GUI 3300. In such embodiments, the GUI 3300 may query the user for information about the patient when a user touches, taps, etc. the BSA parameter input field 3322. For example, the user may be asked to define a patient's height and body weight. After the user defines these values they may be run through a suitable formula to find the patient's BSA. The calculated BSA may then be used to populate the BSA parameter input field 3322 on the GUI 3300.

In operation, the values displayed in the parameter input fields may change throughout the course of a programmed infusion to reflect the current state of the infusion. For example, as the infusate is infused to a patient, the values displayed by the GUI 3300 in the in container drug amount parameter input field 3304 and total volume in container parameter input field 3306 may decline to reflect the volume of the remaining contents of the container. Additionally, the values in the VTBI parameter input field 3314 and time parameter input field 3316 may also decline as infusate is infused to the patient.

FIG. 317 is an example rate over time graph detailing the one behavioral configuration of a pump 3201, 3202, 3203 (see FIG. 303) over the course of an infusion. The graph in FIG. 317 details an example behavioral configuration of a pump 3201, 3202, 3203 where the infusion is a continuous infusion (an infusion with a dose rate). As shown, the graph in FIG. 317 begins at the initiation of infusion. As shown, the infusion is administered at a constant rate for a period of time. As the infusion progresses, the amount of infusate remaining is depleted. When the amount of infusate remaining reaches a pre-determined threshold, an "INFUSION NEAR END ALERT" may be triggered. The "INFUSION NEAR END ALERT" may be in the form of a message on the GUI 3300 and may be accompanied by flashing lights, and audible noises such as a series of beeps. The "INFUSION NEAR END ALERT" allows time for the care giver and pharmacy to prepare materials to continue the infusion if necessary. As shown, the infusion rate may not change over the "INFUSION NEAR END ALERT TIME".

When the pump 3201, 3202, 3203 (see FIG. 303) has infused the VTBI to a patient a "VTBI ZERO ALERT" may be triggered. The "VTBI ZERO ALERT" may be in the form of a message on the GUI 3300 and may be accompanied by flashing lights and audible noises such as beeps. As shown, the "VTBI ZERO ALERT" causes the pump to switch to a keep-vein-open (hereafter KVO) rate until a new infusate container may be put in place. The KVO rate is a low infusion rate (for example 5-25 mL/hr). The rate is set to keep the infusion site patent until a new infusion may be started. The KVO rate is configurable by the group (elaborated upon later) or medication and can be modified on the pump 3201, 3202, 3203. The KVO rate is not allowed to exceed the continuous infusion rate. When the KVO rate can no longer be sustained and air reaches the pumping channel an "AIR-IN-LINE ALERT" may be triggered. When the "AIR-IN-LINE-ALERT" is triggered, all infusion may stop. The "AIR-IN-LINE ALERT" may be in the form of a message on the GUI 3300 and may be accompanied by flashing lights and audible noises such as beeps.

FIG. 318 shows another example rate over time graph detailing one behavioral configuration of a pump 3201, 3202, 3203 (see FIG. 303) over the course of an infusion. The graph in FIG. 318 details an example behavioral configuration of a pump 3201, 3202, 3203 where the infusion is a continuous infusion (an infusion with a dose rate). The alerts in the graph shown in FIG. 318 are the same as the alerts shown in the graph in FIG. 317. The conditions which propagate the alerts are also the same. The rate, however, remains constant throughout the entire graph until the "AIR-IN-LINE ALERT" is triggered and the infusion is stopped. Configuring the pump to continue infusion at a constant rate may be desirable in situations where the infusate is a drug with a short half-life. By continuing infusion at a constant rate, it is ensured that the blood plasma concentration of the drug remains at therapeutically effective levels.

The pump 3201, 3202, 3203 (see FIG. 303) may also be used to deliver a primary or secondary intermittent infusion. During an intermittent infusion, an amount of a drug (dose) is administered to a patient as opposed to a continuous infusion where the drug is given at a specified dose rate (amount/time). An intermittent infusion is also delivered over a defined period of time, however, the time period and dose are independent of one another. The previously described FIG. 313 shows a setup of the GUI 3300 for a continuous infusion. The previously described FIG. 314 shows a setup of the GUI 3300 for an intermittent infusion.

FIG. 319 is an example rate over time graph detailing the one behavioral configuration of a pump 3201, 3202, 3203 (see FIG. 303) over the course of an intermittent infusion. As shown, the intermittent infusion is given at a constant rate until all infusate programmed for the intermittent infusion has been depleted. In the example behavioral configuration, the pump 3201, 3202, 3203 has been programmed to issue a "VTBI ZERO ALERT" and stop the infusion when all the infusate has been dispensed. In this configuration, the user may be required to manually clear the alert before another infusion may be started or resumed.

Other configurations may cause a pump 3201, 3202, 3203 (see FIG. 303) to behave differently. For example, in scenarios where the intermittent infusion is a secondary infusion, the pump 3201, 3202, 3203 may be configured to communicate with its companion pumps 3201, 3202, 3203 and automatically switch back to the primary infusion after issuing a notification that the secondary intermittent infusion has been completed. In alternate configurations, the pump may be configured issue a "VTBI ZERO ALERT" and drop the infusion rate to a KVO rate after completing the intermittent infusion. In such configurations, the user may be required to manually clear the alert before a primary infusion is resumed.

A bolus may also be delivered as a primary intermittent infusion when it may be necessary or desirable to achieve a higher blood plasma drug concentration or manifest a more immediate therapeutic effect. In such cases, the bolus may be delivered by the pump 3201, 3202, 3203 (see FIG. 303)

executing the primary infusion. The bolus may be delivered from the same container which the primary infusion is being delivery from. A bolus may be performed at any point during an infusion providing there is enough infusate to deliver the bolus. Any volume delivered via a bolus to a patient is included in the value displayed by the VTBI parameter input field 3314 of the primary infusion.

Depending on the infusate, a user may be forbidden from performing a bolus. The dosage of a bolus may be pre-set depending on the specific infusate being used. Additionally, the period of time over which the bolus occurs may be pre-defined depending on the infusate being used. In some embodiments, a user may be capable of adjusting these pre-sets by adjusting various setting on the GUI 3300. In some situations, such as those where the drug being infused has a long half-life (vancomycin, teicoplanin, etc.), a bolus may be given as a loading dose to more quickly reach a therapeutically effective blood plasma drug concentration.

FIG. 320 shows another rate over time graph in which the flow rate of the infusate has been titrated to "ramp" the patient up on the infusate. Titration is often used with drugs which register a fast therapeutic effect, but have a short half life (such as norepinephrine). When titrating, the user may adjust the delivery rate of the infusate until the desired therapeutic effect is manifested. Every adjustment may be checked against a series of limits defined for the specific infusate being administered to the patient. If an infusion is changed by more than a predefined percentage, an alert may be issued. In the exemplary graph shown in FIG. 320, the rate has been up-titrated once. If necessary, the rate may be up-titrated more than one time. Additionally, in cases where titration is being used to "wean" a patient off of a drug, the rate may be down-titrated any suitable number of times.

FIG. 321 is another rate over time graph in which the infusion has been configured as a multi-step infusion. A multi-step infusion may be programmed in a number of different steps. Each step may be defined by a VTBI, time, and a dose rate. Multi-step infusions may be useful for certain types of infusates such as those used for parenteral nutrition applications. In the example graph shown in FIG. 321, the infusion has been configured as a five step infusion. The first step infuses a "VTBI 1" for a length of time, "Time 1", at a constant rate, "Rate 1". When the time interval for the first step has elapsed, the pump moves on to the second step of the multi-step infusion. The second step infuses a "VTBI 2" for a length of time, "Time 2", at a constant rate, "Rate 2". As shown, "Rate 2" is higher than "Rate 1". When the time interval for the second step has elapsed, the pump moves on to the third step of the multi-step infusion. The third step infuses a "VTBI 3" for a length of time, "Time 3", at a constant rate, "Rate 3". As shown "Rate 3" is the highest rate of any steps in the multi-step infusion. "Time 3" is also the longest duration of any step of the multi-step infusion. When the time interval for the third step has elapsed, the pump move on to the fourth step of the multi-step infusion. The fourth step infuses a "VTBI 4" for a length of time, "Time 4", at a constant rate, "Rate 4". As shown, "Rate 4" has been down-titrated from "Rate 3". "Rate 4" is approximately the same as "Rate 2". When the time interval for the fourth step of the multi-step infusion has elapsed, the pump move on to the fifth step. The fifth step infuses a "VTBI 5" for a length of time, "Time 5", at a constant rate, "Rate 5". As shown, "Rate 5" has been down-titrated from "Rate 4" and is approximately the same as "Rate 1".

The "INFUSION NEAR END ALERT" is triggered during the fourth step of the example infusion shown in FIG. 321. At the end of the fifth and final step of the multi-step infusion, the "VTBI ZERO ALERT" is triggered. In the example configuration shown in the graph in FIG. 321, the rate is dropped to a KVO rate after the multi-step infusion has been concluded and the "VTBI ZERO ALERT" has been issued. Other configurations may differ.

Each rate change in a multi-step infusion may be handled in a variety of different ways. In some configurations, the pump 3201, 3202, 3203 (see FIG. 303) may display a notification and automatically adjust the rate to move on to the next step. In other configurations, the pump 3201, 3202, 3203 may issue an alert before changing the rate and wait for confirmation from the user before adjusting the rate and moving on to the next step. In such configurations, the pump 3201, 3202, 3203 may stop the infusion or drop to a KVO rate until user confirmation has been received.

In some embodiments, the user may be capable of pre-programming infusions. The user may pre-program an infusion to automatically being after a fixed interval of time has elapsed (e.g. 2 hours). The infusion may also be programmed to automatically being at a specific time of day (e.g. 12:30 pm). In some embodiments, the user may be capable of programming the pump 3201, 3202, 3203 (see FIG. 303) to alert the user with a callback function when it is time to being the pre-programmed infusion. The user may need to confirm the start of the pre-programmed infusion. The callback function may be a series of audible beeps, flashing lights, or the like.

In arrangements where there are more than one pump 3201, 3202, 3203 (see FIG. 303), the user may be able to program a relay infusion. The relay infusion may be programmed such that after a first pump 3201, 3202, 3203 has completed its infusion, a second pump 3201, 3202, 3203 may automatically being a second infusion and so on. The user may also program a relay infusion such that the user is alerted via the callback function before the relay occurs. In such a programmed arrangement, the relay infusion may not being until confirmation from a user has been received. A pump 3201, 3202, 3203 may continue at a KVO rate until user confirmation has been received.

FIG. 322 shows an example block diagram of a "Drug Administration Library". In the upper right hand corner there is a box which is substantially rectangular, though its edges are rounded. The box is associated with the name "General Settings". The "General Settings" may include settings which would be common to all devices in a facility such as, site name (e.g. XZY Hospital), language, common passwords, and the like.

In FIG. 322, the "Drug Administration Library" has two boxes which are associated with the names "Group Settings (ICU)" and "Group Settings". These boxes form the headings for their own columns. These boxes may be used to define a group within a facility (e.g. pediatric intensive care unit, emergency room, sub-acute care, etc.) in which the device is stationed. Groups may also be areas outside a parent facility, for example, a patient's home or an inter-hospital transport such as an ambulance. Each group may be used to set specific settings for various groups within a facility (weight, titration limits, etc.). These groups may alternatively be defined in other manners. For example, the groups may be defined by user training level. The group may be defined by a prior designated individual or any of a number of prior designated individuals and changed if the associated patient or device is moved from one specific group within a facility to another.

In the example embodiment, the left column is "Group Settings (ICU)" which indicates that the peristaltic pump 2990 is stationed in the intensive care unit of the facility. The right column is "Group Settings" and has not been further defined. In some embodiments, this column may be used to designate a sub group, for example operator training level. As indicated by lines extending to the box off to the left of the block diagram from the "Group settings (ICU)" and "Group Settings" columns, the settings for these groups may include a preset number of default settings.

The group settings may include limits on patient weight, limits on patient BSA, air alarm sensitivity, occlusion sensitivity, default KVO rates, VTBI limits, etc. The group settings may also include parameters such as whether or not a review of a programmed infusion is necessary for high risk infusates, whether the user must identify themselves before initiating an infusion, whether the user must enter a text comment after a limit has been overridden, etc. A user may also define the defaults for various attributes like screen brightness, or speaker volume. In some embodiments, a user may be capable of programming the screen to automatically adjust screen brightness in relation to one or more conditions such as but not limited to time of day.

As also shown to the left of the block diagram in FIG. 322, each facility may have a "Master Medication List" defining all of the infusates which may be used in the facility. The "Master Medication List" may comprise a number of medications which a qualified individual may update or maintain. In the example embodiment, the "Master Medication List" only has three medications: Heparin, 0.9% Normal Saline, and Alteplase. Each group within a facility may have its own list of medications used in the group. In the example embodiment, the "Group Medication List (ICU)" only includes a single medication, Heparin.

As shown, each medication may be associated with one or a number of clinical uses. In FIG. 322 the "Clinical Use Records" are defined for each medication in a group medication list and appear as an expanded sub-heading for each infusate. The clinical uses may be used to tailor limits and pre-defined settings for each clinical use of the infusate. For Heparin, weight based dosing and non-weight based dosing are shown in FIG. 322 as possible clinical uses. In some embodiments, there may be a "Clinical Use Record" setting requiring the user to review or re-enter a patient's weight (or BSA) before beginning an infusion.

Clinical uses may also be defined for the different medical uses of each infusate (e.g. stroke, heart attack, etc.) instead of or in addition to the infusate's dose mode. The clinical use may also be used to define whether the infusate is given as a primary continuous infusion, primary intermittent infusion, secondary infusion, etc. They may also be use to provide appropriate limits on the dose, rate, VTBI, time duration, etc. Clinical uses may also provide titration change limits, the availability of boluses, the availability of loading doses, and many other infusion specific parameters. In some embodiments, it may be necessary to provide at least one clinical use for each infusate in the group medication list.

Each clinical use may additionally comprise another expanded sub-heading in which the concentration may also be defined. In some cases, there may be more than one possible concentration of an infusate. In the example embodiment in FIG. 322, the weight base dosing clinical use has a 400 mg/250 mL concentration and an 800 mg/250 mL concentration. The non-weight based dosing clinical use only has one concentration, 400 mg/mL. The concentrations may also be used to define an acceptable range for instances where the user may customize the concentration of the infusate. The concentration setting may include information on the drug concentration (as shown), the diluents volume, or other related information.

In some embodiments, the user may navigate to the "Drug Administration Library" to populate some of the parameter input fields shown in FIGS. 312-316. The user may also navigate to the "Drug Administration Library" to choose from the clinical uses for each infusate what type of infusion the peristaltic pump 2990 will administer. For example, if a user were to select weight based Heparin dosing on FIG. 322, the GUI 3300 might display the infusion programming screen shown on FIG. 315 with "Heparin" populated into the medication parameter input field 3302. Selecting a clinical use of a drug may also prompt a user to select a drug concentration. This concentration may then be used to populate the concentration parameter input field 3308 (see FIGS. 312-316). In some embodiments, the "Drug Administration Library" may be updated and maintained external to the peristaltic pump 2990 and communicated to the peristaltic pump 2990 via any suitable means. In such embodiments, the "Drug Administration Library" may not be changeable on the peristaltic pump 2990 but may only place limits and/or constraints on programming options for a user populating the parameter input fields shown in FIG. 312-316.

As mentioned above, by choosing a medication and clinical use from the group medication list, a user may also be setting limits on other parameter input fields for infusion programming screens. For example, by defining a medication in the "Drug Administration Library" a user may also be defining limits for the dose parameter input field 3310, dose rate parameter input field 3318, rate parameter input field 3312, VTBI parameter input field 3314, time parameter input field 3316, etc. These limits may be pre-defined for each clinical use of an infusate prior to the programming of an infusion by a user. In some embodiments, limits may have both a soft limit and a hard limit with the hard limit being the ceiling for the soft limit. In some embodiments, the group settings may include limits for all of the medications available to the group. In such cases, clinical use limits may be defined to further tailor the group limits for each clinical usage of a particular medication.

Exemplary Battery and Speaker Test

FIG. 323 shows a circuit diagram 13420 having a speaker 3615 and a battery 3420 in accordance with an embodiment of the present disclosure. The battery 3420 may be a backup battery 3450 (FIG. 325A) and/or the speaker 3615 may be a backup alarm speaker 3468 (FIG. 325B). That is, the circuit 13420 may be a backup alarm circuit, for example, a backup alarm circuit in a medical device, such as a peristaltic pump 2900.

In some embodiments of the present disclosure, the battery 3420 may be tested simultaneously with the speaker 3615. When a switch 13422 is in an open position, a voltmeter 13425 may be used to measure the open circuit voltage of the battery 3420. Thereafter, the switch 13422 may be closed and the closed-circuit voltage from the battery 3420 may be measured. The internal resistance of the battery 3420 may be estimated by using the known impedance, Z, of the speaker 3615. A processor may be used to estimate the internal resistance of the battery 3420 (e.g., a processor of a peristaltic pump 2900). The processor may correlate the internal resistance of the battery 3420 to the battery's 3420 health. In some embodiments of the present disclosure, if the closed-circuit voltage of the battery 3420 is not within a predetermined range (the range may be a function of the open-circuit voltage of the battery 3420), the speaker 3615 may be determined to have failed.

In some additional embodiments of the present disclosure, the switch 13422 may be modulated such that the speaker 3615 is tested simultaneously with the battery 3420. A microphone 3617 may be used to determine if the speaker 3615 is audibly broadcasting a signal within predetermined operating parameters (e.g., volume, frequency, spectral compositions, etc.) and/or the internal impedance of the battery 3420 may be estimated to determine if it is within predetermined operating parameters (e.g., the complex impedance, for example). The microphone 3617 (FIG. 325C) may be coupled to the processor. Additionally or alternatively, a test signal may be applied to the speaker 3615 (e.g., by modulating the switch 13422) and the speaker's 3615 current waveform may be monitored by an current sensor 13426 to determine the total harmonic distortion of the speaker 3615 and/or the magnitude of the current; a processor may be monitored these values using the current sensor 13426 to determine if a fault condition exists within the speaker 3615 (e.g., the total harmonic distortion or the magnitude of the current are not within predetermined ranges).

Various sine waves, periodic waveforms, and/or signals maybe applied to the speaker 3615 to measure its impedance and/or to measure the impedance of the battery 3420. For example, a processor of a peristaltic pump 2900 disclosed herein may modulate the switch 13422 and measure the voltage across the battery 3420 to determine if the battery 3420 and the speaker 3615 has an impedance within predetermined ranges; if the estimated impedance of the battery 3420 is outside a first range, the processor may determine that the battery 3420 is in a fault condition, and/or if the estimated impedance of the speaker 3615 is outside a second range, the processor may determine that the speaker 3615 is in a fault condition. Additionally or alternatively, if the processor cannot determine if the battery 3420 or the speaker 3615 has a fault condition, but has determined that at least one exists in a fault condition, the processor may issue an alert or alarm that the circuit 13420 is in a fault condition. The processor may alarm or alert a user or a remote server of the fault condition. In some embodiments of the present disclosure, the peristaltic pump 2990 will not operate until the fault is addressed, mitigated and/or corrected.

Electrical System

The electrical system 4000 of the peristaltic pump 2990 is described in a block schematic in FIGS. 324, 325A-325G. The electrical system 4000 controls the operation of the peristaltic pump 2990 based on inputs from the user interface 3700 and sensors 3501. The electrical system 4000 may be a power system comprised of a rechargeable main battery 3420 and battery charging 3422 that plugs into the AC mains. The electrical system 4000 may be architected to provide safe operation with redundant safety checks, and allow the peristaltic pump 2990 to operate in fail operative modes for some errors and fail safe for the rest.

The high level architecture of an electrical system 4000 is shown in FIG. 324. The electrical system 4000 may be used to control, operate, monitor, or is used with the pump 2990 shown in FIG. 255 (or any other pump described herein). In one example, the electrical system 4000 is comprised of two main processors, a real time processor 3500 and a User Interface and Safety Processor 3600. The electrical system may also comprise a watch-dog circuit 3460, motor control elements 3431, sensors 3501 and input/output elements. One main processor, referred to as the Real Time Processor (RTP) 3500 may controls the speed and position of the motor 3072 that actuates the plunger 3091, and valves 3101,3111. The RTP 3500 controls the motor 3072 based on input from the sensors 3501 and commands from the User Interface & Safety processor (UIP) 3600. The UIP 3600 may manage telecommunications, manage the user interface 3701, and provide safety checks on the RTP 3500. The UIP 3600 estimates the volume pumped based on the output of a motor encoder 3438 and may signal an alarm or alert when the estimated volume differs by more than a specified amount from a desired volume or the volume reported by the RTP 3500. The watch dog circuit 3460 monitors the functioning of the RTP 3500. If the RTP 3500 fails to clear the watch dog 3460 on schedule, the watch dog 3460 may disable the motor controller, sound an alarm and turn on failure lights at the user interface 3701. The sensor 3130 may measure the rotational position of the cam shaft 3080 and the plunger 3901. The RTP 3500 may use the sensor inputs to control the motor 3072 position and speed in a closed-loop controller as described below. The telecommunications may include a WIFI driver and antenna to communicate with a central computer or accessories, a bluetooth driver and antenna to communicate with accessories, tablets, cell-phones etc. and a Near Field Communication (NFC) driver and antenna for RFID tasks and a bluetooth. In FIG. 324 these components are collectively referred to with the reference number 3721. The user interface 3701 may include a display, a touch screen and one or more buttons to communicate with the user.

Figure 325A:
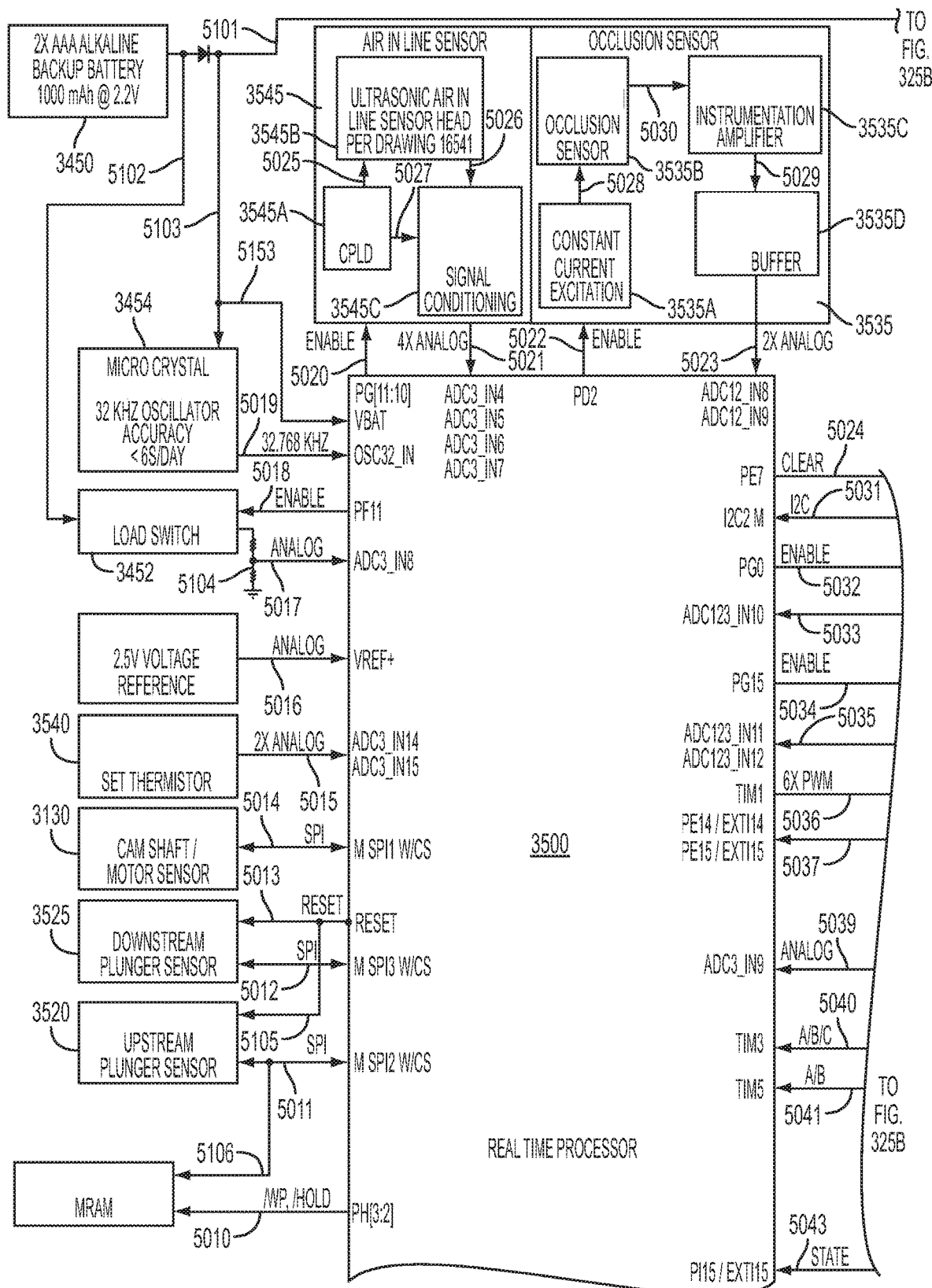
Figure 325B:
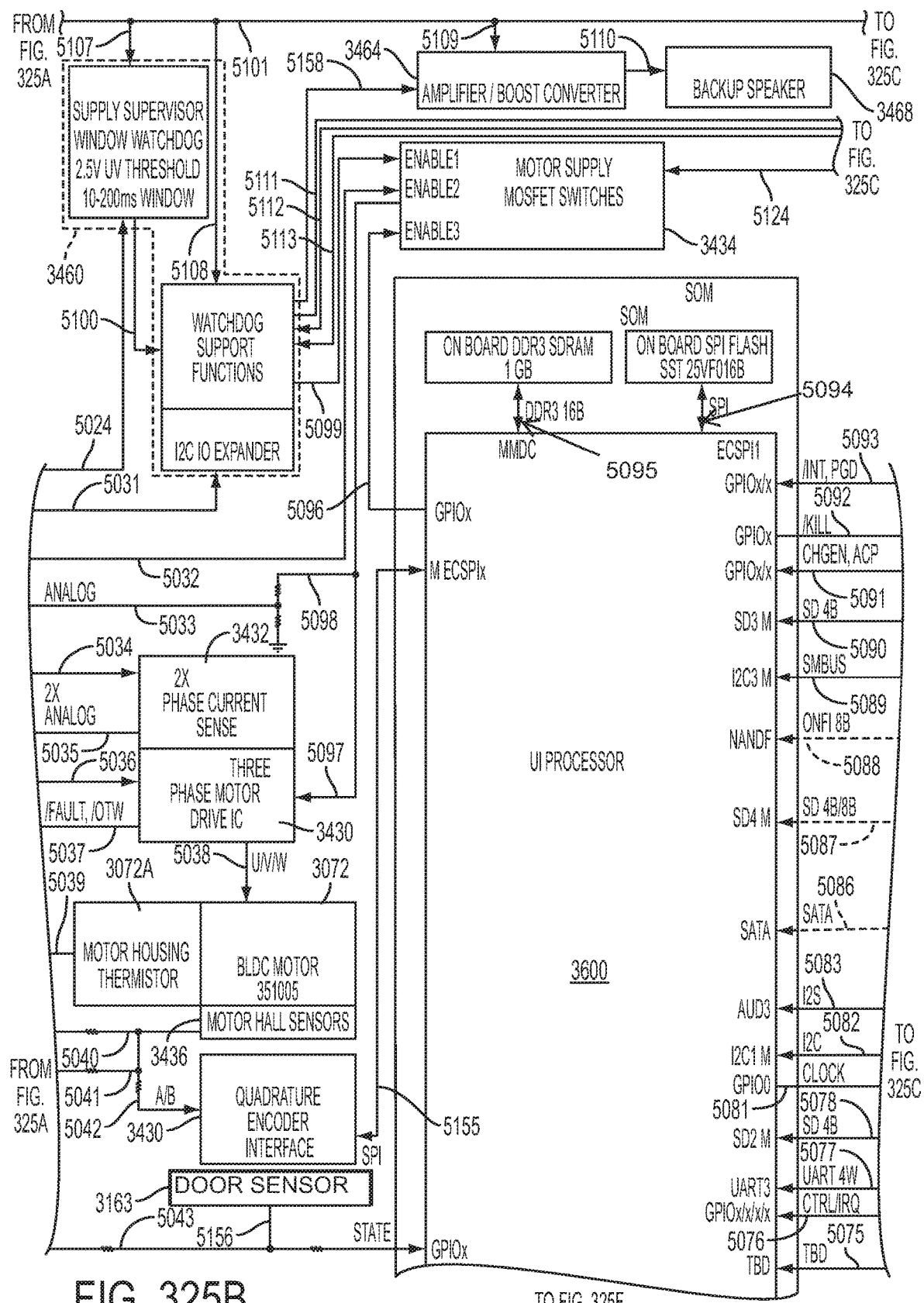

The detailed electrical connections and components of the electrical system 4000 are shown in FIG. 325A-325G. The sensors 3130, 3530, 3525, 3520 and part of the RTP 3500 are shown in FIG. 325A. The sensors monitoring the peristaltic pump 2990 that are connected to the RTP 3500 may comprise the rotary position sensor 3130 monitoring the cam shaft position and two linear encoders 3520, 3525 that measure the position of the plunger 3091 as shown. One linear encoder 6001 measures the position of the magnet (3196 in FIGS. 268 and 282) upstream side of the plunger 3091. The other linear encoder 6002 measures the position of a second magnet 3197 (see FIGS. 268 and 282) on the downstream side of the plunger 3091. In another embodiment, the position of the plunger may be measured with a single magnet and linear encoder. Alternatively, RTP 3500 may use output of only one linear encoder if the other fails. A thermistor 3540 provides a signal to the RTP 3500 indicative of the infusion tube 3210 temperature. Alternatively the thermistor 3540 may measure a temperature in the peristaltic pump 2990.

As shown, the electrical system 4000 any suitable component part numbers may be used. For example, the thermistor 3540 may be a "2X SEMITEC 103JT-050 ADMIN Set THERMISTOR." However, the electrical system 4000 is not limited to any particular set of part numbers and the present disclosure should not be construed as limiting the components of the electrical system 4000 to a particular part number. In various embodiments, suitable replacement components may be used in place of a component of the electrical system 4000 shown in the FIGS. 325A-325G. In some embodiments, the electrical system 4000 may comprise additional components. In some embodiments, the electrical system 4000 may comprises fewer components than the number of components shown in FIGS. 325A-325G.

The two infusion tube sensors located downstream of the peristaltic pump 2990, an air-in-line sensor 3545 and an occlusion sensor 3535 may be connected to the RTP 3500.

An air-in-line sensor 3545 detects the presence of air in the section of infusion tube 3210 near the air-in-line sensor 3545. In one example, the air-in-line sensor 3545 may comprise an ultra-sonic sensor 3545B, a logic unit 3545A and a signal conditioning unit 3545C.

The occlusion sensor 3535 measures the internal pressure of fluid in the infusion tube 3535. In an example embodiment, the occlusion sensor 3535 may comprise a force sensor 3535B, a current excitation IC 3535A, a signal amplifier 3535C and a data buffer 3535D. The data buffer chip 3535D may protect the RTP 3500 from over-voltages due to high forces form pressures applied to the force sensor 3535B.

Figure 325C:
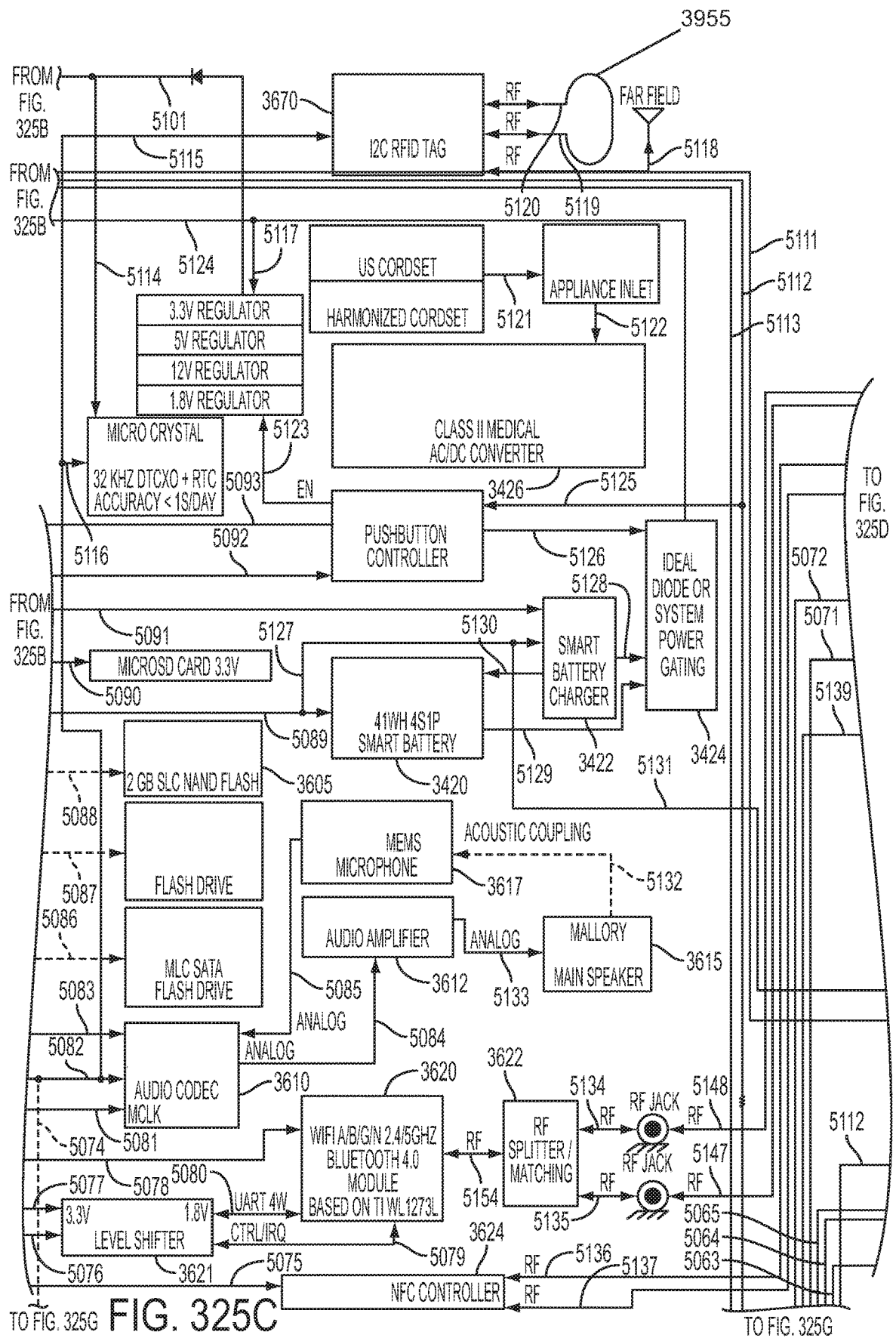
Figure 325D:
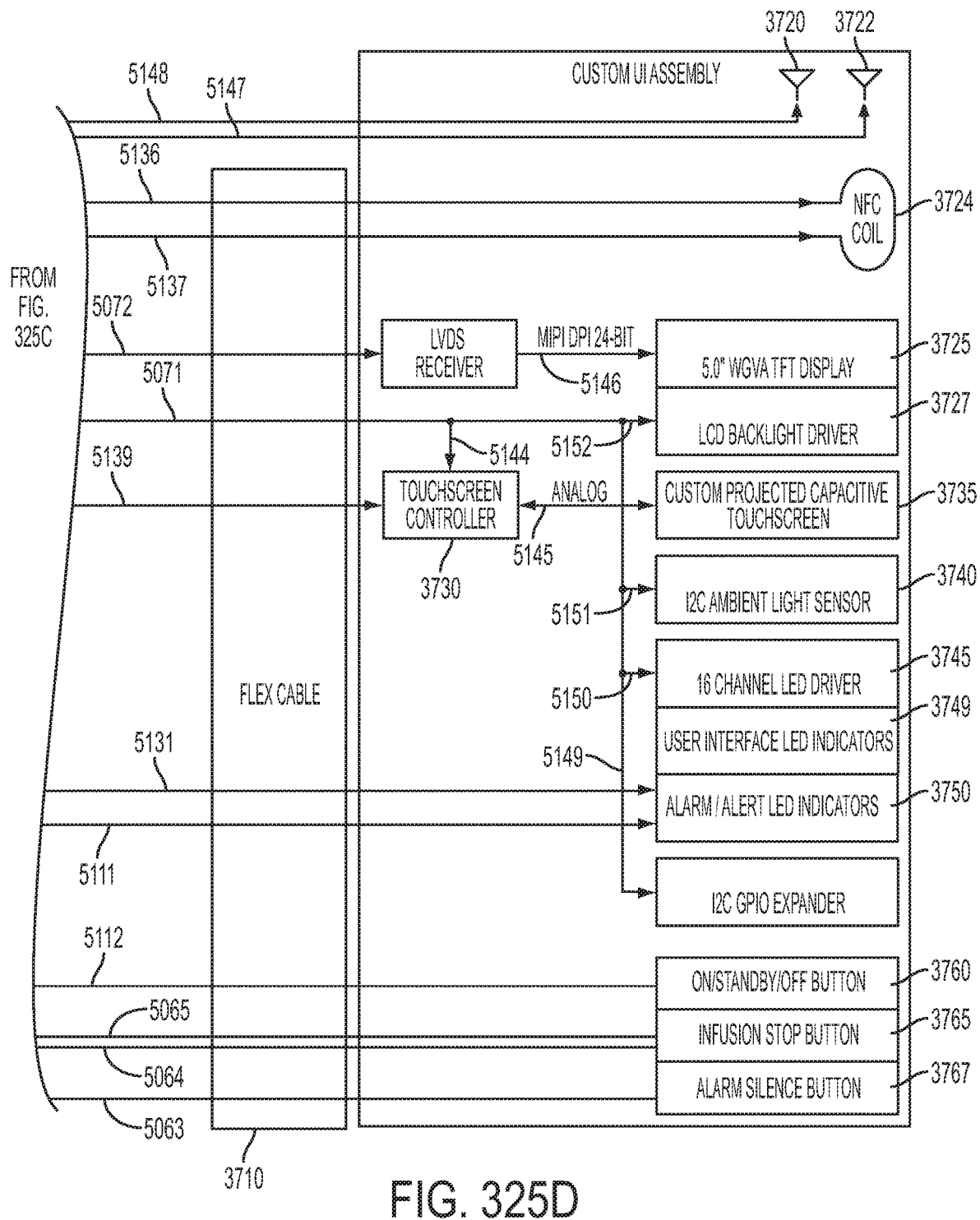
Figure 325E:
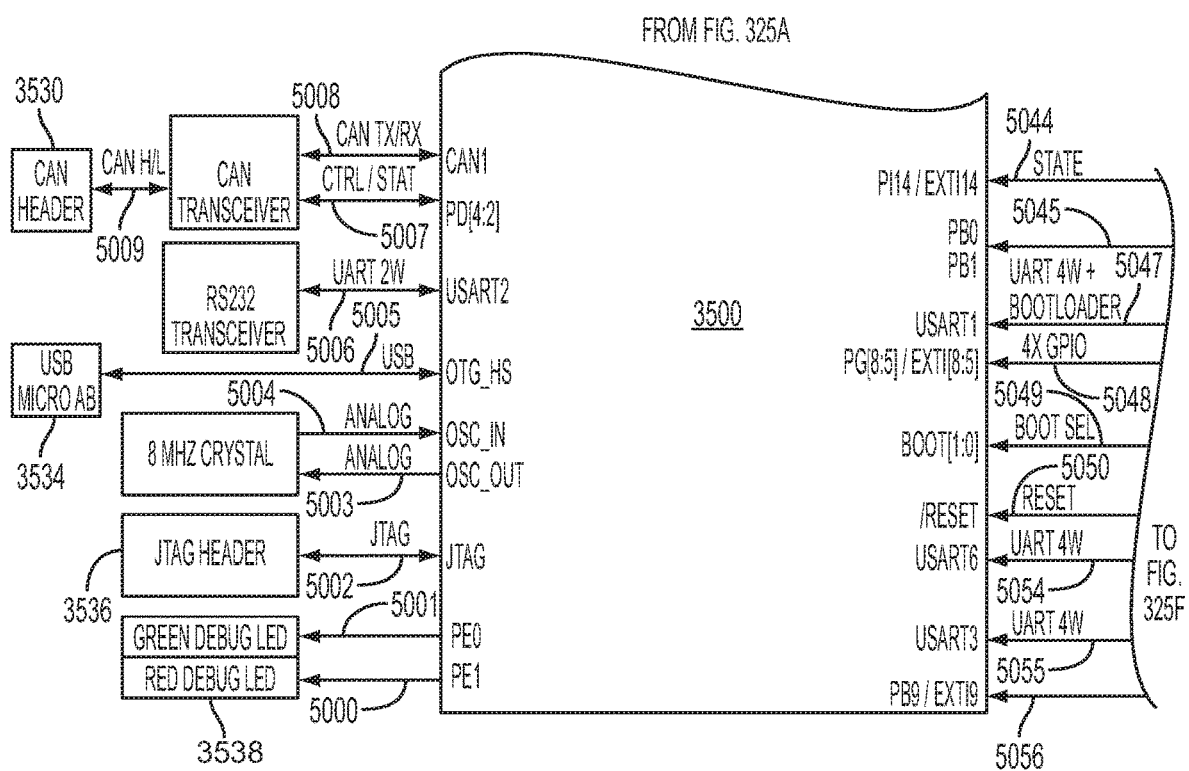

The watchdog circuit 3460 is shown in FIGS. 325A-325C. The watch dog circuit is enabled by an I2C command from the RTP 3500. The watch dog circuit 3460 may signal an error and disable the motor control 3430 if it does not receive a signal from the RTP 3500 at a specified frequency. The watch dog circuit 3460 may signal the user via an audible alarm. The audible alarm may be issued via an amplifier 3464 and/or backup speaker 3468. The watch dog circuit 3460 may signal the user with visual alarm LEDs 3750 (shown in FIG. 325D). In one embodiment, the RTP 3500 must "clear" the watch dog circuit 3460 between 10 ms and 200 ms after the watch dog circuit's last clear. In one embodiment, the watch dog circuit 3460 is comprised of a window watchdog 3450A, a logic circuit 3460B including one or more flip-flop switches and an IO expander 3460C that communicates with the RTP 3500 over an I2C bus. A backup battery 3450 provides power to the watchdog circuit 3460 and backup speaker system (which may comprise an audio amplifier 3464, and a backup speaker 3468) in case the main battery 3420 fails. The backup battery 3450 provides power to the RTP 3500 and UIP 3600 to maintain the internal timekeeping, which may be especially desirable when the main battery 3420 is changed. The RTP 3500 may also monitor the voltage of the backup battery 3450 with a switch such as the "FAIRCHILD FPF1005 LOAD SWITCH" 3452 shown in FIG. 325A.

The RTP 3500 directly controls the speed and position of the motor 3072 which controls the position and speed of the plunger and valves. The motor 3072 may be any of a number of types of motors including a brushed DC motor, a stepper motor or a brushless DC motor. In the embodiment illustrated in FIGS. 325-325G, the peristaltic pump 2990 is driven by a brushless direct current (BLDC) servo motor 3072 where the rotary position sensor 3130 measures the position of the cam-shaft. In one example embodiment, the RTP 3500 receives the signals from the hall-sensors 3436 of a brushless DC motor 3072 and does the calculations to commutate power to the windings of the motor 3072 to achieve a desired speed or position. The commutation signals are sent to the motor driver 3430 which selectively connects the windings to the motor power supply 3434. The motor 3072 is monitored for damaging or dangerous operation via current sensors 3432 and a temperature sensor 3072a.

The signals from the hall sensors 3436 may be supplied to both the RTP 3500 and to an encoder 3438. In one embodiment, three hall sensor signals are generated. Any two of the three hall signals are sent to the encoder 3438. The encoder 3438 may use these signals to provide a position signal to the UIP 3600. The UIP 3600 estimates the total volume of fluid dispensed by the peristaltic pump 2990 by interpreting the position signal of the encoder 3438. The UIP 3600 estimates the total volume by multiplying the number of complete cam-shaft revolutions times a given stroke volume. The total volume estimate of the UIP 3600 assumes each plunger stroke supplies the given amount of fluid. The amount of fluid supplied per stroke is determined empirically during development and stored in memory. Alternatively, each peristaltic pump 2990 may be calibrated during assembly to establish the nominal volume/stroke that may be stored in memory. The UIP 3600 estimated volume may then be compared at regular intervals to the expected volume from the commanded therapy. In some embodiments, the interval between comparisons may be shorter for specific infusates, for example short-half life infusates. The therapy may specify, among other parameters, a flow rate, a duration, or a total volume to be infused (VTBI). In any case, the expected volume for a programmed therapy at a given time during that therapy may be calculated and compared to the volume estimated by the UIP 3600. The UIP 3600 may signal an alert if the difference between UIP 3600 estimated volume and the therapy expected volume is outside a predefined threshold. The UIP 3600 may signal an alarm if the difference between UIP 3600 estimated volume and the therapy expected volume is outside of another predefined threshold.

The UIP 3600 may also compare the estimated volume to the volume reported by the RTP 3500. The UIP 3600 may signal an alert if the difference between UIP 3600 estimated volume and the RTP 3500 reported volume is outside a predefined threshold. The UIP 3600 may signal an alarm if the difference between UIP 3600 estimated volume and the RTP 3500 reported volume is outside a second threshold.

The UIP 3600 may also compare the estimated angles of rotation or number of rotation pulses reported by the RTP 3500. The UIP 3600 may signal an alert if the difference between the UIP 3600 estimated angles of rotation or number of rotation pulses and the RTP 3500 reported value is outside a predefined threshold. The UIP 3600 may signal an alarm if the difference between UIP 3600 and the RTP 3500 value is outside a third threshold.

In some embodiments, the UIP 3600 may compare the RTP 3500 reported volume to therapy expected volume and signal an alert if the two values differ by more than a predefined threshold. The UIP 3600 may signal an alarm if the difference between the RTP 3500 reported volume and the therapy expected volume differ by more than a predefined threshold. The values of the alert and alarm thresholds may be different for comparisons between different sets of volumes including the UIP 3600 estimated volume, the RTP 3500 calculated volume and the therapy expected volume. The thresholds may be stored memory. The thresholds may vary depending on a number of other parameters, such as but not limited to, medication, medication concentration, therapy type, clinical usage, patient or location. The thresholds may be included in the DERS database and downloaded from the device gateway server.

Figure 325F:
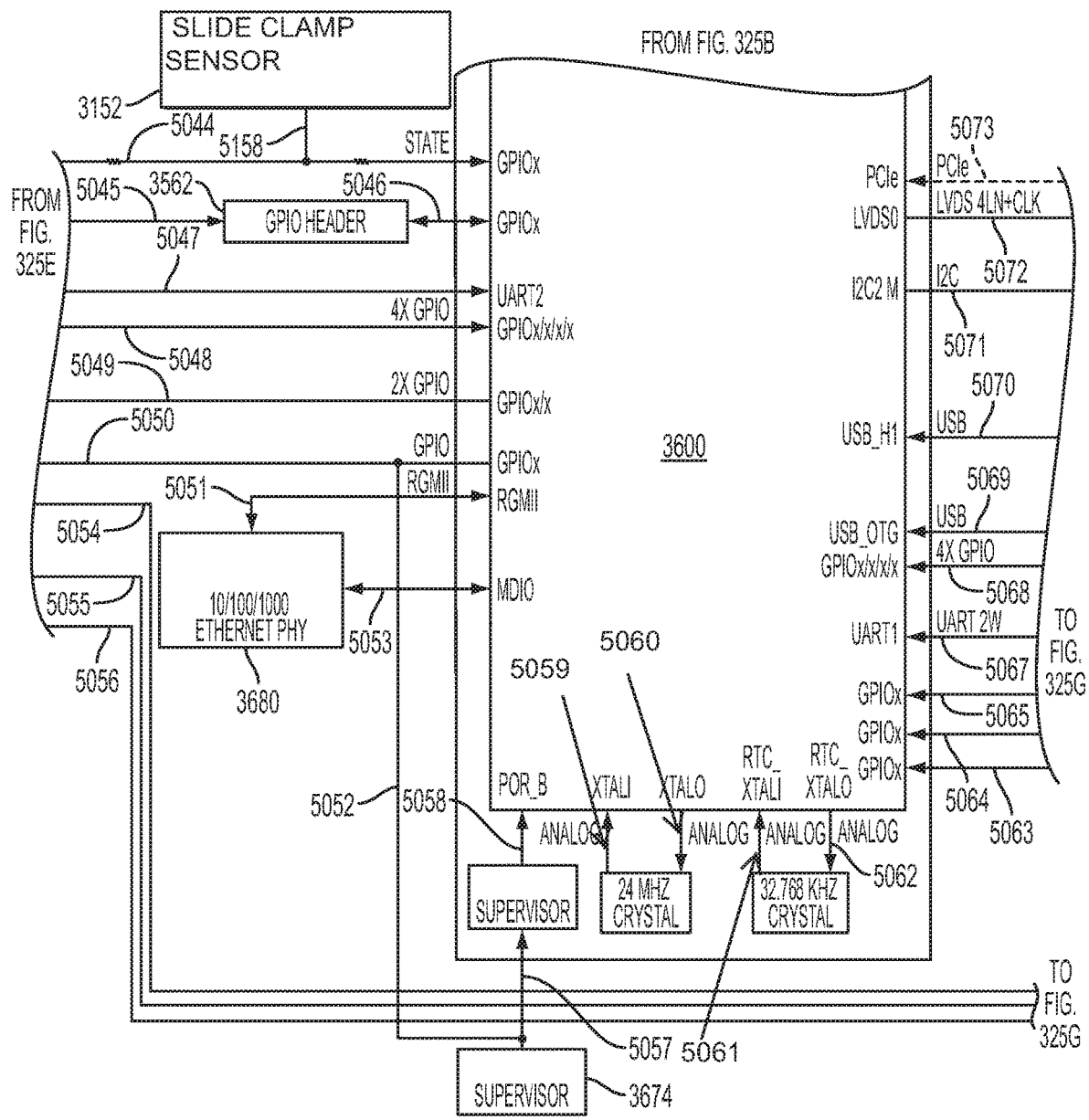
Figure 325G:
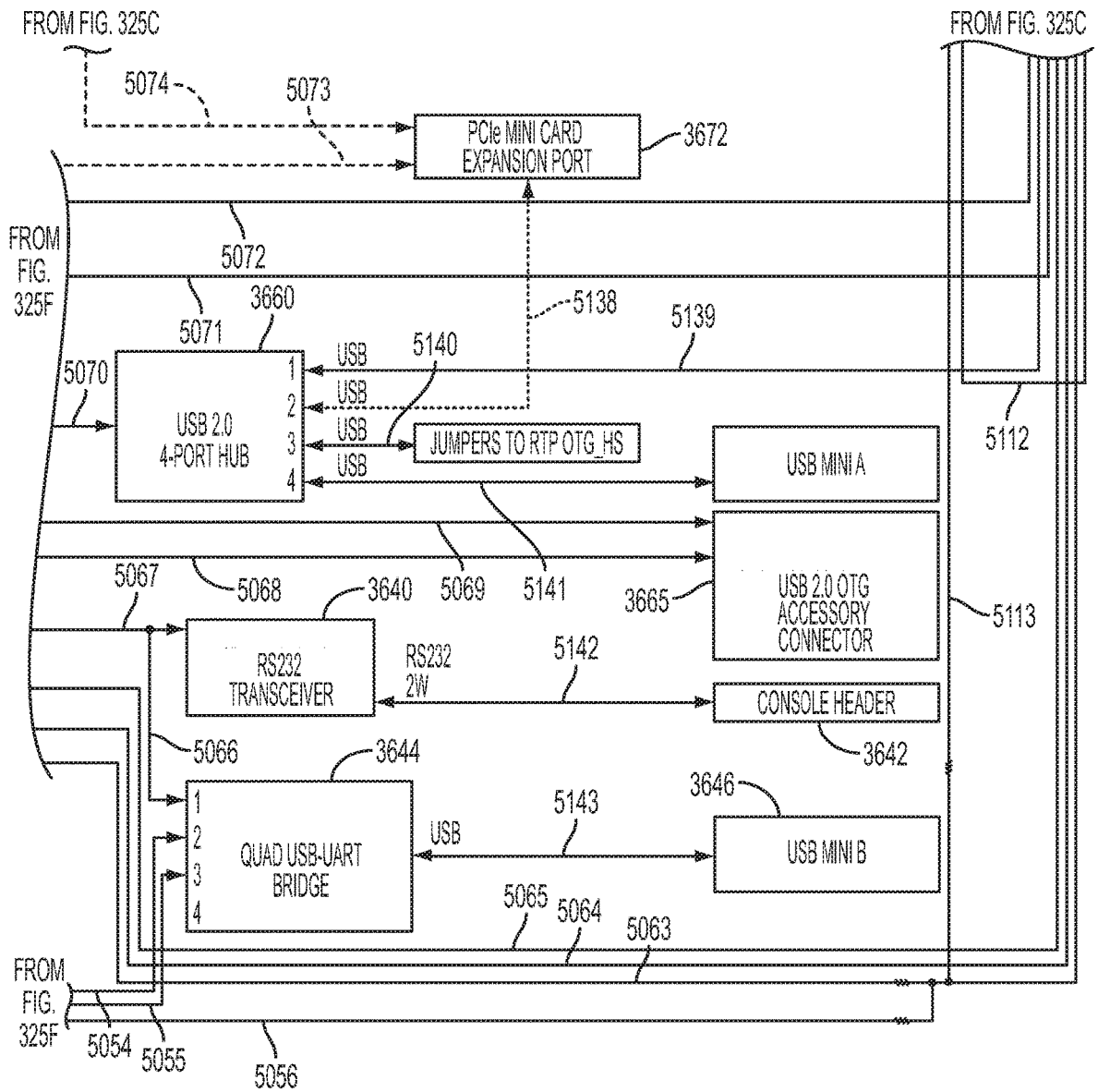

The slide clamp or slide occluder sensor 3152 and the door sensor 3162 communicate with both the RTP 3500 and the UIP 3600 as shown in FIGS. 325B, 325F. In one embodiment the sensors are magnetic null sensors that change state when for example the slide occluder 3200 is detected or the door latch hook 3025C engages the pump body. The RTP 3500 or the UIP 3600 may enable the motor power supply 3434 only while the processors receive signals indicating that the slide occluder 3200 is in place and the door assembly 3021 is properly closed.

An RFID tag 3670 (FIG. 325C) may be connected by an I2C bus to the UIP 3600 and to a near field antenna 3955. The RFID tag 3670 may be used by med-techs or other users or personnel to acquire or store information when the peristaltic pump 2990 is in an unpowered state. The UIP 3600 may store service logs or error codes in the RFID tag 3670 that can be accessed by an RFID reader. A med-tech, for example, could inspect unpowered peristaltic pumps 2990 in storage or evaluate non-functioning peristaltic pumps 2990 by using an RFID reader to interrogate the RFID tag 3670. In another example, a med-tech may perform service on the peristaltic pump 2990 and store the related service information in the RFID tag 3670. The UIP 3600 may then pull the latest service information from the RFID tag 3670 and store it in memory 3605.

The main battery 3420 may supply all the power to the peristaltic pump 2990. The main battery 3420 is connected via a system power gating element 3424 to the motor power supply 3434. All of the sensors and processors may be powered by one of the several voltage regulators 3428. The main battery 3420 is charged from AC power via a battery charger 3422 and an AC/DC converter 3426. The UIP 3600 may be connected to one or more memory chips 3605.

The UIP 3600 controls the main audio system which comprise a main speaker 3615 and the audio-chips 3610, 3612. The main audio system may be capable of producing a range of sounds indicating, for example, alerts and alarms. The audio system may also provide confirmatory sounds to facilitate and improve user interaction with the touch screen 3755 and display 3725. The main audio system may include a microphone 3617 that may be used to confirm the operation of the main speaker 3615 as well as the backup speaker 3468. The main audio system may produce one or more tones, modulation sequences and/or patterns of sound and the audio codec chip 3610 may compare the signal received from the microphone 3617 to the signal sent to the main speaker 3615. The use of one or more tones and comparison of signals may allow the system to confirm main speaker 3615 function independently of ambient noise. Alternatively the UIP 3600 or the audio codec 3610 may confirm that the microphone 3617 produced a signal at the same time a signal was sent to the speaker amplifier 3612.

The UIP 3600 may provide a range of different wireless signals for different uses. The UIP 3600 may communicate with the hospital wireless network via a dual band wifi using chips 3621, 3620 and 3622 and antennas 3720, 3722. The spatially diverse dual antenna may be desirable because it may be capable of overcoming dead spots within a room due to multiple paths and cancellation. A hospital device gateway may communicate DERS (Drug Error Reduction System), CQI (Continuous Quality Improvement), prescriptions, etc. to the peristaltic pump 2990 via the wifi system.

The bluetooth system, using the same chips 3621, 3620 and 3622 and antennas 3720, 3722, provides a convenient method to connect auxiliaries to the peristaltic pump 2990 that may include pulse-oximeters, blood pressure readers, bar-code readers, tablets, phones, etc. The bluetooth may include version 4.0 to allow low power auxiliaries which may communicate with the peristaltic pump 2990 periodically such as, for example, a continuous glucose meter that sends an update once a minute.

The NFC system is comprised of an NFC controller 3624 and an antenna 3724. The controller 3624 may also be referred to as an RFID reader. The NFC system may be used to read RFID chips identifying drugs or other inventory information. The RFID tags may also be used to identify patients and caregivers. The NFC controller 3624 may also interact with a similar RFID reader on, for example, a phone or tablet computer to input information including prescriptions, bar-code information, patient, care-giver identities, etc. The NFC controller 3624 may also provide information to the phone or tablet computers such as the peristaltic pump 2990 history or service conditions. The RFID antennas 3720 and 3722 or NFC antenna 3724 may preferably be located around or near the display screen, so all interaction with the pump occurs on or near the screen face whether reading an RFID tag or interacting with the display touch screen 3725, 3735.

The UIP 3600 may include a medical grade connector 3665 so that other medical devices may plug into the peristaltic pump 2990 and provide additional capabilities. The connector 3665 may implement a USB interface.

The display 3700 includes the antennas 3720, 3722, 3725, the touch screen 3735, LED indicator lights 3747 and three buttons 3760, 3765, 3767. The display 3700 may include a backlight 3727 and an ambient light sensor 3740 to allow the screen brightness to automatically respond to ambient light. The first button 3760 may be the "Power" button, while another button 3765 may be an infusion stop button. These buttons 3760, 3765, 3767 may not provide direct control of the peristaltic pump 2990, but rather provide a signal to the UIP 3600 to either initiate or terminate infusion. The third button 3767 will silence the alarm at the main speaker and at the secondary speaker. Silencing the alarm will not clear the fault, but will end the audible alarm. The electric system 4000 described above, or an alternative embodiment of the electrical system 4000 described above, may be used with any of peristaltic pumps with linear position sensors.

Controls

The pumping algorithms provide substantially uniform flow by varying the rotation speed of the motor 3072 over a complete revolution. At low flows, the motor 3072 turns at a relatively high rate of speed during portions of the revolution when the plunger 3091 is not moving fluid toward the patient. At higher flow rates, the motor 3072 turns at a nearly constant speed throughout the revolution to minimize power consumption. At the high flow rates, the motor 3072 rotation rate is proportional to the desired the flow rate. The pump algorithm use linear encoders 3520, 3525 (FIG. 325A) above the plunger 3091 to measure volume of fluid pumped toward the patient. The pump algorithm use linear encoders 3520, 3525 (FIG. 325A) above the plunger 3091, the rotation encoder 3130 (FIG. 325A) near the cam-shaft 3080 and the air-in-line sensor 3545 downstream of the plunger 3091 to detect one or more of the following conditions: downstream occlusions, upstream occlusions/empty bag, leaks and the amount of air directed toward the patient.

One embodiment of the valve 3101, 3111 openings and plunger 3091 position is plotted in FIG. 326. Three time periods are identified in FIG. 326 including a refill 826, pressurization 835 and a deliver period 840. In addition, period "A" occurs between the pressurization period 835 and Delivery period 840, and period "B" occurs between the Delivery period 840 and Refill period 830. The inlet valve position 820, outlet valve position 825 and plunger position 815 are plotted on a sensor signal over cam angle graph over a complete cam shaft 3080 rotation.

The refill period 830 occurs while the inlet valve 820 is held off the infusion tube 3210 and the plunger 3091 is lifted off the infusion tube 3210 by the plunger cam 3083. The refill period 830 ends and the pressurization period 835 begins as the inlet valve 3101 is closing. The plunger cam 3083 is full retracted during the pressurization period 835 to allow the plunger 3091 to land on the filled infusion tube 3210. The pressurization period 835 ends several cam angle degrees past the point where the plunger cam 3083 reaches its minimum value. After a waiting period "A," the plunger cam 3083 lifts until it reaches the height where the plunger 3091 is expected to be. The delivery period 840 begins when the outlet valve 3111 starts to open and lasts until the outlet valve 3111 closes again. The plunger cam 3083 rotates causing the plunger 3091 to descend during the delivery period 840 pushing fluid toward the patient.

In some embodiments, if the plunger 3091 moves toward the platen 3022 (see FIGS. 257 and 259) beyond a predetermined rate (i.e., a plunger's 3091 speed) during the pressurization period 837, the RTP 3500 may determine that at least one of the inlet valve 3101 and the outlet valve 3111 is leaking. Additionally, alternatively, or optionally, an underfill condition (a type of anomaly) may be considered by the RTP 3500 to have occurred if the static position of the plunger 3091 is beyond a threshold toward a platen 3022 (see FIG. 296) during the pressurization period 837. The static position of the plunger 3091 during the pressurization period 837 is related to the amount of fluid within the tube. Therefore, if the tube did not fill up with an expected amount of fluid, the plunger's 3091 position during the pressurization period 837 will be closer to the platen 3022 (see FIGS. 257 and 259). The underfill condition may be due to air in the tube, an upstream occlusion, or an empty fluid source coupled to the tube. Air is easily compressed within the tube by the plunger 3091. The air-in-line detector 3066 (see FIG. 257) may be used by the processor to distinguish between an underfill caused by air within the tube under the plunger 3091 vs. an underfill caused by an upstream occlusion or an empty fluid source (such as an IV bag). The RTP 3500 may be coupled to the air-in-line detector 3066 to determine a cause of the underfill by examining how much air is within the discharged fluid when the fluid is discharged downstream by the plunger 3091 when the outlet valve 3111 (see FIGS. 257 and 260) is opened. If the underfill was cause by air, the RTP 3500 should detect an amount of air that corresponds to the amount of movement of the plunger 3091 beyond the threshold. The RTP 3500 may use a lookup table to determine if the amount of plunger 3091 movement beyond the threshold corresponds to a range within the lookup table. If it does, the RTP 3500 may determine that air caused the underfill. If it does not, the RTP 3500 may determine that an upstream occlusion and/or an empty fluid source caused the underfill. The cause of the underfill may be displayed on the pump's 2990 display 2994 (see FIG. 255).

The RTP 3500 may determine the volume of fluid delivered toward the patient for each stroke based on signals from the rotary encoder 3130 measuring the angle of the camshaft 3080 and from the linear encoder 3525, 3520 measurements plunger 3091 position. The volume of each stroke may be measured by subtracting the height of the plunger 3091 at the end of the delivery period 840 from the height of the plunger 3091 at the end of pressurization period 835. The height of the plunger 3091 may be determined from signals of one or both of the linear encoders 3020, 3025, where the height approximates the distance of the plunger tip 3091B from the platen 3022. The end of the delivery period 840 and the end of the pressurization period 835 may be determined from the rotary encoder 3130 measuring the angle of the crank shaft. The measured height difference 845 may be empirically associated with pumped volumes and the result stored in a lookup table or in memory in the controller. The volume vs. stroke table may be determined during development and be programmed into each peristaltic pump 2990 during manufacture. Alternatively, the measured change in plunger 3091 height may be calibrated to pumped volume for each peristaltic pump 2990 or pumping mechanism 3000 during the manufacturing process.

In one embodiment, the pumped volume is calibrated plunger 3091 positions as:

$$V_i = A + B^*(h_P - h_D)$$

where $V_i$ is the pumped volume, A and B are fitting coefficients, $h_P$ is the plunger 3091 position at the end of the pressurization period 835 and $h_D$ is the plunger 3091 position at the end of the delivery period 840.

The speed of the motor 3072 varies with the flow rate and it varies over a single revolution for lower flow rates. In one example, the motor 3072 rotation is relatively constant for commanded flow rates above approximately 750 ml/hr. The motor 3072 speed is controlled to relatively slower speeds during intake and deliver flow rates for commanded flow rates below approximately 750 ml/hr.

The motor 3072 moves at a constant speed during the pressurization period 835 for all pumping rates. In one example the motor 3072 turns at the speed required to deliver fluid at the highest flow rate. In one example the motor 3072 turns at 800°/second during the pressurization period 835, which corresponds to the peristaltic pump 2990 to delivering 1200 mL/Hr. Running the motor 3072 at a fixed high speed during the pressurization period 835 may advantageously minimize no-flow periods which improves uniformity of fluid flow. Running the motor 3072 at a fixed high speed during the pressurization period 835 may advantageously create a consistent measurement of the filled infusion tube 3210 height by compressing the plastic walls of the infusion tube 3210 at the same rate each time. Not being limited to a single theory, one theory holds that the plastic infusion tube 3210 continues to yield after being compressed, which would produce a lower height for the filled infusion tube 3210 the longer the time between compression and measurement. The plastic may exhibit visco-elastic properties so that the amount of strain in the plastic changes with the rate of compression, which in turn would change the measured height of the plastic infusion tube 3210.

Low Flow Mode

The pumping algorithm to produce a desired flow rate may control motor 3072 speed differently during the refill and delivery periods 830,840 for relatively lower flow rates as compared to higher flow.

In the low flow mode the motor 3072 is controlled during the delivery period 840 to control the cam-shaft 3080 position in order to produce a predefined volume trajectory. The volume trajectory is the volume of fluid delivered to the patient verses time. The predefined volume trajectory usually occurs over many cam-shaft 3080 rotations, so that the delivery period 840 must deliver a full revolution's worth of fluid at the trajectory speed in the shorter delivery period 840.

The motor 3072 speed during the refill period 830 is adjusted to produce a full infusion tube 3210 as measured at the plunger 3091 position at the end of the pressurization period 835. The controller will slow the motor 3072 speed if the infusion tube 3210 is not full in the previous pump cycle. The refill period 830 is selected such that the plunger 3091 lifts off of the hard stop 3022A (FIG. 277) slowly (at lower flow rates) in order to minimize cavitation and air bubble generation.

At all other times the motor 3072 spins at the Delivery Stroke Velocity. In short, this is the velocity at which the cam shaft 3080 must complete a revolution in order to keep up with the trajectory volume, limited to values greater than 500° per second.

High Flow Mode

In high flow mode, the refill and delivery periods 830, 840 occur at the Delivery Stroke Velocity. The pressurization period 835 continues to occur at 800° per second. The Delivery Stroke Speed is continuously updated based on the previous volume measurement.

Delivery Stroke Velocity

The Delivery Stroke Velocity is the velocity at which the cam shaft 3080 needs to rotate in order for the controller to maintain the requested flow rate. This value is limited to speeds greater than 500° per second (approx. 700 mL per Hr). This value is also limited to less than the velocity required to maintain the requested flow rate in the case where the peristaltic pump 2990 is only delivering 80 uLs per stroke. This would be a significant under-fill and likely the result of some issue upstream of the peristaltic pump 2990. The velocity is calculated using the current volume delivered, requested volume delivered, previous stroke volume, and requested flow rate as pictured in FIG. 327.

A=Trajectrory Volume, at end of previous stroke
B=Measured Delivered Volume, as of previous stroke
D=Expected Stroke Volume
C=B+D-A
T=Requested Trajectory Flow Rate $$C = T(t)$$
$$t = \frac{C}{T} = \frac{B+D-A}{T}$$
$$\theta = \text{Cam Shaft Velocity}, \frac{deg}{sec}$$
$$\dot{\theta} = \frac{360°}{t} = \frac{360° * T}{B+D-A}$$

In order to achieve a consistent flow rate, particularly during low flow rate deliveries, the rate at which the plunger 3091 descends must be controlled. The goal is to keep the flow as continuous and as close to the trajectory volume as possible. This is complicated by periods where the peristaltic pump 2990 does not deliver (refill, pressurize, etc).

To achieve continuous flow, at the start of the delivery stroke the volume delivered as part of the previous stroke should be equal the trajectory volume. This ensures a smooth initial delivery (avoiding an initial "rush" to catch up). In order to accomplish this, by the end of the previous stroke the peristaltic pump 2990 must have over-delivered by the volume that is accrued during the Refill and Pressurization 830, 835 phases. This Over-Delivery volume is applied throughout the delivery stroke, such that at the start none of it is applied, but by the end the full volume is added.

An additional consideration is the fill volume. Shown in FIG. 328 is a graph of the volume delivered versus the cam angle over various fill volumes for several pump cycles. In the case of a completely full pumping chamber (approx. 150 uLs), there is a spurt of fluid as the outlet valve 3111 first opens. Alternatively, in the case of fill volumes lower than about 130 uLs, there is a tendency to pull fluid. Both of these occurrences negatively affect flow continuity. In to temper this, in some embodiments a target fill volume is set to minimize these effects.

The graph in FIG. 328 shows multiple delivery strokes, with the volume delivered normalized to 135 uLs. Most of the stroke is repeatable, once adjusting for the fill volume. The result of all of this is a third-order function that calculates a desired cam shaft 3080 angle given a requested volume. See below for the pertinent equations.

Variables
n=Current Delivery Stroke
i=Current Motor Control ISR cycle
f(x)=3rd Order Polynomial Fit
$E_n$=Expected Pulse Volume given a Fill Volume per current delivery stroke
$P_n$=Pulse Volume per f(x) per delivery stroke (this is a constant)
$S_n$=Expected Volume Shortage of current stroke
$T_i$=Current Target Volume via Trajectory
$V_{n-1}$=Measured Delivered Volume as of completion of previous delivery stroke
$Q_i$=Target Volume to be Delivered at time i
$F_i$=Fraction of Stroke completed at time i
$O_n$=Overhead Volume (Trajectory volume increase during non-delivery portions of cycle)
$\theta_i$=Requested Can Shaft Angle
$\theta_0$=Inital Cam Shaft Angle at start of delivery stroke Equations $$S_n = P_n - E_n$$
$$Q_i = T_i - V_{n-1}$$
$$F_i = \frac{Q_i}{E_n}$$
$$\theta_i = f(Q_i + S_n + O_n F_i) + \theta_0$$

In some embodiments, the motor 3072 velocity during the delivery stroke is limited to no faster than the Delivery Stroke Velocity. The result of this is that at high speeds, the requested position is always ahead of the speed-limited position. At lower flow rates, the cam shaft 3080 position quickly reaches the calculated position and subsequently follows the above algorithm.

Down-stream Occlusion Detection

The controller may determine whether a downstream occlusion exists by comparing the pressures or forces measured at the occlusion detector 3535 (3068 in FIG. 257) during the delivery period 840, during the previous refill period 830 and the filtered pressure data from previous pump cycles. Here a pump cycle is a complete revolution of the cam-shaft 3080 producing a refill, a pressurization and a delivery period (830, 835, 840). A downstream occlusion will be determined to exist by the processor if an occlusion condition occurs. In some embodiments, the occlusion condition may be determined to exist using the equations described in the following paragraphs. The variables of the occlusion equations are as follows:

f=low pass filter constant,
$IP_{MIN}$=sum of changes in $P_{MIN}$ since therapy started,
$P_{MIN\ i}$=minimum pressure while outlet valve is closed during pump cycle i, $P_{MAX\ i}$=maximum pressure while outlet valve is open during pump cycle i, $\Delta FP_{MIN\ i}$=change in minimum pressure in cycle i less the low-pass filtered change in minimum pressure, $\Delta P_L$=the minimum pressure for the first pump cycle minus the lowest pressure recorded during the therapy, $\Delta P_{MIN\ i}$=change in minimum pressure equal to the difference between the minimum pressure of pump cycle i ($P_{MIN\ i}$) and the minimum pressure of the previous pump cycle $P_{MINi-1}$, $\Delta P^*_{MIN\ i}$=low pass filtered value of the change in minimum pressure, $\Delta P_{P\ i}$=maximum change in pressure over a cycle, and $\Sigma\Delta P_{MIN}$ i=sum of the change in minimum pressure ($\Delta P_{MIN}$) from the start of therapy through the current cycle i.

The pressures or forces measured by the sensor 3545B may be low pass filtered to reject spurious noise. In one embodiment, the low pass filter may reject noise above 1000 Hz. A plot of filtered hypothetical pressures over time is plotted in FIG. 329, where the pressure oscillates between lower pressures 850 when outlet valve 3111 (FIG. 259) is closed and high pressures 851 when the outlet valve 3111 is open and flow is being forced through the infusion tube 3210 that is pressed against the pressure sensor 3535B. A downstream occlusion may create greater flow resistance as fluid is pushed toward the patient resulting in higher peak pressures and/or higher pressures when the outlet valve 3111 is closed as the restricted fluid slowly flows past a partial occlusion.

An exemplary embodiment of a downstream occlusion test compares $\Delta P_{MIN\ i}$ to a constant value, where $\Delta P_{MIN\ i}$ is the change in minimum pressure of sequential cycles that is equal to the difference between: (1) the minimum pressure of a pump cycle i ($P_{MIN\ i}$) and (2) the minimum pressure of the previous pump cycle $P_{MINi-1}$. If the $\Delta P_{MIN\ i}$ is greater than a predefined value, the processor may declare an occlusion. That is, the processor (e.g., the RTP 3500 of FIG. 324) is configured to, using the pressure signal from the pressure sensor 368 (see FIG. 357), determine that a downstream occlusion exists when a difference between a first trough pressure level of a first cycle and a second trough pressure level of a second cycle is greater than a predetermined threshold. The pressure signal from the pressure sensor 368 may be filtered (analog or digital filtering) or unfiltered. The first and second cycles may be sequential to each other. The terms "first" and "second" are not meant to indicate order or precedence of the cycles, but these terms are used to indicate that there are two cycles used for the determination. The pressure or volume data of each cycle may be referenced by a counter that increments with each pump cycle from 0 to n cycles. The current pump cycle is referred to as cycle i. Herein, the pressure, volume or other data value for a given cycle will be identified with a subscript such that $P_{MIN\ i}$ is the minimum pressure during cycle i. The $\Delta P_{MIN\ i}$ is the difference between the minimum pressure of the current pump cycle ($P_{MIN\ i}$) and the minimum pressure of the previous pump cycle $P_{MINi-1}$.

Alternatively, the processor may declare a downstream occlusion for cycle i, if the low-pass filtered value of change in minimum pressure ($\Delta P^*_{MIN\ i}$) exceeds a first given threshold. The asterisk indicates that the series pressure data is low-passed filtered in the time domain. The low-pass filtered value of change in minimum pressure (trough-to-trough pressure) is calculated by adding a weighted value of the new change in minimum pressure ($\Delta P^*_{MIN\ i}$) to a weighted value of the previous filtered value of the change in minimum pressure ($\Delta P^*_{MIN\ i-1}$):

$$\Delta P^*_{min\ i}=f^*\Delta P_{min\ i}+(1-f)^*\Delta P^*_{min\ i-1}$$

where f is the weighting value for the newest data. In one example, the weighting value for f is 0.05. The very first sample of the filtered pressure data $\Delta P^*_{MIN1}$ may be set to $\Delta P_{MIN1}$ (where i=1, 2, 3, etc.). In another embodiment, the following equation is used to perform the low-pass filtering:

$$\Delta P^*_{min\ i}=\Delta P^*_{min\ i-1}+f((P_{min\ i}-P_{min\ i-1})-2\Delta P^*_{min\ i-1}).$$

In another embodiment, the processor may declare a downstream occlusion for cycle i, if the difference between the current change in minimum pressure ($\Delta P_{MIN\ i}$) and the low-pass filtered change in minimum pressure ($\Delta P^*_{MIN\ i}$) is larger than a second given threshold. The difference between the current change in minimum pressure and the low-pass filtered change in minimum pressure is calculated as: $\Delta FP_{MIN\ i}=\Delta P_{MIN\ i}-\Delta P^*_{MIN\ i}$. That is, the processor (e.g., the RTP 3500 of FIG. 324) is configured to, using the pressure signal from the pressure sensor 368 (see FIG. 357), determine a downstream occlusion exists when a difference is greater than a predetermined threshold, wherein the difference is a subtraction of: (1) a filtered value of a sequential series of sequential trough-to-trough pressure values of the plurality of cycles from (2) a trough-to-trough value. The pressure signal from the pressure sensor 368 may be filtered (analog or digital filtering) or unfiltered.

In another embodiment, a downstream occlusion is declared when the sum of the changes in minimum pressure (cycle-to-cycle change) exceeds a third given threshold, where the sum of the changes in $P_{MIN}$ ($IP_{MIN}$) is calculated by summing all the changes in minimum pressures from the start of therapy, the adding the difference between the minimum pressure of the first pump cycle ($P_{MIN\ 0}$) and the minimum pressure recorded during the current therapy:

$$IP_{MIN}=\Sigma\Delta P_{MIN\ i}+\Delta P_L.$$

where $\Delta P_L$ is the initial pressure minus the lowest pressure recorded. If $IP_{MIN}$ exceeds a third given value, then the controller may declare an occlusion. That is, the processor (e.g., the RTP 3500 of FIG. 324) is configured to, using the pressure signal from the pressure sensor 368 (see FIG. 357), determine a downstream occlusion exists when a summation of each sequential trough-to-trough pressure value of the plurality of cycles is greater than a predetermined threshold. The processor (e.g., the RTP 3500 of FIG. 324) may perform this test, in some specific embodiments, by comparing the current minimum pressure of the current cycle to the lowest monitored minimum pressure of all of the previous cycles. For example, the processor (e.g., the RTP 3500 of FIG. 324) may be configured to, using the pressure signal from the pressure sensor 368 (see FIG. 357), determine a downstream occlusion exists when a trough of a cycle of the plurality of cycles is greater than a lowest trough of all of the plurality of cycles by a predetermined amount. The pressure signal from the pressure sensor 368 may be filtered (analog or digital filtering) or unfiltered.

A fourth example of a downstream occlusion test evaluates the maximum change in pressure over a cycle ($\Delta P_{P\ i}$) by subtracting the minimum pressure of the current cycle ($P_{MIN\ i}$) from the maximum pressure of the same cycle ($P_{MIN\ i}$):

$$\Delta P_{P\ i}=P_{MAX\ i}-P_{MIN\ i-1}$$

where $P_{MAX\ I}$ is the maximum pressure during the delivery period 840. The controller may declare a downstream occlusion if the maximum change in pressure over a cycle ($\Delta P_{P\ i}$) exceeds a fourth given threshold. That is, the processor (e.g., the RTP 3500 of FIG. 324) is configured to, using the pressure signal from the pressure sensor 368 (see FIG. 357), determine a downstream occlusion exists when a difference between a peak pressure level and a trough pressure level is greater than a predetermined threshold in a cycle of the plurality of cycles. The pressure signal from the pressure sensor 368 may be filtered (analog or digital filtering) or unfiltered. In the event of a downstream occlusion, the controller may command the pump to backflow fluid through the peristaltic pump 2990 in order to relieve the pressure on the occlusion. It may be beneficial to relieve the pressure on the occlusion to avoid a bolus of fluid to be directed to the patient when the occlusion is relieved. In one example, the occlusion may be cleared by unpinching or unkinking the infusion tube 3210 between the peristaltic pump 2990 and the patient.

Upstream Occlusion/Air-in-Line Measurement

The controller may detect an upstream occlusion or determine the volume of air pumped toward the patient based on the measured volume per stroke and historical volume per stroke average. The controller calculates an under-deliver volume for each stroke $V_{UD\ i}$ as:

$$V_{UD_i} = V_{avg_i} - V_i$$

$$V_{avg_i} = fv * V_i + (1-fv) * V_{avg_{i-1}}$$

where fv is a weighting factor for the volume and $V_i$ is the volume of fluid pumped during cycle i. In yet additional embodiments, the controller calculates Vavgi as follows:

$$V_{avg_i} = V_{avg_{i-1}} + f_v(V_i - 2V_{avg_{i-1}}).$$

The controller maintains a buffer of several $V_{UD}$ values, dropping the oldest one as the newest $V_{UD}$ is added. If the air-in-line detector 3545 (3066 in FIG. 257) detects a bubble, the controller will assume the $V_{UD\ i}$ represents an air bubble. If the air-in-line detector 3545 does not detect air, then the $V_{UD\ i}$ is assumed to be under-delivered volume. The controller may declare an upstream occlusion, if $V_{UD\ i}$ is greater than a given value the air-in-line detector 3545 does not detect air. The controller may determine the volume of air pumped toward the patient and may signal an alert if the air volume exceeds a first value over a first time period and alarm if air volume exceeds a second value over a second time period. In one example, the controller calculates the volume of the air bubble ($V_{BUBBLE}$) by summing the under-deliver volumes ($V_{UD\ i}$) for each stroke when the air-in-line detector 3545 signals the presence of air and some number of $V_{UD\ i}$ before the first detection of air:

$$V_{BUBBLE} = \Sigma V_{UD\ i}.$$

In one example, $V_{BUBBLE}$ is calculated for each stroke when the air-in-line detector 3545 signals the presence of air and the three $V_{UD\ i}$ before the first detection of air.

In an alternative embodiment, the controller calculates a under-deliver volume for each stroke $V_{UD\ i}$ as:

$$V_{UD\ i} = V_T - V_i$$

where $V_T$ is the nominal volume of one pump cycle that is stored in the controller. In this alternative embodiment, the controller calculates the total volume of the air bubble ($V_{BUBBLE}$) by summing the under-deliver volumes ($V_{UD\ i}$) for each stroke when the air-in-line detector 3545 signals the presence of air and some number of $V_{UD\ i}$ before the first detection of air:

$$V_{BUBBLE} = \Sigma(V_{UD\ i} - V^*_{UD\ i})$$

$$V^*_{UD\ i} = fv * V^*_{UD\ i} + (1-fv) * V_{UD\ i-1}$$

where $V^*_{UD\ i}$ is the filtered value of $V_{UD}$ and fv is the weighting average. In another embodiment, $V^*_{UD\ i}$ is calculated as follows:

$$V^*_{UD_i} = V^*_{UD_{i-1}} + (fv * ((V_{UD_i} + V_{UD_{i-1}}) - (2 * V^*_{UD_{i-1}}))).$$

In one example, $V_{BUBBLE}$ is calculated for each stroke when the air-in-line detector 3545 signals the presence of air and the three $V_{UD\ i}$ before the first detection of air. In one embodiment, each bubble volume $V_{BUBBLE}$ is added to a buffer of bubble volumes covering a set period of time and the sum of the bubble volumes in the buffer are evaluated against a standard. If the sum of the bubble volumes exceeds a given threshold, then the controller alarms for air in line (i.e., air in the tube). The controller may reverse the peristaltic pump 2990 to pull the air back from the patient. In one example, the buffer captures the most recent 15 minutes of operation and the air volume threshold is set to a value between 50 and 1000 microliters. In one example, bubble volumes smaller than a given value may be counted in the summation of the bubble volume. In one example, bubble volumes less than 10 microliters may be ignored. The air volume threshold may be user settable, or may be part of the DERS data that is downloaded from the device server gateway. The DERS and device server gateway are described in detail in the cross referenced nonprovisional application for SYSTEM, METHOD, AND APPARATUS FOR ELECTRONIC PATIENT CARE.

Leak Test

A leak is determined at the end of the pressurization period 835 by monitoring the plunger 3091 position while the plunger L-shaped cam follower 3090 is not resting on the plunger cam 3083 and the plunger tip 3091B is resting on the infusion tube 3210. If the plunger 3091 moves by more than a given value over a given time indicating that fluid has leaked past the valves 3101, 3111. In one embodiment, the peristaltic pump 2990 is stopped for half a second every six seconds at the end of pressurization period 835 to monitor the plunger 3091 position to determine if a leak exists between the valves 3101, 3111.

State Diagram for Delivery of Fluid by the Peristaltic Pump

The state diagram for the software that controls the delivery of fluid is pictured in FIG. 330. The Delivery Top State (capitalized phases herein may refer to variables, processes, or data structures, etc. depending on context) is the SuperState for the entire pump controller 3430 and comprises the Idle State and the Running State. The Idle State is entered upon starting the pump controller 3430, completing a delivery, or stopping/aborting a delivery. The Running State is the SuperState for all states that involve actuating the motor 3072 or performing a delivery. The Running State also handles Freeze commands.

The Delivery State is the SuperState for all states involving performing a delivery. This state handles Stop commands, which had two behaviors depending on the current state. If commanded during an active delivery the peristaltic pump 2990 will finish delivery after current stroke is completed. If the peristaltic pump 2990 is currently in the freeze state, it will immediately end the delivery.

The Start Deliver State signifies the beginning of a delivery cycle, or one rotation of the cam shaft 3080. The peristaltic pump 2990 will transition to one of three states depending on the current conditions. If enough time has elapsed since the previous leak check, the Moving to Leak Check Position State is called. If the previous delivery was frozen and aborted mid-stroke, the Moving to Plunger Down State is entered in order to resume delivering where the previous delivery ended. Otherwise, the motor controller 3430 transitions to the Moving to Pressurized Position State.

The Moving to Leak Check Position State commands the motor controller 3430 to move to and hold position at the Valves Closed Plunger Down position. The motor 3072 velocity is commanded to move at 800° per second. Upon receiving notification that the cam shaft 3080 has reached the desired position the Pressurized Position measurement is taken for volume calculations and the Waiting for Leak Check State is called.

The Waiting for Leak Check State idles until a set amount of time has elapsed, allowing the infusion tube 3210 to settle and, in the case of a leak, fluid to escape the pumping chamber. Once the time has elapsed, the plunger 3091 position is measured again and compared to the Pressurized Position in order to determine the presence of a leak condition. The Fault Detector is told that the delivery stroke is starting in order to monitor for air and occlusions and the Moving to Plunger Down Position State is called.

The Moving to Pressurized Position State commands the motor controller 3430 to move towards and send a notification upon reaching the Valves Closed Plunger Down position. It will continue to move upon reaching this position until a new command is issued. The motor 3072 velocity is commanded to move at 800° per second.

Upon receiving notification that the cam shaft 3080 has reached the desired position the Pressurized Position measurement is taken for volume calculations and the Moving to Plunger Down Position State is called. The Fault Detector is told that the delivery stroke is starting in order to monitor for air and occlusions.

The Moving to Plunger Down Position State controls the cam shaft 3080 position throughout the portion of the cam shaft 3080 rotation that the outlet valve 3111 is open. The cam shaft 3080 position is controlled in such a way as to attempt to keep the flow as consistent as possible. During this state, the motor 3072 velocity is again limited to no greater than the calculated Delivery Stroke Velocity. There are two paths by which the motor controller 3430 can exit this state. In the first case, the state is notified once the cam shaft 3080 reaches the Outlet Open Plunger Down position. Alternatively, if the total delivery volume reaches the commanded volume during the stroke, the cam shaft 3080 position is frozen and the state is notified that the stroke is complete.

Upon being notified that cam shaft 3080 has reached the Outlet Open Plunger Down position, the plunger 3091 position is stored as the Post Delivery Position measurement and the Fault Detector is told that the delivery stroke is complete. Using this measurement, the volume delivered is calculated (using the calibration in Section 3). If the peristaltic pump 2990 was stopped mid-stroke, the volume delivered is estimated using the current position and the fill volume. Using the updated delivery volume information, the updated Delivery Stroke Velocity is calculated. Finally, in the case where the delivery volume has been reached, the peristaltic pump 2990 calls the End Deliver State. Otherwise the Moving to Fill Position State is entered.

The Moving to Fill Position State commands the motor controller 3430 to move towards and send a notification upon reaching the Inlet Valve Open Plunger Up position (minus the Pre-Fill Window). It will continue to move upon reaching this position until a new command is issued. The motor 3072 velocity is commanded to move at the calculated Delivery Stroke Velocity. Once the desired position is reached, the Moving Through Fill Position State is called.

The Moving to Fill Position State commands the motor controller 3430 to move towards and send a notification upon reaching the Inlet Valve Open Plunger Up position (plus the Post-Fill Window). It will continue to move upon reaching this position until a new command is issued. The motor 3072 velocity is commanded to move at the calculated Refill Stroke Velocity (see Section 8.3). The Refill Stroke Velocity is calculated upon entering this state prior to issuing a new motor 3072 command. Once the desired position is reached, the End Deliver State is called.

The End Deliver State checks if the delivery volume has been attained or a stop has been requested. If so, the motor controller 3430 enters the Idle State and the cam shaft 3080 position is commanded to go to the Inlet Valve Open Plunger Up position. Otherwise the Start Deliver State is called, and a new delivery cycle begins.

The Freeze State is called when the Running State processes a Freeze command. The cam shaft 3080 position is frozen at its current position and the Fault Detector and Volume Estimator are notified that the delivery if frozen.

If a Resume Delivery command is received while in the Freeze State, the state machine is returned to the state which it was in prior to entering the Freeze State. The Fault Detector and Volume Estimator are both informed that the delivery is resuming. If a Stop Delivery command is received, the Idle State is called.

The Calibration State is the SuperState for the states involved in calibrating the cam shaft 3080 and plunger 3091 positions.

The Finding Home State performs the cam shaft 3080 calibration. Entering this state, the IO Access class is notified that a calibration is beginning so certain sensor protections can be turned off. The state receives a notification once the process is completed. Upon receiving this notification, the calibration values are sent to the non-volatile memory. Finally, the Moving to Home State is called.

The Moving to Home State simply commands the peristaltic pump 2990 to move to the Inlet Valve Open Plunger Up position. Upon reaching this position the peristaltic pump 2990 returns to the Idle State.

FIG. 331 rates a possible state chart of the code to detect to detect a fault of the peristaltic pump 2990 and FIG. 332 illustrates a occlusion detection state chart to detect an occlusion of the peristaltic pump 2990 in accordance with an embodiment of the present disclosure. FIG. 33 shows a feedback control loop to control the speed the peristaltic pump 2990 motor 3072 in a peristaltic pump 2990 in accordance with an embodiment of the present disclosure.

Software Architecture

The software architecture of the peristaltic pump 2990 is shown schematically in FIG. 334. The software architecture divides the software into cooperating subsystems that interact to carry out the required pumping action. The software may be equally applicable to all the embodiments described herein. The software may also be used for other pump embodiments which may not be described herein. Each subsystem may be composed of one or more execution streams controlled by the underlying operating system. Useful terms used in the art include operating system, subsystem, process, thread and task.

Asynchronous messages 4130 are used to 'push' information to the destination task or process. The sender process or task does not get confirmation of message delivery. Data delivered in this manner is typically repetitive in nature. If messages are expected on a consistent schedule, the receiver process or task can detect a failure if a message does not arrive on time.

Synchronous messages 4120 may be used to send a command to a task or process, or to request (pull) information from a process or task. After sending the command (or request), the originating task or process suspends execution while awaiting a response. The response may contain the requested information, or may simply acknowledge the receipt of the sent message. If a response is not received in a timely manner, the sending process or task may time out. In such an event the sending process or task may resume execution and/or may signal an error condition.

An operating system (OS) is a collection of software that manages computer hardware resources and provides common services for computer programs. The operating system acts as an intermediary between programs and the computer hardware. Although some application code is executed directly by the hardware, the application code may frequently make a system call to an OS function or be interrupted by it.

The RTP 3500 runs on a Real Time Operating System ("RTOS") that has been certified to a safety level for medical devices. An RTOS is a multitasking operating system that aims at executing real-time applications. Real-time operating systems often use specialized scheduling algorithms so that they can achieve a deterministic nature of behavior. The UIP 3600 runs on a Linux operating system. The Linux operating system is a Unix-like computer operating system.

A subsystem is a collection of software (and perhaps hardware) assigned a specific set of (related) system functionality. A subsystem has clearly defined responsibilities and a clearly defined interface to other subsystems. A subsystem is an architectural division of the software that uses one or more processes, threads or tasks.

A process is an independent executable running on a Linux operating system which runs in its own virtual address space. The memory management hardware on the CPU may be used to enforce the integrity and isolation of this memory, by write protecting code-space, and disallowing data access outside of the process' memory region. Processes can only pass data to other processes using inter-process communication facilities.

In Linux, a thread is a separately scheduled, concurrent path of program execution. On Linux, a thread is always associated with a process (which must have at least one thread and can have multiple threads). Threads share the same memory space as its 'parent' process. Data can be directly shared among all of the threads belonging to a process but care must be taken to properly synchronize access to shared items. Each thread has an assigned execution priority.

A task on an RTOS (Real Time Operating System) is a separately scheduled, concurrent path of program execution, analogous to a Linux 'thread'. All tasks share the same memory address space which consists of the entire CPU memory map. When using an RTOS that provides memory protection, each task's effective memory map is restricted by the Memory Protection Unit (MPU) hardware to the common code space and the task's private data and stack space.

The processes on the UIP 3600, communicate via IPC calls as shown by the one-way arrows in FIG. 334. Each solid-lined arrow represents a synchronous message 4120 call and response, and dotted-line arrows are asynchronous messages 4130. The tasks on the RTP 3500 similarly communicate with each other. The RTP 3500 and UIP 3600 are bridged by an asynchronous serial line 3601, with one of an InterComm Process 4110 or InterComm Task 4210 on each side. The InterComm Process 4110 presents the same communications API (Application Programming Interface) on both sides of the bridge, so all processes and tasks can use the same method calls to interact.

Referring now to also FIG. 324, the RTP 3500 receives data from the Hall sensors 3436 (i.e., rotation sensors) and the UI 3600 receives data from the encoder 3438 (i.e., a counter). The RTP 3500 and UI 3600 are in operative communication with each other and are configured to determine whether the monitored plurality of pulses determined by the RTP 3500 corresponds to the counted pulses as received by the UI 3600 processor from the encoder 3438. This may be done by determining whether they agree by a predetermined amount, such as a percentage amount, a predetermined number of pulses, a predetermined angular value, and/or a predetermined number of degrees of rotation by the motor.

In another embodiment, the RTP 3500 and UI 3600 each estimate an amount of fluid pumped and determine whether the estimated volumes of fluid pumped is within a predetermined range relative to each other. This may be done by determining whether they agree by a predetermined range, such as a percentage amount.

The Executive Process 4320 may be invoked by the Linux system startup scripts after all of the operating system services have started. The Executive Process 4320 may then start the various executable files that comprise the software on the UIP 3600. If any of the software components should exit or fail unexpectedly, the Executive Process 4320 may be notified, and may generate the appropriate alarm.

While the system is running, the Executive Process 4320 may act as a software 'watchdog' for various system components. After registering with the Executive process 4320, a process may be required to 'check in' or send a signal periodically to the executive process 4320. Failure to 'check in' at the required interval may be detected by the Executive Process 4320. Upon detection of a failed subsystem, the Executive Process 4320 may take remedial action of either: do nothing, declaring an alarm, or restarting the failed process. The remedial action taken may be predetermined by a table entry compiled into the Executive Process 4320. The 'check-in' interval may vary from process to process based in part on the importance of the process. The check-in interval may also vary during peristaltic pump 2990 operation to optimize the pump controller 4256 response by minimizing computer processes. In one example embodiment, during tube loading, the pump controller 4256 may check-in less frequently than during active pumping.

In response to the required check-in message, the Executive Process 4320 may return various system status items to processes that checked-in. The system status items may be the status of one or more components on the pump and/or errors. The system status items may include: battery status, WiFi connection status, device gateway connection status, device status (Idle, Infusion Running, Diagnostic Mode, Error, Etc.), technical error indications, and engineering log levels.

A thread running in the Executive Process 4320 may be used to read the state of the battery 3420 from an internal monitor chip in the battery 3420. This may be done at a relatively infrequent interval such as every 10 seconds.

The UI View 4330 may implement the graphical user interface (GUI), rendering the display graphics on the display screen 3725, and responding to inputs on the touchscreen 3735 or other data input means. The UI View 4330 design may be stateless. The screen being displayed may be commanded by the UI Model process 4340, along with any variable data to be displayed. The commanded display is refreshed periodically regardless of data changes.

The style and appearance of user input dialogs (Virtual keyboard, drop down selection list, check box etc.) may be specified by the screen design, and implemented entirely by the UI View 4330. User input may be collected by the UI View 4330, and sent to the UI Model 4340 for interpretation. The UI View 4330 may provide for multi-region, multilingual support with facilities for the following list including but not limited to: virtual keyboards, unicode strings, loadable fonts, right to left entry, translation facility (loadable translation files), and configurable numbers and date formats.

The UI Model 4340 may implement the screen flows, and so control the user experience. The US Model 4340 may interact with the UI View 4330, specifying the screen to display, and supply any transient values to be displayed on the screen. Here screen refers the image displayed on the physical display screen 3725 and the defined interactive areas or user dialogs i.e. buttons, sliders, keypads etc, on the touch screen 3735. The UI Model 4340 may interpret any user inputs sent from the UI View 4330, and may either update the values on the current screen, command a new screen, or pass the request to the appropriate system service (i.e. 'start pumping' is passed to the RTP 3500).

When selecting a medication to infuse from the Drug Administration Library, the UI Model 4340 may interact with the Drug Administration Library stored in the local data base which may be part of the Database System 4350. The user's selections may setup the run time configurations for programming and administering the desired medication.

While the operator may be entering an infusion program, the UI Model 4340 relays the user's input values to the Infusion Manager 4360 for validation and interpretation. Therapeutic decisions may not be made by the UI Model 4340. The treatment values may be passed from the Infusion Manager 4360 to the UI Model 4340 to the UI View 4330 to be displayed for the user.

The UI Model 4340 may continuously monitor the device status gathered from the Infusion Manager 4360 (current infusion progress, alerts, door sensor 3163 and slide clamp sensor 3152, etc.) for possible display by the UI View 4330. Alerts/Alarms and other changes in system state may provoke a screen change by the UI Model 4340.

Additional Dosage Safety Software Algorithm(s)

The Infusion Manager Process (IM) 4360 may validate and control the infusion delivered by the peristaltic pump 2990. To start an infusion, the user may interact with the UI View/Model 4330/4340 to select a specific medication and clinical use. This specification may select one specific Drug Administration Library (DAL) entry for use. The IM 4360 may load this DAL entry from the database 4350, for use in validating and running the infusion.

Once a Drug Administration Library entry is selected, the IM 4340 may pass the dose mode, limits for all user enterable parameters, and the default values (if set) up to the UI Model 4340. Using this data, the UI Model 4340 may guide the user in entering the infusion program.

As each parameter is entered by the user, the value may be sent from the UI View/Model 4330/4340 to the IM 4360 for verification. The IM 4360 may echo the parameters back to the UI View/Model 4330/4340, along with an indication of the parameter's conformance to the DAL limits. This may allow the UI View/Model 4330/4340 to notify the user of any values that are out of bounds.

When a complete set of valid parameters has been entered, the IM 4360 may also return a valid infusion indicator, allowing the UI View/Model 4330/4340 to present a 'Start' control to the user.

The IM 4360 may simultaneously make the infusion/pump status available to the UI View/Model 4330/4340 upon request. If the UI View/Model 4330/4340 is displaying a 'status' screen, it may request this data to populate it. The data may be a composite of the infusion state, and the pump state.

When requested to run the (valid) infusion, the IM 4360 may pass the 'Infusion Worksheet' containing user specified data and the 'Infusion Template' containing the read-only limits from the DAL as a CRC'd binary block to the Infusion Control Task 4220 running on the RTP 3500. The Infusion Control Task 4220 on the RTP 3500 may take the same user inputs, conversions and DERS inputs and recalculate the Infusion Worksheet. The Infusion Control Task 4220 calculated results may be stored in a second CRC'd binary block and compared to the first binary block from the UIP 3600. The infusion calculations performed on the UIP 3600 may be recalculated and double checked on the RTP 3500 before the infusion is run.

Coefficients to convert the input values (i.e. □1, grams, %) to a standard unit such as ml may be stored in the UIP 3600 memory or database system 4350. The coefficients may be stored in a lookup table or at specific memory locations. The lookup table may contain 10's of conversion values. In order to reduce the chance that flipping a single bit will resulting in the wrong conversion factor being used, the addresses for the conversion values may be distributed among the values from zero to 4294967296 or $2^{32}$. The addresses may be selected so that the binary form of one address is never just one bit different from a second address.

While an infusion is running, the IM 4360 may monitor its progress, sequences, pauses, restarts, secondary infusions, boluses and KVO (keep vein open) scenarios as needed. Any user alerts requested during the infusion (Infusion near complete, KVO callback, Secondary complete callback, etc) may be tracked and triggered by the IM 4360.

Processes on the UIP 3600 may communicate with each other via a proprietary messaging scheme based on a message queue library that is available with Linux. The system may provide for both acknowledged (synchronous message 4120) and unacknowledged (asynchronous message 4130) message passing.

Messages destined for the Real-time Processor (RTP) 3500 may be passed to the InterComm Process 4310 which may forward the messages to the RTP 3500 over a serial link 3601. A similar InterComm Task 4210 on the RTP 3500 may relay the message to its intended destination via the RTP 3500 messaging system.

The messaging scheme used on this serial link 3601 may provide for error detection and retransmission of flawed messages. This may be needed to allow the system to be less susceptible to electrical disturbances that may occasionally 'garble' inter-processor communications.

To maintain a consistent interface across all tasks, the message payloads used with the messaging system may be data classes derived from a common baseclass (MessageBase). This class adds both data identity (message type) and data integrity (CRC) to messages.

The Audio Server Process 4370 may be used to render sounds on the system. All user feedback sounds (key press beeps) and alarm or alert tones may be produced by playing pre-recorded sound files. The sound system may also be used to play music or speech if desired.

Sound requests may be symbolic (such as "Play High Priority Alarm Sound"), with the actual sound file selection built into the Audio Server process 4370. The ability to switch to an alternative soundscape may be provided. This ability may be used to customize the sounds for regional or linguistic differences.

The Device Gateway Communication Manager Process (DGCM) 4380 may manage communications with the Device Gateway Server over a Wi-Fi network 3620, 3622, 3720. The DGCM 4380 may be started and monitored by the Executive Process 4320. If the DGCM 4380 exits unexpectedly, it may be restarted by the Executive Process 4320 but if the failures are persistent the system may continue to function without the gateway running.

It may be the function of the DGCM 4380 to establish and maintain the Wi-Fi connection and to then establish a connection to the Device Gateway. All interactions between the DGCM 4380 and the Device Gateway may system such as the system described in the cross-referenced nonprovisional application for System, Method, and Apparatus for Electronic Patient Care.

If the connection to the gateway is unavailable or becomes unavailable, the DGCM 4380 may discontinue any transfers in progress, and attempt to reconnect the link. Transfers may be resumed when the link is reestablished. Network and Gateway operational states may be reported periodically to the Executive Process 4320. The Executive Process 4320 may distribute this information for display to the user.

The DGCM 4380 may function as an autonomous subsystem, polling the Device Gateway Server for updates, and downloading newer items when available. In addition the DGCM 4380 may monitor the logging tables in the database, uploading new log events as soon as they are available. Events that are successfully uploaded may be flagged as such in the database. After a reconnection to the Device Gateway Server, the DGCM 4380 may 'catch up' with the log uploads, sending all items that were entered during the communications disruption. Firmware and Drug Administration Library updates received from the Gateway may be staged in the UIP's 3600 file system for subsequent installation. Infusion programs, clinical advisories, patient identification and other data items destined for the device may be staged in the database.

The DGCM 4380 may report connection status and date/time updates to the Executive Process 4320. There may be no other direct connections between the DGCM 4380 and any of the other operational software. Such a design decouples the operational software from the potentially transient availability of the Device Gateway and Wi-Fi network.

The Motor Check 4383 software reads a hardware counter or encoder 3438 (FIG. 325) that reports motor 3072 rotation. The software in this module independently estimates the motor's 3072 movements, and compares them to the expected motion based on the user inputs for rate of infusion. This is an independent check for proper motor control. However, the primary motor control software may be executed on the RTP 3500.

Event information may be written to a log via the Logging Process 4386 during normal operation. These events may consist of internal machine status and measurements, as well as therapy history events. Due to the volume and frequency of event log data, these logging operations may be buffered in a FIFO queue while waiting to be written to the database.

A SQL database (PostgreSQL) may be used to store the Drug Administration Library, Local Machine Settings, Infusion History and Machine Log data. Stored procedures executed by the database server may be used to insulate the application from the internal database structures.

The database system 4350 may be used as a buffer for log data destined for the Device Gateway server, as well as a staging area for infusion settings and warnings sent to the pump from the Gateway.

Upon requesting the start of an infusion, the DAL entry and all user selected parameters may be sent to the Infusion Control Task 4220. All of the DAL validations and a recalculation of the infusion rate and volume based upon the requested dose may be performed. The result may be checked against the results calculated by the IM 4360 on the UIP 3600. These results may be required to match to continue.

When running an infusion, the Infusion Control Task 4220 may control the delivery of each infusion 'segment'; i.e. one part of an infusion consisting of a volume and a rate. Examples of segments are: a primary infusion, KVO, bolus, remainder of primary after bolus, primary after titration, etc. The infusion segments are sequenced by the IM Process 4360 on the UIP 3600.

The Pump Control task 4250 may incorporate the controllers that drive the pumping mechanism. The desired pumping rate and amount (VTBI) may be specified in commands sent from the Infusion Control Task 4220.

The Pump Control 4250 may receive periodic sensor readings from the Sensor Task 4264. The new sensor readings may be used to determine the motor 3072 speed and position, and to calculate the desired command to send to the Brushless Motor Control IRQ 4262. The receipt of the sensor message may trigger a recalculation of the controller output.

While pumping fluid, the Pump Control Task 4250 may perform at least one of the following tasks: controlling pumping speed, measuring volume delivered, measuring air detected (over a rolling time window), measuring fluid pressure or other indications of occlusions, and detecting upstream occlusions.

Relevant measurements may be reported to the RTP Status Task 4230 periodically. The Pump Control 4250 may execute one infusion segment at a time, stopping when the commanded delivery volume has been reached. The Sensor Task 4264 may read and aggregate the sensor data used for the dynamic control of the pumping system. The sensor data may include the rotary encoder 3130 measuring the camshaft, the linear encoders 3520, 3525 measuring the position of the plunger 3091.

The sensor task 4264 may be scheduled to run at a consistent 1 kHz rate (every 1.0 ms) via a dedicated counter/timer. After all of the relevant sensors are read, the data may be passed to the Pump Control Task 4250 via an asynchronous message 4120. The periodic receipt of this message may be used as the master time base to synchronize the peristaltic pump's 2990 control loops.

The RTP Status Task 4230 may be the central repository for both the state and the status of the various tasks running on the RTP 3500. The RTP Status Task 4230 may distribute this information to both the IM 4360 running on the UIP 3600, as well as to tasks on the RTP 3500 itself.

The RTP Status Task 4230 may also be charged with fluid accounting for the ongoing infusion. Pump starts and stops, as well as pumping progress may be reported to RTP Status 4230 by the Pump Control Task 4256. The RTP Status Task 4230 may account for at least one of the following: total volume infused, primary volume delivered, primary VTBI (counted down), volume delivered and VTBI of a bolus while the bolus is in progress, and volume delivered and VTBI of a secondary infusion while the secondary infusion is in progress.

All alerts or alarms originating on the RTP 3500 may be funneled through the RTP Status Task 4230, and subsequently passed up to the UIP 3600.

While the unit is in operation, the program flash, and RAM memory may be continually tested by the Memory Checker Task 4240. This non-destructive test may be scheduled so that the entire memory space on the RTP 3500 is tested every few hours. Additional periodic checks may be scheduled under this task if needed.

Tasks running on the RTP 3500 may be required to communicate with each other as well as to tasks that are executing on the UIP 3600.

The RTP messaging system may use a unified global addressing scheme to allow messages to be passed to any task in the system. Local messages may be passed in memory utilizing the facilities of the RTOS' message passing, with off-chip messages routed over the (asynchronous serial 3601) communications link by the InterComm Task 4210.

The InterComm Task 4210 may manage the RTP 3500 side of the serial link 3601 between the two processors. It is the RTP 3500 equivalent of the InterComm Process 4310 on the UIP 3600. Messages received from the UIP 3600 may be relayed to their destination on the RTP 3500. Outbound messages may be forwarded to InterComm Process 4310 on the UIP 3600.

All messages between the RTP 3500 and the UIP 3600 may be checked for data corruption using an error-detecting code (32 bit CRC). Messages sent over the serial link 3601 may be re-sent if corruption is detected. This provides a communications system that may be reasonably tolerant to ESD. Corrupted messages within the processor between processes may be handled as a hard system failure. All of the message payloads used with the messaging system may be data classes derived from a common baseclass (MessageBase) to assure consistency across all possible message destinations.

Brushless Motor control 4262 may not run as a task; it may be implemented as a strict foreground (interrupt context) process. Interrupts may be generated from the commutator or hall sensors 3436, and the commutation algorithm may be run entirely in the interrupt service routine.

FIGS. 335 and 336 illustrate the geometry of two dualband antennas that may be used with the peristaltic pump 2990 in accordance with en embodiment of the present disclosure. FIG. 335 shows a top and a bottom view of the antenna, which may be fabricated using metallic layers on a substrate, such as is typically made when manufacturing a printed circuit board. FIG. 336 may also be fabricated using a printed circuit board manufacturing method.

FIG. 337 shows a state diagram illustrating a method 5065 of providing a watchdog functionality in accordance with an embodiment of the present disclosure. The method 5065 is shown as a state diagram and includes states, 5067, 5069, 5099, 5072, 5075, 5077 and 5079, and transition conditions 5066, 5068, 5070, 5071, 5073, 5074, 5076, 5078, 5080, and 5081.

The method 5065 may be implemented by software, hardware, software in execution, or some combination thereof (e.g., as a hardware watchdog system). The method 5065 may be implemented by the watchdog 3460 of FIG. 324 such that it provides a motor enable signal to the motor controller 3431. FIGS. 338A-338F show one specific embodiment of a system that implements the method 5065 of FIG. 337.

Refer now to FIGS. 337, and 338A-338F. When the power is supplied to the watchdog system (e.g., system 5003), the method 5065 transitions 5066 to the watchdog system off state 5067 where the motor enable signal is off (e.g., line 5015), the alarm is off (e.g., line 5016), and the timer is in an unknown state. The timer may be part of the watchdog IC 5012. The watchdog IC 5012 is a window watchdog. The system 5003 also includes I2C control lines 5013 (however, other control lines may be used) that interface with an I/O expander 5004 (or other hardware latches). The I2C control lines 5013 may be part of the connections from the RTP 3500 to the watchdog 3460 of FIG. 324. Additionally, a watchdog clear signal (line 5014 of FIG. 338) may also be received from the RTP 3500 to the watchdog 3460. That is, the watchdog clear line 5014 "pets" the watchdog IC 5012.

In transition 5068, the RTP 3500 (see FIG. 324) clears the watchdog IC's 5012 timer via the watchdog clear line 5014 and the RTP 3500 enables the watchdog IC's 5012 output via the I2C control lines 5013 by instructing the I/O expander 5004 to enable a watchdog enable line 5018. This causes the method 5065 to enter into the state 5069. In state 5069, the timer is initialized (set to zero), the motor enable line 5015 is set to off and the alarm line 5016 is set to off.

The RTP 3500 enables the motor power via the I2C control lines 5013 by setting the D-flip-flop to true (using the preset pin of a D-flip-flop 5005) and pauses for 1 ms in transition 5070. The method 5065 transitions to state 5099 where the watchdog IC's 5012 timer is running, the motor enable line 5015 is enabled, and the timer is less than 200 milliseconds. If the RTP 3500 sets the watchdog clear line 5014 when the watchdog is greater than 10 milliseconds and less than 200 milliseconds, the transition 5071 transitions the method 5065 to state 5072 wherein the timer is reset. The method 5065 will transition back to state 5099.

If the timer reaches 200 milliseconds or the timer is less than or equal to 10 milliseconds and the RTP 3500 sets the watchdog clear line 5014, transition 5074 transitions the method to state 5075. In state 5075, the watchdog IC 5012 sends out a fault signal that is buffered by a buffer 5009 which clears the D-flip-flop 5005 thereby turning the motor line 5015 off. In state 5075, the watchdog IC 5012 also sends out the fault signal which is received by a NAND gate 5008 via an inverted input, which outputs a signal that is amplified by a buffer 5009 which clears a D-flip-flip 5007 and thereby turns on the a alarm line 5016. The output of the D-dlip-flop 5007 is amplified by a load switch 5006.

When the motor enable signal line 5015 is set to turn the motor off, the off signal propagates through the non-inverting input of the NAND gate 5008 after about 1 millisecond, which causes the transition 5076 to transition to state 5077 thereby allowing the alarm to be disabled. An I2C command may cause transition 5080 to reset the system 5003 back to state 5067.

Otherwise, the alarm line 5016 will continue to alarm until a silence button 5017 is pressed which is coupled to the preset of the D-flip-flop 5007 to set the alarm line 5016 to off. That is, the button will cause the transition 5078 to transition the method 5065 to state 5079. An I2C signal via the I2C control lines 5014 to the IO expander 5004 may cause the method 5065 to transition to state 5067.

FIG. 339 shows another embodiment of a peristaltic pump 5020 having an L-shaped plunger in accordance with an embodiment of the present disclosure. The pump 5020 may couple to a pole via the clamp 5028. The pump 5020 includes a lever 5022 and a door 5100 that include a cutout portion 5023. The cutout portion 5023 accommodates a bumper 5021.

The pump 5020 also includes a touchscreen 5024 coupled to the pump 5020 via an outer periphery 5025. The outer periphery 5025 includes an indicator light 5026. The indicator light 5026 may wholly wrap around the touchscreen 5024. The indicator light 5026 may include a diffuser wrapped around the touchscreen 5024 with a plurality of LED lights embedded therein (or optically coupled thereto). The indicator light 5026 may blink when the pump 5020 is running and/or it may be a specific color when the pump is running (e.g., red, blue, green, yellow, etc.). The indicator light 5026 may be continuously on when the pump is not running or is in a standby state. Additionally, alternatively, or optionally, the indicator light 5026 may be a specific color when the pump is not running or is in a standby state (e.g., red, blue, green, yellow, etc.).

The pump 5020 may also include a gesture-recognition apparatus 5094, which may be a camera. A processor of the pump 5020 may be coupled to the gesture-recognition apparatus 5094 to receive user input from a gesture by a user. That is, the processor may be configured to present a user with at least one option via the user interface 5024 and receive a selected one of the at least one option via the gesture-recognition apparatus 5094. The processor coupled to the user interface 5024 may be configured provide a plurality of pump parameter inputs where each of the plurality of pump parameter inputs is configured to receive a user inputted parameter. The processor may be configured to determine whether all of the user inputted parameters of all of the plurality of pump parameters meets at least one predetermined safety criterion. Each of the plurality of pump parameter inputs may be present without another one of the plurality of pump parameters inputs.

The processor may be configured to provide a plurality of pump parameter inputs where each of the plurality of pump parameter inputs is configured to receive a user inputted parameter. The processor may be configured to require that all of the plurality of pump parameter inputs are inputted within a predetermined amount of time. The processor may be configured to receive a corresponding user inputted parameter for the plurality of pump parameter inputs in any order.

FIG. 340 shows an exploded view of the peristaltic pump 5020 of FIG. 339 in accordance with an embodiment of the present disclosure. The pump 5020 includes an upper housing portion 5029 and a lower portion housing 5030. Additionally or alternatively, the upper portion 5029 and the lower portion 5030 of the housing 5029, 5030 may be unitarily formed in some specific embodiments. A module pumping mechanism 5103 may be coupled to the housing 5029, 5030. A motor 5101 actuates the module pumping mechanism 5103. The motor may be controlled via a circuit board 5102 that is coupled to the motor and to various sensors, actuators, the touchscreen 5024, etc. The pump 5020 also includes cabling 5031 and a battery 5027 disposed behind the touchscreen 5024 (when assembled). FIG. 341 shows a close-up view of the upper housing 5029, the lower housing 5030, and the power supply 5032. Note how the power supply is thermally coupled to the lower housing portion 5060 via the conductive path 5033.

The pump 5020 includes a power supply 5032. The power supply 5032 is coupled to a conductive path 5033 to the housing 5030, 5029 (when assembled). The conductive path 5033 may be a piece of metal and may be unitarily formed with the housing 5030 (or 5029). The power supply 5032 may use the housing 5029, 5030 as a heat sink. The power supply 5032 may use any surface of the housing 5029, 5030 so that it is thermally coupled thereto and/or may be thermally coupled to the housing 5029, 5030 via the thermally conductive path 5033.

FIG. 342A shows a front view of the display of the pump 5020 and FIG. 342B shows a back view of the display of the pump 5020 in accordance with an embodiment of the present disclosure. On the back of the touchscreen 5024 (seen easily in FIG. 342B) a near-field antenna 5034 is disposed. FIG. 343 shows the sensor portion 5105 of the touchscreen with the near-filed antenna 5034 disposed adjacent to the backside of the sensor portion 5105 of the touchscreen 5024 (see FIGS. 342A-342B). A frame 5035 is shown that forms a loop of metal with a gap 5104 having a dielectric 5036 disposed within the gap 5104. The frame 5035 may be a frame of the sensor 5105 and/or the touchscreen 5024. The antenna 5034 may operate at 13.56 Megahertz and/or may be an NFC antenna. The metal frame 5035 in conjunction with the gap 5104 and the dielectric 5026 disposed within the gap may form a split-ring resonator. The metal frame 5035 forms an inductive element of the split-ring resonator, and the gap 5014 with the dielectric 5036 disposed therein form a capacitive element of the split-ring resonator.

FIG. 344 shows a close-up, side view of the pump 5020 showing a rotation sensor 5037 to measure rotation of the cam shaft 5106 (viewable in FIG. 345) in accordance with an embodiment of the present disclosure. A magnet may be coupled to the cam shaft 345 such that the rotation sensor 5037 can measure the rotation of the cam shaft 5106. The rotation sensor 5037 may be a hall-effect sensor. The rotation sensor 5037 may be coupled to the processor 3500 of FIG. 324.

FIG. 345 shows a close-up, side view of the pump 5020 with a cut plane in accordance with an embodiment of the present disclosure. As the cam shaft 5106 rotates, the rotation sensor 5037 of FIG. 344 senses the rotation of the cam shaft 5106. Rotation of the cam shaft 5106 causes the plunger 5039 to actuate toward or away from the cam shaft 5106. As the plunger 5039 actuates, magnets 5041, 5107 move therewith. A hall-effect sensor 5040 detects movement of the magnet 5041 and another hall-effect sensor (not viewable in FIG. 345) detects movement of the magnet 5107.

FIG. 346 shows a chart diagram illustrating the use of the sensors of the pump of FIG. 399 when one or more of the sensors are unavailable in accordance with an embodiment of the present disclosure. FIG. 345 shows sensors 5042, 5043, 5044, 5045. The rotary position sensor 5042 may be the rotation sensor 5037 of FIG. 355. The motor hall sensors 5043 may be sensors on the motor 5101. The plunger position sensors 5044 and 5045 may be Hall Effect sensors that measure the position of the magnets 5040 and 5107 (e.g., the Hall Effect sensor 5040 of FIG. 345 may be the plunger position sensor 5044).

FIG. 346 may be implemented as a method of using feedback sensors of a peristaltic pump 5020. The RTP 3500 of FIG. 324 may receive the sensors 5042, 5043, 5044, 5045. That is, the sensors 5042, 5043, 5044, 5045 may be the pump sensors 3501.

The RTP 3500 may cross-check the position of the plunger 5039 as indicated by the sensors 5044, 5045 relative to each other. If they are out of agreement by a predetermined amount, the processor will compare them to one or both of the rotary position sensors 5042 and the Hall Effect sensors 5043 to determine the operating one of the plunger position sensors 5044, 5045. Thereafter, the RTP 3500 will use the operating one of the plunger position sensors 5044, 5045. If both of the plunger positions sensors 5044, 5045 are unavailable (e.g., are not working), then the RTP 3500 will use the rotation position sensor 5042 or the motor hall sensor 5043 to estimate the flow rate of the pump 5020. In this case, the RTP 3500 will correlate an RPM of the rotary position sensor 5042 to estimate a flow rate or will correlate the RPM of the motor based upon the motor hall sensor 5043 to estimate the flow rate.

The RTP 3500 also cross checks the rotary position sensor 5042 with the motor hall sensors 5043. If the rotary position sensor 5042 is inoperative, the RTP 3500 uses the motor hall sensor 5043.

FIGS. 347-350 show the operation of the door latch of the pump of FIG. 399 in accordance with an embodiment of the present disclosure. Shown in FIGS. 347-350 are cross-sectional views to illustrate a latching operation of the door 5108 being latched onto the housing 5109 of the pump 5020. FIGS. 347-350 show a sequential progression of using the lever 5046 to latch the door 5108 onto the housing 5109.

The lever 5046 is pivotally coupled to the door 5108 via a pin 5058. When the lever 5046 is in the fully open position (as shown in FIG. 347), an interlock 5047 has an angle of rotation about a pivot 5095 such that a pointed end 5048 engages with a detent 5052 of the lever such that the lever 5046 cannot rotate about its axis of rotation via the pivot 5058 toward the housing 5009. That is, when the top 5048 of the interlock 5047 is positioned within the detent 5052 of the lever 5046, the lever 5046 cannot be closed unless the interlock 5047 is disengaged.

As the door 5108 is closed toward the housing 5109, an end 5110 contacts the housing 5109 thereby disengaging the pointed end 5048 from the detect 5052, as shown in FIG. 348. A spring 5096 biases the interlock 5047 to rotate the end 5110 toward the housing 5109 (counterclockwise in FIGS. 347-350).

As the lever 5046 is actuated toward the door 5108 (and housing 5109), the carriage 5055 (i.e., carrier), is actuated into a slot of the housing 5109. The lever 5046 is pivotally coupled to a first link 5056, which is pivotally coupled to a second link 5057, which is pivotally coupled to the carriage 5055. As the lever 5046 is actuated toward the door 5108, the carriage 5055 is pushed into a slot of the housing 5109 as shown in FIGS. 348 and 349.

As the lever 5046 is rotated toward the door 5108 and the housing 5109, a hook 5053 hooks onto a pin 5054 to secure the door 5108 to the housing 5109. FIG. 350 shows the lever 5046 in a fully closed position. Also note a sensor 5050 pivots along a pivot 5111 such that the hook 5053 engages an end 5051 of the sensor 5050 to rotate the sensor 5050 along the pivot 5111 to thereby move a magnet 5112. Movement of the magnet 5112 may be detected by a Hall Effect sensor to determine whether or not the lever 5046 is the fully closed position.

In some embodiments, an initial actuation of the lever handle 5046 toward the housing 5108 actuates a valve (e.g., working ends 3100 or 3111 of FIG. 274) to occlude the tube prior to actuation of the carrier 5055 into the first slot of the door 5109 such that the tube is unoccluded by the slide occluder.

In some embodiments, the lever handle 5046 is operatively coupled to the carrier 5055 such that actuation of the lever handle away from the housing moves the carrier 5055 away from the first slot to thereby move a slide occluder disposed within the carrier 5055 into an occluded position such that at least some actuation of the lever handle 5046 away from the housing occurs without moving the slide occluder.

In another embodiment, an initial actuation of the lever handle 5046 when the lever handle 5046 is in a fully closed position away from the housing 5109 actuates the carrier 5055 to an occluding position prior to actuating the valve into a non-occluding position.

In another embodiment, an initial actuation of the lever handle 5046 away from the housing 5109 actuates the carrier to an occluding position prior to actuating the valve into a non-occluding position.

FIG. 351 shows an optical sensor 5113 for estimating parameters of a fluid line in accordance with an embodiment of the present disclosure. FIG. 352 shows the optical sensor 5113 of FIG. 351 with a fluid line 5063. Light is shined into a waveguide 5059. The position of the tube 5063 affects the light that travels within the waveguide 5059. A diffuser 5061 causes some of the light to leave the waveguide 5059. That is, total internal reflection prevents light from leaving the bottom surface of the waveguide 5059 into the air. As shown in FIG. 352, the tube 5063 greatly increases the amount of light that leaves the waveguide 5059, which affects the amount of light that leaves the diffuser 5060 at various positions. The light out 5061 is monitored by an image sensor 5062 to determine where and how much of the light leaves the diffuser 5060, which is used to measure the contact of the tube 5063 with the diffuser 506. As shown in FIG. 352, there will be less light out as the tube 5063 pulls in light which results in dimmed light on the right side (of FIG. 352) of the diffuser 5060. The image sensor 5062 may use this data to determine the shape of the tube 5063 and to estimate its volume. The image sensor 5062 may be coupled to the RTP 3500 of FIG. 324. In some embodiments, a plunger (e.g., plunger 3091 of FIG. 297) includes the waveguide 5059, the diffuser 5060, and/or the image sensor 5062 to measure a tube 5063 parameter. The plunger may be clear. In yet additional embodiments, the waveguide 5059, the diffuser 5060, and/or the image sensor 5062 may be positioned in a platen (e.g., platen 3022 of FIG. 297). The platen may be clear.

The image data from the image sensor 5062 may be used to measure the volume delivered, the extent of change in a tube 5063 that is being crushed as part of the pumping mechanism, and/or the extent of water boundaries in a contained portion of the tube 5063 (e.g., between inlet and outlet valves). A polarizer may be used in front of the image sensor 5062 to enhance the image.

In some embodiments, two polarizes are used on both sides of the tube 5063 to determine the edges of the tube 5063 (e.g., using a birefringence effect) as determined by analyzing the image data of the image sensor 5062. The polarizers may polarize light orthogonal to each other. Stress birefringence creates colored interference pattern with a light source, e.g., white light source. The varying indices of refraction through the material of the tube 5063 cause differing patterns of constructive and destructive interference. In some embodiments, monochromatic light may used. In yet additional embodiment, the image data of the image sensor 5062 is used to estimate the width of the tube 5063 using its stress profile. In yet additional embodiments, two patterns (e.g., grid patterns) are used on both sides of the tube 5063 to determine the edges of the tube 5063 (e.g., using Moiré patterns) as determined by analyzing the image data of the image sensor 5062. In yet additional embodiments, the image sensor 5062 detects particles within the tube 5063.

As shown in FIG. 353, light guides can be layered 5064 to provide a variety of information to the images sensor 5062. Each layer can use different polarizations, orientations colors, etc. to provide a suite of spatially distinct information to the camera 5062.

FIGS. 354-355 show the operation of a tube restoring apparatus 5088 in accordance with an embodiment of the present disclosure. The apparatus 5088 includes a first end 5083 and a second end 5082 that squeeze a tube 5082 to ensure its round shape. The ends 5082, 5083 may be coupled to a back 5088. As a plunger 5085 compresses the tube 5082 (see FIG. 355), the plunger 5085 pushes the ends 5082, 5083 away from the tube 5082. When the plunger 5085 is retracted, a spring action causes the ends 5082, 5083 to restore the shape of the tube 5082.

FIGS. 356-357 show the operation of a tube restoring apparatus 5114 in accordance with an embodiment of the present disclosure. The apparatus 5114 includes a first end 5091 and a second end 5092 that squeeze a tube 5090 to help the tube 5090 maintain a round shape. The ends 5091, 5092 may be coupled to a common point 5089. As a plunger 5093 compresses the tube 5090 (see FIG. 357), the plunger 5093 pushes the ends 5091, 5092 away from the tube 5091. When the plunger 5093 is retracted, a spring action causes the ends 5091, 5092 to restore the shape of the tube 5090 as shown in FIG. 356.

FIG. 358 shows a circuit 7000 for storing data within an RFID tag 7008 associated with an infusion pump (e.g., the infusion pump 2990 of FIG. 255) in accordance with an embodiment of the present disclosure. The RFID tag 7009 of FIG. 358 may be the RFID tag 3670 of FIG. 325C. The antenna 7001 of FIG. 358 may be the antenna 3955 of FIG. 325C.

The antenna 7001 is coupled to an RFID tag 7008 such that an RFID reader (i.e., RFID interrogator) can communicate with the RFID tag 7008. The circuit 7000 may be placed on a 1×1 PCB inch board with a solid-metal ground plane of the back side.

An inner loop 7002 with a capacitor 7003 may form a split-ring resonator to enhance the read range capability of the circuit 7000. The RFID tag 7008 may be coupled to the antenna 7001 via an impedance matching network 7004, 7005, 7006, 7007. The circuit 7000 may be configured for use with a 900 Megahertz RFID reader.

A reader chip 7009 may interface with the RFID tag 7008 to write data (e.g., log data) thereto. The reader chip 7009 may communicate with the RFID tag 7008 using I2C, a CAN bus, or other communications link. Alternatively, 7009 may be a electrical connector, in some embodiments.

FIG. 359 shows an equivalent circuit 7010 for impedance as seen from the RFID tag 7008 of FIG. 358 in accordance with an embodiment of the present disclosure. A loop 7011 shows the antenna 7001 of FIG. 358. The inductor 7012 shows the inductor 7004 of FIG. 358. The resistors 7013 and 7014 are schematic representations of the resistors 7006 and 7005, respectively. The capacitor 7015 shows the capacitor 7007 of FIG. 359. The circuit elements 7012-7015 are used for impedance matching so that the RFID tag 7008 is efficiently coupled to the loop antenna 7001 such as in the circuit 7000 of FIG. 358.

FIG. 360 shows another circuit 7016 for storing data within an RFID tag 7022 associated with an infusion pump (e.g., the infusion pump 2990 of FIG. 255) in accordance with an embodiment of the present disclosure. The antenna 7017 is shown. The RFID tag 7022 of FIG. 360 may be the RFID tag 3670 of FIG. 325C. The antenna 7017 of FIG. 360 may be the antenna 3955 of FIG. 325C.

The antenna 7017 may have capacitors coupled to the gaps in the antenna 7017, in some embodiments. An impedance matching network 7018, 7020, 7021 may be used to efficiently couple the RFID tag 7022 to the antenna 7017. An interface 7023 may be used to communicate with the RFID tag 7022 (e.g., an I2C interface, a CAN interface, etc.). FIG. 361 shows a split-ring resonator 7026 used with the circuit of FIG. 360 in accordance with an embodiment of the present disclosure. The split-ring resonator 7026 may be printed on a PCB board with an inner loop 7025 and an outer loop 7024. The splint-ring resonator 7026 may be placed adjacent to the circuit 7016 of FIG. 260 to enhance its read range (e.g., the two planes defined by the two circuit's PCB boards may be parallel to each other).

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in the drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g., "a," "an," or "the," this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B. This expression signifies that, with respect to the present disclosure, the only relevant components of the device are A and B.

Furthermore, the terms "first," "second," "third," and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

What is claimed is:

1. A pump for pumping fluid, the pump comprising:
   a tube platen;
   a plunger configured for actuation toward and away from the tube platen when the tube platen is disposed opposite to the plunger;
   a bias member configured to urge the plunger toward the tube platen;
   an inlet valve upstream of the plunger configured for actuation between an occluding position and a non-occluding position;
   an outlet valve downstream of the plunger configured for actuation between an occluding position and a non-occluding position;
   an actuator mechanism configured to control the actuation of the plunger, the inlet valve and the outlet valve, wherein the actuator mechanism is configured to mechanically engage and disengage from the plunger to pump fluid toward a patient, wherein when the actuator mechanism is disengaged from the plunger, the actuator mechanism is configured to mechanically discharge the bias member such that the bias member acting upon the plunger is a sole force driving the plunger toward the tube platen, wherein the actuator mechanism is configured to engage the plunger to lift the plunger away from the tube platen to thereby mechanically charge the bias member, wherein the actuator mechanism comprises a cam shaft and a plunger cam coupled to the cam shaft configured to actuate the plunger;
   a pressure sensor disposed adjacent to at least one of the inlet valve, the outlet valve, and the plunger;
   a position sensor configured to estimate a position of the plunger; and
   a processor coupled to the position sensor to receive the estimated position of the plunger therefrom, wherein the processor is configured to detect an anomaly based in part on the estimated plunger position when:
      the inlet valve is in the occluding position,
      the outlet valve is in the occluding position,
      the actuator mechanism is mechanically disengaged from the plunger thereby making the bias member the sole source of actuation force of the plunger toward the tube platen, wherein the plunger cam is not in contact with a plunger-cam follower of the plunger when the plunger position is estimated; and
      the bias member urges the plunger toward the tube platen,
   wherein the processor is further coupled to the pressure sensor to receive a pressure signal from the pressure sensor, the processor is configured to, using the pressure signal, to determine a downstream occlusion exists if a subtraction of a filtered value of a sequential series of sequential trough-to-trough pressure values of a plurality of cycles from a trough-to-trough value is greater than a predetermined threshold.

2. The pump according to claim 1, wherein the processor is configured to detect a leak based on a rate of change of the estimated position of the plunger.

3. The pump according to claim 1, the pump further comprising an ultrasonic sensor sensitive to gas in an infusion tube, the ultrasonic sensor located downstream of the plunger and configured communicate with the processor, wherein the processor is configured to distinguish between an upstream occlusion and a presence of air in the fluid using the ultrasonic sensor.

4. The pump according to claim 1, the pump further comprising an ultrasonic sensor sensitive to gas in an infusion tube, the ultrasonic sensor located downstream of the plunger and configured communicate with the processor, wherein the processor is configured to determine a volume of air pumped downstream based on the plunger position when both the inlet and outlet valves occlude the infusion tube and on the sensed gas.

5. The pump according to claim 1, wherein the tube platen is configured to hold an intravenous infusion tube.

6. The pump according to claim 1, further comprising:
   a housing; and
   a door pivotally coupled to the housing, the door configured to pivot to an open position and to a closed position, wherein the tube platen is disposed on the door.

7. The pump according to claim 6, wherein the tube platen, the door, and the plunger are configured such that the plunger is configured for actuation toward and away from the infusion-tube when the door is in the closed position.

8. The pump according to claim 7, further comprising:
   a lever pivotally coupled to the door, the lever having first and second positions; and
   a latch coupled to the door, wherein the lever is configured to latch the door onto the housing when in the first position.

9. The pump according to claim 8, wherein the first position is defined as a position in which the lever is pivoted toward to the door.

10. The pump according to claim 8, further comprising a carrier having first and second portions pivotally coupled together, wherein:
    the door and the carrier co-pivot together,
    the housing includes a first slot in which the first portion of the carrier is at least partially disposed when the door is in the open position,
    the door includes a second slot in which the second portion of the carrier is disposed within when the door is in the open position, and
    the lever is operatively coupled to the second portion of the carrier such that when the door is in the closed position, lever actuation toward the first position pushes the first and second portions of the carrier into the first slot of the housing.

11. The pump according to claim 1, wherein the plunger cam is configured to lift the plunger away from the tube platen.

12. The pump according to claim 1, wherein the processor detects the anomaly when only a force of the bias member forces the plunger toward the tube platen.

13. The pump according to claim 1, wherein the processor detects the anomaly when only a force of the bias member forces the plunger toward the tube platen.

14. The pump according to claim 1, wherein the processor is configured to communicate data to a monitoring client.

15. The pump according to claim 14, wherein the data includes an indication of the anomaly.

16. A pump for pumping fluid, the pump comprising:
    a tube platen;
    a plunger configured for actuation toward and away from the tube platen when the tube platen is disposed opposite to the plunger;

a bias member configured to urge the plunger toward the tube platen;

an inlet valve upstream of the plunger configured for actuation between an occluding position and a non-occluding position;

an outlet valve downstream of the plunger configured for actuation between an occluding position and a non-occluding position;

an actuator mechanism configured to control the actuation of the plunger, the inlet valve and the outlet valve, wherein the actuator mechanism comprises a cam shaft and a plunger cam coupled to the cam shaft configured to actuate the plunger, wherein:
- the actuator mechanism is configured to mechanically engage and disengage from the plunger to pump fluid toward a patient,
- when the actuator mechanism is disengaged from the plunger, the actuator mechanism is configured to mechanically discharge the bias member such that the bias member acting upon the plunger is a sole force driving the plunger toward the tube platen, and
- the actuator mechanism is configured to engage the plunger to lift the plunger away from the tube platen to thereby mechanically charge the bias member;

a pressure sensor disposed adjacent to at least one of the inlet valve, the outlet valve, and the plunger;

a position sensor to estimate the position of the plunger; and a processor coupled to the position sensor and configured to estimate fluid flow in accordance with the estimated position of the plunger when the inlet and outlet valves are closed and the plunger cam is not in contact with a plunger-cam follower of the plunger, the processor is further coupled to the pressure sensor to receive a pressure signal from the pressure sensor, wherein:
- the inlet valve, the outlet valve, and the plunger are configured to pump fluid in a plurality of cycles, each cycle having a trough pressure level and a peak pressure level, and
- the processor is configured to, using the pressure signal, to determine a downstream occlusion exists if a subtraction of a filtered value of a sequential series of sequential trough-to-trough pressure values of the plurality of cycles from a trough-to-trough value is greater than a predetermined threshold.

17. The pump according to claim 16, wherein the pressure signal is filtered prior to being received by the processor.

18. The pump according to claim 16, further comprising an analog filter configured to filter the pressure signal prior to being received by the processor.

19. The pump according to claim 16, wherein the processor is configured to communicate data to a monitoring client.

* * * * *